(12) United States Patent
Akahoshi et al.

(10) Patent No.: US 12,421,225 B2
(45) Date of Patent: Sep. 23, 2025

(54) HETEROAROMATIC AMIDE DERIVATIVE AND MEDICAMENT CONTAINING THE SAME

(71) Applicant: KAKEN PHARMACEUTICAL CO., LTD., Tokyo (JP)

(72) Inventors: Issei Akahoshi, Kyoto (JP); Yoshitake Sumikawa, Kyoto (JP); Sadayoshi Furuta, Tokyo (JP); Keiichiro Fukushima, Kyoto (JP); Takuya Imazu, Kyoto (JP); Ryota Kotaka, Kyoto (JP)

(73) Assignee: KAKEN PHARMACEUTICAL CO., LTD., Tokyo (JP)

( * ) Notice: Subject to any disclaimer, the term of this patent is extended or adjusted under 35 U.S.C. 154(b) by 792 days.

(21) Appl. No.: 17/268,649

(22) PCT Filed: Sep. 9, 2019

(86) PCT No.: PCT/JP2019/035354
§ 371 (c)(1),
(2) Date: Feb. 16, 2021

(87) PCT Pub. No.: WO2020/054657
PCT Pub. Date: Mar. 19, 2020

(65) Prior Publication Data
US 2023/0086366 A1 Mar. 23, 2023

(30) Foreign Application Priority Data
Sep. 10, 2018 (JP) .................... 2018-169104

(51) Int. Cl.
*C07D 471/04* (2006.01)
*A61P 25/04* (2006.01)
(Continued)

(52) U.S. Cl.
CPC ............ *C07D 471/04* (2013.01); *A61P 25/04* (2018.01); *C07D 487/04* (2013.01); *C07D 498/04* (2013.01)

(58) Field of Classification Search
None
See application file for complete search history.

(56) References Cited

U.S. PATENT DOCUMENTS 8,883,840 B2 11/2014 Chafeev et al.
2007/0037974 A1 2/2007 Brotherton-Pleiss et al.
(Continued)

FOREIGN PATENT DOCUMENTS

JP 2014-101287 A 6/2014
JP 2016-526571 A 9/2016
(Continued)

OTHER PUBLICATIONS

CAS STNext Registry for Registry Nos. 2224029-00-7 published Mar. 19, 2018; 2193883-73-5 published Mar. 19, 2018; 1944645-45-7 published Jul. 4, 2016; 440110-80-5 published Jul. 25, 2002. Retrieved from STN Registry on Jan. 4, 2024. (Year: 2018).*
SciFinder. CAS Registry No. 493-08-03. Retrieved from the Internet on Mar. 5, 2024, https://scifinder-n.cas.org/searchDetail/substance/65e6e8fca9414c0bb59e7e81/substanceDetails. (Year: 2024).*
STN International, 2023, File Registry, CAS Registry No. 1957374-74-1, 1956882-96-4, 1956614-99-5, 1953690-86-2, 1952842-99-7, 1951042-02-6, 1950531-37-9, 1948866-33-8, 1948047-30-0, 1946161-06-3 (5 pages total).
STN International, 2023, File Registry, CAS Registry No. 2813995-75-2, 2806651-16-9, 2806186-38-7, 2804660-55-5, 2800695-08-1, 2799132-89-9, 2470292-78-3, 2398205-30-4, 2398113-55-6, 2369392-55-0 (6 pages total).
STN International, 2023, File Registry, CAS Registry No. 2469333-53-5, 2406846-52-2, 2406099-31-6, 2403988-07-6, 2371031-70-6, 2370270-31-6, 2060587-19-9 (4 pages total).
(Continued)

*Primary Examiner* — James H Alstrum-Acevedo
*Assistant Examiner* — Lauren Wells
(74) *Attorney, Agent, or Firm* — Sughrue Mion, PLLC

(57) ABSTRACT

A heteroaromatic amide derivative or salt thereof showing high efficacy for diseases associated with Nav1.7 is represented by general formula (I)

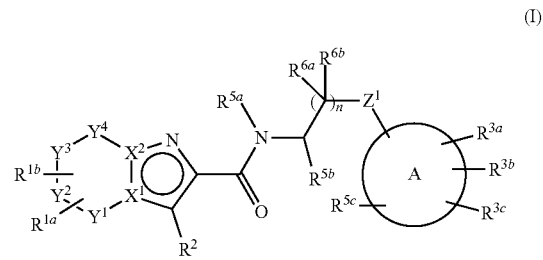

wherein, $X^1$-$X^2$ is N—C or C—N, $Y^1$, $Y^2$, $Y^3$ and $Y^4$ are —$CH_2$—, —$CR^{4a}H$— or —O— and so on, $Z^1$ is —O— and so on, ring A is a 3- to 7-membered monocyclic aromatic ring and so on, $R^{1a}$ and $R^{1b}$ are a hydrogen atom or a halogen atom and so on, $R^2$ is a hydrogen atom and so on, $R^{3a}$, $R^{3b}$ and $R^{3c}$ are a hydrogen atom or an optionally substituted $C_1$-$C_6$ haloalkyl group and so on, $R^{4a}$, $R^{4b}$ and $R^{4c}$ are, an optionally substituted $C_1$-$C_6$ haloalkyl group or $C_1$-$C_6$ haloalkoxy group and so on, $R^{5a}$ is a hydrogen atom and so on, $R^{5a}$ and $R^{5b}$ together form —$CH_2O$— and so on, $R^{6a}$ and $R^{6b}$ are a hydrogen atom and so on, n is 1 or 2.

8 Claims, No Drawings

(51) Int. Cl.
   C07D 487/04    (2006.01)
   C07D 498/04    (2006.01)

(56) References Cited

U.S. PATENT DOCUMENTS

| | | |
|---|---|---|
| 2009/0186902 A1 | 7/2009 | Merla et al. |
| 2013/0324522 A1 | 12/2013 | Vosshall et al. |
| 2017/0362253 A1 | 12/2017 | Xiao et al. |

FOREIGN PATENT DOCUMENTS

| | | |
|---|---|---|
| WO | 01/58869 A2 | 8/2001 |
| WO | 2008/008020 A1 | 1/2008 |
| WO | 2008/130319 A2 | 10/2008 |
| WO | 2008/130320 A2 | 10/2008 |
| WO | 2008/130321 A2 | 10/2008 |
| WO | 2008/130322 A1 | 10/2008 |
| WO | 2008/130323 A1 | 10/2008 |
| WO | 2009/144494 A1 | 12/2009 |
| WO | 2009/145720 A1 | 12/2009 |
| WO | 2009/145721 A1 | 12/2009 |
| WO | 2012/039657 A1 | 3/2012 |
| WO | 2012/083190 A1 | 6/2012 |
| WO | 2013/161928 A1 | 10/2013 |
| WO | 2014/025651 A1 | 2/2014 |
| WO | 2014/151472 A1 | 9/2014 |
| WO | 2015/006280 A1 | 1/2015 |
| WO | 2015/119998 A1 | 8/2015 |
| WO | 2016/117647 A1 | 7/2016 |
| WO | 2017/004500 A1 | 1/2017 |
| WO | 2017/108744 A1 | 6/2017 |
| WO | 2017/136727 A2 | 8/2017 |
| WO | 2017/145013 A1 | 8/2017 |
| WO | 2018/023029 A1 | 2/2018 |
| WO | 2018/109097 A1 | 6/2018 |
| WO | 2019/204537 A1 | 10/2019 |

OTHER PUBLICATIONS

P. Yogeeswari et al., "Ion Channels as Important Targets for Antiepileptic Drug Design", Current Drug Targets, 2004, vol. 5, No. 7, pp. 589-602 (14 pages).

Denis Noble, "Unraveling the genetics and mechanisms of cardiac arrhythmia", Proc Natl Acad Sci, 2002, vol. 99, No. 9, pp. 5755-5756 (2 pages).

Stephen C. Cannon, "Spectrum of sodium channel disturbances in the nondystrophic myotonias and periodic paralyses", Kidney International, 2000, vol. 57, No. 3, pp. 772-779 (8 pages total).

John N. Wood et al., "Voltage-Gated Sodium Channels and Pain Pathways", J. Neurobiol., 2004, vol. 61, No. 1, pp. 55-71 (17 pages total).

William A. Catterall et al., "International Union of Pharmacology. XLVII. Nomenclature and Structure-Function Relationships of Voltage-Gated Sodium Channels", Pharmacological Reviews, 2005, vol. 57, No. 4, pp. 397-409 (13 pages total).

Stephen G. Waxman, MD, PhD, "Nav1.7, its mutations, and the syndromes that they cause", Neurology, 2007, vol. 7, No. 69 (6), pp. 505-507 (5 pages total).

James J. Cox et al., "An SCN9A channelopathy causes congenital inability to experience pain", Nature, 2006, vol. 444, pp. 894-898 (5 pages total).

Jun-Ho Lee et al., "A Monoclonal Antibody that Targets a Nav1.7 Channel Voltage Sensor for Pain and Itch Relief", Cell, 2014, vol. 157, pp. 1393-1404 (12 pages total).

Erin McGowan et al., "A Peripherally Acting Nav1.7 Sodium Channel Blocker Reverses Hyperalgesia and Allodynia on Rat Models of Inflammatory and Neuropathic Pain", International Anesthesia Research Society, 2009, vol. 109, No. 3, pp. 951-958 (8 pages total).

Guillaume Duvey et al., "A novel series of metabotropic glutamate receptor 5 negative allosteric modulators based on a 4,5,6,7-tetrahydropyrazolo [1,5-a]pyridine core" Bioorganic & Medicinal Chemistry Letters, 2013, vol. 23, No. 16, pp. 4523-4527 (5 pages total).

STN International, 2011, File Registry, CAS Registry No. 1309257-05-3, 1309231-46-6.

STN International, 2015, File Registry, CAS Registry No. 1795487-06-7, 1795267-01-4, 1795259-58-3.

STN International, 2015, File Registry, CAS Registry No. 1789032-35-4.

STN International, 2012, File Registry, CAS Registry No. 1380773-67-0, 1380748-43-5.

STN International, 2018, File Registry, CAS Registry No. 2242295-07-2.

STN International, 2018, File Registry, CAS Registry No. 2241890-76-4.

STN International, 2015, File Registry, CAS Registry No. 1775525-83-1.

STN International, 2016, File Registry, CAS Registry No. 1944645-45-7.

STN International, 2018, File Registry, CAS Registry No. 2200697-80-7, 1945459-43-7, 1956914-79-6, 1951559-45-7.

STN International, 2011, File Registry, CAS Registry No. 1269245-68-2, 1269117-64-7, 1269059-85-9.

STN International, 2017, File Registry, CAS Registry No. 2108827-53-6.

STN International, 2015, File Registry, CAS Registry No. 1775531-76-4, 1582767-49-4, 2184583-31-9.

Sulayman D. Dib-Hajj et al., "From genes to pain: Nav1.7 and human pain disorders", Trends in Neurosciences, 2007, vol. 30, No. 11, ppl 555-563 (9 pages total).

International Search Report (PCT/ISA/210) issued in PCT/JP2019/035354 on Dec. 10, 2019.

STN International, 2022, File Registry, CAS Registry No. 2224029-00-7 (1 page total).

* cited by examiner

HETEROAROMATIC AMIDE DERIVATIVE AND MEDICAMENT CONTAINING THE SAME

CROSS REFERENCE TO RELATED APPLICATIONS

This application is a National Stage of International Application No. PCT/JP2019/035354 filed on Sep. 9, 2019, claiming priority based on Japanese Patent Application No. 2018-169104 filed on Sep. 10, 2018.

TECHNICAL FIELD

The present invention relates to a compound or a pharmaceutical composition useful for treating or preventing a disease associated with a voltage-gated sodium channel Nav1.7 (hereinafter referred to as Nav1.7).

BACKGROUND ART

Voltage-gated sodium channels (Nav) are present in excitable cells including neuronal cells in the central and peripheral nervous systems as well as cardiomyocytes. Its role is to control the rising phase of action potential generated by depolarization of cell membrane potential to participate in the generation and propagation of electrical signals. The Nav are essential for maintaining the physiological functions of excitable cells such as those in the neurons and myocardia. Nav abnormalities are associated with diseases such as epilepsy (Non-Patent document 1), arrhythmia (Non-Patent document 2), myotonia (Non-Patent document 3), and chronic pain (Non-Patent document 4).

The Nav are composed of a subunits which form an ion channel pore and β subunits which supplementarily works. There are at least nine a subunits known to date (Nav1.1 to Nav1.9). These subtypes are classified as TTX-sensitive Nav (Nav1.1, Nav1.2, Nav1.3, Nav1.4, Nav1.6, Nav1.7), which are functionally inhibited by the puffer toxin tetrodotoxin (TTX) and TTX-resistant Nav (Nav1.5, Nav1.8, Nav1.9). It is known that Nav1.1, Nav1.2, Nav1.3 are mostly expressed in the central nervous system, Nav1.4 is mostly expressed in skeletal muscles, Nav1.5 is mostly expressed in myocardia, Nav1.6 is mostly expressed in the nervous system, and Nav1.7, Nav1.8 and Nav1.9 are mostly expressed in the peripheral nervous system (Non-Patent document 5).

Nav1.7 is a TTX-sensitive sodium channel distributed in the peripheral nervous system such as autonomic and sensory neurons. Recently, mutations in the gene encoding Nav1.7 (SCN9A) have been shown to change the pain threshold. Namely, it has been reported that a gain of function mutation occurred in SCN9A, based on the analysis of the family history of erythromelalgia with increased flushing at the distal extremities and pain sensation (Non-Patent document 6); and also it has been reported that a loss of function mutation occurred in SCN9A, based on a pedigree analysis of insensitivity to pain in which only pain sensation had disappeared even though other sensations are normal (Non-Patent document 7).

It is also known that inhibition of Nav1.7 achieves analgesic effects on nociceptive pain and neuropathic pain from studies using an anti-Nav1.7 antibody (Non-Patent document 8) and Nav1.7 inhibitory compounds (Non-Patent document 9, Patent document 1, and Patent document 2).

Thus, since Nav1.7 is suggested of its relevance in particular to pain sensation, Nav1.7 inhibitors are considered to be useful as therapeutic or preventive drugs for diseases associated with pain, in particular, nociceptive pain and neuropathic pain.

Furthermore, since pruritus sensation is transmitted by peripheral sensory neurons and Nav1.7 is distributed in the peripheral nervous system, Nav1.7 is thought to be involved in acute and chronic pruritus; inhibition of Nav1.7 is considered to exert an anti-pruritic effect against acute or chronic pruritus (Non-Patent document 7).

Nav inhibitors are effective in the treatment of various disease states. For example, subtype-non-selective Nav inhibitors include lidocaine, a local anesthetic, mexiletine, an antiarrhythmic drug, and carbamazepine, an antiepileptic drug and so on.

Subtype-non-specific Nav inhibitors are known clinically to have an analgesic effect and are used as analgesics. However, these subtype-non-selective Nav inhibitors also exert an inhibitory action on Nav1.5 expressed in the myocardia, and thus have a concern about adversely affecting cardiac function, which function is particularly important in life support. To date, there is no selective Nav1.7 inhibitor to be clinically used.

Based on the above, Nav1.7 inhibitors that are selective for Nav1.5 are thought to be very useful as therapeutic or preventive drugs for various painful pathologies with less concern about side effects derived from Nav1.5 inhibition.

To date, various heteroaromatic amide derivatives having Nav1.7 inhibitory action have been reported (Patent document 3 to Patent document 10).

In addition, various amide compounds having Nav1.7 inhibitory activity are disclosed in Patent document 11 to Patent document 15. For example, Patent document 15 describes a compound represented by

[Chem 1]

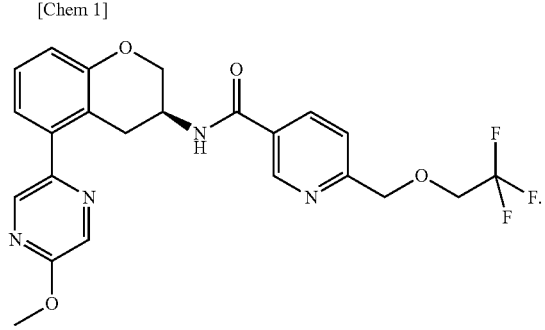

Patent document 16 describes a compound represented by

[Chem 2]

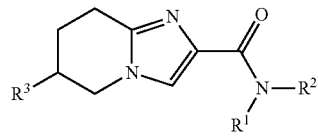

(wherein, each symbol is as defined in Patent document 16), as a compound having affinity to KCNQ2/3 potassium channel and being useful as an analgesic agent.

Patent document 17 describes a compound represented by

[Chem 3]

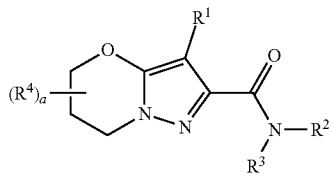

(wherein, each symbol is as defined in Patent document 17), as a compound having PDE4B inhibitory activity and being effective for various disorders including pain.

Non-Patent document 10 describes a compound represented by

[Chem 4]

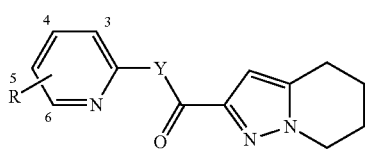

(wherein, each symbol is as defined in Non-Patent document 10.), as a negative allosteric modulator of metabotropic glutamate receptor 5 and a compound applicable to chronic pain.

PRIOR ART DOCUMENTS

Patent Documents

Patent document 1: WO2014/151472
Patent document 2: U.S. Pat. No. 8,883,840
Patent document 3: WO2008/008020
Patent document 4: WO2009/145720
Patent document 5: WO2009/145721
Patent document 6: WO2013/161928
Patent document 7: JP2014-101287A
Patent document 8: WO2015/119998
Patent document 9: WO2016/117647
Patent document 10: WO2008/130319
Patent document 11: WO2008/130320
Patent document 12: WO2008/130321
Patent document 13: WO2008/130322
Patent document 14: WO2008/130323
Patent document 15: WO2012/039657
Patent document 16: US20090186902A
Patent document 17: WO2017/145013

Non-Patent Documents

Non-Patent document 1: Yogeeswari et al., Curr. Drug Targets 2004, 5 (7), 589-602.
Non-Patent document 2: Noble D., Proc Natl Acad Sci USA. 2002, 99 (9): 5755-5756.
Non-Patent document 3: Cannon S C, Kidney Int. 2000, 57 (3), 772-779.
Non-Patent document 4: Wood, J N et al., J. Neurobiol. 2004, 61 (1), 55-71.
Non-Patent document 5: Catterall, W A et al., Pharmacol Rev. 2005, 57: 397-409.
Non-Patent document 6: Waxman, S G Neurology. 2007, 7, 69 (6), 505-507.
Non-Patent document 7: Cox et al., Nature 2006, 444, 894-898.
Non-Patent document 8: Lee J H et al., Cell 2014, 157, 1393-1404.
Non-Patent document 9: Erin McGowan B S et al., Anesth Analg 2009, 109, 951-958.
Non-Patent document 10: G. Duvey et al., Bioorg. Med. Chem. Lett. 2013, 23 (16), 4523.

DISCLOSURE OF THE INVENTION

Problems to be Solved by the Invention

An object of the present invention is to provide novel compounds having Nav1.7 inhibitory action and pharmaceutical compositions containing the same.

Means to Solve the Problem

The present inventors have conducted intensive research to solve the aforementioned problems, found out that the following novel heteroaromatic amide derivative represented by the general formula (I) has Nav1.7 inhibitory action selective over Nav1.5, and completed the present invention.

(0) The present invention relates to a heteroaromatic amide derivative represented by the general formula (I) or pharmaceutically acceptable salt thereof:

[Chem 5]

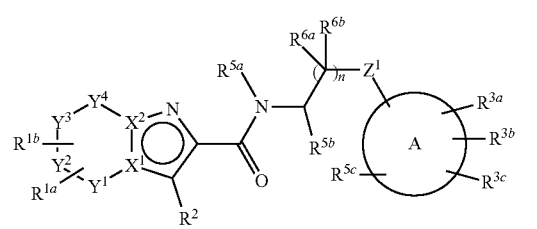

(I)

[wherein,
$X^1$-$X^2$ is N—C or C—N,
$Y^1$, $Y^2$, $Y^3$ and $Y^4$ are, independently each other, a single bond, —$CH_2$—, —$CH_2CH_2$—, —$CR^{4a}R^{4b}$—, —$CR^{4a}H$—, —$CR^{4b}H$—, —$CH_2CR^{4a}R^{4b}$—, —$CH_2CR^{4a}H$—, —$NR^{4c}$—, —NH—, —S—, —$SO_2$—, or —O—,
$Z^1$ is a single bond, —$CR^{7a}R^{7b}$—, —O—, —S—, —NH—, —$NR^{7a}$—, —$NR^{7a}CH_2$—, —$CH_2NR^{7a}$—, —CO—, or —$SO_2$—,
ring A is a 3- to 7-membered monocyclic aromatic ring, or a 8- to 12-membered bicyclic aromatic ring,
$R^{1a}$ and $R^{1b}$ are, independently each other, a hydrogen atom, a halogen atom, a hydroxyl group, a cyano group, a $C_1$-$C_4$ alkyl group, a $C_1$-$C_4$ haloalkyl group, a $C_1$-$C_4$ alkoxy group, a $C_1$-$C_4$ haloalkoxy group, a $C_3$-$C_7$ cycloalkyl group, a $C_1$-$C_4$ alkoxy-$C_1$-$C_4$ alkyl group, or a $C_1$-$C_4$ haloalkoxy-$C_1$-$C_4$ alkyl group,
$R^2$ is a hydrogen atom, a halogen atom, a hydroxyl group, a cyano group, an optionally substituted $C_1$-$C_6$ alkyl group, an optionally substituted $C_1$-$C_6$ haloalkyl group, an optionally substituted $C_2$-$C_6$ alkenyl group, an optionally substituted $C_2$-$C_6$ alkynyl group, or an optionally substituted saturated, partially saturated or unsaturated 3- to 7-membered monocyclic ring, $R^{3a}$, $R^{3b}$ and $R^{3c}$ are, independently each other, a hydrogen atom, a halogen atom, a cyano group, a cyanomethyl group, a formyl group, a nitro group, a carboxamide group, a hydroxyl group, an optionally substituted $C_1$-$C_6$ alkyl group, an optionally substituted $C_1$-$C_6$ haloalkyl group, an optionally substituted $C_1$-$C_6$ alkoxy group, an optionally substituted $C_1$-$C_6$ haloalkoxy group, an optionally substituted $C_1$-$C_4$ alkoxy-$C_1$-$C_4$ alkyl group, an optionally substituted $C_1$-$C_4$ haloalkoxy-$C_1$-$C_4$ alkyl group, an optionally substituted $C_1$-$C_4$ alkoxy-$C_1$-$C_4$ haloalkyl group, an optionally substituted $C_1$-$C_4$ haloalkoxy-$C_1$-$C_4$ haloalkyl group, an optionally substituted $C_1$-$C_6$ alkylcarbonyl group, an optionally substituted $C_1$-$C_6$ alkoxycarbonyl group, an optionally substituted $C_1$-$C_6$ alkylcarbonyloxy group, an optionally substituted $C_1$-$C_6$ haloalkylcarbonyl group, an optionally substituted $C_1$-$C_6$ haloalkoxycarbonyl group, an optionally substituted $C_1$-$C_6$ haloalkylcarbonyloxy group, an optionally substituted $C_3$-$C_7$ cycloalkyl group, an optionally substituted heterocycloalkyl group, an optionally substituted $C_3$-$C_7$ cycloalkyloxy group, an optionally substituted heterocycloalkyloxy group, an optionally substituted $C_2$-$C_6$ alkenyl group, an optionally substituted $C_2$-$C_6$ alkenyloxy group, an optionally substituted $C_2$-$C_6$ alkenyloxy-$C_1$-$C_4$ alkyl group, an optionally substituted $C_2$-$C_6$ alkenyloxy-$C_1$-$C_4$ haloalkyl group, an optionally substituted $C_2$-$C_6$ alkynyl group, an optionally substituted $C_2$-$C_6$ alkynyloxy group, an optionally substituted $C_2$-$C_6$ alkynyloxy-$C_1$-$C_4$ alkyl group, an optionally substituted $C_2$-$C_6$ alkynyloxy-$C_1$-$C_4$ haloalkyl group, an optionally substituted $C_1$-$C_4$ alkoxy-$C_1$-$C_4$ alkoxy group, an optionally substituted $C_1$-$C_4$ haloalkoxy-$C_1$-$C_4$ alkoxy group, an optionally substituted $C_2$-$C_6$ alkenyloxy-$C_1$-$C_4$ alkoxy group, an optionally substituted $C_2$-$C_6$ alkynyloxy-$C_1$-$C_4$ alkoxy group, an optionally substituted $C_2$-$C_6$ alkenyloxy-$C_1$-$C_4$ haloalkoxy group, an optionally substituted $C_2$-$C_6$ alkynyloxy-$C_1$-$C_4$ haloalkoxy group, an optionally substituted $C_1$-$C_6$ alkylthio group, an optionally substituted $C_1$-$C_6$ haloalkylthio group, an optionally substituted $C_1$-$C_4$ alkylthio-$C_1$-$C_4$ alkyl group, an optionally substituted $C_1$-$C_4$ haloalkylthio-$C_1$-$C_4$ alkyl group, an optionally substituted $C_1$-$C_4$ alkylthio-$C_1$-$C_4$ haloalkyl group, an optionally substituted $C_1$-$C_4$ haloalkylthio-$C_1$-$C_4$ haloalkyl group, an optionally substituted $C_1$-$C_6$ alkylsulfonyl group, —$(CH_2)_p NR^{a1}R^{a2}$ ($R^{a1}$ and $R^{a2}$ are, independently each other, a hydrogen atom, a $C_1$-$C_4$ alkyl group, or a $C_1$-$C_4$ haloalkyl group, and p is 0, 1, or 2.), or a group represented by the general formula (I-A)

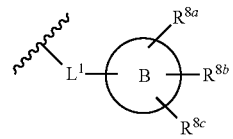

(I-A)

{wherein,
ring B is a saturated, partially saturated or unsaturated 3- to 7-membered monocyclic ring, $L^1$ is a single bond, —$CR^{a3}R^{a4}$—, —O—, —$NR^{a1}$, —$CR^{a3}R^{a4}O$—, —$OCR^{a3}R^{a4}$—, —$CH_2CH_2$—, —CH═CH—, —C≡C—, or —$CH_2OCH_2$— ($R^{a3}$ and $R^{a4}$ are, independently each other, a hydrogen atom, a $C_1$-$C_4$ alkyl group, or a $C_1$-$C_4$ haloalkyl group.), $R^{8a}$, $R^{8b}$ and $R^{8c}$ are, independently each other, a hydrogen atom, a halogen atom, a cyano group, a $C_1$-$C_6$ alkyl group, a $C_1$-$C_6$ haloalkyl group, a $C_1$-$C_6$ alkoxy group, a $C_1$-$C_6$ haloalkoxy group, a $C_3$-$C_7$ cycloalkyl group, a $C_3$-$C_7$ cycloalkyloxy group, a heterocycloalkyl group, a heterocycloalkyloxy group, a $C_2$-$C_6$ alkenyl group, or a $C_2$-$C_6$ alkynyl group.}, $R^{4a}$, $R^{4b}$ and $R^{4c}$ are, independently each other, a halogen atom, a cyano group, a cyanomethyl group, a formyl group, a nitro group, a carboxamide group, a hydroxyl group, an optionally substituted $C_1$-$C_6$ alkyl group, an optionally substituted $C_1$-$C_6$ haloalkyl group, an optionally substituted $C_1$-$C_6$ alkoxy group, an optionally substituted $C_1$-$C_6$ haloalkoxy group, an optionally substituted $C_1$-$C_4$ alkoxy-$C_1$-$C_4$ alkyl group, an optionally substituted $C_1$-$C_4$ haloalkoxy-$C_1$-$C_4$ alkyl group, an optionally substituted $C_1$-$C_4$ alkoxy-$C_1$-$C_4$ haloalkyl group, an optionally substituted $C_1$-$C_4$ haloalkoxy-$C_1$-$C_4$ haloalkyl group, an optionally substituted $C_1$-$C_6$ alkylcarbonyl group, an optionally substituted $C_1$-$C_6$ alkoxycarbonyl group, an optionally substituted $C_1$-$C_6$ alkylcarbonyloxy group, an optionally substituted $C_1$-$C_6$ haloalkylcarbonyl group, an optionally substituted $C_1$-$C_6$ haloalkoxycarbonyl group, an optionally substituted $C_1$-$C_6$ haloalkylcarbonyloxy group, an optionally substituted $C_3$-$C_7$ cycloalkyl group, an optionally substituted heterocycloalkyl group, an optionally substituted $C_3$-$C_7$ cycloalkyloxy group, an optionally substituted heterocycloalkyloxy group, an optionally substituted $C_2$-$C_6$ alkenyl group, an optionally substituted $C_2$-$C_6$ alkenyloxy group, an optionally substituted $C_2$-$C_6$ alkenyloxy-$C_1$-$C_4$ alkyl group, an optionally substituted $C_2$-$C_6$ alkenyloxy-$C_1$-$C_4$ haloalkyl group, an optionally substituted $C_2$-$C_6$ alkynyl group, an optionally substituted $C_2$-$C_6$ alkynyloxy group, an optionally substituted $C_2$-$C_6$ alkynyloxy-$C_1$-$C_4$ alkyl group, an optionally substituted $C_2$-$C_6$ alkynyloxy-$C_1$-$C_4$ haloalkyl group, an optionally substituted $C_1$-$C_4$ alkoxy-$C_1$-$C_4$ alkoxy group, an optionally substituted $C_1$-$C_4$ haloalkoxy-$C_1$-$C_4$ alkoxy group, an optionally substituted $C_2$-$C_6$ alkenyloxy-$C_1$-$C_4$ alkoxy group, an optionally substituted $C_2$-$C_6$ alkynyloxy-$C_1$-$C_4$ alkoxy group, an optionally substituted $C_2$-$C_6$ alkenyloxy-$C_1$-$C_4$ haloalkoxy group, an optionally substituted $C_2$-$C_6$ alkynyloxy-$C_1$-$C_4$ haloalkoxy group, an optionally substituted $C_1$-$C_6$ alkylthio group, an optionally substituted $C_1$-$C_6$ haloalkylthio group, an optionally substituted $C_1$-$C_4$ alkylthio-$C_1$-$C_4$ alkyl group, an optionally substituted $C_1$-$C_4$ haloalkylthio-$C_1$-$C_4$ alkyl group, an optionally substituted $C_1$-$C_4$ alkylthio-$C_1$-$C_4$ haloalkyl group, an optionally substituted $C_1$-$C_4$ haloalkylthio-$C_1$-$C_4$ haloalkyl group, a pentafluorosulfanyl group, —$(CH_2)_q NR^{b1}R^{b2}$ ($R^{b1}$ and $R^{b2}$ are, independently each other, a hydrogen atom, a $C_1$-$C_4$ alkyl group, or a $C_1$-$C_4$ haloalkyl group, and q is 0, 1, 2, or 3.), or the general formula (I-B)

[Chem 7]

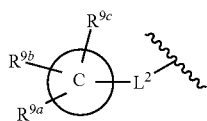

(I-B)

{wherein,
ring C is a saturated, partially saturated or unsaturated 3- to 7-membered monocyclic ring, or a saturated, partially saturated or unsaturated 7- to 12-membered bicyclic ring,
$L^2$ is a single bond, —CH=CH—, —C≡C—,
—$(CR^{10a}R^{10b})_{r1}(CR^{10c}R^{10d})_{r2}(CR^{10e}R^{10f})_{r3}(CR^{10g}R^{10h})_{r4}$—,
—$(CR^{10a}R^{10b})_{r1}(CR^{10c}R^{10d})_{r2}O(CR^{10e}R^{10f})_{r3}(CR^{10g}R^{10h})_{r4}$—,
—$(CR^{10a}R^{10b})_{r1}(CR^{10c}R^{10d})_{r2}NR^c(CR^{10e}R^{10f})_{r3}(CR^{10g}R^{10h})_{r4}$—,
—$(CR^{10a}R^{10b})_{r1}(CR^{10c}R^{10d})_{r2}CO(CR^{10e}R^{10f})_{r3}(CR^{10g}R^{10h})_{r4}$—,
—$(CR^{10a}R^{10b})_{r1}(CR^{10c}R^{10d})_{r2}CONR^c(CR^{10e}R^{10f})_{r3}(CR^{10g}R^{10h})_{r4}$—,
—$(CR^{10a}R^{10b})_{r1}(CR^{10c}R^{10d})_{r2}NR^cCO(CR^{10e}R^{10f})_{r3}(CR^{10g}R^{10h})_{r4}$—,
—$(CR^{10a}R^{10b})_{r1}(CR^{10c}R^{10d})_{r2}S(CR^{10e}R^{10f})_{r3}(CR^{10g}R^{10h})_{r4}$—,
—$(CR^{10a}R^{10b})_{r1}(CR^{10c}R^{10d})_{r2}SO(CR^{10e}R^{10f})_{r3}(CR^{10g}R^{10h})_{r4}$—,
—$(CR^{10a}R^{10b})_{r1}(CR^{10c}R^{10d})_{r2}SO_2(CR^{10e}R^{10f})_{r3}(CR^{10g}R^{10h})_{r4}$—,
—$(CR^{10a}R^{10b})_{r1}(CR^{10c}R^{10d})_{r2}SO_2NR^c(CR^{10e}R^{10f})_{r3}(CR^{10g}R^{10h})_{r4}$—, or
—$(CR^{10a}R^{10b})_{r1}(CR^{10c}R^{10d})_{r2}NR^cSO_2(CR^{10e}R^{10f})_{r3}(CR^{10g}R^{10h})_{r4}$—,
($R^c$ is hydrogen atom, a $C_1$-$C_4$ alkyl group, or a $C_1$-$C_4$ haloalkyl group,
$R^{10a}$, $R^{10b}$, $R^{10c}$, $R^{10d}$, $R^{10e}$, $R^{10f}$, $R^{10g}$, and $R^{10h}$ are, independently each other, a hydrogen atom, a halogen atom, a $C_1$-$C_4$ alkyl group, or a $C_3$-$C_7$ cycloalkyl group,
$R^{10a}$ and $R^{10b}$ optionally form, together with the carbon atom bonded thereto, a 3- to 7-membered monocyclic ring,
$R^{10c}$ and $R^{10d}$ optionally form, together with the carbon atom bonded thereto, a 3- to 7-membered monocyclic ring,
$R^{10e}$ and $R^{10f}$ optionally form, together with the carbon atom bonded thereto, a 3- to 7-membered monocyclic ring,
$R^{10g}$ and $R^{10h}$ optionally form, together with the carbon atom bonded thereto, a 3- to 7-membered monocyclic ring,
r1, r2, r3 and r4 are, independently each other, 0, 1, or 2.),
$R^{9a}$, $R^{9b}$ and $R^{9c}$ are, independently each other, a hydrogen atom, a halogen atom, a hydroxyl group, a cyano group, a formyl group, a $C_1$-$C_6$ alkyl group, a $C_1$-$C_6$ haloalkyl group, a $C_1$-$C_6$ alkoxy group, a $C_1$-$C_6$ haloalkoxy group, a $C_1$-$C_4$ alkoxy-$C_1$-$C_4$ alkyl group, a $C_1$-$C_4$ haloalkoxy-$C_1$-$C_4$ alkyl group, a $C_1$-$C_4$ alkoxy-$C_1$-$C_4$ haloalkyl group, a $C_1$-$C_6$ alkylcarbonyl group, a $C_1$-$C_6$ alkoxycarbonyl group, a $C_1$-$C_6$ haloalkylcarbonyl group, a $C_3$-$C_7$ cycloalkyl group, a heterocycloalkyl group, a $C_3$-$C_7$ cycloalkyloxy group, a heterocycloalkyloxy group, a $C_2$-$C_6$ alkenyl group, —$(CH_2)_s NR^{d1}R^{d2}$ ($R^{d1}$ and $R^{d2}$ are, independently each other, a hydrogen atom, a $C_1$-$C_4$ alkyl group, or a $C_1$-$C_4$ haloalkyl group, and s is 0, 1, or 2.), or a group represented by the general formula (I-C)

[Chem 8]

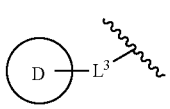

(I-C)

{wherein,
ring D is a 3- to 7-membered monocyclic ring optionally substituted by a halogen atom, a hydroxyl group, a $C_1$-$C_4$ alkyl group, a $C_1$-$C_4$ haloalkyl group, a $C_1$-$C_4$ alkoxy group, or a $C_1$-$C_4$ haloalkoxy group,
$L^3$ is a single bond, or an oxygen atom.}, or
$R^{4a}$ and $R^{4b}$ optionally form, together with the carbon atom bonded thereto, a 3- to 7-membered monocyclic ring, or
$R^{4a}$ and $R^{4b}$ together optionally form the general formula (I-D):

[Chem 9]

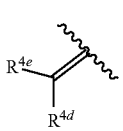

(I-D)

($R^{4d}$ and $R^{4e}$ are, independently each other, a hydrogen atom, a halogen atom, or a $C_1$-$C_4$ alkyl group, or $R^{4d}$ and $R^{4e}$ optionally form, together with the carbon atom bonded thereto, a 3- to 7-membered monocyclic ring.),
$R^{5a}$, $R^{5b}$, $R^{6a}$, $R^{6b}$ and n fulfill either one of the following constitutions indicated in (i) to (v)
{(i) $R^{5b}$ and $R^{5c}$ together form a single bond, —$CH_2$—, —$OCH_2$—, —$CH_2O$—, —$CH_2S$—, —$SCH_2$—, —$CH_2NR^{e1}$—, —$NR^{e1}CH_2$—, —$CH_2CH_2$—, —$CONR^{e1}$—, —$NR^{e1}CO$—, or —$OCR^{e1}R^{e2}$— ($R^{e1}$ and $R^{e2}$ are a hydrogen atom or a $C_1$-$C_4$ alkyl group.), and
$R^{5a}$ is a hydrogen atom, a $C_1$-$C_6$ alkyl group, a $C_1$-$C_6$ haloalkyl group, a $C_3$-$C_7$ cycloalkyl group, a heterocycloalkyl group, a $C_3$-$C_7$ cycloalkyl-$C_1$-$C_4$ alkyl group, a heterocycloalkyl-$C_1$-$C_4$ alkyl group, or an aralkyl group, and $R^{6a}$ and $R^{6b}$, independently each other, are a hydrogen atom, a halogen atom, a hydroxyl group, a cyano group, a $C_1$-$C_4$ alkyl group, a $C_1$-$C_4$ haloalkyl group, a $C_1$-$C_4$ alkoxy group, or a $C_1$-$C_4$ haloalkoxy group, and n is 1 or 2.

(ii) $R^{5a}$ and $R^{6a}$ together form —$CH_2$—, —$CH_2CH_2$—, —$CH_2CR^{e1}R^{e2}$—, —$CR^{e1}R^{e2}CH_2$—, —$CH_2CH_2CH_2$—, —$CH_2CH_2O$—, or —$CH_2CH_2CH_2O$— ($R^{e1}$ and $R^{e2}$ are the same as the definition given in the (i).), and $R^{5b}$ is a hydrogen atom, a $C_1$-$C_4$ alkyl group, or a $C_1$-$C_4$ haloalkyl group, $R^{5c}$ and $R^{6b}$ are a hydrogen atom, a halogen atom, a hydroxyl group, a $C_1$-$C_4$ alkyl group, a $C_1$-$C_4$ haloalkyl group, a $C_1$-$C_4$ alkoxy group, a $C_1$-$C_4$ haloalkoxy group or, alternatively, $R^{5c}$ and $R^{6b}$ together form —$(CH_2)_t$—, —$O(CH_2)_t$—, —$(CH_2)_tO$—, —$(CH_2)_tO(CH_2)_u$—, —$(CH_2)_tNR^{e3}(CH_2)_u$—, —$(CH_2)_tCONR^{e3}(CH_2)_u$—, or —$(CH_2)_tNR^{e3}CO(CH_2)_u$— (t and u are, independently each other, 0, 1, 2, or 3, and $R^{e3}$ is a hydrogen atom or a $C_1$-$C_4$ alkyl group.), and n is 1.

(iii) $R^{5a}$ is a hydrogen atom, a $C_1$-$C_6$ alkyl group, a $C_1$-$C_6$ haloalkyl group, a $C_3$-$C_7$ cycloalkyl group, a heterocycloalkyl group, a $C_3$-$C_7$ cycloalkyl-$C_1$-$C_4$ alkyl group, a heterocycloalkyl-$C_1$-$C_4$ alkyl group, or an aralkyl group, and $R^{5b}$ is a hydrogen atom or a $C_1$-$C_4$ alkyl group, $R^{5c}$ is a hydrogen atom, a $C_1$-$C_4$ alkyl group, or a halogen atom, $R^{6a}$ and $R^{6b}$ are, independently each other, a hydrogen atom, a halogen atom, a $C_1$-$C_6$ alkyl group, a $C_3$-$C_7$ cycloalkyl group, or a $C_1$-$C_6$ haloalkyl group or, alternatively, $R^{6a}$ and $R^{6b}$ optionally form, together with the carbon atom bonded thereto, a 3- to 7-membered monocyclic ring, and n is 1 or 2.

(iv) $R^{5a}$ and $R^{5b}$ together form —$CH_2CH_2$—, —$CH_2CH_2CH_2$—, or —$CH_2CH_2CH_2CH_2$—, and $R^{5c}$, $R^{6a}$ and $R^{6b}$, independently each other, are a hydrogen atom or a halogen atom, and n is 1 or 2.

(v) $R^{6a}$ and $R^{5c}$ together form —$OCH_2$—, —$CH_2O$—, —$CH_2S$—, —$SCH_2$—, —$CH_2NH$—, —$NHCH_2$—, or —$CH_2CH_2$—, and $R^{5a}$ and $R^{5b}$ are a hydrogen atom, and $R^{6b}$ is a hydrogen atom or a halogen atom, and n is 1.}, and $R^{7a}$ and $R^{7b}$ are, independently each other, a hydrogen atom, a halogen atom, or a $C_1$-$C_4$ alkyl group.].

Namely, the present invention includes the following inventions.

(1) A pharmaceutical composition comprising a heteroaromatic amide derivative represented by the general formula (I) or salt thereof:

[Chem 10]

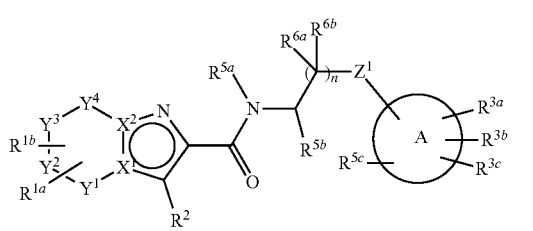

(I)

[wherein, $X^1$-$X^2$, $Y^1$, $Y^2$, $Y^3$, $Y^4$, $Z^1$, ring A, $R^{1a}$, $R^{1b}$, $R^2$, $R^{3a}$, $R^{3b}$, $R^{3c}$, $R^{5a}$, $R^{5b}$, $R^{5c}$, $R^{6a}$, $R^{6b}$, n have the same definition as given in the (0) (with a proviso that ring C is not a phenyl ring when $X^1$-$X^2$ is N—C, $Y^1$, $Y^2$, $Y^3$ and $Y^4$ together form —$CH_2CR^{4a}HCH_2CH_2$—, $R^2$ is a hydrogen atom, $R^{4a}$ is a group represented by the general formula (I-B), and $L^2$ is a single bond. Alternatively, when ring C is a phenyl ring, $X^1$-$X^2$ is C—N.)].

(4) A heteroaromatic amide derivative or salt thereof represented by the general formula (I):

[Chem 11]

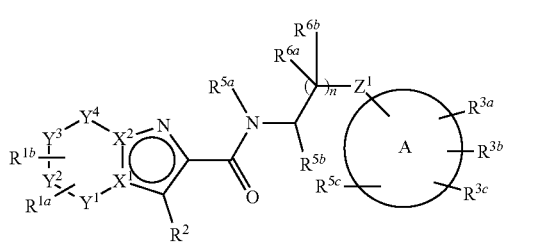

(I)

[wherein, $X^1$-$X^2$, $Y^1$, $Y^2$, $Y^3$, $Y^4$, $Z^1$, ring A, $R^{1a}$, $R^{1b}$, $R^2$, $R^{3a}$, $R^{3b}$, $R^{3c}$ have the same definition as given in the (0) (with a proviso that at least one of $Y^1$, $Y^2$, $Y^3$, or $Y^4$ is —$CR^{4a}R^{4b}$—, —$CR^{4a}H$—, —$CH_2CR^{4a}R^{4b}$—, —$CH_2CR^{4a}H$—, or —$NR^{4c}$— ($R^{4a}$, $R^{4b}$ and $R^{4c}$ have the same definition as given in the (0) when $R^2$ is a hydrogen atom.).), and $R^{5a}$, $R^{5b}$, $R^{5c}$, $R^{6a}$, $R^{6b}$ and n fulfill either one of the above constitutions (i) and (ii) (with a proviso that $Y^1$, $Y^2$, $Y^3$ and $Y^4$ do not together form —$CH_2NR^{4a}HCH_2CH_2$— when $R^{5a}$, $R^{5b}$, $R^{5c}$, $R^{6a}$, $R^{6b}$ and n fulfill the constitution (ii).).].

(5) The heteroaromatic amide derivative or salt thereof described in the (4) (with a proviso that ring C is not a phenyl ring when $X^1$-$X^2$ is N—C, $Y^1$, $Y^2$, $Y^3$ and $Y^4$ together form —$CH_2CR^{4a}HCH_2CH_2$—, $R^2$ is a hydrogen atom, $R^{4a}$ is a group represented by the general formula (I-B), and $L^2$ is a single bond. Alternatively, when ring C is a phenyl ring, $X^1$-$X^2$ is C—N), wherein in the general formula (I), $Y^1$, $Y^2$, $Y^3$ and $Y^4$ together form
—$OCR^{4a}HCH_2CH_2$—, —$OCR^{4a}R^{4b}CH_2CH_2$—,
—$OCH_2CH_2$—, —$OCR^{4a}HCH_2$—, —$OCR^{4a}R^{4b}CH_2$—,
—$OCH_2CH_2CH_2CH_2$—, —$OCR^{4a}HCH_2CH_2$—,
—$OCR^{4a}R^{4b}CH_2CH_2$—,
—$OCH_2CR^{4a}HCH_2CH_2$—, —$OCH_2CR^{4a}R^{4b}CH_2CH_2$—, —CH$_2$OCH$_2$CH$_2$—, —CH$_2$OCH$_2$CH$_2$CH$_2$—, —CH$_2$CH$_2$OCH$_2$—, —CH$_2$CR$^{4a}$HOCH$_2$— —CH$_2$CH$_2$CH$_2$CH$_2$—, —CH$_2$CR$^{4a}$HCH$_2$CH$_2$—, —CH$_2$CR$^{4a}$R$^{4b}$CH$_2$CH$_2$—, —CH$_2$CH$_2$CR$^{4a}$HCH$_2$—, —CH$_2$CH$_2$CR$^{4a}$R$^{4b}$CH$_2$—, —CH$_2$SCH$_2$CH$_2$—, —CH$_2$SO$_2$CH$_2$CH$_2$—, —NHCH$_2$CH$_2$CH$_2$—, —NR$^{4c}$CH$_2$CH$_2$CH$_2$—, —NR$^{4c}$CR$^{4a}$HCH$_2$CH$_2$—, —NHCR$^{4a}$HCH$_2$CH$_2$—, —CH$_2$NR$^{4c}$CH$_2$CH$_2$—, —CH$_2$NR$^{4c}$CR$^{4a}$HCH$_2$—, —CH$_2$NHCR$^{4a}$HCH$_2$—, —CH$_2$CH$_2$NR$^{4c}$CH$_2$—, —CH$_2$CR$^{4a}$HNR$^{4c}$CH$_2$—, or —CH$_2$CR$^{4a}$HNHCH$_2$— (R$^{4a}$, R$^{4b}$ and R$^{4c}$ have the same definition as given in the (0).), and R$^2$ is a hydrogen atom, a halogen atom, a hydroxyl group, a cyano group, or an optionally substituted saturated, partially saturated or unsaturated 3- to 7-membered monocyclic ring (with a proviso that R$^2$ is a hydrogen atom when X$^1$-X$^2$ is C—N and Y$^1$, Y$^2$, Y$^3$ and Y$^4$ together form —OCR$^{4a}$HCH$_2$CH$_2$—, —OCR$^{4a}$R$^{4b}$CH$_2$CH$_2$—.).

(6) The heteroaromatic amide derivative or salt thereof described in the (4) or (5), wherein in the general formula (I),
X$^1$-X$^2$ is C—N, and
Y$^1$, Y$^2$, Y$^3$ and Y$^4$ together form
—OCR$^{4a}$HCH$_2$CH$_2$—, —OCR$^{4a}$R$^{4b}$CH$_2$CH$_2$—, —OCH$_2$CH$_2$—, —OCR$^{4a}$HCH$_2$—, —OCR$^{4a}$R$^{4b}$CH$_2$—, —OCH$_2$CH$_2$CH$_2$CH$_2$—, —OCR$^{4a}$HCH$_2$CH$_2$CH$_2$—, —OCH$_2$CR$^{4a}$HCH$_2$CH$_2$—, CH$_2$OCH$_2$CH$_2$—, —CH$_2$OCH$_2$CH$_2$CH$_2$—, —CH$_2$CR$^{4a}$HCH$_2$CH$_2$—, —CH$_2$CR$^{4a}$R$^{4b}$CH$_2$CH$_2$—, —CH$_2$CH$_2$CR$^{4a}$HCH$_2$—, —NHCH$_2$CH$_2$CH$_2$—, —NR$^{4c}$CR$^{4a}$HCH$_2$CH$_2$—, —NHCR$^{4a}$HCH$_2$CH$_2$—, or —CH$_2$NR$^{4c}$CH$_2$CH$_2$— (R$^{4a}$, R$^{4b}$ and R$^{4c}$ have the same definition as given in the (0).),
R$^{5a}$, R$^{5b}$, R$^{5c}$, R$^{6a}$, R$^{6b}$ and n fulfill the constitution (i) in the (0).

(7) A heteroaromatic amide derivative or salt thereof represented by the general formula (I-E2):

[Chem 12]

(I-E2)

[wherein,
X$^1$, X$^2$, Y$^1$, Y$^2$, Y$^3$, Y$^4$, R$^{1a}$, R$^{1b}$, R$^2$ have the same definition as given in the (0),
Z$^2$-Z$^3$ is —CH$_2$—, —OCH$_2$—, —CH$_2$O—, —SCH$_2$—, —CH$_2$S—, —CH$_2$NR$^{f1}$, —NR$^{f1}$CH$_2$—, —CH$_2$CH$_2$—, —CONR$^{f1}$—, —NR$^{f1}$CO—, —OCR$^{f1}$R$^{f2}$—, or —CR$^{f1}$R$^{f2}$O— (R$^{f1}$ and R$^{f2}$ are a hydrogen atom, a C$_1$-C$_4$ alkyl group, or a C$_1$-C$_4$ haloalkyl group.), R$^{5a}$ is a hydrogen atom, a C$_1$-C$_6$ alkyl group, a C$_1$-C$_6$ haloalkyl group, a C$_3$-C$_7$ cycloalkyl group, a heterocycloalkyl group, a C$_3$-C$_7$ cycloalkyl-C$_1$-C$_4$ alkyl group, a heterocycloalkyl-C$_1$-C$_4$ alkyl group, or an aralkyl group, R$^{6a}$ and R$^{6b}$ are, independently each other, a hydrogen atom, a halogen atom, a hydroxyl group, a cyano group, a C$_1$-C$_4$ alkyl group, a C$_1$-C$_4$ haloalkyl group, a C$_1$-C$_4$ alkoxy group, or a C$_1$-C$_4$ haloalkoxy group, Z$^4$ is C—R$^{11a}$ or a nitrogen atom, R$^{11a}$ is a hydrogen atom, a halogen atom, a cyano group, a cyanomethyl group, a formyl group, a nitro group, a carboxamide group, a hydroxyl group, a C$_1$-C$_6$ alkyl group, a C$_1$-C$_6$ haloalkyl group, a C$_1$-C$_6$ alkoxy group, a C$_1$-C$_6$ haloalkoxy group, a C$_1$-C$_4$ alkoxy-C$_1$-C$_4$ alkyl group, a C$_1$-C$_4$ haloalkoxy-C$_1$-C$_4$ alkyl group, a C$_3$-C$_7$ cycloalkyl group, a C$_2$-C$_6$ alkenyl group, a C$_2$-C$_6$ alkenyloxy group, a C$_2$-C$_6$ alkynyl group, or a C$_2$-C$_6$ alkynyloxy group, R$^{11b}$ has the same definition as given to R$^{3b}$ in the (0), and R$^{11c}$ has the same definition as given to R$^{3c}$ in the (0) (with a proviso that at least one of Y$^1$, Y$^2$, Y$^3$, or Y$^4$ is —CR$^{4a}$R$^{4b}$—, —CR$^{4a}$H—, —CH$_2$CR$^{4a}$R$^{4b}$—, —CH$_2$CR$^{4a}$H—, or —NR$^{4c}$— (R$^{4a}$, R$^{4b}$ and R$^{4c}$ have the same definition as given in the (0).) when R$^2$ is a hydrogen atom.).].

(8) The heteroaromatic amide derivative or salt thereof described in the (7) (with a proviso that R$^2$ is a hydrogen atom when X$^1$-X$^2$ is C—N and Y$^1$, Y$^2$, Y$^3$ and Y$^4$ together form —OCR$^{4a}$HCH$_2$CH$_2$— or —OCR$^{4a}$R$^{4b}$CH$_2$CH$_2$—.),
wherein in the general formula (I-E2),
X$^1$-X$^2$ is C—N, and
Y$^1$, Y$^2$, Y$^3$ and Y$^4$ together form
—OCR$^{4a}$HCH$_2$CH$_2$—, —OCR$^{4a}$R$^{4b}$CH$_2$CH$_2$—, —OCH$_2$CH$_2$—, —OCR$^{4a}$HCH$_2$—, —OCR$^{4a}$R$^{4b}$CH$_2$—, —OCH$_2$CH$_2$CH$_2$CH$_2$—, —OCR$^{4a}$HCH$_2$CH$_2$CH$_2$—, —OCH$_2$CR$^{4a}$HCH$_2$CH$_2$—, —CH$_2$OCH$_2$CH$_2$—, —CH$_2$OCH$_2$CH$_2$CH$_2$—, —CH$_2$CR$^{4a}$HCH$_2$CH$_2$—, —CH$_2$CR$^{4a}$R$^{4b}$CH$_2$CH$_2$—, —CH$_2$CH$_2$CR$^{4a}$HCH$_2$—, —NHCH$_2$CH$_2$CH$_2$—, —NR$^{4c}$CR$^{4a}$HCH$_2$CH$_2$—, —NHCR$^{4a}$HCH$_2$CH$_2$—, or —CH$_2$NR$^{4c}$CH$_2$CH$_2$— (R$^{4a}$, R$^{4b}$ and R$^{4c}$ have the same definition as given in the (0).).

(9) The heteroaromatic amide derivative or salt thereof described in the (7) or (8), wherein in the general formula (I-E2),
Z$^2$-Z$^3$ is —CH$_2$O—,
R$^{6a}$ and R$^{6b}$, independently each other, are a hydrogen atom, a fluorine atom, a hydroxyl group, or a methoxy group,
R$^{11a}$ and R$^{11c}$ are each a hydrogen atom.

(10) The heteroaromatic amide derivative or salt thereof described in any one of the (7) to (9), wherein in the general formula (I-E2),
X$^1$-X$^2$ is C—N,
Y$^1$, Y$^2$, Y$^3$ and Y$^4$ together form
—OCR$^{4a}$HCH$_2$CH$_2$—, —OCR$^{4a}$HCH$_2$—, —OCR$^{4a}$HCH$_2$CH$_2$CH$_2$—, —CH$_2$CR$^{4a}$HCH$_2$CH$_2$—, —NR$^{4c}$CR$^{4a}$HCH$_2$CH$_2$—, —NHCR$^{4a}$HCH$_2$CH$_2$—, or —CH$_2$NR$^{4c}$CH$_2$CH$_2$—, and
R$^{4a}$ is a halogen atom, a hydroxyl group, a cyano group, a C$_1$-C$_6$ alkyl group, a C$_1$-C$_6$ alkyl group optionally substituted by a hydroxyl group, a C$_1$-C$_6$ haloalkyl group, a C$_1$-C$_6$ haloalkyl group optionally substituted by a hydroxyl group, a $C_1$-$C_6$ alkoxy group, a $C_1$-$C_6$ haloalkoxy group, a $C_1$-$C_4$ alkoxy-$C_1$-$C_4$ alkyl group optionally substituted by a $C_1$-$C_4$ haloalkoxy group, a $C_1$-$C_4$ haloalkoxy-$C_1$-$C_4$ alkyl group, a $C_1$-$C_4$ alkoxy-$C_1$-$C_4$ haloalkyl group, a $C_1$-$C_4$ haloalkoxy-$C_1$-$C_4$ haloalkyl group, a $C_1$-$C_6$ alkylcarbonyl group, a $C_1$-$C_6$ alkoxycarbonyl group, a $C_1$-$C_6$ haloalkylcarbonyl group, a $C_3$-$C_7$ cycloalkyl group, a $C_3$-$C_7$ cycloalkyl group optionally substituted by a halogen atom or a $C_1$-$C_4$ haloalkyl group, a heterocycloalkyl group, a $C_2$-$C_6$ alkenyl group, a $C_2$-$C_6$ alkenyloxy group, a $C_2$-$C_6$ alkenyloxy-$C_1$-$C_4$ alkyl group, a $C_2$-$C_6$ alkenyloxy-$C_1$-$C_4$ alkyl group optionally substituted by a halogen atom, a $C_2$-$C_6$ alkynyl group, a $C_2$-$C_6$ alkynyl group optionally substituted by a halogen atom or a methoxy group, a $C_2$-$C_6$ alkynyloxy-$C_1$-$C_4$ alkyl group, a $C_1$-$C_4$ haloalkoxy-$C_1$-$C_4$ alkoxy group, a $C_1$-$C_6$ alkylthio group, a $C_1$-$C_6$ haloalkylthio group, a $C_1$-$C_4$ alkylthio-$C_1$-$C_4$ alkyl group, a $C_1$-$C_4$ haloalkylthio-$C_1$-$C_4$ alkyl group, —$(CH_2)_q NR^{b1}R^{b2}$ (q, $R^{b1}$ and $R^{b2}$ have the same definition as given in the (0).), or the general formula (I-B)

[Chem 13]

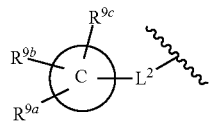

(I-B)

{wherein,
ring C is a $C_3$-$C_7$ cycloalkyl, an azetidinyl, a pyrrolidinyl, a piperidyl, a piperazinyl, a morpholino, a phenyl, a pyrrolyl, a furyl, a thienyl, an imidazolyl, a pyrazolyl, an oxazolyl, a thiazolyl, a triazolyl, a pyridyl, a pyrazinyl, a pyridazinyl, or a pyrimidinyl, $L^2$ is a single bond, —CH=CH—, —C≡C—, —$(CR^{10a}R^{10b})_{r1}(CR^{10c}R^{10d})_{r2}(CR^{10e}R^{10g})_{r3}(CR^{10g}R^{10h})_{r4}$—,
—$(CR^{10a}R^{10b})_{r1}(CR^{10c}R^{10d})_{r2}O(CR^{10e}R^{10g})_{r3}(CR^{10g}R^{10h})_{r4}$—,
—$(CR^{10a}R^{10b})_{r1}(CR^{10c}R^{10d})_{r2}NR^c(CR^{10e}R^{10g})_{r3}(CR^{10g}R^{10h})_{r4}$—,
—$(CR^{10a}R^{10b})_{r1}(CR^{10c}R^{10d})_{r2}CO(CR^{10e}R^{10g})_{r3}(CR^{10g}R^{10h})_{r4}$—,
—$(CR^{10a}R^{10b})_{r1}(CR^{10c}R^{10d})_{r2}S(CR^{10e}R^{10g})_{r3}(CR^{10g}R^{10h})_{r4}$—, or
—$(CR^{10a}R^{10b})_{r1}(CR^{10c}R^{10d})_{r2}SO(CR^{10e}R^{10g})_{r3}(CR^{10g}R^{10h})_{r4}$— ($R^{10a}$, $R^{10b}$, $R^{10c}$, $R^{10d}$, $R^{10e}$, $R^{10f}$, $R^{10g}$, $R^{10h}$, r1, r2, r3, r4 and $R^c$ have the same definition as given in the (0).), and $R^{9a}$, $R^{9b}$ and $R^{9c}$ are, independently each other, a hydrogen atom, a halogen atom, a hydroxyl group, a cyano group, a $C_1$-$C_6$ alkyl group, a $C_1$-$C_6$ haloalkyl group, a $C_1$-$C_6$ alkoxy group, a $C_1$-$C_6$ haloalkoxy group, a $C_1$-$C_6$ alkoxycarbonyl group, a heterocycloalkyloxy group, or —$(CH_2)_s NR^{d1}R^{d2}$ (s, $R^{d1}$ and $R^{d2}$ have the same definition as given in the (0).).}

(11) The heteroaromatic amide derivative or salt thereof described the (7) (with a proviso that ring C is not a phenyl ring when $Y^1$, $Y^2$, $Y^3$ and $Y^4$ together form —$CH_2CR^{4a}HCH_2CH_2$—, $R^2$ is a hydrogen atom, $R^{4a}$ is a group represented by the general formula (I-B), and $L^2$ is a single bond. Alternatively, when ring C is a phenyl ring, $X^1$-$X^2$ is C—N.), wherein in the general formula (I-E2), $X^1$-$X^2$ is N—C, and
$Y^1$, $Y^2$, $Y^3$ and $Y^4$ together form
—$CH_2CR^{4a}HOCH_2$—,   —$CH_2CR^{4a}HCH_2CH_2$—,
—$CH_2CR^{4a}R^{4b}CH_2CH_2$—,
$CH_2CH_2NR^{4c}CH_2$—,   —$CH_2CR^{4a}HNR^{4c}CH_2$—,   or
—$CH_2CR^{4a}HNHCH_2$— ($R^{4a}$, $R^{4b}$ and $R^{4c}$ have the same definition as given in the (0).).

(12) The heteroaromatic amide derivative or salt thereof described in the (7) or (11), wherein in the general formula (I-E2), $Z^2$-$Z^3$ is —$CH_2O$—, and
$R^{6a}$, $R^{6b}$ and $R^{11c}$ are each a hydrogen atom, and $R^{11a}$ is a hydrogen atom or a halogen atom.

(13) The heteroaromatic amide derivative or salt thereof described in any one of the (7), (11) or (12), wherein in the general formula (I-E2), $X^1$-$X^2$ is N—C,
$Y^1$, $Y^2$, $Y^3$ and $Y^4$ together form
—$CH_2CR^{4a}HOCH_2$—,   —$CH_2CR^{4a}HCH_2CH_2$—,
—$CH_2CH_2NR^{4c}CH_2$—,
—$CH_2CR^{4a}HNR^{4c}CH_2$—, or —$CH_2CR^{4a}HNHCH_2$—, and
$R^{4a}$ and $R^{4c}$, independently each other, are a halogen atom, a hydroxyl group, a cyano group, a $C_1$-$C_6$ alkyl group, a $C_1$-$C_6$ alkyl group optionally substituted by a hydroxyl group, a $C_1$-$C_6$ haloalkyl group, a $C_1$-$C_6$ haloalkyl group optionally substituted by a hydroxyl group, a $C_1$-$C_6$ alkoxy group, a $C_1$-$C_6$ haloalkoxy group, a $C_1$-$C_4$ alkoxy-$C_1$-$C_4$ alkyl group optionally substituted by a $C_1$-$C_4$ haloalkoxy group, a $C_1$-$C_4$ haloalkoxy-$C_1$-$C_4$ alkyl group, a $C_1$-$C_4$ alkoxy-$C_1$-$C_4$ haloalkyl group, a $C_1$-$C_4$ haloalkoxy-$C_1$-$C_4$ haloalkyl group, a $C_1$-$C_6$ alkylcarbonyl group, a $C_1$-$C_6$ alkoxycarbonyl group, a $C_1$-$C_6$ haloalkylcarbonyl group, a $C_3$-$C_7$ cycloalkyl group, a $C_3$-$C_7$ cycloalkyl group optionally substituted by a halogen atom or a $C_1$-$C_4$ haloalkyl group, a heterocycloalkyl group, a $C_2$-$C_6$ alkenyl group, a $C_2$-$C_6$ alkenyloxy group, a $C_2$-$C_6$ alkenyloxy-$C_1$-$C_4$ alkyl group, a $C_2$-$C_6$ alkenyloxy-$C_1$-$C_4$ alkyl group optionally substituted by a halogen atom, a $C_2$-$C_6$ alkynyl group, a $C_2$-$C_6$ alkynyl group optionally substituted by a halogen atom or a methoxy group, a $C_2$-$C_6$ alkynyloxy-$C_1$-$C_4$ alkyl group, a $C_1$-$C_4$ haloalkoxy-$C_1$-$C_4$ alkoxy group, a $C_1$-$C_6$ alkylthio group, a $C_1$-$C_6$ haloalkylthio group, a $C_1$-$C_4$ alkylthio-$C_1$-$C_4$ alkyl group, a $C_1$-$C_4$ haloalkylthio-$C_1$-$C_4$ alkyl group, —$(CH_2)_q NR^{b1}R^{b2}$ (q, $R^{b1}$ and $R^{b2}$ have the same definition as given in the (0).), or the general formula (I-B)

[Chem 14]

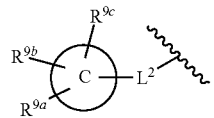

(I-B)

{wherein,
ring C is a $C_3$-$C_7$ cycloalkyl, an azetidinyl, a pyrrolidinyl, a piperidyl, a piperazinyl, a morpholino, a phenyl, a pyrrolyl, a furyl, a thienyl, an imidazolyl, a pyrazolyl, an oxazolyl, a thiazolyl, a triazolyl, a pyridyl, a pyrazinyl, a pyridazinyl, or a pyrimidinyl, $L^2$ is a single bond, —CH=CH—, —C≡C—, —(CR$^{10a}$R$^{10b}$)$_{r1}$(CR$^{10c}$R$^{10d}$)$_{r2}$(CR$^{10e}$R$^{10f}$)$_{r3}$(CR$^{10g}$R$^{10h}$)$_{r4}$—,
—(CR$^{10a}$R$^{10b}$)$_{r1}$(CR$^{10c}$R$^{10d}$)$_{r2}$O(CR$^{10e}$R$^{10f}$)$_{r3}$(CR$^{10g}$R$^{10h}$)$_{r4}$—,
—(CR$^{10a}$R$^{10b}$)$_{r1}$(CR$^{10c}$R$^{10d}$)$_{r2}$NR$^c$(CR$^{10e}$R$^{10f}$)$_{r3}$(CR$^{10g}$R$^{10h}$)$_{r4}$—,
—(CR$^{10a}$R$^{10b}$)$_{r1}$(CR$^{10c}$R$^{10d}$)$_{r2}$CO(CR$^{10e}$R$^{10f}$)$_{r3}$(CR$^{10g}$R$^{10h}$)$_{r4}$—,
—(CR$^{10a}$R$^{10b}$)$_{r1}$(CR$^{10c}$R$^{10d}$)$_{r2}$S(CR$^{10e}$R$^{10f}$)$_{r3}$(CR$^{10g}$R$^{10h}$)$_{r4}$—,
—(CR$^{10a}$R$^{10b}$)$_{r1}$(CR$^{10c}$R$^{10d}$)$_{r2}$SO(CR$^{10e}$R$^{10f}$)$_{r3}$(CR$^{10g}$R$^{10h}$)$_{r4}$—(R$^{10a}$, R$^{10b}$, R$^{10c}$, R$^{10d}$, R$^{10e}$, R$^{10f}$, R$^{10g}$, R$^{10h}$, r1, r2, r3, r4 and R$^c$ have the same definition as given in the (0).),
R$^{9a}$, R$^{9b}$ and R$^{9c}$ are, independently each other, a hydrogen atom, a halogen atom, a hydroxyl group, a cyano group, a C$_1$-C$_6$ alkyl group, a C$_1$-C$_6$ haloalkyl group, a C$_1$-C$_6$ alkoxy group, a C$_1$-C$_6$ haloalkoxy group, a C$_1$-C$_6$ alkoxycarbonyl group, a heterocycloalkyloxy group, or —(CH$_2$)$_s$NR$^{d1}$R$^{d2}$ (s, R$^{d1}$ and R$^{d2}$ have the same definition as given in the (0).).}.

(14) The heteroaromatic amide derivative or salt thereof described in any one of the (7) to (13), wherein in the general formula (I-E2),
R$^{11b}$ is a hydrogen atom, a halogen atom, a cyano group, a cyanomethyl group, a formyl group, a nitro group, a carboxamide group, a hydroxyl group, a C$_1$-C$_6$ alkyl group, a C$_1$-C$_6$ haloalkyl group, a C$_1$-C$_6$ alkoxy group, a C$_1$-C$_6$ haloalkoxy group, a C$_1$-C$_4$ alkoxy-C$_1$-C$_4$ alkyl group, a C$_1$-C$_4$ alkoxy-C$_1$-C$_4$ alkyl group optionally substituted by a dimethylaminocarbonyl group or a dimethylamino group, a C$_1$-C$_4$ haloalkoxy-C$_1$-C$_4$ alkyl group, a C$_1$-C$_4$ alkoxy-C$_1$-C$_4$ haloalkyl group, a C$_1$-C$_4$ haloalkoxy-C$_1$-C$_4$ haloalkyl group, a C$_1$-C$_6$ alkylcarbonyl group, a C$_2$-C$_6$ alkenyl group, a C$_2$-C$_6$ alkynyl group, a C$_2$-C$_6$ alkynyl group optionally substituted by a halogen atom, a C$_1$-C$_6$ alkylthio group, a C$_1$-C$_6$ haloalkylthio group, —(CH$_2$)$_p$NR$^{a1}$R$^{a2}$ (p, R$^{a1}$ and R$^{a2}$ have the same definition as given in the (0).), or the general formula (I-A)

[Chem 15]

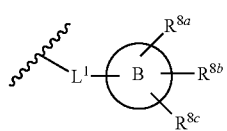

(I-A)

{wherein,
ring B is a C$_3$-C$_7$ cycloalkyl, an azetidinyl, a pyrrolidinyl, a piperidyl, a piperazinyl, a morpholino, a phenyl, a pyrrolyl, a furyl, a thienyl, an imidazolyl, a pyrazolyl, a oxazolyl, an isoxazolyl, a thiazolyl, a isothiazolyl, a triazolyl, a tetrazolyl, a pyridyl, a pyrazinyl, a pyridazinyl, or a pyrimidinyl,
L$^1$ is a single bond, —CH$_2$—, —CH$_2$O—, —OCH$_2$—, —CH$_2$CH$_2$—, or —CH$_2$OCH$_2$—, R$^{8a}$, R$^{8b}$ and R$^{8c}$ are, independently each other, a hydrogen atom, a halogen atom, a cyano group, a C$_1$-C$_6$ alkyl group, a C$_1$-C$_6$ haloalkyl group, a C$_1$-C$_6$ alkoxy group, a C$_1$-C$_6$ haloalkoxy group, a C$_3$-C$_7$ cycloalkyl group, a C$_3$-C$_7$ cycloalkyloxy group, a heterocycloalkyl group, a heterocycloalkyloxy group, a C$_2$-C$_6$ alkenyl group, or a C$_2$-C$_6$ alkynyl group.}.

(15) The heteroaromatic amide derivative or salt thereof described in the (7), wherein the compound represented by the general formula (I-E2) (the asterisks (*) shown in the structural formulae denote that the corresponding asymmetric carbon has a single steric structure. The number indicates the Example number. Regarding the notations of "isomer A", "isomer B", "isomer C" and "isomer D", among the plural compounds indicated by the same Example number, the isomers are specified as "isomer A", "isomer B", "isomer C" and "isomer D" in accordance with the order of collection by high performance liquid chromatography in the Example.) is any one of the following:

[Chem 16]

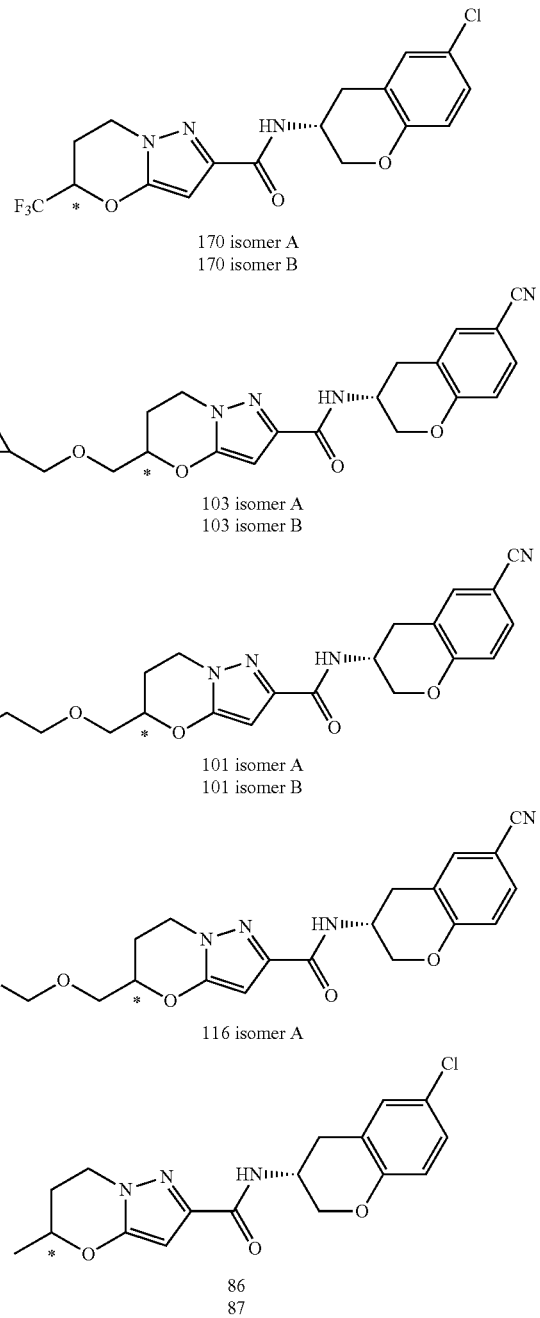

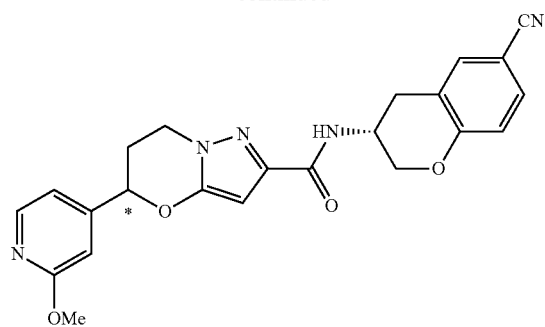
74 isomer A

92 isomer A
92 isomer B
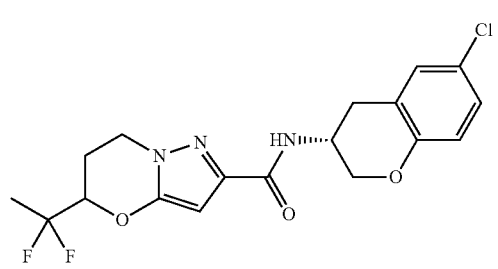
167

177
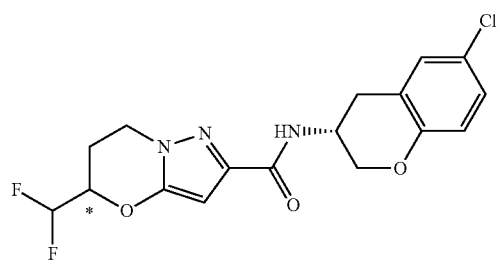
168 isomer A

70
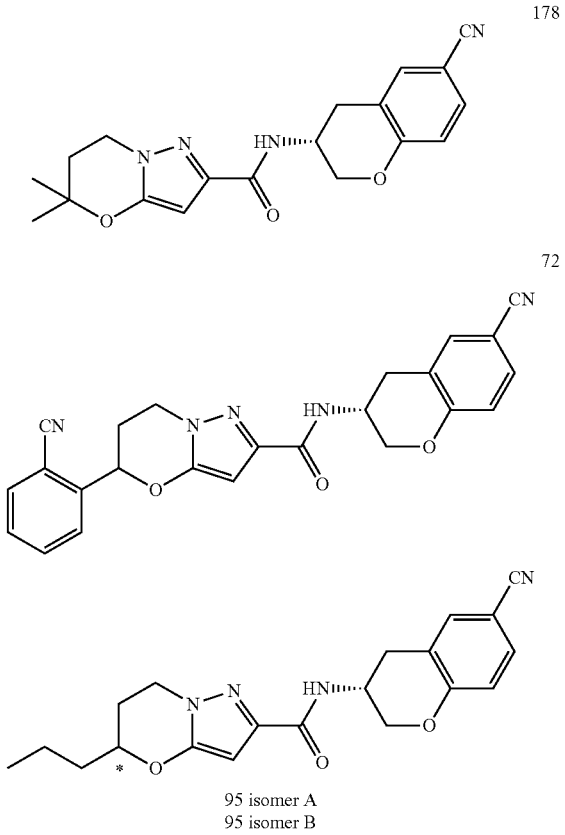
178
72
95 isomer A
95 isomer B
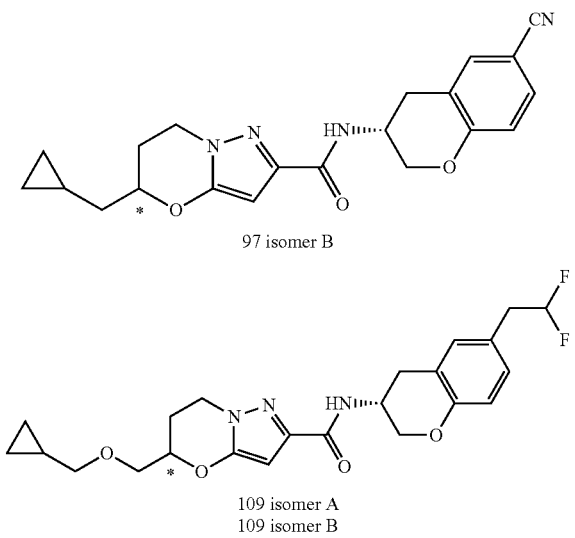
97 isomer B
109 isomer A
109 isomer B -continued

113 isomer A
113 isomer B
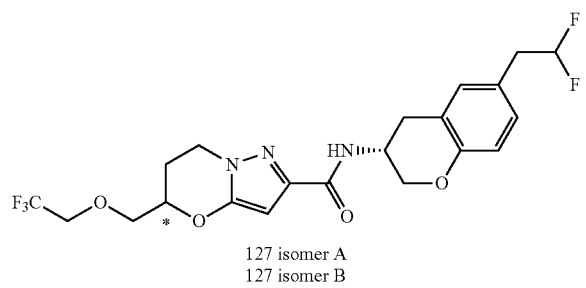
127 isomer A
127 isomer B
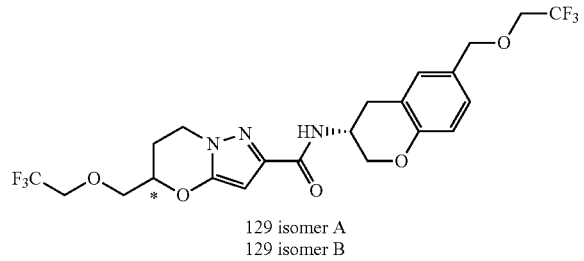
129 isomer A
129 isomer B
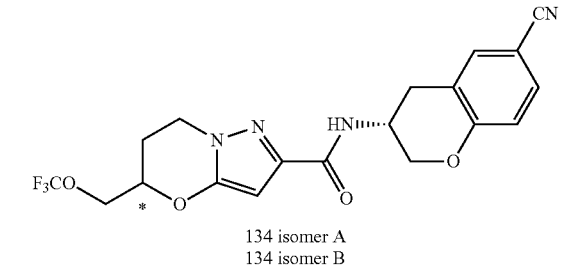
134 isomer A
134 isomer B
[Chem 17]
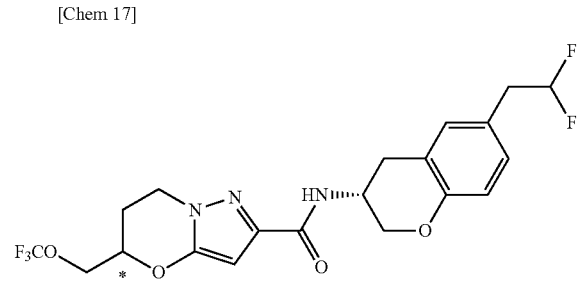
136 isomer A
136 isomer B

140 isomer A
140 isomer B
-continued
142 isomer A
142 isomer B
144 isomer B
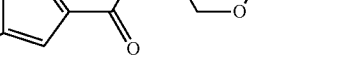
146 isomer B
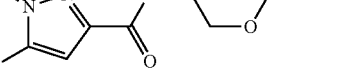
148 isomer B
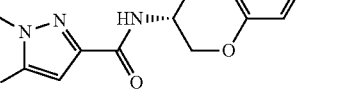
150 isomer B
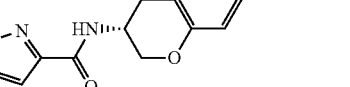
152 isomer A
152 isomer B

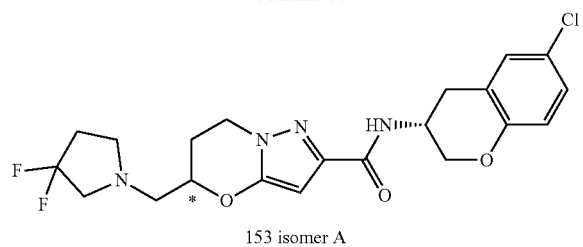
153 isomer A
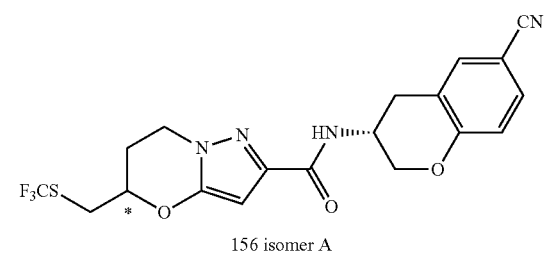
156 isomer A
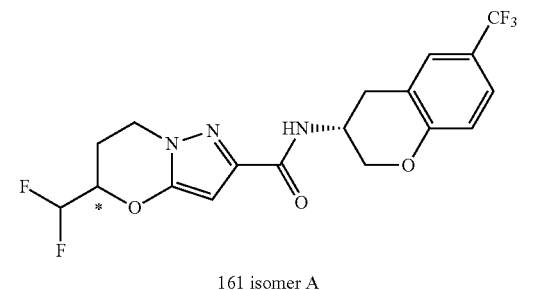
161 isomer A
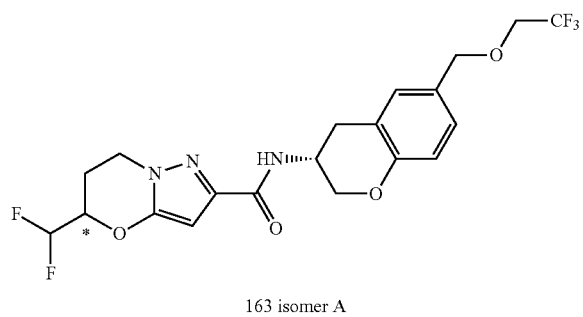
163 isomer A
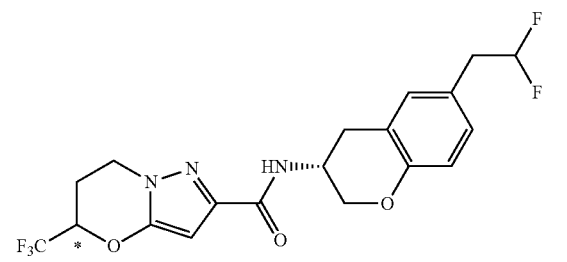
173 isomer A
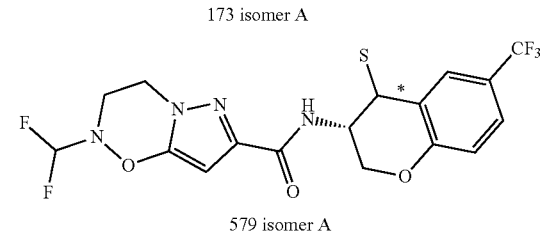
579 isomer A
579 isomer B
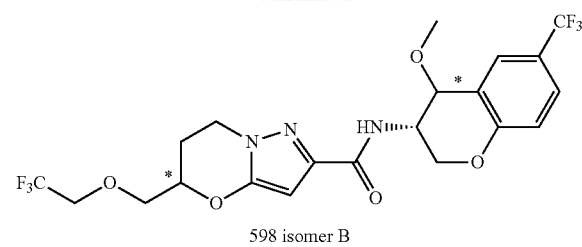
598 isomer B
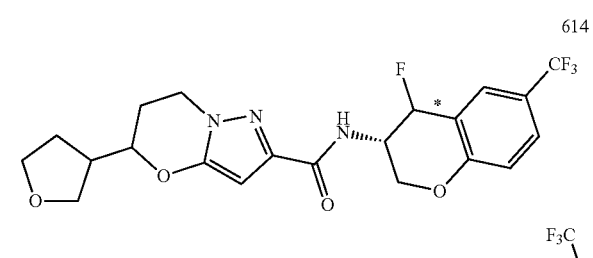
614
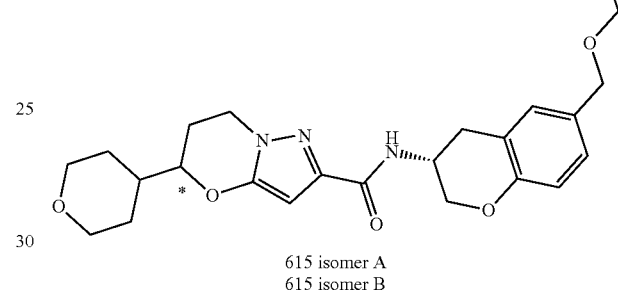
615 isomer A
615 isomer B
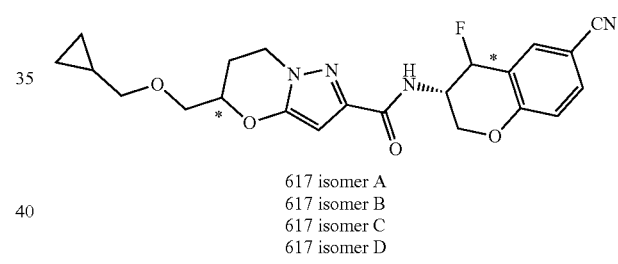
617 isomer A
617 isomer B
617 isomer C
617 isomer D
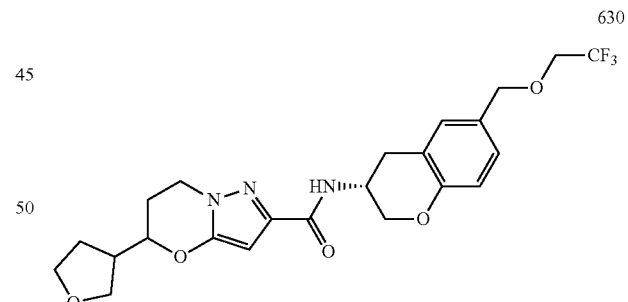
630
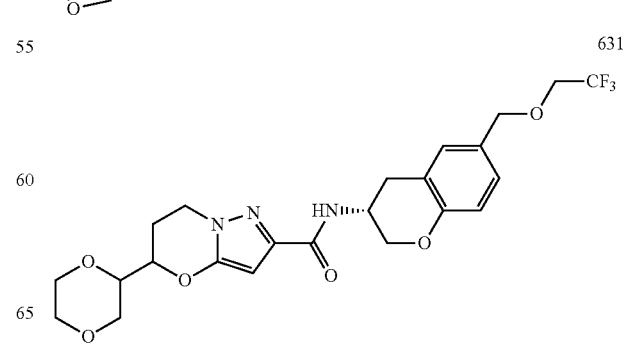
631

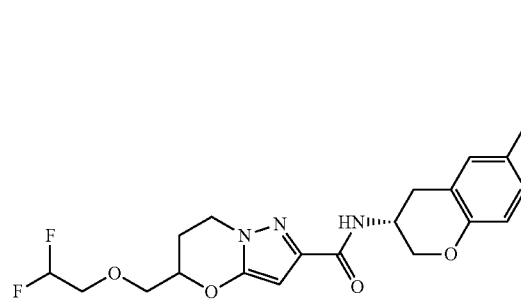
635
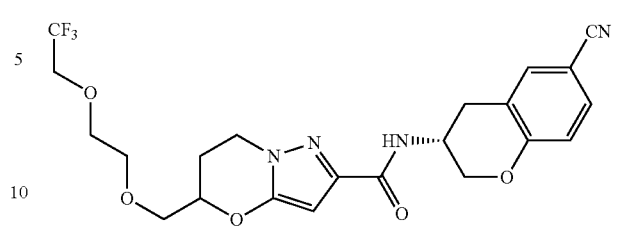
664
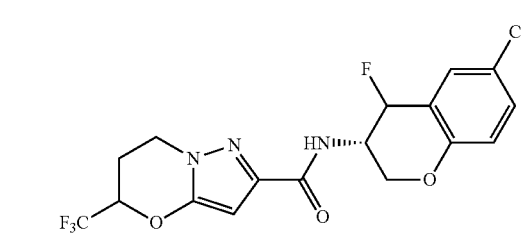
648
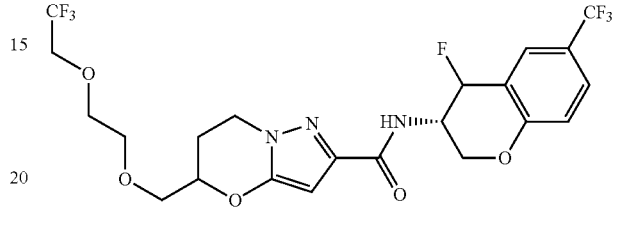
665
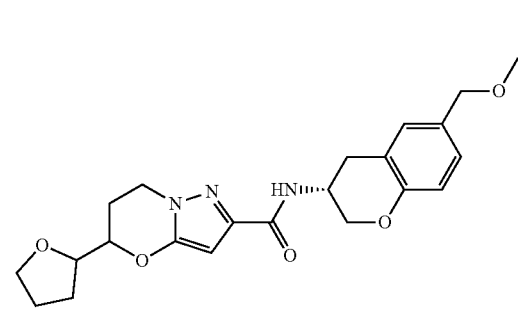
651
[Chem 18]
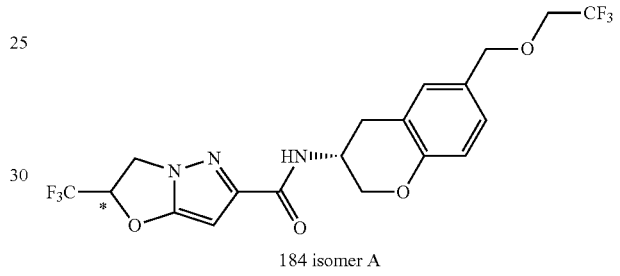
184 isomer A
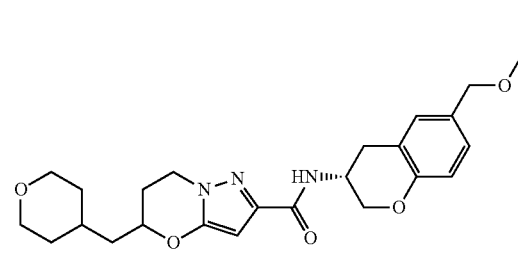
655
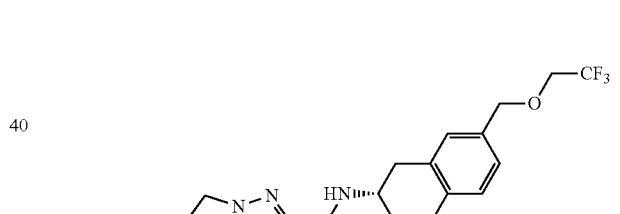
186 isomer A
186 isomer B
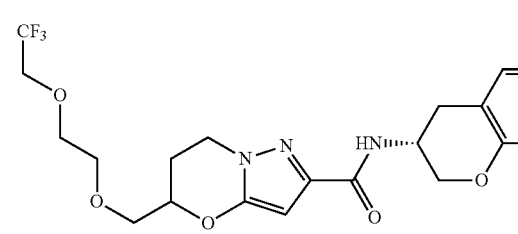
662
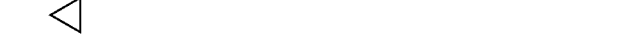
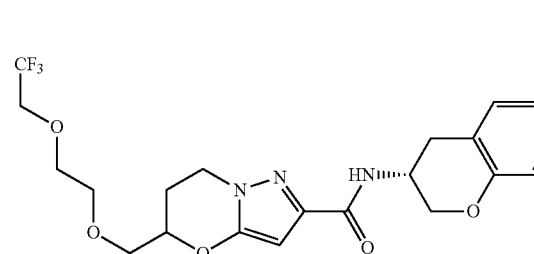
663
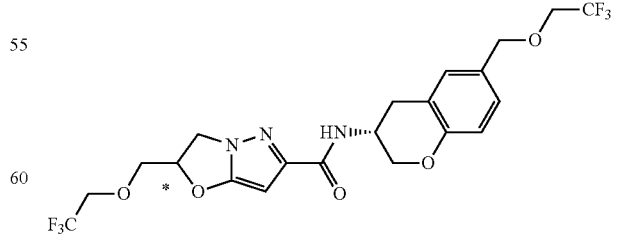
188 isomer A
188 isomer B

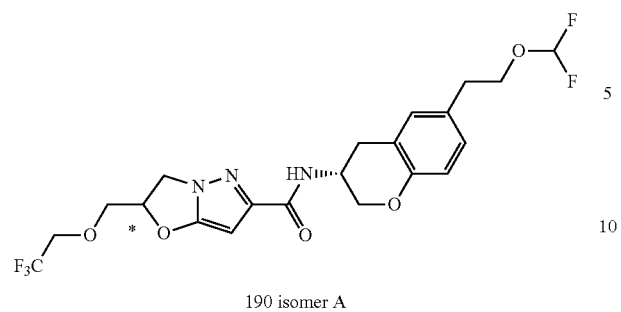
190 isomer A
190 isomer B
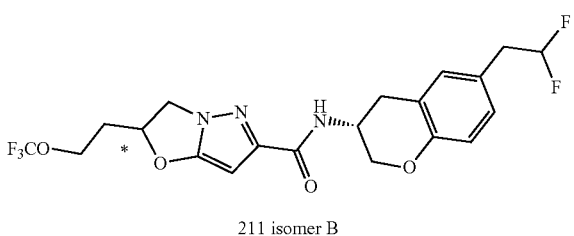
211 isomer B
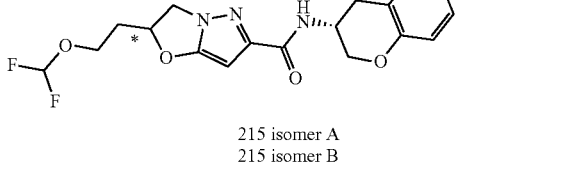
215 isomer A
215 isomer B
196 isomer A
196 isomer B
217 isomer A
217 isomer B
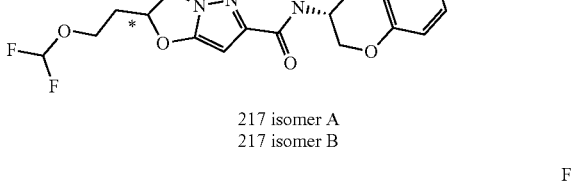
198 isomer B
219 isomer A
219 isomer B
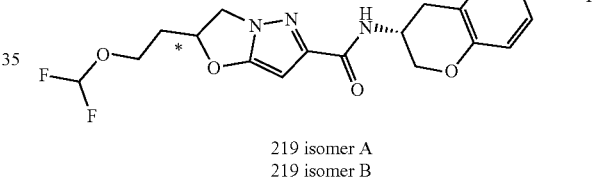
200 isomer A
200 isomer B
224 isomer A
224 isomer B
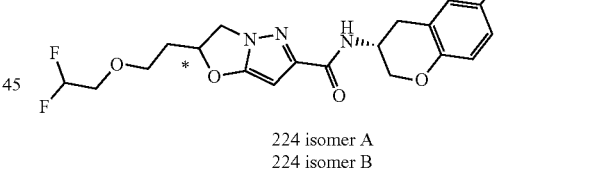
202 isomer A
202 isomer B
226 isomer A
226 isomer B
209 isomer B
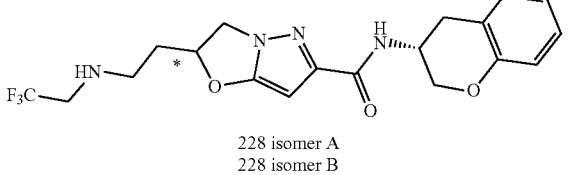
228 isomer A
228 isomer B

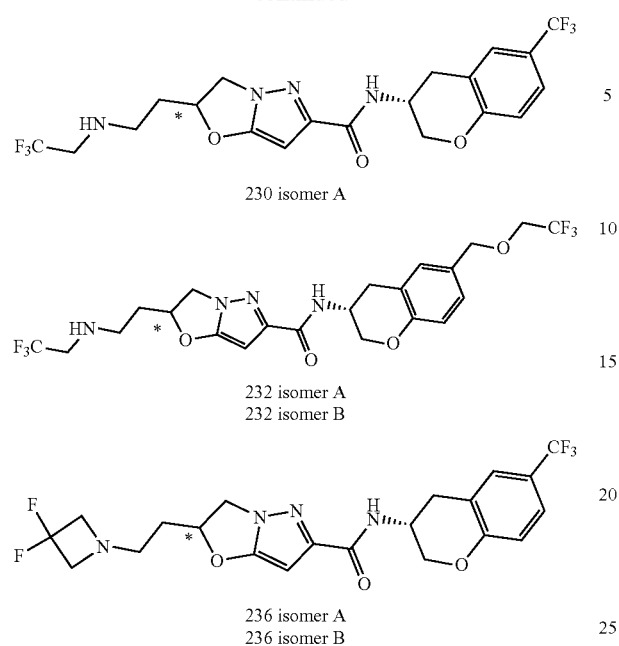
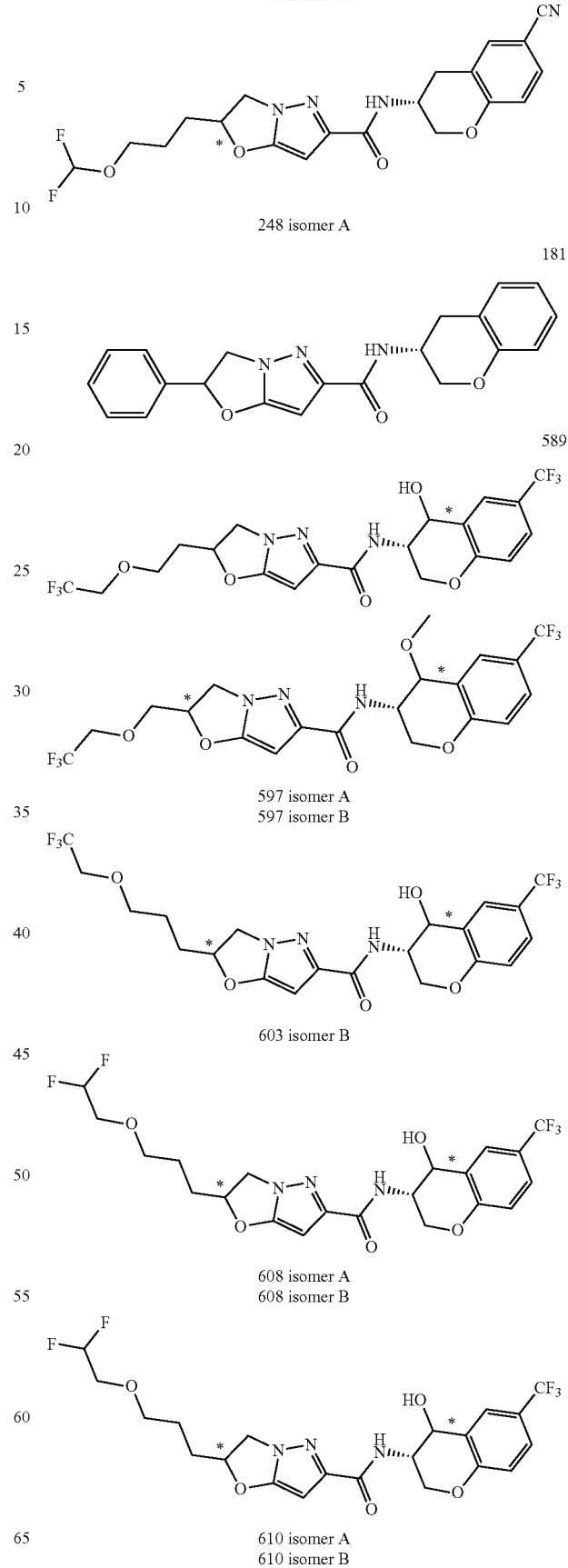

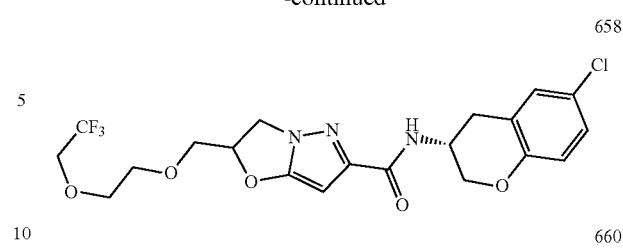
621
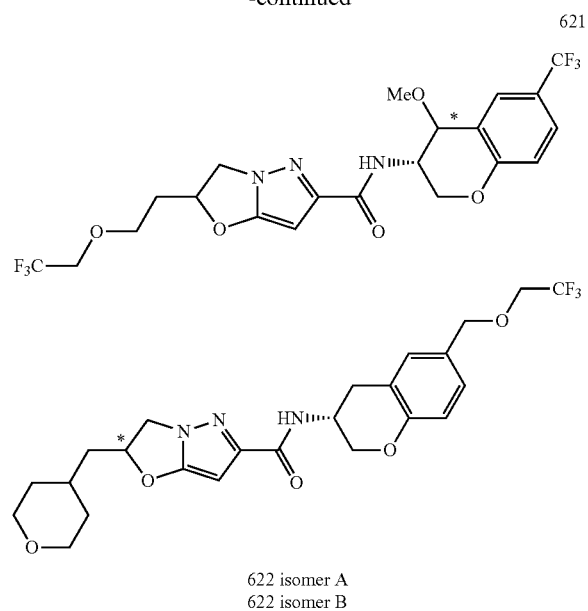
622 isomer A
622 isomer B
623
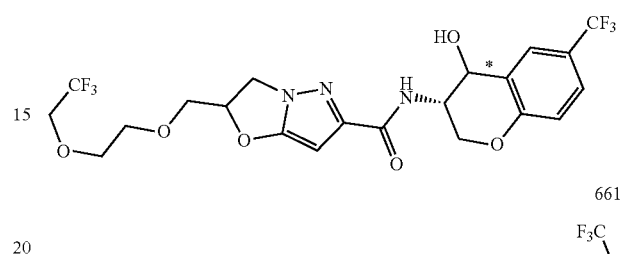
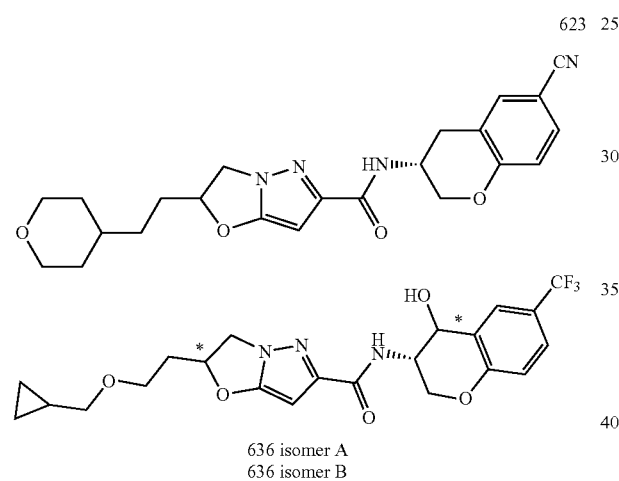
636 isomer A
636 isomer B
641 isomer A
641 isomer B
650
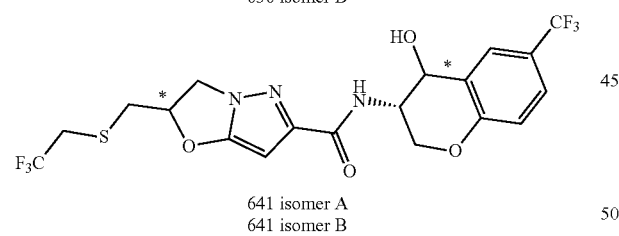
657
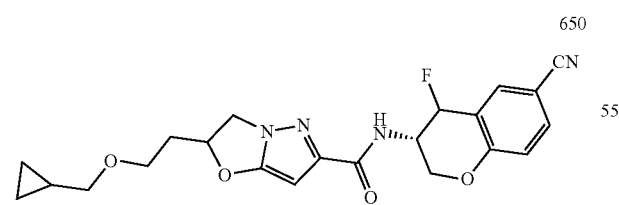
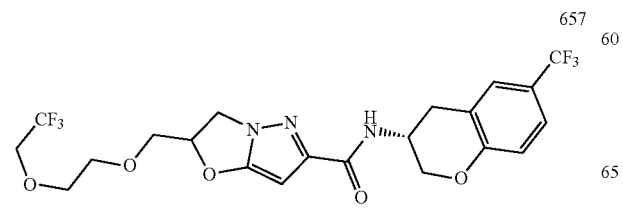
658
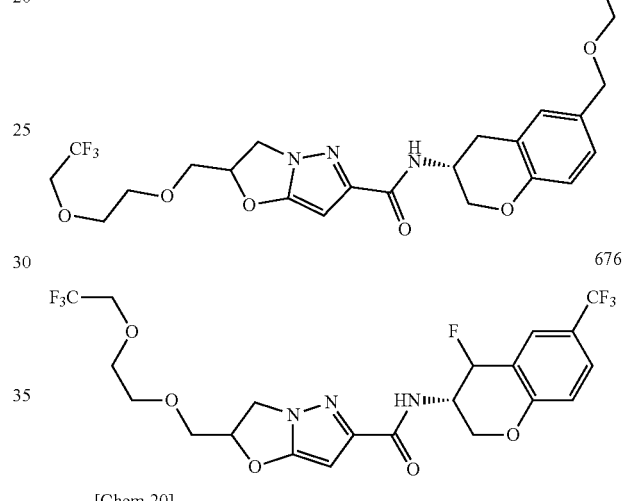
660
661
676
[Chem 20]
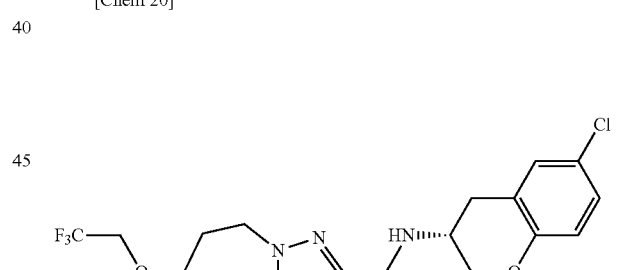
256 isomer A
256 isomer B
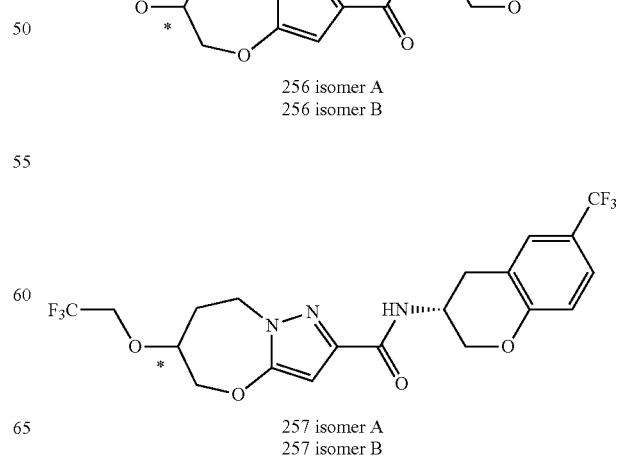
257 isomer A
257 isomer B

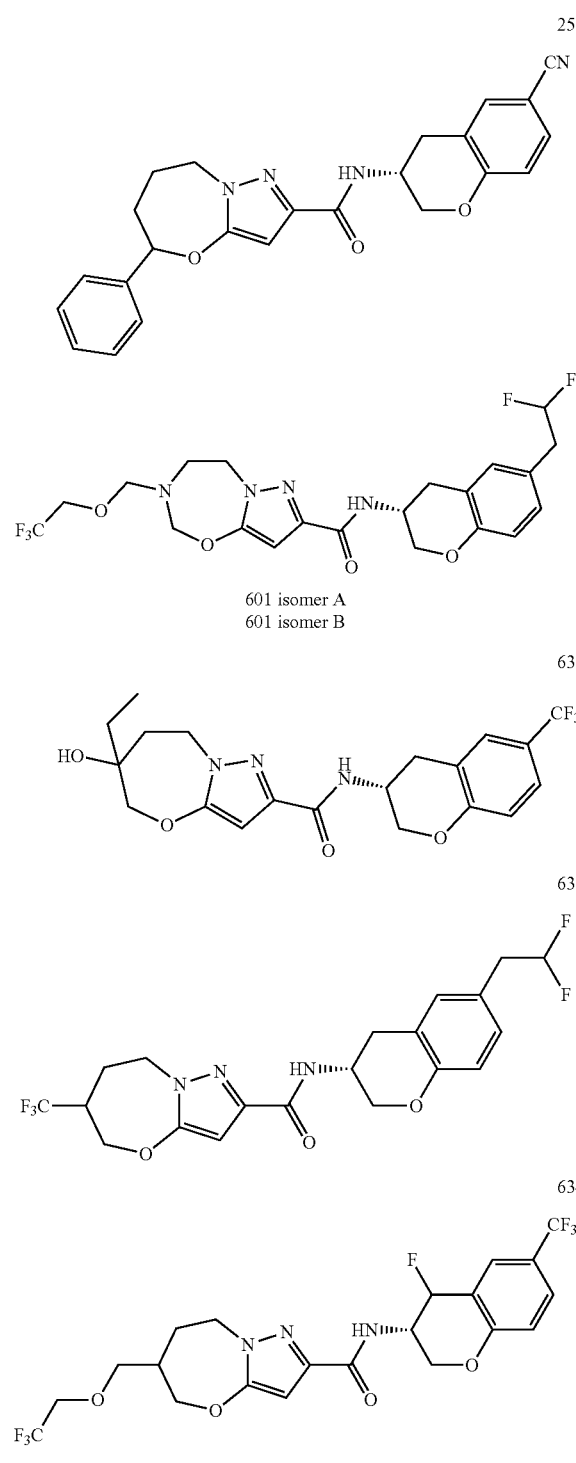
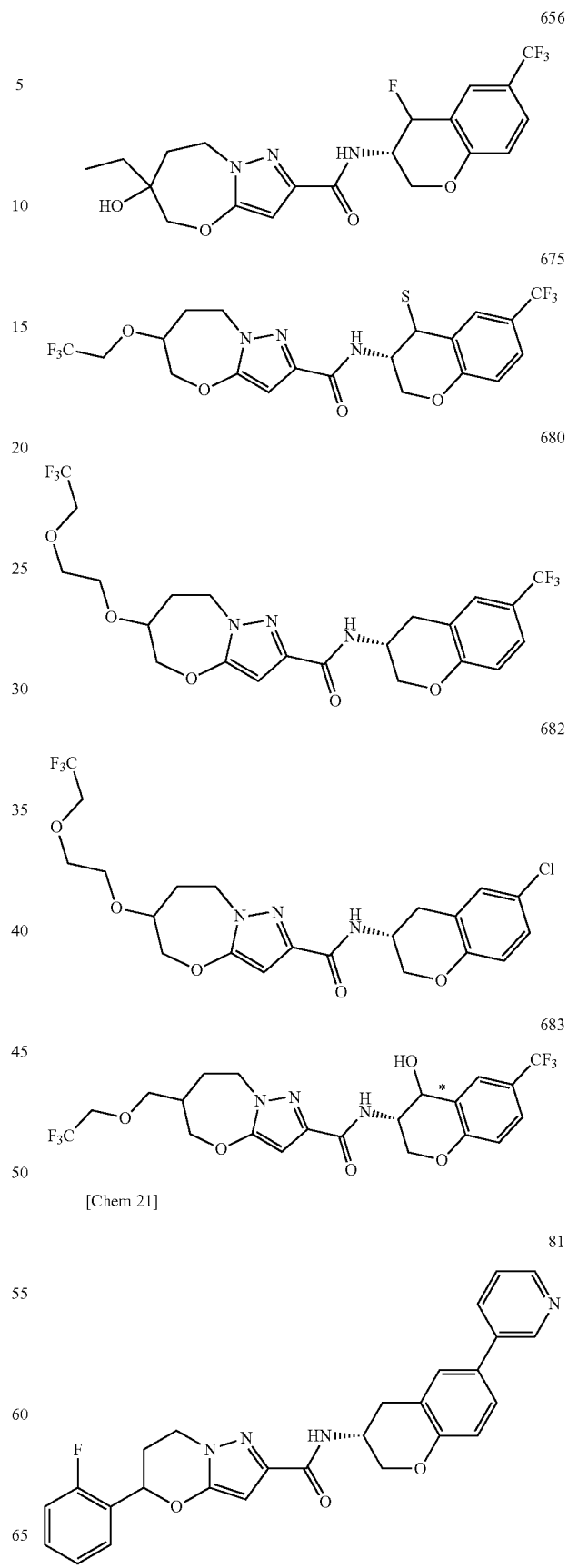

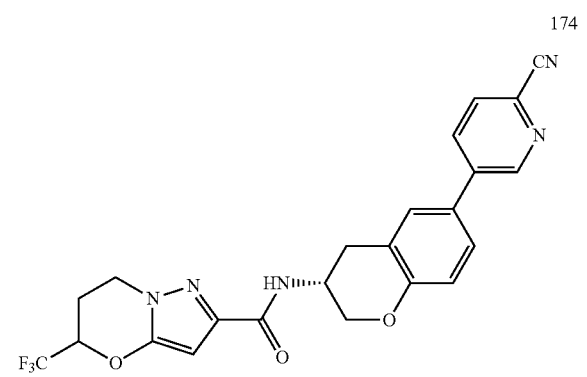
174
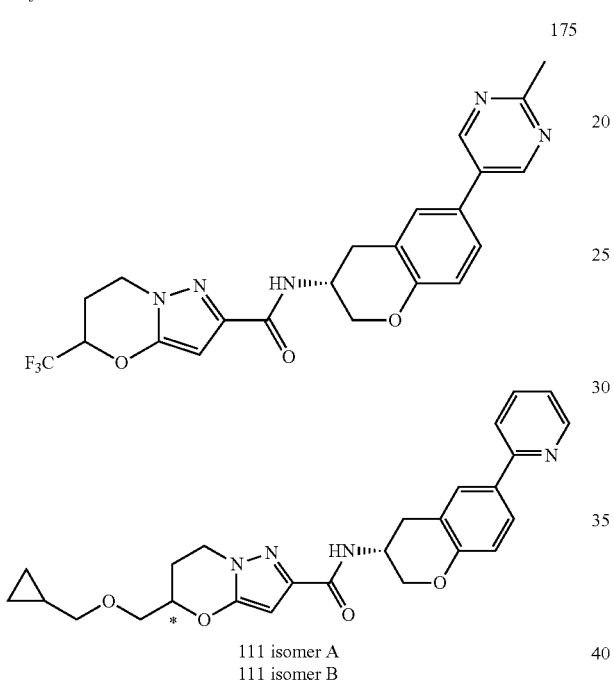
175
111 isomer A
111 isomer B
124 isomer A
124 isomer B
131 isomer A
131 isomer B
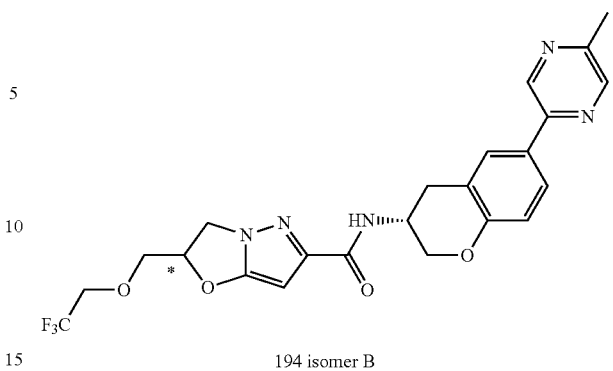
194 isomer B
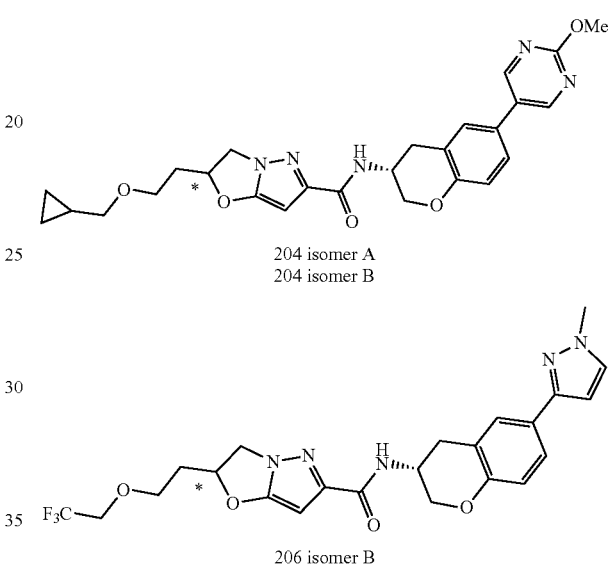
204 isomer A
204 isomer B
206 isomer B
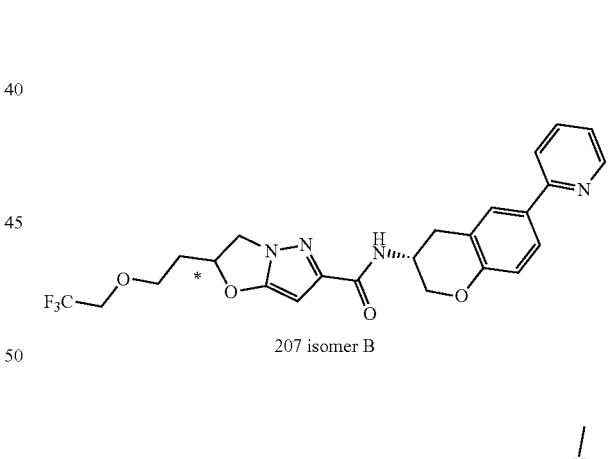
207 isomer B
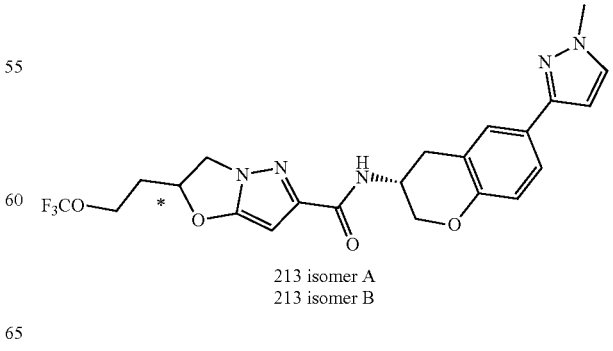
213 isomer A
213 isomer B

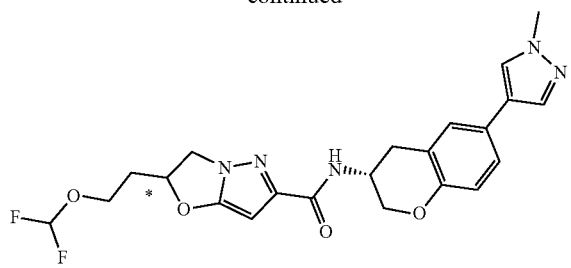
221 isomer A
221 isomer B
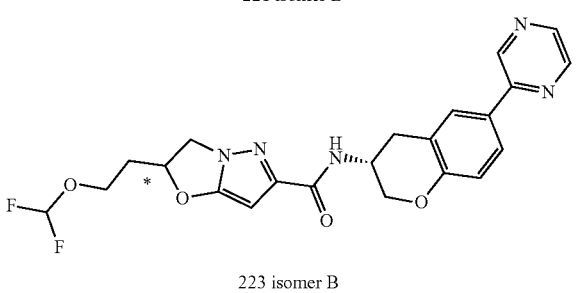
223 isomer B
[Chem 22]
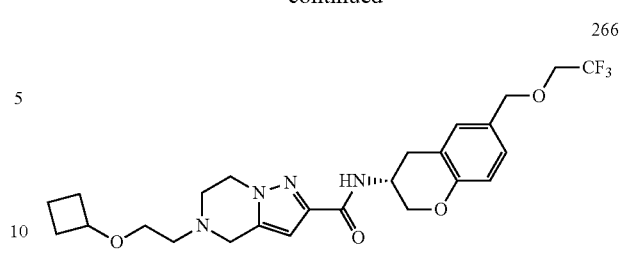
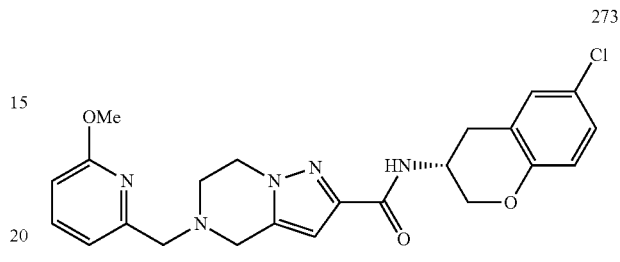
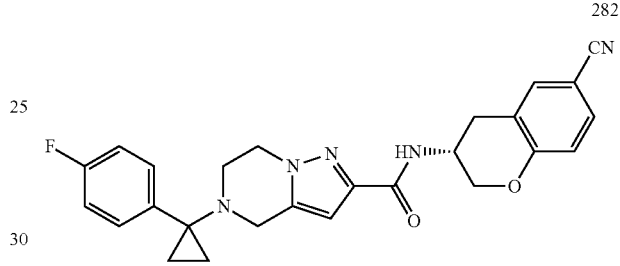
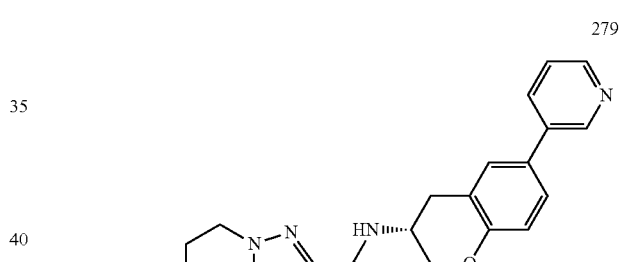
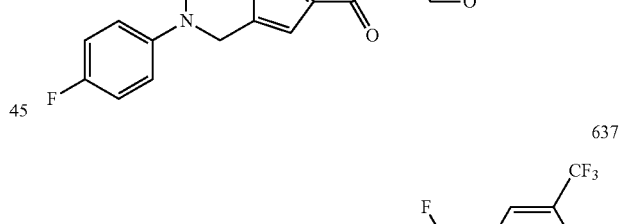
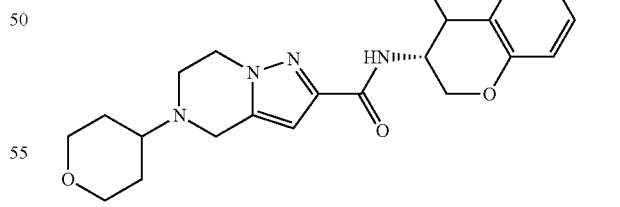
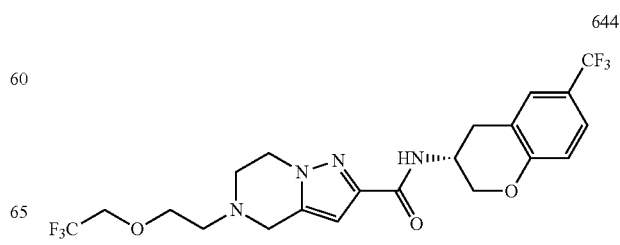

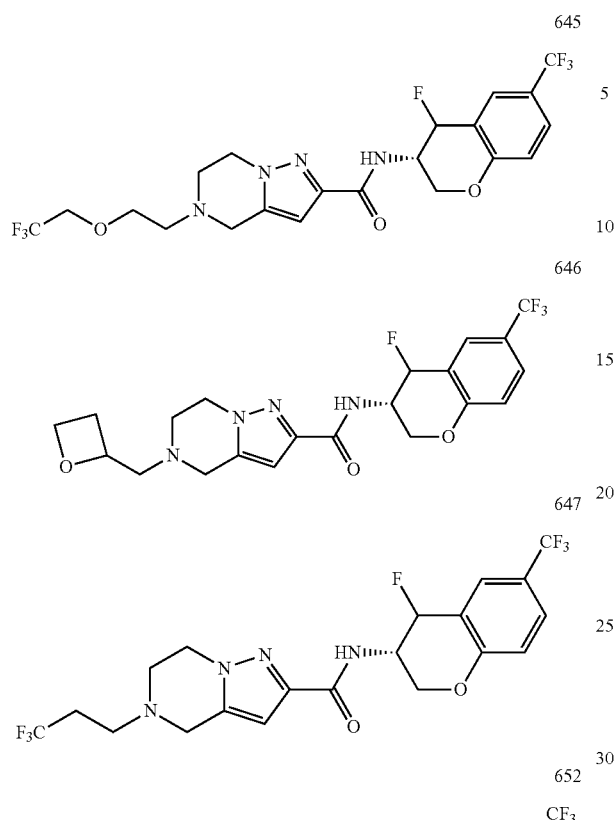
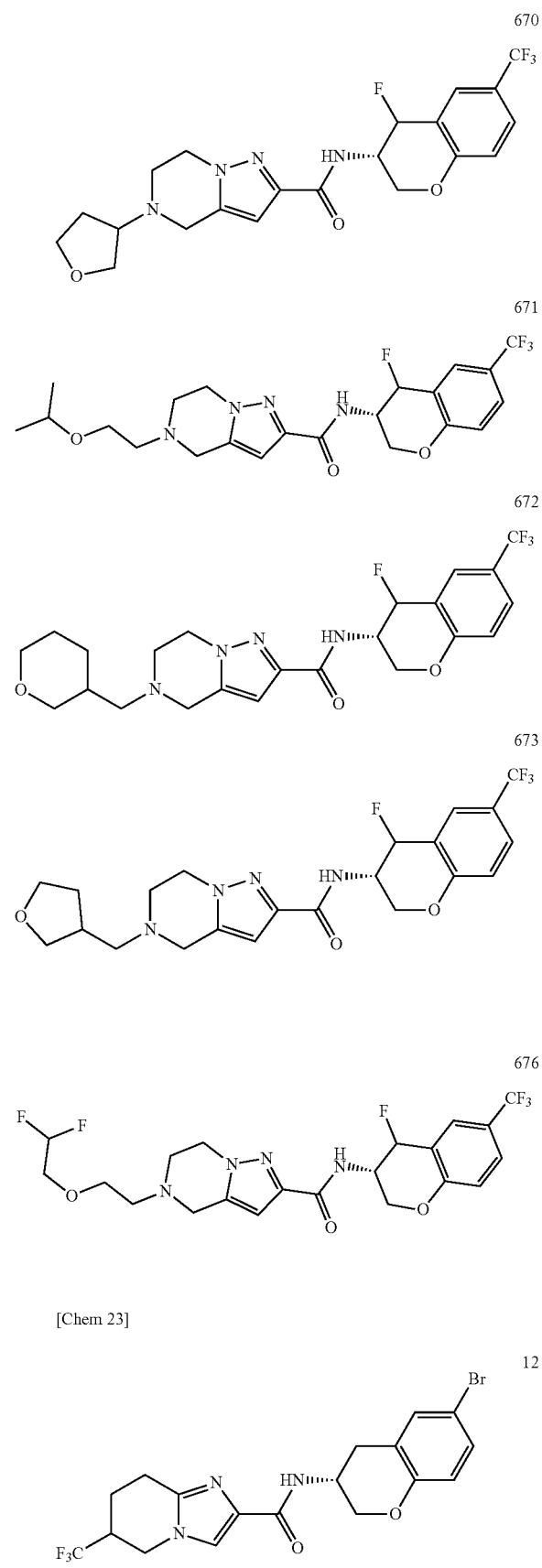

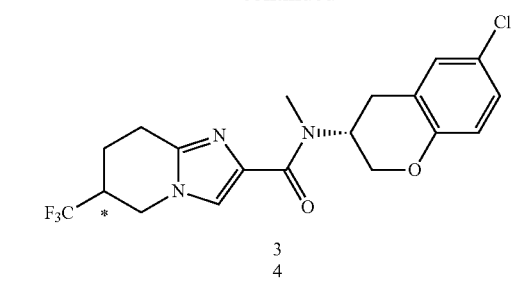
3
4
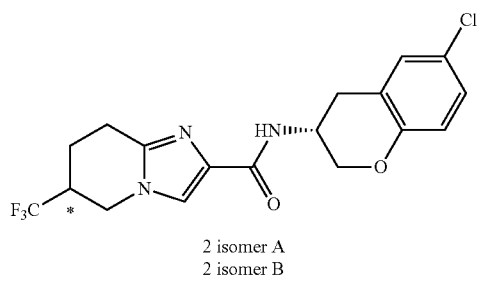
2 isomer A
2 isomer B
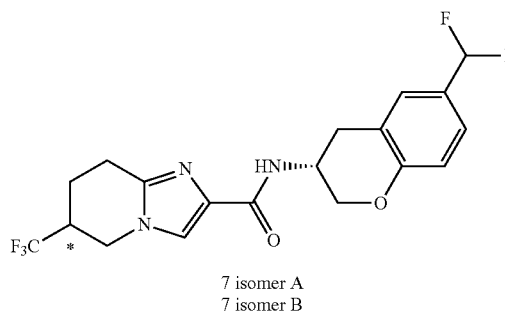
7 isomer A
7 isomer B
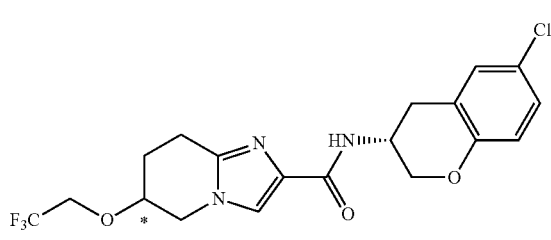
39 isomer A
39 isomer B
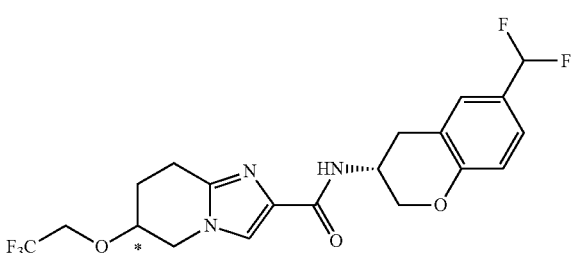
37
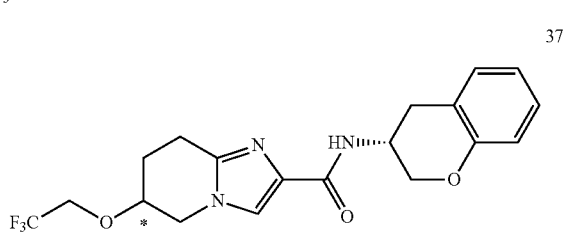
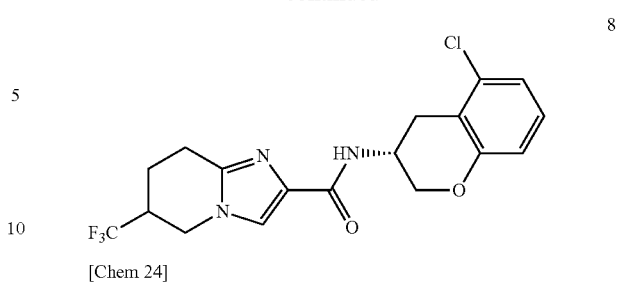
8
[Chem 24]
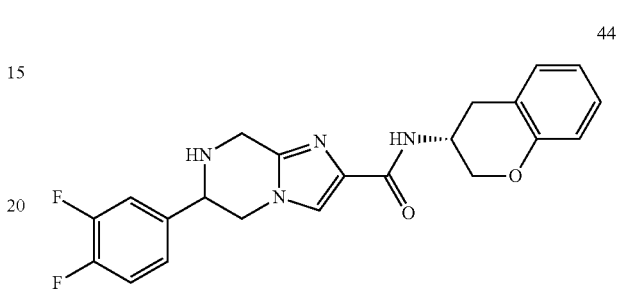
44
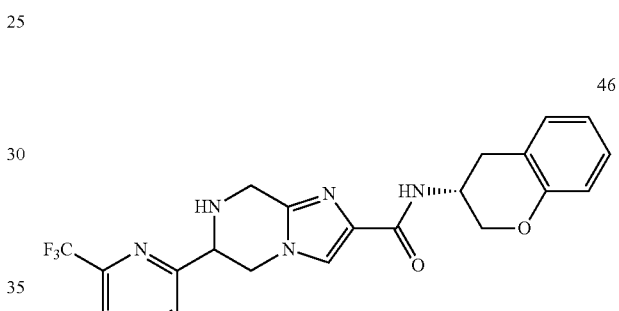
46
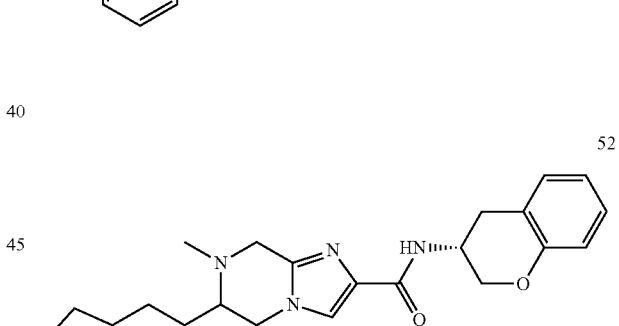
52
[Chem 25]
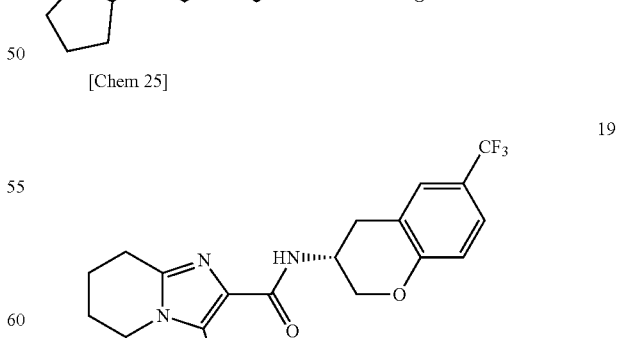
19

-continued

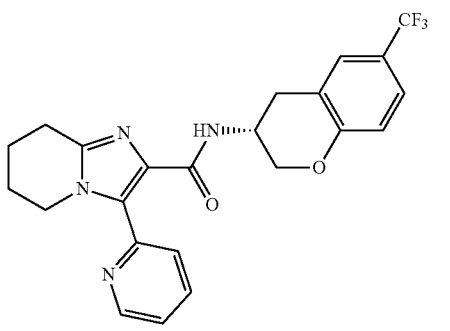
67

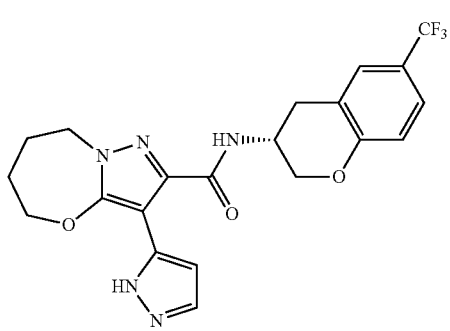
258

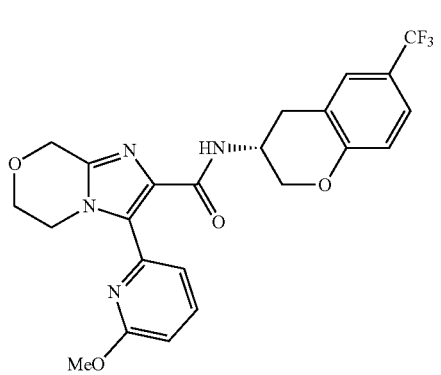
65

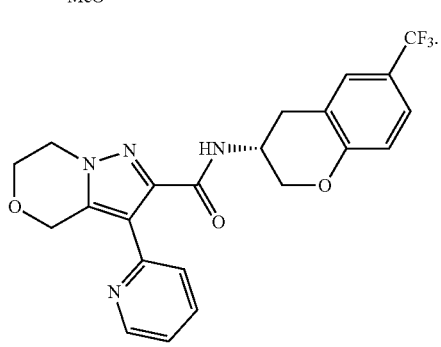
260

(16) A pharmaceutical composition containing the heteroaromatic amide derivative or salt thereof described in any one of the (4) to (15).

(17) A pharmaceutical composition for preventing or treating a disorder associated with voltage-gated sodium channel Nav1.7, containing as an active ingredient the heteroaromatic amide derivative represented by the general formula (I) or salt thereof contained in the pharmaceutical composition described in the (1), or the heteroaromatic amide derivative or salt thereof described in any one of the (4) to (15) (hereinafter sometimes referred to as "the heteroaromatic amide derivative or salt thereof described in any one of the (1) to (15)").

(18) A preventing or treating agent for a disorder with pain, a disorder with pruritus, or an autonomic nervous system disorder, containing as an active ingredient the heteroaromatic amide derivative or salt thereof described in any one of the (1) to (15).

(19) A preventing or treating agent for a disorder with pain, containing as an active ingredient the heteroaromatic amide derivative or salt thereof described in any one of the (1) to (15).

(20) An analgesic agent containing as an active ingredient the heteroaromatic amide derivative or salt thereof described in any one of the (1) to (15).

(21) A preventing or treating agent for nociceptive pain or neuropathic pain, containing as an active ingredient the heteroaromatic amide derivative or salt thereof described in any one of the (1) to (15).

(22) Use of the heteroaromatic amide derivative or salt thereof described in any one of the (1) to (15) for manufacturing a pharmaceutical composition used for preventing or treating pain.

(23) Use of the heteroaromatic amide derivative or salt thereof described in any one of the (1) to (15) for manufacturing an analgesic agent.

Effect of the Invention

Since the present inventive heteroaromatic amide derivative or salt thereof has strong Nav1.7 inhibitory activity, it is useful as an active ingredient for a therapeutic and/or preventive agent for various disorders associated with Nav1.7. For example, it is useful as an analgesic for diseases with various pain.

The present inventive heteroaromatic amide derivative or salt thereof has little concern about side effects derived from Nav1.5, and is useful as an active ingredient for therapeutic and/or preventive agents for a wide range of pathology associated with Nav1.7.

The compounds described in Patent Document 3 to Patent Document 15 are largely different in structure from the present inventive compounds.

In addition, Patent document 16, Patent document 17 and Non-Patent document 10 fail to describe a sodium channel, and let alone neither to describe or suggest the compounds having Nav1.7 inhibitory activity selective over Nav1.5.

Modes for Carry Out the Invention

The present invention is hereinafter explained in more detail.

First, the substituent which the compound of this invention may have is explained.

Specific examples of the "halogen atom" are a fluorine atom, a chlorine atom, a bromine atom and an iodine atom.

The "$C_1$-$C_6$ alkyl group" means a straight or branched alkyl group having 1-6 carbon atoms, specific examples including a methyl group, an ethyl group, a n-propyl group, an isopropyl group, a n-butyl group, an isobutyl group, a tert-butyl group, a sec-butyl group, a n-pentyl group, a tert-pentyl group, a 3-methylbutyl group (an isopentyl group), a neopentyl group, a n-hexyl group, a 3,3-dimethylbutyl group and so on.

The "$C_1$-$C_4$ alkyl group" means a straight or branched alkyl group having 1-4 carbon atoms, specific examples including a methyl group, an ethyl group, a n-propyl group, a n-butyl group and so on.

The "$C_1$-$C_6$ haloalkyl group" means an alkyl group in which the hydrogen atoms on the aforementioned "$C_1$-$C_6$ alkyl group" are substituted by one or more of halogen atom, specific examples including a monofluoromethyl group, a difluoromethyl group, a trifluoromethyl group, a 2-fluoroethyl group, a 2,2-difluoroethyl group, a 2,2,2-trifluoroethyl group, a 1-fluoroethyl group, a 1,1-difluoroethyl group, a 3,3,3-trifluoropropyl group, a 3,3-difluoropropyl group, a 2-fluoroisopropyl group, a 2,3,3,3-tetrafluoropropyl group, a 2,2,3,3-tetrafluoropropyl group, a 2,2,3,3,3-pentafluoropropyl group, a 1,1,2,2,3,3,3-heptafluoropropyl group, a 1,1,1,3,3,3-hexafluoroisopropyl group, a 4,4,4-trifluorobutyl group, a 2,2,3,4,4-pentafluorobutyl group, a 2,2,3,4,4,4-hexafluorobutyl group, a 2,2,3,3,4,4,4-heptafluorobutyl group, a 3,3-difluorobutyl group, a 3,3,3-trifluoro-2-(trifluoromethyl)-propyl group, a 3-fluoro-3-methylbutyl group and so on.

The "$C_1$-$C_4$ haloalkyl group" means an alkyl group in which one or more of the hydrogen atoms on the aforementioned "$C_1$-$C_4$ alkyl group" are substituted by halogen atoms.

The "$C_1$-$C_6$ alkoxy group" means an alkoxy group in which the alkyl moiety has the same definition as given for the "$C_1$-$C_6$ alkyl group", specific examples including a methoxy group, an ethoxy group, a n-propoxy group, an isopropoxy group, a n-butoxy group, an isobutoxy group, a tert-butoxy group, a sec-butoxy group, a n-pentyloxy group, a tert-amyloxy group, a 3-methylbutoxy group, a neopentyloxy group, a n-hexyloxy group and so on.

The "$C_1$-$C_4$ alkoxy group" means an alkoxy group in which the alkyl moiety has the same definition as given for the aforementioned "$C_1$-$C_4$ alkyl group".

The "$C_1$-$C_6$ haloalkoxy group" means a haloalkoxy group in which the haloalkyl moiety has the same definition as given for the "$C_1$-$C_6$ haloalkyl group", specific examples including a trifluoromethoxy group, a difluoromethoxy group, a 2-fluoroethoxy group, a 2,2-difluoroethoxy group, a 2,2,2-trifluoroethoxy group, a 3,3,3-trifluoropropoxy group, a 2,2,3,3-tetrafluoropropoxy group, a 2,2,3,3,3-pentafluoropropoxy group, a 1,1,1,3,3,3-hexafluoroisopropoxy group, a 2,2,3,4,4,4-hexafluorobutoxy group and so on.

The "$C_1$-$C_4$ haloalkoxy group" means a haloalkoxy group in which the haloalkyl moiety has the same definition as given for the aforementioned "$C_1$-$C_4$ haloalkyl group".

The "$C_1$-$C_4$ alkoxy-$C_1$-$C_4$ alkyl group" is the aforementioned "$C_1$-$C_4$ alkyl group" substituted by the aforementioned "$C_1$-$C_4$ alkoxy group", and these can bind at any substitutionable position. Specific examples include a methoxymethyl group, an ethoxymethyl group, an isopropoxymethyl group, a n-propoxymethyl group, a tert-butoxymethyl group, an isobutoxymethyl group, a 2-methoxyethyl group, a 2-ethoxyethyl group, a 1-ethoxyethyl group, an isobutoxyethyl group, a tert-butoxyethyl group and so on.

The "$C_1$-$C_4$ haloalkoxy-$C_1$-$C_4$ alkyl group" is the aforementioned "$C_1$-$C_4$ alkyl group" substituted by the aforementioned "$C_1$-$C_4$ haloalkoxy group", and these can bind at any substitutionable position. Specific examples include a trifluoromethoxymethyl group, a difluoromethoxymethyl group, a monofluoromethoxymethyl group, a 2,2,2-trifluoroethoxymethyl group, a 2,2-difluoroethoxymethyl group, a 3,3,3-trifluoropropoxymethyl group, a 4,4,4-trifluorobutoxymethyl group, a 1,1,1,3,3,3-pentafluoroisopropoxymethyl group, a 3,3,3-trifluoro-2-(trifluoromethyl)-propoxymethyl group, a 2-(trifluoromethoxy)ethyl group, a 2-(difluoromethoxy)ethyl group, a 2-(2',2',2'-trifluoroethoxy)ethyl group, 2-(2',2'-difluoroethoxy)ethyl group, a 2-(1',1',1',3',3',3'-pentafluoroisopropoxy)ethyl group, a 3-(trifluoromethoxy)propyl group, a 3-(difluoromethoxy)propyl group, a 3-(2',2',2'-trifluoroethoxy)propyl group, a 3-(2',2'-difluoroethoxy)propyl group, a 3-(1',1',1',3',3',3'-pentafluoroisopropoxy)propyl group and so on.

The "$C_1$-$C_4$ alkoxy-$C_1$-$C_4$ haloalkyl group" is the aforementioned "$C_1$-$C_4$ haloalkyl group" substituted by the aforementioned "$C_1$-$C_4$ alkoxy group", and these can bind at any substitutionable position. Specific examples include an ethoxymonofluoromethyl group and so on.

The "$C_1$-$C_4$ haloalkoxy-$C_1$-$C_4$ haloalkyl group" is the aforementioned "$C_1$-$C_4$ haloalkyl group" substituted by the aforementioned "$C_1$-$C_4$ haloalkoxy group", and these can bind at any substitutionable position.

The "$C_1$-$C_6$ alkylcarbonyl group" means an alkylcarbonyl group in which the alkyl moiety is the aforementioned "$C_1$-$C_6$ alkyl group", specific examples including a methylcarbonyl group, an ethylcarbonyl group, a n-propylcarbonyl group and so on.

"$C_1$-$C_6$ alkoxycarbonyl group" means an alkoxycarbonyl group in which the alkoxy moiety is the aforementioned "$C_1$-$C_6$ alkoxy group", specific examples including a methoxycarbonyl group, an ethoxycarbonyl group, a n-propoxycarbonyl group, a tert-butoxycarbonyl and so on.

The "$C_1$-$C_6$ alkylcarbonyloxy group" means an alkylcarbonyloxy group in which the alkylcarbonyl moiety is the aforementioned "$C_1$-$C_6$ alkylcarbonyl group", specific examples including a methylcarbonyloxy group, an ethylcarbonyloxy group, a n-propylcarbonyloxy group and so on.

The "$C_1$-$C_6$ haloalkylcarbonyl group" means a haloalkylcarbonyl group in which the haloalkyl moiety is the aforementioned "$C_1$-$C_6$ haloalkyl group", specifically being a trifluoromethylcarbonyl group and so on.

The "$C_1$-$C_6$ haloalkoxycarbonyl group" means a haloalkoxycarbonyl group in which the haloalkoxy moiety is the aforementioned "$C_1$-$C_6$ haloalkoxy group".

The "$C_1$-$C_6$ haloalkylcarbonyloxy group" means a haloalkylcarbonyloxy group in which the halolkylcarbonyl moiety is the aforementioned "$C_1$-$C_6$ haloalkylcarbonyl group".

The "$C_3$-$C_7$ cycloalkyl group" means a monocyclic saturated carbon ring group having 3 to 7 carbon atoms. Specific examples include a cyclopropyl group, a cyclobutyl group, a cyclopentyl group, a cyclohexyl group and so on.

The "monocyclic saturated heteroring" means a 3- to 7-membered saturated monocyclic ring comprising at least one of an oxygen atom, a nitrogen atom or a sulfur atom, specific examples including an aziridine, an azetidine, a pyrrolidine, a piperidine, a piperazine, an azepan, an oxetane, a tetrahydrofuran, a tetrahydropyran, a morpholine, a thiomorpholine and so on.

The "heterocycloalkyl group" means a monocyclic saturated heteroring group, in which at least one of the carbon atoms in the "$C_3$-$C_7$ cycloalkyl group" is replaced with an oxygen atom, a nitrogen atom or a sulfur atom. Specific examples of the "heterocycloalkyl group" include an azetidinyl group, a pyrrolidinyl group, a piperidyl group, a piperazinyl group, a morpholino group and so on.

The "$C_3$-$C_7$ cycloalkyloxy group" means a cycloalkyloxy group in which the cycloalkyl moiety is the aforementioned "$C_3$-$C_7$ cycloalkyl group".

The "heterocycloalkyloxy group" means a heterocycloalkyloxy group in which the heterocycloalkyl moiety is the aforementioned "heterocycloalkyl group".

The "$C_2$-$C_6$ alkenyl group" means a straight or branched alkenyl group having 2-6 carbon atoms with one or more double bonds. Positions of the double bonds are not limited. Specific examples include a vinyl group, an allyl group, a 1-propenyl group, a 2-propenyl group, an isopropenyl group, an isobutenyl group, a 3-methyl-3-butenyl group and so on.

The "$C_2$-$C_6$ alkenyloxy group" means an alkenyloxy group in which the alkenyl moiety is the aforementioned "$C_2$-$C_6$ alkenyl group", specific examples including a vinyloxy group, an allyloxy group, a 1-butenyloxy group, a 2-butenyloxy group, a 3-butenyloxy group and so on.

The "$C_2$-$C_6$ alkenyloxy-$C_1$-$C_4$ alkyl group" means the aforementioned "$C_1$-$C_4$ alkyl group" substituted by the aforementioned "$C_2$-$C_6$ alkenyloxy group", and these can bind at any substitutionable position. For example, vinyloxymethyl group, allyloxymethyl group and so on can be recited.

The "$C_2$-$C_6$ alkenyloxy-$C_1$-$C_4$ haloalkyl group" means the aforementioned "$C_1$-$C_4$ haloalkyl group" substituted by the aforementioned "$C_2$-$C_6$ alkenyloxy group", and these can bind at any substitutionable position.

The "$C_2$-$C_6$ alkynyl group" means a straight or branched alkynyl group having 2-6 carbon atoms with one or more triple bonds. Positions of the triple bonds are not limited. Specific examples include an ethynyl group, a 1-propynyl group, a 2-propynyl group, a 3-methyl-1-butynyl group and so on.

The "$C_2$-$C_6$ alkynyloxy group" means an alkynyloxy group in which the alkynyl moiety is the aforementioned "$C_2$-$C_6$ alkynyl group".

The "$C_2$-$C_6$ alkynyloxy-$C_1$-$C_4$ alkyl group" means the aforementioned "$C_1$-$C_4$ alkyl group" substituted by the aforementioned "$C_2$-$C_6$ alkynyloxy group", and these can bind at any substitutionable position.

The "$C_2$-$C_6$ alkynyloxy-$C_1$-$C_4$ haloalkyl group" means the aforementioned "$C_1$-$C_4$ haloalkyl group" substituted by the aforementioned "$C_2$-$C_6$ alkynyloxy group", and these can bind at any substitutionable position.

The "$C_1$-$C_4$ alkoxy-$C_1$-$C_4$ alkoxy group" means the aforementioned "$C_1$-$C_4$ alkoxy group" substituted by the aforementioned "$C_1$-$C_4$ alkoxy group", and these can bind at any substitutionable position.

The "$C_1$-$C_4$ haloalkoxy-$C_1$-$C_4$ alkoxy group" means the aforementioned "$C_1$-$C_4$ alkoxy group" substituted by the aforementioned "$C_1$-$C_4$ haloalkoxy group", and these can bind at any substitutionable position. Specific examples include a 2-(trifluoromethoxy)ethoxy group and so on.

The "$C_2$-$C_6$ alkenyloxy-$C_1$-$C_4$ alkoxy group" means the aforementioned "$C_1$-$C_4$ alkoxy group" substituted by the aforementioned "$C_2$-$C_6$ alkenyloxy group", and these can bind at any substitutionable position.

The "$C_2$-$C_6$ alkynyloxy-$C_1$-$C_4$ alkoxy group" means the aforementioned "$C_1$-$C_4$ alkoxy group" substituted by the aforementioned "$C_2$-$C_6$ alkynyloxy group", and these can bind at any substitutionable position. For example, an allyloxymethoxy group and so on can be recited.

The "$C_2$-$C_6$ alkenyloxy-$C_1$-$C_4$ haloalkoxy group" means the aforementioned "$C_1$-$C_4$ haloalkoxy group" substituted by the aforementioned "$C_2$-$C_6$ alkenyloxy group", and these can bind at any substitutionable position.

The "$C_2$-$C_6$ alkynyloxy-$C_1$-$C_4$ haloalkoxy group" means the aforementioned "$C_1$-$C_4$ haloalkoxy group" substituted by the aforementioned "$C_2$-$C_6$ alkynyloxy group", and these can bind at any substitutionable position.

The "$C_1$-$C_6$ alkylthio group" means an alkylthio group in which the alkyl moiety has the same definition as given for the aforementioned "$C_1$-$C_6$ alkyl group", specific examples including a methylthio group, an ethylthio group, a n-propylthio group, an isopropylthio group, a n-butylthio group and so on.

The "$C_1$-$C_4$ alkylthio group" means an alkylthio group in which the alkyl moiety has the same definition as given for the aforementioned "$C_1$-$C_4$ alkyl group".

The "$C_1$-$C_6$ haloalkylthio group" means an alkylthio group in which one or more of the hydrogen atoms in the aforementioned "$C_1$-$C_6$ alkylthio group" are substituted by halogen atoms, specific examples including a trifluoromethylthio group, a 2,2,2-trifluoroethylthio group and so on.

The "$C_1$-$C_4$ haloalkylthio group" means an alkylthio group in which one or more of the hydrogen atoms in the aforementioned "$C_1$-$C_4$ alkylthio group" are substituted by halogen atoms.

The "$C_1$-$C_4$ alkylthio-$C_1$-$C_4$ alkyl group" means the aforementioned "$C_1$-$C_4$ alkyl group" substituted by the aforementioned "$C_1$-$C_4$ alkylthio group", and these can bind at any substitutionable position.

The "$C_1$-$C_4$ haloalkylthio-$C_1$-$C_4$ alkyl group" means the aforementioned "$C_1$-$C_4$ alkyl group" substituted by the aforementioned "$C_1$-$C_4$ haloalkylthio group", and these can bind at any substitutionable position. Specific examples include a trifluoromethylthiomethyl group, a ((2',2',2'-trifluoroethyl)thio)methyl group, a 2-((trifluoromethyl)thio)ethyl group, a 2-((2',2',2'-trifluoroethyl)thio)ethyl group and so on.

The "$C_1$-$C_4$ alkylthio-$C_1$-$C_4$ haloalkyl group" means the aforementioned "$C_1$-$C_4$ haloalkyl group" substituted by the aforementioned "$C_1$-$C_4$ alkylthio group", and these can bind at any substitutionable position.

The "$C_1$-$C_4$ haloalkylthio-$C_1$-$C_4$ haloalkyl group" means the aforementioned "$C_1$-$C_4$ haloalkyl group" substituted by the aforementioned "$C_1$-$C_4$ haloalkylthio group", and these can bind at any substitutionable position.

The "$C_1$-$C_6$ alkylsulfonyl group" means the aforementioned "$C_1$-$C_6$ alkyl group" is substituted by a sulfonyl group, and these can bind at any substitutionable position.

The "$C_3$-$C_7$ cycloalkyl-$C_1$-$C_4$ alkyl group" means the aforementioned "$C_1$-$C_4$ alkyl group" substituted by the aforementioned "$C_3$-$C_7$ cycloalkyl group", and these can bind at any substitutionable position. Specific examples include a cyclopropylmethyl group and so on.

The "heterocycloalkyl-$C_1$-$C_4$ alkyl group" means the aforementioned "$C_1$-$C_4$ alkyl group" substituted by the aforementioned "heterocycloalkyl group", and these can bind at any substitutionable position. Specific examples include an oxetanylmethyl group, a pyrrolidinylmethyl group, a morpholinomethyl group and so on.

The "aralkyl group" means the aforementioned "$C_1$-$C_6$ alkyl group" substituted by a phenyl group, a 5-membered heteroaryl group, or a 6-membered heteroaryl group. These can bind at any substitutionable position. Specific examples include a benzyl group, a fenetyl group and so on.

The "5-membered heteroaryl" means a 5-membered monocyclic aromatic heteroring comprising one or more (for example, one to four) hetero atoms selected from a nitrogen atom, a sulfur atom and an oxygen atom in addition to carbon atoms. Specific examples include a pyrrol, a furan, a thiophen, an imidazole, a pyrazole, an oxazole, an isoxazole, a thiazole, an isothiazole, a thiadiazole, an oxadiazole, a triazole, a tetrazole and so on.

The "5-membered heteroaryl group" means a group of the aforementioned "5-membered heteroaryl", specific examples including a pyrrolyl group (for example, a 2-pyrrolyl group), a furyl group (for example, a 3-furyl group), a thienyl group (for example, a 2-thienyl group), an imidazolyl group (for example, a 4-imidazolyl group), a pyrazolyl group (for a example, 3-pyrazolyl group) and so on.

The "6-membered heteroaryl" means a 6-membered monocyclic aromatic heteroring comprising one or more (for example, one to three) nitrogen atoms in addition to carbon atoms. Specific examples include a pyridine, a pyridazine, a pyrimidine, a pyrazine, a triazine and so on.

The "6-membered heteroaryl group" means a group of the "6-membered heteroaryl", specific examples including a pyridyl group (for example, a 2-pyridyl group, a 3-pyridyl group, a 4-pyridyl group), pyridazinyl group (for example, a 3-pyridazinyl group), a pyrimidinyl group (for example, a 5-pyrimidinyl group), a pyrazinyl group (for example, a 2-pyrazinyl group) and so on.

In the present specification, the "monocyclic ring" includes all of a monocyclic saturated carbocyclic ring, a monocyclic partially saturated carbocyclic ring, a monocyclic unsaturated carbocyclic ring, a monocyclic saturated heterocyclic ring, a monocyclic partially saturated heterocycles, a monocyclic unsaturated heterocyclic ring, and a monocyclic aromatic ring unless otherwise described.

In the present specification, the "bicyclic ring" includes all of a bicyclic saturated carbocyclic ring, a bicyclic partially saturated carbocyclic ring, a bicyclic unsaturated carbocyclic ring, a bicyclic saturated heterocyclic ring, a bicyclic partially saturated heterocyclic ring, a bicyclic unsaturated heterocycles, and a bicyclic aromatic ring unless otherwise described.

The meaning of substituents with the term "optionally substituted" in the present specification is then explained. Meanwhile, the term "substituted" means that one or more hydrogen atoms at any position are substituted by an atom or a functional group other than a hydrogen atom unless otherwise specified.

In $R^2$ of the general formula (I) or the general formula (I-E2), the substituent of the "optionally substituted $C_1$-$C_6$ alkyl group", "optionally substituted $C_1$-$C_6$ haloalkyl group", "optionally substituted $C_2$-$C_6$ alkenyl group", "optionally substituted $C_2$-$C_6$ alkynyl group", or "optionally substituted saturated, partially saturated or unsaturated 3- to 7-membered monocyclic ring" denotes one selected from the group consisting of a halogen atom, a cyano group, a carboxyl group, a carboxamide group, a hydroxy group, a $C_1$-$C_4$ alkyl group, a $C_1$-$C_4$ haloalkyl group, a $C_1$-$C_4$ alkoxy group, a $C_1$-$C_4$ haloalkoxy group, a $C_3$-$C_7$ cycloalkyl group, a heterocycloalkyl group, a $C_3$-$C_7$ cycloalkyloxy group, a heterocycloalkyloxy group, a $C_1$-$C_4$ alkylthio group, a $C_1$-$C_4$ haloalkylthio group and —$NR^{d1}R^{d2}$ ($R^{d1}$ and $R^{d2}$ are, independently each other, a hydrogen atom, a $C_1$-$C_4$ alkyl group, or a $C_1$-$C_4$ haloalkyl group.). These can substitute at all the substitutable positions by one or more.

In $R^{3a}$, $R^{3b}$, $R^{3c}$, $R^{11b}$ and $R^{11c}$ of the general formula (I) or the general formula (I-E2), the substituent of the "optionally substituted $C_1$-$C_6$ alkyl group", "optionally substituted $C_1$-$C_6$ haloalkyl group", "optionally substituted $C_1$-$C_6$ alkoxy group", "optionally substituted $C_1$-$C_6$ haloalkoxy group", "optionally substituted $C_1$-$C_4$ alkoxy-$C_1$-$C_4$ alkyl group", "optionally substituted $C_1$-$C_4$ haloalkoxy-$C_1$-$C_4$ alkyl group", "optionally substituted $C_1$-$C_4$ alkoxy-$C_1$-$C_4$ haloalkyl group", "optionally substituted $C_1$-$C_4$ haloalkoxy-$C_1$-$C_4$ haloalkyl group", "optionally substituted $C_1$-$C_6$ alkylcarbonyl group", "optionally substituted $C_1$-$C_6$ alkoxycarbonyl group", "optionally substituted $C_1$-$C_6$ alkylcarbonyloxy group", "optionally substituted $C_1$-$C_6$ haloalkylcarbonyl group", "optionally substituted $C_1$-$C_6$ haloalkoxycarbonyl group", "optionally substituted $C_1$-$C_6$ haloalkylcarbonyloxy group", "optionally substituted $C_3$-$C_7$ cycloalkyl group", "optionally substituted heterocycloalkyl group", "optionally substituted $C_3$-$C_7$ cycloalkyloxy group", "optionally substituted heterocycloalkyloxy group", "optionally substituted $C_2$-$C_6$ alkenyl group", "optionally substituted $C_2$-$C_6$ alkenyloxy group", "optionally substituted $C_2$-$C_6$ alkenyloxy-$C_1$-$C_4$ alkyl group", "optionally substituted $C_2$-$C_6$ alkenyloxy-$C_1$-$C_4$ haloalkyl group", "optionally substituted $C_2$-$C_6$ alkynyl group", "optionally substituted $C_2$-$C_6$ alkynyloxy group", "optionally substituted $C_2$-$C_6$ alkynyloxy-$C_1$-$C_4$ alkyl group", "optionally substituted $C_2$-$C_6$ alkynyloxy-$C_1$-$C_4$ haloalkyl group", "optionally substituted $C_1$-$C_4$ alkoxy-$C_1$-$C_4$ alkoxy group", "optionally substituted $C_1$-$C_4$ haloalkoxy-$C_1$-$C_4$ alkoxy group", "optionally substituted $C_2$-$C_6$ alkenyloxy-$C_1$-$C_4$ alkoxy group", "optionally substituted $C_2$-$C_6$ alkynyloxy-$C_1$-$C_4$ alkoxy group", "optionally substituted $C_2$-$C_6$ alkenyloxy-$C_1$-$C_4$ haloalkoxy group", "optionally substituted $C_2$-$C_6$ alkynyloxy-$C_1$-$C_4$ haloalkoxy group", "optionally substituted $C_1$-$C_6$ alkylthio group", "optionally substituted $C_1$-$C_6$ haloalkylthio group", "optionally substituted $C_1$-$C_4$ alkylthio-$C_1$-$C_4$ alkyl group", "optionally substituted $C_1$-$C_4$ haloalkylthio-$C_1$-$C_4$ alkyl group", "optionally substituted $C_1$-$C_4$ alkylthio-$C_1$-$C_4$ haloalkyl group", "optionally substituted $C_1$-$C_4$ haloalkylthio-$C_1$-$C_4$ haloalkyl group", "optionally substituted $C_1$-$C_6$ alkylsulfonyl group" denotes one selected from the group consisting of a halogen atom, a cyano group, a carboxyl group, a carboxamide group, a hydroxy group, a $C_1$-$C_4$ alkyl group, a $C_1$-$C_4$ haloalkyl group, a $C_1$-$C_4$ alkoxy group, a $C_1$-$C_4$ haloalkoxy group, a $C_3$-$C_7$ cycloalkyl group, a heterocycloalkyl group, a $C_3$-$C_7$ cycloalkyloxy group, a heterocycloalkyloxy group, a $C_1$-$C_4$ alkylthio group, a $C_1$-$C_4$ haloalkylthio group, a methylamino group, a dimethylamino group, an ethylamino group, a diethylamino group, an ethylmethylamino group, a (2,2,2-trifluoroethyl)amino group, a methyl (2,2,2-trifluoroethyl)amino group, an ethyl (2,2,2-trifluoroethyl)amino group, a bis(2,2,2-trifluoroethyl)amino group, a methylaminocarbonyl group, a dimethylaminocarbonyl group, an ethylaminocarbonyl group, a diethylaminocarbonyl group and an ethylmethylaminocarbonyl group. These can substitute at all the substitutable positions by one or more.

In $R^{4a}$, $R^{4b}$ or $R^{4c}$ of the general formula (I) or the general formula (I-E2), the substituent of the "optionally substituted $C_1$-$C_6$ alkyl group", "optionally substituted $C_1$-$C_6$ haloalkyl group", "optionally substituted $C_1$-$C_6$ alkoxy group", "optionally substituted $C_1$-$C_6$ haloalkoxy group", "optionally substituted $C_1$-$C_4$ alkoxy-$C_1$-$C_4$ alkyl group", "optionally substituted $C_1$-$C_4$ haloalkoxy-$C_1$-$C_4$ alkyl group", "optionally substituted $C_1$-$C_4$ alkoxy-$C_1$-$C_4$ haloalkyl group", "optionally substituted $C_1$-$C_4$ haloalkoxy-$C_1$-$C_4$ haloalkyl group", "optionally substituted $C_1$-$C_6$ alkylcarbonyl group", "optionally substituted $C_1$-$C_6$ alkoxycarbonyl group", "optionally substituted $C_1$-$C_6$ alkylcarbonyloxy group", "optionally substituted $C_1$-$C_6$ alkoxycarbonyloxy group", "optionally substituted $C_1$-$C_6$ haloalkylcarbonyl group", "optionally substituted $C_1$-$C_6$ haloalkoxycarbonyl group", "optionally substituted $C_1$-$C_6$ haloalkylcarbonyloxy group", "optionally substituted $C_3$-$C_7$ cycloalkyl group", "optionally substituted heterocycloalkyl group", "optionally substituted $C_3$-$C_7$ cycloalkyloxy group", "optionally substituted heterocycloalkyloxy group", "optionally substituted $C_2$-$C_6$ alkenyl group", "optionally substituted $C_2$-$C_6$ alkenyloxy group", "optionally substituted $C_2$-$C_6$ alkenyloxy-$C_1$-$C_4$ alkyl group", "optionally substituted $C_2$-$C_6$ alkenyloxy-$C_1$-$C_4$ haloalkyl group", "optionally substituted $C_2$-$C_6$ alkynyl group", "optionally substituted $C_2$-$C_6$ alkynyloxy group", "optionally substituted $C_2$-$C_6$ alkynyloxy-$C_1$-$C_4$ alkyl group", "optionally substituted $C_2$-$C_6$ alkynyloxy-$C_1$-$C_4$ haloalkyl group", "optionally substituted $C_1$-$C_4$ alkoxy- $C_1$-$C_4$ alkoxy group", "optionally substituted $C_1$-$C_4$ haloalkoxy-$C_1$-$C_4$ alkoxy group", "optionally substituted $C_2$-$C_6$ alkenyloxy-$C_1$-$C_4$ alkoxy group", "optionally substituted $C_2$-$C_6$ alkynyloxy-$C_1$-$C_4$ alkoxy group", "optionally substituted $C_2$-$C_6$ alkenyloxy-$C_1$-$C_4$ haloalkoxy group", "optionally substituted $C_2$-$C_6$ alkynyloxy-$C_1$-$C_4$ haloalkoxy group", "optionally substituted $C_1$-$C_6$ alkylthio group", "optionally substituted $C_1$-$C_6$ haloalkylthio group", "optionally substituted $C_1$-$C_4$ alkylthio-$C_1$-$C_4$ alkyl group", "optionally substituted $C_1$-$C_4$ haloalkylthio-$C_1$-$C_4$ alkyl group", "optionally substituted $C_1$-$C_4$ alkylthio-$C_1$-$C_4$ haloalkyl group", "optionally substituted $C_1$-$C_4$ haloalkylthio-$C_1$-$C_4$ haloalkyl group" denotes one selected from the group consisting of a halogen atom, a cyano group, a carboxyl group, carboxamide group, a hydroxy group, a $C_1$-$C_4$ alkyl group, a $C_1$-$C_4$ haloalkyl group, a $C_1$-$C_4$ alkoxy group, a $C_1$-$C_4$ haloalkoxy group, a $C_3$-$C_7$ cycloalkyl group, a heterocycloalkyl group, a $C_3$-$C_7$ cycloalkyloxy group, a heterocycloalkyloxy group, a $C_1$-$C_4$ alkylthio group and a $C_1$-$C_4$ haloalkylthio group. These can substitute at all the substitutable positions by one or more.

As regards the present inventive heteroaromatic amide derivative or salt thereof of the general formula (I) or the general formula (I-E2), preferable atoms, substituent groups, and rings are then hereinbelow explained. The present inventive compound having at least one of preferable atoms, substituents, or rings is preferable; the present inventive compound having plural preferable atoms, substituents, or rings is more preferable.

Preferable $Y^1$, $Y^2$, $Y^3$ and $Y^4$ together form
—OCH$_2$CH$_2$CH$_2$—, —OCR$^{4a}$HCH$_2$CH$_2$—, —OCR$^{4a}$R$^{4b}$CH$_2$CH$_2$—
—OCH$_2$CH$_2$—, —OCR$^{4a}$HCH$_2$—, —OCR$^{4a}$R$^{4b}$CH$_2$—,
—OCH$_2$CH$_2$CH$_2$CH$_2$—, —OCR$^{4a}$HCH$_2$CH$_2$CH$_2$—,
—OCR$^{4a}$R$^{4b}$CH$_2$CH$_2$CH$_2$—,
—OCH$_2$CR$^{4a}$HCH$_2$CH$_2$—,
—OCH$_2$CR$^{4a}$R$^{4b}$CH$_2$CH$_2$—,
—CH$_2$OCH$_2$CH$_2$—, —CH$_2$OCH$_2$CH$_2$CH$_2$—,
—CH$_2$CH$_2$OCH$_2$—, —CH$_2$CR$^{4a}$HOCH$_2$—
—CH$_2$CH$_2$CH$_2$CH$_2$—, —CH$_2$CR$^{4a}$HCH$_2$CH$_2$—,
—CH$_2$CR$^{4a}$R$^{4b}$CH$_2$CH$_2$—,
—CH$_2$CH$_2$CR$^{4a}$HCH$_2$—, —CH$_2$CH$_2$CR$^{4a}$R$^{4b}$CH$_2$—,
—CH$_2$SCH$_2$CH$_2$—, —CH$_2$SO$_2$CH$_2$CH$_2$—,
—NHCH$_2$CH$_2$CH$_2$—, —NR$^{4c}$CH$_2$CH$_2$CH$_2$—,
—NR$^{4c}$CR$^{4a}$HCH$_2$CH$_2$—,
—NHCR$^{4a}$HCH$_2$CH$_2$—,
—CH$_2$NR$^{4c}$CH$_2$CH$_2$—, —CH$_2$NR$^4$CCR$^{4a}$HCH$_2$—,
—CH$_2$NHCR$^{4a}$HCH$_2$—,
—CH$_2$CH$_2$NR$^{4c}$CH$_2$—, —CH$_2$CR$^{4a}$HNR$^4$CCH$_2$—, or
—CH$_2$CR$^{4a}$HNHCH$_2$—;

more preferable $Y^1$, $Y^2$, $Y^3$ and $Y^4$ together form
—OCR$^{4a}$HCH$_2$CH$_2$—, —OCR$^{4a}$R$^{4b}$CH$_2$CH$_2$—
—OCH$_2$CH$_2$—, —OCR$^{4a}$HCH$_2$—, —OCR$^{4a}$R$^{4b}$CH$_2$—,
—OCH$_2$CH$_2$CH$_2$CH$_2$—, —OCR$^{4a}$HCH$_2$CH$_2$CH$_2$—,
—OCR$^{4a}$R$^{4b}$CH$_2$CH$_2$CH$_2$—,
—OCH$_2$CR$^{4a}$HCH$_2$CH$_2$—,
—OCH$_2$CR$^{4a}$R$^{4b}$CH$_2$CH$_2$—,
—CH$_2$OCH$_2$CH$_2$—, —CH$_2$OCH$_2$CH$_2$CH$_2$—,
—CH$_2$CH$_2$OCH$_2$—, —CH$_2$CR$^{4a}$HOCH$_2$—
—CH$_2$CH$_2$CH$_2$CH$_2$—, —CH$_2$CR$^{4a}$HCH$_2$CH$_2$—,
—CH$_2$CR$^{4a}$R$^{4b}$CH$_2$CH$_2$—,
—CH$_2$CH$_2$CR$^{4a}$HCH$_2$—, —CH$_2$CH$_2$CR$^{4a}$R$^{4b}$CH$_2$—,
—CH$_2$SCH$_2$CH$_2$—, —CH$_2$SO$_2$CH$_2$CH$_2$—,
—NHCH$_2$CH$_2$CH$_2$—, —NR$^{4c}$CH$_2$CH$_2$CH$_2$—,
—NR$^{4c}$CR$^{4a}$HCH$_2$CH$_2$—,
—NHCR$^{4a}$HCH$_2$CH$_2$—,
—CH$_2$NR$^{4c}$CH$_2$CH$_2$—, —CH$_2$NR$^{4c}$CR$^{4a}$HCH$_2$—,
—CH$_2$NHCR$^{4a}$HCH$_2$—,
—CH$_2$CH$_2$NR$^{4c}$CH$_2$—, —CH$_2$CR$^{4a}$HNR$^{4c}$CH$_2$—, or
—CH$_2$CR$^{4a}$HNHCH$_2$—.

Meanwhile, for example, "$Y^1$, $Y^2$, $Y^3$ and $Y^4$ together form —OCR$^{4a}$HCH$_2$CH$_2$—" means that $Y^1$ is —O—, $Y^2$ is —CR$^{4a}$H—, $Y^3$ is —CH$_2$—, and $Y^4$ is —CH$_2$—.

When $X^1$-$X^2$ is C—N, (namely, in the case where $X^1$ is a carbon atom, and $X^2$ is a nitrogen atom.), preferable $Y^1$, $Y^2$, $Y^3$ and $Y^4$ together form
—OCH$_2$CH$_2$CH$_2$—, —OCR$^{4a}$HCH$_2$CH$_2$—,
—OCR$^{4a}$R$^{4b}$CH$_2$CH$_2$—, —OCH$_2$CH$_2$—,
—OCR$^{4a}$HCH$_2$—, —OCR$^{4a}$R$^{4b}$CH$_2$—,
—OCH$_2$CH$_2$CH$_2$CH$_2$—, —OCR$^{4a}$HCH$_2$CH$_2$CH$_2$—,
—OCH$_2$CR$^{4a}$HCH$_2$CH$_2$—,
—CH$_2$OCH$_2$CH$_2$—, —CH$_2$OCH$_2$CH$_2$CH$_2$—,
—CH$_2$CR$^{4a}$HCH$_2$CH$_2$—, —CH$_2$CR$^{4a}$R$^{4b}$CH$_2$CH$_2$—,
—CH$_2$CH$_2$CR$^{4a}$HCH$_2$—,
—NHCH$_2$CH$_2$CH$_2$—, —NR$^{4c}$CR$^{4a}$HCH$_2$CH$_2$—,
—NHCR$^{4a}$HCH$_2$CH$_2$—, or —CH$_2$NR$^{4c}$CH$_2$CH$_2$—.

In this case, more preferable $Y^1$, $Y^2$, $Y^3$ and $Y^4$ together form
—OCR$^{4a}$HCH$_2$CH$_2$—, —OCR$^{4a}$R$^{4b}$CH$_2$CH$_2$—,
—OCH$_2$CH$_2$—,
—OCR$^{4a}$HCH$_2$—, —OCR$^{4a}$R$^{4b}$CH$_2$—,
—OCH$_2$CH$_2$CH$_2$CH$_2$—, —OCR$^{4a}$HCH$_2$CH$_2$CH$_2$—,
—OCH$_2$CR$^{4a}$HCH$_2$CH$_2$—,
—CH$_2$OCH$_2$CH$_2$—, —CH$_2$OCH$_2$CH$_2$CH$_2$—,
—CH$_2$CR$^{4a}$HCH$_2$CH$_2$—, —CH$_2$CR$^{4a}$R$^{4b}$CH$_2$CH$_2$—,
—CH$_2$CH$_2$CR$^{4a}$HCH$_2$—,
—NHCH$_2$CH$_2$CH$_2$—, —NR$^{4c}$CR$^{4a}$HCH$_2$CH$_2$—,
—NHCR$^{4a}$HCH$_2$CH$_2$—, or —CH$_2$NR$^{4c}$CH$_2$CH$_2$—.

In this case, further more preferable $Y^1$, $Y^2$, $Y^3$ and $Y^4$ together form
—OCR$^{4a}$HCH$_2$CH$_2$—, —OCR$^{4a}$R$^{4b}$CH$_2$CH$_2$—,
—OCH$_2$CH$_2$—, —OCR$^{4a}$HCH$_2$—,
—OCR$^{4a}$R$^{4b}$CH$_2$—,
—OCH$_2$CH$_2$CH$_2$CH$_2$—, —OCR$^{4a}$HCH$_2$CH$_2$CH$_2$—,
—OCH$_2$CR$^{4a}$HCH$_2$CH$_2$—, —CH$_2$CR$^{4a}$HCH$_2$CH$_2$—,
—NR$^{4c}$CR$^{4a}$HCH$_2$CH$_2$—, —NHCR$^{4a}$HCH$_2$CH$_2$—, or
—CH$_2$NR$^{4c}$CH$_2$CH$_2$—.

In this case, still further more preferable $Y^1$, $Y^2$, $Y^3$ and $Y^4$ together form
—OCR$^{4a}$HCH$_2$CH$_2$—, —OCR$^{4a}$HCH$_2$—,
—OCR$^{4a}$HCH$_2$CH$_2$CH$_2$—, —CH$_2$CR$^{4a}$HCH$_2$CH$_2$—,
—NR$^{4c}$CR$^{4a}$HCH$_2$CH$_2$—, —NHCR$^{4a}$HCH$_2$CH$_2$—, or
—CH$_2$NR$^{4c}$CH$_2$CH$_2$—.

In this case, particularly preferable $Y^1$, $Y^2$, $Y^3$ and $Y^4$ together form
—OCR$^{4a}$HCH$_2$CH$_2$—.

Additionally, in this case, in another aspect of the present invention, particularly preferable $Y^1$, $Y^2$, $Y^3$ and $Y^4$ together form —CH$_2$NR$^{4c}$CH$_2$CH$_2$—.

When $X^1$-$X^2$ is N—C (namely, in the case where $X^1$ is a nitrogen atom, and $X^2$ is a carbon atom), preferable $Y^1$, $Y^2$, $Y^3$ and $Y^4$ together form
—CH$_2$CH$_2$OCH$_2$—, —CH$_2$CR$^{4a}$HOCH$_2$—
—CH$_2$CH$_2$CH$_2$CH$_2$—, —CH$_2$CR$^{4a}$HCH$_2$CH$_2$—,
—CH$_2$CR$^{4a}$R$^{4b}$CH$_2$CH$_2$—,
—CH$_2$CH$_2$NR$^{4c}$CH$_2$—, —CH$_2$CR$^{4a}$HNR$^{4c}$CH$_2$—, or
—CH$_2$CR$^{4a}$HNHCH$_2$—.

In this case, more preferable $Y^1$, $Y^2$, $Y^3$ and $Y^4$ together form
—CH$_2$CH$_2$OCH$_2$—, —CH$_2$CR$^{4a}$HOCH$_2$—,
—CH$_2$CR$^{4a}$HCH$_2$CH$_2$—,
—CH$_2$CH$_2$NR$^{4c}$CH$_2$—, —CH$_2$CR$^{4a}$HNR$^{4c}$CH$_2$—, or
—CH$_2$CR$^{4a}$HNHCH$_2$—.

In this case, further more preferable $Y^1$, $Y^2$, $Y^3$ and $Y^4$ together form —$CH_2CR^{4a}HOCH_2$—, —$CH_2CR^{4a}HCH_2CH_2$—, —$CH_2CH_2NR^{4c}CH_2$—,
—$CH_2CR^{4a}HNR^{4c}CH_2$—, or —$CH_2CR^{4a}HNHCH_2$—.

$Z^1$ is preferably a single bond, —$CR^{7a}R^{7b}$—, —O—, or —S—, and more preferably a single bond.

Ring A is a 3- to 7-membered monocyclic aromatic ring, or 8- to 12-membered bicyclic aromatic ring.

In one embodiment of the present invention, preferable ring A is a 3- to 7-membered monocyclic aromatic ring; for example, in this case, ring A is a phenyl, a pyrrolyl, a furyl, a thienyl, an imidazolyl, a pyrazolyl, an oxazolyl, a thiazolyl, a triazolyl, a pyridyl, a pyrazinyl, a pyridazinyl, a pyrimidinyl, a tetrazolyl, an isothiazolyl, an oxadiazolyl, an isoxazolyl, or a thiadiazolyl.

In this case, preferably, ring A is a phenyl, a pyrrolyl, a furyl, a thienyl, a imidazolyl, a pyrazolyl, a oxazolyl, a thiazolyl, a triazolyl, a pyridyl, a pyrazinyl, a pyridazinyl, or a pyrimidinyl;

in this case, more preferably, ring A is a phenyl, a pyridyl, a pyrazinyl, a pyridazinyl, or a pyrimidinyl;

in this case, further more preferably, ring A is a phenyl.

In one embodiment of the present invention, preferable ring A is a 8- to 12-membered bicyclic aromatic ring;

for example, in this case, ring A is a quinolinyl, an isoquinolylphthaladinyl, a naphthyridinyl, a quinoxalinyl, a quinazolinyl, a cinnolinyl, a benzoimidazolyl, an indolyl, an isoindolyl, a benzooxazolinyl, a benzofuranyl, an isobenzofuranyl, or an indazolyl.

In this case, preferably, ring A is a quinolyl, a benzoimidazolyl, an indolyl, or a benzooxazolinyl, In this case, more preferably, ring A is an 8-quinolyl, a 1-benzoimidazolyl, a 3-indolyl, or a 2-benzooxazolinyl.

$R^{1a}$ and $R^{1b}$ are, independently each other, a hydrogen atom, a halogen atom, a hydroxy group, a cyano group, a $C_1$-$C_4$ alkyl group, a $C_1$-$C_4$ haloalkyl group, a $C_1$-$C_4$ alkoxy group, a $C_1$-$C_4$ haloalkoxy group, a $C_3$-$C_7$ cycloalkyl group, a $C_1$-$C_4$ alkoxy-$C_1$-$C_4$ alkyl group, or a $C_1$-$C_4$ haloalkoxy-$C_1$-$C_4$ alkyl group;

preferably, $R^{1a}$ and $R^{1b}$ are, independently each other, a hydrogen atom, a halogen atom, a $C_1$-$C_4$ alkyl group, or a $C_1$-$C_4$ haloalkyl group, more preferably, $R^{1a}$ and $R^{1b}$ are, independently each other, a hydrogen atom or a halogen atom.

$R^2$ is a hydrogen atom, a halogen atom, a hydroxy group, a cyano group, an optionally substituted $C_1$-$C_6$ alkyl group, an optionally substituted $C_1$-$C_6$ haloalkyl group, an optionally substituted $C_2$-$C_6$ alkenyl group, an optionally substituted $C_2$-$C_6$ alkynyl group, or an optionally substituted saturated, partially saturated or unsaturated 3- to 7-membered monocyclic ring.

Preferably, $R^2$ is a hydrogen atom, a halogen atom, a hydroxy group, a cyano group, or an optionally substituted saturated, partially saturated or unsaturated 3- to 7-membered monocyclic ring;

more preferably, $R^2$ is a hydrogen atom or an optionally substituted saturated, partially saturated or unsaturated 3- to 7-membered monocyclic ring.

In one embodiment of the present invention, preferable $R^2$ is a hydrogen atom, a halogen atom, a hydroxy group, or a cyano group; in this case, more preferably, $R^2$ is a hydrogen atom.

Further, in another aspect of the present invention, when $R^2$ is an optionally substituted saturated, partially saturated or unsaturated 3- to 7-membered monocyclic ring, $R^2$ is preferably an optionally substituted 3- to 7-membered monocyclic aromatic ring.

Still further, in another aspect of the present invention, when $R^2$ is an optionally substituted saturated, partially saturated or unsaturated 3- to 7-membered monocyclic ring, $R^2$ is preferably a saturated, partially saturated or unsaturated 3- to 7-membered monocyclic ring optionally substituted by a halogen atom, a cyano group, a carboxyl group, carboxamide group, a hydroxy group, a $C_1$-$C_4$ alkyl group, a $C_1$-$C_4$ haloalkyl group, a $C_1$-$C_4$ alkoxy group, a $C_1$-$C_4$ haloalkoxy group, a $C_3$-$C_7$ cycloalkyl group, a heterocycloalkyl group, a $C_3$-$C_7$ cycloalkyloxy group, a heterocycloalkyloxy group, a $C_1$-$C_4$ alkylthio group, a $C_1$-$C_4$ haloalkylthio group, or —$NR^{d1}R^{d2}$ ($R^{d1}$ and $R^{d2}$ are, independently each other, a hydrogen atom, a $C_1$-$C_4$ alkyl group, or a $C_1$-$C_4$ haloalkyl group.).

In this case, more preferably, $R^2$ is an unsaturated 3- to 7-membered monocyclic ring optionally substituted by a halogen atom, a cyano group, a $C_1$-$C_4$ alkyl group, a $C_1$-$C_4$ haloalkyl group, a $C_1$-$C_4$ alkoxy group, a $C_1$-$C_4$ haloalkoxy group, or —$NR^{d1}R^{d2}$ ($R^{d1}$ and $R^{d2}$ are, independently each other, a hydrogen atom, a $C_1$-$C_4$ alkyl group, or a $C_1$-$C_4$ haloalkyl group.).

$R^{3a}$, $R^{3b}$ and $R^{3c}$ are, preferably, independently each other, a hydrogen atom, a halogen atom, a cyano group, a cyanomethyl group, a formyl group, a nitro group, a carboxamide group, a hydroxy group, a $C_1$-$C_6$ alkyl group, a $C_1$-$C_6$ alkyl group substituted by a heterocyclooxy group, a $C_1$-$C_6$ alkyl group substituted by a cyano group, a $C_1$-$C_6$ alkyl group substituted by a morpholino group, a $C_1$-$C_6$ haloalkyl group, a $C_1$-$C_6$ alkoxy group, a $C_1$-$C_6$ haloalkoxy group, a $C_1$-$C_4$ alkoxy-$C_1$-$C_4$ alkyl group, a $C_1$-$C_4$ alkoxy-$C_1$-$C_4$ alkyl group substituted by a dimethylamino group, a $C_1$-$C_4$ alkoxy-$C_1$-$C_4$ alkyl group substituted by a dimethylaminocarbonyl group, a $C_1$-$C_4$ haloalkoxy-$C_1$-$C_4$ alkyl group, a $C_1$-$C_4$ alkoxy-$C_1$-$C_4$ haloalkyl group, a $C_1$-$C_4$ haloalkoxy-$C_1$-$C_4$ haloalkyl group, a $C_1$-$C_6$ alkylcarbonyl group, a $C_1$-$C_6$ alkoxycarbonyl group, a $C_1$-$C_6$ alkylcarbonyloxy group, a $C_1$-$C_6$ haloalkylcarbonyl group, a $C_1$-$C_6$ haloalkoxycarbonyl group, a $C_1$-$C_6$ haloalkylcarbonyloxy group, a $C_3$-$C_7$ cycloalkyl group, a heterocycloalkyl group, a $C_3$-$C_7$ cycloalkyloxy group, a heterocycloalkyloxy group, a $C_2$-$C_6$ alkenyl group, a $C_2$-$C_6$ alkenyloxy group, a $C_2$-$C_6$ alkenyloxy-$C_1$-$C_4$ alkyl group, a $C_2$-$C_6$ alkenyloxy-$C_1$-$C_4$ haloalkyl group, a $C_2$-$C_6$ alkynyl group, a $C_2$-$C_6$ alkynyl group optionally substituted by a halogen atom, a $C_2$-$C_6$ alkynyloxy group, a $C_2$-$C_6$ alkynyloxy-$C_1$-$C_4$ alkyl group, a $C_2$-$C_6$ alkynyloxy-$C_1$-$C_4$ haloalkyl group, a $C_1$-$C_4$ alkoxy-$C_1$-$C_4$ alkoxy group, a $C_1$-$C_4$ haloalkoxy-$C_1$-$C_4$ alkoxy group, a $C_2$-$C_6$ alkenyloxy-$C_1$-$C_4$ alkoxy group, a $C_2$-$C_6$ alkynyloxy-$C_1$-$C_4$ alkoxy group, a $C_2$-$C_6$ alkenyloxy-$C_1$-$C_4$ haloalkoxy group, a $C_2$-$C_6$ alkynyloxy-$C_1$-$C_4$ haloalkoxy group, a $C_1$-$C_6$ alkylthio group, a $C_1$-$C_6$ haloalkylthio group, a $C_1$-$C_4$ alkylthio-$C_1$-$C_4$ alkyl group, a $C_1$-$C_4$ haloalkylthio-$C_1$-$C_4$ alkyl group, a $C_1$-$C_4$ alkylthio-$C_1$-$C_4$ haloalkyl group, a $C_1$-$C_4$ haloalkylthio-$C_1$-$C_4$ haloalkyl group, a $C_1$-$C_6$ alkylsulfonyl group, —$(CH_2)_pNR^{a1}R^{a2}$ ($R^{a1}$ and $R^{a2}$ are, independently each other, a hydrogen atom, a $C_1$-$C_4$ alkyl group, or a $C_1$-$C_4$ haloalkyl group, and p is 0, 1, or 2.), or a group represented by the general formula (I-A)

[Chem 26]

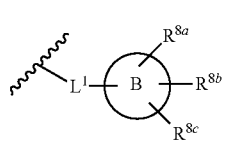

(I-A)

{wherein,
ring B, $L^1$, $R^{8a}$, $R^{8b}$, and $R^{8c}$ have the same definition as the (0).}.

$R^{3a}$, $R^{3b}$ and $R^{3c}$ are, more preferably, independently each other, a hydrogen atom, a halogen atom, a cyano group, a cyanomethyl group, a formyl group, a nitro group, a carboxamide group, a hydroxy group, a $C_1$-$C_6$ alkyl group, a $C_1$-$C_6$ haloalkyl group, a $C_1$-$C_6$ alkoxy group, a $C_1$-$C_6$ haloalkoxy group, a $C_1$-$C_4$ alkoxy-$C_1$-$C_4$ alkyl group, a $C_1$-$C_4$ alkoxy-$C_1$-$C_4$ alkyl group optionally substituted by a dimethylaminocarbonyl group or a dimethylamino group, a $C_1$-$C_4$ haloalkoxy-$C_1$-$C_4$ alkyl group, a $C_1$-$C_4$ alkoxy-$C_1$-$C_4$ haloalkyl group, a $C_1$-$C_4$ haloalkoxy-$C_1$-$C_4$ haloalkyl group, a $C_1$-$C_6$ alkylcarbonyl group, a $C_2$-$C_6$ alkenyl group, a $C_2$-$C_6$ alkynyl group, a $C_2$-$C_6$ alkynyl group optionally substituted by a halogen atom, a $C_1$-$C_6$ alkylthio group, a $C_1$-$C_6$ haloalkylthio group, —$(CH_2)_pNR^{a1}R^{a2}$ (p, $R^{a1}$ and $R^{a2}$ have the same definition as given in the (0).), or a group represented by the general formula (I-A)

[Chem 27]

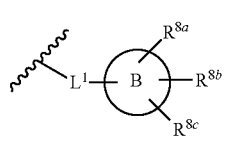

(I-A)

{wherein,
ring B is a $C_3$-$C_7$ cycloalkyl, an azetidinyl, a pyrrolidinyl, a piperidyl, a piperazinyl, a morpholino, a phenyl, a pyrrolyl, a furyl, a thienyl, an imidazolyl, a pyrazolyl, an oxazolyl, a thiazolyl, a triazolyl, a pyridyl, a pyrazinyl, a pyridazinyl, or a pyrimidinyl,
$L^1$ is a single bond, —$CH_2$—, —$CH_2O$—, —$OCH_2$—, —$CH_2CH_2$—, or —$CH_2OCH_2$—,
$R^{8a}$, $R^{8b}$ and $R^{8c}$ are, independently each other, a hydrogen atom, a halogen atom, a cyano group, a $C_1$-$C_6$ alkyl group, a $C_1$-$C_6$ haloalkyl group, a $C_1$-$C_6$ alkoxy group, a $C_1$-$C_6$ haloalkoxy group, a $C_3$-$C_7$ cycloalkyl group, a $C_3$-$C_7$ cycloalkyloxy group, a heterocycloalkyl group, a heterocycloalkyloxy group, a $C_2$-$C_6$ alkenyl group, or a $C_2$-$C_6$ alkynyl group.}.

More preferably, $R^{3a}$, $R^{3b}$ and $R^{3c}$ are, independently each other, a hydrogen atom, a halogen atom, a cyano group, a cyanomethyl group, a $C_1$-$C_6$ alkyl group, a $C_1$-$C_6$ haloalkyl group, a $C_1$-$C_6$ alkoxy group, a $C_1$-$C_6$ haloalkoxy group, a $C_1$-$C_4$ alkoxy-$C_1$-$C_4$ alkyl group, a $C_1$-$C_4$ haloalkoxy-$C_1$-$C_4$ alkyl group, a $C_2$-$C_6$ alkenyl group, a $C_2$-$C_6$ alkynyl group, —$(CH_2)_pNR^{a1}R^{a2}$ (p is 1, and $R^{a1}$ and $R^{a2}$ are, independently each other, a hydrogen atom, a methyl group, an ethyl group, or a 2,2,2-trifluoroethyl group.), or a group represented by the general formula (I-A)

[Chem 28]

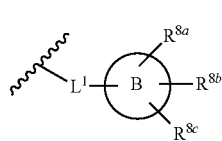

(I-A)

{wherein,
ring B is a $C_3$-$C_7$ cycloalkyl, a morpholino, a phenyl, a pyrazolyl, a pyridyl, a pyrazinyl, a pyridazinyl, or a pyrimidinyl,
$L^1$ is a single bond,
$R^{8a}$, $R^{8b}$ and $R^{8c}$ are, independently each other, a hydrogen atom, a halogen atom, a cyano group, a $C_1$-$C_6$ alkyl group, a $C_1$-$C_6$ haloalkyl group, a $C_1$-$C_6$ alkoxy group, or a $C_1$-$C_6$ haloalkoxy group.}.

Further more preferably, $R^{3a}$, $R^{3b}$ and $R^{3c}$ are, independently each other, a hydrogen atom, a halogen atom, a cyano group, a $C_1$-$C_6$ alkyl group, a $C_1$-$C_6$ haloalkyl group, a $C_1$-$C_6$ alkoxy group, or a $C_1$-$C_6$ haloalkoxy group.

$R^{4a}$, $R^{4b}$ and $R^{4c}$ are, preferably, independently each other, a halogen atom, a cyano group, a cyanomethyl group, a formyl group, a nitro group, a carboxamide group, a hydroxy group, a $C_1$-$C_6$ alkyl group, a $C_1$-$C_6$ alkyl group optionally substituted by a hydroxy group, a $C_1$-$C_6$ haloalkyl group, a $C_1$-$C_6$ haloalkyl group optionally substituted by a hydroxy group, a $C_1$-$C_6$ alkoxy group, a $C_1$-$C_6$ haloalkoxy group, a $C_1$-$C_4$ alkoxy-$C_1$-$C_4$ alkyl group optionally substituted by a $C_1$-$C_4$ haloalkoxy group, a $C_1$-$C_4$ haloalkoxy-$C_1$-$C_4$ alkyl group, a $C_1$-$C_4$ alkoxy-$C_1$-$C_4$ haloalkyl group, a $C_1$-$C_4$ haloalkoxy-$C_1$-$C_4$ haloalkyl group, a $C_1$-$C_6$ alkylcarbonyl group, a $C_1$-$C_6$ alkoxycarbonyl group, a $C_1$-$C_6$ alkylcarbonyloxy group, a $C_1$-$C_6$ haloalkylcarbonyl group, a $C_1$-$C_6$ haloalkoxycarbonyl group, a $C_1$-$C_6$ haloalkylcarbonyloxy group, a $C_3$-$C_7$ cycloalkyl group, a $C_3$-$C_7$ cycloalkyl group optionally substituted by a halogen atom, a heterocycloalkyl group, a $C_3$-$C_7$ cycloalkyloxy group, a heterocycloalkyloxy group, a $C_2$-$C_6$ alkenyl group, a $C_2$-$C_6$ alkenyloxy group, a $C_2$-$C_6$ alkenyloxy-$C_1$-$C_4$ alkyl group, a $C_2$-$C_6$ alkenyloxy-$C_1$-$C_4$ alkyl group optionally substituted by a halogen atom, a $C_2$-$C_6$ alkenyloxy-$C_1$-$C_4$ haloalkyl group, a $C_2$-$C_6$ alkynyl group, a $C_2$-$C_6$ alkynyl group optionally substituted by a halogen atom or a methoxy group, a $C_2$-$C_6$ alkynyloxy group, a $C_2$-$C_6$ alkynyloxy-$C_1$-$C_4$ alkyl group, a $C_2$-$C_6$ alkynyloxy-$C_1$-$C_4$ haloalkyl group, a $C_1$-$C_4$ alkoxy-$C_1$-$C_4$ alkoxy group, a $C_1$-$C_4$ haloalkoxy-$C_1$-$C_4$ alkoxy group, a $C_2$-$C_6$ alkenyloxy-$C_1$-$C_4$ alkoxy group, a $C_2$-$C_6$ alkynyloxy-$C_1$-$C_4$ alkoxy group, a $C_2$-$C_6$ alkenyloxy-$C_1$-$C_4$ haloalkoxy group, a $C_2$-$C_6$ alkynyloxy-$C_1$-$C_4$ haloalkoxy group, a $C_1$-$C_6$ alkylthio group, a $C_1$-$C_6$ haloalkylthio group, a $C_1$-$C_4$ alkylthio-$C_1$-$C_4$ alkyl group, a $C_1$-$C_4$ haloalkylthio-$C_1$-$C_4$ alkyl group, a $C_1$-$C_4$ alkylthio-$C_1$-$C_4$ haloalkyl group, a $C_1$-$C_4$ haloalkylthio-$C_1$-$C_4$ haloalkyl group, a pentafluorosulfanyl group, —$(CH_2)_qNR^{b1}R^{b2}$ ($R^{b1}$ and $R^{b2}$ are, independently each other, a hydrogen atom, a $C_1$-$C_4$ alkyl group, or a $C_1$-$C_4$ haloalkyl group, and q is, 0, 1, 2, or 3.), or a group represented by the general formula (I-B)

[Chem 29]

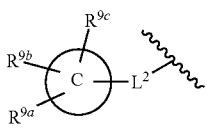

(I-B)

{wherein,
ring C, $L^2$, $R^{9a}$, $R^{9b}$, $R^{9c}$ have the same definition as the (0).}.

$R^{4a}$, $R^{4b}$ and $R^{4c}$ are, more preferably, independently each other, a halogen atom, a hydroxy group, a cyano group, a $C_1$-$C_6$ alkyl group, a $C_1$-$C_6$ alkyl group optionally substituted by a hydroxy group, $C_1$-$C_6$ haloalkyl group, a $C_1$-$C_6$ haloalkyl group optionally substituted by a hydroxy group, a $C_1$-$C_6$ alkoxy group, a $C_1$-$C_6$ haloalkoxy group, a $C_1$-$C_4$ alkoxy-$C_1$-$C_4$ alkyl group optionally substituted by a $C_1$-$C_4$ haloalkoxy group, a $C_1$-$C_4$ haloalkoxy-$C_1$-$C_4$ alkyl group, a $C_1$-$C_4$ alkoxy-$C_1$-$C_4$ haloalkyl group, a $C_1$-$C_4$ haloalkoxy-$C_1$-$C_4$ haloalkyl group, a $C_1$-$C_6$ alkylcarbonyl group, a $C_1$-$C_6$ alkoxycarbonyl group, a $C_1$-$C_6$ haloalkylcarbonyl group, a $C_3$-$C_7$ cycloalkyl group, a $C_3$-$C_7$ cycloalkyl group optionally substituted by a halogen atom or a $C_1$-$C_4$ haloalkyl group, a heterocycloalkyl group, a $C_2$-$C_6$ alkenyl group, a $C_2$-$C_6$ alkenyloxy group, a $C_2$-$C_6$ alkenyloxy-$C_1$-$C_4$ alkyl group, a $C_2$-$C_6$ alkenyloxy-$C_1$-$C_4$ alkyl group optionally substituted by a halogen atom, a $C_2$-$C_6$ alkynyl group, a $C_2$-$C_6$ alkynyl group optionally substituted by a halogen atom or a methoxy group, a $C_2$-$C_6$ alkynyloxy-$C_1$-$C_4$ alkyl group, a $C_1$-$C_4$ haloalkoxy-$C_1$-$C_4$ alkoxy group, a $C_1$-$C_6$ alkylthio group, a $C_1$-$C_6$ haloalkylthio group, a $C_1$-$C_4$ alkylthio-$C_1$-$C_4$ alkyl group, a $C_1$-$C_4$ haloalkylthio-$C_1$-$C_4$ alkyl group, —$(CH_2)_qNR^{b1}R^{b2}$ (q, $R^{b1}$ and $R^{b2}$ have the same definition as given in the (0).), or the general formula (I-B)

[Chem 30]

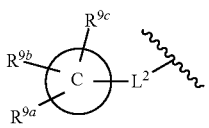

(I-B)

{wherein,
ring C is a $C_3$-$C_7$ cycloalkyl, an azetidinyl, a pyrrolidinyl, a piperidyl, a piperazinyl, a morpholino, a phenyl, a pyrrolyl, a furyl, a thienyl, an imidazolyl, a pyrazolyl, an oxazolyl, a thiazolyl, a triazolyl, a pyridyl, a pyrazinyl, a pyridazinyl, or a pyrimidinyl,
$L^2$ is a single bond, —CH=CH—, —C≡C—,
—$(CR^{10a}R^{10b})_{r1}(CR^{10c}R^{10d})_{r2}(CR^{10e}R^{10f})_{r3}(CR^{10g}R^{10h})_{r4}$—,
—$(CR^{10a}R^{10b})_{r1}(CR^{10c}R^{10d})_{r2}O(CR^{10e}R^{10f})_{r3}(CR^{10g}R^{10h})_{r4}$—,
—$(CR^{10a}R^{10b})_{r1}(CR^{10c}R^{10d})_{r2}NR^c(CR^{10e}R^{10f})_{r3}(CR^{10g}R^{10h})_{r4}$—,
—$(CR^{10a}R^{10b})_{r1}(CR^{10c}R^{10d})_{r2}CO(CR^{10e}R^{10f})_{r3}(CR^{10g}R^{10h})_{r4}$—,
—$(CR^{10a}R^{10b})_{r1}(CR^{10c}R^{10d})_{r2}S(CR^{10e}R^{10f})_{r3}(CR^{10g}R^{10h})_{r4}$—, or
—$(CR^{10a}R^{10b})_{r1}(CR^{10c}R^{10d})_{r2}SO(CR^{10e}R^{10f})_{r3}(CR^{10g}R^{10h})_{r4}$—($R^{10a}$, $R^{10b}$, $R^{10c}$, $R^{10d}$, $R^e$, $R^{10f}$, $R^{10g}$, $R^{10h}$, r1, r2, r3, r4 and $R^c$ have the same definition as given in the (0).), $R^{9a}$, $R^{9b}$ and $R^{9c}$ are, independently each other, a hydrogen atom, a halogen atom, a hydroxy group, a cyano group, a $C_1$-$C_6$ alkyl group, a $C_1$-$C_6$ haloalkyl group, a $C_1$-$C_6$ alkoxy group, a $C_1$-$C_6$ haloalkoxy group, a $C_1$-$C_6$ alkoxycarbonyl group, a heterocycloalkyloxy group, or —$(CH_2)_sNR^{d1}R^{d2}$ (s, $R^{d1}$ and $R^{d2}$ have the same definition as given in the (0).).}.

In one embodiment of the present invention, preferable $R^{4a}$, $R^{4b}$ and $R^{4c}$ are, independently each other, a halogen atom, a hydroxy group, a cyano group, a $C_1$-$C_6$ alkyl group, a $C_1$-$C_6$ haloalkyl group, a $C_1$-$C_6$ alkoxy group, a $C_1$-$C_6$ haloalkoxy group, a $C_1$-$C_4$ alkoxy-$C_1$-$C_4$ alkyl group optionally substituted by a $C_1$-$C_4$ haloalkoxy group, a $C_1$-$C_4$ haloalkoxy-$C_1$-$C_4$ alkyl group, a $C_1$-$C_4$ haloalkoxy-$C_1$-$C_4$ alkoxy group, a $C_1$-$C_4$ alkylthio-$C_1$-$C_4$ alkyl group, a $C_1$-$C_4$ haloalkylthio-$C_1$-$C_4$ alkyl group, or —$(CH_2)_qNR^{b1}R^{b2}$ (q, $R^{b1}$ and $R^{b2}$ have the same definition as given in the (0).), more preferably, a halogen atom, a cyano group, a $C_1$-$C_6$ alkyl group, a $C_1$-$C_6$ haloalkyl group, a $C_1$-$C_4$ alkoxy-$C_1$-$C_4$ alkyl group optionally substituted by a $C_1$-$C_4$ haloalkoxy group, or a $C_1$-$C_4$ haloalkoxy-$C_1$-$C_4$ alkyl group, or a $C_1$-$C_4$ haloalkoxy-$C_1$-$C_4$ alkoxy group.

In addition, in another aspect of the present invention, when $R^{4a}$, $R^{4b}$ and $R^{4c}$ are groups represented by the general formula (I-B), $R^{4a}$, $R^{4b}$ and $R^{4c}$ are more preferably a substituent selected from the group consisting of the following formulae:

[Chem 31]

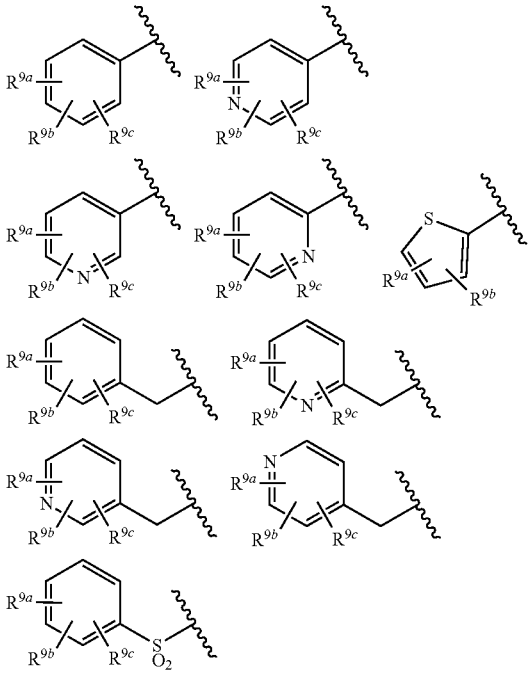

[Chem 32]

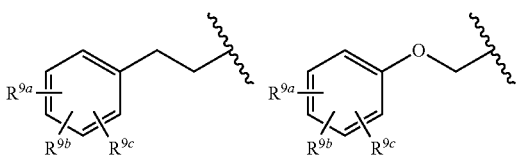

[Chem 33]
[Chem 34]
[Chem 35]
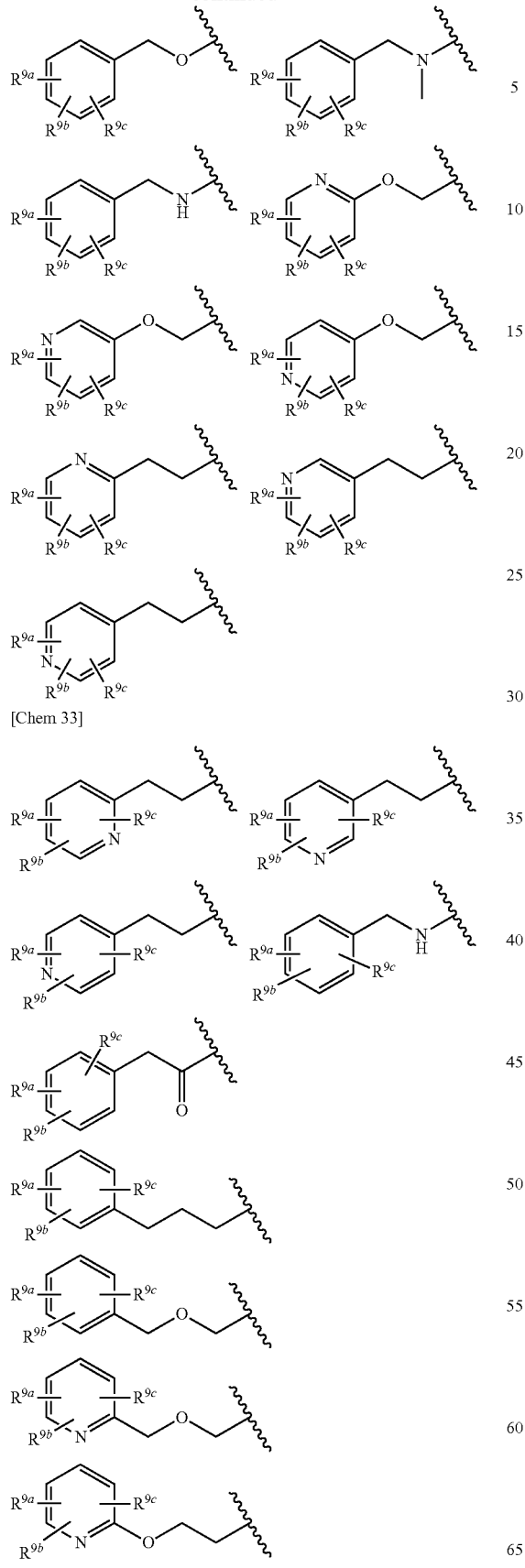
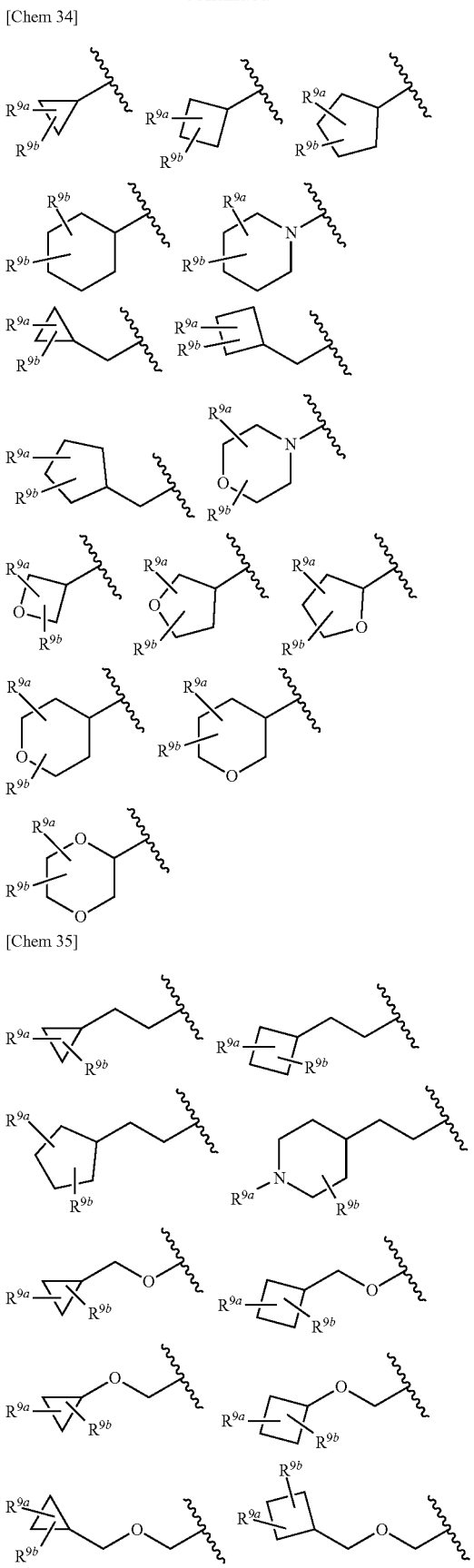

-continued
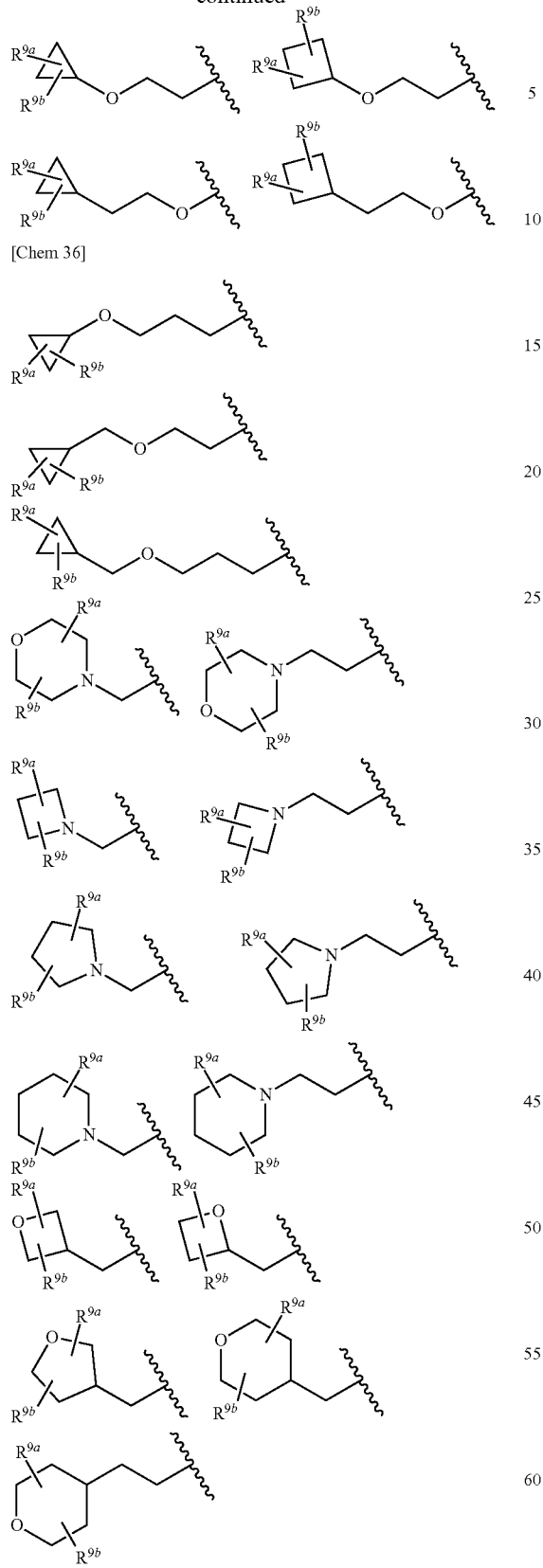
[Chem 36]
(wherein $R^{9a}$, $R^{9b}$ and $R^{9c}$ have the same definition as given in the (0).),
in this case, $R^{4a}$, $R^{4b}$ and $R^{4c}$ are more preferably a substituent selected from the group consisting of the following formulae:
[Chem 37]
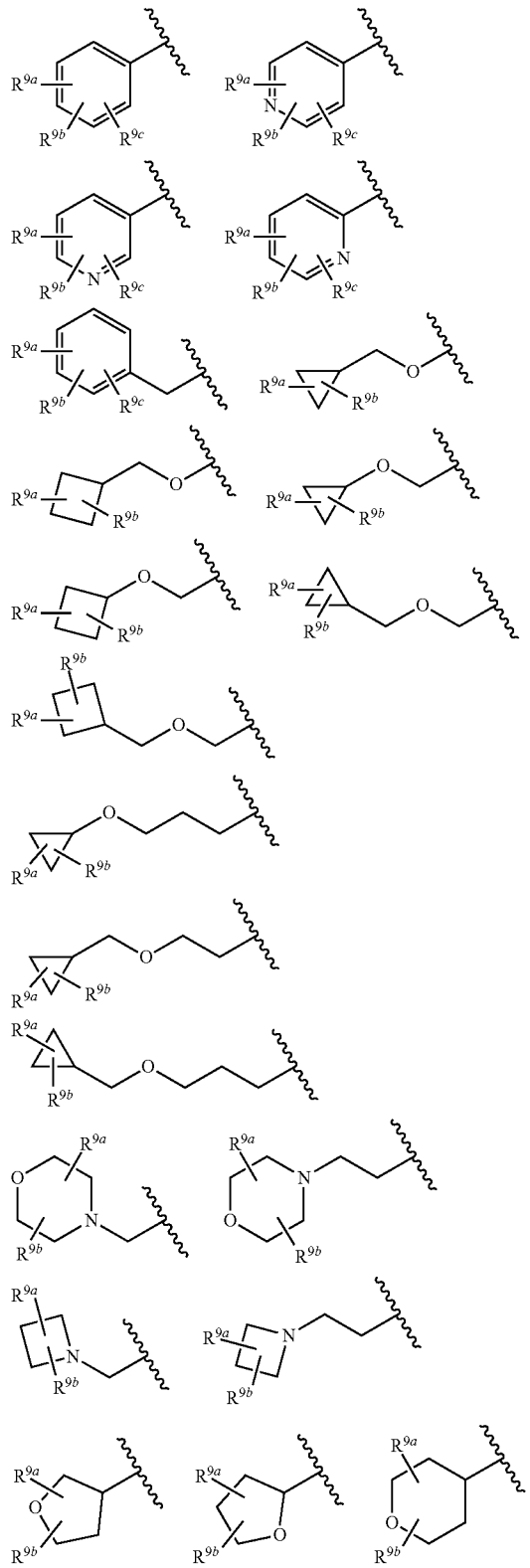

-continued

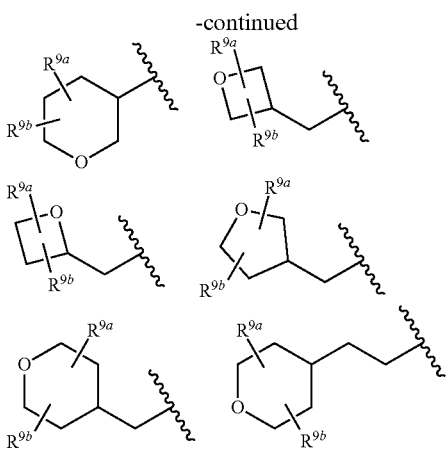

(wherein $R^{9a}$, $R^{9b}$ and $R^{9c}$ have the same definition as given in the (0).), in this case, $R^{4a}$, $R^{4b}$ and $R^{4c}$ are further more preferably a substituent selected from the group consisting of the following:

[Chem 38]

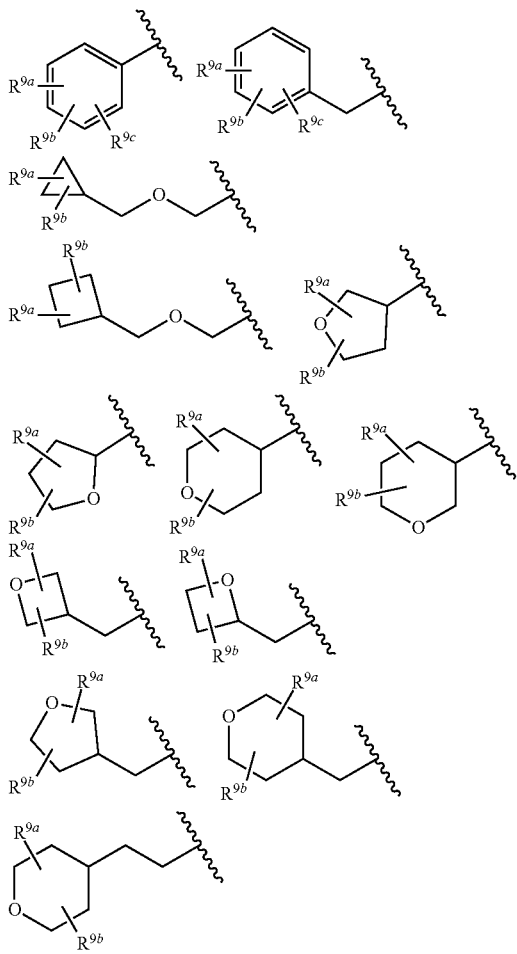

(wherein $R^{9a}$, $R^{9b}$ and $R^{9c}$ are, independently each other, a hydrogen atom, a halogen atom, a hydroxy group, a cyano group, a $C_1$-$C_6$ alkyl group, a $C_1$-$C_6$ haloalkyl group, a $C_1$-$C_6$ alkoxy group, or a $C_1$-$C_6$ haloalkoxy group.).

In addition, in another aspect of the present invention, preferable $R^{4a}$, $R^{4b}$ and $R^{4c}$ are, independently each other, a halogen atom, a hydroxy group, a cyano group, a $C_1$-$C_6$ alkyl group, a $C_1$-$C_6$ haloalkyl group, a $C_1$-$C_6$ alkoxy group, a $C_1$-$C_6$ haloalkoxy group, a $C_1$-$C_4$ alkoxy-$C_1$-$C_4$ alkyl group optionally substituted by a $C_1$-$C_4$ haloalkoxy group, a $C_1$-$C_4$ haloalkoxy-$C_1$-$C_4$ alkyl group, a $C_1$-$C_4$ haloalkoxy-$C_1$-$C_4$ alkoxy group, a $C_1$-$C_4$ alkylthio-$C_1$-$C_4$ alkyl group, a $C_1$-$C_4$ haloalkylthio-$C_1$-$C_4$ alkyl group, —$(CH_2)_q NR^{b1}R^{b2}$ (q, $R^{b1}$ and $R^{b2}$ have the same definition as given in the (0).), or a substituent selected from the group consisting of the following formulae:

[Chem 39]

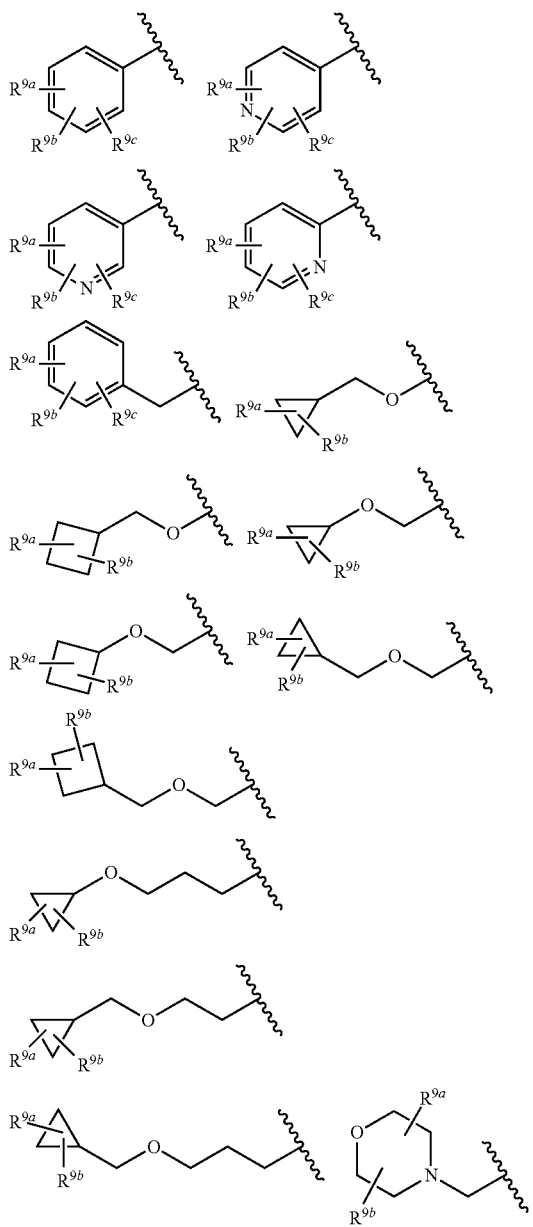

-continued

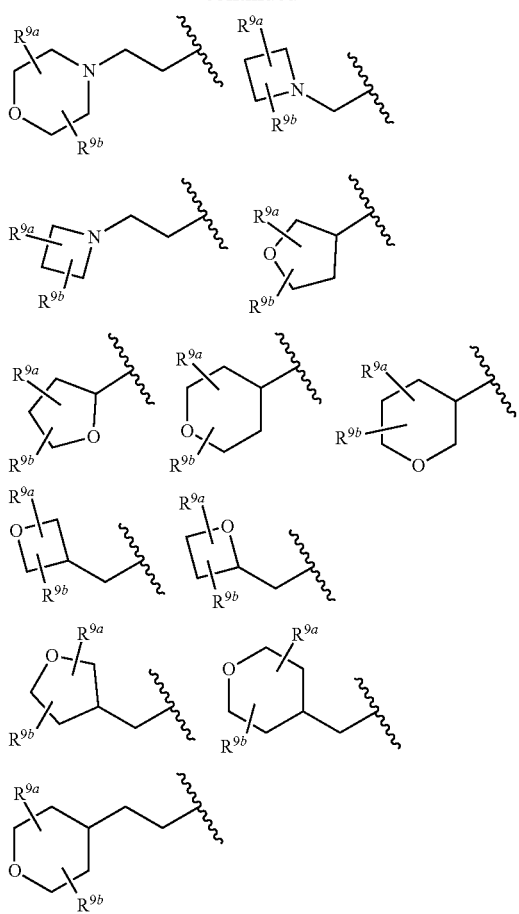

(wherein $R^{9a}$, $R^{9b}$ and $R^{9c}$ have the same definition as given in the (0).), more preferable $R^{4a}$, $R^{4b}$ and $R^{4c}$ are, independently each other, a halogen atom, a cyano group, a $C_1$-$C_6$ alkyl group, a $C_1$-$C_6$ haloalkyl group, a $C_1$-$C_4$ alkoxy-$C_1$-$C_4$ alkyl group optionally substituted by a $C_1$-$C_4$ haloalkoxy group, a $C_1$-$C_4$ haloalkoxy-$C_1$-$C_4$ alkyl group, a $C_1$-$C_4$ haloalkoxy-$C_1$-$C_4$ alkoxy group, or a substituent selected from the group consisting of the following formulae:

[Chem 40]

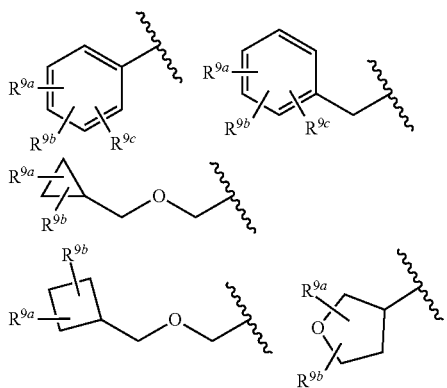

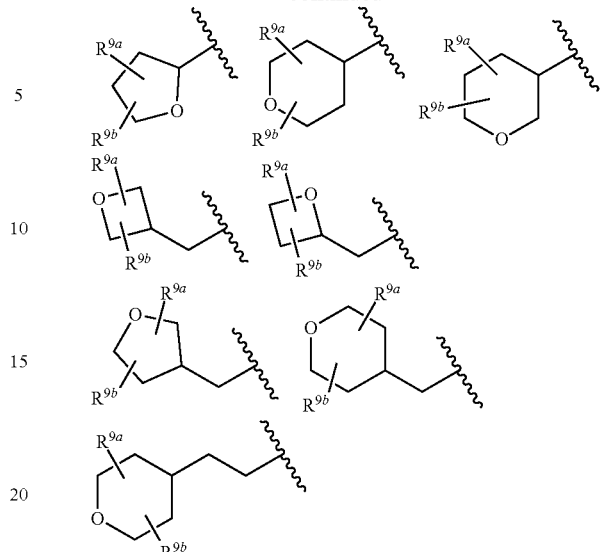

(wherein $R^{9a}$, $R^{9b}$ and $R^{9c}$ are, independently each other, a hydrogen atom, a halogen atom, a hydroxy group, a cyano group, a $C_1$-$C_6$ alkyl group, a $C_1$-$C_6$ haloalkyl group, a $C_1$-$C_6$ alkoxy group, or a $C_1$-$C_6$ haloalkoxy group.).

When $R^{5a}$, $R^{5b}$, $R^{5c}$, $R^{6a}$, $R^{6b}$ and n fulfill the constitution (i) in the (0), the present inventive compounds are preferable, wherein $R^{5b}$ and $R^{5c}$ together form a single bond, —$CH_2O$—, —$CH_2S$—, —$CH_2NR^{e1}$—, —$CH_2CH_2$—, or —$CONR^{e1}$— ($R^{e1}$ and $R^{e2}$ have the same definition as given in the (0).), $R^{5a}$ is a hydrogen atom or a $C_1$-$C_6$ alkyl group, $R^{6a}$ and $R^{6b}$ are, independently each other, a hydrogen atom, a fluorine atom, a hydroxy group, or a methoxy group, and n is 1 or 2.

More preferably, the present inventive compounds are preferable, wherein, among $R^{5a}$, $R^{5b}$, $R^{5c}$, $R^{6a}$ and $R^{6b}$, $R^{5b}$ and $R^{5c}$ together form —$CH_2O$—, $R^{5a}$, $R^{6a}$ and $R^{6b}$ are hydrogen atoms, and n is 1.

In the general formula (I-E2), $Z^2$-$Z^3$ is preferably —$CH_2O$—, —$CH_2S$—, —$CH_2NR^{f1}$—, —$CH_2CH_2$—, or —$CONR^{f1}$— ($R^{f1}$ and $R^{f2}$ is a hydrogen atom or a $C_1$-$C_4$ alkyl group.), more preferably, $Z^2$-$Z^3$ forms —$CH_2O$—.

In the general formula (I) or the general formula (I-E2), $R^{5a}$ is more preferably a hydrogen atom, a $C_1$-$C_6$ alkyl group, a $C_1$-$C_6$ haloalkyl group, a $C_3$-$C_7$ cycloalkyl group, or a heterocycloalkyl group, more preferably, $R^{5a}$ is a hydrogen atom.

In the general formula (I-E2), when $Z^4$ is C—$R^{11a}$, $R^{11a}$ is preferably a hydrogen atom, a halogen atom, a cyano group, a cyanomethyl group, a $C_1$-$C_6$ alkyl group, a $C_1$-$C_6$ haloalkyl group, a $C_1$-$C_6$ alkoxy group, or a $C_1$-$C_6$ haloalkoxy group, more preferably, $R^{11a}$ is a hydrogen atom, a halogen atom, a cyano group, a $C_1$-$C_6$ alkyl group, or a $C_1$-$C_6$ haloalkyl group, further preferably, $R^{11a}$ is a hydrogen atom.

In the general formula (I-E2), $R^{11b}$ is $R^{3b}$ in the (0); preferable substituent thereof is the above mentioned preferable $R^{3b}$.

In the general formula (I-E2), $R^{11c}$ is $R^{3c}$ in the (0); preferable substituent thereof is the above mentioned preferable $R^{3c}$.

As regards the present inventive heteroaromatic amide derivative or salt thereof of the general formula (I-E2), preferable combinations of atoms, substituent groups, or rings are then hereinbelow explained.

In one embodiment of the present invention, in a compound represented by the general formula (I-E2) having $R^{11a}$, $R^{11b}$, $R^{11c}$ and at least one of $R^{4a}$, $R^{4b}$ and $R^{4c}$, preferable combinations of these substituents are selected from the group consisting of the following:

$R^{11a}$ is a hydrogen atom, a halogen atom, a cyano group, a cyanomethyl group, a $C_1$-$C_6$ alkyl group, a $C_1$-$C_6$ haloalkyl group, a $C_1$-$C_6$ alkoxy group, or a $C_1$-$C_6$ haloalkoxy group, $R^{11b}$ and $R^{11c}$ are, independently each other, a hydrogen atom, a halogen atom, a cyano group, a cyanomethyl group, a formyl group, a nitro group, a carboxamide group, a hydroxy group, a $C_1$-$C_6$ alkyl group, a $C_1$-$C_6$ haloalkyl group, a $C_1$-$C_6$ alkoxy group, a $C_1$-$C_6$ haloalkoxy group, a $C_1$-$C_4$ alkoxy-$C_1$-$C_4$ alkyl group, a $C_1$-$C_4$ alkoxy-$C_1$-$C_4$ alkyl group optionally substituted by a dimethylaminocarbonyl group or a dimethylamino group, a $C_1$-$C_4$ haloalkoxy-$C_1$-$C_4$ alkyl group, a $C_1$-$C_4$ alkoxy-$C_1$-$C_4$ haloalkyl group, a $C_1$-$C_4$ haloalkoxy-$C_1$-$C_4$ haloalkyl group, a $C_1$-$C_6$ alkylcarbonyl group, a $C_2$-$C_6$ alkenyl group, a $C_2$-$C_6$ alkynyl group, a $C_2$-$C_6$ alkynyl group optionally substituted by a halogen atom, a $C_1$-$C_6$ alkylthio group, a $C_1$-$C_6$ haloalkylthio group, —$(CH_2)_pNR^{a1}R^{a2}$ (p, $R^{a1}$ and $R^{a2}$ have the same definition as given in the (0).), or a group represented by the general formula (I-A)

[Chem 41]

(I-A)

{wherein,
ring B is a $C_3$-$C_7$ cycloalkyl, an azetidinyl, a pyrrolidinyl, a piperidyl, a piperazinyl, a morpholino, a phenyl, a pyrrolyl, a furyl, a thienyl, an imidazolyl, a pyrazolyl, an oxazolyl, a thiazolyl, a triazolyl, a pyridyl, a pyrazinyl, a pyridazinyl, or a pyrimidinyl, $L^1$ is a single bond, —$CH_2$—, —$CH_2O$—, —$OCH_2$—, —$CH_2CH_2$—, or —$CH_2OCH_2$—, $R^{8a}$, $R^{8b}$ and $R^{8c}$ are, independently each other, a hydrogen atom, a halogen atom, a cyano group, a $C_1$-$C_6$ alkyl group, a $C_1$-$C_6$ haloalkyl group, a $C_1$-$C_6$ alkoxy group, a $C_1$-$C_6$ haloalkoxy group, a $C_3$-$C_7$ cycloalkyl group, a $C_3$-$C_7$ cycloalkyloxy group, a heterocycloalkyl group, a heterocycloalkyloxy group, a $C_2$-$C_6$ alkenyl group, or a $C_2$-$C_6$ alkynyl group.}, $R^{4a}$, $R^{4b}$ and $R^{4c}$ are, independently each other, a halogen atom, a hydroxy group, a cyano group, a $C_1$-$C_6$ alkyl group, a $C_1$-$C_6$ haloalkyl group, a $C_1$-$C_6$ alkoxy group, a $C_1$-$C_6$ haloalkoxy group, a $C_1$-$C_4$ alkoxy-$C_1$-$C_4$ alkyl group optionally substituted by a $C_1$-$C_4$ haloalkoxy group, a $C_1$-$C_4$ haloalkoxy-$C_1$-$C_4$ alkyl group, a $C_1$-$C_4$ haloalkoxy-$C_1$-$C_4$ alkoxy group, a $C_1$-$C_4$ alkylthio-$C_1$-$C_4$ alkyl group, a $C_1$-$C_4$ haloalkylthio-$C_1$-$C_4$ alkyl group, —$(CH_2)_qNR^{b1}R^{b2}$ (q, $R^{b1}$ and $R^{b2}$ have the same definition as given in the (0).), or a substituent selected from the group consisting of the following formulae:

[Chem 42]

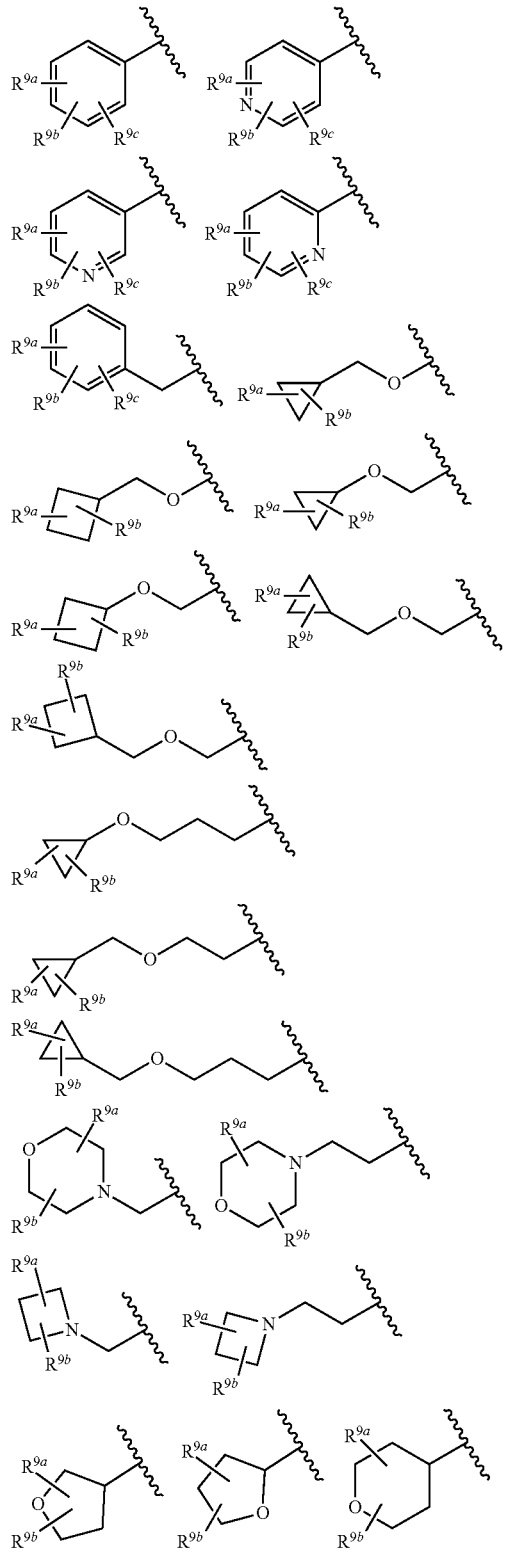

-continued

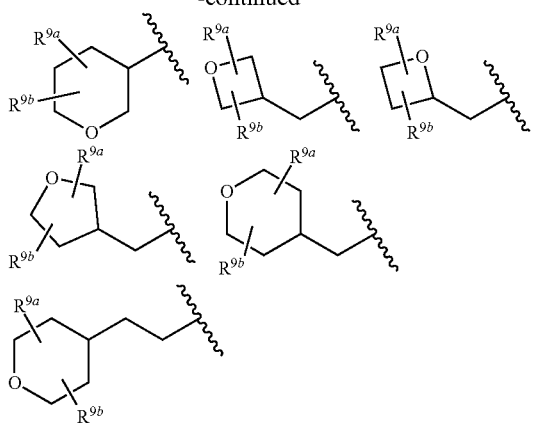

(wherein $R^{9a}$, $R^{9b}$ and $R^{9c}$ have the same definition as given in the (0).).

In one embodiment of the present invention, in a compound represented by the general formula (I) or the general formula (I-E2) having $R^2$ and at least one of $R^{4a}$, $R^{4b}$ and $R^{4c}$, preferable combinations of these substituents are selected from the group consisting of the following:

$R^2$ is a hydrogen atom, a halogen atom, a hydroxy group, or a cyano group, $R^{4a}$, $R^{4b}$ and $R^{4c}$ are, independently each other, a halogen atom, a hydroxy group, a cyano group, a $C_1$-$C_6$ alkyl group, a $C_1$-$C_6$ alkyl group optionally substituted by a hydroxy group, a $C_1$-$C_6$ haloalkyl group, a $C_1$-$C_6$ haloalkyl group optionally substituted by a hydroxy group, a $C_1$-$C_6$ alkoxy group, a $C_1$-$C_6$ haloalkoxy group, a $C_1$-$C_4$ alkoxy-$C_1$-$C_4$ alkyl group optionally substituted by a $C_1$-$C_4$ haloalkoxy group, a $C_1$-$C_4$ haloalkoxy-$C_1$-$C_4$ alkyl group, a $C_1$-$C_4$ alkoxy-$C_1$-$C_4$ haloalkyl group, a $C_1$-$C_4$ haloalkoxy-$C_1$-$C_4$ haloalkyl group, a $C_1$-$C_6$ alkylcarbonyl group, a $C_1$-$C_6$ alkoxycarbonyl group, a $C_1$-$C_6$ haloalkylcarbonyl group, a $C_3$-$C_7$ cycloalkyl group, a $C_3$-$C_7$ cycloalkyl group optionally substituted by a halogen atom or a $C_1$-$C_4$ haloalkyl group, a heterocycloalkyl group, a $C_2$-$C_6$ alkenyl group, a $C_2$-$C_6$ alkenyloxy group, a $C_2$-$C_6$ alkenyloxy-$C_1$-$C_4$ alkyl group, a $C_2$-$C_6$ alkenyloxy-$C_1$-$C_4$ alkyl group optionally substituted by a halogen atom, a $C_2$-$C_6$ alkynyl group, a $C_2$-$C_6$ alkynyl group optionally substituted by a halogen atom or a methoxy group, a $C_2$-$C_6$ alkynyloxy-$C_1$-$C_4$ alkyl group, a $C_1$-$C_4$ haloalkoxy-$C_1$-$C_4$ alkoxy group, a $C_1$-$C_6$ alkylthio group, a $C_1$-$C_6$ haloalkylthio group, a $C_1$-$C_4$ alkylthio-$C_1$-$C_4$ alkyl group, a $C_1$-$C_4$ haloalkylthio-$C_1$-$C_4$ alkyl group, —$(CH_2)_q NR^{b1}R^{b2}$ (q, $R^{b1}$ and $R^{b2}$ have the same definition as given in the (0).), or the general formula (I-B)

[Chem 43]

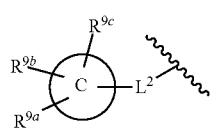

(I-B)

{wherein,
ring C is a $C_3$-$C_7$ cycloalkyl, an azetidinyl, a pyrrolidinyl, a piperidyl, a piperazinyl, a morpholino, a phenyl, a pyrrolyl, a furyl, a thienyl, an imidazolyl, a pyrazolyl, an oxazolyl, a thiazolyl, a triazolyl, a pyridyl, a pyrazinyl, a pyridazinyl, or a pyrimidinyl, $L^2$ is a single bond, —CH=CH—, —C≡C—,
—$(CR^{10a}R^{10b})_{r1}(CR^{10c}R^{10d})_{r2}(CR^{10e}R^{10f})_{r3}(CR^{10g}R^{10h})_{r4}$—,
—$(CR^{10a}R^{10b})_{r1}(CR^{10c}R^{10d})_{r2}NR^c(CR^{10e}R^{10f})_{r3}(CR^{10g}R^{10h})_{r4}$—,
—$(CR^{10a}R^{10b})_{r1}(CR^{10c}R^{10d})_{r2}CO(CR^{10e}R^{10f})_{r3}(CR^{10g}R^{10h})_{r4}$—,
—$(CR^{10a}R^{10b})_{r1}(CR^{10c}R^{10d})_{r2}S(CR^{10e}R^{10f})_{r3}(CR^{10g}R^{10h})_{r4}$—, or
—$(CR^{10a}R^{10b})_{r1}(CR^{10c}R^{10d})_{r2}SO(CR^{10e}R^{10f})_{r3}(CR^{10g}R^{10h})_{r4}$—($R^{10a}$, $R^{10b}$, $R^{10c}$, $R^{10d}$, $R^{10e}$, $R^{10f}$, $R^{10g}$, $R^{10h}$, r1, r2, r3, r4 and $R^c$ have the same definition as given in the (0).), $R^{9a}$, $R^{9b}$ and $R^{9c}$ are, independently each other, a hydrogen atom, a halogen atom, a hydroxy group, a cyano group, a $C_1$-$C_6$ alkyl group, a $C_1$-$C_6$ haloalkyl group, a $C_1$-$C_6$ alkoxy group, a $C_1$-$C_6$ haloalkoxy group, a $C_1$-$C_6$ alkoxycarbonyl group, a heterocycloalkyloxy group, or —$(CH_2)_s NR^{d1}R^{d2}$ (s, $R^{d1}$ and $R^{d2}$ have the same definition as given in the (0).).}.

In one embodiment of the present invention, in a compound represented by the general formula (I-E2) having $Z^2$-$Z^3$, $R^{6a}$, $R^{6b}$, $R^{11a}$, $R^{11b}$ and $R^{11c}$, preferable combinations of these substituents are selected from the group consisting of the following:

$Z^2$-$Z^3$ is —$CH_2O$—, —$CH_2S$—, —$CH_2NR^{f1}$—, —$CH_2CH_2$—, or —$CONR^{f1}$— ($R^{f1}$ and $R^{f2}$ is a hydrogen atom or a $C_1$-$C_4$ alkyl group.), $R^{6a}$ and $R^{6b}$ are, independently each other, a hydrogen atom, a fluorine atom, a hydroxy group, or a methoxy group, $R^{11a}$ is a hydrogen atom, a halogen atom, a cyano group, a cyanomethyl group, a $C_1$-$C_6$ alkyl group, a $C_1$-$C_6$ haloalkyl group, a $C_1$-$C_6$ alkoxy group, or a $C_1$-$C_6$ haloalkoxy group, $R^{11b}$ and $R^{11c}$ are, independently each other, a hydrogen atom, a halogen atom, a cyano group, a cyanomethyl group, a formyl group, a nitro group, a carboxamide group, a hydroxy group, a $C_1$-$C_6$ alkyl group, a $C_1$-$C_6$ haloalkyl group, a $C_1$-$C_6$ alkoxy group, a $C_1$-$C_6$ haloalkoxy group, a $C_1$-$C_4$ alkoxy-$C_1$-$C_4$ alkyl group, a $C_1$-$C_4$ alkoxy-$C_1$-$C_4$ alkyl group optionally substituted by a dimethylaminocarbonyl group or a dimethylamino group, a $C_1$-$C_4$ haloalkoxy-$C_1$-$C_4$ alkyl group, a $C_1$-$C_4$ alkoxy-$C_1$-$C_4$ haloalkyl group, a $C_1$-$C_4$ haloalkoxy-$C_1$-$C_4$ haloalkyl group, a $C_1$-$C_6$ alkylcarbonyl group, a $C_2$-$C_6$ alkenyl group, a $C_2$-$C_6$ alkynyl group, a $C_2$-$C_6$ alkynyl group optionally substituted by a halogen atom, a $C_1$-$C_6$ alkylthio group, a $C_1$-$C_6$ haloalkylthio group, —$(CH_2)_p NR^{a1}R^{a2}$ (p, $R^{a1}$ and $R^{a2}$ have the same definition as given in the (0).), or the general formula (I-A)

[Chem 44]

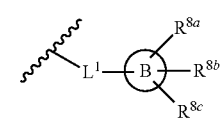

(I-A)

{wherein,
ring B is a $C_3$-$C_7$ cycloalkyl, an azetidinyl, a pyrrolidinyl, a piperidyl, a piperazinyl, a morpholino, a phenyl, a pyrrolyl, a furyl, a thienyl, an imidazolyl, a pyrazolyl, an oxazolyl, a thiazolyl, a triazolyl, a pyridyl, a pyrazinyl, a pyridazinyl, or a pyrimidinyl, $L^1$ is a single bond, —$CH_2$—, —$CH_2O$—, —$OCH_2$—, —$CH_2CH_2$—, or —$CH_2OCH_2$—, $R^{8a}$, $R^{8b}$ and $R^{8c}$ are, independently each other, a hydrogen atom, a halogen atom, a cyano group, a $C_1$-$C_6$ alkyl group, a $C_1$-$C_6$ haloalkyl group, a $C_1$-$C_6$ alkoxy group, a $C_1$-$C_6$ haloalkoxy group, a $C_3$-$C_7$ cycloalkyl group, a $C_3$-$C_7$ cycloalkyloxy group, a heterocycloalkyl group, a heterocycloalkyloxy group, a $C_2$-$C_6$ alkenyl group, or a $C_2$-$C_6$ alkynyl group.}.

Regarding the heteroaromatic amide derivative represented by the general formula (I) or (I-E2) of the present invention, preferable compounds are then explained.

In one embodiment of the present invention, preferable compounds of the heteroaromatic amide derivative represented by the general formula (I-E2) are the heteroaromatic amide derivatives or salt thereof set forth in the above described (4) to (15).

In another embodiment of the present invention, for example, the present inventive compounds belonging to the following "derivative" are preferable in the compounds of the heteroaromatic amide derivative represented by the general formula (I) or the general formula (I-E2). Any "derivative" includes pharmaceutically acceptable salt thereof, and one compound can belong to plural "derivative" groups.

Type (a) Derivative:
A group of compounds wherein, in the general formula (I) or the general formula (I-E2), $X^1$-$X^2$ is C—N, and $Y^1$ is —O—; specifically, a 2,3-dihydropyrazolo[5,1-b]oxazole derivative, a 6,7-dihydro-5H-pyrazolo[5,1-b][1,3]oxazine derivative, a 5,6,7,8-tetrahydropyrazolo[5,1-b][1,3]oxepin derivative and so on.

Type (b) Derivative:
A group of compounds wherein, in the general formula (I) or the general formula (I-E2), $X^1$-$X^2$ is C—N, and $Y^1$ is —$CH_2$—; specifically, a 4,5,6,7-tetrahydropyrazolo[1,5-a]pyrazine derivative, a 4,5,6,7-tetrahydropyrazolo[1,5-a]pyridine derivative, a 6,7-dihydro-4H-pyrazolo[5,1-c][1,4]oxazine derivative and so on.

Type (c) Derivative:
A group of compounds wherein, in the general formula (I) or the general formula (I-E2), $X^1$-$X^2$ is N—C, and $Y^1$ is —$CH_2$—; specifically, a 5,6,7,8-tetrahydroimidazo[1,2-a]pyridine derivative, a 5,6,7,8-tetrahydroimidazo[1,2-a]pyrazine derivative, a 5, 6-dihydro-8H-imidazo[2,1-c][1,4]oxazine derivative and so on.

Type (d) Derivative:
Heteroaromatic amide derivatives of the general formula (I) or the general formula (I-E2), wherein $R^2$ is an optionally substituted saturated, partially saturated or unsaturated 3- to 7-membered monocyclic ring.

Each "derivative" is then explained separately to show compounds in preferable embodiments. Meanwhile, any compound in each "derivative" comprises optically active substances and pharmaceutically acceptable salt thereof.

As type (a) derivatives in the present inventive general formula (I) or general formula (I-E2), the following compounds are preferable:

a1) A heteroaromatic amide derivative or salt thereof represented by the general formula (I-G) below:

[Chem 45]

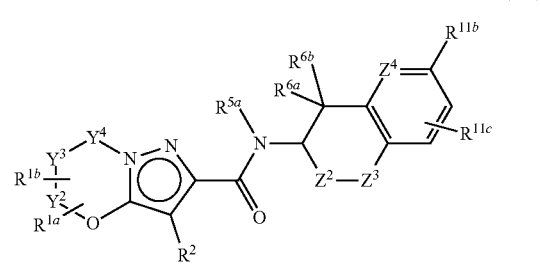

(I-G)

[wherein,
$Y^2$, $Y^3$, $Y^4$, $R^{1a}$, $R^{1b}$, $R^{6a}$, and $R^{6b}$ have the same definition as given in the (0), $Z^2$-$Z^3$, $Z^4$, $R^{5a}$, $R^{11b}$, and $R^{11c}$ have the same definition as given in the (7), $R^2$ is a hydrogen atom, a halogen atom, a hydroxy group, or a cyano group, with a proviso that at least one of $Y^2$, $Y^3$, or $Y^4$ is —$CR^{4a}R^{4b}$—, $CR^{4a}H$—, —$CH_2CR^{4a}R^{4b}$—, —$CH_2CR^{4a}H$—, or —$NR^{4c}$— ($R^{4a}$, $R^{4b}$ and $R^{4c}$ have the same definition as given in the (0).).]

a2) The heteroaromatic amide derivative or salt thereof described in the a1), wherein in the general formula (I-G),
$Y^2$, $Y^3$ and $Y^4$ together form
—$CR^{4a}HCH_2CH_2$—, —$CR^{4a}R^{4b}CH_2CH_2$—, —$CH_2CH_2$—, —$CR^{4a}HCH_2$—, —$CR^{4a}R^{4b}CH_2$—, —$CH_2CH_2CH_2CH_2$—, —$CR^{4a}HCH_2CH_2CH_2$—, or —$CH_2CR^{4a}HCH_2CH_2$— ($R^{4a}$, $R^{4b}$ have the same definition as given in the (0).).

a3) The heteroaromatic amide derivative or salt thereof described in the a1) or a2), wherein in the general formula (I-G),
$Z^2$-$Z^3$ is —$CH_2O$—, —$CH_2S$—, —$CH_2NR^{f1}$—, —$CH_2CH_2$—, or —$CONR^{f1}$— ($R^{f1}$ and $R^{f2}$ have the same definition as given in the (7).),
$R^{5a}$, $R^{6a}$ and $R^{6b}$ are hydrogen atoms.

a4) The heteroaromatic amide derivative or salt thereof in any one of the a1) to a3), wherein in the general formula (I-G),
$Z^2$-$Z^3$ is —$CH_2O$—,
$R^{11a}$ is a hydrogen atom, a halogen atom, a cyano group, a $C_1$-$C_6$ alkyl group, or a $C_1$-$C_6$ haloalkyl group,
$R^{11b}$ and $R^{11c}$ are, independently each other, a hydrogen atom, a halogen atom, a cyano group, a cyanomethyl group, a formyl group, a nitro group, a carboxamide group, a hydroxy group, a $C_1$-$C_6$ alkyl group, a $C_1$-$C_6$ haloalkyl group, a $C_1$-$C_6$ alkoxy group, a $C_1$-$C_6$ haloalkoxy group, a $C_1$-$C_4$ alkoxy-$C_1$-$C_4$ alkyl group, a $C_1$-$C_4$ alkoxy-$C_1$-$C_4$ alkyl group optionally substituted by a dimethylaminocarbonyl group or a dimethylamino group, a $C_1$-$C_4$ haloalkoxy-$C_1$-$C_4$ alkyl group, a $C_1$-$C_4$ alkoxy-$C_1$-$C_4$ haloalkyl group, a $C_1$-$C_4$ haloalkoxy-$C_1$-$C_4$ haloalkyl group, a $C_1$-$C_6$ alkylcarbonyl group, a $C_2$-$C_6$ alkenyl group, a $C_2$-$C_6$ alkynyl group, a $C_2$-$C_6$ alkynyl group optionally substituted by a halogen atom, a $C_1$-$C_6$ alkylthio group, a $C_1$-$C_6$ haloalkylthio group, —$(CH_2)_pNR^{a1}R^{a2}$ (p, $R^{a1}$ and $R^{a2}$ have the same definition as given in the (0).), or a group represented by the general formula (I-A)

[Chem 46]

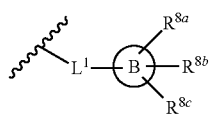

(I-A)

{wherein,
ring B is a $C_3$-$C_7$ cycloalkyl, an azetidinyl, a pyrrolidinyl, a piperidyl, a piperazinyl, a morpholino, a phenyl, a pyrrolyl, a furyl, a thienyl, an imidazolyl, a pyrazolyl, an oxazolyl, a thiazolyl, a triazolyl, a pyridyl, a pyrazinyl, a pyridazinyl, or a pyrimidinyl, $L^1$ is a single bond, —$CH_2$—, —$CH_2O$—, —$OCH_2$—, —$CH_2CH_2$—, or —$CH_2OCH_2$—($R^{a1}$ and $R^{a2}$ have the same definition as given in the (0).), $R^{8a}$, $R^{8b}$ and $R^{8c}$ are, independently each other, a hydrogen atom, a halogen atom, a cyano group, a $C_1$-$C_6$ alkyl group, a $C_1$-$C_6$ haloalkyl group, a $C_1$-$C_6$ alkoxy group, a $C_1$-$C_6$ haloalkoxy group, a $C_3$-$C_7$ cycloalkyl group, a $C_3$-$C_7$ cycloalkyloxy group, a heterocycloalkyl group, a heterocycloalkyloxy group, a $C_2$-$C_6$ alkenyl group, or a $C_2$-$C_6$ alkynyl group.}.

a5) The heteroaromatic amide derivative or salt thereof in any one of the a1) to a4), wherein in the general formula (I-G), $R^{4a}$ is a halogen atom, a hydroxy group, a cyano group, a $C_1$-$C_6$ alkyl group, a $C_1$-$C_6$ alkyl group optionally substituted by a hydroxy group, a $C_1$-$C_6$ haloalkyl group, a $C_1$-$C_6$ haloalkyl group optionally substituted by a hydroxy group, a $C_1$-$C_6$ alkoxy group, a $C_1$-$C_6$ haloalkoxy group, a $C_1$-$C_4$ alkoxy-$C_1$-$C_4$ alkyl group optionally substituted by a $C_1$-$C_4$ haloalkoxy group, a $C_1$-$C_4$ haloalkoxy-$C_1$-$C_4$ alkyl group, a $C_1$-$C_4$ alkoxy-$C_1$-$C_4$ haloalkyl group, a $C_1$-$C_4$ haloalkoxy-$C_1$-$C_4$ haloalkyl group, a $C_1$-$C_6$ alkylcarbonyl group, a $C_1$-$C_6$ alkoxycarbonyl group, a $C_1$-$C_6$ haloalkylcarbonyl group, a $C_3$-$C_7$ cycloalkyl group, a $C_3$-$C_7$ cycloalkyl group optionally substituted by a halogen atom or a $C_1$-$C_4$ haloalkyl group, a heterocycloalkyl group, $C_2$-$C_6$ alkenyl group, a $C_2$-$C_6$ alkenyloxy group, a $C_2$-$C_6$ alkenyloxy-$C_1$-$C_4$ alkyl group, a $C_2$-$C_6$ alkenyloxy-$C_1$-$C_4$ alkyl group optionally substituted by a halogen atom, a $C_2$-$C_6$ alkynyl group, a $C_2$-$C_6$ alkynyl group optionally substituted by a halogen atom or methoxy group, a $C_2$-$C_6$ alkynyloxy-$C_1$-$C_4$ alkyl group, a $C_1$-$C_4$ haloalkoxy-$C_1$-$C_4$ alkoxy group, a $C_1$-$C_6$ alkylthio group, $C_1$-$C_6$ haloalkylthio group, a $C_1$-$C_4$ alkylthio-$C_1$-$C_4$ alkyl group, a $C_1$-$C_4$ haloalkylthio-$C_1$-$C_4$ alkyl group, —$(CH_2)_q NR^{b1}R^{b2}$ (q, $R^{b1}$ and $R^{b2}$ have the same definition as given in the (0).), or a group represented by the general formula (I-B)

[Chem 47]

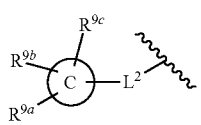

(I-B)

{wherein,
ring C is a $C_3$-$C_7$ cycloalkyl, an azetidinyl, a pyrrolidinyl, a piperidyl, a piperazinyl, a morpholino, a phenyl, a pyrrolyl, a furyl, a thienyl, an imidazolyl, a pyrazolyl, an oxazolyl, a thiazolyl, a triazolyl, a pyridyl, a pyrazinyl, a pyridazinyl, or a pyrimidinyl, $L^2$ is a single bond, —CH=CH—, —C≡C—, —$(CR^{10a}R^{10b})_{r1}(CR^{10c}R^{10d})_{r2}(CR^{10e}R^{10f})_{r3}(CR^{10g}R^{10h})_{r4}$—,
—$(CR^{10a}R^{10b})_{r1}(CR^{10c}R^{10d})_{r2}O(CR^{10e}R^{10f})_{r3}(CR^{10g}R^{10h})_{r4}$—,
—$(CR^{10a}R^{10b})_{r1}(CR^{10c}R^{10d})_{r2}NR^c(CR^{10e}R^{10f})_{r3}(CR^{10g}R^{10h})_{r4}$—,
—$(CR^{10a}R^{10b})_{r1}(CR^{10c}R^{10d})_{r2}CO(CR^{10e}R^{10f})_{r3}(CR^{10g}R^{10h})_{r4}$—,
—$(CR^{10a}R^{10b})_{r1}(CR^{10c}R^{10d})_{r2}S(CR^{10e}R^{10f})_{r3}(CR^{10g}R^{10h})_{r4}$—, or
—$(CR^{10a}R^{10b})_{r1}(CR^{10c}R^{10d})_{r2}SO(CR^{10e}R^{10f})_{r3}(CR^{10g}R^{10h})_{r4}$—($R^{10a}$, $R^{10b}$, $R^{10c}$, $R^{10d}$, $R^{10e}$, $R^{10f}$, $R^{10g}$, $R^{10h}$, r1, r2, r3, r4 and $R^c$ have the same definition as given in the (0).), $R^{9a}$, $R^{9b}$ and $R^{9c}$ are, independently each other, a hydrogen atom, a halogen atom, a hydroxy group, a cyano group, a $C_1$-$C_6$ alkyl group, a $C_1$-$C_6$ haloalkyl group, a $C_1$-$C_6$ alkoxy group, a $C_1$-$C_6$ haloalkoxy group, a $C_1$-$C_6$ alkoxycarbonyl group, a heterocycloalkyloxy group, or —$(CH_2)_s NR^{d1}R^{d2}$ (s, $R^{d1}$ and $R^{d2}$ have the same definition as given in the (0).).}.

a6) The heteroaromatic amide derivative or salt thereof in any one of the a1) to a5), wherein in the general formula (I-G), $Y^2$, $Y^3$ and $Y^4$ together form —$CR^{4a}HCH_2CH_2$—, $R^{4a}$ is a halogen atom, a hydroxy group, a cyano group, a $C_1$-$C_6$ alkyl group, a $C_1$-$C_6$ haloalkyl group, a $C_1$-$C_6$ alkoxy group, a $C_1$-$C_6$ haloalkoxy group, a $C_1$-$C_4$ alkoxy-$C_1$-$C_4$ alkyl group optionally substituted by a $C_1$-$C_4$ haloalkoxy group, a $C_1$-$C_4$ haloalkoxy-$C_1$-$C_4$ alkyl group, a $C_1$-$C_4$ haloalkoxy-$C_1$-$C_4$ alkoxy group, a $C_1$-$C_4$ alkylthio-$C_1$-$C_4$ alkyl group, a $C_1$-$C_4$ haloalkylthio-$C_1$-$C_4$ alkyl group, —$(CH_2)_q NR^{b1}R^{b2}$ (q, $R^{b1}$ and $R^{b2}$ have the same definition as given in the (0).), or substituents selected from the group consisting of the following formulae:

[Chem 48]

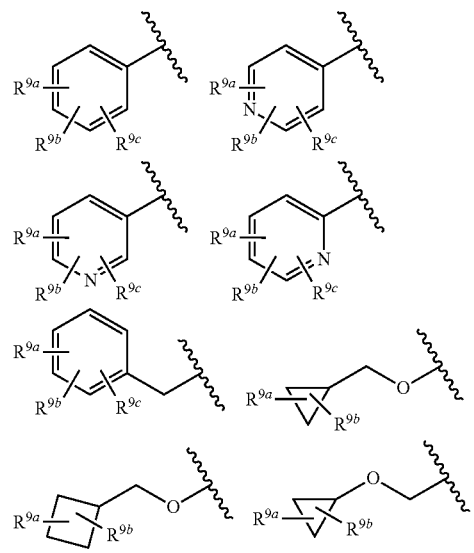

-continued

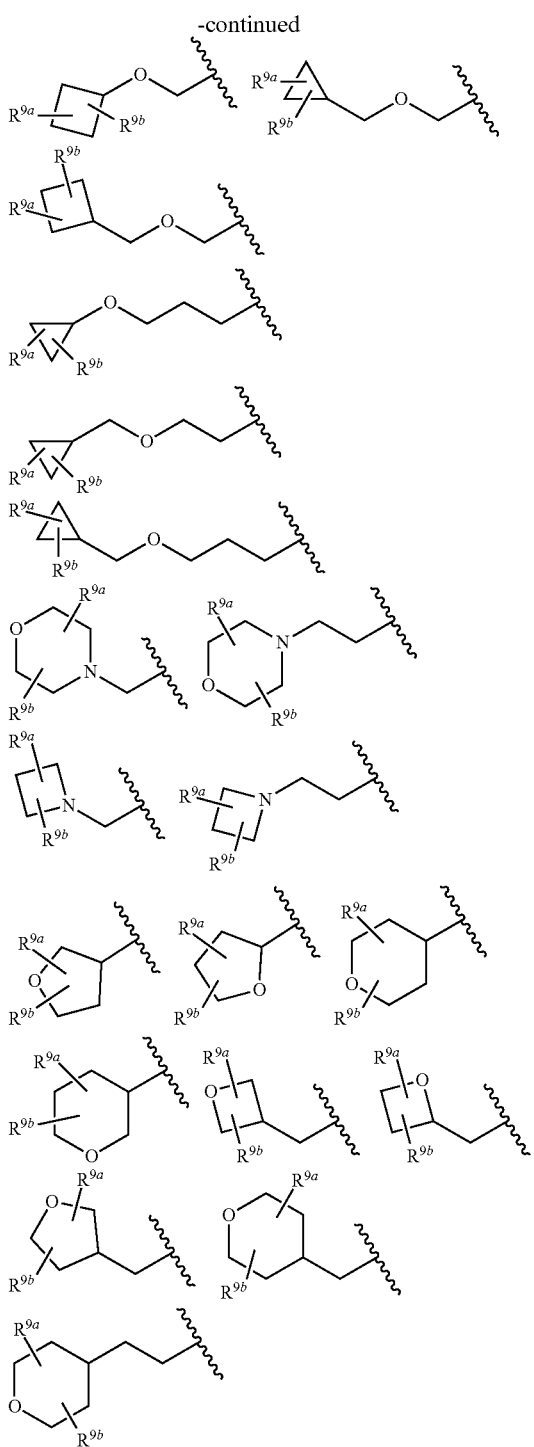

(wherein $R^{9a}$, $R^{9b}$ and $R^{9c}$ have the same definition as given in the (0).), $R^{11a}$ is a hydrogen atom, $R^{11b}$ and $R^{11c}$ are, independently each other, a hydrogen atom, a halogen atom, a cyano group, a cyanomethyl group, a $C_1$-$C_6$ alkyl group, a $C_1$-$C_6$ haloalkyl group, a $C_1$-$C_6$ alkoxy group, a $C_1$-$C_6$ haloalkoxy group, a $C_1$-$C_4$ alkoxy-$C_1$-$C_4$ alkyl group, a $C_1$-$C_4$ haloalkoxy-$C_1$-$C_4$ alkyl group, a $C_2$-$C_6$ alkenyl group, a $C_2$-$C_6$ alkynyl group, —$(CH_2)_p NR^{a1}R^{a2}$ (p is 1, and $R^{a1}$ and $R^{a2}$ are, independently each other, a hydrogen atom, a methyl group, an ethyl group, or a 2,2,2-trifluoroethyl group.), or a group represented by the general formula (I-A)

[Chem 49]

(I-A)

{wherein, ring B is a $C_3$-$C_7$ cycloalkyl, a morpholino, a phenyl, a pyrazolyl, a pyridyl, a pyrazinyl, a pyridazinyl, or a pyrimidinyl, $L^1$ is a single bond, $R^{8a}$, $R^{8b}$ and $R^{8c}$ are, independently each other, a hydrogen atom, a halogen atom, a cyano group, a $C_1$-$C_6$ alkyl group, a $C_1$-$C_6$ haloalkyl group, a $C_1$-$C_6$ alkoxy group, or a $C_1$-$C_6$ haloalkoxy group.}.

a7) The heteroaromatic amide derivative or salt thereof in the a1), wherein the compound represented by the general formula (I-G) is the following (the meaning of the numbers and asterisks (*) are as those given in the (15)):

[Chem 50]

170 isomer A
170 isomer B 103 isomer A
103 isomer B 101 isomer A
101 isomer B

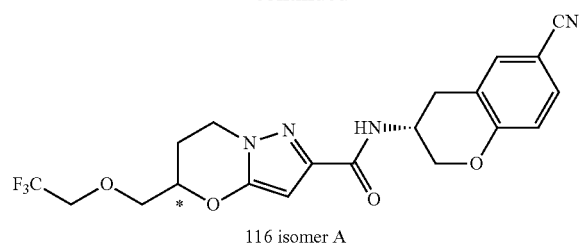
116 isomer A
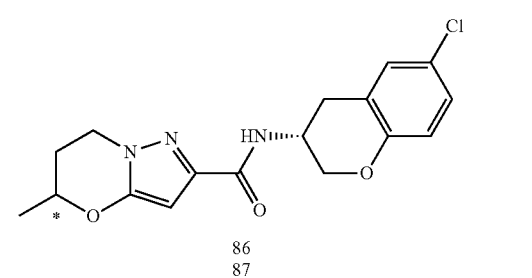
86
87
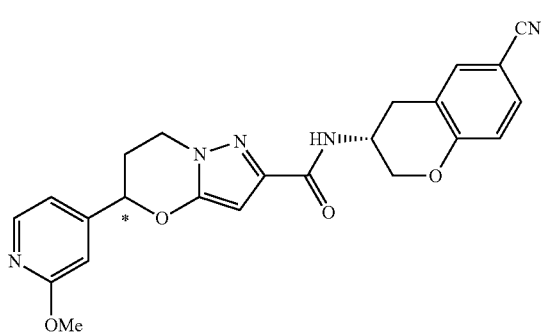
74 isomer A
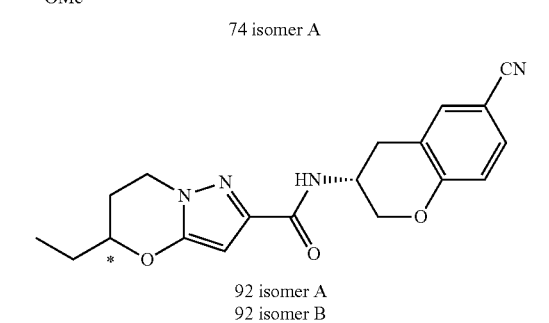
92 isomer A
92 isomer B
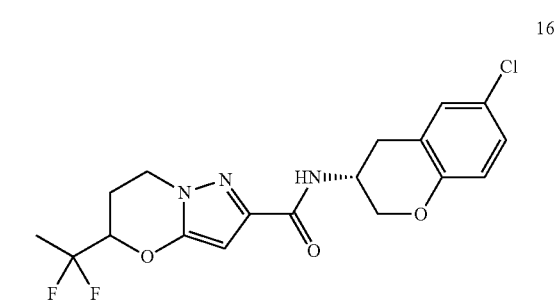
167
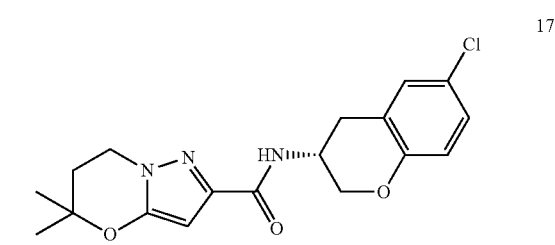
177
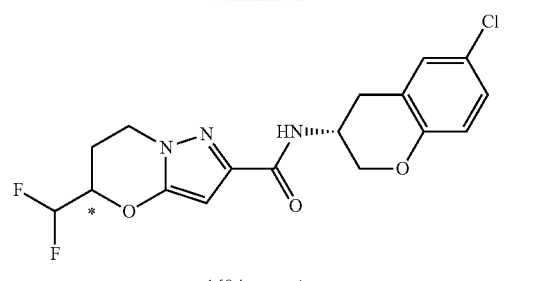
168 isomer A
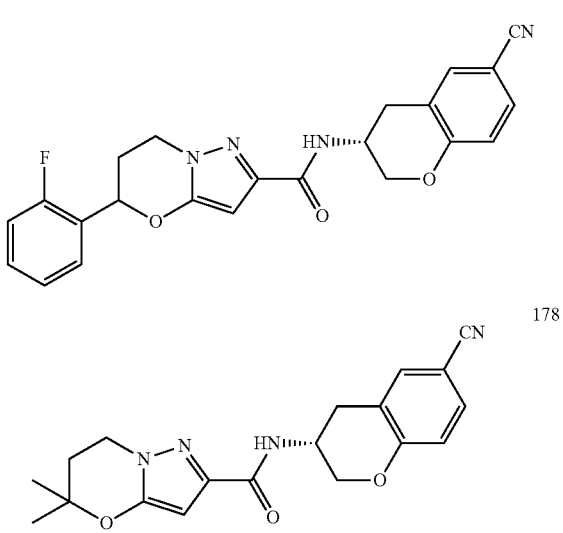
70
178
72
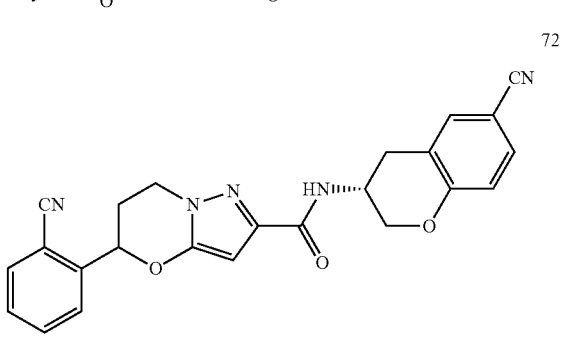
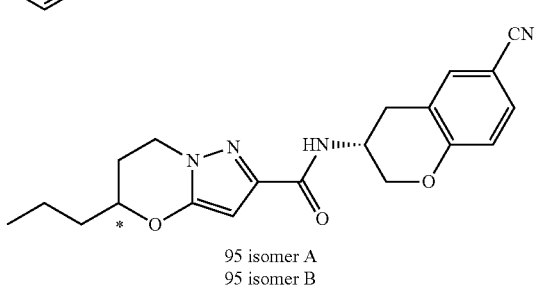
95 isomer A
95 isomer B
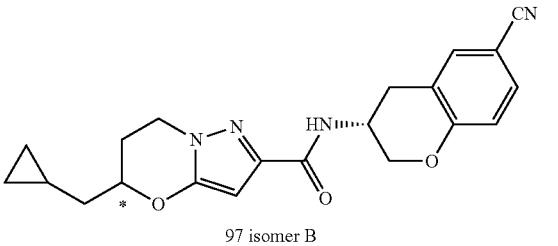
97 isomer B

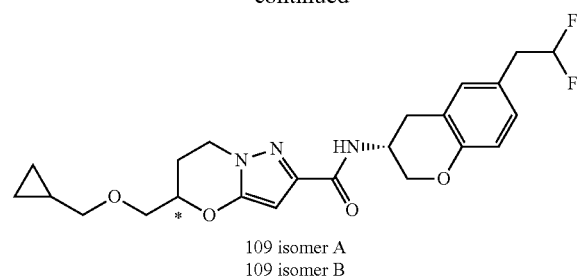
109 isomer A
109 isomer B
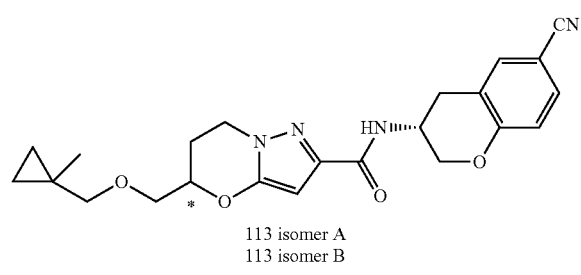
113 isomer A
113 isomer B
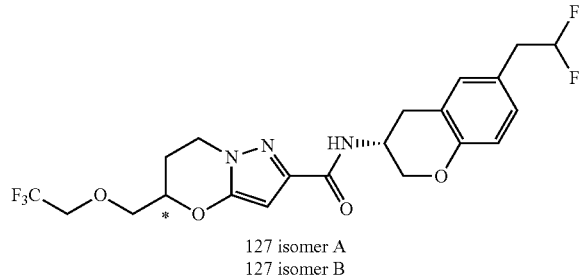
127 isomer A
127 isomer B
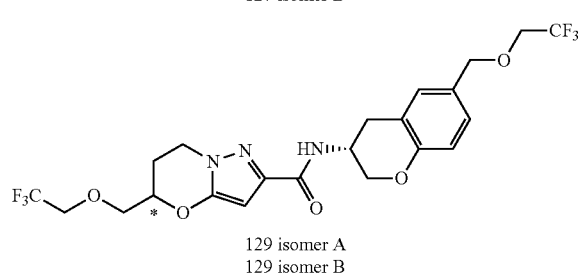
129 isomer A
129 isomer B
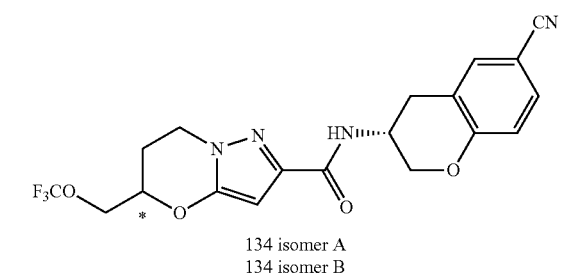
134 isomer A
134 isomer B
[Chem 51]
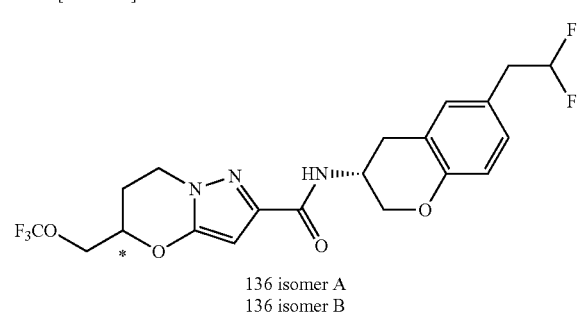
136 isomer A
136 isomer B
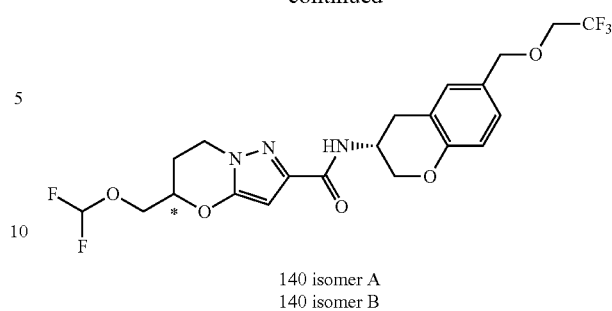
140 isomer A
140 isomer B
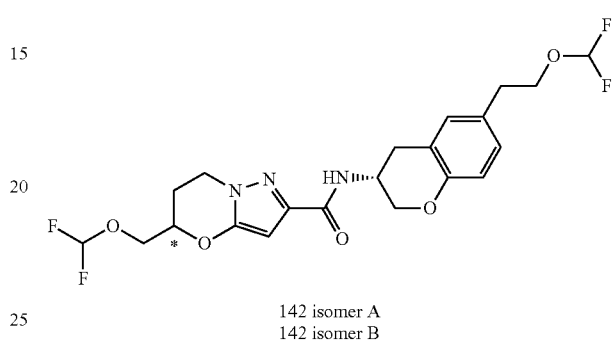
142 isomer A
142 isomer B
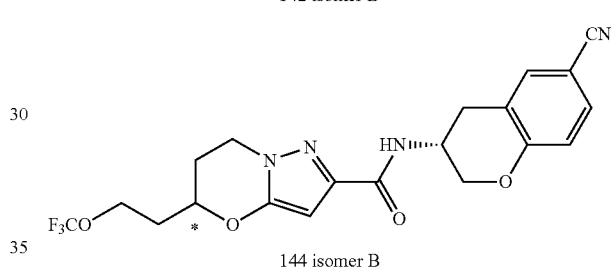
144 isomer B
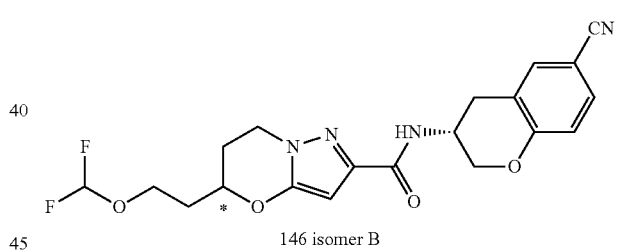
146 isomer B
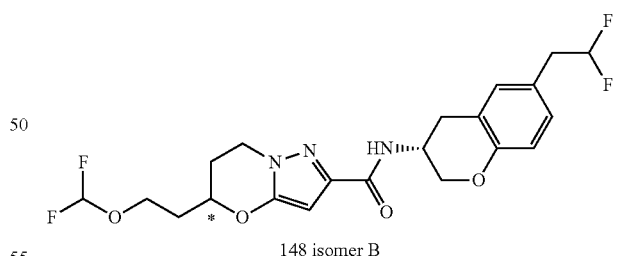
148 isomer B
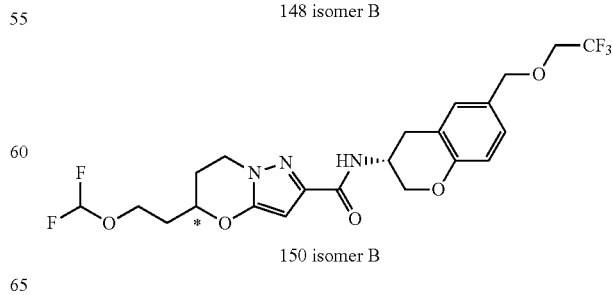
150 isomer B

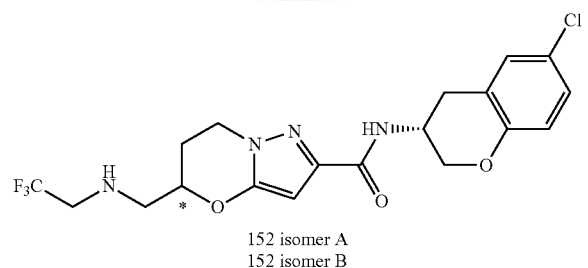
152 isomer A
152 isomer B
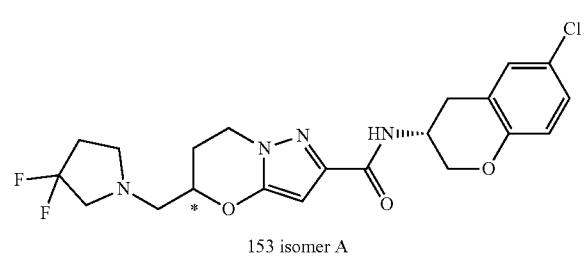
153 isomer A
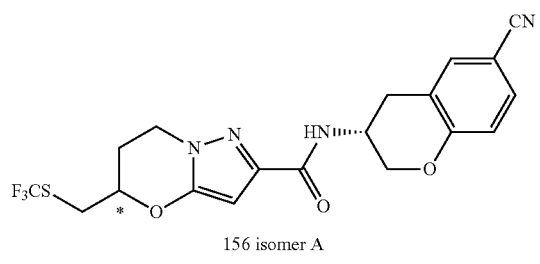
156 isomer A
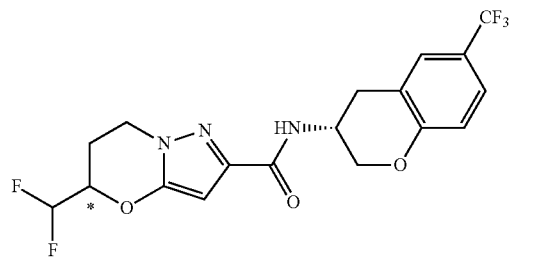
161 isomer A
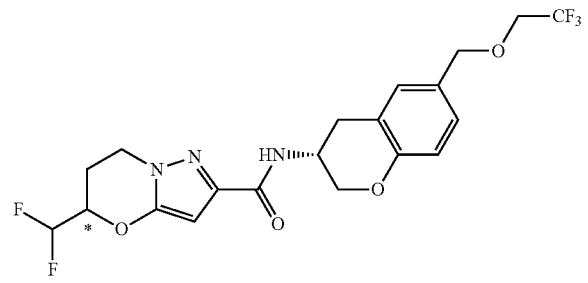
163 isomer A
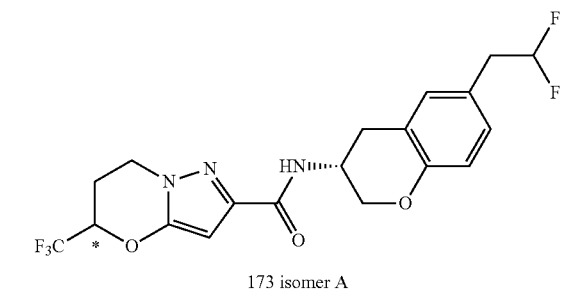
173 isomer A
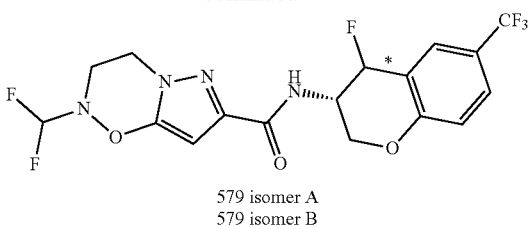
579 isomer A
579 isomer B
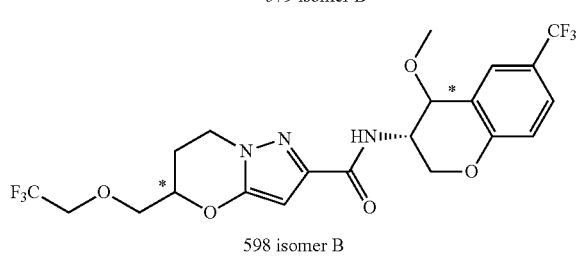
598 isomer B
614
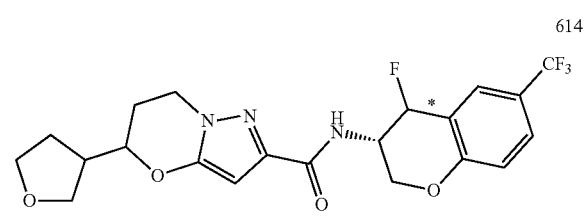
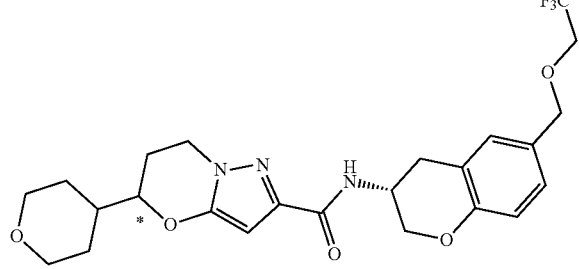
615 isomer A
615 isomer B
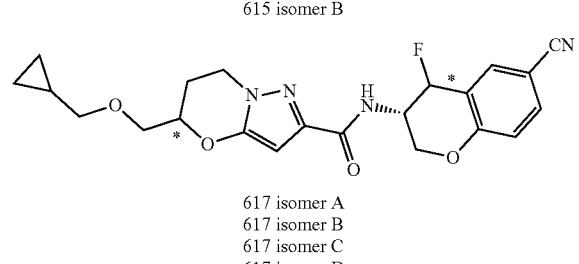
617 isomer A
617 isomer B
617 isomer C
617 isomer D
630
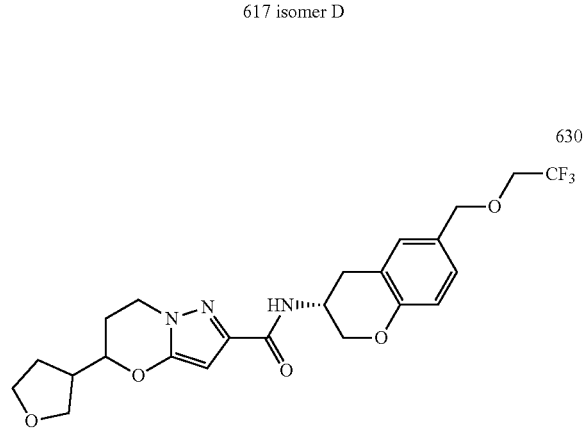

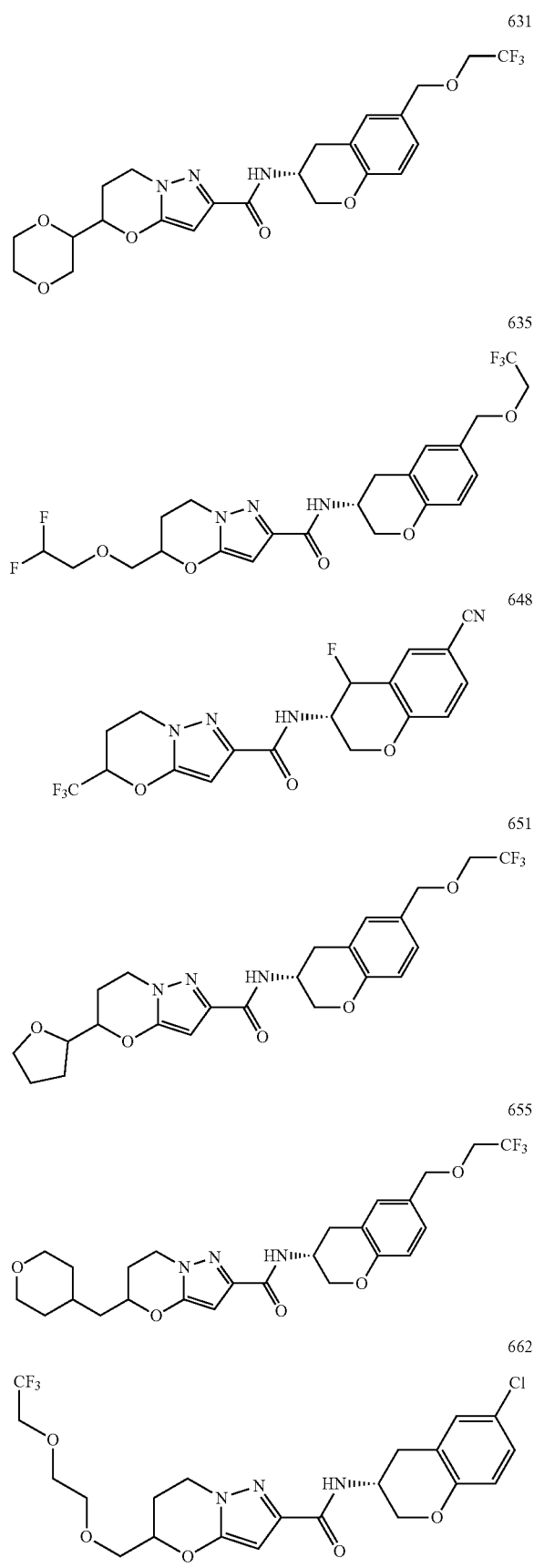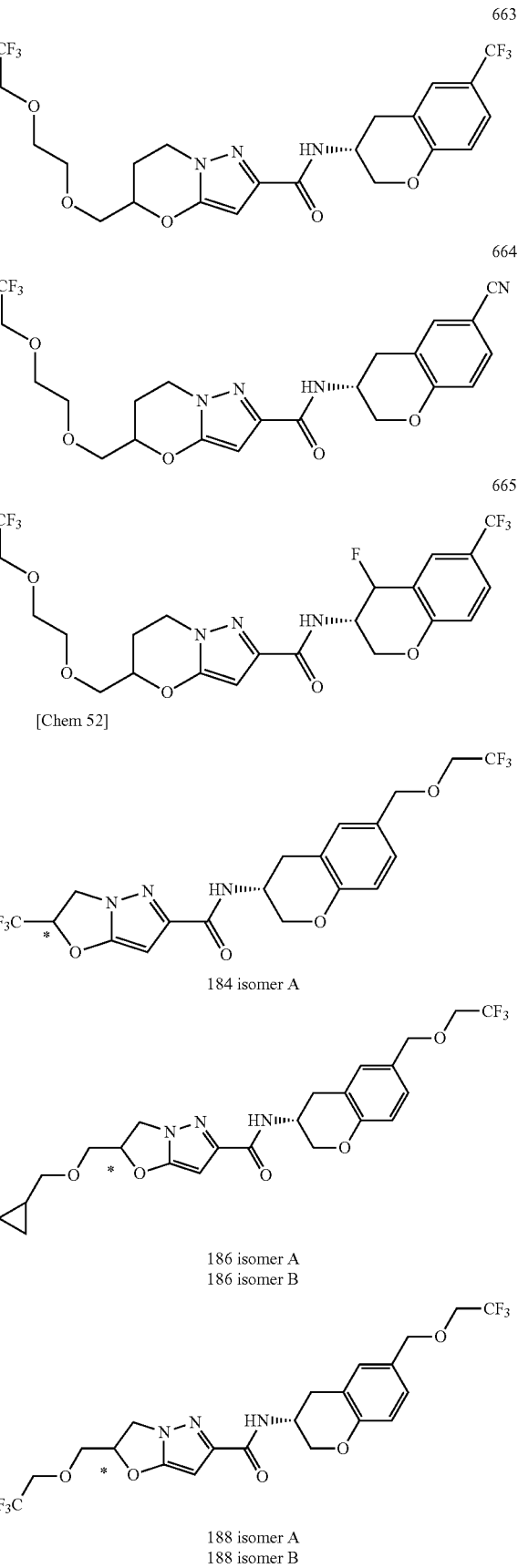

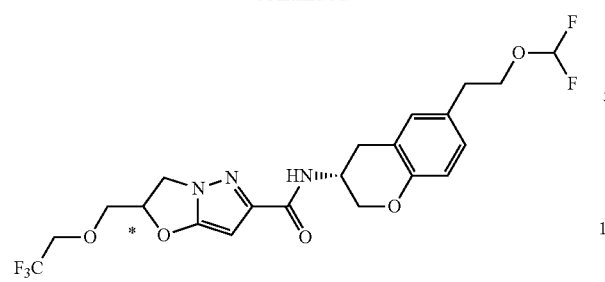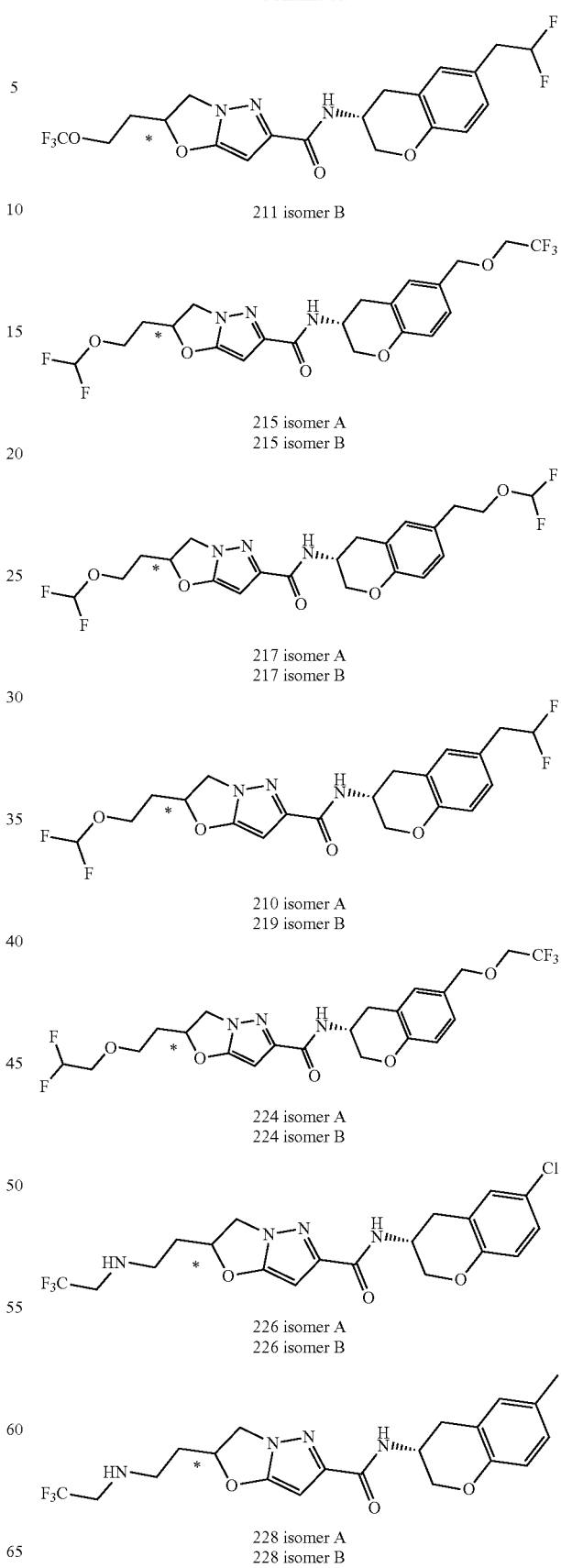

-continued
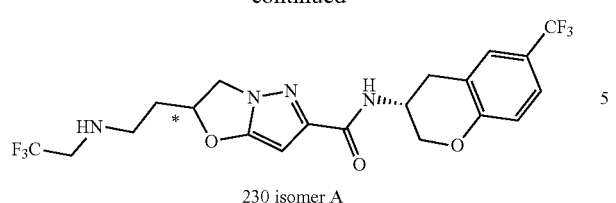
230 isomer A
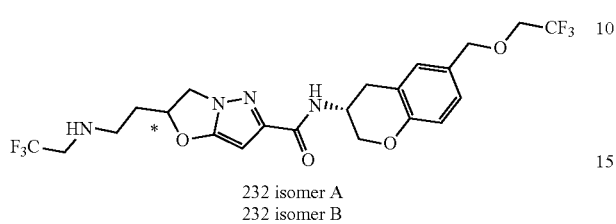
232 isomer A
232 isomer B
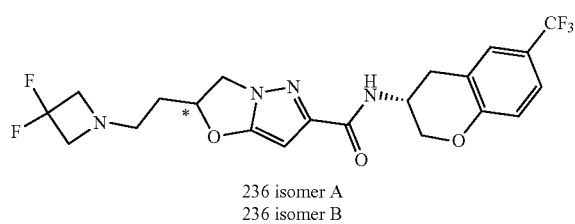
236 isomer A
236 isomer B
[Chem 53]
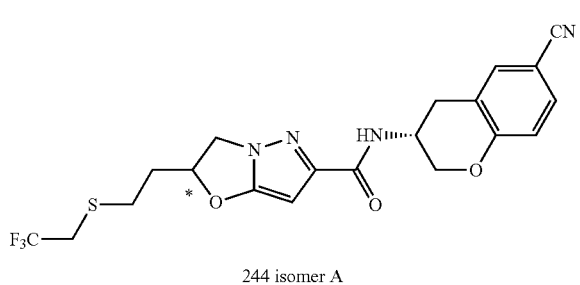
244 isomer A
244 isomer B
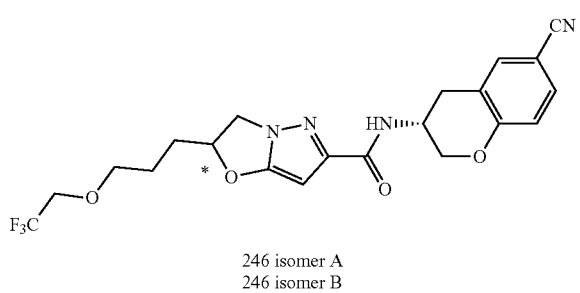
246 isomer A
246 isomer B
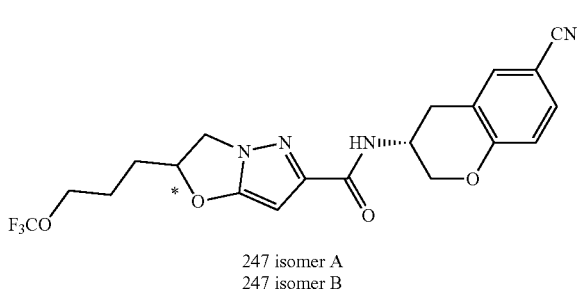
247 isomer A
247 isomer B
-continued
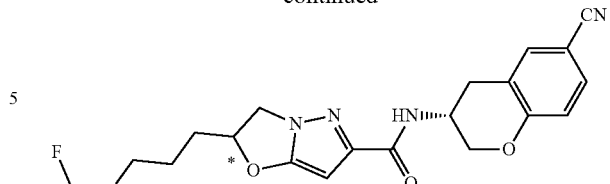
248 isomer A
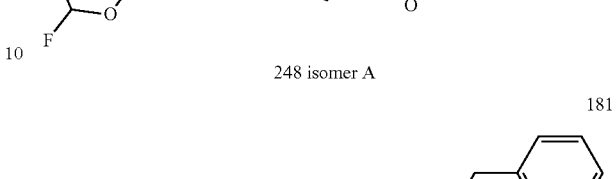
181
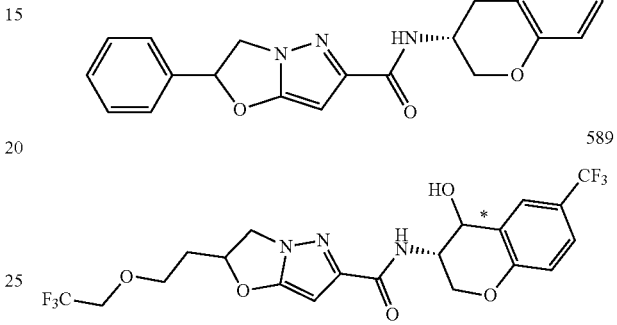
589
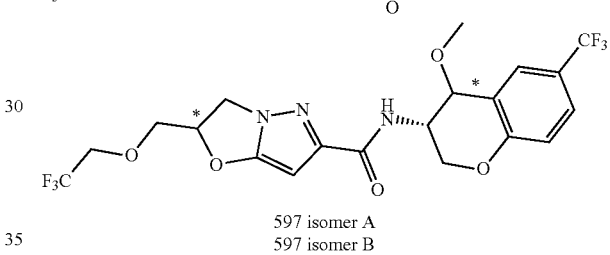
597 isomer A
597 isomer B
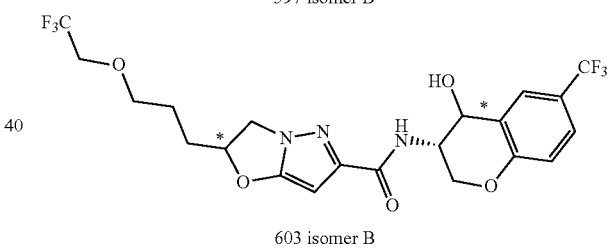
603 isomer B
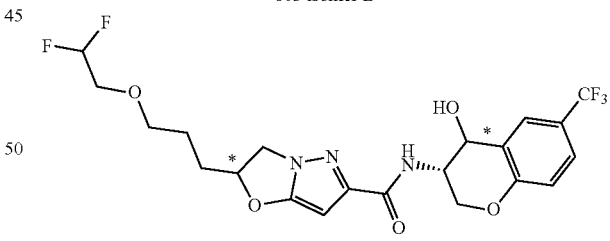
608 isomer A
608 isomer B
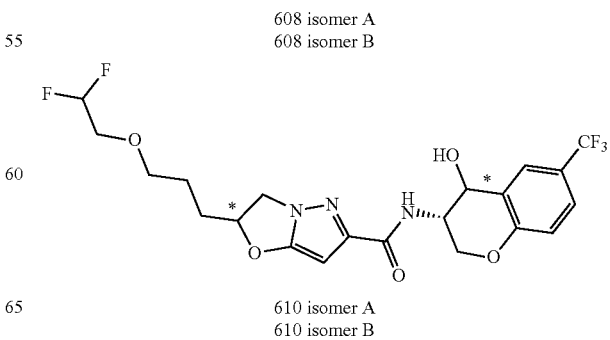
610 isomer A
610 isomer B

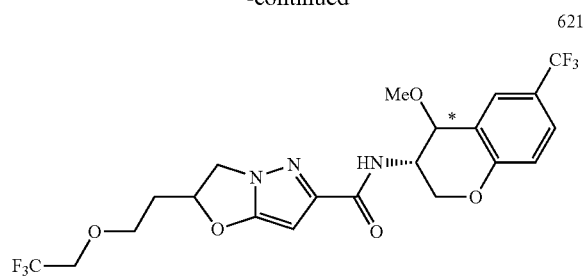
621
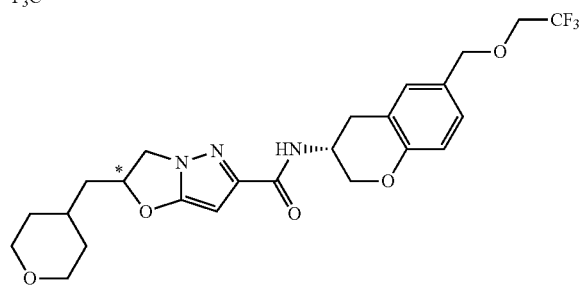
622 isomer A
622 isomer B
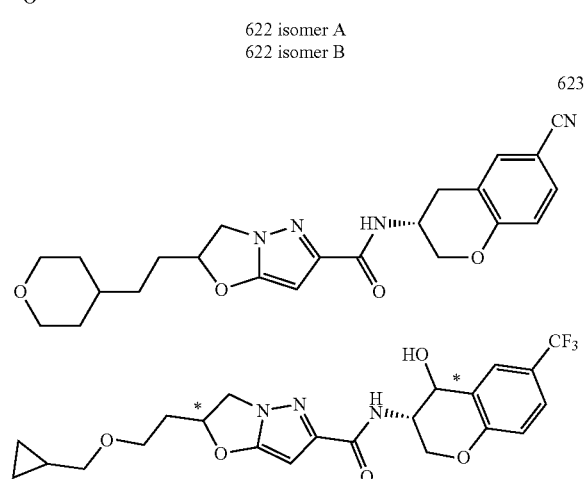
623
636 isomer A
636 isomer B
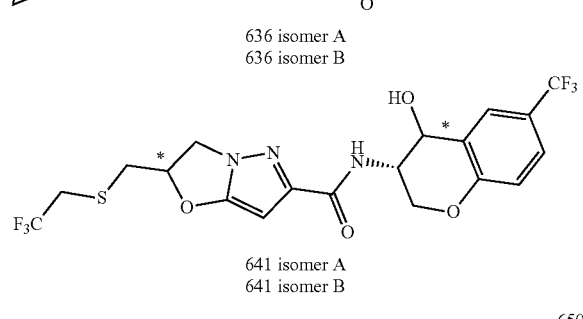
641 isomer A
641 isomer B
650
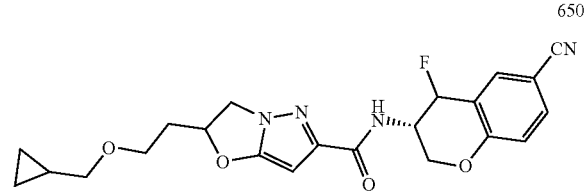
657
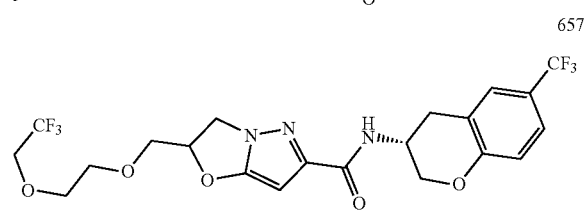
658
660
661
676
[Chem 54]
256 isomer A
256 isomer B
257 isomer A
257 isomer B -continued
251
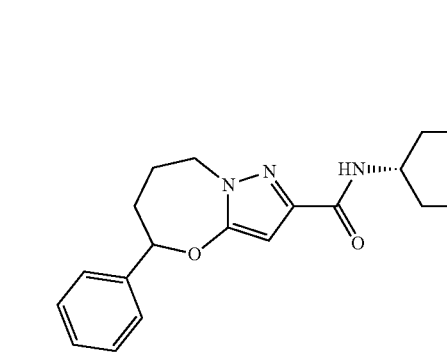
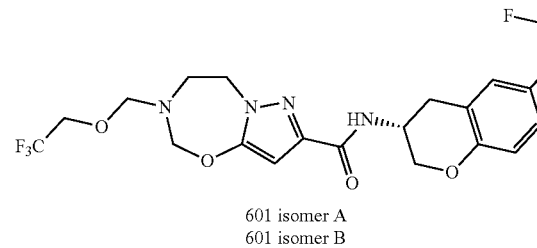
601 isomer A
601 isomer B
632
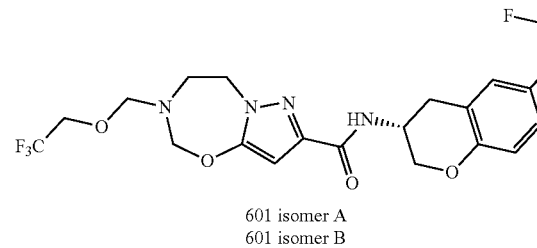
633
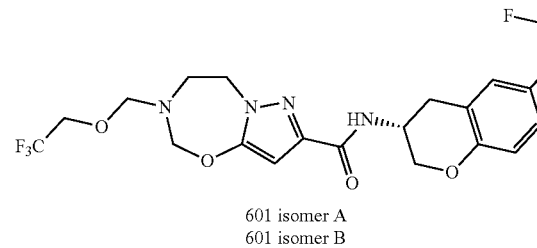
634
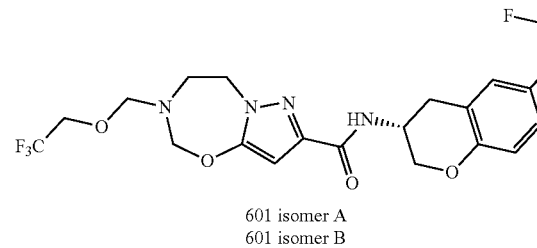
649
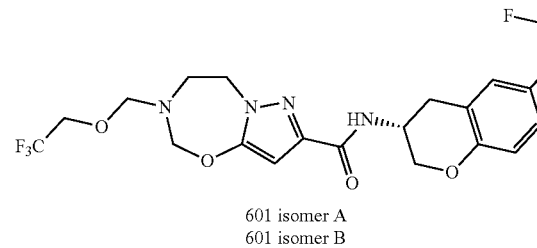
-continued
656
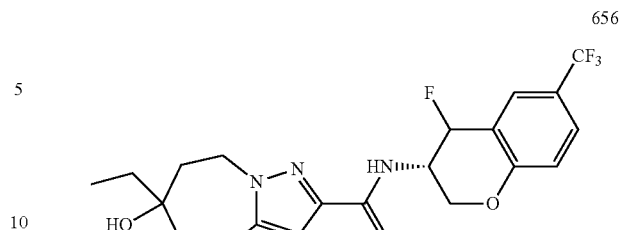
679
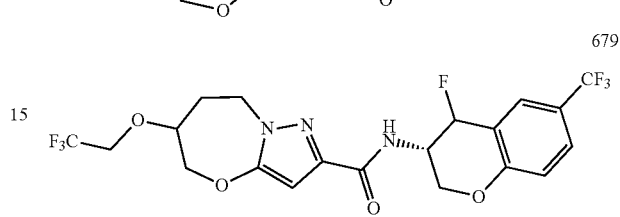
680
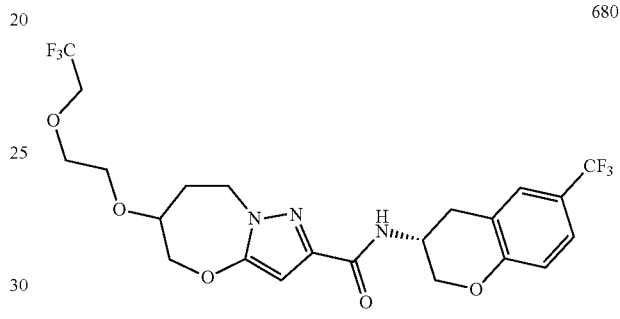
682
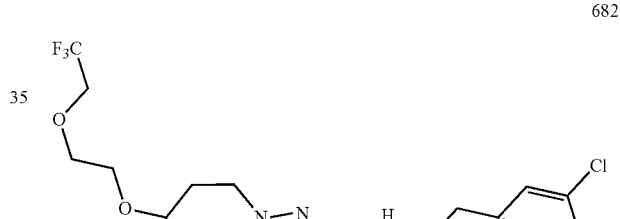
683
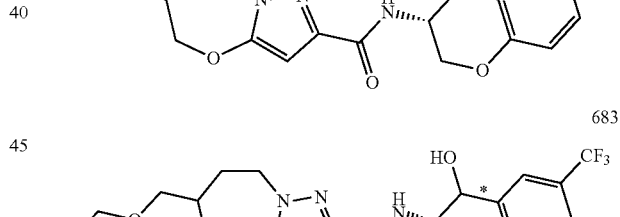
[Chem 55]
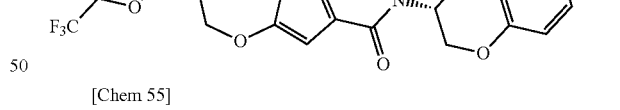

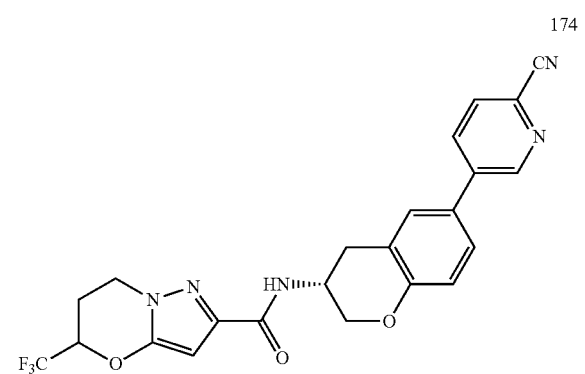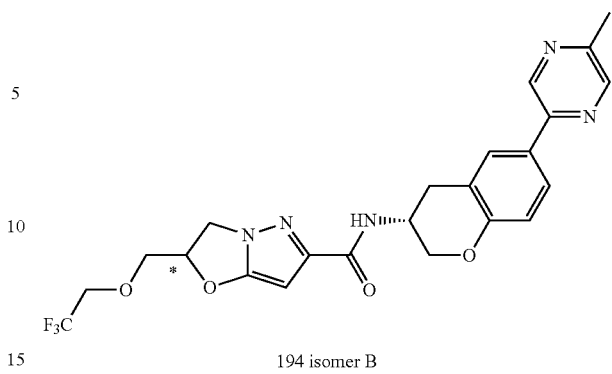

-continued

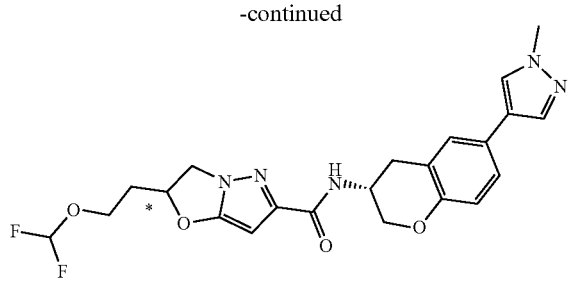

221 isomer A
221 isomer B

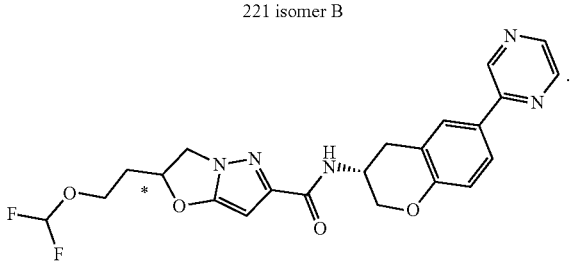

223 isomer B

As type (b) derivatives in the present inventive general formula (I) or general formula (I-E2), the following compounds are preferable:

b1) A heteroaromatic amide derivative or salt thereof represented by the general formula (I-I):

[Chem 56]

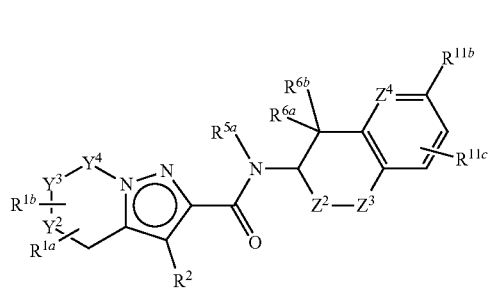

(I-I)

[wherein,
Y$^2$, Y$^3$, Y$^4$, R$^{1a}$, R$^{1b}$, R$^2$, R$^{6a}$, and R$^{6b}$ have the same definition as given in the (0),
Z$^2$-Z$^3$, Z$^4$, R$^{5a}$, R$^{11b}$, and R$^{11c}$ have the same definition as given in in the (7) (with a proviso that at least one of Y$^2$, Y$^3$, or Y$^4$ is —CR$^{4a}$R$^{4b}$—, —CR$^{4a}$H—, —CH$_2$CR$^{4a}$R$^{4b}$—, —CH$_2$CR$^{4a}$H—, or —NR$^{4c}$— (R$^{4a}$, R$^{4b}$ and R$^{4c}$ have the same definition as given in in the (0).).].

b2) The heteroaromatic amide derivative or salt thereof set forth in the b1), wherein in the general formula (I-I),
Y$^2$, Y$^3$ and Y$^4$ together form
—OCH$_2$CH$_2$—, —OCH$_2$CH$_2$CH$_2$—,
—CR$^{4a}$HCH$_2$CH$_2$—, —CR$^{4a}$R$^{4b}$CH$_2$CH$_2$—,
—CH$_2$CR$^{4a}$HCH$_2$—, or —NR$^{4a}$CH$_2$CH$_2$— (R$^{4a}$, R$^{4b}$ and R$^{4c}$ have the same definition as given in the (0).).

b3) The heteroaromatic amide derivative or salt thereof of the b1) or b2), wherein in the general formula (I-I),
Z$^2$-Z$^3$ is —CH$_2$O—, —CH$_2$S—, —CH$_2$NR$^{f1}$—, —CH$_2$CH$_2$—, or —CONR$^{f1}$— (R$^{f1}$ and R$^{f2}$ have the same definition as given in the (7).),
R$^{5a}$, R$^{6a}$ and R$^{6b}$ are hydrogen atoms.

b4) The heteroaromatic amide derivative or salt thereof set forth in the b1), wherein the compound represented by the general formula (I-I) is the following (the meaning of the numbers is as those given in the (15)),

[Chem 57]

278

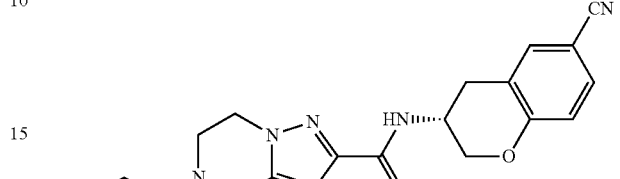

268

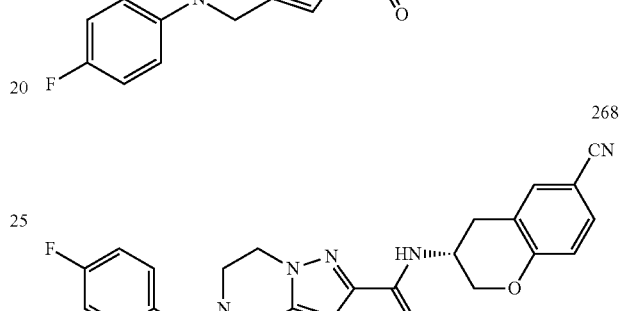

261

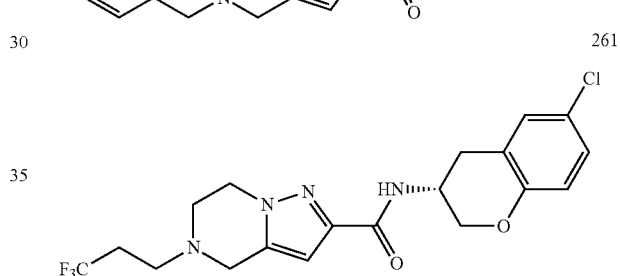

265

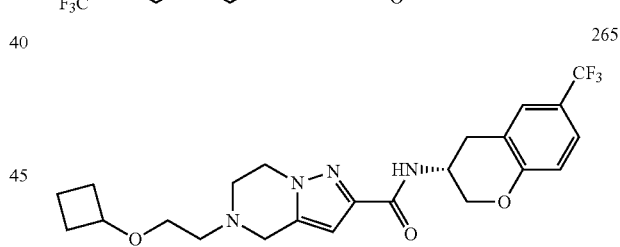

266

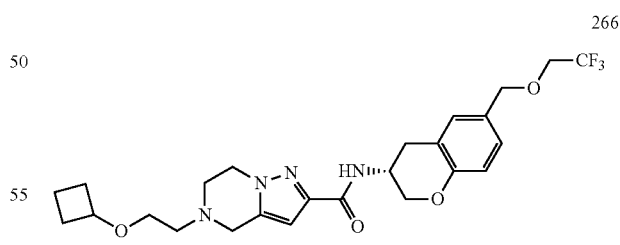

273

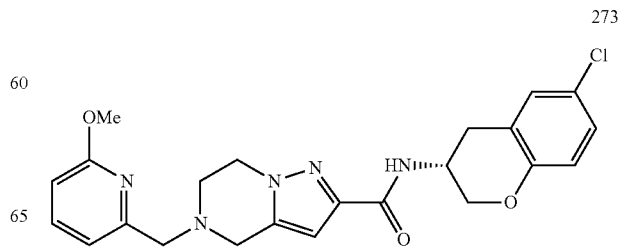

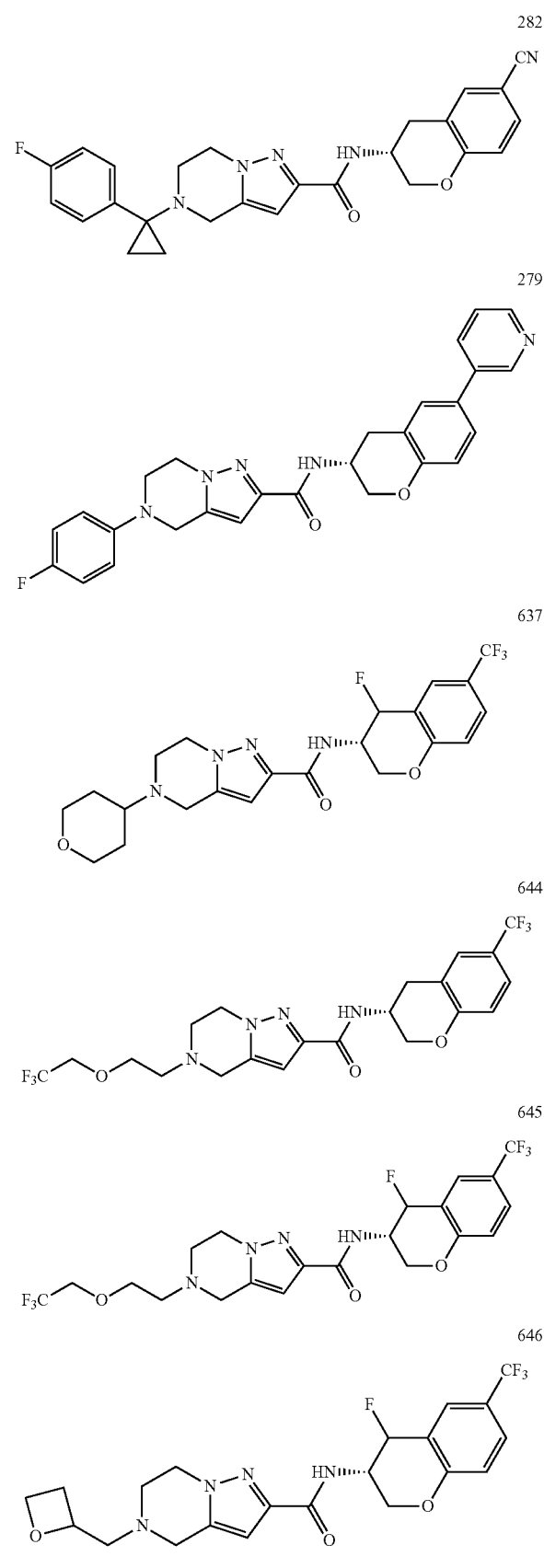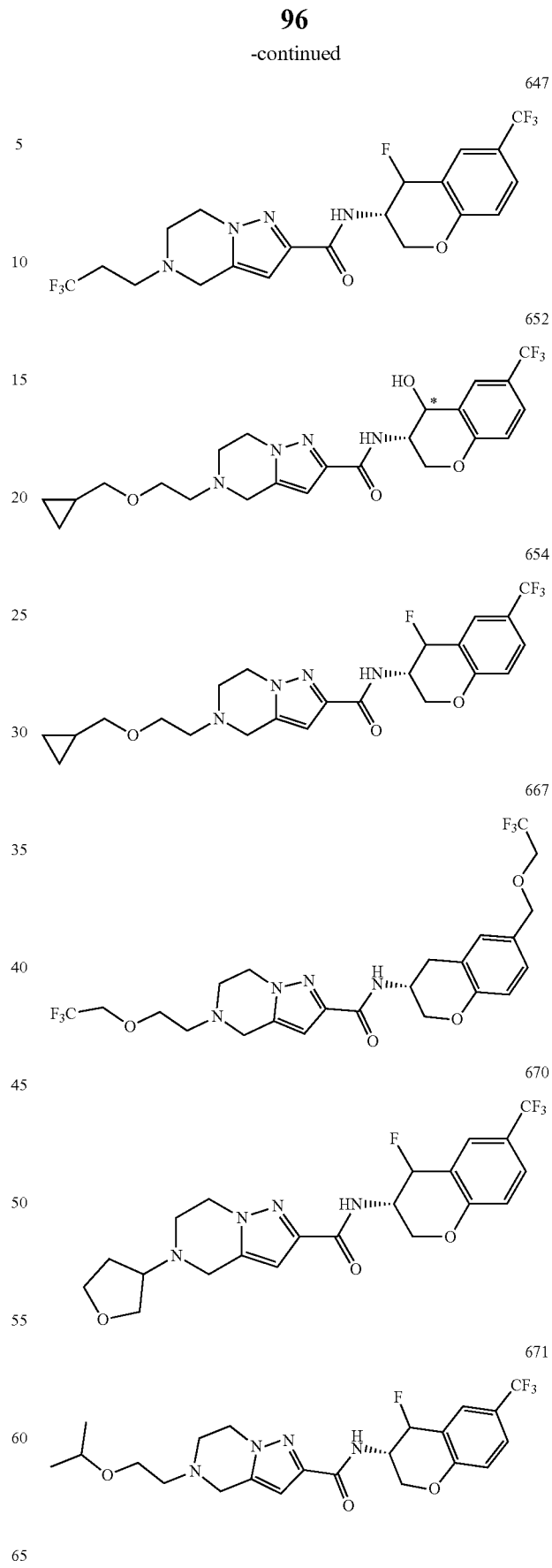

c2) The heteroaromatic amide derivative or salt thereof set forth in the c1), wherein in the general formula (I-K), Y², Y³ and Y⁴ together form
—CR⁴ᵃHOCH₂—, —CR⁴ᵃHCH₂CH₂—, —CH₂NR⁴ᶜCH₂—, —CR⁴ᵃHNR⁴ᶜCH₂—, or —CR⁴ᵃHNHCH₂— (R⁴ᵃ and R⁴ᵇ have the same definition as given in the (0).).

c3) The heteroaromatic amide derivative or salt thereof of the c1) or c2), wherein in the general formula (I-K), Z²-Z³ is —CH₂O—, —CH₂S—, —CH₂NR^f¹—, —CH₂CH₂—, or —CONR^f¹— (R^f¹ and R^f² have the same definition as given in the (7).), R⁵ᵃ, R⁶ᵃ and R⁶ᵇ are a hydrogen atom.

c4) The heteroaromatic amide derivative or salt thereof of the c1), wherein the compound represented by the general formula (I-K) is the following (the meaning of the numbers is as those given in the (15)):

[Chem 59]

As type (c) derivatives in the present inventive general formula (I) or general formula (I-E2), the following compounds are preferable:

c1) A heteroaromatic amide derivative or salt thereof represented by the general formula (I-K):

[Chem 58]

(I-K)

[wherein,

Y², Y³, Y⁴, R¹ᵃ, R¹ᵇ, R², R⁶ᵃ, and R⁶ᵇ have the same definition as given in the (0), Z²-Z³, Z⁴, R⁵ᵃ, R¹¹ᵇ, and R¹¹ᶜ have the same definition as given in the (7) (with a proviso that ring C is not a phenyl ring when Y², Y³ and Y⁴ together form —CR⁴ᵃHCH₂CH₂—, R² is a hydrogen atom, R⁴ᵃ is a group represented by the general formula (I-B), and L² is a single bond, and with a proviso that at least one of Y², Y³, or Y⁴ is —CR⁴ᵃR⁴ᵇ—, —CR⁴ᵃH—, —CH₂CR⁴ᵃR⁴ᵇ—, —CH₂CR⁴ᵃH—, or —NR⁴ᶜ— (R⁴ᵃ, R⁴ᵇ and R⁴ᶜ have the same definition as given in the (0).).].

As type (d) derivatives in the present inventive general formula (I) or general formula (I-E2), the following compounds are preferable:

d1) A heteroaromatic amide derivative or salt thereof represented by the general formula (I-E2):

[Chem 60]

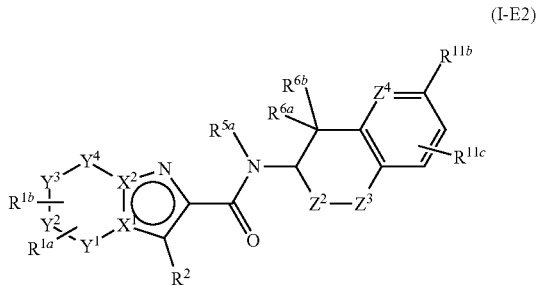

(I-E2)

[wherein, $R^{1a}$, $R^{1b}$, $R^{6a}$, and $R^{6b}$ have the same definition as given in the (0), $Z^2-Z^3$, $Z^4$, $R^{5a}$, $R^{11b}$, and $R^{11c}$ have the same definition as given in the (7), $R^2$ is an optionally substituted saturated, partially saturated or unsaturated 3- to 7-membered monocyclic ring, and $Y^1$, $Y^2$, $Y^3$ and $Y^4$ together form
—OCH$_2$CH$_2$CH$_2$—, —OCR$^{4a}$HCH$_2$CH$_2$—, —OCR$^{4a}$R$^{4b}$CH$_2$CH$_2$—
—OCH$_2$CH$_2$—, —OCR$^{4a}$HCH$_2$—, —OCR$^{4a}$R$^{4b}$CH$_2$—,
—OCH$_2$CH$_2$CH$_2$CH$_2$—, —OCR$^{4a}$HCH$_2$CH$_2$CH$_2$—,
—OCR$^{4a}$R$^{4b}$CH$_2$CH$_2$CH$_2$—,
—OCH$_2$CR$^{4a}$HCH$_2$CH$_2$—,
—OCH$_2$CR$^{4a}$R$^{4b}$CH$_2$CH$_2$—,
—CH$_2$OCH$_2$CH$_2$—, —CH$_2$OCH$_2$CH$_2$CH$_2$—,
—CH$_2$CH$_2$OCH$_2$—, —CH$_2$CR$^{4a}$HOCH$_2$—
—CH$_2$CH$_2$CH$_2$CH$_2$—, —CH$_2$CR$^{4a}$HCH$_2$CH$_2$—,
—CH$_2$CR$^{4a}$R$^{4b}$CH$_2$CH$_2$—,
—CH$_2$CH$_2$CR$^{4a}$HCH$_2$—, —CH$_2$CH$_2$CR$^{4a}$R$^{4b}$CH$_2$—,
—CH$_2$SCH$_2$CH$_2$—, —CH$_2$SO$_2$CH$_2$CH$_2$—,
—NHCH$_2$CH$_2$CH$_2$—, —NR$^{4c}$CH$_2$CH$_2$CH$_2$—,
—NR$^{4c}$CR$^{4a}$HCH$_2$CH$_2$—, —NHCR$^{4a}$HCH$_2$CH$_2$—,
—CH$_2$NR$^{4c}$CH$_2$CH$_2$—, —CH$_2$NR$^{4c}$CR$^{4a}$HCH$_2$—,
—CH$_2$NHCR$^{4a}$HCH$_2$—,
—CH$_2$CH$_2$NR$^{4c}$CH$_2$—, —CH$_2$CR$^{4a}$HNR$^{4c}$CH$_2$—, or —CH$_2$CR$^{4a}$HNHCH$_2$— ($R^{4a}$, $R^{4b}$ and $R^{4c}$ have the same definition as given in the (0).), $X^1$-$X^2$ is N—C or C—N (with a proviso that $Y^1$, $Y^2$, $Y^3$ and $Y^4$ do not together form —OCH$_2$CH$_2$CH$_2$—, —OCR$^{4a}$HCH$_2$CH$_2$—, or —OCR$^{4a}$R$^{4b}$CH$_2$CH$_2$— in the case of C—N.).].

d2) The heteroaromatic amide derivative or salt thereof set forth in the d1), wherein in the general formula (I-E2), $Z^2$-$Z^3$ is —CH$_2$O—, —CH$_2$S—, —CH$_2$NR$^{f1}$—, —CH$_2$CH$_2$—, or —CONR$^{f1}$— ($R^{f1}$ and $R^{f2}$ have the same definition as given in the (7).), $R^{5a}$, $R^{6a}$ and $R^{6b}$ are a hydrogen atom.

d3) The heteroaromatic amide derivative or salt thereof set forth in any one of the d1) to d2), wherein, in the general formula (I-E2), $R^2$ is a phenyl, a pyrrolyl, a furyl, a thienyl, an imidazolyl, a pyrazolyl, an oxazolyl, a thiazolyl, a triazolyl, a pyridyl, a pyrazinyl, a pyridazinyl, a pyrimidinyl, a tetrazolyl, an isothiazolyl, an oxazolyl, an isoxazolyl, or a thiadiazolyl, wherein each is optionally substituted by a halogen atom, a cyano group, a C$_1$-C$_4$ alkyl group, a C$_1$-C$_4$ haloalkyl group, a C$_1$-C$_4$ alkoxy group, a C$_1$-C$_4$ haloalkoxy group or —NR$^{d1}$R$^{d2}$ (R$^{d1}$ and R$^{d2}$ are, independently each other, a hydrogen atom, a C$_1$-C$_4$ alkyl group, or a C$_1$-C$_4$ haloalkyl group.).

d4) The heteroaromatic amide derivative or salt thereof set forth in any one of the d1) to d3), wherein in the general formula (I-E2), $R^2$ is a phenyl, a pyrazolyl, a triazolyl, a pyridyl, or a pyrazinyl, wherein each is optionally substituted by a halogen atom, a cyano group, a C$_1$-C$_4$ alkyl group, a C$_1$-C$_4$ haloalkyl group, a C$_1$-C$_4$ alkoxy group, a C$_1$-C$_4$ haloalkoxy group or —NR$^{d1}$R$^{d2}$ (R$^{d1}$ and R$^{d2}$ are, independently each other, a hydrogen atom, a C$_1$-C$_4$ alkyl group, or a C$_1$-C$_4$ haloalkyl group.).

d5) The heteroaromatic amide derivative or salt thereof set forth in any one of the d1) to d4), wherein in the general formula (I-E2), $R^2$ is a phenyl, a pyrazolyl, or a pyridyl, wherein each is optionally substituted by a halogen atom, a methyl group, an ethyl group, a trifluoromethyl group, a trifluoromethoxy group, a trifluoroethyl group, a trifluoroethoxy group or —NHR$^{d2}$ (R$^{d2}$ is a methyl group, an ethyl group, a trifluoromethyl group, or a trifluoroethyl group.).

d6) The heteroaromatic amide derivative or salt thereof set forth in the d1), wherein the compound represented by the general formula (I) or the general formula (I-E2) is the following (the meaning of the numbers is as those given in the (15)):

[Chem 61]

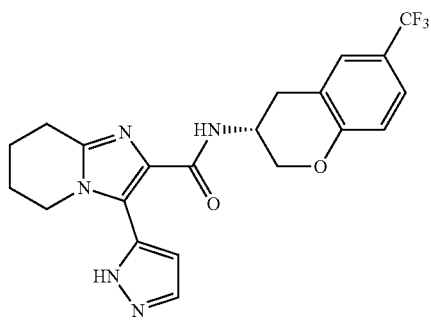 [SMILES: O=C(N[C@H]1COc2ccc(C(F)(F)F)cc2C1)c1nc2n(c1-c1ccn[nH]1)CCCC2]

19

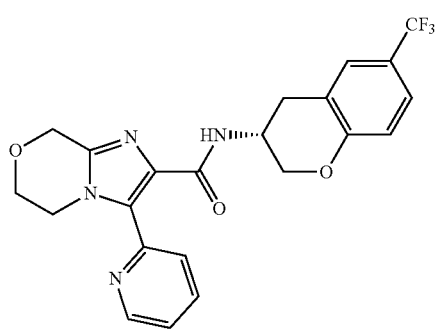

67

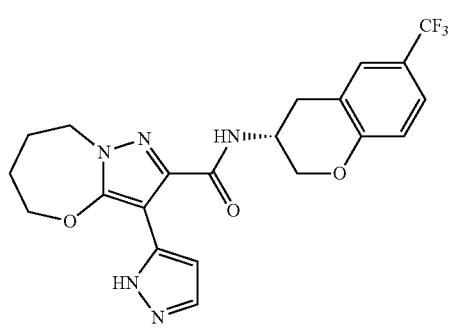

258

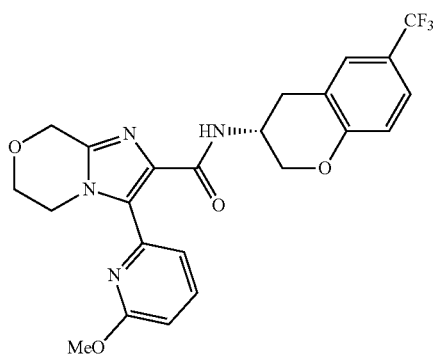

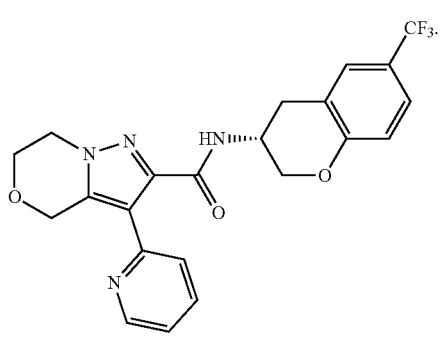

As the salt of the present inventive compound represented by the general formula (I), the pharmaceutically acceptable salt is preferable. The "pharmacologically acceptable salt" is not particularly limited as long as it is a pharmacologically acceptable salt. It includes inorganic acid salts such as hydrochloride, hydrobromide, nitrate, sulfate, phosphate; organic carboxylic acid salts such as acetate, oxalate, fumarate, maleate, malonate, citrate, succinate, lactate, tartrate and malate; aromatic carboxylic acid salts such as salicylate and benzoate; organic sulfonates such as methanesulfonate, tosylate and benzenesulfonate; alkali metal salts such as lithium salt, sodium salt and potassium salt; alkaline earth metal salts such as calcium salt, magnesium salt and so on.

In the present inventive compound represented by the general formula (I), a racemate, diastereo isomers and each optically active substance thereof are included in the present invention when an asymmetric carbon exists, and any of (E) isomer, (Z) isomer and a mixture thereof are included in the present invention when geometrical isomers exist.

In the present inventive compound represented by the general formula (I), the solvates such a hydrate and so on are also included in the present invention when these exist.

The compounds represented by the general formula (I), that is the heteroaromatic amide derivative of the present invention, can be produced by various methods; it can be produced, for example, by the methods shown below, methods similar to the methods shown below, or by appropriately combining synthesis methods known to those skilled in the art. Any of the starting materials and reaction reagents used in these syntheses is commercially available or can be prepared by using commercially available compounds according to methods well known to those skilled in the art. In addition, extraction, purification and so on may be performed in the usual organic chemistry experiments. Furthermore, the order of the steps to be performed can appropriately be changed for all the following steps.

The compound represented by the general formula (I) can be produced, for example, by a method shown by the following reaction scheme-1.

<Reaction Scheme-1>

[Chem 62]

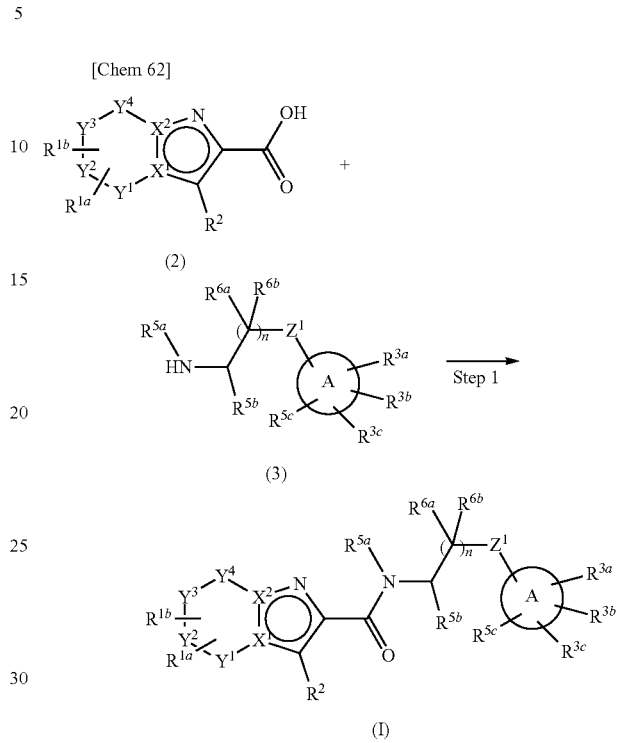

[wherein, ring A, $R^{1a}$, $R^{1b}$, $R^2$, $R^{3a}$, $R^{3b}$, $R^{3c}$, $R^{5a}$, $R^{5b}$, $R^{5c}$, $R^{6a}$, $R^{6b}$, n, $X^1$, $X^2$, $Y^1$, $Y^2$, $Y^3$, $Y^4$ and $Z^1$ are as defined for the general formula (I) in the (0)]

Step 1

In Step 1, the compound represented by the general formula (I) can be produced by condensation reaction of the compound represented by the general formula (2) and the compound represented by the general formula (3), wherein condensation reaction uses a condensing reagent in the presence or absence of a base. As the condensing reagents, N,N'-dicyclohexylcarbodiimide (DCC), 1-ethyl-3-(3-dimethylaminopropyl)carbodiimide hydrochloride (EDC), 1,1'-carbonyldiimidazole (CDI), 2-chloro-1-methylpyridinium iodide, propylphosphonic anhydride (cyclic trimer), O-(7-azabenzotriazol-1-yl)-N,N,N',N'-tetramethyluronium hexafluorophosphate (HATU) and so on can be recited.

As the base, organic bases such as trimethylamine, triethylamine, diisopropylethylamine, tripropylamine, triisopropylamine, tributylamine, N-methylmorpholine, pyridine, 4-(N,N-dimethylamino)pyridine, N,N-dimethylaniline, N,N-diethylaniline, 1,5-diazabicyclo[4.3.0]non-5-ene, 1,4-diazabicyclo[2.2.2]octane (DABCO), 1,1,3,3-tetramethylguanidine, or 1,8-diazabicyclo[5.4.0]-7-undecene (DBU) can be recited.

As the reaction solvent, halogenated hydrocarbon solvents such as dichloromethane and so on; esters such as ethylacetate and so on; ethers such as tetrahydrofuran and so on; amides such as N,N-dimethylformamide, N,N-dimethylacetoamide and so on; ketones such as acetone, methylethylketone and so on; aromatic hydrocarbon solvents such as toluene and so on; and a mixed solvent of these and so on can be recited. If necessary, a reaction reagent such as 1-hydroxybenzotriazole (HOBt) and so on may be added.

Reaction temperature is not particularly limited; the reaction is normally performed at 0° C. to 100° C. Reaction time is not particularly limited; 1 hour to 24 hours is preferable.

In addition, after the reaction intermediate is derivatized from the compound represented by the general formula (2) by using an activator for a carboxyl group, the compound represented by general formula (I) can be produced by reacting with the compound represented by the general formula (3).

As the activator for a carboxylic group, thionyl chloride, oxalyl chloride, phosphorus oxychloride, phosgene, triphosgene, 1,1'-carbonyldiimidazole, ethyl chlorocarbonate and so on can be recited.

As the reaction solvent, aromatic hydrocarbon solvents such as benzene, toluene, chlorobenzene, nitrobenzene, xylene and so on; halogenated hydrocarbon solvents such as chloroform, dichloromethane and so on; ethers such as tetrahydrofuran and so on; ketones such as acetone, methylethylketone and so on; nitriles such as acetonitrile, propionitrile and so on; and a mixed solvent of these and so on can be recited.

Reaction temperature is not particularly limited; the reaction is normally performed at 0° C. to 100° C. Reaction time is not particularly limited; 1 hour to 24 hours is preferable.

Among the compounds represented by the general formula (2) in the reaction scheme-1, the compound represented by the general formula (2-c) can be produced, for example, by the method indicated by the following reaction scheme-3.

<Reaction Scheme-3> example, chlorine atom, bromine atom, iodine atom, methanesulfonyloxy group, trifluoromethanesulfonyloxy group, or p-toluenesulfonyloxy group and so on), $Y^{1a}$ is O, or NH, and $Y^{3a}$ is a single bond, methylene or ethylene.]

The protecting group represented by P are not particularly limited as long as it is generally used as a protecting group for a hydroxy group, the following can be recited for example: lower alkyl groups such as a methyl group and so on; lower alkoxyalkyl groups such as a methoxymethyl group, an ethoxyethyl group and so on; optionally substituted benzyl groups (as the substituent, a nitro group, a lower alkoxy group and so on can be recited); lower alkoxycarbonyl groups; halogeno lower alkoxycarbonyl groups; optionally substituted bezyloxy benzyloxycarbonyl groups (as the substituent, a nitro group, lower alkoxy group and so on can be recited); acyl groups such as an acetyl group, a benzoyl group and so on; a triphenylmethyl group; a tetrahydropyranyl group; tri-substituted silyl groups such as a trimethylsilyl group, triethylsilyl group, a t-butyldimethylsilyl group, a triisopropylsilyl group, a dimethylhexylsilyl group, a t-butyldiphenylsilyl group and so on.

Step 7

In Step 7, the compound represented by the general formula (13) can be produced by reacting the compound represented by the general formula (11) and the compound represented by the general formula (12) with an azodicarboxylic acid derivative and phosphine derivative.

As the azodicarboxylic acid derivative, ethyl azodicarboxylate, isopropyl azodicarboxylate, 1,1'-(azodicarbonyl)dipyperidine and so on can be recited.

[Chem 63]

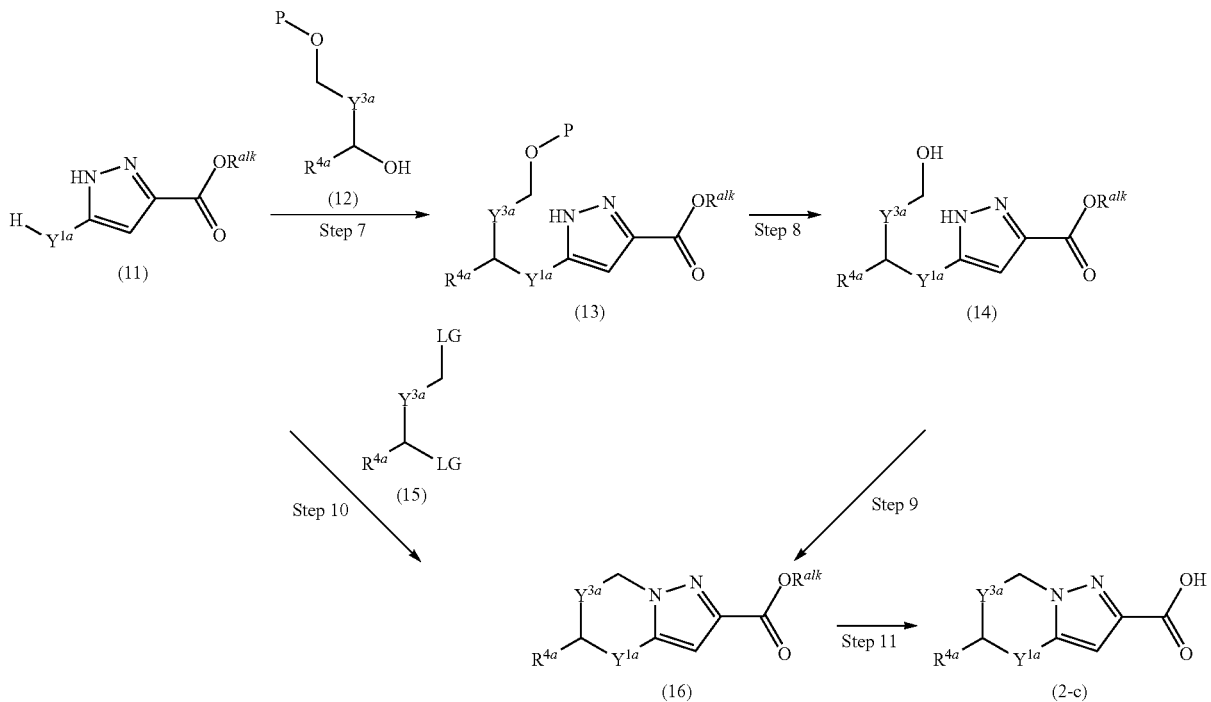

[wherein,
$R^{4a}$ is as defined for the general formula (I) in the (0).
$R^{alk}$ is an alkyl group having 1 to 8 carbon atoms, P is a protecting group, LG is a leaving group (for As the phosphine derivative, triphenylphosphine, tri-n-butylphosphine and so on can be recited. In addition, a phosphorane reagent such as cyanomethylenetributylphosphorane, cyanomethylenetrimethylphosphorane and so on can be used for performing the similar reaction instead of the azodicarboxylic acid derivative and the phosphine derivative.

The reaction solvent is not particularly limited as long as it is a neutral solvent; for example, tetrahydrofuran, toluene or a mixture thereof can be recited.

Reaction temperature is not particularly limited; the reaction is normally performed at 0° C. to 80° C. Reaction time is not particularly limited; 1 hour to 24 hours is preferable.

In addition, the compound represented by the general formula (13) can also be produced by reacting with the compound represented by the general formula (11) in the presence of a base after the hydroxy group in the compound represented by the general formula (12) is converted into a leaving group by a method well known to those skilled in the art.

As the reagent converting into the leaving group, the following can be recited: Thionyl chloride, sulfuryl chloride, oxalyl chloride, phosphorus trichloride, phosphorus pentachloride, phosphorus tribromide, phosphorus pentabromide, carbon tetrabromide, dimethylbromosulfonium bromide, thionyl bromide, phosphorus triiodide, p-toluene sulfonyl chloride, methanesulfonyl chloride, trifluoromethanesulfonyl chloride, trifluoromethanesulfonic anhydride and so on.

As the base, the following can be recited: Inorganic bases such as potassium carbonate, potassium bicarbonate, potassium acetate, sodium acetate, sodium carbonate, sodium bicarbonate, cesium carbonate, lithium carbonate, tripotassium phosphate, potassium tert-butoxide, sodium tert-butoxide, potassium fluoride, potassium hexamethyldisilazane or sodium hydride and so on; organic bases described in the above (Step 1).

As the reaction solvent, aromatic hydrocarbons such as benzene, toluene, xylene and so on; halogenated hydrocarbons such as dichloromethane, chloroform, 1,2-dichloroethane and so on; nitriles such as acetonitrile, propionitrile and so on; ethers such as diethyl ether, tetrahydrofuran, 1,4-dioxane, 1,2-dimethoxyethane and so on; aprotic polar solvents such as N,N-dimethylformamide, N,N-dimethylacetamide, N-methylpyrrolidone, dimethylsulfoxide and so on; and mixture solvents thereof and so on can be recited without being limited thereto.

Reaction temperature is not particularly limited; the reaction is normally performed at room temperature to 140° C. Reaction time is not particularly limited; 1 hour to 24 hours is preferable.

Step 8

In step 8, the compound represented by the general formula (14) can be produced by the deprotecting reaction for the compound represented by the general formula (13). Such deprotecting reactions may be performed according to methods well known to those skilled in the art (for example, methods described in Green and Wuts, "Protective Groups in Organic Synthesis (3rd edition, 1999)").

Step 9

In Step 9, the compound represented by the general formula (16) can be produced by reacting the compound represented by the general formula (14) in the presence or absence of a base with a halogenating reagent and a phosphine derivative.

As the base, the base described in the above (Step 7) is preferable for example.

As the halogenating reagent, carbon tetrachloride, carbon tetrabromide, hexachloroacetone, hexabromoacetone, triphosgene, lithium bromide, methyl iodide, bromine and iodine and so on can be recited.

As the phosphine derivative, triphenylphosphine, tri-n-butylphosphine and so on can be recited.

The reaction solvent is not particularly limited as long as it does not significantly inhibit the reaction, and the solvents described in (Step 7) can be recited for example.

Reaction temperature is not particularly limited; the reaction is normally performed at room temperature to 120° C. Reaction time is not particularly limited; 1 hour to 24 hours is preferable.

Step 10

In Step 10, the compound represented by the general formula (16) can be produced by a cyclization reaction of the compound represented by the general formula (11) and the compound represented by the general formula (15) in the presence or absence of a base.

The bases described in the (Step 7) above are preferable for example.

To smoothly perform the reaction, an additive may be co-present. As the additive, potassium iodide, sodium iodide, tetrabutylammonium iodide, potassium bromide, sodium bromide, tetrabutylammonium bromide and so on can be recited.

The reaction solvent is not particularly limited as long as it does not significantly inhibit the reaction, and the solvents described in (Step 7) can be recited for example.

Reaction temperature is not particularly limited; the reaction is normally performed at room temperature to 120° C. Reaction time is not particularly limited; 1 hour to 24 hours is preferable.

Step 11

In Step 11, the compound represented by the general formula (2-c) can be produced by hydrolyzing the compound represented by general formula (16) in the presence of a base or acid, which is a method similar to one described in step 4 in reaction scheme-1.

Among the compounds represented by the general formula (2) in the reaction scheme-1, the compound represented by the general formula (2-d) can be produced by the method shown by the following reaction scheme-5 for example.

<Reaction Scheme-5>

[Chem 64]

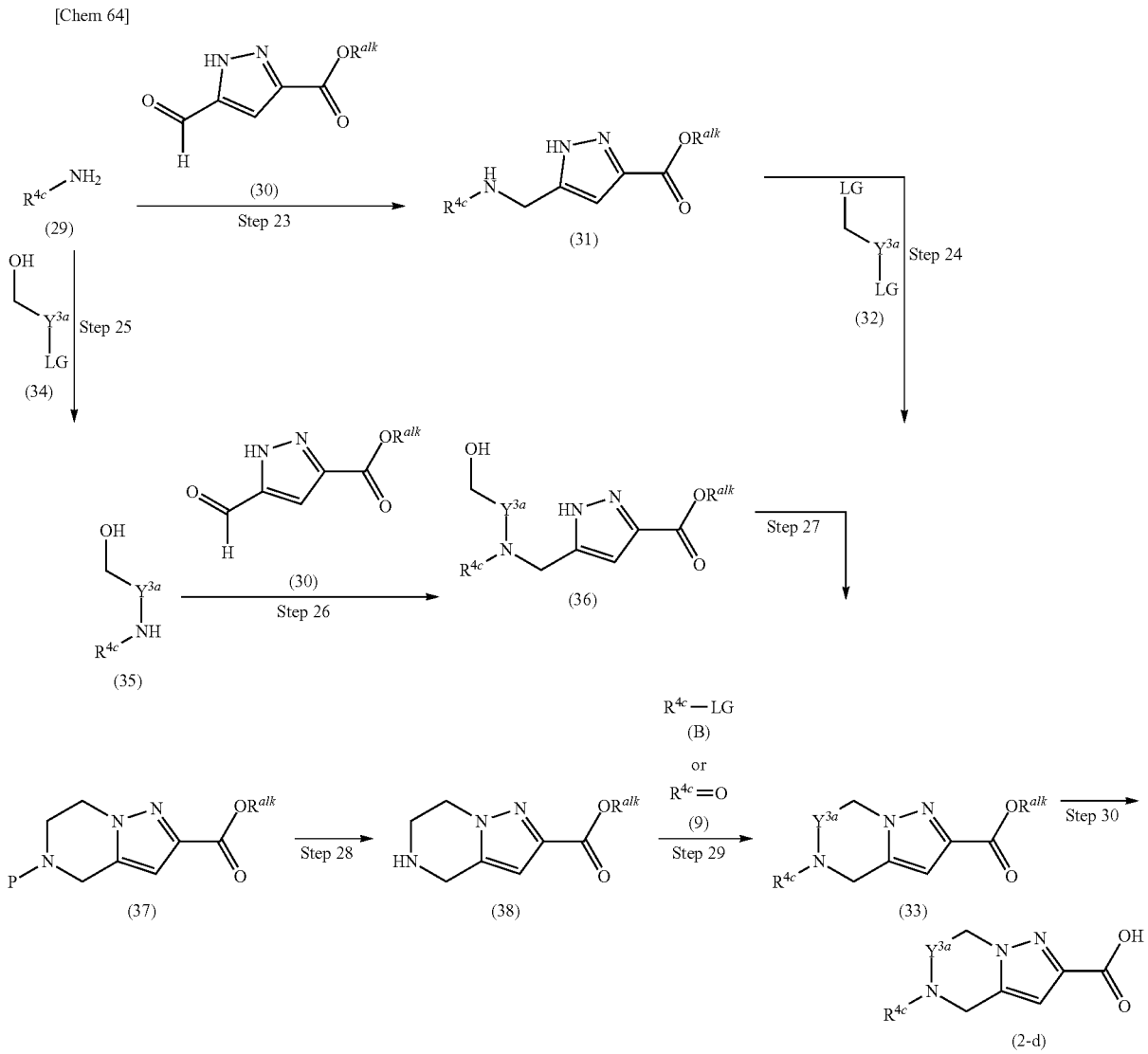

[wherein, $R^{4c}$ is as defined for the general formula (I) in the (0). In addition, $R^{alk}$ (is an alkyl group having 1 to 8 carbon atoms, P is a protecting group, LG is a leaving group (for example, a chlorine atom, a bromine atom, an iodine atom, a methanesulfonyloxy group, a trifluoromethanesulfonyloxy group, or a p-toluene sulfonyloxy group and so on), $Y^{3a}$ is a methylene or an ethylene.]

As the protecting group represented by P, being not particularly limited as long as it is generally used as a protecting group for an amino group, for example, the following can be recited: A tert-butoxycarbonyl (Boc) group, a benzyloxycarbonyl (Cbz), a 9-fluorenylmethyloxycarbonyl (fmoc), an acetyl (Ac) group, a trifluoroacetyl group, benzyl (Bn) group, a 4-methoxybenzyl (PMB) group and so on.

Step 23

In Step 23, the compound represented by the general formula (31) can be produced by a reductive alkylization reaction with the compound represented by the general formula (29) and the compound represented by the general formula (30) in the presence or absence of an acid or a base, using a reducing reagent.

As the base, the bases described in the (Step 7) above are preferable for example.

As the acid to be used, formic acid, acetic acid, propionic acid, isobutyric acid, hexanic acid, p-toluenesulfonic acid or benzoic acid and so on can be recited.

As the reducing reagent, sodium borohydride, sodium triacetoxyborohydride, sodium cyanoborohydride, dimethylamine borane, triethylamine borane, trimethylamine borane, tert-butylamine borane, N,N-diethylaniline borane or 2-picoline borane and so on can be recited.

The reaction solvent is not particularly limited as long as it does not significantly inhibit the reaction, and the solvents described in (Step 7) can be recited for example.

Reaction temperature is not particularly limited; the reaction is normally performed at 0° C. to 100° C. Reaction time is not particularly limited; 1 hour to 24 hours is preferable.

Step 24

In Step 24, the compound represented by the general formula (33) can be produced by a cyclization reaction with the compound represented by the general formula (31) and the compound represented by the general formula (32) in the presence or absence of a base, which is a method similar to one described in Step 10 in reaction scheme-3.

Step 25

In Step 25, the compound represented by the general formula (35) can be produced by the reaction with the compound represented by the general formula (29) and the compound represented by the general formula (34) in the presence or absence of a base.

As the base, the base described in the above (Step 7) is preferable for example.

To smoothly perform the reaction, an additive may be co-present; as the additive, the additive described in (Step 10) can be recited.

The reaction solvent is not particularly limited as long as it does not significantly inhibit the reaction, and the solvents shown in (Step 7) can be recited for example.

Reaction temperature is not particularly limited; the reaction is normally perfomed at room temperature to 120° C. Reaction time is not particularly limited; 1 hour to 24 hours is preferable.

Step 26

In Step 26, the compound represented by the general formula (36) can be produced by a reductive alkylization reaction with the compound represented by the general formula (35) and the compound represented by the general formula (30) in the presence or absence of an acid or base by using a reducing reagent, which is a method similar to one described in Step 23 in reaction scheme-5.

Step 27

In Step 27, the compound represented by the general formula (33) can be produced by reacting the compound represented by the general formula (36) in the presence or absence of a base with a halogenating reagent and phosphine derivative, which is a method similar to one described in Step 9 in reaction scheme-3.

Step 28

In step 28, the compound represented by the general formula (38) can be produced by a deprotecting reaction with the compound represented by the general formula (37). Such deprotecting reactions may be performed according to methods well known to those skilled in the art (for example, methods described in Green and Wuts, "Protective Groups in Organic Synthesis (3rd edition, 1999)").

Step 29

In Step 29, the compound represented by the general formula (33) can be produced by reacting the compound represented by the general formula (38) with the compound represented by the general formula (8) or the compound represented by the general formula (9), which is a method similar to one described in Step 5 in scheme-2.

Step 30

In Step 30, the compound represented by the general formula (2-d) can be produced by hydrolyzing the compound represented by the general formula (33) in the presence of a base or acid, which is a method similar to one described in Step 4 in scheme-2.

Among the compounds represented by the general formula (2) in the reaction scheme-1, the compound represented by the general formula (2-e) can be produced by the method shown by the following reaction scheme-6 for example.

<Reaction Scheme-6>

[Chem 65]

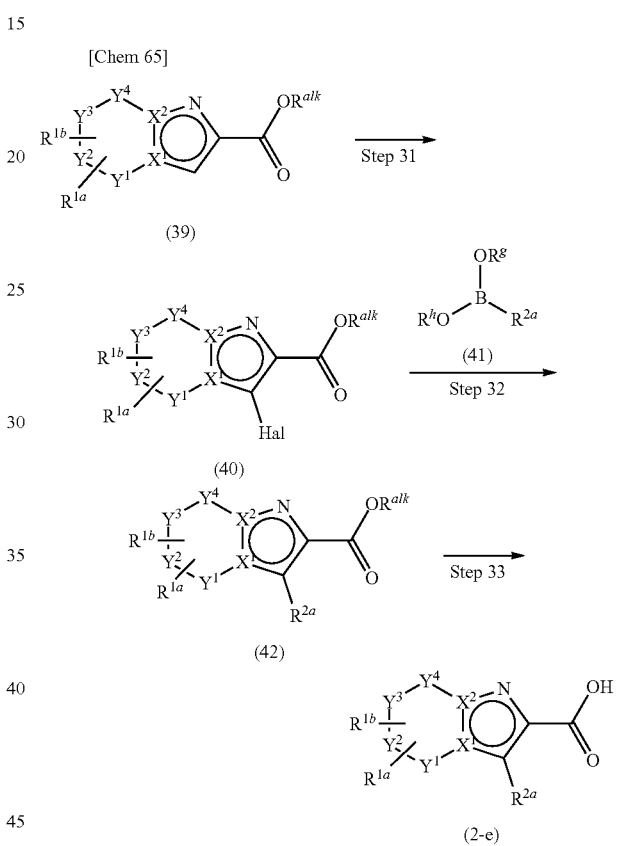

[wherein,
$R^{1a}$, $R^{1b}$, $X^1$, $X^2$, $Y^1$, $Y^2$, $Y^3$ and $Y^4$ are as defined for the general formula (I) in the (0).
$R^{alk}$ is an alkyl group having 1 to 8 carbon atoms,
$R^g$ and $R^h$ are, independently each other, a hydrogen atom or an optionally substituted alkyl group, or
$R^g$ and $R^h$ form an optionally substituted non-aromatic hetero ring with the oxygen atoms bonded thereto and the boron atom bonded to the oxygen atom,
$R^{2a}$ is an optionally substituted partially-saturated or unsaturated 3- to 7-membered monocyclic ring,
Hal is a halogen atom (for example, chlorine atom, bromine atom, iodine atom).]

Step 31

In Step 31, the compound represented by the general formula (40) can be produced by subjecting the compound represented by the general formula (39) to a halogenating reagent.

As the halogenating reagent, chlorine, bromine, iodine, N-chlorosuccinimide, N-bromosuccinimide, N-iodosuccinimide, 1,3-dichloro-5,5-dimethylhydantoin, 1,3-dibromeo-5,5-dimethylhydantoin and so on can be recited.

An appropriate acid such as acetic acid, trifluoroacetic acid, hydrochloric acid and so on may be added at this reaction.

The reaction solvent is not particularly limited as long as it does not significantly inhibit the reaction, and the solvents described in (Step 7) can be recited for example.

Reaction temperature is not particularly limited; the reaction is normally performed at room temperature to 140° C. Reaction time is not particularly limited; 1 hour to 24 hours is preferable.

Step 32

In Step 32, the compound represented by the general formula (42) can be produced by reacting the compound represented by the general formula (41) with the compound represented by the general formula (40) in the co-presence of a palladium catalyst and base.

As the palladium catalyst, the following can be recited: Palladium metals such as palladium-carbon and palladium black and so on; organic palladium salt such as tetrakis(triphenylphosphine)palladium, dichlorobis(triphenylphosphine)palladium, palladium acetate, palladium chloride-1,1'-bis(diphenylphosphino)ferrocene or bis(di-tert-butyl (4-dimethylaminophenyl) phosphine) dichloropalladium (II); and polymer-supported organic palladium complexes such as polymer-supported bis(acetate) triphenylphosphine palladium (II) and polymer-supported di(acetate)dicyclohexylphenylphosphine palladium (II), and so on. These may be used in combination.

The addition amount of the palladium catalyst relative to the compound represented by the general formula (40) normally is 1 to 50 mol %, preferably 5 to 20 mol %.

As the base, for example, the base described in the above (Step 7) is preferable.

To smoothly perform the reaction, an additive may be co-present; as the additive, the following can be recited: Trialkylphosphines such as trimethylphosphine and tritert-butylphosphine and so on; tricycloalkylphosphines such as tricyclohexylphosphine and so on; triarylphosphines such as triphenylphosphine and tritolylphosphine and so on; trialkylphosphites such as trimethylphosphite, triethylphosphite and tributylphosphite and so on; tricycloalkylphosphites such as tricyclohexylphosphite and so on; triarylphosphites such as triphenylphosphite and so on; imidazolium salt such as 1,3-bis(2,4,6-trimethylphenyl)imidazolium chloride and so on; diketones such as acetylacetone and octafluoro acetylacetone and so on; amines such as trimethylamine, triethylamine, tripropylamine, triisopropylamine and tributylamine and so on; 1,1'-bis(diphenylphosphino)ferrocene; 2,2'-bis(diphenylphosphino)-1,1'-binaphtyl; 2-dicyclohexylphosphino-2',6'-dimethoxybiphenyl; 2-dicyclohexylphosphino-2',4',6'-triisopropylbiphenyl; 2-(di-tert-butylphosphino)-2',4',6'-triisopropylbiphenyl; 2-dicyclohexylphosphino-2'-(N,N-dimethylamino)biphenyl; 4,5-bis(diphenylphosphino)-9,9-dimethylxanthene; and 2-(di-tert-butylphosphino)biphenyl. These additives may be used in combination.

The reaction solvent is not particularly limited as long as it does not significantly inhibit the reaction, and the solvents described in (Step 7) can be recited for example.

Reaction temperature is not particularly limited; the reaction is normally performed at room temperature to 140° C. Reaction time is not particularly limited; 1 hour to 24 hours is preferable.

Step 33

In Step 33, the compound represented by the general formula (2-e) can be produced by hydrolyzing the compound represented by the general formula (42) in the presence of a base or acid, which is a method similar to one described in Step 4 in scheme-2.

Among the compounds represented by the general formula (3) in the reaction scheme-1, the compound represented by the general formula (3-a) can be produced, for example, by the method shown by the following reaction scheme-7.

<Reaction Scheme-7>

[Chem 66]

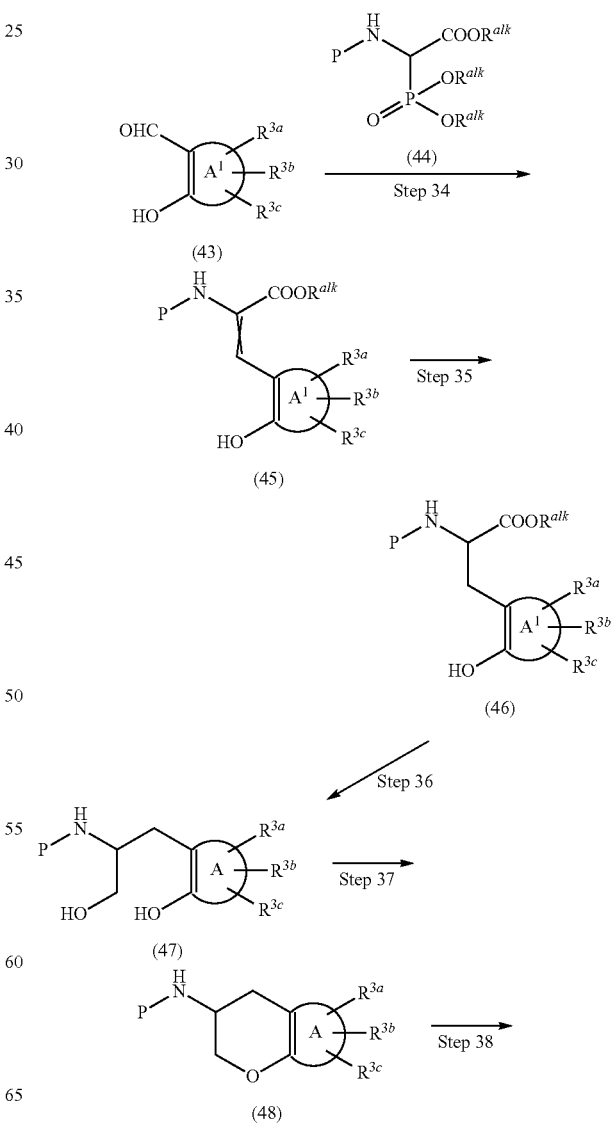

-continued

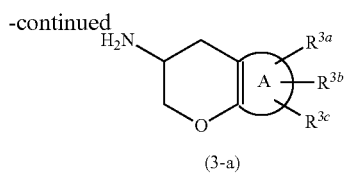

(3-a)

[wherein,
R³ᵃ, R³ᵇ, R³ᶜ are as defined for the general formula (I) in the (0).
Ring A¹ is a 3- to 7-membered monocyclic aromatic ring, Rᵃˡᵏ (is an alkyl group having 1 to 8 carbon atoms, and P is a protecting group.]

As the protecting group represented by P, protecting groups described in <Reaction scheme-5> can be recited.

Step 34

In Step 34, the compound represented by the general formula (45) can be produced by reacting the compound represented by the general formula (44) with the compound represented by the general formula (43) in the presence of a base.

As the base, for example, the bases described in (Step 1) are preferable.

The reaction solvent is not particularly limited as long as it does not significantly inhibit the reaction. For example, the solvents described in (Step 7), esters such as ethyl acetate and so on and a mixed solvent thereof can be recited.

Reaction temperature is not particularly limited; the reaction is normally performed at room temperature to 120° C. Reaction time is not particularly limited; 1 hour to 24 hours is preferable.

Step 35

In Step 35, the compound represented by the general formula (46) can be produced by a catalytic reduction reaction with the compound represented by the general formula (45) in the presence of a transition metal catalyst and hydrogen.

As the transition metal catalyst, palladium on carbon, palladium hydroxide, Raney nickel, platinum oxide and so on can be recited.

The amount of the transition metal catalyst added is, relative to the weight of the compound represented by the general formula (45), normally five times or less, and preferably 0.01 to 0.5 times.

The reaction solvent is not particularly limited as long as it does not significantly inhibit the reaction, the following can be recited: Alcohols such as methanol and ethanol; esters such as methyl acetate and ethyl acetate; ethers such as diethyl ether, tetrahydrofuran, 1,4-dioxane and 1,2-dimethoxyethane; aprotic polar solvents such as N,N-dimethylformamide, N,N-dimethylacetamide, N-methylpyrrolidone and dimethylsulfoxide; protic polar solvents such as acetic acid; water; and mixed solvents thereof.

Reaction temperature is not particularly limited; the reaction is normally performed at 0° C. to 80° C. under the normal pressure or pressurized conditions. Reaction time is not particularly limited; 1 hour to 24 hours is preferable.

Step 36

In Step 36, the compound represented by the general formula (47) can be produced by the reduction of an ester of the compound represented by the general formula (46) using a reducing reagent to an alcohol.

As the reductant, lithium aluminum hydride, sodium borohydride, lithium borohydride, borane and so on can be recited.

The reaction solvent is not particularly limited as long as it does not significantly inhibit the reaction, the following can be recited: Aromatic hydrocarbons such as benzene, toluene and xylene; alcohols such as methanol, ethanol and 2-propanol; ethers such as diethyl ether, tetrahydrofuran, and 1,4-dioxane; aprotic polar solvents such as N,N-dimethylformamide, N,N-dimethylacetamide, N-methylpyrrolidone, and dimethylsulfoxide; and mixed solvents thereof.

Reaction temperature is not particularly limited; the reaction is normally performed at 0° C. to 100° C. Reaction time is not particularly limited; 1 hour to 24 hours is preferable.

Step 37

In Step 37, the compound represented by the general formula (48) can be produced by reacting an azodicarboxylic acid derivative and phosphine derivative with the compound represented by the general formula (47).

As the azodicarboxylic acid derivative, ethyl azodicarboxylate, isopropyl azodicarboxylate, 1,1'-(azodicarbonyl)dipiperizine and so on can be recited.

As the phosphine derivative, triphenylphosphine, tri-n-butylphosphine and so on can be recited.

In addition, a phosphorane reagent such as cyanomethylenetributylphosphorane, cyanomethylenetrimethylphosphorane and so on can be used for performing the similar reaction instead of the azodicarboxylic acid derivative and phosphine derivative.

The reaction solvent is not particularly limited as long as it is a neutral solvent; for example, tetrahydrofuran, toluene or a mixture thereof can be recited.

Reaction temperature is not particularly limited; the reaction is normally performed at 0° C. to 80° C. Reaction time is not particularly limited; 1 hour to 24 hours is preferable.

Step 38

In Step 38, the compound represented by the general formula (3-a) can be produced by a deprotecting reaction of the compound represented by the general formula (48). Such deprotecting reactions may be performed according to methods well known to those skilled in the art (for example, methods described in Green and Wuts, "Protective Groups in Organic Synthesis (3rd edition, 1999)").

In the above production method, the starting material, intermediate or final product can also be induced to other compounds included by the present invention by appropriately converting the functional group. Conversion of the functional group can be performed by a method well known to those skilled in the art (for example, the method described in "Comprehensive Organic Transformations" by R. C. Larock, 1989 and so on).

The compound represented by the general formula (I) produced by the aforementioned method may be isolated and purified as a free compound, salt thereof, solvate such as a hydrate or ethanol solvate thereof or crystal polymorphic substance. The pharmaceutically acceptable salt of the compound of the present invention can be produced by a conventional salt formation reaction. The isolation and purification may be performed by applying chemical operations such as extraction fractionation, crystallization, and various fractional chromatographies.

In addition, an optically active compound can be obtained as a stereochemically pure isomer by selecting an appropriate raw material compound or by a conventional optical resolution of a racemate. For example, in the case of optical resolution of a racemate using a chiral column, a method known to those skilled in the art (see, for example, "Separation of optical isomers" Quarterly Chemical Review No. 6, 1989, Chemical Society of Japan, Society Publishing Center) can be employed. Furthermore, as chiral columns, various ones are commercially available and suitable one may appropriately be selected; as preferred examples, CHIRALPAK IA, CHIRALPK IB, and CHIRALPAK IC manufactured by Daicel Corporation can be recited.

The present inventive compounds may have optical isomers, stereoisomers, tautomers and/or geometric isomers; in addition, the present inventive compounds include all possible isomers including the above mentioned isomers and mixtures thereof. Likewise, raw materials and intermediates for synthesizing the present inventive compounds may also have optical isomers, stereoisomers, tautomers and/or geometric isomers, and the raw materials and intermediates for producing the present inventive compound also includes all possible isomers including the above mentioned isomers and mixtures thereof.

Prodrugs of the present inventive compound can be produced, for example, by substituting an appropriate functional group existing on the present inventive compound with an appropriate protecting group in accordance with a method known to those skilled in the art (for example, a method described in "Design of Prodrugs" by H. Bundgaard, Elseverer, 1985 and so on).

Because the present inventive compounds or salts thereof selectively inhibit Nav1.7 over Nav1.5, they have little concern about a side effects derived from Nav1.5 inhibition and very effectively act on a wide range of pathological conditions associated with Nav1.7. Even though various pathological conditions are associated with Nav1.7, the present inventive compounds or salts thereof are, for example, effective for treating or preventing pain. More specifically, the present inventive compounds or salts thereof are useful, in particular, for treating or preventing acute pain, chronic pain, nociceptive pain, neuropathic pain and headache.

In addition, the present inventive compounds or salts thereof are useful, in particular, for treating or preventing acute or chronic pruritus and autonomic nervous system disorder.

Nociceptive pain is pain caused by tissue injury or by intense stimuli with the potential to cause injury, including the following pain:

Perioperative pain; chronic postsurgical pain; posttraumatic pain; inflammatory pain; cancer-related pain; pain associated with osteoarthritis; herpes zoster pain; renal colics; bladder pain; visceral pain; toothache; pain after tooth extraction; pain related to heart disease; pain associated with pancreatitis; pain associated with contusion or sprain; back pain; pain associated with musculoskeletal disorders and pain associated with chronic arthropathy.

Inflammatory pain includes pain associated with pathological conditions associated with the following inflammatory factors:

Rheumatoid arthritis; interstitial cystitis; skin diseases (for example, sunburn, burns, eczema, dermatitis, or psoriasis); eye diseases (for example, glaucoma, retinitis, retinopathy, uveitis or acute ocular tissue disorders); lung diseases (for example, asthma, bronchitis, allergic rhinitis, chronic obstructive pulmonary disease, acute respiratory distress syndrome or farmer's lung); pathological conditions associated with infections such as influenza or colds; digestive tract diseases (for example, aphthous ulcer, irritable bowel syndrome, inflammatory bowel syndrome, atopic gastritis, functional gastrointestinal disorder, gastroesophageal reflux disease, Crohn's disease, ileitis or ulcerative colitis); dysmenorrhea; organ transplantation; vascular diseases; periarteritis nodosa; thyroiditis; aplastic anemia; Hodgkin's disease; scleroderma; myasthenia gravis; systemic lupus erythematosus; Behcet's disease; Sjogren's syndrome; nephrotic syndrome; polymyositis; gingivitis; and fever.

Cancer-related pain includes pain associated with tumors, pain associated with cancer therapy.

Pain associated with musculoskeletal disorders includes myalgia, fibromyalgia, polymyositis, purulent myositis, temporomandibular myofascial pain. The back pain includes pain due to disc herniation, abnormalities in lumbar spine joint, sacroiliac joint, paraspinal muscles or posterior longitudinal ligament.

The chronic arthropathy includes rheumatoid arthritis, osteoarthritis, rheumatoid spondylitis, gouty arthritis and juvenile arthritis.

Neuropathic pain is pain caused by damage in the nervous system by trauma or disease, and neuropathic pain includes many disorders derived from various causes. Neuropathic pain includes the following pain without being limited thereto:

Peripheral neuropathic pain; central neuropathic pain; postherpetic neuralgia; diabetic neuropathy; trigeminal neuralgia; nonspecific low back pain; cancer neuropathic pain; pain associated with Parkinson's disease; pain associated with multiple neurosclerosis; HIV-related neuropathic pain; sciatica; complex regional pain syndrome; spinal canal stenosis; carpal tunnel syndrome; phantom limbpain; post-stroke pain; pain associated with spinal cord injury; pain associated with epilepsy; pain associated with convulsions; pain associated with vitamin deficiency; familial erythromelalgia; primary erythromelalgia; paroxysmal extreme pain disorder, orofacial pain; and pain resulted from burning mouth syndrome, toxins or chronic inflammatory conditions.

These neuropathic pain include spontaneous pain, sensory disturbance and sensory abnormalities, hyperesthesia, high sensitivity to noxious stimuli (heat, cold, mechanical hyperalgesia), painful sensation to innocuous stimuli (dynamic, static, thermal or cold allodynia), hypoalgesia and so on.

The headaches include migraine, cluster headache, tension headache, combined headache, headache associated with vascular disorders, secondary headache, autonomic cephalalgias and so on.

Pruritus includes itching associated with skin disease, drug eruption, pruritus in hemodialysis, eye pruritus, ear pruritus, pruritus caused by an insect bite, opioid-induced pruritus, pruritus associated with infections virus and so on, cutaneous lymphoma and neuropathic pruritus.

Autonomic nervous system disorder includes autonomic dysfunction, neurological gastritis, irritable bowel syndrome, Meniere's disease, hyperventilation syndrome and autonomic neuropathy.

Note that the diseases mediated by the action of Nav1.7 are recited above as examples and said diseases are not limited to those described above.

The medicament comprising the compound of the present invention or salt thereof as an active ingredient is formulated from the compound of the present invention or salt thereof alone or as a mixture with a pharmacologically acceptable solid or liquid carrier to be used in formulating. It can be formulated by conventional methods in the technical field. Examples of the pharmacologically acceptable solid or liquid carrier to be used in formulating include the following:

For example, excipients, binders, disintegrants, disintegration aids, fluidizers, lubricants, stabilizers, coating agents, plasticizers, brighteners, bases, emulsifiers, thickeners, suspension agents, dispersants, solvents, solubilizers, solubilization aids, surfactants, antioxidants, buffers, isotonic agents, pH adjusters, preservatives, antiseptic agents, fragrances, colorants, sweeteners, flavoring agents and other additives.

The present inventive medicament can be administered orally or parenterally to mammals (e.g. humans, monkeys, cows, horses, pigs, dogs, cats, rabbits, guinea pigs, rats, mice and so on). As examples of dosage forms for administering present inventive medicament the following can be recited:

For example, tablets (including sugar-coated tablets, film-coated tablets), capsules, granules, powders, oral liquid medicines, syrups, oral jelly agents, tablets for oral cavity, liquid medicines for oral cavity, sprays for oral cavity, semisolids for oral cavity, injections, dialysis agents, inhalants, eye drops, eye ointments, ear drops, nasal drops, suppositories, semi-solid preparations for rectum, enemas, tablets for vagina, suppositories for vagina, topical solid agent, topical liquids agent (including liniments and lotions), sprays, ointments, creams, gels, patches and so on.

In addition, if necessary, another drug may be blended to the present inventive medicament.

When the present inventive compound is orally administered, the dosage form is not particularly limited as long as the dosage form is used as a pharmaceutical composition for oral administration; for example, it is possible to prepare a dosage form such as tablets, capsules, granules or syrups and so on. When the present inventive medicament including these dosage forms is prepared, each dosage form can be prepared by a conventional method in the present technical field.

In addition, the dose and frequency of administration of the present inventive medicament are not limited, and can be determined and/or adjusted with considering the age and weight of the subject to be administered. For example, in orally administering to an adult patient, an active ingredient, the compound of the present invention or salt thereof, is normally administered in a dose of about 0.001 mg to about 1000 mg per kg body weight at a time and it may be administered at a normal frequency.

EXAMPLE

Hereinbelow, features of the present invention will more specifically be explained by reciting examples and test examples.

The materials, the amount used, the ratios, the processing content, the processing procedures and so on indicated in the following Examples can appropriately be changed as long as not departing from the subject matter of the present invention.

Hence the scope of the present invention should not be interpreted limitatively by the specific examples shown hereinbelow.

The $^1$H-NMR spectra shown hereinbelow were measured by a JNM-ECA400 type spectrometer (400 MHz, manufactured by JEOL Ltd.) or AVANCEIII HD400 type (400 MHz, manufactured by Bruker BioSpin Co., Ltd.), by using deuterated chloroform (CDCl$_3$), deuterated dimethyl sulfoxide (DMSO-d$_6$), deuterated methanol (CD$_3$OD) as a solvent, and tetramethylsilane (TMS) as an internal standard. In the measurement results for the chemical shift, the δ value was expressed in ppm and the J value of the coupling constant was expressed in Hz. In the abbreviation, "s" means "singlet", "d" means "doublet", "t" means "triplet", "q" means "quartert", "m" means "multiplet" and "br" means "broad". Mass spectrum (ESI-MS) was measured by electrospray ionization with Exactive (manufactured by Thermo Fisher Scientific Co., Ltd.). The chemical structural formulae and physical property values of the compound in each Example are shown in the tables shown below.

Ac: acetyl
ADDP: 1,1'-(azodicarbonyl) dipiperidine
(A$^{ta}$Phos)$_2$PdCl$_2$: bis(di-tert-butyl(4-dimethylaminophenyl)phosphine)dichloropalladium(II)
Bn: benzyl
Boc: tert-butoxycarbonyl
Bu: butyl
CAN: ammonium cerium (IV) nitrate
DAST: N,N-diethylaminosulfur trifluoride
DBU: diazabicycloundecene
DCE: 1,2-dichloroethane
DCM: dichloromethane
DDQ: 2,3-dichloro-5,6-dicyano-p-benzoquinone
DIAD: diisopropyl azodicarboxylate
DIEA: N,N-diisopropylethylamine
DMAP: N,N-dimethyl-4-aminopyridine
DME: 1,2-dimethoxyethane
DMF: N,N-dimethylformamide
DMSO: dimethyl sulfoxide
Et: ethyl
EDCI: 1-(3-dimethylaminopropyl)-3-ethylcarbodiimide
HATU: O-(7-azabenzotriazol-1-yl)-N,N,N',N'-tetramethyluronium hexafluorophosphate
HOBt: 1-hydroxybenzotriazole
HPLC: high performance liquid chromatography
i: iso
IPA: isopropyl alcohol
Me: methyl
Ms: methanesulfonyl
n: normal
NBS: N-bromosuccinimide
NCS: N-chlorosuccinimide
NIS: N-iodosuccinimide
NMM: N-methylmorpholine
nor-AZADO: 9-azanor adamantane N-oxyl
p: para
Ph: phenyl
PTSA: p-toluenesulfonic acid
TBAB: tetrabutylammonium bromide
TBA-HS: tetrabutylammonium hydrogen sulfate
TBAI: tetrabutylammonium iodide
TBAF: tetrabutylammonium fluoride
TBDPS: tert-butyldiphenylsilyl
tert: tertiary
tBuXphos: 2-di-tert-butylphosphino-2',4',6'-triisopropylbiphenyl
Tf: trifluoromethylsulfonyl
TEA: triethylamine
TFA: trifluoroacetic acid
TFAA: trifluoroacetic anhydride
THF: tetrahydrofuran
TMEDA: tetramethylethylenediamine
TMS: trimethylsilyl
TMG: 1,1,3,3-tetramethylguanidine
Ts: p-toluenesulfonyl Xantphos Pd G3: [(4,5'-bis(diphenylphosphino)-9,9'-dimethylxanthene)-2-(2'-amino-1,1'-biphenyl)]palladium(II) methanesulfonate The asterisks (*) appearing in the structural formulae in the Examples denote that the corresponding asymmetric carbon has a single steric structure. Regarding the notations of "isomer A", "isomer B", "isomer C" and "isomer D", among the plural compounds indicated by the same Example number, the isomers are specified as "isomer A", "isomer B", "isomer C" and "isomer D" in accordance with the order of collection by the high performance liquid chromatography in the Example.

Example 1

Production of N-(6-fluorochroman-3-yl)-6-(trifluoromethyl)-5,6,7,8-tetrahydroimidazo[1,2-a]pyridine-2-carboxamide

[Chem 67]

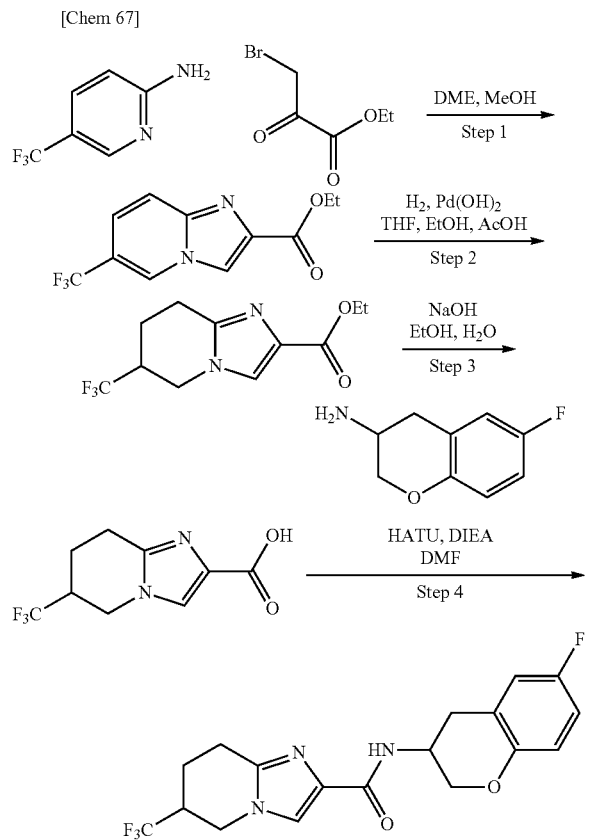

Step 1

To a mixed solution of 5-(trifluoromethyl)pyridin-2-amine (835 mg, 5.15 mmol) in 1,2-dimethoxyethane (12.9 mL) and methanol (12.9 mL) was added ethyl bromopyruvate (776 µL, 6.18 mmol), and the mixture was stirred for 14 hours at 80° C. After concentrating the reaction solution under reduced pressure, the residue was purified by silica gel column chromatography to give ethyl 6-(trifluoromethyl)imidazo[1,2-a]pyridine-2-carboxylate (amount 557 mg, yield 42%).

Step 2

To a mixed solution of ethyl 6-(trifluoromethyl)imidazo[1,2-a]pyridine-2-carboxylate (5.96 g, 23.1 mmol) in tetrahydrofuran (100 mL), ethanol (100 mL) and acetic acid (11.9 mL) was added 20% palladium hydroxide on carbon (2.43 g). The mixture was stirred under pressurized conditions (about 3 atm) at hydrogen atmosphere for 16 hours at room temperature. The reaction solution was filtered through celite and the solvent was evaporated off under reduced pressure. To the residue was added toluene, and the solvent was evaporated off under reduced pressure to give ethyl 6-(trifluoromethyl)-5,6,7,8-tetrahydroimidazo[1,2-a]pyridine-2-carboxylate (amount 6.42 g) as a crude product.

Step 3

To a solution of ethyl 6-(trifluoromethyl)-5,6,7,8-tetrahydroimidazo[1,2-a]pyridine-2-carboxylate (6.42 g, 24.5 mmol) in ethanol (49 mL) was added 4 mol/L aqueous solution of sodium hydroxide (24.5 mL, 98.0 mmol), and the mixture was stirred for 3 hours at room temperature. To the reaction solution, 1 mol/L hydrochloric acid (98.0 mL, 98.0 mmol) was added, and then the solvent was evaporated off under reduced pressure. To the residue was added toluene, the solvent was evaporated off under reduced pressure, and the procedure was repeated three times to give 6-(trifluoromethyl)-5,6,7,8-tetrahydroimidazo[1,2-a]pyridine-2-carboxylic acid (amount 11.2 g, yield 98%) as a mixture with 4 equivalents of sodium chloride.

Step 4

To a suspension of 6-(trifluoromethyl)-5,6,7,8-tetrahydroimidazo[1,2-a]pyridine-2-carboxylic acid (a mixture with 4 equivalents of sodium chloride) (30.0 mg, 0.0641 mmol) in N,N-dimethylformamide (641 µL) were added HATU (29.2 mg, 0.0769 mmol), N,N-diisopropylethylamine (55 µL, 0.32 mmol) and 6-fluorochroman-3-amine hydrochloride (14.4 mg, 0.0705 mmol), and the mixture was stirred for 6 hours at 40° C. To the reaction solution, water and ethyl acetate were added, and the mixture was partitioned. Thereafter, the organic layer was washed with saturated brine and dried over anhydrous magnesium sulfate. After the solvent was evaporated off under reduced pressure, the residue was purified by silica gel column chromatography to give N-(6-fluorochroman-3-yl)-6-(trifluoromethyl)-5,6,7,8-tetrahydroimidazo[1,2-a]pyridine-2-carboxamide (amount 17.9 mg, yield 73%).

Reference Example 1

Production of (R)-6-chlorochroman-3-amine hydrochloride

[Chem 68]

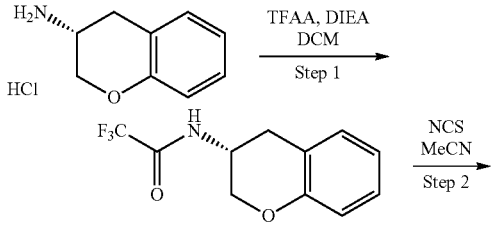

-continued

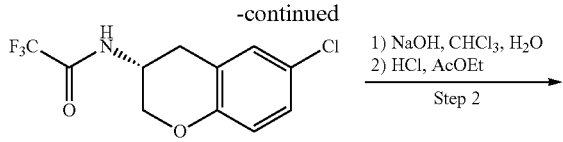

Step 1

To a suspension of (R)-chroman-3-amine hydrochloride (200 mg, 1.08 mmol) in dichloromethane (11 mL) were added N,N-diisopropylethylamine (555 µL, 3.23 mmol) and trifluoroacetic anhydride (180 µL, 1.29 mmol), and the mixture was stirred for 2 hours at room temperature. After concentrating the reaction solution under reduced pressure, the residue was purified by silica gel column chromatography to give (R)—N-(chroman-3-yl)-2,2,2-trifluoroacetamide (amount 245 mg, yield 93%).

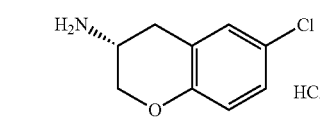

Step 2

To a solution of (R)—N-(chroman-3-yl)-2,2,2-trifluoroacetamide (4.00 g, 16.3 mmol) in acetonitrile (100 mL), N-chlorosuccineimide (2.60 g, 19.5 mmol) was added, and the mixture was stirred for 6 hours at 70° C. To the reaction solution were added saturated aqueous solution of sodium hydrogen carbonate and ethyl acetate, and the mixture was partitioned. Thereafter, the organic layer was washed with saturated brine and dried over anhydrous magnesium sulfate. The solvent was evaporated off under reduced pressure to give (R)—N-(6-chlorochroman-3-yl)-2,2,2-trifluoroacetamide (amount 4.60 g, yield 100%).

Step 3

To a solution of (R)—N-(6-chlorochroman-3-yl)-2,2,2-trifluoroacetamide (297 mg, 1.06 mmol) in chloroform (2.7 mL), 4 mol/L aqueous solution of sodium hydroxide (2.7 mL, 10.8 mmol) was added, and the mixture was stirred for 17 hours at room temperature. Water and chloroform were added to the reaction solution, and the mixture was partitioned. The organic layer was dried over anhydrous sodium sulfate. The solvent was evaporated off under reduced pressure and the residue was purified by silica gel column chromatography. To a solution of the purified compound in ethyl acetate, 4 mol/L hydrogen chloride-ethyl acetate solution was added, and then precipitated solid was filtered to give (R)-6-chlorochroman-3-amine hydrochloride (amount 60.9 mg, yield 67%).

Example 2

Production and isomeric separation of N—((R)-6-chlorochroman-3-yl)-6-(trifluoromethyl)-5,6,7,8-tetrahydroimidazo[1,2-a]pyridine-2-carboxamide

[Chem 69]

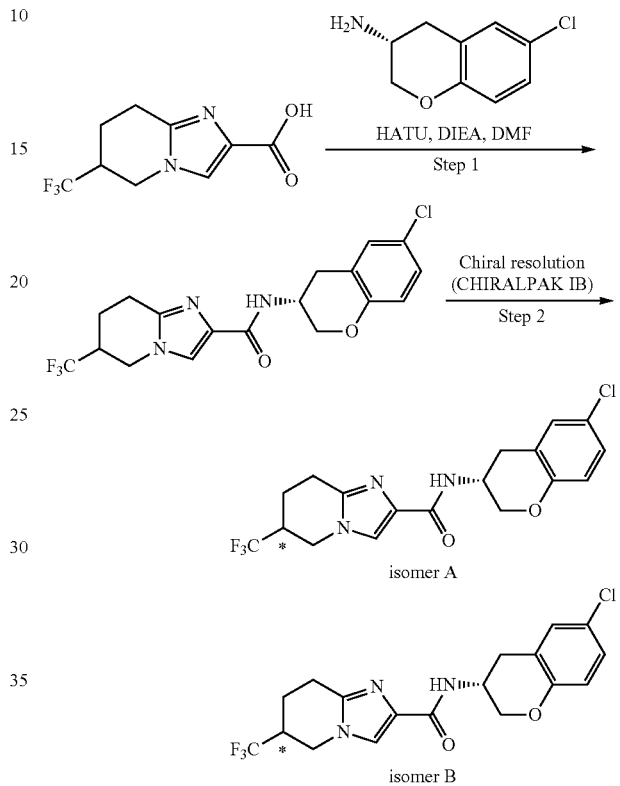

Step 1

To a suspension of 6-(trifluoromethyl)-5,6,7,8-tetrahydroimidazo[1,2-a]pyridine-2-carboxylic acid (a mixture with 4 equivalents of sodium chloride) (128 mg, 0.273 mmol) synthesized by a method described in Step 3 in Example 1 in N,N-dimethylformamide (2.27 mL) were added HATU (95.0 mg, 0.250 mmol), N,N-diisopropylethylamine (195 µL, 1.14 mmol) and (R)-6-chlorochroman-3-amine hydrochloride (50.0 mg, 0.227 mmol) synthesized by a method described in Reference Example 1, and the mixture was stirred for 15 hours at room temperature. Water was added to the reaction solution, and the precipitated solid was collected by filtration. The obtained solid was purified by silica gel column chromatography to give N—((R)-6-chlorochroman-3-yl)-6-(trifluoromethyl)-5,6,7,8-tetrahydroimidazo[1,2-a]pyridine-2-carboxamide (amount 60.9 mg, yield 67%).

Step 2

N—((R)-6-Chlorochroman-3-yl)-6-(trifluoromethyl)-5,6,7,8-tetrahydroimidazo[1,2-a]pyridine-2-carboxamide (50.0 mg, 0.125 mmol) was dissolved into ethanol (20 mL), and the solution was subjected to HPLC fractionation (column: CHIRALPAK IB, developing solvent: ethanol/n- hexane=50/50, flow rate: 5.0 mL/min, room temperature) to give isomer A (amount 16.8 mg, yield 34%) and isomer B (amount 14.3 mg, yield 29%).

The compound of Example 3 was synthesized from the compound of Example 2 (isomer A) under the scheme depicted in the figure below.

[Chem 70]

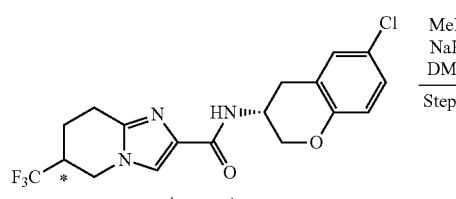

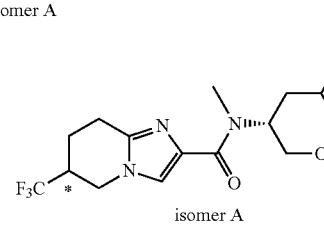

The compound of Example 4 was synthesized from the compound of Example 2 (isomer B) by a method similar to Example 3.

The compound of Reference Example 2 ((R)-6-bromochroman-3-amine hydrochloride) was synthesized under the scheme depicted in the figure below.

[Chem 71]

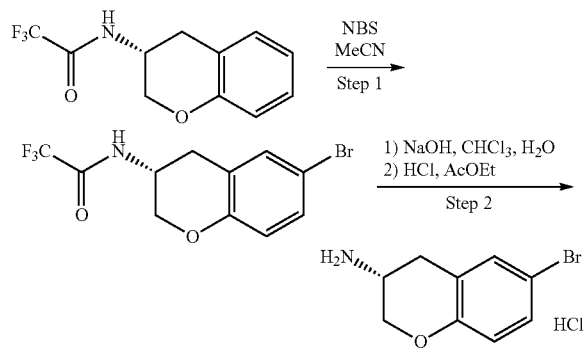

The compound of Example 5 was synthesized by methods similar to those described in Example 1 and Reference Example 2.

Reference Example 3

Production of (R)-6-(difluoromethyl)chroman-3-amine hydrochloride

[Chem 72]

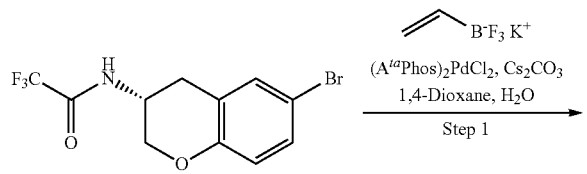

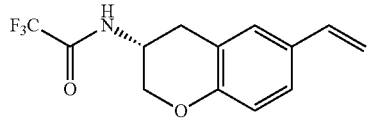

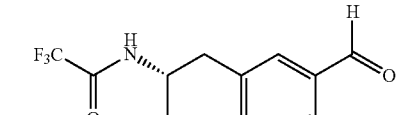

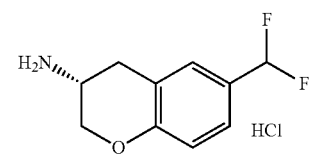

Step 1

A mixed suspension of (R)—N-(6-bromochroman-3-yl)-2,2,2-trifluoroacetamide (6.47 g, 20.0 mmol), potassium vinyl trifluoroborate (4.01 g, 29.9 mmol), cesium carbonate (13.0 g, 39.9 mmol) and bis(di-tert-butyl (4-dimethylaminophenyl)phosphine)dichloropalladium (II) (707 mg, 0.998 mmol) in 1,4-dioxane (167 mL) and water (33 mL) was stirred for 15 hours at 100° C. To the reaction solution, water and ethyl acetate were added, and the mixture was partitioned. Thereafter, the organic layer was washed with saturated brine and dried over anhydrous sodium sulfate. After the solvent was evaporated off under reduced pressure, the residue was purified by silica gel column chromatography to obtain (R)-2,2,2-trifluoro-N-(6-vinylchroman-3-yl)acetamide (amount 3.03 g, yield 56%).

Step 2

To a solution of (R)-2,2,2-trifluoro-N-(6-vinylchroman-3-yl)acetamide (3.03 g, 11.2 mmol) in 1,4-dioxane were added water (37 mL), 2,6-lutidine (2.6 mL, 22.3 mmol), sodium periodate (9.56 g, 44.7 mmol) and 2.5w/v % osmium tetroxide t-butanol solution (5.7 mL, 0.56 mmol), and the mixture was stirred for 3 hours at room temperature. Water and ethyl acetate was added to the reaction solution and the mixture was filtered. After the filtrate was partitioned, the organic layer was washed with saturated brine and dried over anhydrous sodium sulfate. After the solvent was evaporated off under reduced pressure, the residue was purified by silica gel column chromatography to to obtain (R)-2,2,2-trifluoro-N-(6-formylchroman-3-yl)acetamide (amount 2.56 g, yield 84%).

Step 3

To (R)-2,2,2-trifluoro-N-(6-formylchroman-3-yl)acetamide (1.45 g, 5.31 mmol), N,N-diethylaminosulfur trifluoride (2.8 mL, 21.2 mmol) was added, and the mixture was stirred for 5 days at room temperature. The reaction solution was diluted with dichloromethane, added dropwise to a mixed liquid of chloroform and water, and then the mixture was partitioned. The organic layer was dried over anhydrous magnesium sulfate, and the solvent was evaporated off under reduced pressure. The residue was purified by silica gel column chromatography to give (R)—N-(6-(difluoromethyl)chroman-3-yl)-2,2,2-trifluoroacetamide (amount 1.11 g, yield 71%).

Step 4

(R)-6-(Difluoromethyl)chroman-3-amine hydrochloride was obtained by a method similar to Step 3 in Reference Example 1, using (R)—N-(6-(difluoromethyl)chroman-3-yl)-2,2,2-trifluoroacetamide instead of (R)—N-(6-chlorochroman-3-yl)-2,2,2-trifluoroacetamide The compound of Example 6 was synthesized by methods similar to those described in Example 1 and Reference Example 3.

The compounds of Example 7 were obtained by separating the compound of Example 6.

The compound of Reference Example 4 (5-chlorochroman-3-amine hydrochloride) was synthesized under the scheme depicted in the figure below.

[Chem 73]

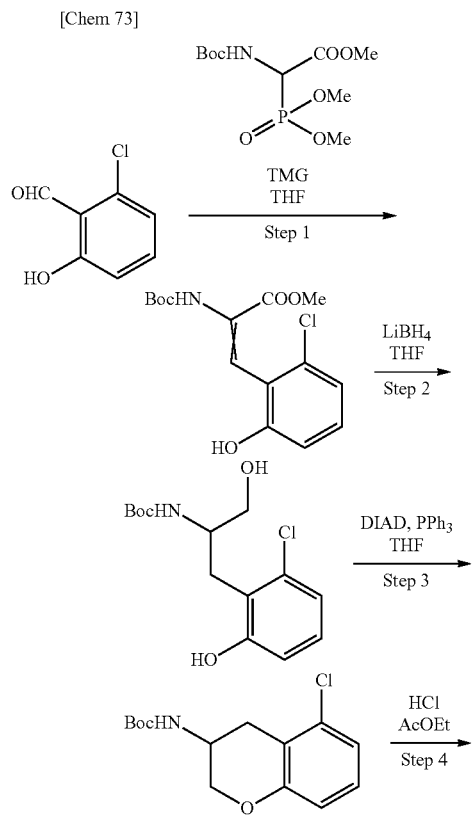

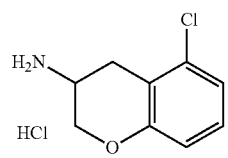

The compound of Example 8 was synthesized by methods similar to those described in Example 1 and Reference Example 4.

The compounds of Example 9 (isomer A and isomer B) were synthesized by a method similar to Example 1.

The compound of Example 10 was synthesized from the compound of Example 9 under the scheme depicted in the figure below.

[Chem 74]

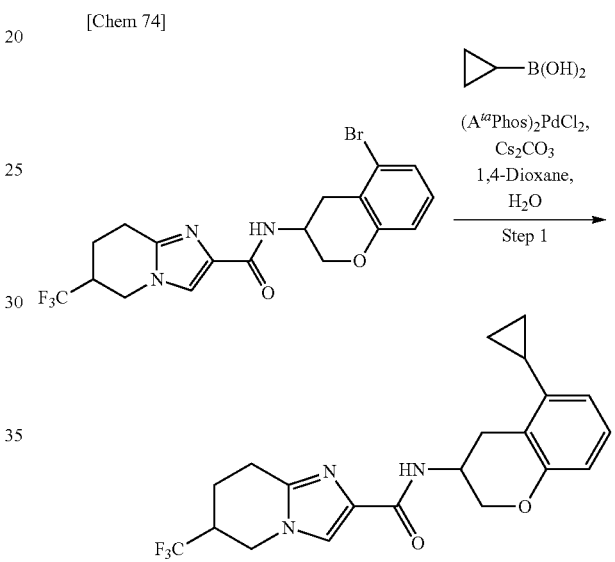

The compound of Reference Example 5 ((R)-6-ethylchroman-3-amine hydrochloride) was synthesized under the scheme depicted in the figure below.

[Chem 75]

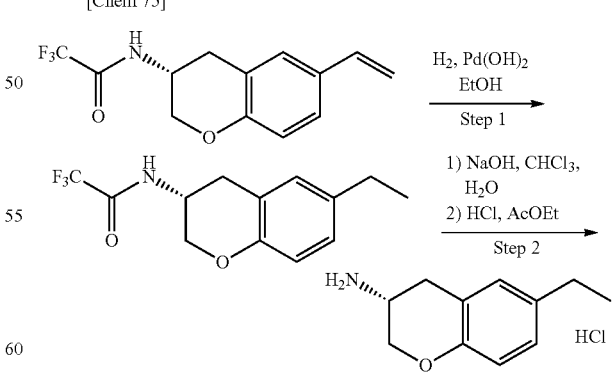

The compound of Example 11 was synthesized by methods similar to those described in Example 1 and Reference Example 5.

The compound of Example 12 was synthesized by a method similar to Example 1.

The compound of Example 13 was synthesized from the compound of Example 12 under the scheme depicted in the figure below.

[Chem 76]

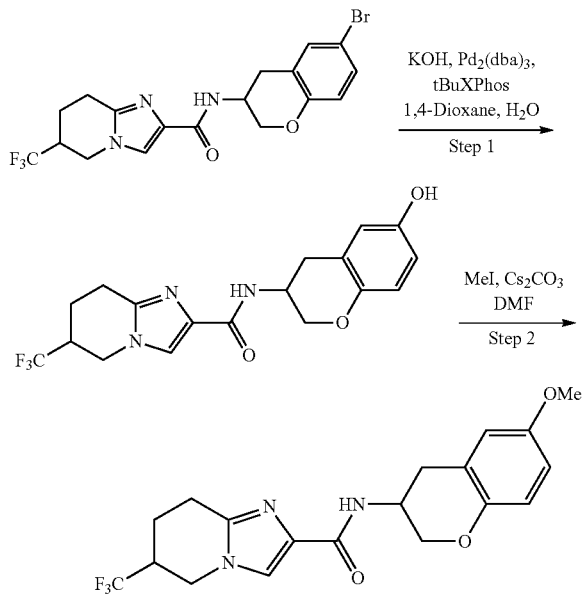

The compound of Reference Example 7 (shown in the figure below.) was synthesized by a method similar to Example 1, using (R)-chroman-3-amine hydrochloride instead of 6-fluorochroman-3-amine hydrochloride in Step 4

[Chem 77]

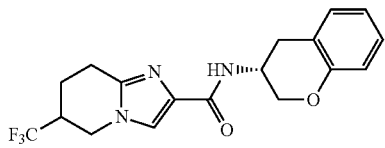

Example 14

Production of N—((R)-chroman-3-yl)-3-iodo-6-(trifluoromethyl)-5,6,7,8-tetrahydroimidazo[1,2-a]pyridine-2-carboxamide

[Chem 78]

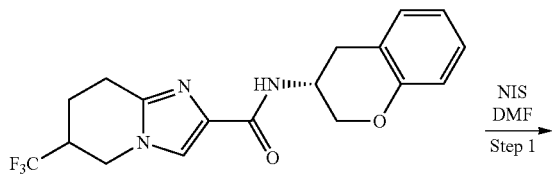

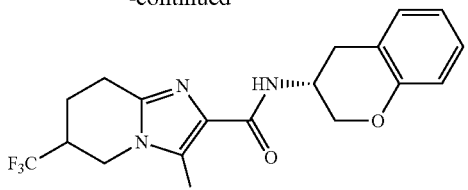

To a solution of N—((R)-chroman-3-yl)-6-(trifluoromethyl)-5,6,7,8-tetrahydroimidazo[1,2-a]pyridine-2-carboxamide synthesized by the method described in Reference Example 7 (79.7 mg, 0.218 mmol) in N,N-dimethylformamide (2.2 mL), N-iodosuccineimide (73.6 mg, 0.327 mmol) was added, and the mixture was stirred for 14 hours at 80° C. In addition, N-iodosuccineimide (73.6 mg, 0.327 mmol) was added, and the mixture was stirred for 8 hours at 100° C. Water and ethyl acetate were added to the reaction solution, and the mixture was partitioned. After the organic layer was washed with saturated brine, dried over anhydrous sodium sulfate and the solvent was evaporated off under reduced pressure. The residue was purified by silica gel column chromatography to give N—((R)-chroman-3-yl)-3-iodo-6-(trifluoromethyl)-5,6,7,8-tetrahydroimidazo[1,2-a]pyridine-2-carboxamide (amount 97.5 mg, yield 91%).

The compound of Example 15 was synthesized from the compound of Example 14 under the scheme depicted in the figure below.

[Chem 79]

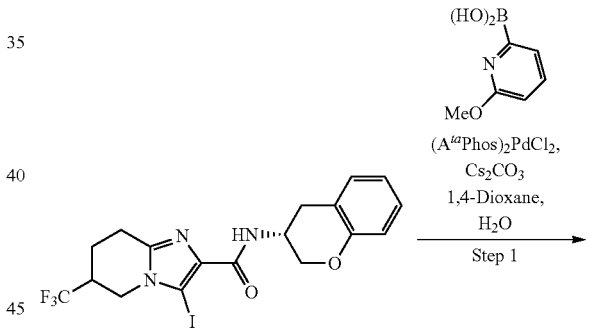

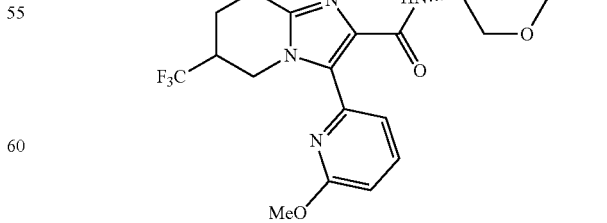

The compound of Example 16 was synthesized from the compound of Reference Example 9 under the scheme depicted in the figure below.

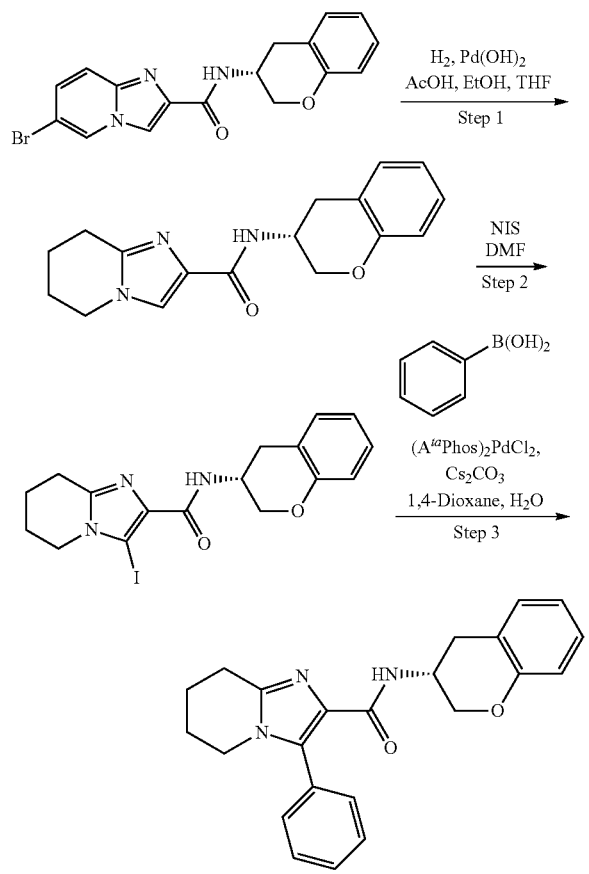

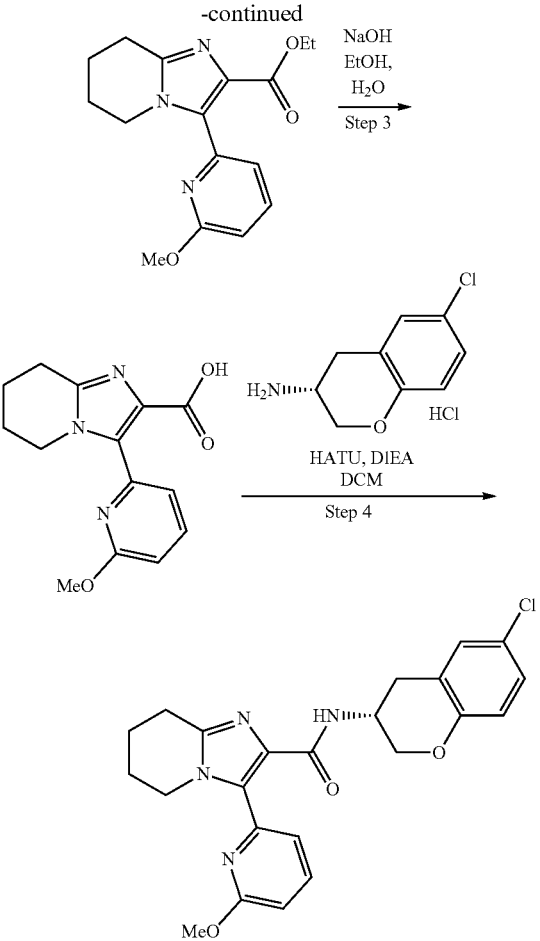

Example 17

Production of (R)—N-(6-chlorochroman-3-yl)-3-(6-methoxypyridin-2-yl)-5,6,7,8-tetrahydroimidazo[1,2-a]pyridine-2-carboxamide

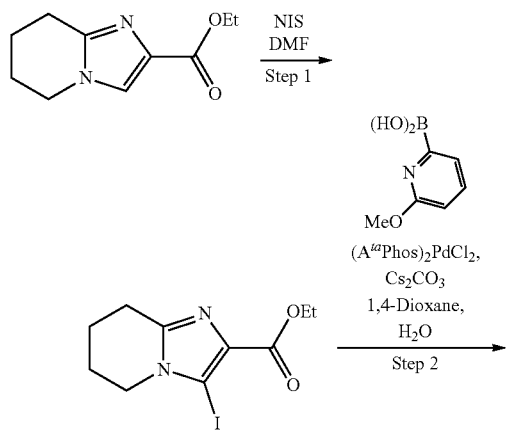

Step 1

Ethyl 3-iodo-5,6,7,8-tetrahydroimidazo[1,2-a]pyridine-2-carboxylate was obtained by a method similar to Example 14, using ethyl 5,6,7,8-tetrahydroimidazo[1,2-a]pyridine-2-carboxylate instead of N—((R)-chroman-3-yl)-6-(trifluoromethyl)-5,6,7,8-tetrahydroimidazo[1,2-a]pyridine-2-carboxamide.

Step 2

Ethyl 3-(6-methoxypyridin-2-yl)-5,6,7,8-tetrahydroimidazo[1,2-a]pyridine-2-carboxylate was obtained by a method similar to Example 15, using ethyl 3-iodo-5,6,7,8-tetrahydroimidazo[1,2-a]pyridine-2-carboxylate instead of N—((R)-chroman-3-yl)-3-iodo-6-(trifluoromethyl)-5,6,7,8-tetrahydroimidazo[1,2-a]pyridine-2-carboxamide.

Step 3

3-(6-Methoxypyridin-2-yl)-5,6,7,8-tetrahydroimidazo[1,2-a]pyridine-2-carboxylic acid was obtained as a mixture with 4 equivalents of sodium chloride by a method similar to Step 3 in Example 1, using ethyl 3-(6-methoxypyridin-2-yl)-5,6,7,8-tetrahydroimidazo[1,2-a]pyridine-2-carboxylate instead of ethyl 6-(trifluoromethyl)-5,6,7,8-tetrahydroimidazo[1,2-a]pyridine-2-carboxylate.

Step 4

(R)—N-(6-Chlorochroman-3-yl)-3-(6-methoxypyridin-2-yl)-5,6,7,8-tetrahydroimidazo[1,2-a]pyridine-2-carboxamide was obtained by a method similar to Step 4 in Example 1, using 3-(6-methoxypyridin-2-yl)-5,6,7,8-tetrahydroimidazo[1,2-a]pyridine-2-carboxylic acid instead of 6-(trifluoromethyl)-5,6,7,8-tetrahydroimidazo[1,2-a]pyridine-2-carboxylic acid, and using (R)-6-chlorochroman-3-amine hydrochloride synthesized by a method described in Reference Example 1 instead of 6-fluorochroman-3-amine hydrochloride.

Example 18

Production of (R)—N-(6-chlorochroman-3-yl)-3-(pyridin-2-yl)-5,6,7,8-tetrahydroimidazo[1,2-a]pyridine-2-carboxamide

[Chem 82]

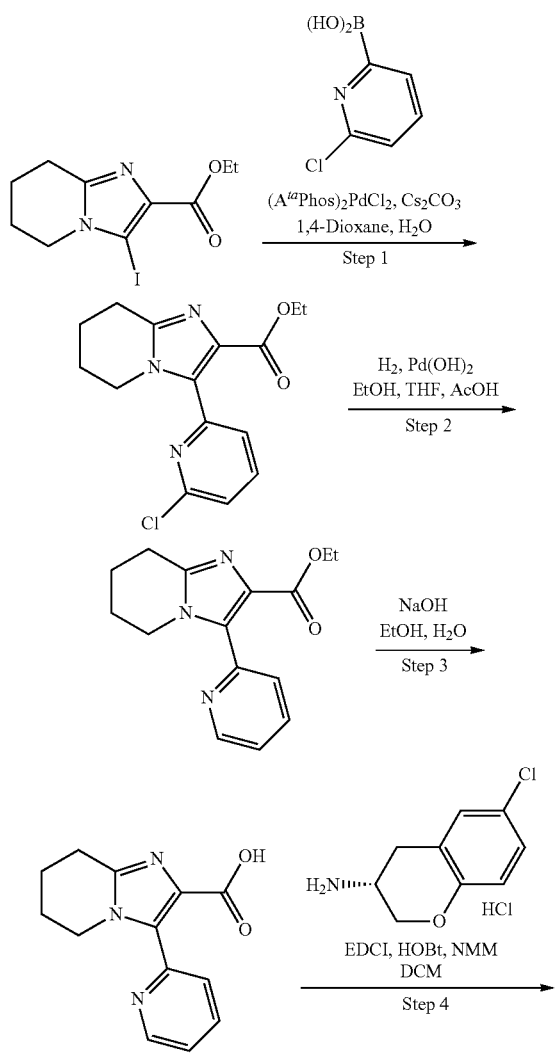

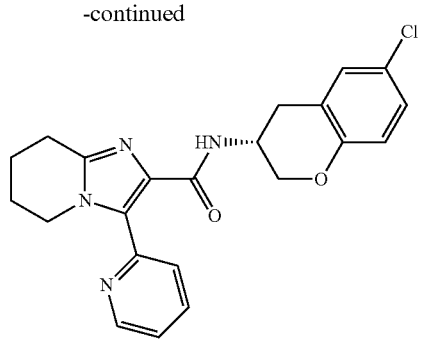

Step 1

Ethyl 3-(6-chloropyridin-2-yl)-5,6,7,8-tetrahydroimidazo[1,2-a]pyridine-2-carboxylate was obtained by a method similar to Step 2 in Example 17, using 6-(chloropyridin-2-yl)boronic acid instead of 6-methoxypyridine-2-boronic acid.

Step 2

To a solution of ethyl 3-(6-chloropyridin-2-yl)-5,6,7,8-tetrahydroimidazo[1,2-a]pyridine-2-carboxylate (1.05 g, 3.43 mmol) in tetrahydrofuran (10 mL) were added ethanol (10 mL), acetic acid (1.8 mL) and 20% palladium hydroxide on carbon (0.72 g), and the mixture was stirred for 2 hours in hydrogen atmosphere (under balloon pressure) at 50° C. The reaction solution was filtered through Celite, and then the solvent was evaporated off under reduced pressure. The residue was purified by silica gel column chromatography to give ethyl 3-(pyridin-2-yl)-5,6,7,8-tetrahydroimidazo[1,2-a]pyridine-2-carboxylate (amount 900 g, yield 97%).

Step 3

3-(Pyridin-2-yl)-5,6,7,8-tetrahydroimidazo[1,2-a]pyridine-2-carboxylic acid was obtained as a mixture with 4 equivalents of sodium chloride by a method similar to Step 3 in Example 1, using ethyl 3-(pyridin-2-yl)-5,6,7,8-tetrahydroimidazo[1,2-a]pyridine-2-carboxylate instead of ethyl 6-(trifluoromethyl)-5,6,7,8-tetrahydroimidazo[1,2-a]pyridine-2-carboxylate.

Step 4

To suspension of 3-(pyridin-2-yl)-5,6,7,8-tetrahydroimidazo[1,2-a]pyridine-2-carboxylic acid (4 equivalents sodium chloride mixture) (15 mg, 0.031 mmol), (R)-6-chlorochroman-3-amine hydrochloride synthesized by a method described in Reference Example 1 (6.9 mg, 0.031 mmol), 1-hydroxybenzotriazole (7.2 mg, 0.047 mmol) and 1-ethyl-3-(3-dimethylaminopropyl)carbodiimide hydrochloride (9.0 mg, 0.047 mmol) in dichloromethane (1 mL), 4-methylmorpholine (21 μL, 0.19 mmol) was added, and the mixture was stirred for 2 hours at room temperature. Water and ethyl acetate was added to the reaction solution, and the mixture was partitioned. After drying the organic layer with anhydrous sodium sulfate, the solvent was evaporated off under reduced pressure. The residue was purified by silica gel column chromatography to give (R)—N-(6-chlorochroman-3-yl)-3-(pyridin-2-yl)-5,6,7,8-tetrahydroimidazo[1,2-a]pyridine-2-carboxamide (amount 8.0 mg, yield 62%).

The compound of Reference Example 8 (shown in the figure below.) was synthesized by a method similar to Step 2 to Step 3 in Example 17.

[Chem 83]

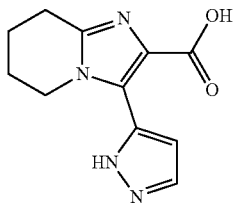

The compound of Example 19 was synthesized from the compound of Reference Example 8 and the compound of Reference Example 43 by a method similar to Step 4 in Example 18.

The compound of Example 20 was synthesized from the compound of Reference Example 8 and the compound of Reference Example 44 by a method similar to Step 4 in Example 18.

The compound of Example 21 was synthesized by a method similar to Example 17.

The compound of Example 22 was synthesized by a method similar to Example 17.

The compound of Reference Example 9 (shown in the figure below.) was synthesized by a method similar to Step 4 in Example 1.

[Chem 84]

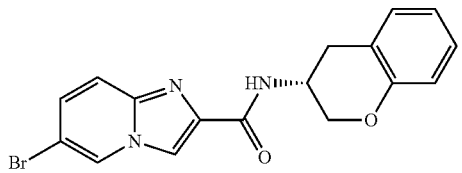

The compound of Example 23 was synthesized from the compound of Reference Example 9 under the scheme depicted in the figure below.

[Chem 85]

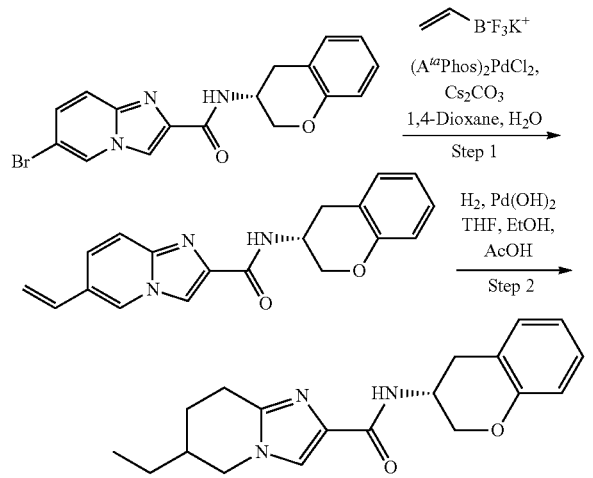

The compound of Example 24 was synthesized by a method similar to Example 23.

The compound of Reference Example 10 (shown in the figure below.) was synthesized by a method similar to Example 23.

[Chem 86]

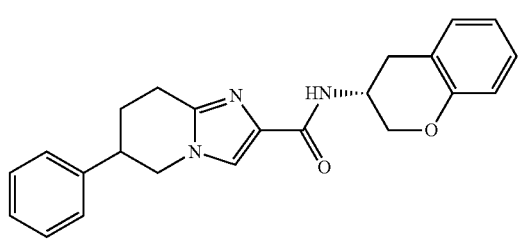

The compound of Example 25 was synthesized from the compound of Reference Example 10 under the scheme depicted in the figure below.

[Chem 87]

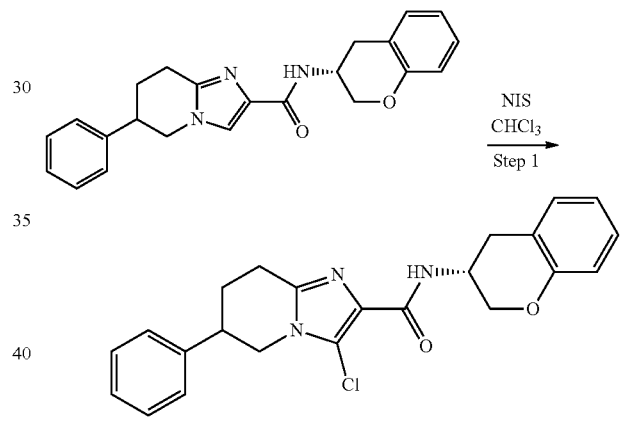

The compound of Reference Example 11 (shown in the figure below.) was synthesized by a method similar to Reference Example 9.

[Chem 88]

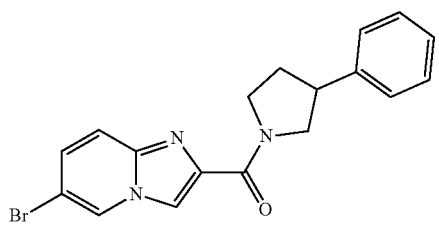

The compound of Example 26 was synthesized from the compound of Reference Example 11 by a method similar to Example 23.

The compound of Reference Example 12 (shown in the figure below.) was synthesized by a method similar to Step 4 in Example 1.

[Chem 89]

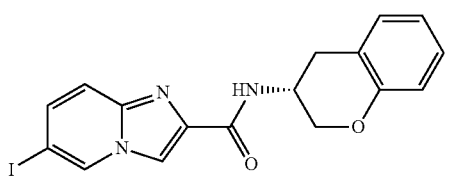

The compound of Example 27 was synthesized from the compound of Reference Example 12 by a method similar to Example 23.

The compound of Reference Example 13 (shown in the figure below.) was synthesized by a method similar to Reference Example 12.

[Chem 90]

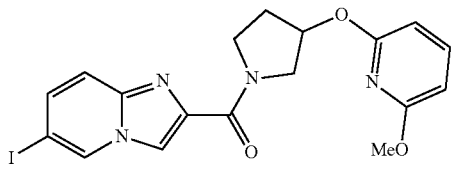

The compound of Example 28 was synthesized from the compound of Reference Example 13 by a method similar to Example 23.

The compound of Reference Example 14 (shown in the figure below.) was synthesized by a method similar to Reference Example 12.

[Chem 91]

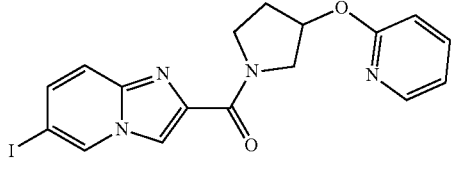

The compound of Example 29 was synthesized from the compound of Reference Example 14 under the scheme depicted in the figure below.

[Chem 92]

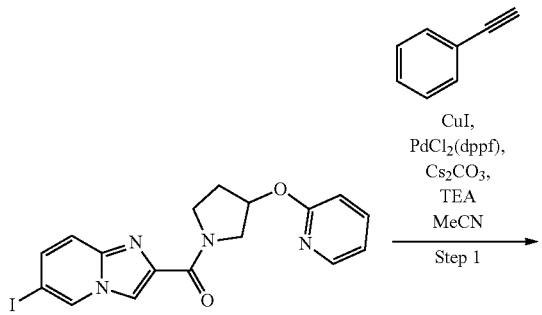

The compound of Example 30 was synthesized under the scheme depicted in the figure below.

[Chem 93]

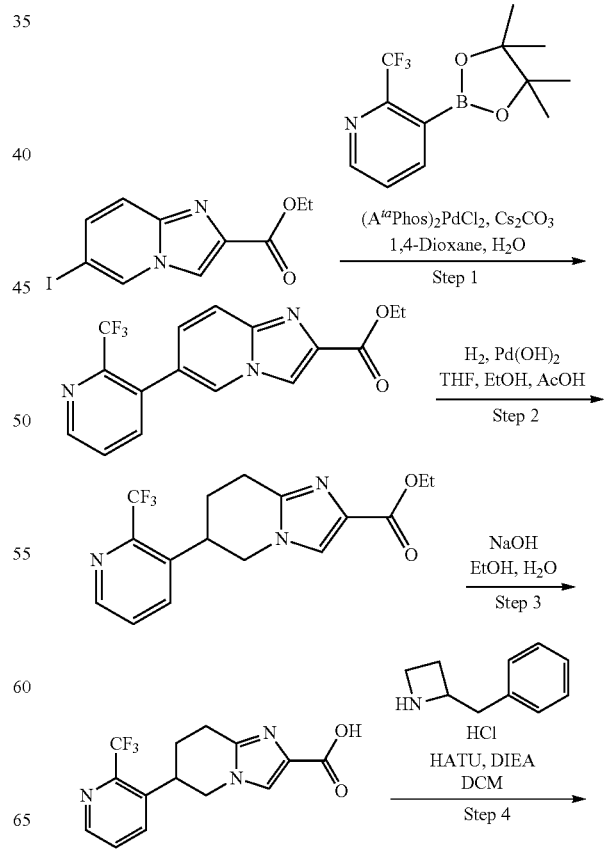

-continued
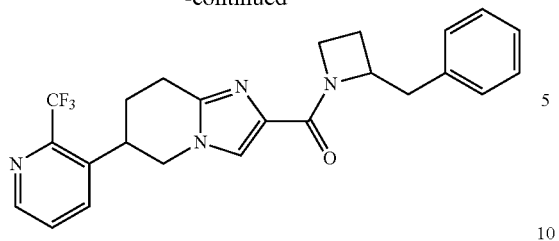
-continued
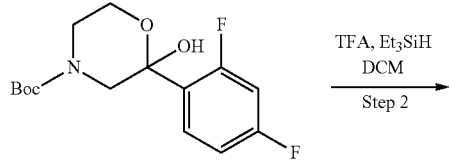
The compound of Example 31 was produced under the scheme depicted in the figure below.
[Chem 94]
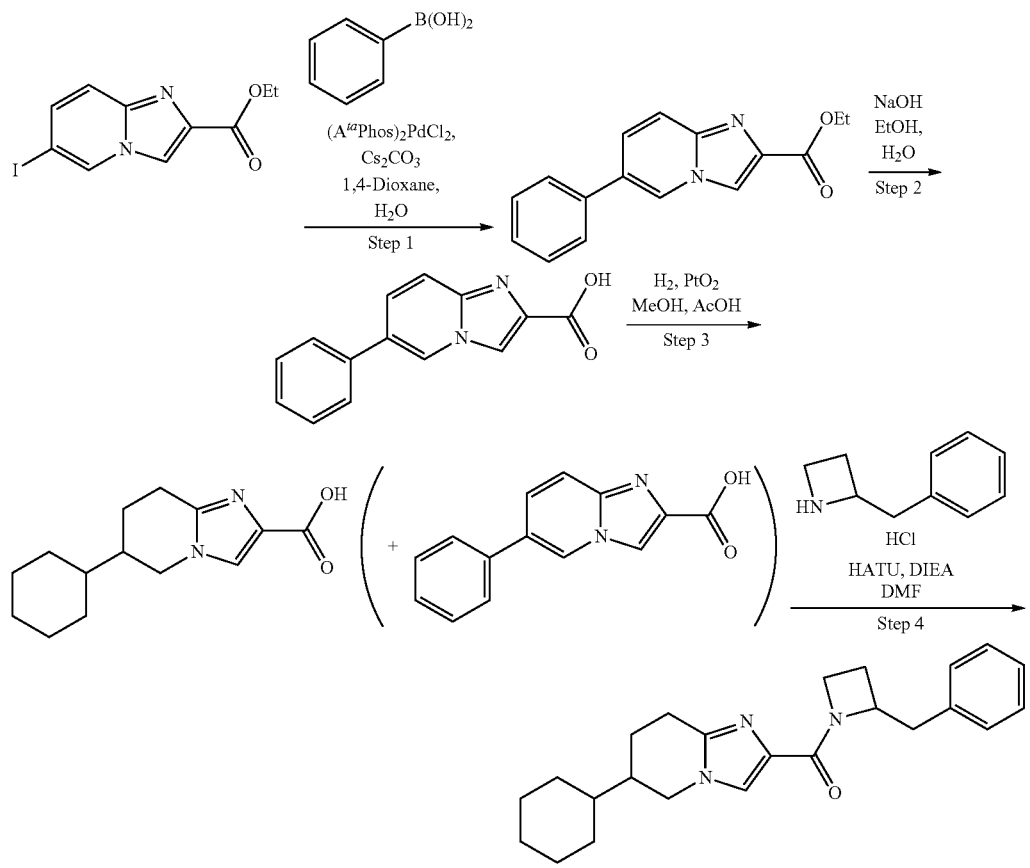
The compound of Reference Example 15 (2-(2,4-difluorophenyl)morpholine) was synthesized under the scheme depicted in the figure below.
[Chem 95]
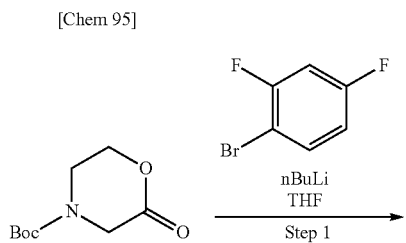
-continued
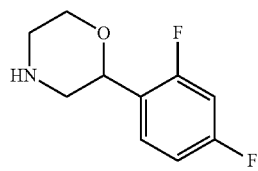
The compound of Example 32 was synthesized under the scheme depicted in the figure below.

[Chem 96]
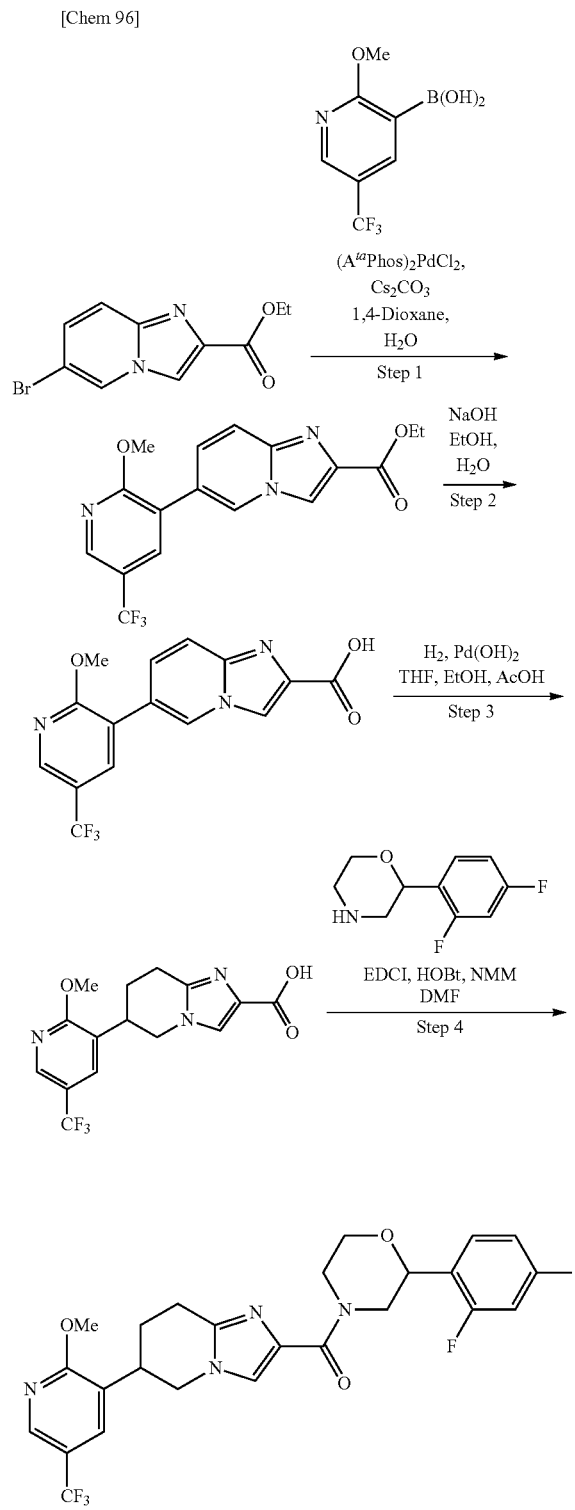
The compound of Example 33 was synthesized under the scheme depicted in the figure below.
[Chem 97]
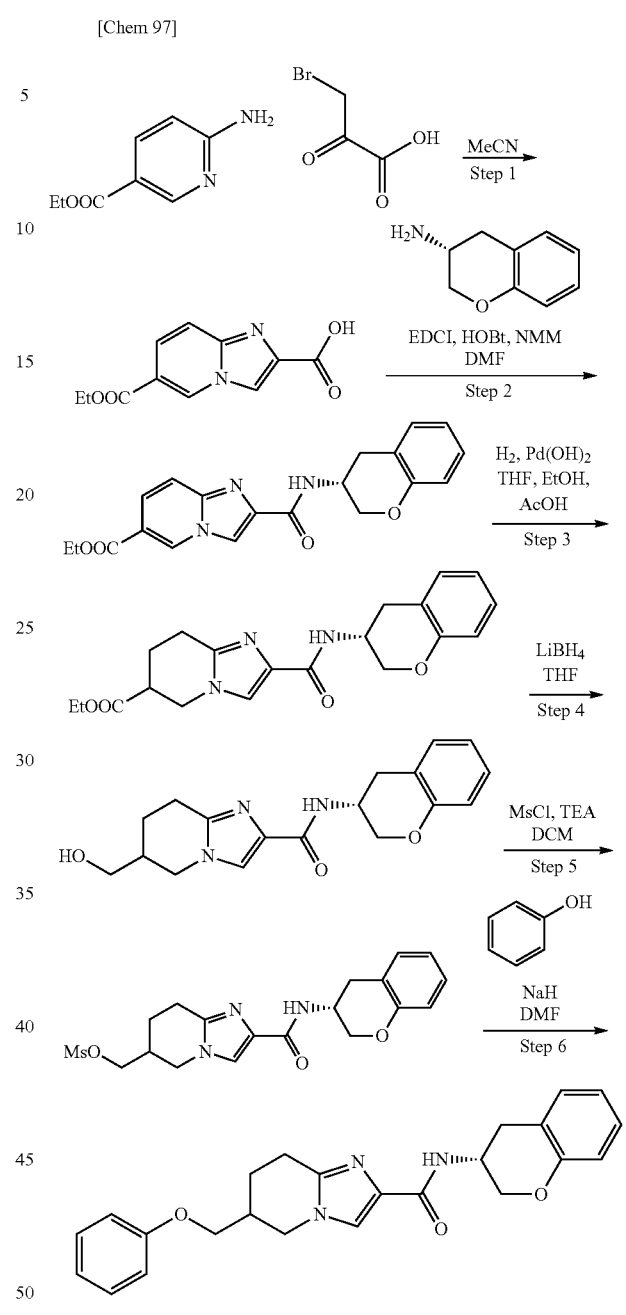
The compound of Example 34 was synthesized from the compound synthesized in Step 4 in Example 33 under the scheme depicted in the figure below.
[Chem 98]
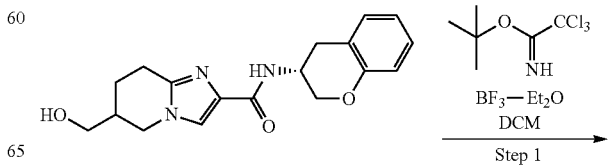

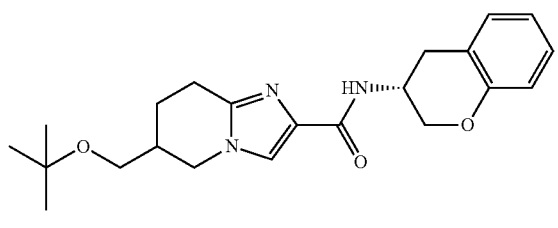
The compound of Example 35 was synthesized from the compound of Reference Example 9 under the scheme depicted in the figure below.
[Chem 99]
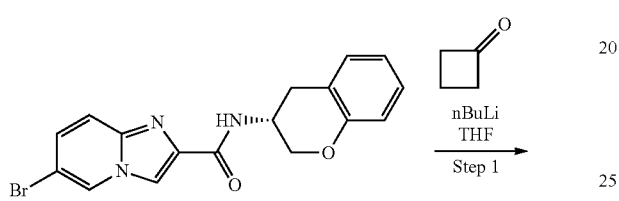
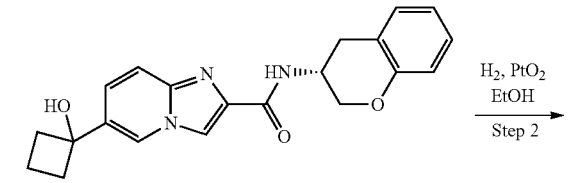
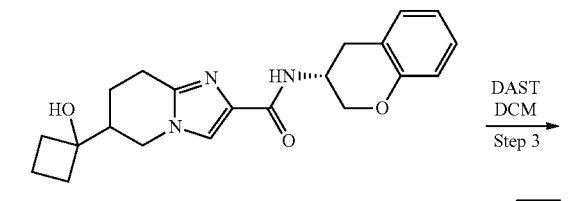
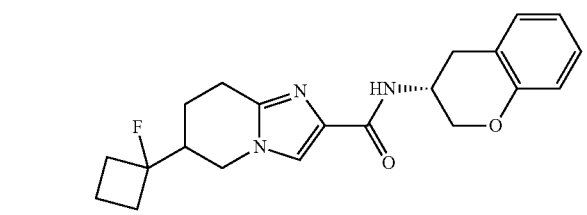
The compound of Example 36 was synthesized under the scheme depicted in the figure below.
[Chem 100]
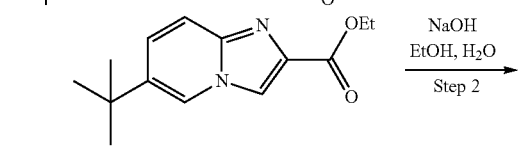
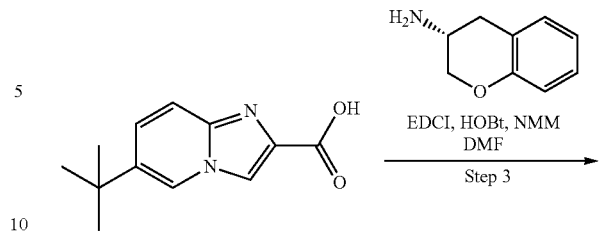
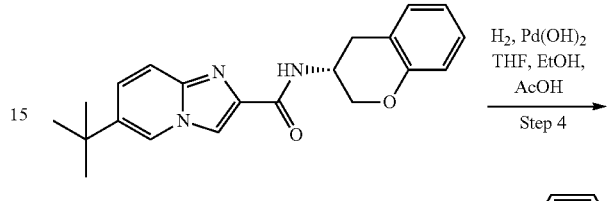
Example 37
Production of N—((R)-chroman-3-yl)-6-(2,2,2-trifluoroethoxy)-5,6,7,8-tetrahydroimidazo[1,2-a]pyridine-2-carboxamide
[Chem 101]
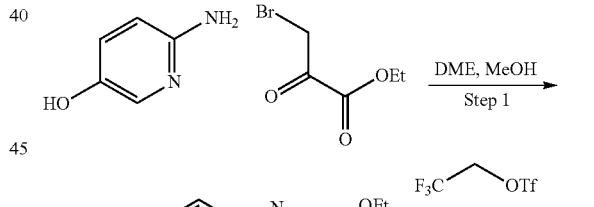
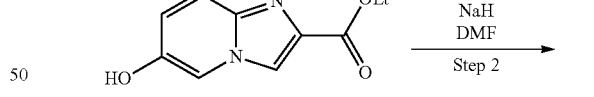
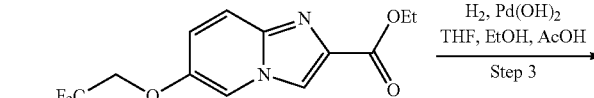
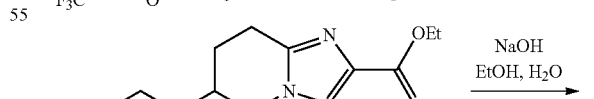
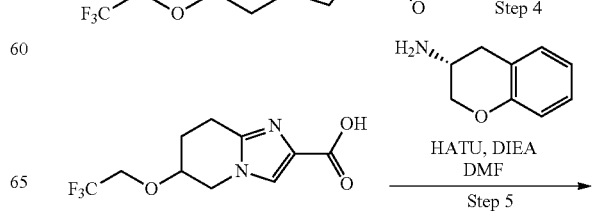

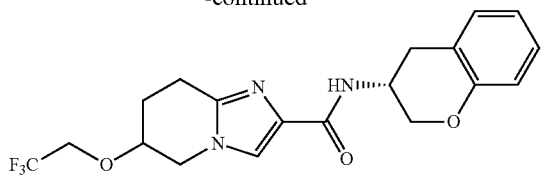

Step 1

Ethyl 6-hydroxyimidazo[1,2-a]pyridine-2-carboxylate was obtained by a method similar to Step 1 in Example 1, using 6-aminopyridin-3-ol instead of 5-(trifluoromethyl)pyridin-2-amine.

Step 2

To ice cold solution of ethyl 6-hydroxyimidazo[1,2-a]pyridine-2-carboxylate (1.38 g, 6.69 mmol) in N,N-dimethylformamide (34 mL), sodium hydride (60% in oil) (535 mg, 13.4 mmol) was added. After stirring for 5 minutes, 2,2,2-trifluoroethyl trifluoromethanesulphonate (1.93 mL, 13.4 mmol) was added, and the mixture was stirred for 1 hour at 80° C. Water and ethyl acetate were added to the reaction solution, and then the mixture was partitioned. The organic layer was washed with saturated brine and dried over anhydrous sodium sulfate. The solvent was evaporated off under reduced pressure. The residue was purified by silica gel column chromatography to give ethyl 6-(2,2,2-trifluoroethoxy)imidazo[1,2-a]pyridine-2-carboxylate (amount 1.55 g, yield 80%).

Step 3

Ethyl 6-(2,2,2-trifluoroethoxy)-5,6,7,8-tetrahydroimidazo[1,2-a]pyridine-2-carboxylate was obtained by a method similar to Step 2 in Example 1, using ethyl 6-(2,2,2-trifluoroethoxy)imidazo[1,2-a]pyridine-2-carboxylate instead of ethyl 6-(trifluoromethyl)imidazo[1,2-a]pyridine-2-carboxylate.

Step 4

6-(2,2,2-Trifluoroethoxy)-5,6,7,8-tetrahydroimidazo[1,2-a]pyridine-2-carboxylic acid was obtained by a method similar to Step 3 in Example 1, using ethyl 6-(2,2,2-trifluoroethoxy)-5,6,7,8-tetrahydroimidazo[1,2-a]pyridine-2-carboxylate instead of ethyl 6-(trifluoromethyl)-5,6,7,8-tetrahydroimidazo[1,2-a]pyridine-2-carboxylate.

Step 5

N—((R)-Chroman-3-yl)-6-(2,2,2-trifluoroethoxy)-5,6,7,8-tetrahydroimidazo[1,2-a]pyridine-2-carboxamide was obtained by a method similar to Step 4 in Example 1, using 6-(2,2,2-trifluoroethoxy)-5,6,7,8-tetrahydroimidazo[1,2-a]pyridine-2-carboxylic acid instead of 6-(trifluoromethyl)-5,6,7,8-tetrahydroimidazo[1,2-a]pyridine-2-carboxylic acid, and, using (R)-chroman-3-amine hydrochloride instead of 6-fluorochroman-3-amine hydrochloride.

The compound of Example 38 was synthesized from the compound synthesized in Step 4 in Example 37 and the compound of Reference Example 1 by a method similar to Step 4 in Example 1.

The compounds of Example 39 were obtained by separating the compound of Example 38.

The compound of Example 40 was synthesized from the compound synthesized in Step 4 in Example 37 and the compound of Reference Example 3 by a method similar to Step 4 in Example 1.

The compound of Example 41 was synthesized under the scheme depicted in the figure below.

[Chem 102]

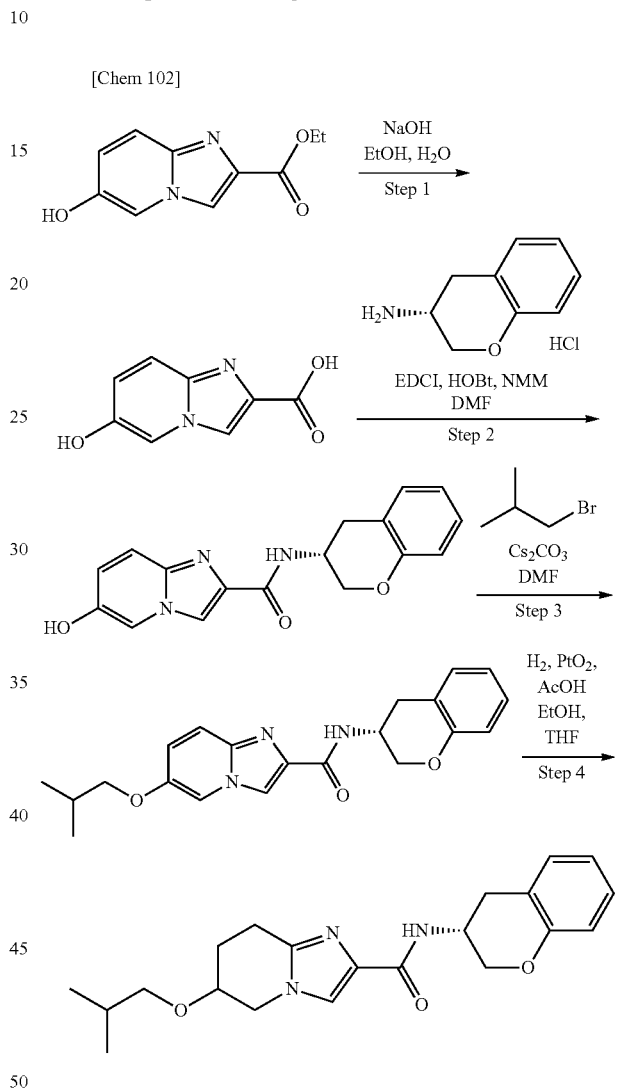

The compound of Reference Example 16 (shown in the figure below.) was synthesized by a method similar to Step 1 in Example 1.

[Chem 103]

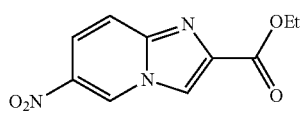

The compound of Reference Example 17 (shown in figure below.) was synthesized from the compound of Reference Example 16 by a method similar to Step 1 to Step 2 in Example 41.

[Chem 104]

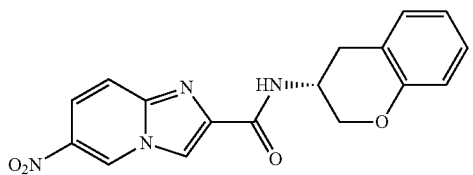

The compound of Example 42 was synthesized under the scheme depicted in the figure below.

[Chem 105]

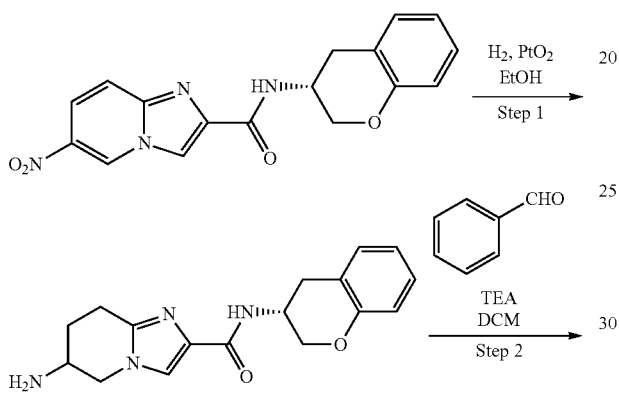

The compound of Example 43 was synthesized under the scheme depicted in the figure below.

[Chem 106]

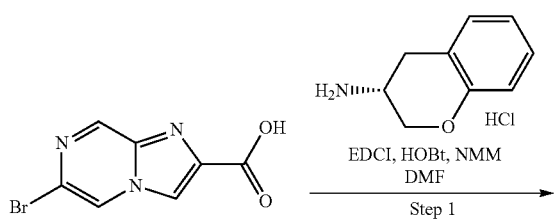

The compound of Example 44 was synthesized by a method similar to Example 43.

The compound of Example 45 was synthesized from the compound of Example 44 under the scheme depicted in the figure below.

[Chem 107]

The compound of Example 46 was synthesized by a method similar to Example 43.

The compound of Example 47 was synthesized from the compound of Example 46 by a method similar to Example 45.

The compound of Example 48 was synthesized by a method similar to Example 43.

The compound of Example 49 was synthesized under the scheme depicted in the figure below.

[Chem 108]

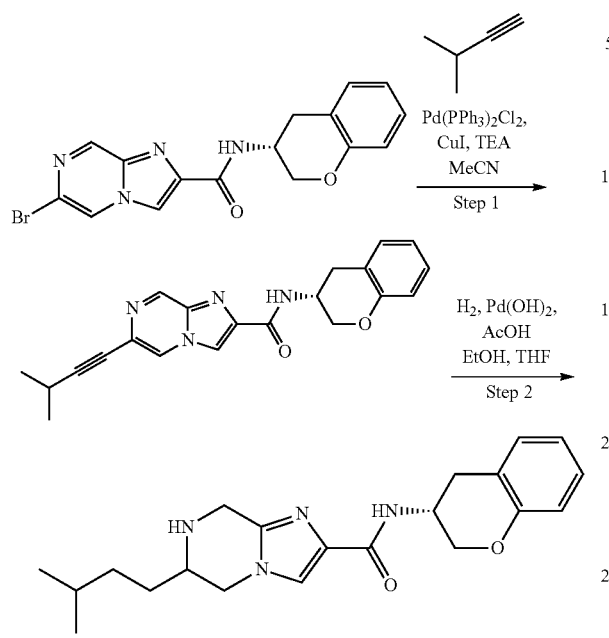

The compound of Example 50 was synthesized from the compound of Example 49 by a method similar to Example 45.

The compound of Example 51 was synthesized by a method similar to Example 49.

The compound of Example 52 was synthesized from the compound of Example 51 by a method similar to Example 45.

The compound of Example 53 was synthesized by a method similar to Example 49.

The compound of Example 54 was synthesized from the compound of Example 53 by a method similar to Example 45.

The compound of Example 55 was synthesized by a method similar to Example 49.

The compound of Example 56 was synthesized under the scheme depicted in the figure below.

[Chem 109]

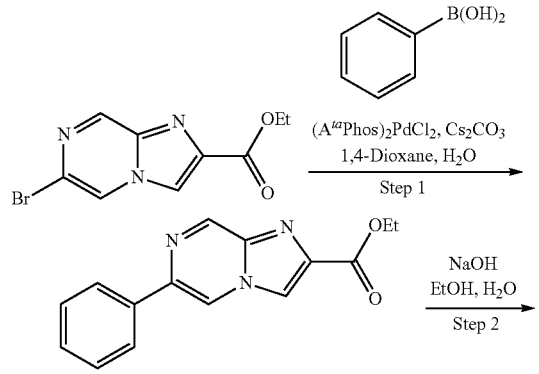

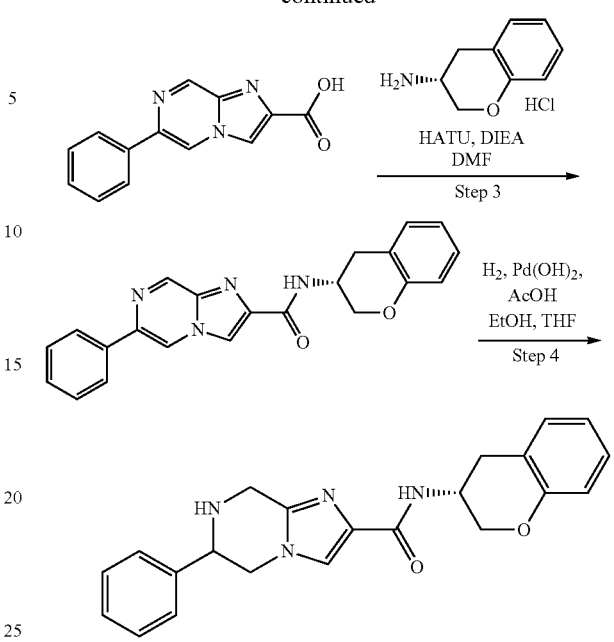

The compound of Example 57 was synthesized from the compound of Example 56 by a method similar to Example 45.

The compound of Reference Example 18 (shown in the figure below.) was synthesized by a method similar to Example 56.

[Chem 110]

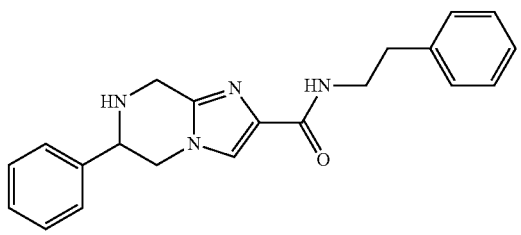

The compound of Example 58 was synthesized from the compound of Reference Example 18 by a method similar to Example 45.

The compound of Example 59 was synthesized under the scheme depicted in the figure below.

[Chem 111]

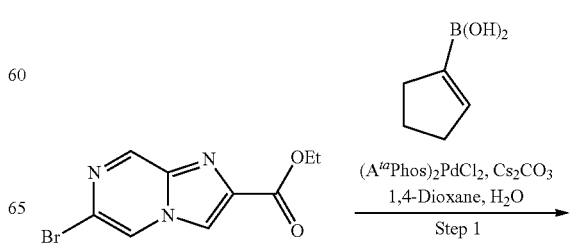

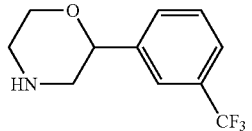

[Chem 113]

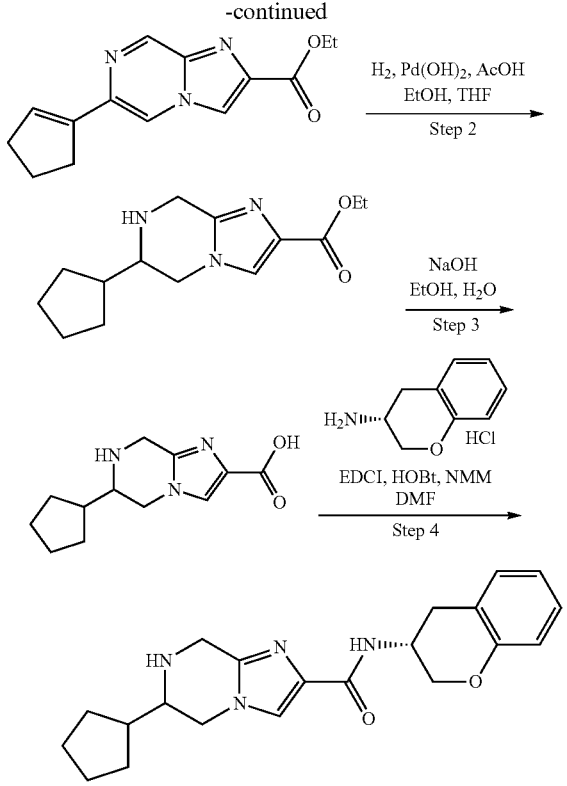

The compound of Example 61 was synthesized from the compound of Reference Example 19 and the compound of Reference Example 20 by a method similar to Step 4 in Example 59.

The compound of Reference Example 21 (shown in the figure below.) was synthesized from the compound synthesized in Step 1 in Reference Example 19 by methods similar to those described in Example 45 and Step 2 in Reference Example 19.

[Chem 114]

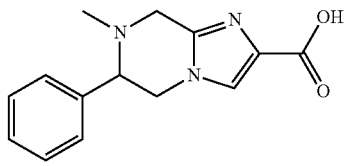

The compound of Reference Example 22 was synthesized under the scheme depicted in the figure below.

The compound of Reference Example 19 was synthesized from the compound synthesized in Step 1 in Example 56 under the scheme depicted in the figure below.

[Chem 115]

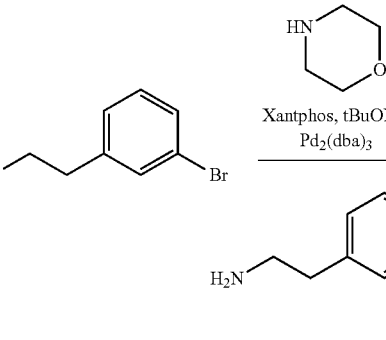

[Chem 112]

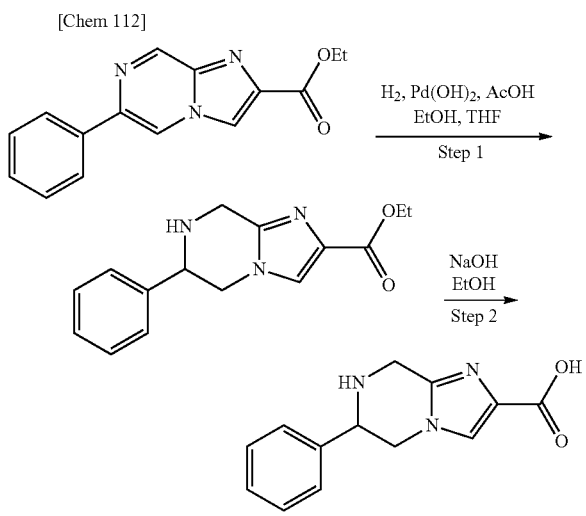

The compound of Example 62 was synthesized from the compound Reference Example 21 and the compound Reference Example 22 by a method similar to Step 3 in Example 56.

The compound of Reference Example 23 (2-(azetidin-3-yloxy)-6-(trifluoromethyl)pyridine dihydrochloride) was synthesized under the scheme depicted in the figure below.

[Chem 116]

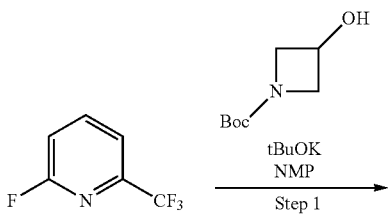

The compound of Example 60 was synthesized from the compound of Reference Example 19 by a method similar to Step 4 in Example 59.

The compound of Reference Example 20 (shown in the figure below.) was synthesized by a method similar to Reference Example 15.

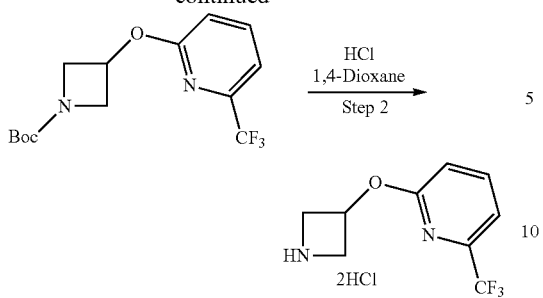

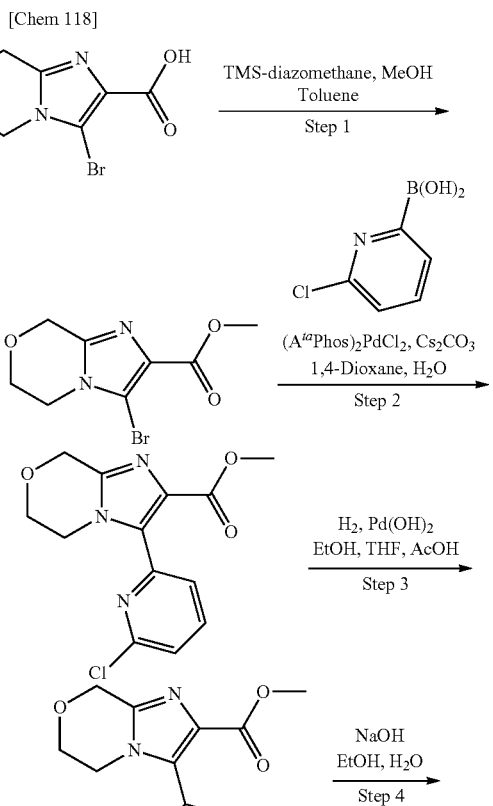

The compound of Example 63 was synthesized from the compound of Reference Example 21 and the compound of Reference Example 23 by a method similar to Step 3 in Example 56.

The compound of Example 64 was synthesized under the scheme depicted in the figure below.

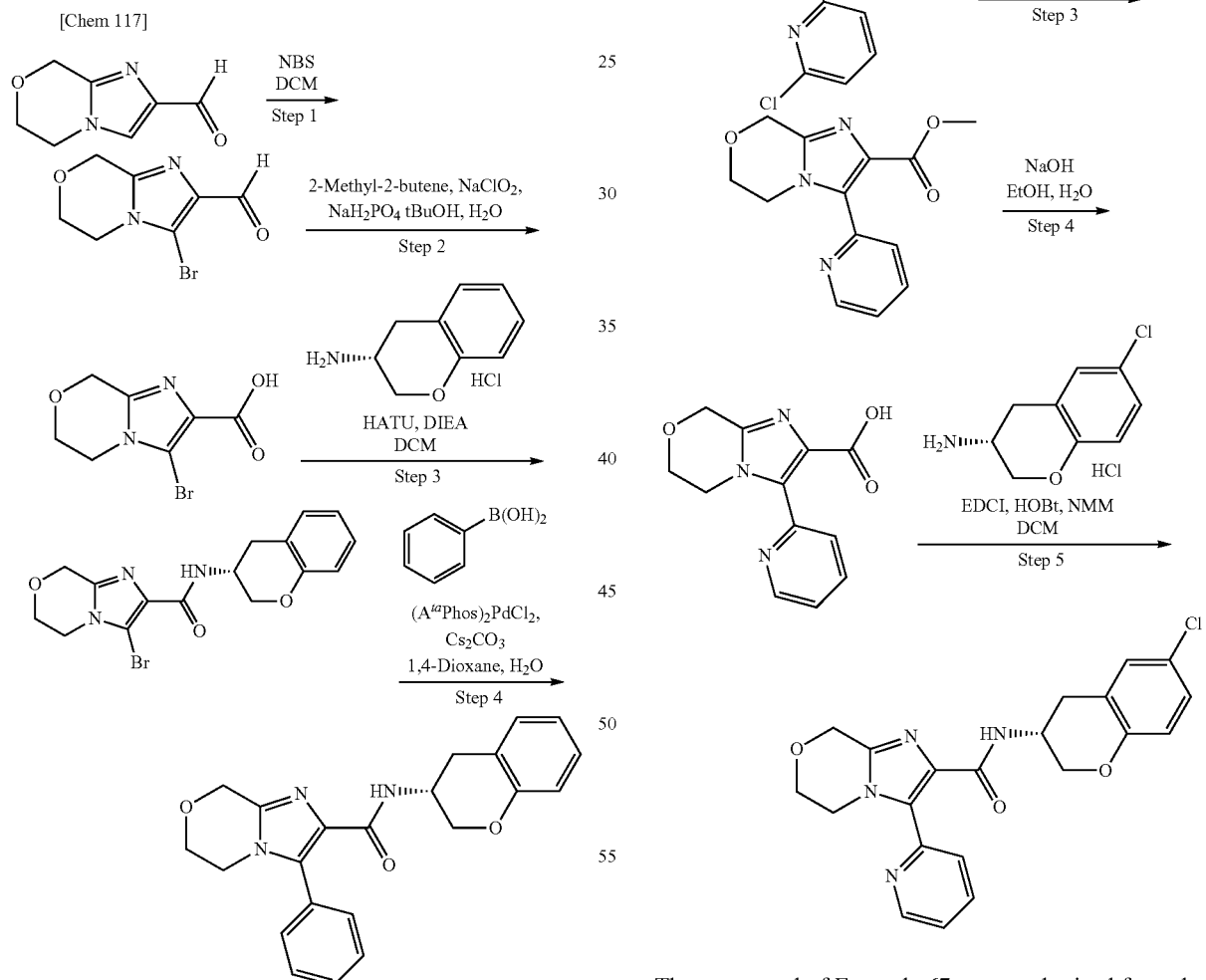

The compound of Example 65 was synthesized by methods similar to those described in Example 64 and Reference Example 1.

The compound of Example 66 was synthesized under the scheme depicted in the figure below.

The compound of Example 67 was synthesized from the compound synthesized in Step 4 in Example 66 and the compound of Reference Example 43 by a method similar to Step 4 in Reference Example 18.

The compound of Example 68 was synthesized by a method similar to Example 32.

The compound of Example 69 was synthesized under the scheme depicted in the figure below.

[Chem 119]

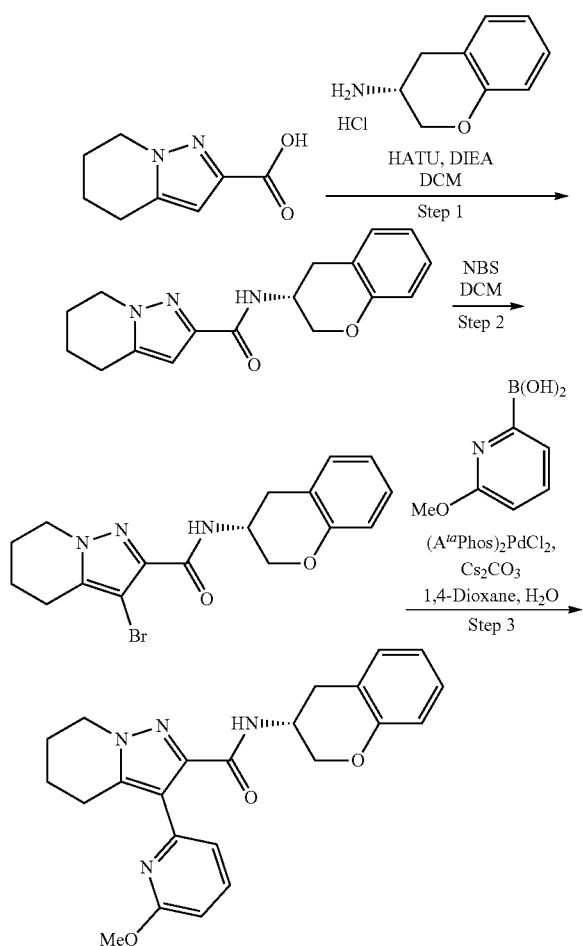

Reference Example 24

Production of (R)-3-aminochroman-6-carbonitrile

[Chem 120]

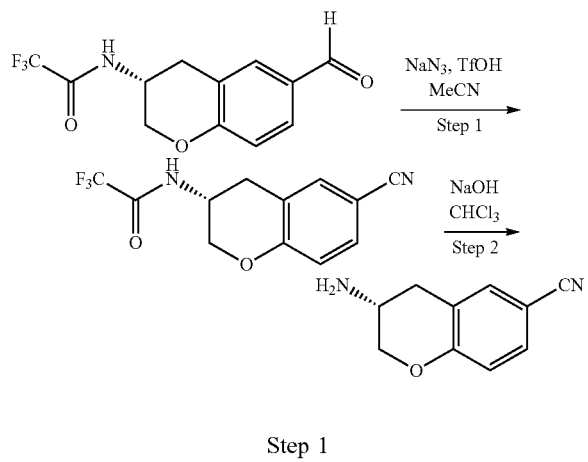

Step 1

To a solution of (R)-2,2,2-trifluoro-N-(6-formylchroman-3-yl)acetamide (1.43 g, 5.23 mmol) synthesized by a method described in Step 2 in Reference Example 3 in acetonitrile (52.3 mL) were added sodium azide (524 mg, 8.06 mmol) and trifluoromethanesulfonic acid (1.61 mL, 18.3 mmol), and the mixture was stirred for 2 hours at room temperature. Saturated aqueous solution of sodium hydrogen carbonate, water and ethyl acetate were added to the reaction solution, and the mixture was partitioned. The organic layer was washed with saturated brine, and then dried over anhydrous sodium sulfate. The solvent was evaporated off under reduced pressure. The residue was purified by silica gel column chromatography to give (R)—N-(6-cyanochroman-3-yl)-2,2,2-trifluoroacetamide (amount 1.40 g, yield 99%).

Step 2

To a solution of (R)—N-(6-cyanochroman-3-yl)-2,2,2-trifluoroacetamide (1.40 g, 5.18 mmol) in chloroform (13 mL), 4 mol/L aqueous solution of sodium hydroxide (13.0 mL, 51.8 mmol) was added, and the mixture was stirred for 13 hours at room temperature. Water and chloroform were added to the reaction solution, and the mixture was partitioned. The organic layer was washed with saturated brine, and then dried over anhydrous sodium sulfate. The solvent was evaporated off under reduced pressure to give (R)-3-aminochroman-6-carbonitrile (amount 505 mg, yield 56%).

Example 70

Production of N—((R)-6-cyanochroman-3-yl)-5-(2-fluorophenyl)-6,7-dihydro-5H-pyrazolo[5,1-b][1,3]oxazine-2-carboxamide

[Chem 121]

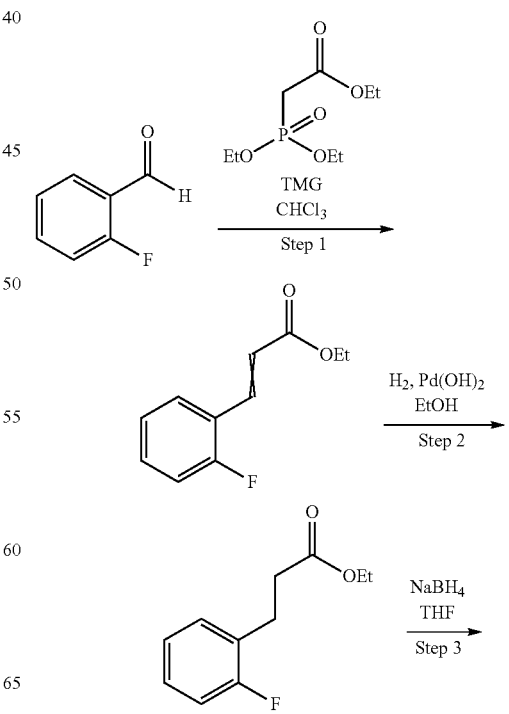

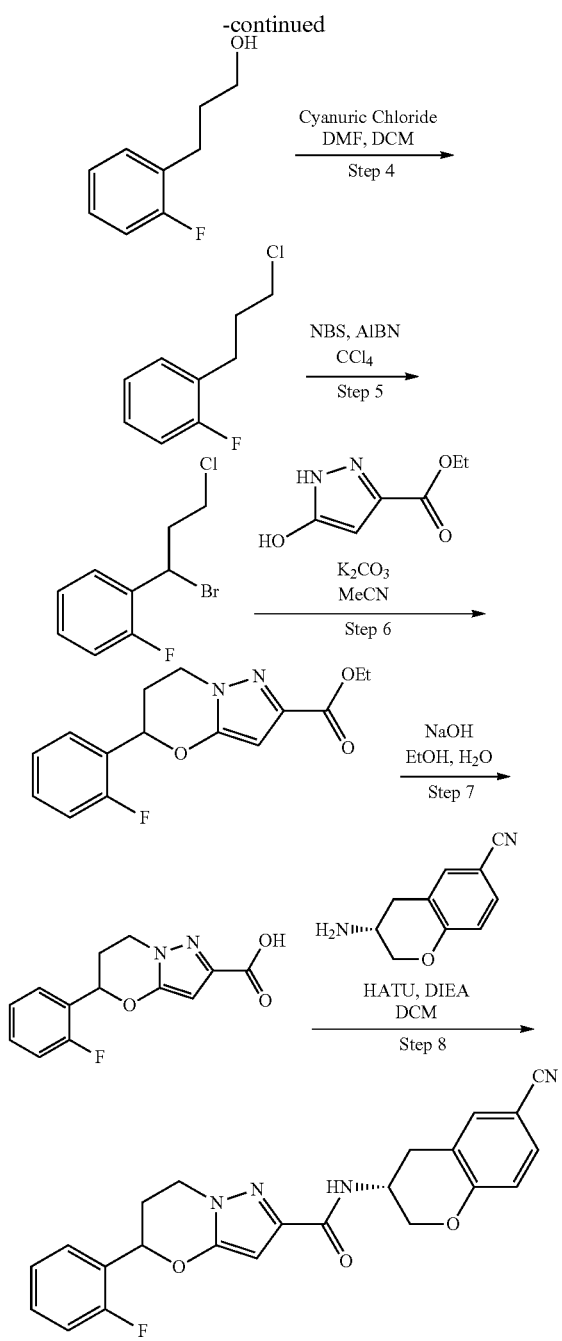

Step 1

To a solution of 2-fluorobenzaldehyde (2.00 g, 16.1 mmol) in chloroform (32.2 mL) were added 1,1,3,3-tetramethylguanidine (3.03 mL, 24.2 mmol) and diethylphosphonoethyl acetate (3.52 mL, 17.7 mmol), and the mixture was stirred for 4 hours at 50° C. After evaporating off the solvent under reduced pressure, the residue was purified by silica gel column chromatography to give ethyl 3-(2-fluorophenyl)acrylate (amount 2.98 g, yield 95%).

Step 2

To a solution of ethyl 3-(2-fluorophenyl)acrylate (2.98 g, 15.3 mmol) in ethanol (76.7 mL), 20% palladium hydroxide on carbon (539 mg) was added, and the mixture was stirred under pressurized conditions (about 3 atm) in hydrogen atmosphere for 3 hours at 50° C. After the reaction solution was filtered through celite, the solvent was evaporated off under reduced pressure to give ethyl 3-(2-fluorophenyl)propanoate (amount 2.79 g, yield 93%).

Step 3

To a solution of ethyl 3-(2-fluorophenyl)propanoate (2.79 g, 14.2 mmol) in tetrahydrofuran (71.1 mL), lithium borohydride (774 mg, 35.5 mmol) was added, and the mixture was stirred for 5 hours at room temperature. Water and ethyl acetate were added to the reaction solution, and the mixture was partitioned. The organic layer was washed with saturated brine, and then dried over anhydrous sodium sulfate. The solvent was evaporated off under reduced pressure. The residue was purified by silica gel column chromatography to give 3-(2-fluorophenyl)propan-1-ol (amount 2.17 g, yield 99%).

Step 4

To a solution of cyanuric chloride (2.86 g, 15.5 mL) in N,N-dimethylformamide (3.3 mL) was added a solution of 3-(2-fluorophenyl)propan-1-ol (2.17 g, 14.1 mmol) in dichloromethane (70.4 mL), and the mixture was stirred for 13 hours at room temperature. Water and chloroform were added to the reaction solution, and the mixture was partitioned. After drying the organic layer with anhydrous sodium sulfate, the solvent was evaporated off under reduced pressure. The residue was purified by silica gel column chromatography to give 1-(3-chloropropyl)-2-fluorobenzene (amount 2.00 g, yield 82%).

Step 5

To a solution of 1-(3-chloropropyl)-2-fluorobenzene (2.00 g, 11.6 mmol) in carbon tetrachloride (39 mL) were added N-bromosuccineimide (2.27 g, 12.7 mmol) and 2,2'-azobis(isobutyropionitrile) (168 μL, 1.16 mmol), and the mixture was stirred for 2 hours at 90° C. Water and chloroform were added to the reaction solution, and the mixture was partitioned. After drying the organic layer with anhydrous sodium sulfate, the solvent was evaporated off under reduced pressure. The residue was purified by silica gel column chromatography to give 1-(1-bromo-3-chloropropyl)-2-fluorobenzene (amount 2.36 g, yield 81%).

Step 6

To a solution of 1-(1-bromo-3-chloropropyl)-2-fluorobenzene (2.36 g, 9.38 mmol) in acetonitrile (31.3 mL) were added ethyl 5-hydroxy-1H-pyrazole-3-carboxylate (1.47 g, 9.38 mmol) and potassium carbonate (3.89 g, 28.1 mmol), and the mixture was stirred for 15 hours at 100° C. After concentrating the reaction solution under reduced pressure, the residue was purified by silica gel column chromatography to give ethyl 5-(2-fluorophenyl)-6,7-dihydro-5H-pyrazolo[5,1-b][1,3]oxazine-2-carboxylate (amount 2.30 g, yield 84%).

Step 7

To a solution of ethyl 5-(2-fluorophenyl)-6,7-dihydro-5H-pyrazolo[5,1-b][1,3]oxazine-2-carboxylate (2.30 g, 7.92 mmol) in ethanol (15.8 mL) was added 4 mol/L aqueous solution of sodium hydroxide (7.92 mL, 31.7 mmol), and the mixture was stirred for 24 hours at room temperature. To the reaction solution, 2 mol/L hydrochloric acid was added, and then the solvent was evaporated off under reduced pressure. Water and ethyl acetate were added to the residue, and the mixture was partitioned. The organic layer was washed with saturated brine, and then dried over anhydrous sodium sulfate, and the solvent was evaporated off under reduced pressure to give 5-(2-fluorophenyl)-6,7-dihydro-5H-pyrazolo[5,1-b][1,3]oxazine-2-carboxylic acid (amount 1.80 g, yield 87%) as a mixture with 4 equivalents of sodium chloride.

Step 8

To a suspension of 5-(2-fluorophenyl)-6,7-dihydro-5H-pyrazolo[5,1-b][1,3]oxazine-2-carboxylic acid (a mixture with 4 equivalents of sodium chloride) (36.1 mg, 0.138 mmol) in dichloromethane (1.2 mL) were added HATU (48.0 mg, 0.126 mmol), N,N-diisopropylethylamine (99 µL, 0.57 mmol) and (R)-3-aminochroman-6-carbonitrile (20.0 mg, 0.115 mmol), and the mixture was stirred for 2 hours at room temperature. The reaction solution was purified by silica gel column chromatography to give N—((R)-6-cyanochroman-3-yl)-5-(2-fluorophenyl)-6,7-dihydro-5H-pyrazolo[5,1-b][1,3]oxazine-2-carboxamide (amount 47.9 mg, yield 100%).

The compound of Example 71 was synthesized by methods similar to those described in Example 70 and Reference Example 2.

The compound of Example 72 was synthesized by a method similar to Example 70.

The compound of Example 73 was synthesized by a method similar to Example 70.

The compounds of Example 74 were obtained by separating the compound of Example 73.

The compound of Example 75 was synthesized by a method similar to Example 70.

The compound of Example 76 was synthesized by methods similar to those described in Example 70 and Reference Example 5.

The compound of Example 77 was synthesized by a method similar to those described in Step 6 to Step 8 in Example 70 and Reference Example 4.

The compound of Reference Example 25 (shown in the figure below.) was synthesized by a method similar to Reference Example 4.

[Chem 122]

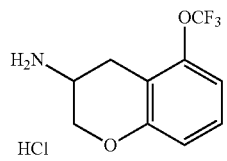

The compound of Example 78 was synthesized by methods similar to those described in Example 77 and Reference Example 25.

The compound of Example 79 was synthesized by a method similar to Example 77.

The compound of Reference Example 27 was synthesized under the scheme depicted in the figure below.

[Chem 123]

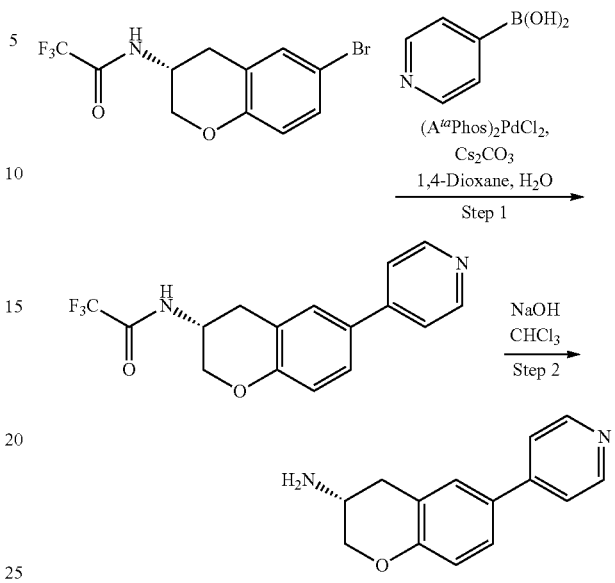

The compound of Example 80 was synthesized by methods similar to those described in Example 70 and Reference Example 27.

Reference Example 28

Production of (R)-6-(pyridin-2-yl)chroman-3-amine dihydrochloride

[Chem 124]

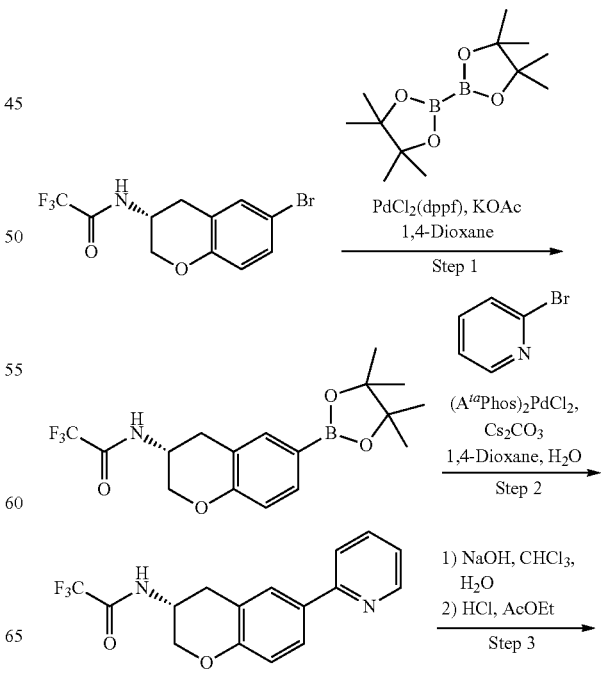

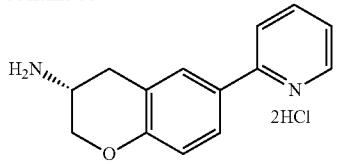

Step 1

To a solution of (R)—N-(6-bromochroman-3-yl)-2,2,2-trifluoroacetamide (500 mg, 1.54 mmol) synthesized by a method described in Step 1 in Reference Example 2 in 1,4-dioxane (10 mL) were added bis(pinacolato)diboron (800 mg, 3.15 mmol), potassium acetate (300 mg, 7.87 mmol) and [1,1'-bis(diphenylphosphino)ferrocene]dichloropalladium (II) (100 mg, 0.14 mmol). The mixture was stirred for 15 hours at 90° C. Water and ethyl acetate were added to the reaction solution, and the mixture was partitioned. After drying the organic layer with anhydrous sodium sulfate, the solvent was evaporated off under reduced pressure. The residue was purified by silica gel column chromatography to give (R)-2,2,2-trifluoro-N-(6-(4,4,5,5-tetramethyl-1,3,2-dioxaborolan-2-yl)chroman-3-yl)acetamide (amount 570 mg, yield 100%).

Step 2

A mixture suspension of (R)-2,2,2-trifluoro-N-(6-(4,4,5,5-tetramethyl-1,3,2-dioxaborolan-2-yl)chroman-3-yl)acetamide (200 mg, 0.539 mmol), 2-bromopyridine (130 mg, 0.823 mmol), cesium carbonate (350 mg, 1.07 mmol) and bis(di-tert-butyl (4-dimethylaminophenyl)phosphine)dichloropalladium (II) (38.0 mg, 0.0537 mmol) in 1,4-dioxane (2.5 mL) and water (0.5 mL) was stirred for 5 hours at 100° C. To the reaction solution, an aqueous solution of saturated ammonium chloride and ethyl acetate were added, and the mixture was partitioned. The organic layer was washed with saturated brine, and then dried over anhydrous sodium sulfate. The solvent was evaporated off under reduced pressure. The residue was purified by silica gel column chromatography to give (R)-2,2,2-trifluoro-N-(6-(pyridin-2-yl)chroman-3-yl)acetamide (amount 82.0 mg, yield 47%).

Step 3

(R)-6-(Pyridin-2-yl)chroman-3-amine dihydrochloride was obtained by a method similar to Step 3 in Reference Example 1, using (R)-2,2,2-trifluoro-N-(6-(pyridin-2-yl)chroman-3-yl)acetamide instead of (R)—N-(6-chlorochroman-3-yl)-2,2,2-trifluoroacetamide.

The compound of Example 81 was synthesized by methods similar to those described in Example 70 and Reference Example 28.

The compound of e Example 82 was synthesized under the scheme depicted in the figure below.

[Chem 125]

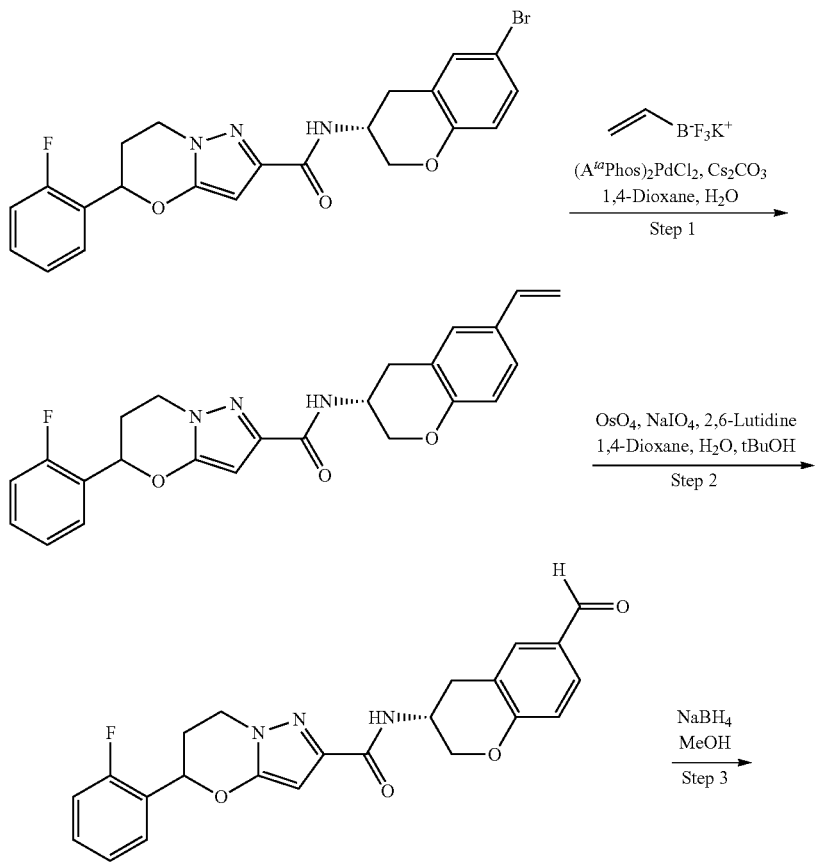

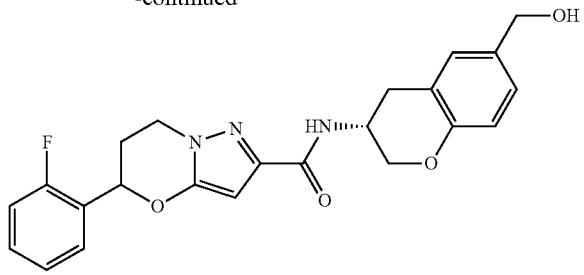

The compound of Example 83 was synthesized under the scheme depicted in the figure below.

[Chem 126]

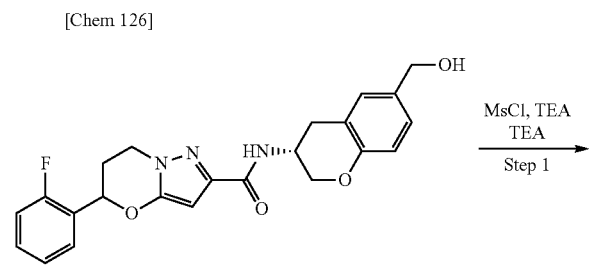 MsCl, TEA
TEA
Step 1

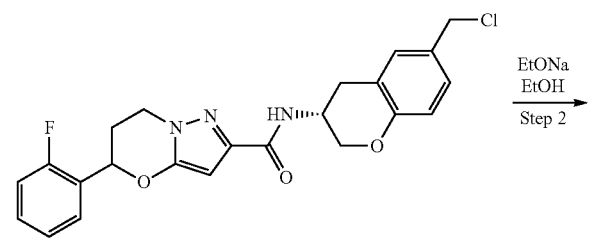 EtONa
EtOH
Step 2

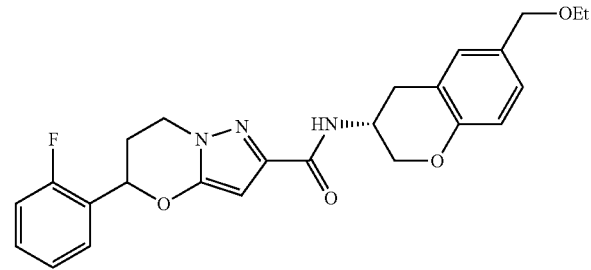

The compound of Example 84 was synthesized under the scheme depicted in the figure below.

[Chem 127]

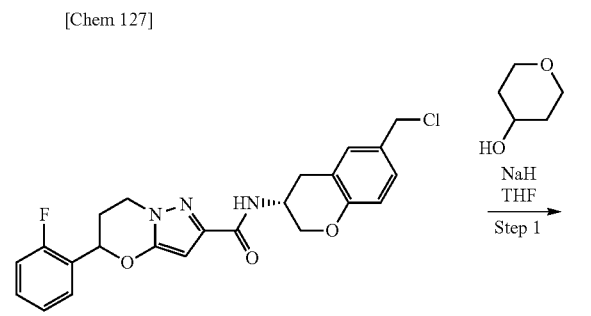 NaH
THF
Step 1

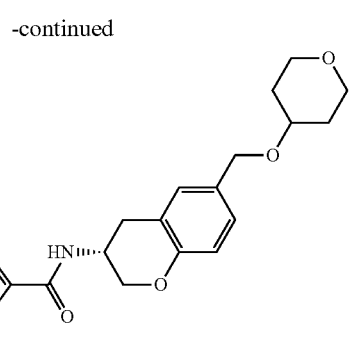

The compound of Example 85 was synthesized under the scheme depicted in the figure below.

[Chem 128]

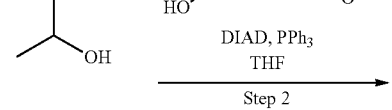 TBDSCl, Imidazole
DCM
Step 1

 DIAD, PPh$_3$
THF
Step 2

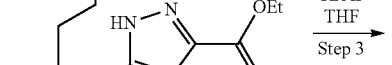 TBAF
THF
Step 3

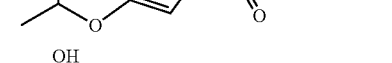 CBr$_4$, PPh$_3$, DIEA
DCM
Step 4

NaOH
EtOH, H$_2$O
Step 5

-continued

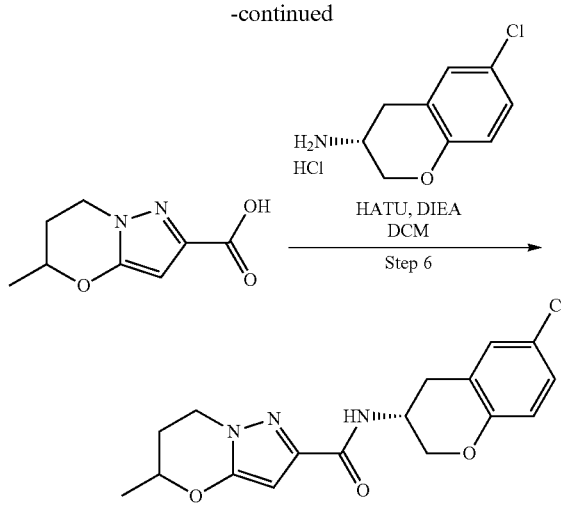

The compound of Example 86 was synthesized by a method similar to Example 85.

The compound of Example 87 was synthesized by a method similar to Example 85.

The compound of Example 88 was synthesized by methods similar to those described in Example 85 and Reference Example 2.

The compound of Example 89 was synthesized by methods similar to those described in Example 85 and Reference Example 2.

The compound of Example 90 was synthesized by a method similar to Example 85.

The compound of Example 91 was synthesized by methods similar to those described in Example 85 and Reference Example 24.

The compounds of Example 92 were obtained by separating the compound of Example 91.

The compound of Reference Example 29 (shown in the figure below.) was synthesized by a method similar to Reference Example 27.

[Chem 129]

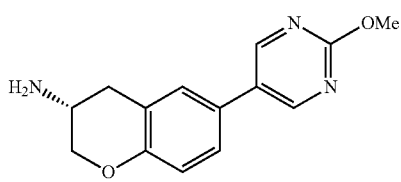

The compound of Example 93 was synthesized by methods similar to those described in Example 85 and Reference Example 29.

The compound of Example 94 was synthesized by methods similar to those described in Example 85 and Reference Example 24.

The compounds of Example 95 were obtained by separating the compound of Example 94.

The compound of Reference Example 30 (4-cyclopropylbutan-1,3-diol) was synthesized under the scheme depicted in the figure below.

[Chem 130]

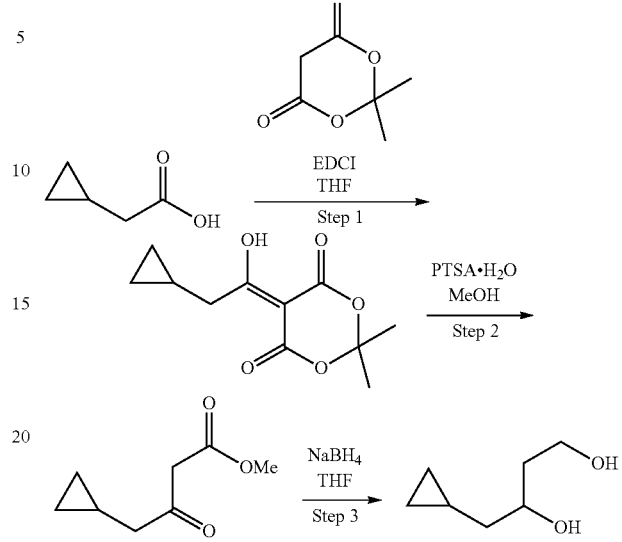

The compound of Example 96 was synthesized by methods similar to those described in Reference Example 30, Example 85 and Reference Example 24.

The compounds of Example 97 were obtained by separating the compound of Example 96.

Reference Example 31

Production of ethyl 5-((benzyloxy)methyl)-6,7-dihydro-5H-pyrazolo[5,1-b][1,3]oxazine-2-carboxylate

[Chem 131]

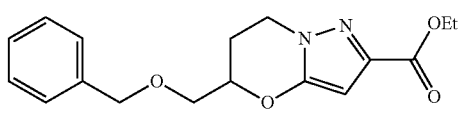

Ethyl 5-((benzyloxy)methyl)-6,7-dihydro-5H-pyrazolo[5,1-b][1,3]oxazine-2-carboxylate was obtained by a method similar to Step 1 to Step 4 in Example 85, using 4-(benzyloxy)butan-1,3-diol instead of butan-1,3-diol in Step 1.

The compound of Example 98 was synthesized from the compound of Reference Example 31 by methods similar to Step 5 and Step 6 in Example 85.

The compound of Example 99 was synthesized by methods similar to Reference Example 31, Step 5 and Step 6 in Example 85 and Example 24.

Example 100

Production of N—((R)-6-cyanochroman-3-yl)-5-(propoxymethyl)-6,7-dihydro-5H-pyrazolo[5,1-b][1,3]oxazine-2-carboxamide

[Chem 132]

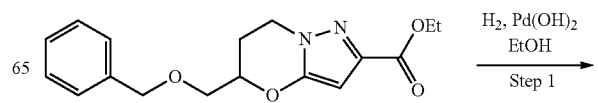

165

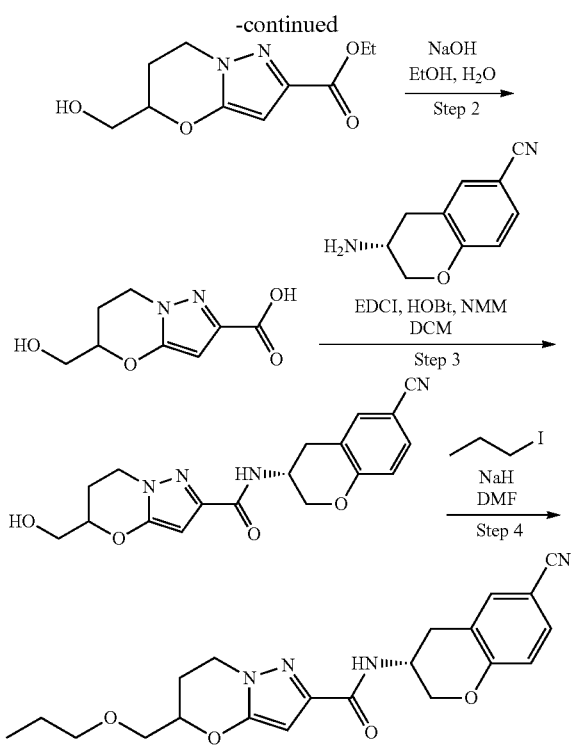

Step 1

To a solution of ethyl 5-((benzyloxy)methyl-6,7-dihydro-5H-pyrazolo[5,1-b][1,3]oxazine-2-carboxylate (12.4 g, 18.4 mmol) synthesized by a method described in Reference Example 31 in ethanol (61 mL), 20% palladium hydroxide on carbon (2.59 mg) was added. The mixture was stirred for 23 hours at 40° C. under pressurized conditions (about 3 atm) in hydrogen atmosphere. After the reaction solution was filtered through celite, the solvent was evaporated off under reduced pressure. The residue was purified by silica gel column chromatography to give ethyl 5-(hydroxymethyl)-6,7-dihydro-5H-pyrazolo[5,1-b][1,3]oxazine-2-carboxylate (amount 2.47 g, yield 59%).

Step 2

To a solution of ethyl 5-(hydroxymethyl)-6,7-dihydro-5H-pyrazolo[5,1-b][1,3]oxazine-2-carboxylate (1.97 g, 8.71 mmol) in ethanol (44 mL), 4 mol/L aqueous solution of sodium hydroxide (8.7 mL, 35 mmol) was added, and the mixture was stirred for 15 hours at room temperature. To the reaction solution, 2 mol/L hydrochloric acid was added, and then the solvent was evaporated off under reduced pressure to give 5-(hydroxymethyl)-6,7-dihydro-5H-pyrazolo[5,1-b][1,3]oxazine-2-carboxylic acid (amount 3.68 g, yield 98%) as a mixture with 4 equivalents of sodium chloride.

Step 3

To a suspension of 5-(hydroxymethyl)-6,7-dihydro-5H-pyrazolo[5,1-b][1,3]oxazine-2-carboxylic acid (a mixture with 4 equivalents of sodium chloride) (450 mg, 1.04 mmol), (R)-3-aminochroman-6-carbonitrile (200 mg, 1.15 mmol) synthesized by a method described in Reference Example 24, 1-hydroxybenzotriazole (169 mg, 1.25 mmol)

166 and 1-ethyl-3-(3-dimethylaminopropyl)carbodiimide hydrochloride (240 mg, 1.25 mmol) in dichloromethane (10 mL), 4-methylmorpholine (573 μL, 5.21 mmol) was added, and the mixture was stirred for 24 hours at room temperature. To the reaction solution, 1 mol/L hydrochloric acid and chloroform was added, and the mixture was partitioned. After drying the organic layer with anhydrous sodium sulfate, the solvent was evaporated off under reduced pressure. The residue was purified by silica gel column chromatography to give N—((R)-6-cyanochroman-3-yl)-5-(hydroxymethyl)-6,7-dihydro-5H-pyrazolo[5,1-b][1,3]oxazine-2-carboxamide (amount 300 mg, yield 81%).

Step 4

To a solution of N—((R)-6-cyanochroman-3-yl)-5-(hydroxymethyl)-6,7-dihydro-5H-pyrazolo[5,1-b][1,3]oxazine-2-carboxamide (330 mg, 0.931 mmol) in N,N-dimethylformamide (8.8 mL) was added sodium hydride (60% in oil) and 1-iodopropane (136 μL, 1.39 mmol). The mixture was stirred for 13 hours at 90° C. Water and ethyl acetate were added to the reaction solution, and the mixture was partitioned. After drying the organic layer with anhydrous sodium sulfate, the solvent was evaporated off under reduced pressure. The residue was purified by silica gel column chromatography to give N—((R)-6-cyanochroman-3-yl)-5-(propoxymethyl)-6,7-dihydro-5H-pyrazolo[5,1-b][1,3]oxazine-2-carboxamide (amount 73.3 mg, yield 20%).

Example 101

Isomeric separation of N—((R)-6-cyanochroman-3-yl)-5-(propoxymethyl)-6,7-dihydro-5H-pyrazolo[5,1-b][1,3]oxazine-2-carboxamide

[Chem 133]

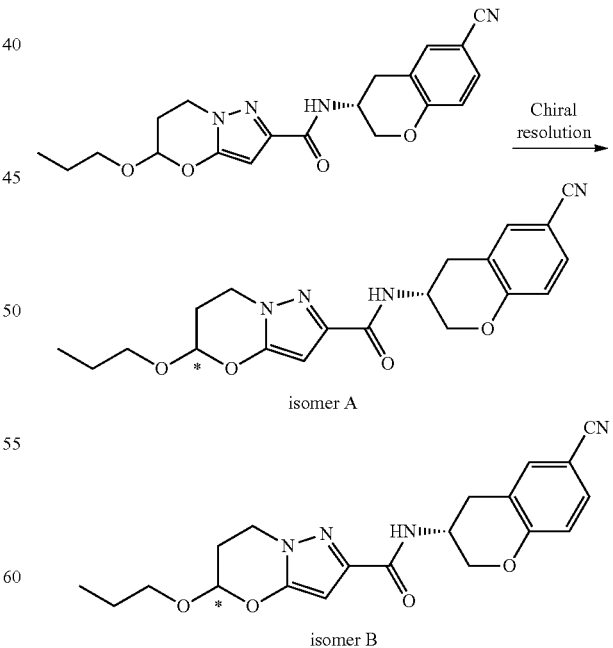

N—((R)-6-Cyanochroman-3-yl)-5-(propoxymethyl)-6,7-dihydro-5H-pyrazolo[5,1-b][1,3]oxazine-2-carboxamide (150 mg, 0.378 mmol) synthesized by a method described in Example 100 was dissolved in ethanol (15 mL), and the solution was subjected to HPLC fractionation (column: CHIRALPAK IB, developing solvent: ethanol, flow rate: 8.0 mL/min, room temperature) to give isomer A (amount 59.9 mg, yield 40%) and isomer B (amount 61.4 mg, yield 41%).

Example 102

Production of N—((R)-6-cyanochroman-3-yl)-5-((cyclopropylmethoxy)methyl)-6,7-dihydro-5H-pyrazolo[5,1-b][1,3]oxazine-2-carboxamide

[Chem 134]

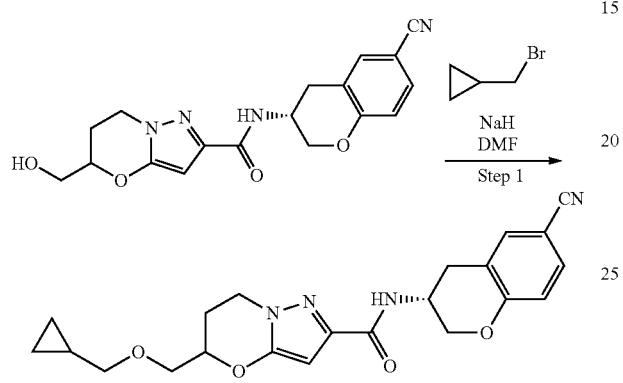

To a solution of N—((R)-6-cyanochroman-3-yl)-5-(hydroxymethyl)-6,7-dihydro-5H-pyrazolo[5,1-b][1,3]oxazine-2-carboxamide (397 mg, 1.12 mmol) synthesized by a method described in Step 3 in Example 100 in N,N-dimethylformamide (11.2 mL), sodium hydride (60% in oil) (179 mg, 4.48 mmol) was added. The mixture was stirred for 10 minutes at room temperature. In addition, (bromomethyl)cyclopropane (215 μL, 2.24 mmol) was added, and the mixture was stirred for 16 hours at 90° C. Water and ethyl acetate were added to the reaction solution, and the mixture was partitioned. After drying the organic layer with anhydrous sodium sulfate, the solvent was evaporated off under reduced pressure. The residue was purified by silica gel column chromatography to give N—((R)-6-cyanochroman-3-yl)-5-((cyclopropylmethoxy)methyl)-6,7-dihydro-5H-pyrazolo[5,1-b][1,3]oxazine-2-carboxamide (amount 136 mg, yield 30%).

Example 103

Isomeric Separation of N—((R)-6-cyanochroman-3-yl)-5-((cyclopropylmethoxy)methyl)-6,7-dihydro-5H-pyrazolo[5,1-b][1,3]oxazine-2-carboxamide

[Chem 135]

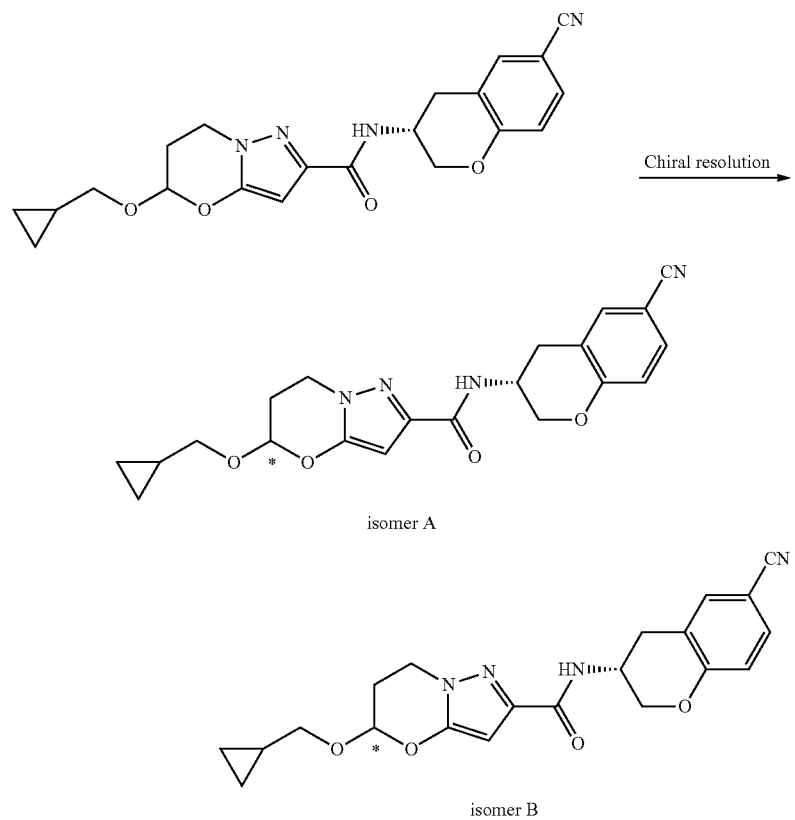

N—((R)-6-Cyanochroman-3-yl)-5-((cyclopropyl-methoxy)methyl)-6,7-dihydro-5H-pyrazolo[5,1-b][1,3]oxazine-2-carboxamide (134 mg, 0.328 mmol) synthesized by a method described in Example 102 was dissolved in ethanol (13 mL), and the solution was subjected to HPLC fractionation (column: CHIRALPAK IB, developing solvent: ethanol, flow rate: 8.0 mL/min, room temperature) to give isomer A (amount 49.3 mg, yield 37%) and isomer B (amount 48.9 mg, yield 37%).

The compound of Example 104 was synthesized by a method similar to Example 100.

The compound of Example 105 was synthesized by methods similar to those described in Example 100 and Reference Example 1.

The compound of Example 106 was synthesized by methods similar to those described in Example 100 and Reference Example 1.

The compound of Reference Example 32 (shown in the figure below.) was synthesized by a method similar to Reference Example 27.

[Chem 136]

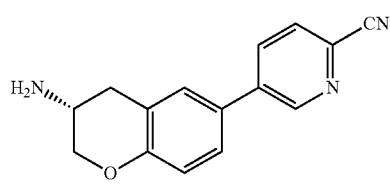

The compound of Example 107 was synthesized by methods similar to those described in Example 100 and Reference Example 32.

The compound of Reference Example 33 (shown in the figure below.) was synthesized by a method similar to Example 100.

[Chem 137]

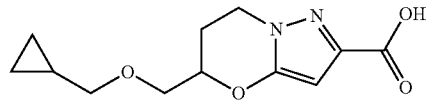

The compound of Example 108 was synthesized from the compound of Reference Example 33 and the compound of Reference Example 48 by a method similar to Step 3 in Example 100.

The compounds of Example 109 were obtained by separating the compound of Example 108.

The compound of Example 110 was synthesized from the compound of Reference Example 33 and the compound of Reference Example 28 by a method similar to Step 3 in Example 100.

The compounds of Example 111 were obtained by separating the compound of Example 110.

The compound of Reference Example 34 (4-((1-methylcyclopropyl)methoxy)butan-1,3-diol) was synthesized under the scheme depicted in the figure below.

[Chem 138]

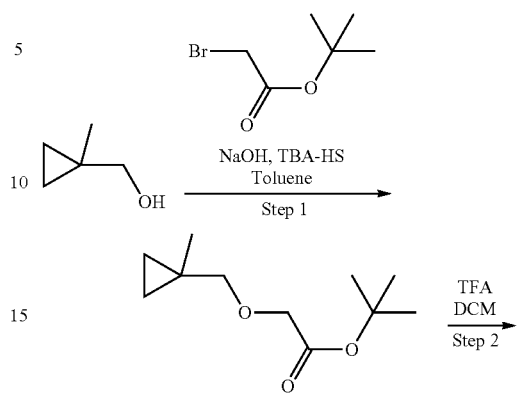

The compound of Example 112 was synthesized by methods similar to those described in Reference Example 34, Example 85 and Reference Example 24.

The compounds of Example 113 were obtained by separating the compound of Example 112.

Example 114

Production of N—((R)-6-cyanochroman-3-yl)-5-((2,2,2-trifluoroethoxy)methyl)-6,7-dihydro-5H-pyrazolo[5,1-b][1,3]oxazine-2-carboxamide

[Chem 139]

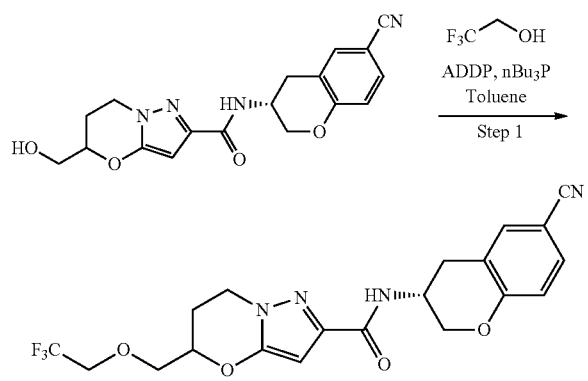

To a solution of N—((R)-6-cyanochroman-3-yl)-5-(hydroxymethyl)-6,7-dihydro-5H-pyrazolo[5,1-b][1,3]oxazine-2-carboxamide (20.0 mg, 0.0564 mmol) synthesized by a method described in Step 3 in Example 100 in toluene (1.1 mL) were added tributylphosphine (28.2 μL, 0.113 mmol), 2,2,2-trifluoroethanol (40.6 μL, 0.564 mmol) and 1,1'-(azodicarbonyl)dipiperizine (28.5 mg, 0.113 mmol). The mixture was stirred for 15 hours at 80° C. The reaction solution was purified by silica gel column chromatography to give N—((R)-6-cyanochroman-3-yl)-5-((2,2,2-trifluoroethoxy)methyl)-6,7-dihydro-5H-pyrazolo[5,1-b][1,3]oxazine-2-carboxamide.

Example 115

Isomeric Separation of N—((R)-6-cyanochroman-3-yl)-5-((2,2,2-trifluoroethoxy)methyl)-6,7-dihydro-5H-pyrazolo[5,1-b][1,3]oxazine-2-carboxamide

[Chem 140]

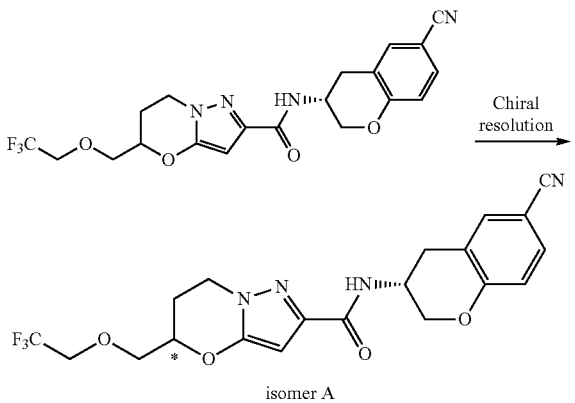

isomer A

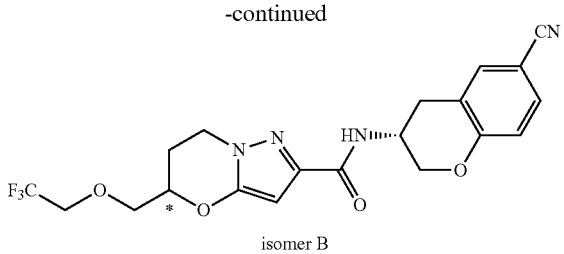

isomer B

N—((R)-6-Cyanochroman-3-yl)-5-((2,2,2-trifluoroethoxy)methyl)-6,7-dihydro-5H-pyrazolo[5,1-b][1,3]oxazine-2-carboxamide (178 mg, 0.408 mmol) synthesized by a method described in Example 114 was dissolved in ethanol (18 mL), and the solution was subjected to HPLC fractionation (column: CHIRALPAK IB, developing solvent: ethanol, flow rate: 8.0 mL/min, room temperature) to give isomer A (amount 74.7 mg, yield 42%) and isomer B (amount 70.5 mg, yield 40%).

The compound of Example 116 was synthesized by a method similar to Example 114.

The compound of Example 117 was synthesized under the scheme depicted in the figure below.

[Chem 141]

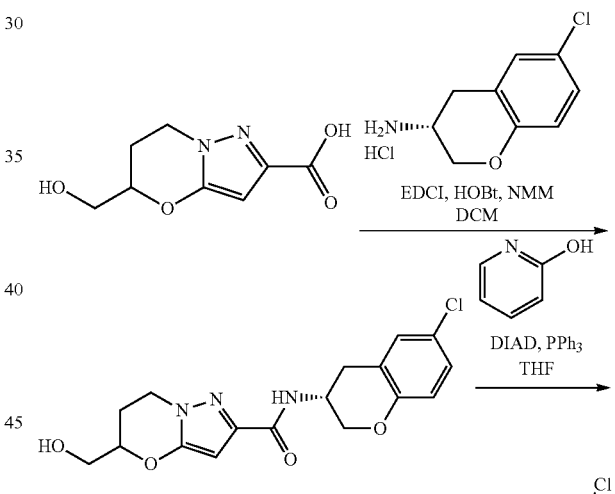

The compound of Example 118 was synthesized from the compound synthesized in Step 3 in Example 100 by a method similar to Step 2 in Example 117.

The compound of Example 119 was synthesized under the scheme depicted in the figure below.

[Chem 142]

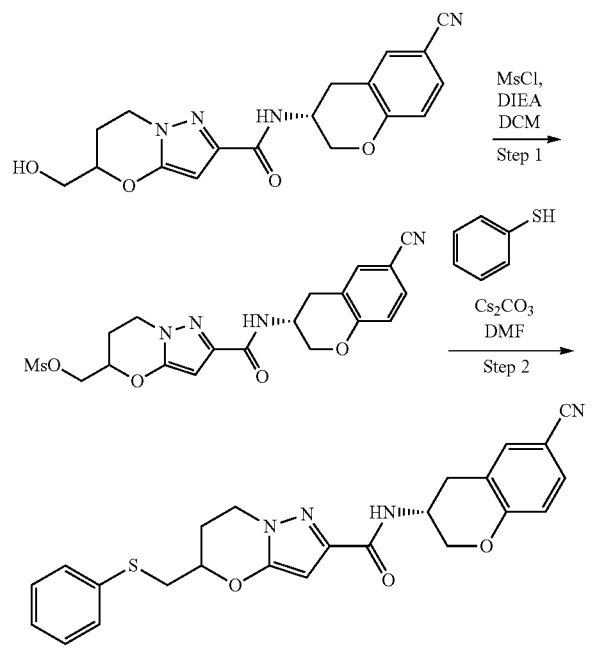

The compound of Example 120 was synthesized from the compound synthesized in Step 1 in Example 117 by a method similar to Example 119.

The compound of Example 121 was synthesized under the scheme depicted in the figure below.

[Chem 143]

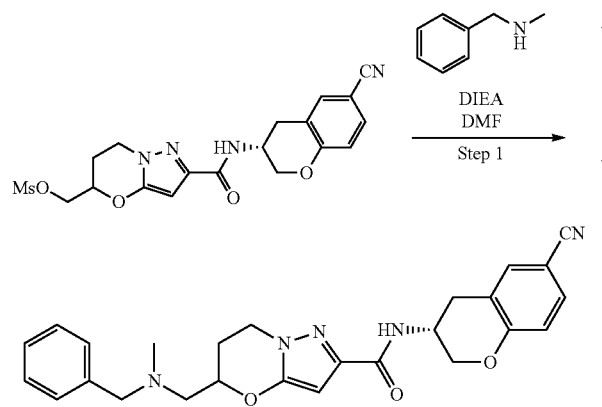

The compound of Example 122 was synthesized under the scheme depicted in the figure below.

[Chem 144]

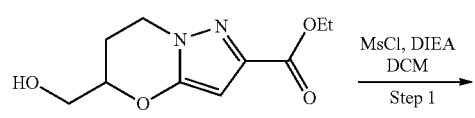

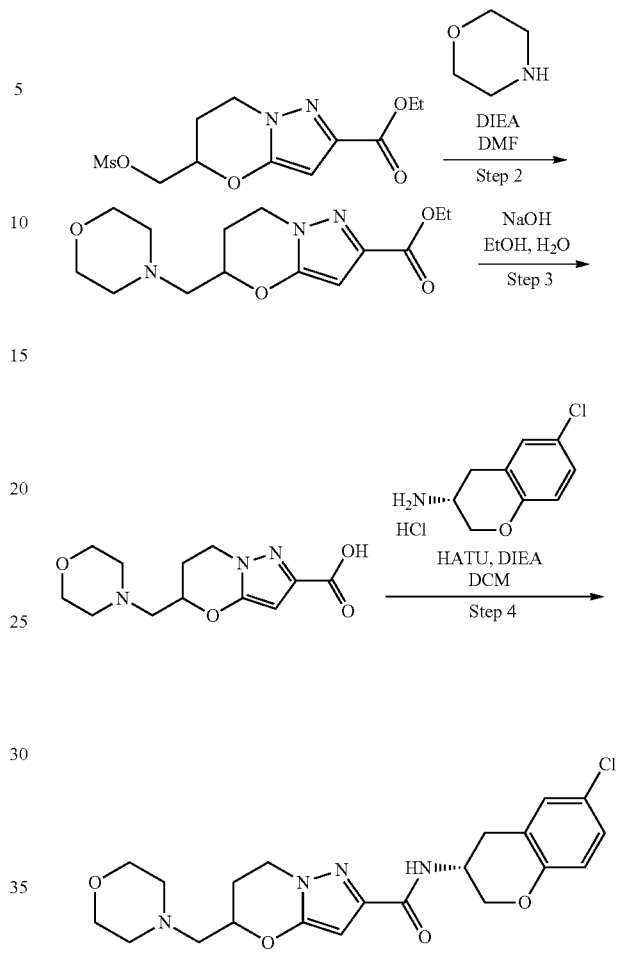

The compound of Reference Example 35 was synthesized from the compound of synthesized in Step 1 in Example 122 under the scheme depicted in the figure below.

[Chem 145]

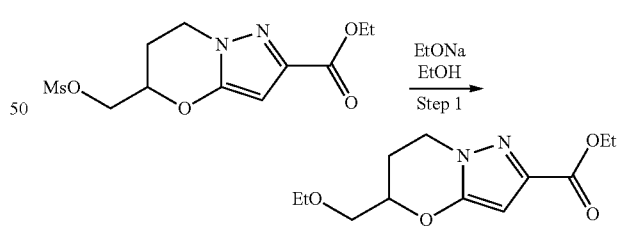

The compound of Example 123 was synthesized from the compound of Reference Example 35 and the compound of Reference Example 28 by methods similar to Step 3 and Step 4 in Example 122.

The compounds of Example 124 were obtained by separating the compound of Example 123.

The compound of Example 125 was synthesized from the compound of Reference Example 35 and the compound of Reference Example 32 by methods similar to Step 3 and Step 4 in Example 122.

Reference Example 36

Ethyl 5-((2,2,2-trifluoroethoxy)methyl)-6,7-dihydro-5H-pyrazolo[5,1-b][1,3]oxazine-2-carboxylate

[Chem 146]

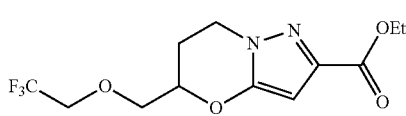

Ethyl 5-((2,2,2-trifluoroethoxy)methyl)-6,7-dihydro-5H-pyrazolo[5,1-b][1,3]oxazine-2-carboxylate was obtained by a method similar to Example 114, using ethyl 5-(hydroxymethyl)-6,7-dihydro-5H-pyrazolo[5,1-b][1,3]oxazine-2-carboxylate synthesized by a method described in Step 1 in Example 100 instead of N—((R)-6-cyanochroman-3-yl)-5-(hydroxymethyl)-6,7-dihydro-5H-pyrazolo[5,1-b][1,3]oxazine-2-carboxamide.

The compound of Example 126 was synthesized from the compound of Reference Example 36 and Reference Example 48 by methods similar to Step 2 and Step 3 in Example 100.

The compounds of Example 127 were obtained by separating the compound of Example 126.

Example 128

Production of 5-((2,2,2-trifluoroethoxy)methyl)-N—((R)-6-((2,2,2-trifluoroethoxy)methyl)chroman-3-yl)-6,7-dihydro-5H-pyrazolo[5,1-b][1,3]oxazine-2-carboxamide

[Chem 147]

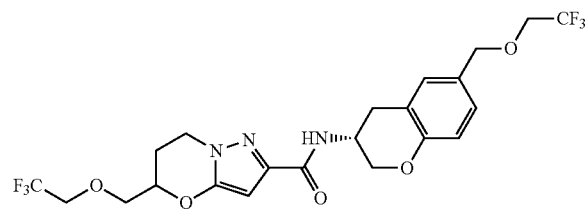

5-((2,2,2-Trifluoroethoxy)methyl)-N—((R)-6-((2,2,2-trifluoroethoxy)methyl)chroman-3-yl)-6,7-dihydro-5H-pyrazolo[5,1-b][1,3]oxazine-2-carboxamide was obtained by a method similar to Step 3 and Step 4 in Example 1, using ethyl 5-((2,2,2-trifluoroethoxy)methyl)-6,7-dihydro-5H-pyrazolo[5,1-b][1,3]oxazine-2-carboxylate synthesized by a method described in Reference Example 36 instead of ethyl 6-(trifluoromethyl)-5,6,7,8-tetrahydroimidazo[1,2-a]pyridine-2-carboxylate in Step 3, and using (R)-6-((2,2,2-trifluoroethoxy)methyl)chroman-3-amine hydrochloride synthesized by a method described in Reference Example 44 instead of 6-fluorochroman-3-amine hydrochloride in Step 4.

Example 129

Isomeric Separation of 5-((2,2,2-trifluoroethoxy)methyl)-N—((R)-6-((2,2,2-trifluoroethoxy)methyl)chroman-3-yl)-6,7-dihydro-5H-pyrazolo[5,1-b][1,3]oxazine-2-carboxamide

[Chem 148]

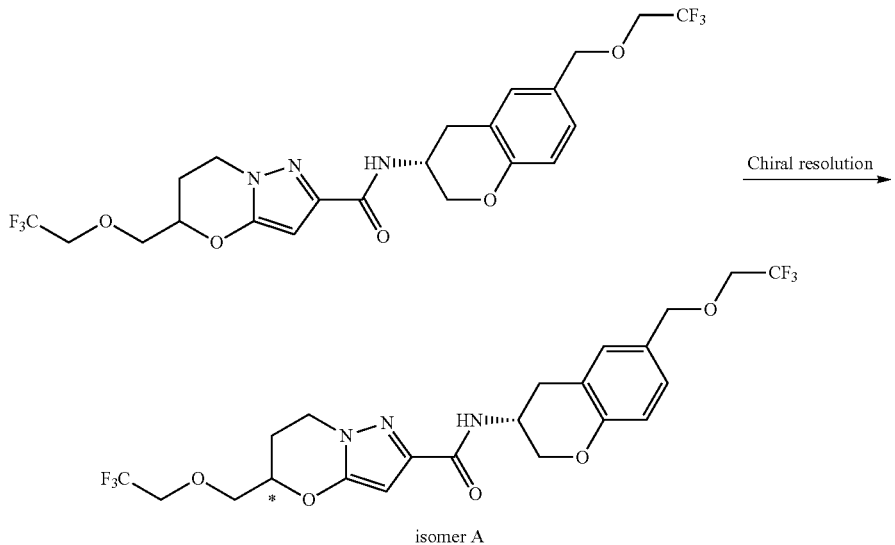

isomer A

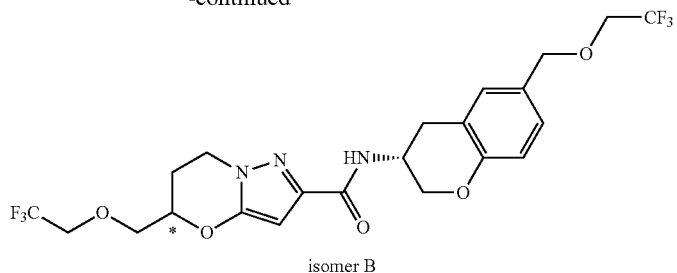

isomer B 5-((2,2,2-Trifluoroethoxy)methyl)-N—((R)-6-((2,2,2-trifluoroethoxy)methyl)chroman-3-yl)-6,7-dihydro-5H-pyrazolo[5,1-b][1,3]oxazine-2-carboxamide synthesized by a method described in Example 128 was dissolved in ethanol, and the solution was subjected to HPLC fractionation (column: CHIRALPAK IC, developing solvent: ethanol/n-hexane=50/50, flow rate: 8.0 mL/min, room temperature) to give isomer A (amount 3.7 mg) and isomer B (amount 3.6 mg).

The compound of Example 130 was synthesized from the compound of Reference Example 36 and the compound of Reference Example 28 by methods similar to Step 2 and Step 3 in Example 100.

The compounds of Example 131 were obtained by separating the compound of Example 130.

The compound of Example 132 was synthesized from the compound of Reference Example 36 and Reference Example 32 by methods similar to Step 3 and Step 4 in Example 122.

The compound of Reference Example 37 (5-((trifluoromethoxy)methyl)-6,7-dihydro-5H-pyrazolo[5,1-b][1,3]oxazine-2-carboxylic acid) was synthesized under the scheme depicted in the figure below.

[Chem 149]

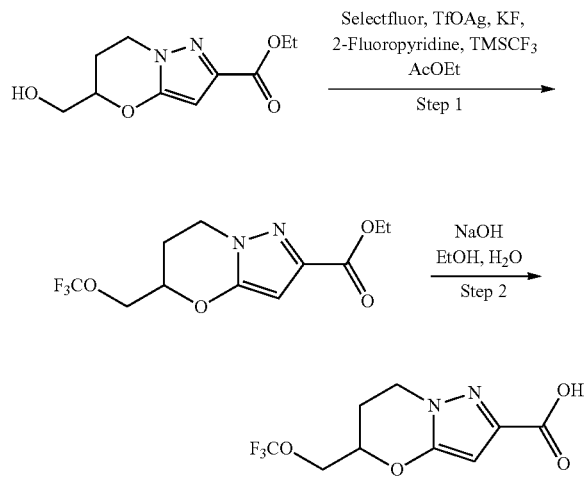

Example 133

Production of N—((R)-6-cyanochroman-3-yl)-5-((trifluoromethoxy)methyl)-6,7-dihydro-5H-pyrazolo[5,1-b][1,3]oxazine-2-carboxamide

[Chem 150]

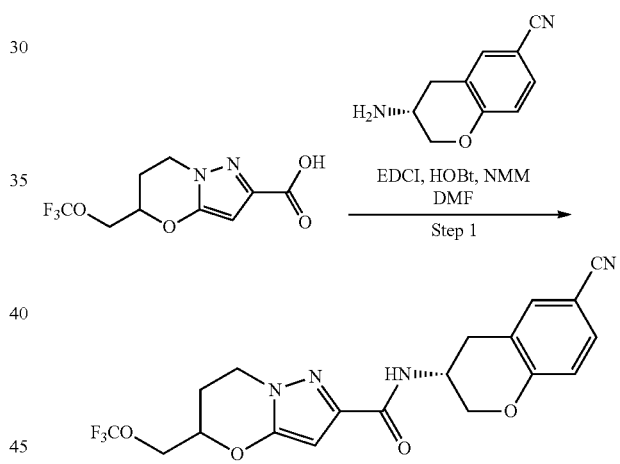

To a suspension of 5-((trifluoromethoxy)methyl)-6,7-dihydro-5H-pyrazolo[5,1-b][1,3]oxazine-2-carboxylic acid (a mixture with 4 equivalents of sodium chloride) (267 mg, 0.534 mmol) synthesized by a method described in Reference Example 37, (R)-3-aminochroman-6-carbonitrile (140 mg, 0.804 mmol) synthesized by a method described in Reference Example 24, 1-hydroxybenzotriazole (123 mg, 0.804 mmol) and 1-ethyl-3-(3-dimethylaminopropyl)carbodiimide hydrochloride (154 mg, 0.804 mmol) in N,N-dimethylformamide (5 mL), 4-methylmorpholine (353 µL, 3.21 mmol) was added. The mixture was stirred for 15 hours at 40° C. Water and ethyl acetate were added to the reaction solution, and the mixture was partitioned. After drying the organic layer with anhydrous sodium sulfate, the solvent was evaporated off under reduced pressure. The residue was purified by silica gel column chromatography to give N—((R)-6-cyanochroman-3-yl)-5-((trifluoromethoxy)methyl)-6,7-dihydro-5H-pyrazolo[5,1-b][1,3]oxazine-2-carboxamide (amount 182 mg, yield 81%).

Example 134

Isomeric Separation of N—((R)-6-cyanochroman-3-yl)-5-((trifluoromethoxy)methyl)-6,7-dihydro-5H-pyrazolo[5,1-b][1,3]oxazine-2-carboxamide

[Chem 151]

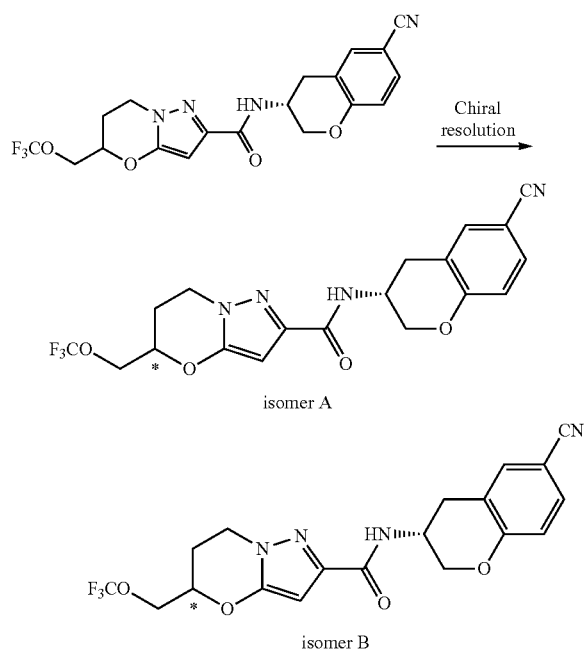

N—((R)-6-Cyanochroman-3-yl)-5-((trifluoromethoxy)methyl)-6,7-dihydro-5H-pyrazolo[5,1-b][1,3]oxazine-2-carboxamide (20 mg) synthesized by a method described in Example 133 was dissolved in ethanol (2 mL), and the solution was subjected to HPLC fractionation (column: CHIRALPAK IB, developing solvent: ethanol, flow rate: 8.0 mL/min, room temperature) to give isomer A (amount 9.4 mg, yield 47%) and isomer B (amount 8.2 mg, yield 41%).

The compound of Example 135 was synthesized from the compound of Reference Example 37 and the compound of Reference Example 48 by a method similar to Step 3 in Example 100.

The compounds of Example 136 were obtained by separating the compound of Example 135.

The compound of Reference Example 38 (5-(((difluoromethoxy)methyl)-6,7-dihydro-5H-pyrazolo[5,1-b][1,3]oxazine-2-carboxylic acid) was synthesized from the compound synthesized in Step 1 in Example 100 under the scheme depicted in the figure below.

[Chem 152]

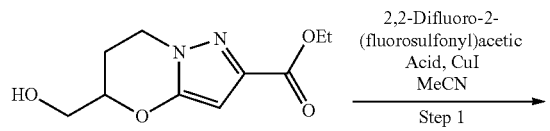

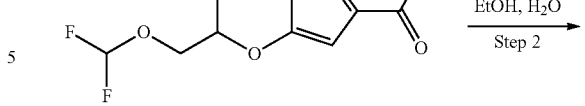

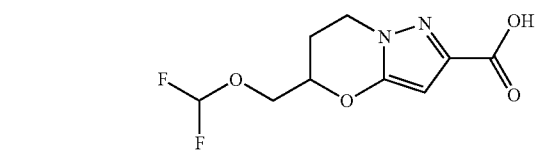

The compound of Example 137 was synthesized from the compound of Reference Example 38 and the compound of Reference Example 48 by a method similar to Step 3 in Example 100.

The compounds of Example 138 were obtained by separating the compound of Example 137.

The compound of Example 139 was synthesized from the compound of Reference Example 38 and the compound of Reference Example 44 by a method similar to Step 3 in Example 100.

The compounds of Example 140 were obtained by separating the compound of Example 139.

The compound of Example 141 was synthesized from the compound of Reference Example 38 and the compound of Reference Example 45 by a method similar to Step 3 in Example 100.

The compounds of Example 142 were obtained by separating the compound of Example 141.

Reference Example 39

Ethyl 5-(2-(benzyloxy)ethyl)-6,7-dihydro-5H-pyrazolo[5,1-b][1,3]oxazine-2-carboxylate

[Chem 153]

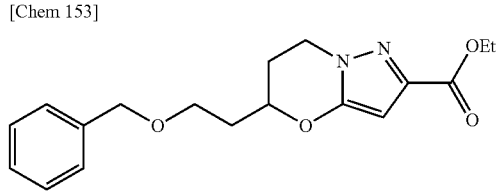

Ethyl 5-(2-(benzyloxy)ethyl)-6,7-dihydro-5H-pyrazolo[5,1-b][1,3]oxazine-2-carboxylate was obtained by a method similar to Step 1 to Step 4 in Example 85, using 5-(benzyloxy)pentane-1,3-diol instead of butan-1,3-diol in Step 1.

Reference Example 40

5-(2-(Trifluoromethoxy)ethyl)-6,7-dihydro-5H-pyrazolo[5,1-b][1,3]oxazine-2-carboxylic acid

[Chem 154]

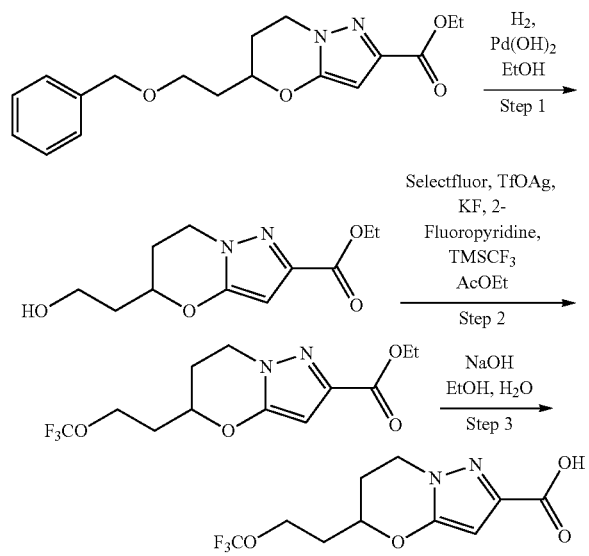

Step 1

Ethyl 5-(2-hydroxyethyl)-6,7-dihydro-5H-pyrazolo[5,1-b][1,3]oxazine-2-carboxylate was obtained by a method similar to Step 1 in Example 100, using ethyl 5-(2-(benzyloxy)ethyl)-6,7-dihydro-5H-pyrazolo[5,1-b][1,3]oxazine-2-carboxylate synthesized by a method described in Reference Example 39 instead of ethyl 5-((benzyloxy)methyl-6,7-dihydro-5H-pyrazolo[5,1-b][1,3]oxazine-2-carboxylate.

Step 2, Step 3

5-(2-(Trifluoromethoxy)ethyl)-6,7-dihydro-5H-pyrazolo[5,1-b][1,3]oxazine-2-carboxylic acid was obtained as a mixture with 2 equivalents of sodium chloride by a method similar to Step 1 and Step 2 in Reference Example 37, using ethyl5-(2-hydroxyethyl)-6,7-dihydro-5H-pyrazolo[5,1-b][1,3]oxazine-2-carboxylate instead of ethyl5-(hydroxymethyl)-6,7-dihydro-5H-pyrazolo[5,1-b][1,3]oxazine-2-carboxylate in Step 1.

The compound of Example 143 was synthesized, from the compound of Reference Example 40 and the compound of Reference Example 24 by a method similar to Step 4 in Example 1.

The compounds of Example 144 were obtained by separating the compound of Example 143.

The compound of Reference Example 41 (shown in the figure below.) was synthesized from the compound synthesized in Step 1 in Reference Example 40 by a method similar to Step 1 to Step 2 in Reference Example 38.

[Chem 155]

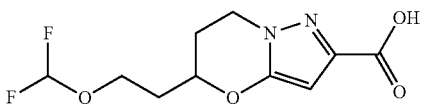

The compound of Example 145 was synthesized from the compound of Reference Example 41 and the compound of Reference Example 24 by a method similar to Step 4 in Example 1.

The compounds of Example 146 were obtained by separating the compound of Example 145.

The compound of Example 147 was synthesized from the compound of Reference Example 41 and the compound of Reference Example 48 by a method similar to Step 4 in Example 1.

The compounds of Example 148 were obtained by separating the compound of Example 147.

The compound of Example 149 was synthesized from the compound of Reference Example 41 and the compound of Reference Example 44 by a method similar to Step 4 in Example 1.

The compounds of Example 150 were obtained by separating the compound of Example 149.

The compound of Reference Example 151 was synthesized from the compound synthesized in Step 1 in Example 117 under the scheme depicted in the figure below.

[Chem 156]

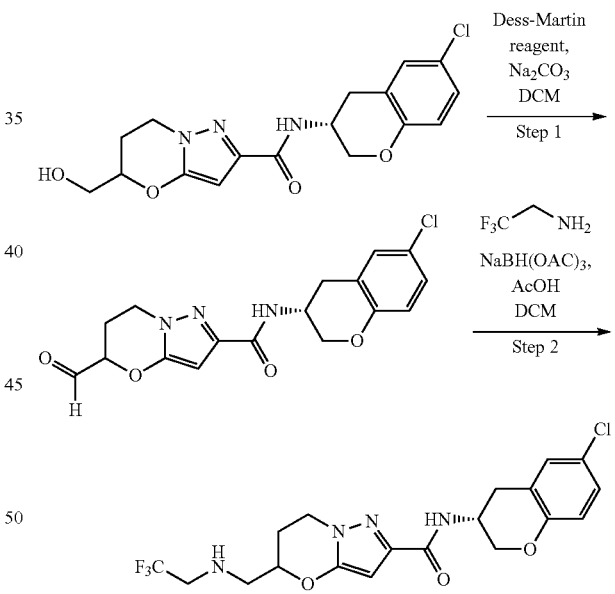

The compounds of Example 152 were obtained by separating the compound of Example 151.

The compound of Reference Example 42 (shown in the figure below.) was synthesized by a method similar to Step 2 to Step 3 in Example 122.

[Chem 157]

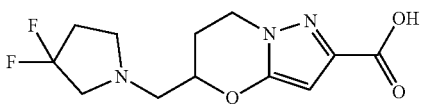

The compound of Example 153 was synthesized from the compound of Reference Example 42 under the scheme depicted in the figure below.
[Chem 158]
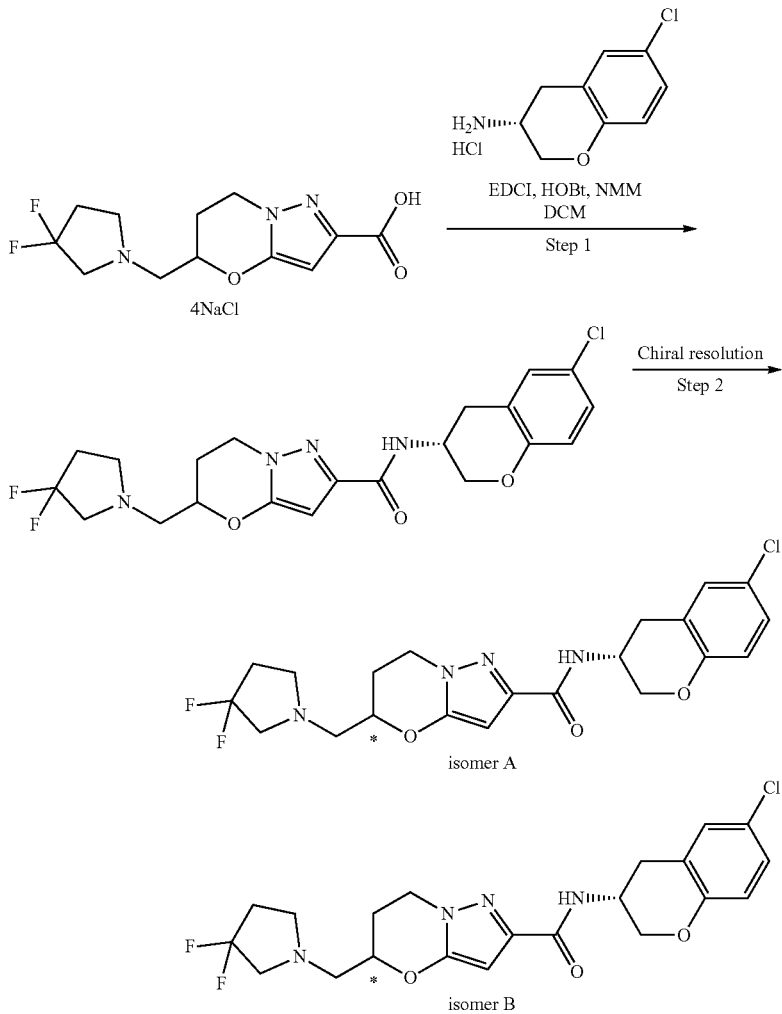
The compound of Example 154 was synthesized from the compound of Reference Example 42 under the scheme depicted in the figure below.
[Chem 159]
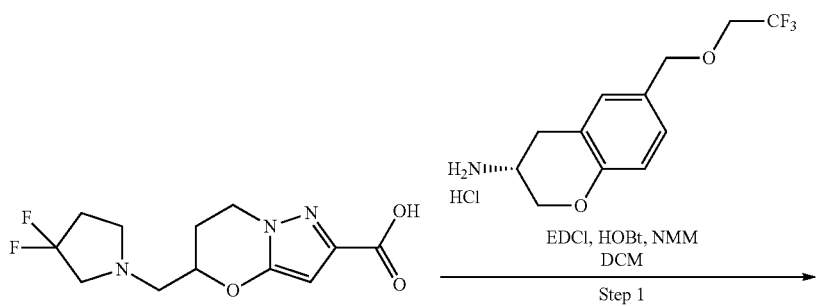

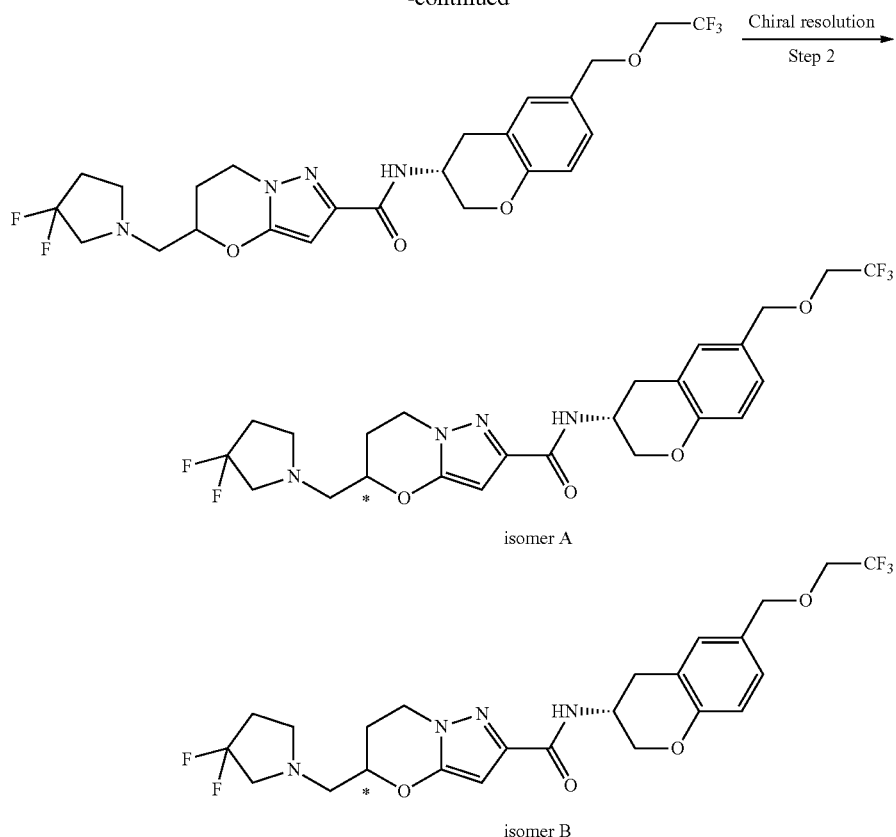

isomer A isomer B

The compound of Example 155 was synthesized under the scheme depicted in the figure below.

[Chem 160]

[Chem 161]

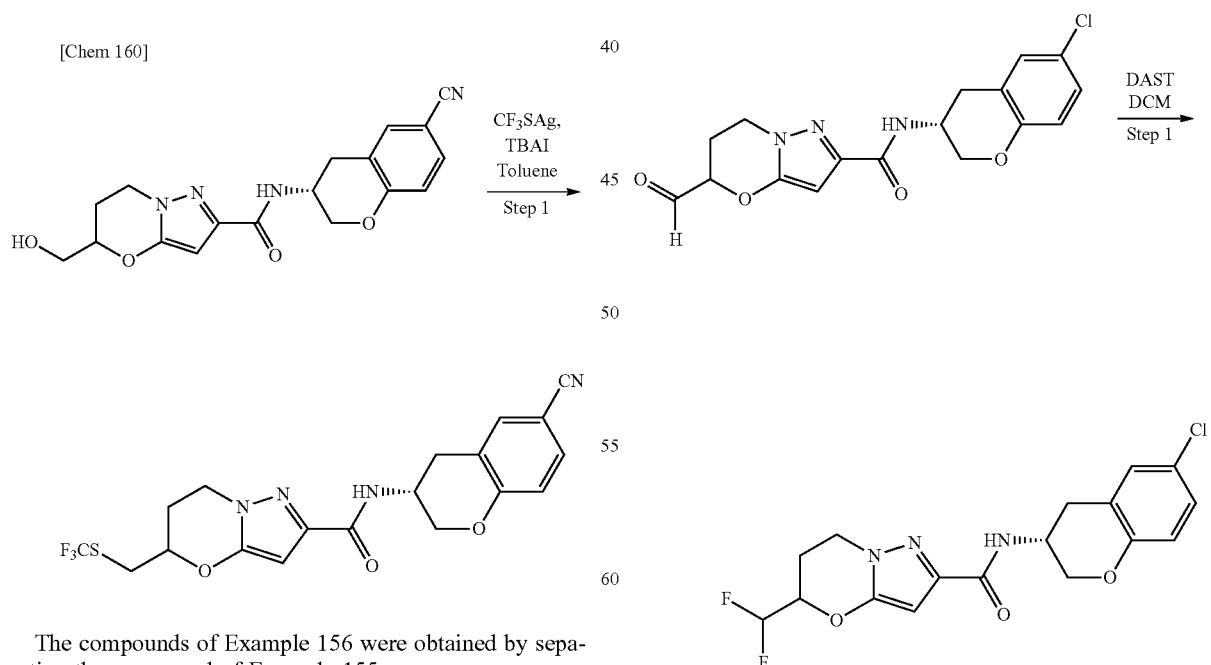

The compounds of Example 156 were obtained by separating the compound of Example 155.

The compound of Reference Example 157 was synthesized from the compound synthesized in Step 1 in Example 151 under the scheme depicted in the figure below.

The compounds of Example 158 were obtained by separating the compound of Example 157.

Example 159

Production of N—((R)-6-bromochroman-3-yl)-5-(difluoromethyl)-6,7-dihydro-5H-pyrazolo[5,1-b][1,3]oxazine-2-carboxamide

[Chem 162]

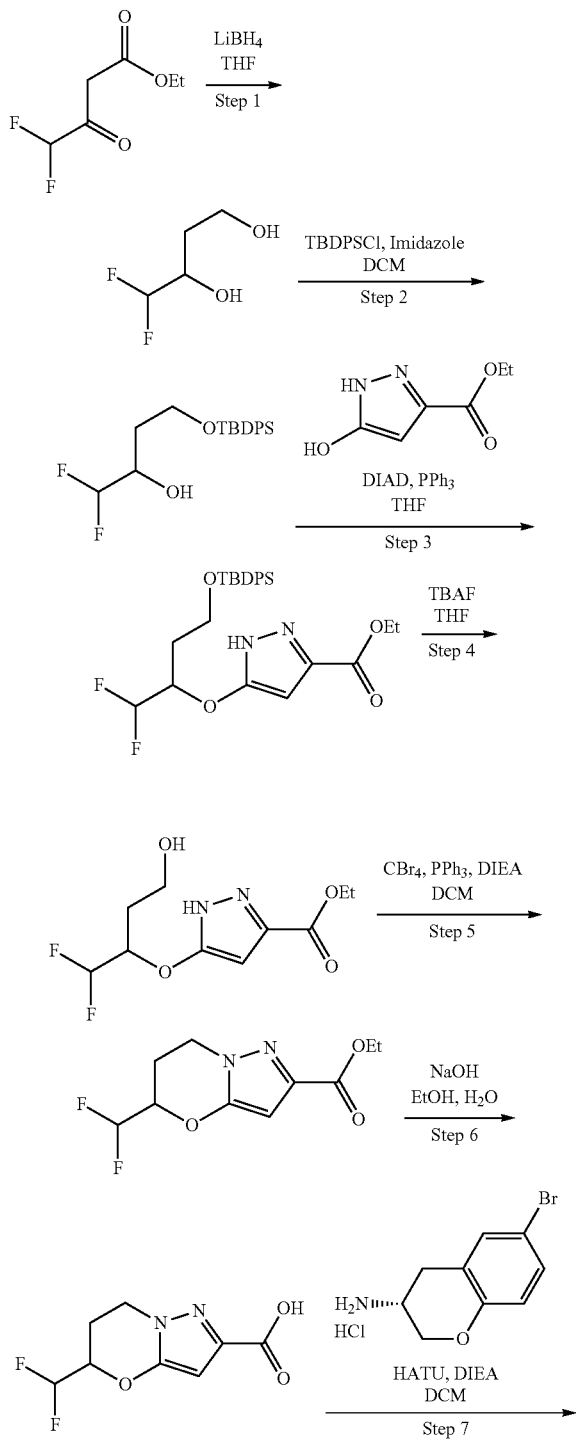

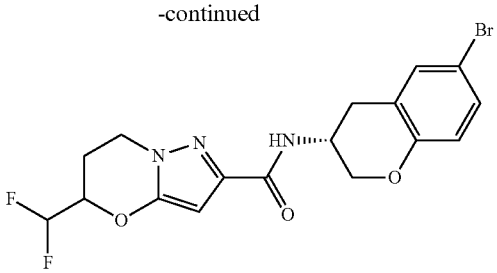

Step 1

To a solution of ethyl 4,4-difluoro3-oxo-butanoate (10.0 g, 60.2 mmol) in tetrahydrofuran (300 mL), lithium borohydride (4.34 g, 199 mmol) was added, and the mixture was stirred for 15 hours at room temperature. Water and ethyl acetate were added to the reaction solution, and the mixture was partitioned. The organic layer was washed with saturated brine and dried over anhydrous sodium sulfate. After the solvent was evaporated off under reduced pressure, the residue was purified by silica gel column chromatography to give 4,4-difluorobutan-1,3-diol (amount 3.37 g, yield 44%).

Step 2

To a solution of 4,4-difluorobutan-1,3-diol (128 mg, 1.02 mmol) in dichloromethane (3.4 mL) were added imidazole (346 mg, 5.08 mmol) and tert-butylchlorodiphenylsilane (263 µL, 1.01 mmol), and the mixture was stirred for 6 hours at room temperature. After the solvent was evaporated off under reduced pressure, the residue was purified by silica gel column chromatography to give 4-(tert-butyl (diphenyl) silyl)oxy-1,1-difluorobutan-2-ol (amount 299 mg, yield 81%).

Step 3

To a solution of 4-(tert-butyl (diphenyl)silyl)oxy-1,1-difluorobutan-2-ol (100 mg, 0.274 mmol) in tetrahydrofuran (1.0 mL) were added ethyl 5-hydroxy-1H-pyrazole-3-carboxylate (42.8 mg, 0.274 mmol), triphenylphosphine (93.6 mg, 0.357 mmol) and 1.9 mol/L azodicarboxylic acid diisopropyl-toluene solution (190 µL, 0.36 mmol). The mixture was stirred for 13 hours at room temperature. The reaction solution was purified by silica gel column chromatography to give ethyl 5-(3-(tert-butyl(diphenylsilyl)oxy)-1-(difluoromethyl)propoxy)-1H-pyrazole-3-carboxylate (amount 33.3 mg, yield 24%).

Step 4

To a solution of ethyl 5-(3-(tert-butyl (diphenylsilyl)oxy)-1-(difluoromethyl)propoxy)-1H-pyrazole-3-carboxylate (9.16 g, 18.2 mmol) in tetrahydrofuran (180 mL), 1 mol/L tetrahydroammoniumfluoride-tetrahydrofuran solution (37 mL, 37 mmol) was added, and the mixture was stirred for 1 hour at room temperature. After concentrating the reaction solution under reduced pressure, the residue was purified by silica gel column chromatography to give ethyl 5-(1-(difluoromethyl)-3-hydroxypropoxy)-1H-pyrazole-3-carboxylate (amount 4.75 g, yield 99%).

Step 5

To a solution of ethyl 5-(1-(difluoromethyl)-3-hydroxypropoxy)-1H-pyrazole-3-carboxylate (93.0 mg, 5.91 mmol)

189 in dichloromethane (3.5 mL) were added N,N-diisopropylethylamine (363 mL, 2.11 mmol), carbon tetrabromide (233 mg, 0.703 mmol) and triphenylphosphine (120 mg, 0.703 mmol). The mixture was stirred for 22 hours at room temperature. 1 mol/L Hydrochloric acid and chloroform were added, and the mixture was partitioned. The organic layer was dried over anhydrous sodium sulfate, and then the solvent was evaporated off under reduced pressure, the residue was purified by silica gel column chromatography to give ethyl 5-(difluoromethyl)-6,7-dihydro-5H-pyrazolo[5,1-b][1,3]oxazine-2-carboxylate (219 mg) as a mixture with triphenylphosphine oxide.

Step 6

To a solution of mixture of ethyl 5-(difluoromethyl)-6,7-dihydro-5H-pyrazolo[5,1-b][1,3]oxazine-2-carboxylate and triphenylphosphine oxide (213 mg) in ethanol (1.7 mL), 4 mol/L aqueous solution of sodium hydroxide (346 µL, 1.38 mmol) was added, and the mixture was stirred for 1 hours at room temperature. 2 mol/L Hydrochloric acid and toluene were added. After the solvent being evaporated off under reduced pressure, the residue was purified by silica gel column chromatography to give 5-(difluoromethyl)-6,7-dihydro-5H-pyrazolo[5,1-b][1,3]oxazine-2-carboxylic acid (20.1 mg).

Step 7

N—((R)-6-bromochroman-3-yl)-5-(difluoromethyl)-6,7-dihydro-5H-pyrazolo[5,1-b][1,3]oxazine-2-carboxamide was obtained by a method similar to Step 3 in Example 100, using 5-(difluoromethyl)-6,7-dihydro-5H-pyrazolo[5,1-b][1,3]oxazine-2-carboxylic acid instead of 5-(hydroxymethyl)-6,7-dihydro-5H-pyrazolo[5,1-b][1,3]oxazine-2-carboxylic acid, and using (R)-6-bromochroman-3-amine hydrochloride synthesized by a method described in Reference Example 2 instead of (R)-3-aminochroman-6-carbonitrile.

Reference Example 43

Production of (R)-6-(trifluoromethyl)chroman-3-amine hydrochloride

[Chem 163]

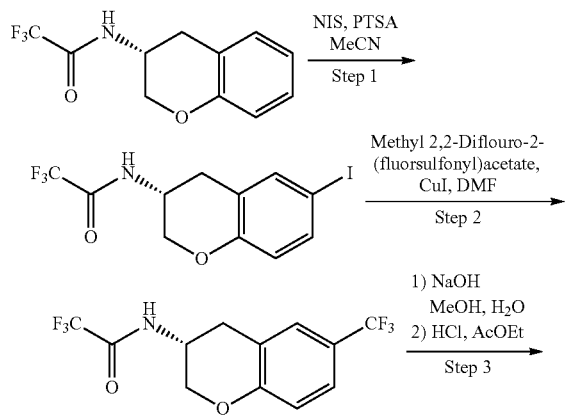

190

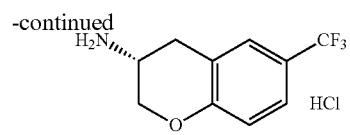

Step 1

To a solution of (R)—N-(chroman-3-yl)-2,2,2-trifluoroacetamide (2.50 g, 16.3 mmol) synthesized by a method described in Step 1 in Reference Example 1 in acetonitrile (26 mL), para-toluene sulfonic acid monohydrate (2.13 g, 11.2 mmol) was added. The mixture was stirred for 10 minutes at room temperature. In addition, a solution of N-iodosuccineimide (2.52 g, 11.2 mmol) in acetonitrile (40 mL) was added, and the mixture was stirred for 16 hours at room temperature. Thereafter, saturated aqueous solution of sodium hydrogen carbonate, an aqueous solution of saturated sodium thiosulfate and ethyl acetate were added to the reaction solution, and the mixture was partitioned. The organic layer was washed with saturated brine and dried over anhydrous magnesium sulfate. n-Hexane and ethyl acetate were added to the residue, and the residue was dissolved by heating, and then the solution was allowed to cool to room temperature. The precipitated solid was collected by filtration to give (R)-2,2,2-trifluoro-N-(6-iodochroman-3-yl)acetamide (amount 1.19 g, yield 32%).

Step 2

To a solution of (R)-2,2,2-trifluoro-N-(6-iodochroman-3-yl)acetamide (1.19 g, 3.21 mmol) in N,N-dimethylformamide (100 mL) were added copper iodide (I) (0.73 g, 3.8 mmol), methyl 2,2-difluoro2-(fluorosulfonyl)acetate (2.04 mL, 16 mmol). The mixture was stirred for 16 hours at 120° C. The reaction solution was allowed to cooled to room temperature thereafter filtered through celite. Thereafter, ethyl acetate, n-hexane and saturated aqueous solution of sodium hydrogen carbonate were added, and the mixture was partitioned. The organic layer was washed with saturated brine, and dried over anhydrous magnesium sulfate. After the solvent was evaporated off under reduced pressure, the residue was purified by silica gel column chromatography to give (R)-2,2,2-trifluoro-N-(6-(trifluoromethyl)chroman-3-yl)acetamide (amount 949 mg, yield 95%).

Step 3

To a solution of (R)-2,2,2-trifluoro-N-(6-(trifluoromethyl)chroman-3-yl)acetamide (133 mg, 0.425 mmol) in methanol (1.1 mL), 2 mol/L aqueous solution of sodium hydroxide (1.1 mL, 2.2 mmol) was added, and the mixture was stirred for 3 hours at room temperature. Water and chloroform was added to the reaction solution, and the mixture was partitioned. Thereafter, the organic layer was dried over anhydrous sodium sulfate. The solvent was evaporated off under reduced pressure, the residue was dissolved in ethyl acetate, 4 mol/L hydrogen chloride-ethyl acetate solution was added, and the mixture was stirred for 1 hour. Under reduced pressure, the solvent was evaporated off to give ((R)-6-(trifluoromethyl)chroman-3-amine hydrochloride (amount 93.8 mg, yield 87%).

Example 160

Production of 5-(difluoromethyl)-N—((R)-6-(trifluoromethyl)chroman-3-yl)-6,7-dihydro-5H-pyrazolo[5,1-b][1,3]oxazine-2-carboxamide

[Chem 164]

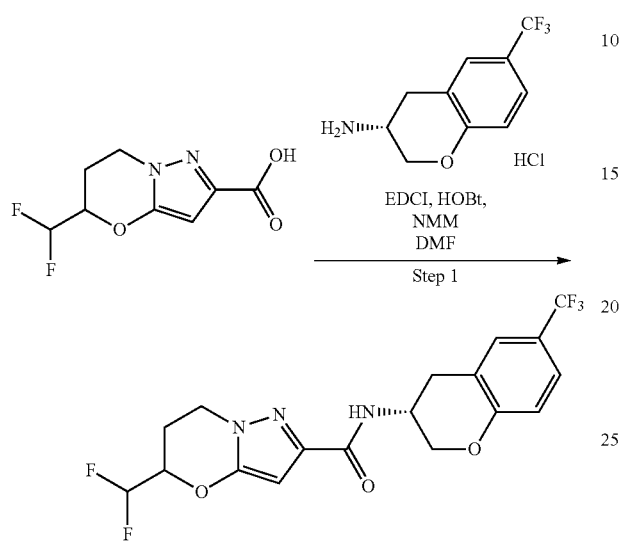

To a solution of 5-(difluoromethyl)-6,7-dihydro-5H-pyrazolo[5,1-b][1,3]oxazine-2-carboxylic acid (51.5 mg, 0.236 mmol) synthesized by a method described in Step 6 in Example 159, (R)-6-(trifluoromethyl)chroman-3-amine hydrochloride (72.0 mg, 0.284 mmol) synthesized by a method described in Reference Example 43, 1-hydroxybenzotriazole (43.4 mg, 0.283 mmol) and 1-ethyl-3-(3-dimethylaminopropyl)carbodiimide hydrochloride (54.5 mg, 0.284 mmol) in N,N-dimethylformamide (787 µL), 4-methylmorpholine (158 µL, 1.44 mmol) was added. The mixture was stirred for 4 hours at room temperature. Water and ethyl acetate was added to the reaction solution, and the mixture was partitioned. After drying the organic layer with anhydrous sodium sulfate, the solvent was evaporated off under reduced pressure. The residue was purified by silica gel column chromatography to give 5-(difluoromethyl)-N—((R)-6-(trifluoromethyl)chroman-3-yl)-6,7-dihydro-5H-pyrazolo[5,1-b][1,3]oxazine-2-carboxamide (amount 91.1 mg, yield 93%).

Example 161

Isomeric Separation of 5-(difluoromethyl)-N—((R)-6-(trifluoromethyl)chroman-3-yl)-6,7-dihydro-5H-pyrazolo[5,1-b][1,3]oxazine-2-carboxamide

[Chem 165]

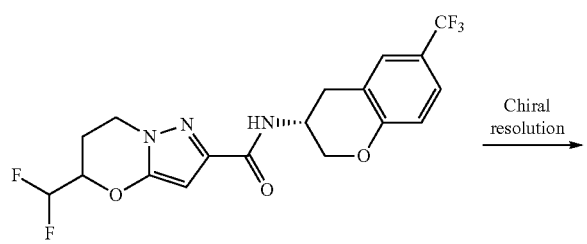

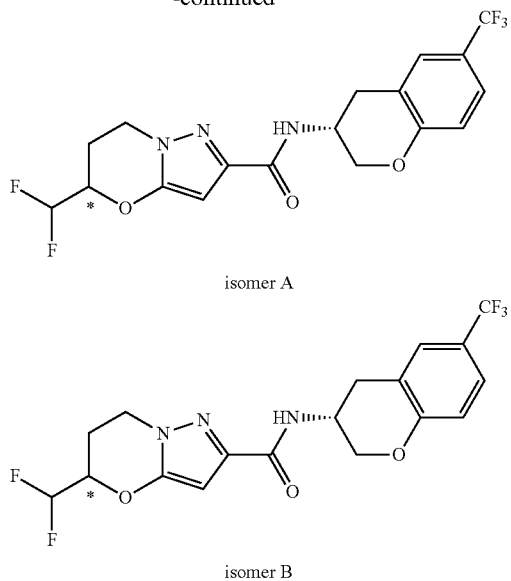

5-(Difluoromethyl)-N—((R)-6-(trifluoromethyl)chroman-3-yl)-6,7-dihydro-5H-pyrazolo[5,1-b][1,3]oxazine-2-carboxamide (14.7 mg, 0.035 mmol) synthesized by a method described in Example 160 was dissolved in ethanol (7 mL), and the solution was subjected to HPLC fractionation (column: CHIRALPAK IC, developing solvent: ethanol/n-hexane=50/50, flow rate: 20.0 mL/min) to give isomer A (amount 6.2 mg, yield 42%) and isomer B (amount 5.2 mg, yield 35%).

Reference Example 44

Production of (R)-6-((2,2,2-trifluoroethoxy)methyl)chroman-3-amine hydrochloride

[Chem 166]

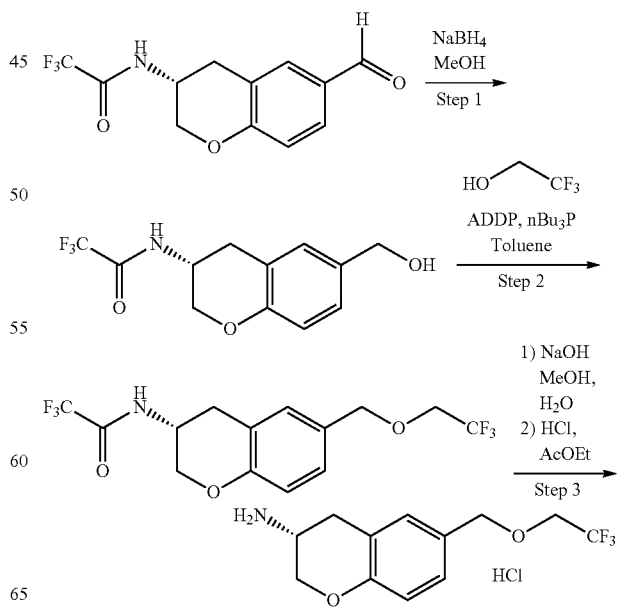

Step 1

To ice cold (R)-2,2,2-trifluoro-N-(6-formylchroman-3-yl)acetamide (3.89 g, 14.2 mmol) synthesized by a method described in Step 2 in Reference Example 3 in methanol (70 mL), sodium borohydride (1.08 g, 28.5 mmol) was added, and the mixture was stirred for 15 minutes under ice cooling. To the reaction solution, 1 mol/L hydrochloric acid and chloroform were added, and the mixture was partitioned. After drying the organic layer with anhydrous sodium sulfate, the solvent was evaporated off under reduced pressure. The residue was purified by silica gel column chromatography to give (R)-2,2,2-trifluoro-N-(6-(hydroxymethyl)chroman-3-yl)acetamide (amount 2.34 g, yield 60%).

Step 2

To a solution of (R)-2,2,2-trifluoro-N-(6-(hydroxymethyl)chroman-3-yl)acetamide (500 mg, 1.82 mmol) in toluene (18 mL) were added tributylphosphine (908 μL, 3.64 mmol), 2,2,2-trifluoroethanol (1.3 mL, 18 mmol) and 1,1'-(azodicarbonyl)dipiperidine (919 mg, 3.64 mmol). The mixture was stirred for 1 hours at 80° C. The reaction solution was allowed to cool to room temperature, water and ethyl acetate were added, and the mixture was partitioned. The organic layer was washed with saturated brine, and then dried over anhydrous magnesium sulfate, and the solvent was evaporated off under reduced pressure. The residue was purified by silica gel column chromatography to give (R)-2,2,2-trifluoro-N-(6-((2,2,2-trifluoroethoxy)methyl)chroman-3-yl)acetamide (amount 409 mg, yield 63%).

Step 3

(R)-6-((2,2,2-Trifluoroethoxy)methyl)chroman-3-amine hydrochloride was obtained by a method similar to Step 3 in Reference Example 1, using (R)-2,2,2-trifluoro-N-(6-((2,2,2-trifluoroethoxy)methyl)chroman-3-yl)acetamide instead of (R)—N-(6-chlorochroman-3-yl)-2,2,2-trifluoroacetamide.

The compound of Example 162 was synthesized by methods similar to those described in Example 159 and Reference Example 44.

The compounds of Example 163 were obtained by separating the compound of Example 162.

The compound of Reference Example 45 ((R)-6-(2-(difluoromethoxy)ethyl)chroman-3-amine hydrochloride) was synthesized from the compound synthesized in Step 1 in Reference Example 3 under the scheme depicted in the figure below.

[Chem 167]

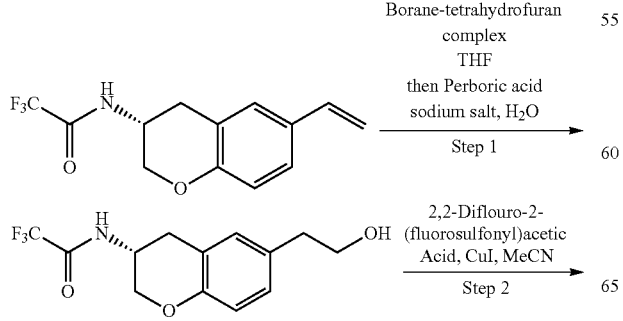

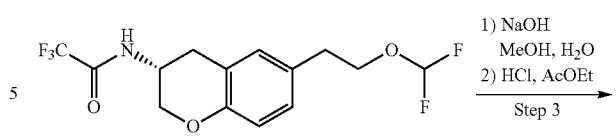

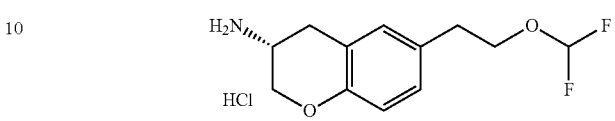

The compound of Example 164 was synthesized by methods similar to those described in Example 159 and Reference Example 45.

The compounds of Example 165 were obtained by separating the compound of Example 164.

The compounds of Reference Example 46 (N—((R)-6-chlorochroman-3-yl)-5-(2-hydroxypropan-2-yl)-6,7-dihydro-5H-pyrazolo[5,1-b][1,3]oxazine-2-carboxamide, and 5-acetyl-N—((R)-6-chlorochroman-3-yl)-6,7-dihydro-5H-pyrazolo[5,1-b][1,3]oxazine-2-carboxamide) were synthesized from the compound synthesized in Step 1 in Example 117 under the scheme depicted in the figure below.

[Chem 168]

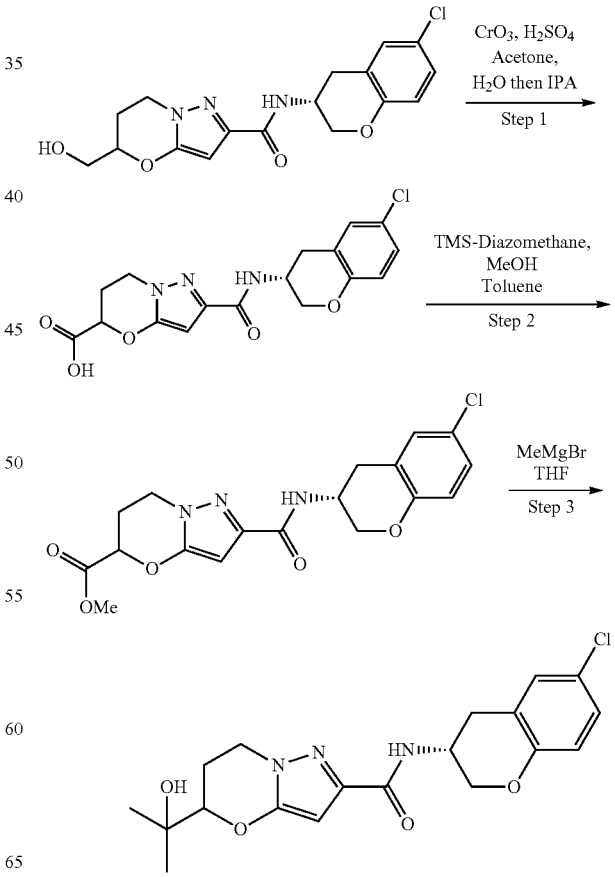

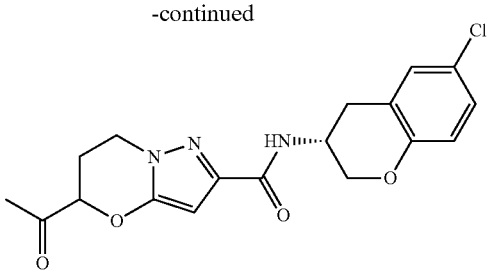

The compound of Example 166 was synthesized from the compound of Reference Example 46 (N—((R)-6-chlorochroman-3-yl)-5-(2-hydroxypropan-2-yl)-6,7-dihydro-5H-pyrazolo[5,1-b][1,3]oxazine-2-carboxamide) by a method similar to Example 157.

The compound of Example 167 was synthesized from the compound of Reference Example 46 (5-acetyl-N—((R)-6-chlorochroman-3-yl)-6,7-dihydro-5H-pyrazolo[5,1-b][1,3]oxazine-2-carboxamide) by a method similar to Example 157.

The compound of Example 168 was synthesized from the compound synthesized in Step 2 in Reference Example 46 under the scheme depicted in the figure below.

[Chem 169]

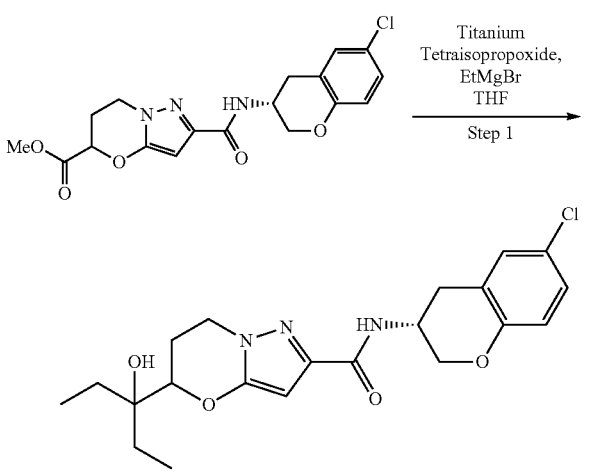

The compound of Example 169 was synthesized under the scheme depicted in the figure below.

[Chem 170]

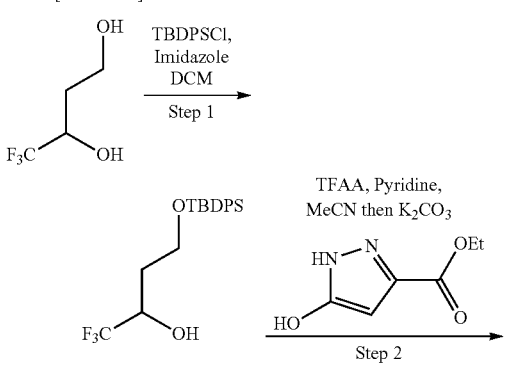

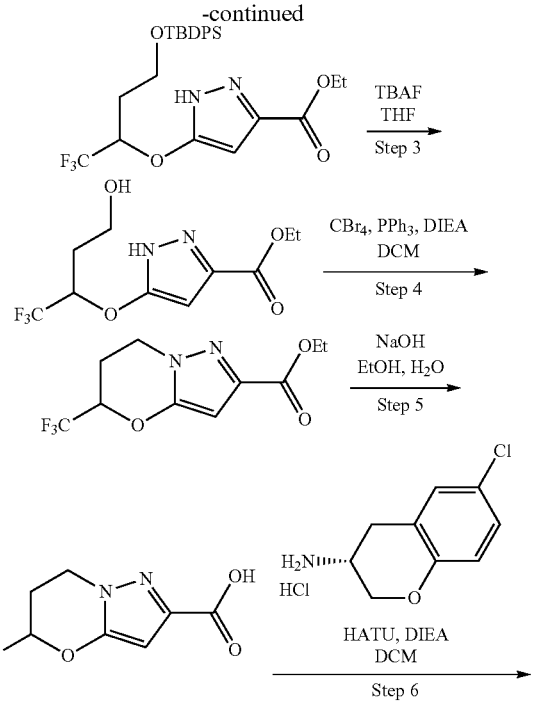

The compounds of Example 170 were obtained by separating the compound of Example 169.

The compound of Example 171 was synthesized by methods similar to those described in Example 169 and Reference Example 2.

The compound of Reference Example 47 (shown in the figure below.) was synthesized by a method similar to Reference Example 4.

[Chem 171]

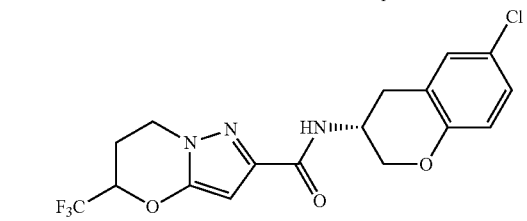

The compound of Reference Example 48 ((R)-6-(2,2-difluoroethyl)chroman-3-amine hydrochloride) was synthesized from the compound synthesized in Step 1 in Reference Example 45 under the scheme depicted in the figure below.

[Chem 172]

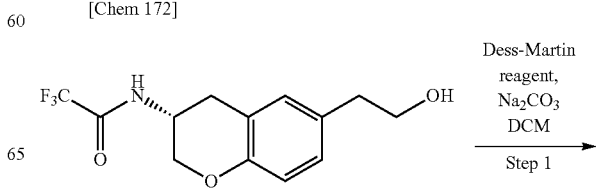

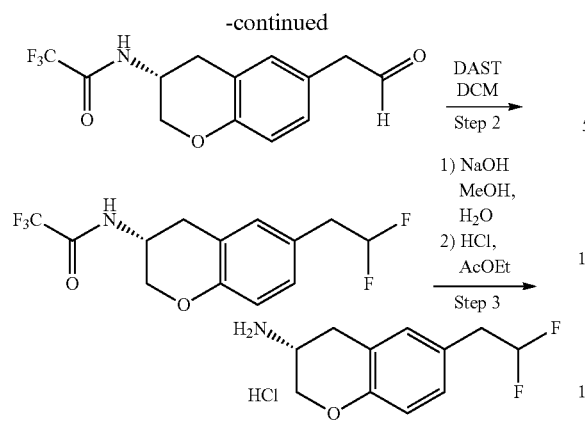

The compound of Example 172 was synthesized by methods similar to those described in Example 169 and Reference Example 48.

The compounds of Example 173 were obtained by separating the compound of Example 172.

The compound of Example 174 was synthesized from the compound of Example 171 by a method similar to Step 1 in Reference Example 27.

The compound of Example 175 was synthesized by a method similar to Example 174.

The compound of Example 176 was synthesized by a method similar to Example 174.

The compound of Example 177 was synthesized under the scheme depicted in the figure below.

[Chem 173]

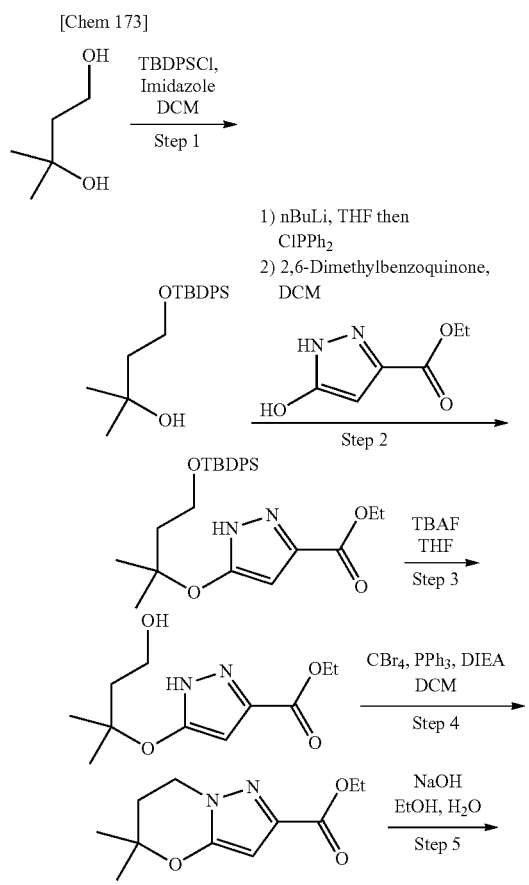

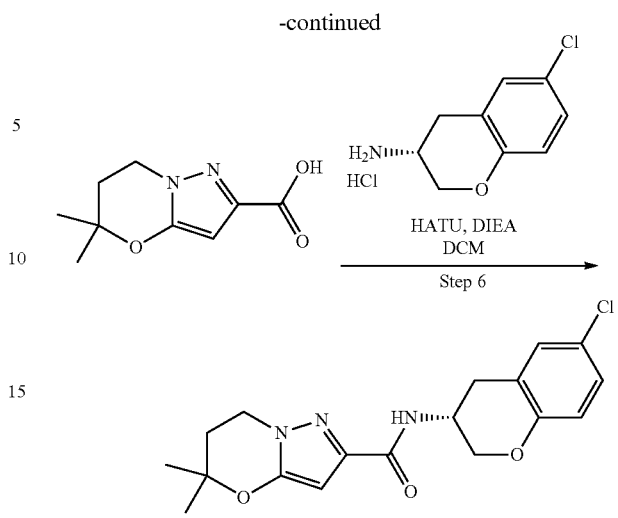

The compound of Example 178 was synthesized by methods similar to those described in Example 177 and Reference Example 24.

The compound of Example 179 was synthesized by methods similar to those described in Example 177 and Reference Example 32.

The compound of Example 180 was synthesized by methods similar to those described in Example 177 and Reference Example 24.

The compound of Example 181 was synthesized by a method similar to Step 6 to Step 8 in Example 70.

The compound of Example 182 was synthesized by methods similar to those described in Example 181 and Reference Example 24.

The compound of Example 183 was synthesized by methods similar to those described in Example 169 and Reference Example 44.

The compounds of Example 184 were obtained by separating the compound of Example 183.

The Reference Example 49 (3-(cyclopropylmethoxy)propane-1,2-diol) was synthesized under the scheme depicted in the figure below.

[Chem 174]

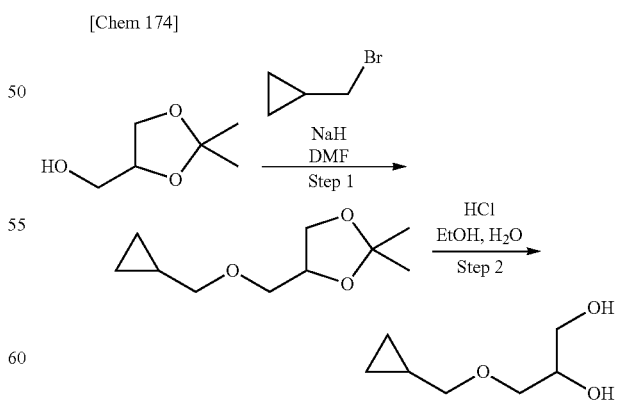

The compound of Reference Example 50 (shown in the figure below.) was synthesized from the compound of Reference Example 49 by a method similar to Step 1 to Step 5 in Example 85.

[Chem 175]

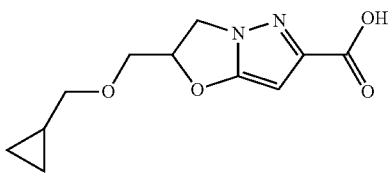

The compound of Example 185 was synthesized from the compound of Reference Example 50 and the compound of Reference Example 44 by a method similar to Step 3 in Example 100.

The compounds of Example 186 were obtained by separating the compound of Example 185.

The compound of Reference Example 51 (shown in the figure below.) was synthesized by a method similar to Step 1 to Step 4 in Example 85.

[Chem 176]

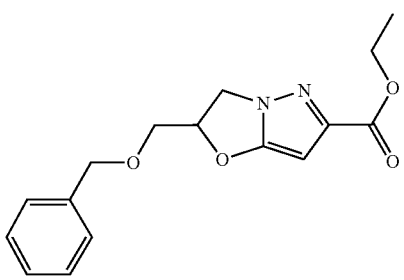

Example 187

Production of 2-((2,2,2-trifluoroethoxy)methyl)-N—((R)-6-((2,2,2-trifluoroethoxy)methyl)chroman-3-yl)-2,3-dihydropyrazolo[5,1-b]oxazole-6-carboxamide

[Chem 177]

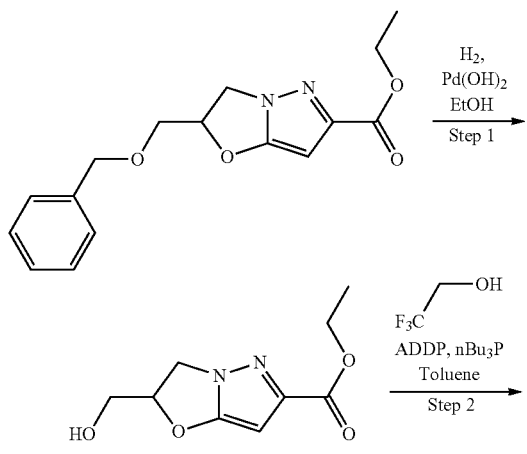

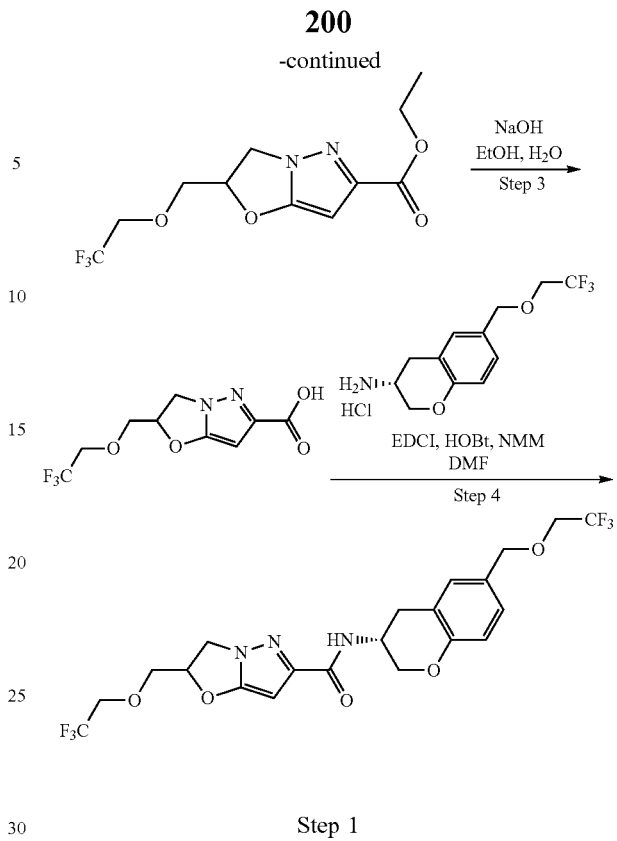

Step 1

Ethyl 2-(hydroxymethyl)-2,3-dihydropyrazolo[5,1-b]oxazole-6-carboxylate was obtained by a method similar to Step 1 in Example 100, using ethyl 2-((benzyloxy)methyl)-2,3-dihydropyrazolo[5,1-b]oxazole-6-carboxylate synthesized by a method described in Reference Example 51 instead of ethyl 5-((benzyloxy)methyl-6,7-dihydro-5H-pyrazolo[5,1-b][1,3]oxazine-2-carboxylate.

Step 2

Ethyl 2-((2,2,2-trifluoroethoxy)methyl)-2,3-dihydropyrazolo[5,1-b]oxazole-6-carboxylate was obtained by a method similar to Example 114, using ethyl 2-(hydroxymethyl)-2,3-dihydropyrazolo[5,1-b]oxazole-6-carboxylate instead of N—((R)-6-cyanochroman-3-yl)-5-(hydroxymethyl)-6,7-dihydro-5H-pyrazolo[5,1-b][1,3]oxazine-2-carboxamide.

Step 3

2-((2,2,2-Trifluoroethoxy)methyl)-2,3-dihydropyrazolo[5,1-b]oxazole-6-carboxylic acid was obtained as a mixture with 4 equivalents of sodium chloride by a method similar to Step 2 in Example 100, using ethyl 2-((2,2,2-trifluoroethoxy)methyl)-2,3-dihydropyrazolo[5,1-b]oxazole-6-carboxylate instead of ethyl 5-(hydroxymethyl)-6,7-dihydro-5H-pyrazolo[5,1-b][1,3]oxazine-2-carboxylate.

Step 4

2-((2,2,2-Trifluoroethoxy)methyl)-N—((R)-6-((2,2,2-trifluoroethoxy)methyl)chroman-3-yl)-2,3-dihydropyrazolo[5,1-b]oxazole-6-carboxamide was obtained by a method similar to Step 3 in Example 100, using 2-((2,2,2-trifluoroethoxy)methyl)-2,3-dihydropyrazolo[5,1-b]oxazole-6-carboxylic acid instead of 5-(hydroxymethyl)-6,7-dihydro-5H-pyrazolo[5,1-b][1,3]oxazine-2-carboxylic acid, and using (R)-6-((2,2,2-trifluoroethoxy)methyl)chroman-3-amine hydrochloride synthesized by a method described in Reference Example 44 instead of (R)-3-aminochroman-6-carbonitrile.

The compounds of Example 188 were obtained by separating the compound of Example 187.

The compound of Example 189 was synthesized by methods similar to those described in Example 187 and Reference Example 45.

The compounds of Example 190 were obtained by separating the compound of Example 189.

The compound of Reference Example 52 ((R)-6-(2,2,2-trifluoroethyl)chroman-3-amine hydrochloride) was synthesized from the compound synthesized in Step 2 in Reference Example 3 under the scheme depicted in the figure below.

[Chem 178]

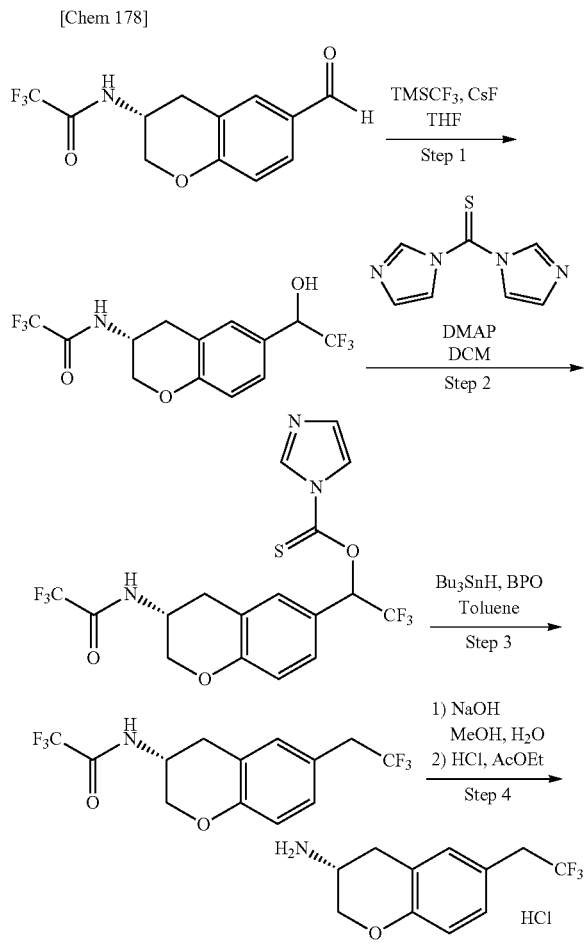

The compound of Example 191 was synthesized by methods similar to those described in Example 187 and Reference Example 52.

The compounds of Example 192 were obtained by separating the compound of Example 191.

Reference Example 53

Production of (R)-6-(5-methylpyrazine-2-yl)chroman-3-amine

[Chem 179]

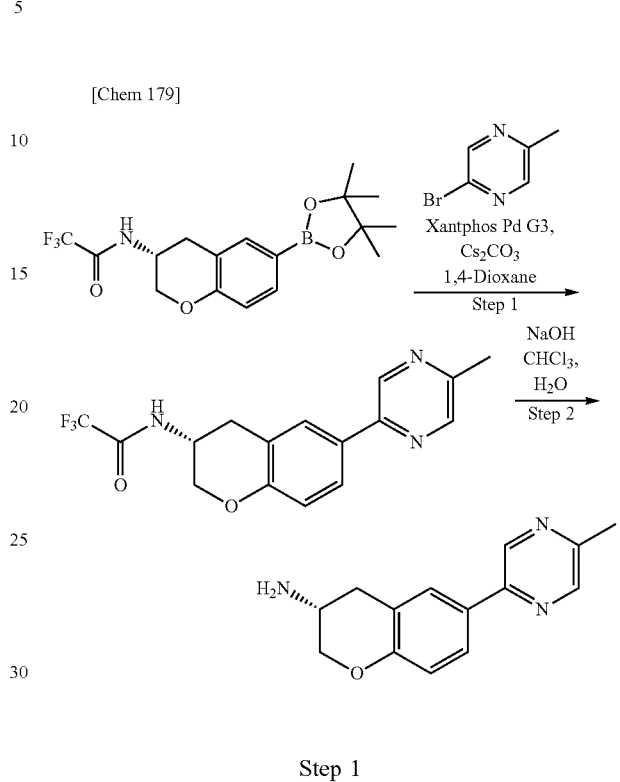

Step 1

To a suspension of (R)-2,2,2-trifluoro-N-(6-(4,4,5,5-tetramethyl-1,3,2-dioxaborolan-2-yl)chroman-3-yl)acetamide (600 mg, 1.62 mmol) synthesized by a method described in Step 1 in Reference Example 28, 2-bromo-5-methylpyrazine (336 mg, 1.94 mmol) cesium carbonate (1.00 g, 3.07 mmol) in 1,4-dioxane (20 mL), Xantphos Pd G3 (15.0 mg, 0.0158 mmol) was added. The mixture was stirred for 4 hours at 125° C. Water and ethyl acetate was added to the reaction solution, and the mixture was partitioned. Thereafter, the organic layer was dried over anhydrous sodium sulfate and the solvent was evaporated off under reduced pressure. The residue was purified by silica gel column chromatography to give (R)-2,2,2-trifluoro-N-(6-(5-methylpyrazine-2-yl)chroman-3-yl)acetamide (amount 224 mg, yield 41%).

Step 2

(R)-6-(5-Methylpyrazine-2-yl)chroman-3-amine was obtained by a method similar to Step 3 in Reference Example 1, using (R)-2,2,2-trifluoro-N-(6-(5-methylpyrazine-2-yl)chroman-3-yl)acetamide instead of (R)—N-(6-chlorochroman-3-yl)-2,2,2-trifluoroacetamide.

The compound of Example 193 was synthesized by methods similar to those described in Example 187 and Reference Example 52.

The compounds of Example 194 were obtained by separating the compound of Example 193.

The compound of Reference Example 54 (shown in the figure below.) was synthesized from the compound synthesized in Step 1 in Example 187 by a method similar to Reference Example 37.

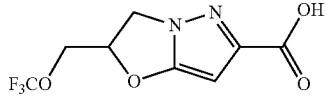

The compound of Example 195 was synthesized from the compound of Reference Example 54 and the compound of Reference Example 44 by a method similar to Step 3 in Example 100.

The compounds of Example 196 were obtained by separating the compound of Example 195.

The compound of Example 197 was synthesized from the compound of Reference Example 54 and the compound of Reference Example 48 by a method similar to Step 3 in Example 100.

The compounds of Example 198 were obtained by separating the compound of Example 197.

The compound of Example 199 was synthesized by methods similar to those described in Example 187 and Reference Example 24.

The compounds of Example 200 were obtained by separating the compound of Example 199.

Example 201

Production of N—((R)-6-cyanochroman-3-yl)-2-(2-(cyclopropylmethoxy)ethyl)-2,3-dihydropyrazolo[5,1-b]oxazole-6-carboxamide

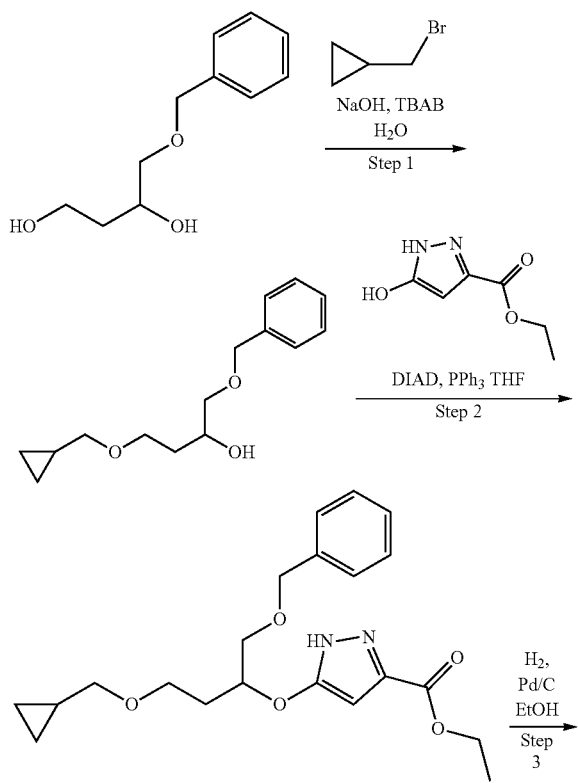

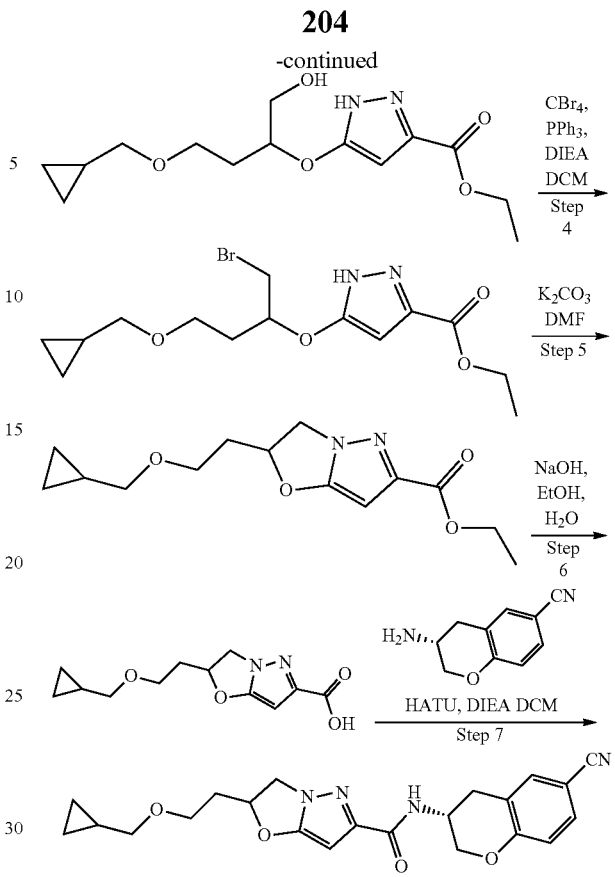

Step 1

To 4 mol/L aqueous solution of sodium hydroxide (1 mL) were added tetrabutylammonium bromide (16.4 mg, 0.0509 mmol), 4-benzyloxybutan-1,3-diol (100 mg, 0.510 mmol) and (bromomethyl)cyclopropane (0.15 mL, 1.6 mmol). The mixture was stirred for 2 hours at 50° C. To the reaction solution, aqueous solution of saturated ammonium chloride and ethyl acetate were added, and the mixture was partitioned. After drying the organic layer with anhydrous sodium sulfate, the solvent was evaporated off under reduced pressure. The residue was purified by silica gel column chromatography to give 1-benzyloxy-4-(cyclopropylmethoxy)butan-2-ol (amount 58 mg, yield 45%).

Step 2

Ethyl 5-(1-benzyloxymethyl)-3-(cyclopropylmethoxy) propoxy)-1H-pyrazole-3-carboxylate was obtained by a method similar to Example 85, using 1-benzyloxy-4-(cyclopropylmethoxy)butan-2-ol instead of 4-((tert-butyldiphenylsilyl)oxy)butan-2-ol.

205

Step 3

To a solution of ethyl 5-(1-benzyloxymethyl)-3-(cyclopropylmethoxy)propoxy)-1H-pyrazole-3-carboxylate (1.3 g, 3.3 mmol) in ethanol (50 mL), 5% palladium on carbon (0.71 g) was added, and the mixture was stirred under hydrogen atmosphere (balloon pressure) for 3 hours at room temperature. After the reaction solution was filtered through celite, the solvent was evaporated off under reduced pressure. The residue was purified by silica gel column chromatography to give ethyl 5-(3-(cyclopropylmethoxy)-1-(hydroxymethyl)propoxy)-1H-pyrazole-3-carboxylate (amount 0.91 g, yield 91%).

Step 4

To a solution of ethyl 5-(3-(cyclopropylmethoxy)-1-(hydroxymethyl)propoxy)-1H-pyrazole-3-carboxylate (0.91 g, 3.1 mmol) in dichloromethane (20 mL) were added N,N-diisopropylethylamine (3.1 mL, 18 mmol), carbon tetrabromide (3.0 g, 9.0 mmol) and triphenylphosphine (1.6 g, 6.1 mmol). The mixture was stirred for 15 hours at room temperature. After concentrating the reaction solution under reduced pressure, the residue was purified by silica gel column chromatography to give ethyl 5-(1-(bromomethyl)-3-(cyclopropylmethoxy)propoxy)-1H-pyrazole-3-carboxylate (amount 0.42 g, yield 38%).

Step 5

To a solution of ethyl 5-(1-(bromomethyl)-3-(cyclopropylmethoxy)propoxy)-1H-pyrazole-3-carboxylate (0.42 g, 1.2 mmol) in N,N-dimethylformamide (12 mL), potassium carbonate (0.40 g, 2.9 mmol) was added, and the mixture was stirred for 3 hours at room temperature. Water and chloroform was added to the reaction solution, and the mixture was partitioned. After the organic layer was dried over anhydrous magnesium sulfate, the solvent was evaporated off under reduced pressure. Ethyl 2-(2-(cyclopropylmethoxy)ethyl)-2,3-dihydropyrazolo[5,1-b]oxazole-6-carboxylate (amount 195 mg, yield 60%) was obtained.

Step 6

2-(2-(Cyclopropylmethoxy)ethyl)-2,3-dihydropyrazolo[5,1-b]oxazole-6-carboxylic acid was obtained as a mixture with 4 equivalents of sodium chloride by a method similar to Step 5 in Example 85, using ethyl 2-(2-(cyclopropylmethoxy)ethyl)-2,3-dihydropyrazolo[5,1-b]oxazole-6-carboxylate instead of ethyl 5-(2-fluorophenyl)-6,7-dihydro-5H-pyrazolo[5,1-b][1,3]oxazine-2-carboxylate.

Step 7

N—((R)-6-Cyanochroman-3-yl)-2-(2-(cyclopropylmethoxy)ethyl)-2,3-dihydropyrazolo[5,1-b]oxazole-6-carboxamide was obtained by a method similar to Step 4 in Example 1, using 2-(2-(cyclopropylmethoxy)ethyl)-2,3-dihydropyrazolo[5,1-b]oxazole-6-carboxylic acid instead of 6-(trifluoromethyl)-5,6,7,8-tetrahydroimidazo[1,2-a]pyridine-2-carboxylic acid, and using (R)-3-aminochroman-6-carbonitrile synthesized by a method described in Reference Example 24 instead of 6-fluorochroman-3-amine hydrochloride.

The compounds of Example 202 were obtained by separating the compound of Example 201.

206

Example 203

Production of 2-(2-(cyclopropylmethoxy)ethyl)-N—((R)-6-(2-methoxypyrimidin-5-yl)chroman-3-yl)-2,3-dihydropyrazolo[5,1-b]oxazole-6-carboxamide

[Chem 182]

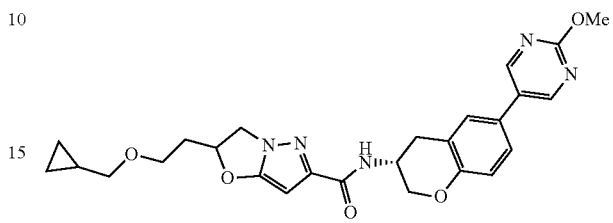

2,2-(2-(Cyclopropylmethoxy)ethyl)-N—((R)-6-(2-methoxypyrimidin-5-yl)chroman-3-yl)-2,3-dihydropyrazolo[5,1-b]oxazole-6-carboxamide was obtained by a method similar to Example 201, using (R)-6-(2-methoxypyrimidin-5-yl)chroman-3-amine synthesized by a method described in Reference Example 29 instead of (R)-3-aminochroman-6-carbonitrile.

Example 204

Isomeric Separation of 2-(2-(cyclopropylmethoxy)ethyl)-N—((R)-6-(2-methoxypyrimidin-5-yl)chroman-3-yl)-2,3-dihydropyrazolo[5,1-b]oxazole-6-carboxamide

[Chem 183]

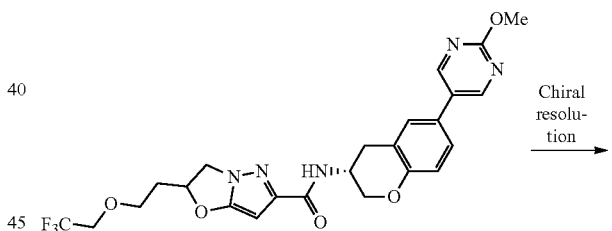

Chiral resolution

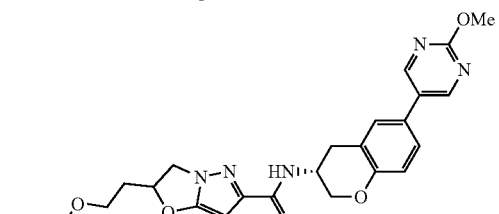

isomer A

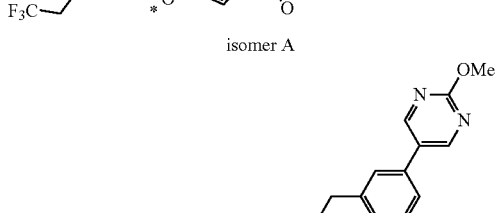

isomer B 2-(2-(Cyclopropylmethoxy)ethyl)-N—((R)-6-(2-methoxypyrimidin-5-yl)chroman-3-yl)-2,3-dihydropyrazolo[5,1-b]oxazole-6-carboxamide (22.0 mg, 0.045 mmol) synthesized by a method described in Example 203 was dissolved in ethanol (7 mL), the solution was subjected to HPLC fractionation (column: CHIRALPAK IB, developing solvent: ethanol, flow rate: 8.0 mL/min, room temperature) to give isomer A (amount 6.4 mg, yield 29%) and isomer B (amount 8.5 mg, yield 39%).

The compound of Reference Example 55 (2-(2-(2,2,2-trifluoroethoxy)ethyl)-2,3-dihydropyrazolo[5,1-b]oxazole-6-carboxylic acid) was synthesized under the scheme depicted in the figure below.

[Chem 184]

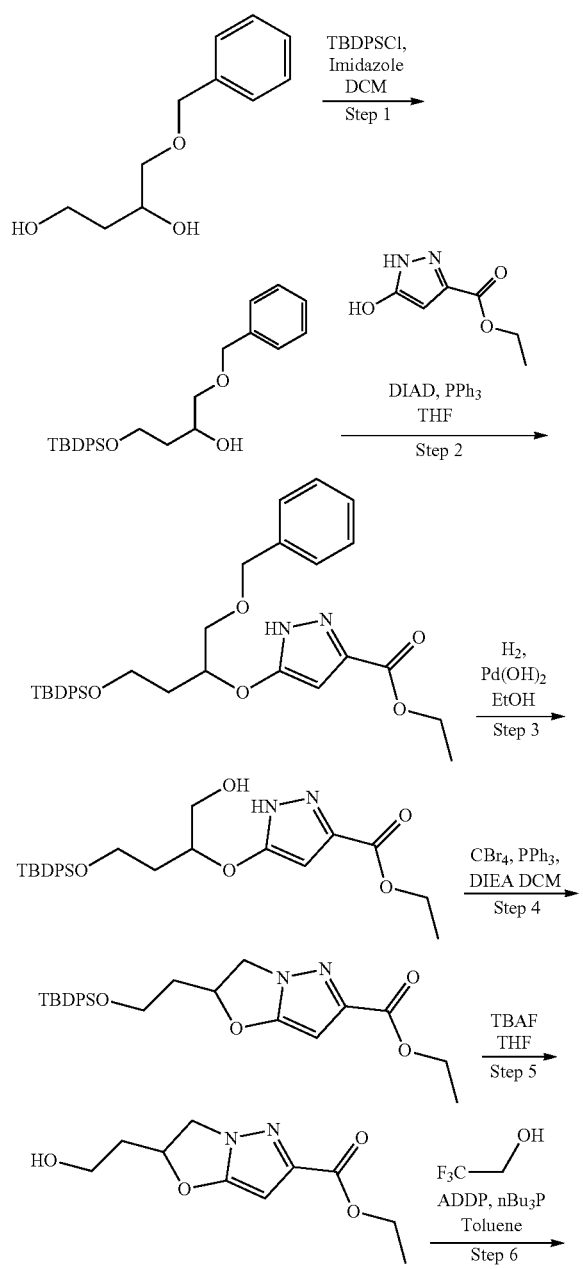

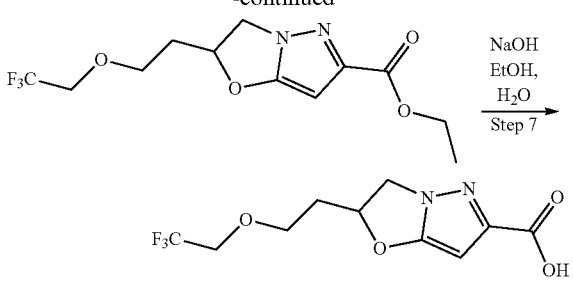

The compound of Reference Example 56 (shown in the figure below.) was synthesized by a method similar to Reference Example 53.

[Chem 185]

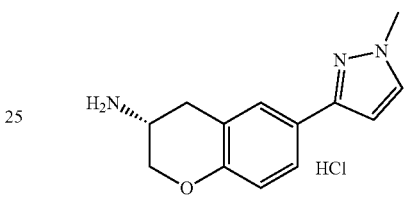

The compound of Example 205 was synthesized from the compound of Reference Example 55 and the compound of Reference Example 56 by a method similar to Step 3 in Example 100.

The compounds of Example 206 were obtained by separating the compound of Example 205.

The compound of Example 207 was synthesized from the compound of Reference Example 55 and the compound of Reference Example 28 under the scheme depicted in the figure below.

[Chem 186]

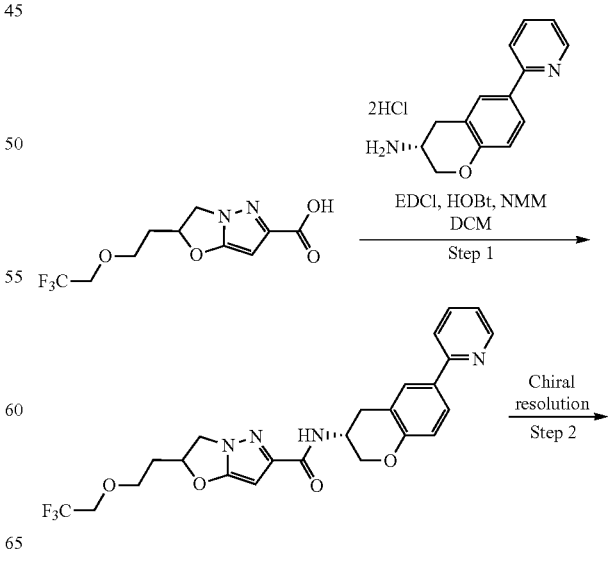

isomer A isomer B

The compound of Reference Example 57 (shown in the figure below.) was synthesized from the compound synthesized in Step 5 in Reference Example 55 by a method similar to Reference Example 37.

[Chem 187]

The compound of Example 208 was synthesized from the compound of Reference Example 57 and the compound of Reference Example 24 by a method similar to Step 4 in Example 1.

The compounds of Example 209 were obtained by separating the compound of Example 208.

The compound of Example 210 was synthesized from the compound of Reference Example 57 and the compound of Reference Example 48 by a method similar to Step 4 in Example 1.

The compounds of Example 211 were obtained by separating the compound of Example 210.

The compound of Example 212 was synthesized from the compound of Reference Example 57 and the compound of Reference Example 56 by a method similar to Step 4 in Example 1.

The compounds of Example 213 were obtained by separating the compound of Example 212.

The compound of Reference Example 58 (shown in the figure below.) was synthesized from the compound synthesized in Step 5 in Reference Example 55 by a method similar to Reference Example 38.

[Chem 188]

The compound of Example 214 was synthesized from the compound of Reference Example 58 and the compound of Reference Example 44 by a method similar to Step 4 in Example 1.

The compounds of Example 215 were obtained by separating the compound of Example 214.

The compound of Example 216 was synthesized from the compound of Reference Example 58 and the compound of Reference Example 45 by a method similar to Step 4 in Example 1.

The compounds of Example 217 were obtained by separating the compound of Example 216.

The compound of Example 218 was synthesized from the compound of Reference Example 58 and the compound of Reference Example 48 by a method similar to Step 4 in Example 1.

The compounds of Example 219 were obtained by separating the compound of Example 218.

The compound of Reference Example 59 (shown in the figure below.) was synthesized by a method similar to Example 53.

[Chem 189]

The compound of Example 220 was synthesized from the compound of Reference Example 58 and the compound of Reference Example 59 by a method similar to Step 4 in Example 1.

The compounds of Example 221 were obtained by separating the compound of Example 220.

The compound of Reference Example 60 (shown in the figure below.) was synthesized by a method similar to Reference Example 53.

[Chem 190]

The compound of Example 222 was synthesized from the compound of Reference Example 58 and the compound of Reference Example 60 by a method similar to Step 4 in Example 1.

The compounds of Example 223 were obtained by separating the compound of Example 222.

The compound of Reference Example 61 was synthesized under the scheme depicted in the figure below.

[Chem 191]

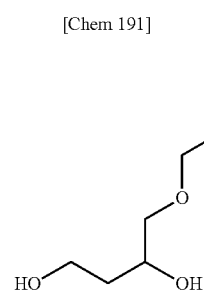

The compound of Reference Example 62 (shown in the figure below.) was synthesized from the compound of Reference Example 61 by a method similar to Step 2 to Step 6 in Example 201.

[Chem 192]

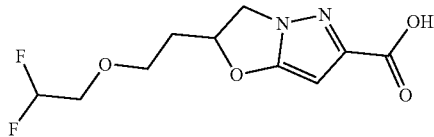

The compound of Example 224 was synthesized from the compound of Reference Example 62 and the compound of Reference Example 44 under the scheme depicted in the figure below.

[Chem 193]

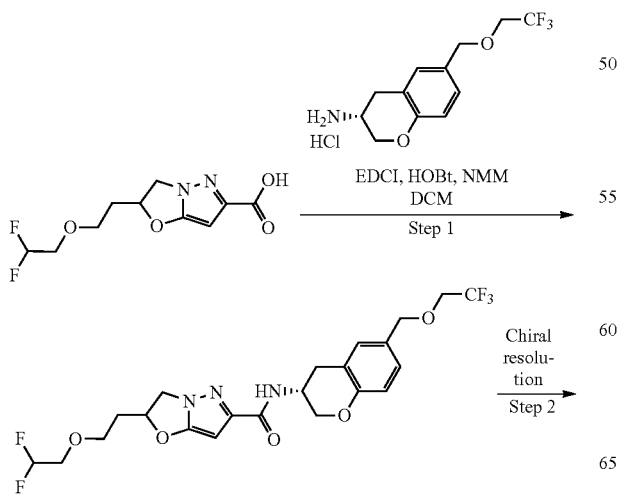

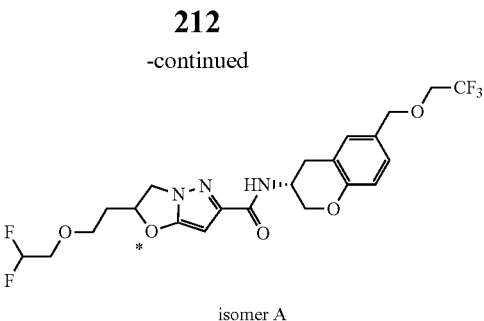

isomer A

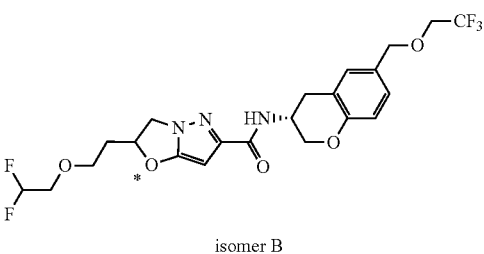

isomer B

The compound of Example 225 was synthesized from the compound synthesized in Step 5 in Reference Example 55 under the scheme depicted in the figure below.

[Chem 194]

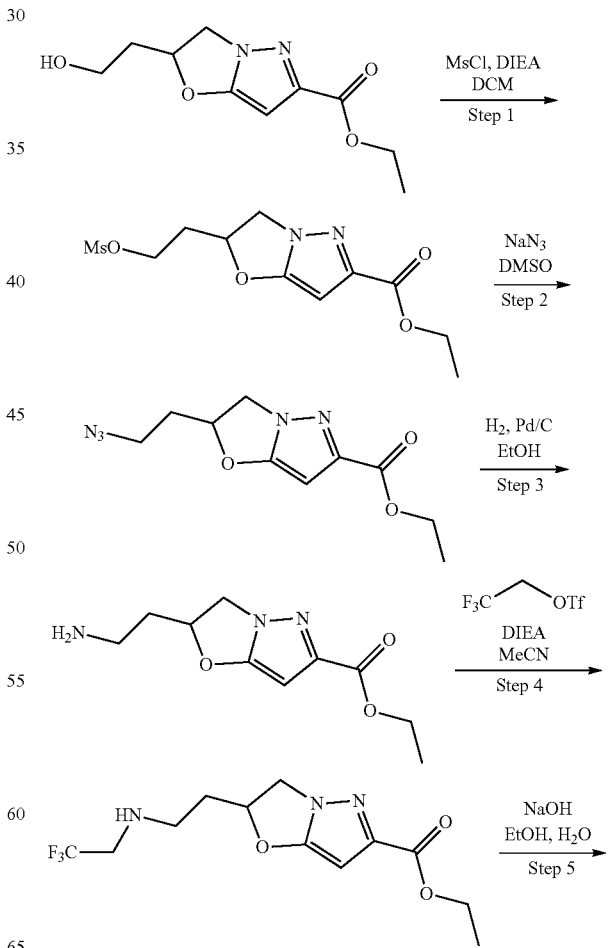

-continued

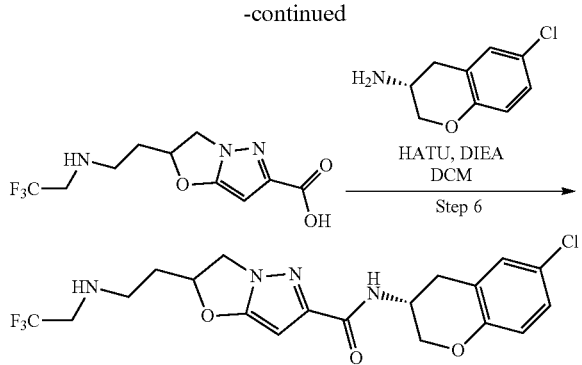

The compounds of Example 226 were obtained by separating the compound of Example 225

The compound of Reference Example 63 (shown in the figure below.) was synthesized by a method similar to Reference Example 27.

[Chem 195]

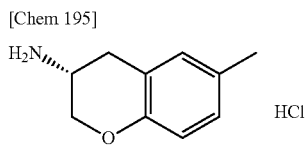

The compound of Example 227 was synthesized by methods similar to those described in Example 225 and Reference Example 63.

The compounds of Example 228 were obtained by separating the compound of Example 227.

The compound of Example 229 was synthesized by methods similar to those described in Example 225 and Reference Example 43.

The compounds of Example 230 were obtained by separating the compound of Example 229.

The compound of Example 231 was synthesized by methods similar to those described in Example 225 and Reference Example 44.

The compounds of Example 232 were obtained by separating the compound of Example 231.

The compound of Reference Example 64 (2-(2-(3,3-difluoroazetidin-1-yl)ethyl)-2,3-dihydropyrazolo[5,1-b]oxazole-6-carboxylic acid) was synthesized from the compound synthesized in Step 1 in Example 225 under the scheme depicted in the figure below.

[Chem 196]

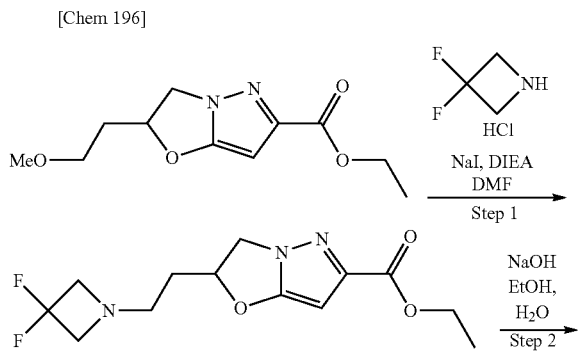

-continued

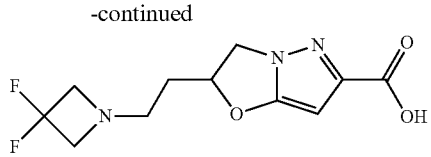

The compound of Example 233 was synthesized from the compound of Reference Example 64 and the compound of Reference Example 1 by a method similar to Step 3 in Example 100.

The compounds of Example 234 were obtained by separating the compound of Example 233.

The compound of Example 235 was synthesized from the compound of Reference Example 64 and the compound of Reference Example 43 by a method similar to Step 3 in Example 100.

The compounds of Example 236 were obtained by separating the compound of Example 235.

The compound of Example 237 was synthesized from the compound of Reference Example 64 and the compound of Reference Example 45 by a method similar to Step 3 in Example 100.

The compounds of Example 238 were obtained by separating the compound of Example 237.

The compound of Reference Example 65 ((R)-6-(2-(trifluoromethoxy)ethyl)chroman-3-amine hydrochloride) was synthesized from the compound synthesized in Step 1 in Reference Example 45 under the scheme depicted in the figure below.

[Chem 197]

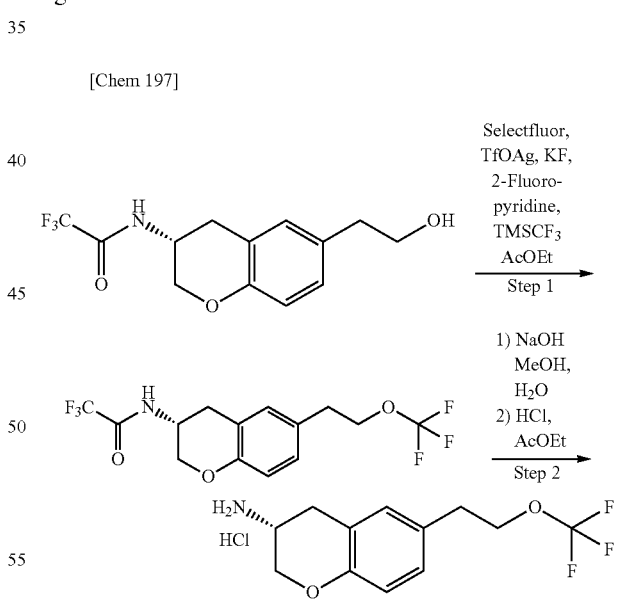

The compound of Example 239 was synthesized by methods similar to those described in Example 233 and Reference Example 65.

The compounds of Example 240 were obtained by separating the compound of Example 239.

The compound of Reference Example 66 (shown in the figure below.) was synthesized by a method similar to Reference Example 64.

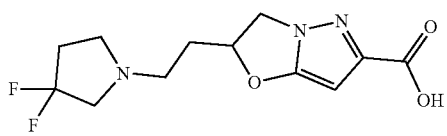

The compound of Example 241 was synthesized from the compound of Reference Example 66 under the scheme depicted in the figure below.

The compound of Reference Example 67 (shown in the figure below.) was synthesized by a method similar to Reference Example 64.

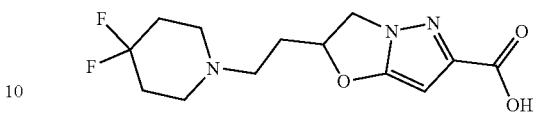

The compound of Example 242 was synthesized from the compound of Reference Example 67 under the scheme depicted in the figure below.

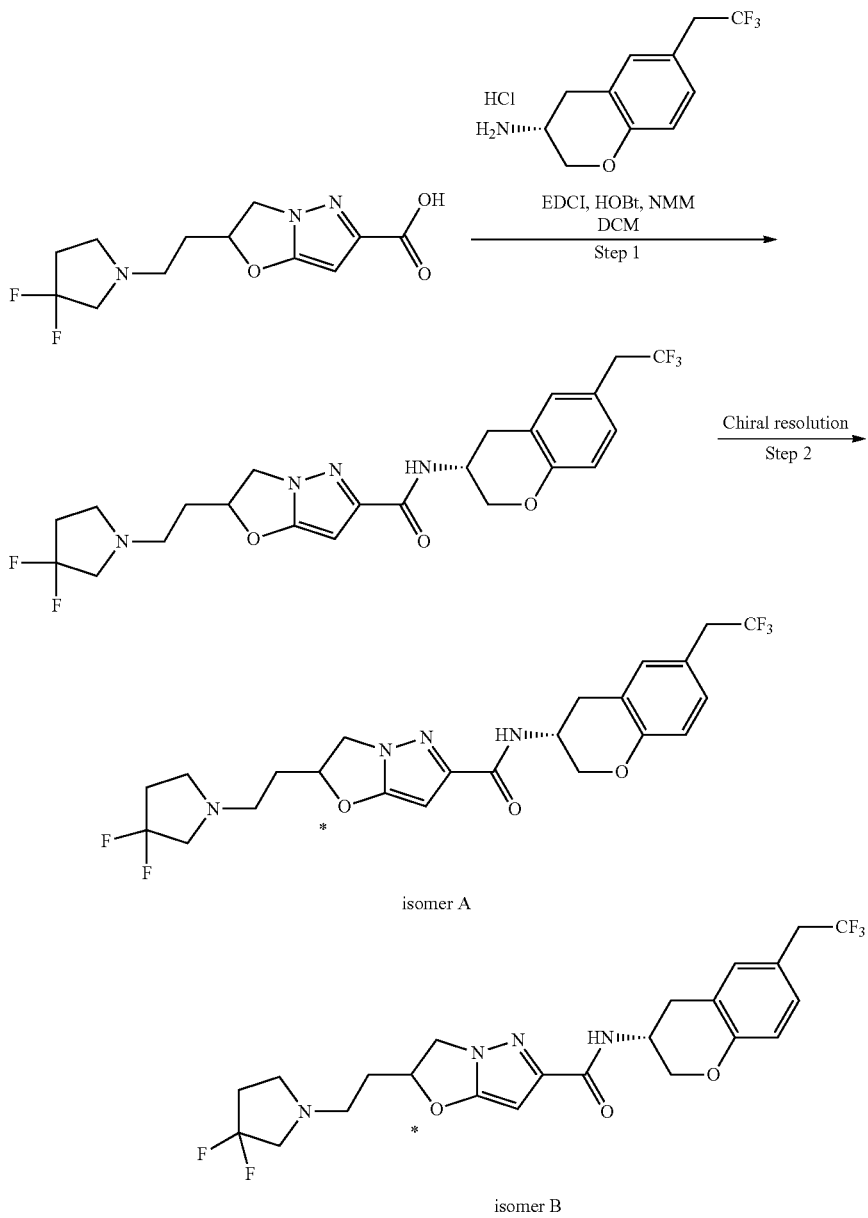

[Chem 201]
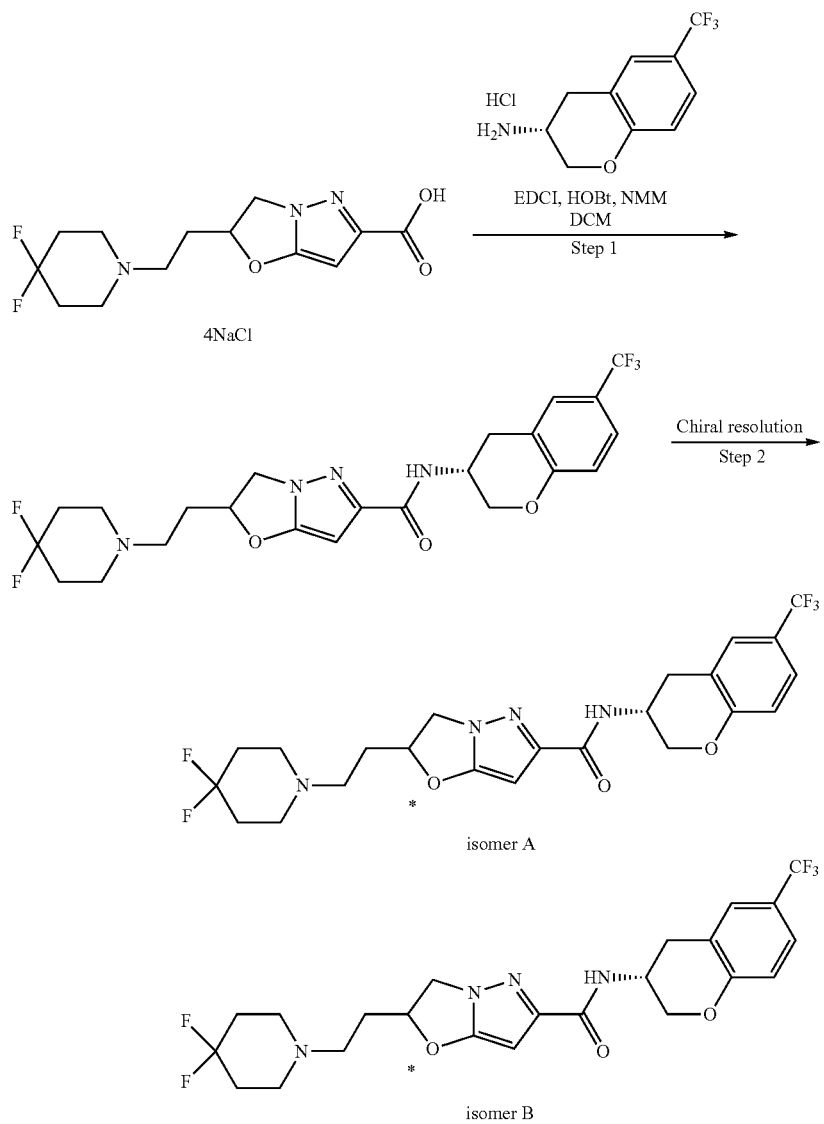
The compound of Example 243 was synthesized from the compound synthesized in Step 5 in Reference Example 55 and the compound of Reference Example 24 by a method similar to Step 2 to Step 4 in Example 187.
The compounds of Example 244 were obtained by separating the compound of Example 243.
The compound of Example 245 was synthesized under the scheme depicted in the figure below.
[Chem 202]
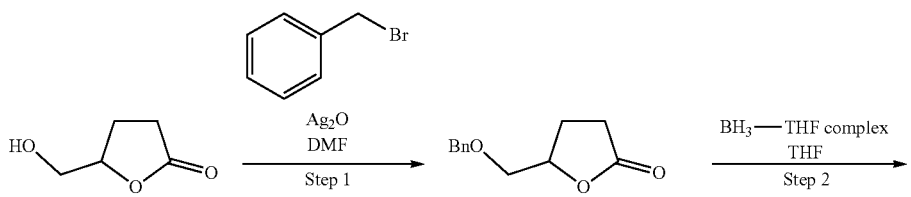

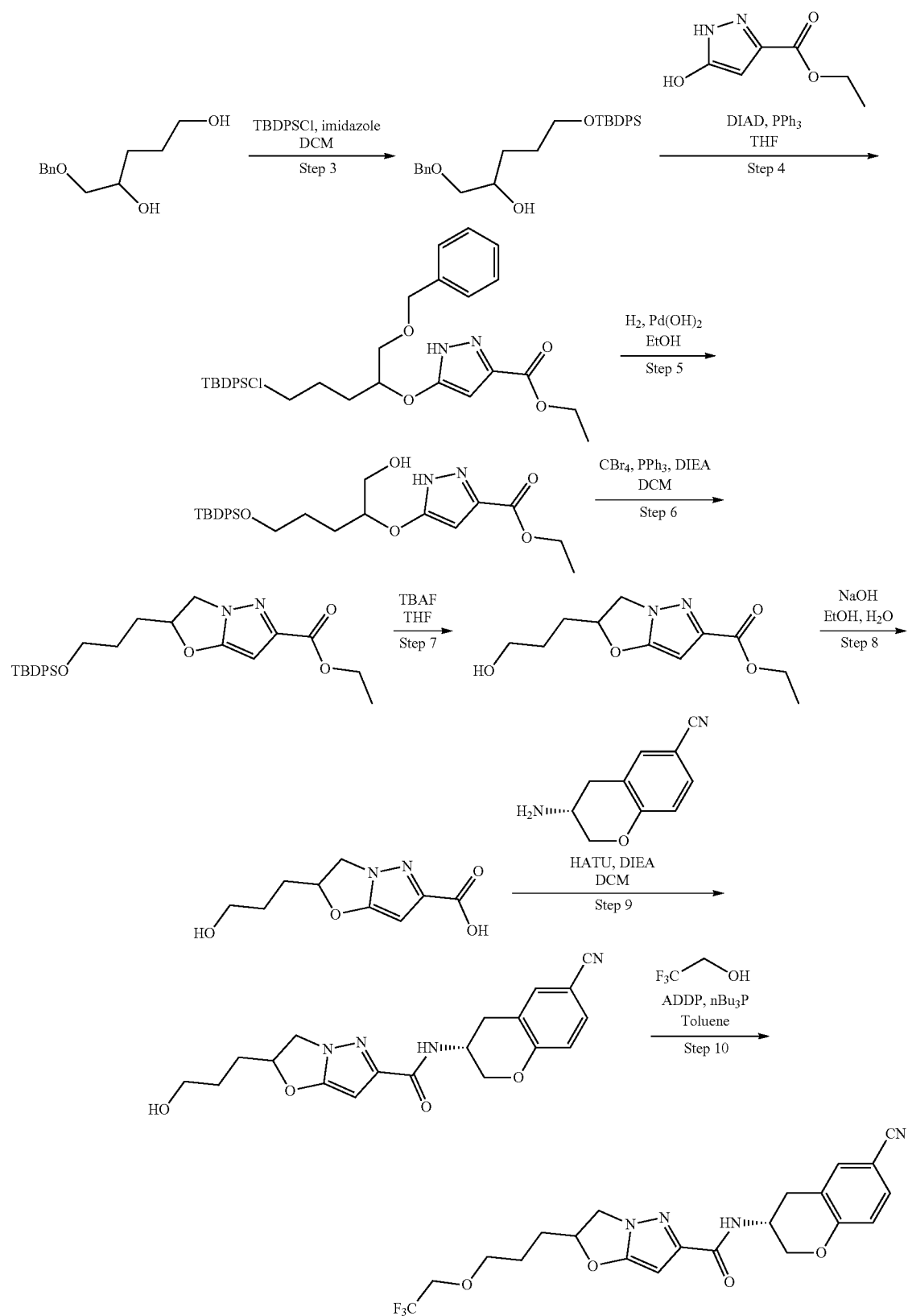

The compounds of Example 246 were obtained by separating the compound of Example 245.

Example 247

Production and isomeric separation of N—((R)-6-cyanochroman-3-yl)-2-(3-(trifluoromethoxy)propyl)-2,3-dihydropyrazolo[5,1-b]oxazole-6-carboxamide

[Chem 203]

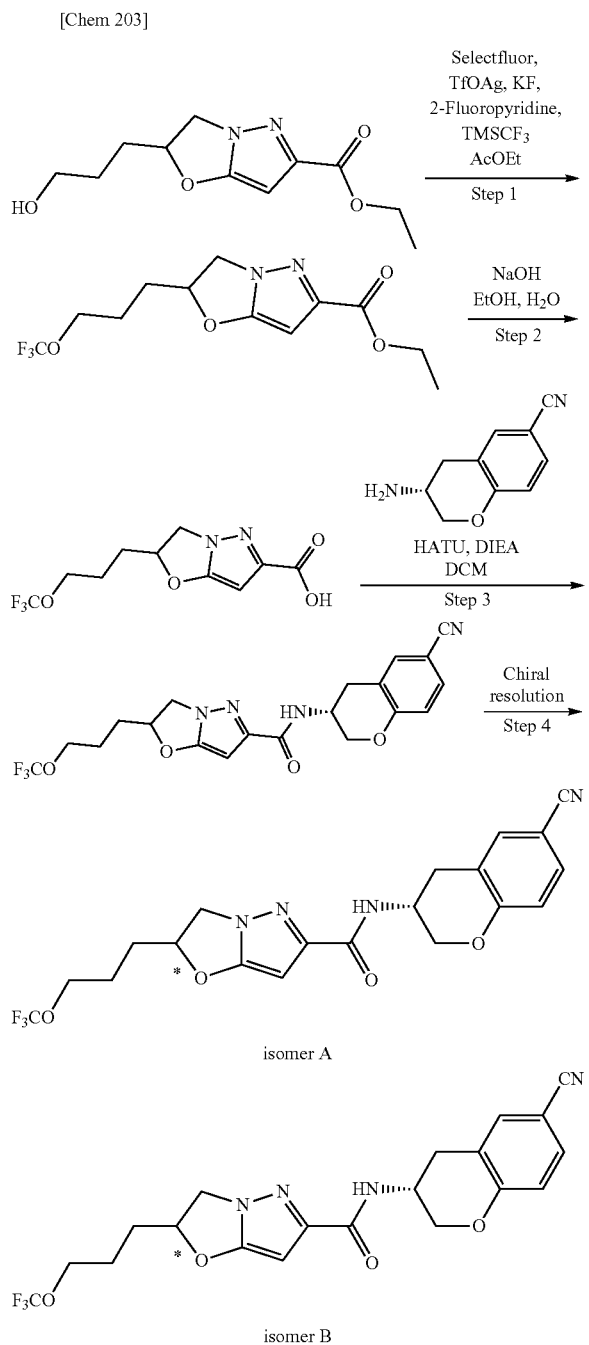

Step 1 to Step 2

2-(3-(Trifluoromethoxy)propyl)-2,3-dihydropyrazolo[5,1-b]oxazole-6-carboxylic acid was obtained by a method similar to Step 1 to Step 2 in Reference Example 37, using ethyl 2-(3-hydroxypropyl)-2,3-dihydropyrazolo[5,1-b]oxazole-6-carboxylate synthesized by a method described in Step 7 in Example 245 instead of ethyl 5-(hydroxymethyl)-6,7-dihydro-5H-pyrazolo[5,1-b][1,3]oxazine-2-carboxylate in Step 1.

Step 3

N—((R)-6-Cyanochroman-3-yl)-2-(3-(trifluoromethoxy)propyl)-2,3-dihydropyrazolo[5,1-b]oxazole-6-carboxamide was obtained by a method similar to Step 4 in Example 1, using 2-(3-(trifluoromethoxy)propyl)-2,3-dihydropyrazolo[5,1-b]oxazole-6-carboxylic acid instead of 6-(trifluoromethyl)-5,6,7,8-tetrahydroimidazo[1,2-a]pyridine-2-carboxylic acid, and using (R)-3-aminochroman-6-carbonitrile synthesized by a method described in Reference Example 24 instead of 6-fluorochroman-3-amine hydrochloride.

Step 4

N—((R)-6-Cyanochroman-3-yl)-2-(3-(trifluoromethoxy)propyl)-2,3-dihydropyrazolo[5,1-b]oxazole-6-carboxamide (126 mg, 0.289 mmol) was dissolved in ethanol (12 mL), and the solution was subjected to HPLC fractionation (column: CHIRALPAK IB N-5, developing solvent: ethanol, flow rate: 8.0 mL/min, room temperature) to give isomer A (amount 57.7 mg, yield 46%) and isomer B (amount 52.5 mg, yield 42%).

The compound of Reference Example 248 was synthesized from the compound synthesized in Step 7 in Example 245 under the scheme depicted in the figure below.

[Chem 204]

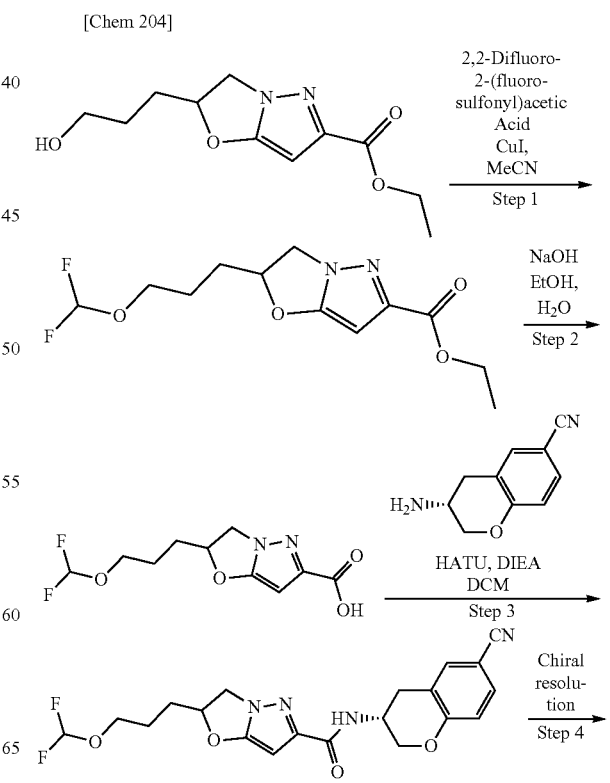

-continued

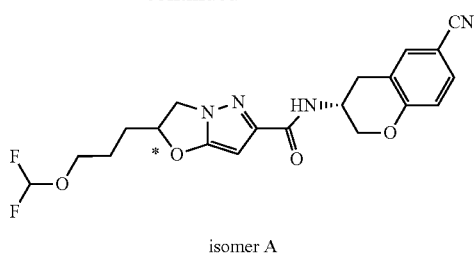

isomer A

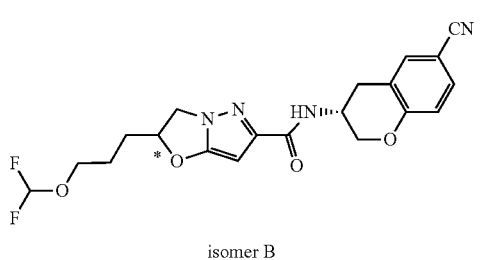

isomer B

The compound of Example 249 was synthesized under the scheme depicted in the figure below.

[Chem 205]

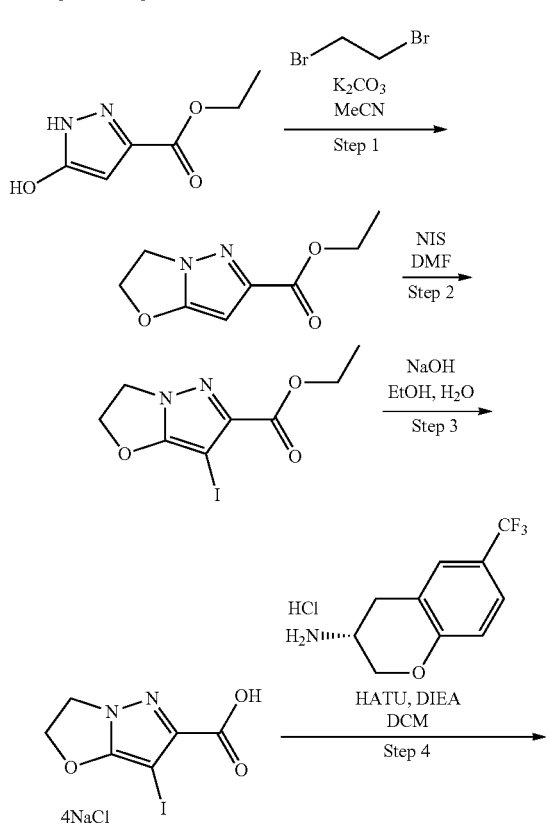

-continued

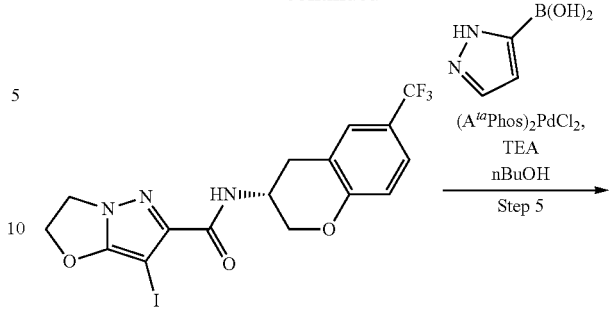

The compound of Reference Example 68 (ethyl 2,2-dimethyl-2,3-dihydropyrazolo[5,1-b]oxazole-6-carboxylate) was synthesized under the scheme depicted in the figure below.

[Chem 206]

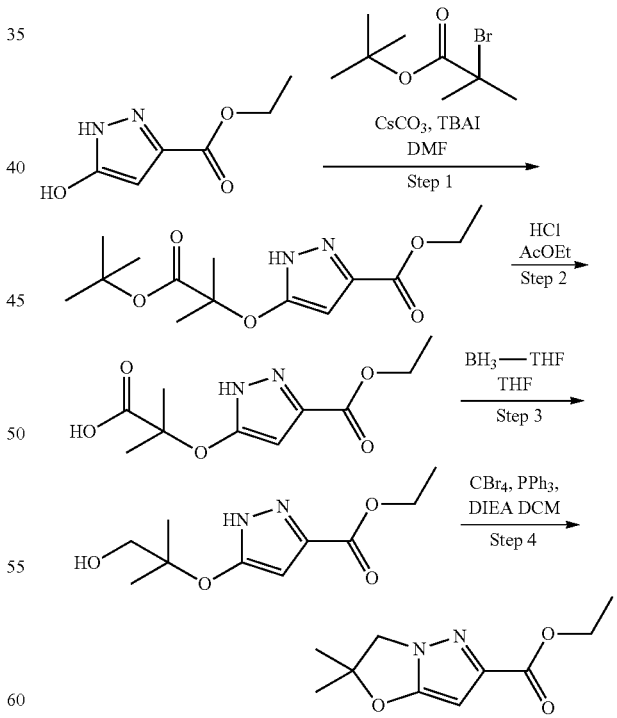

The compound of Example 250 was synthesized from the compound of Reference Example 68 by a method similar to Step 2 to Step 5 in Example 249.

The compound of Example 251 was synthesized by a method similar to Step 5 to Step 8 in Example 70.

Example 252

Production of N—((R)-6-cyanochroman-3-yl)-6-(trifluoromethoxy)-5,6,7,8-tetrahydropyrazolo[5,1-b][1,3]oxazepine-2-carboxamide

[Chem 207]

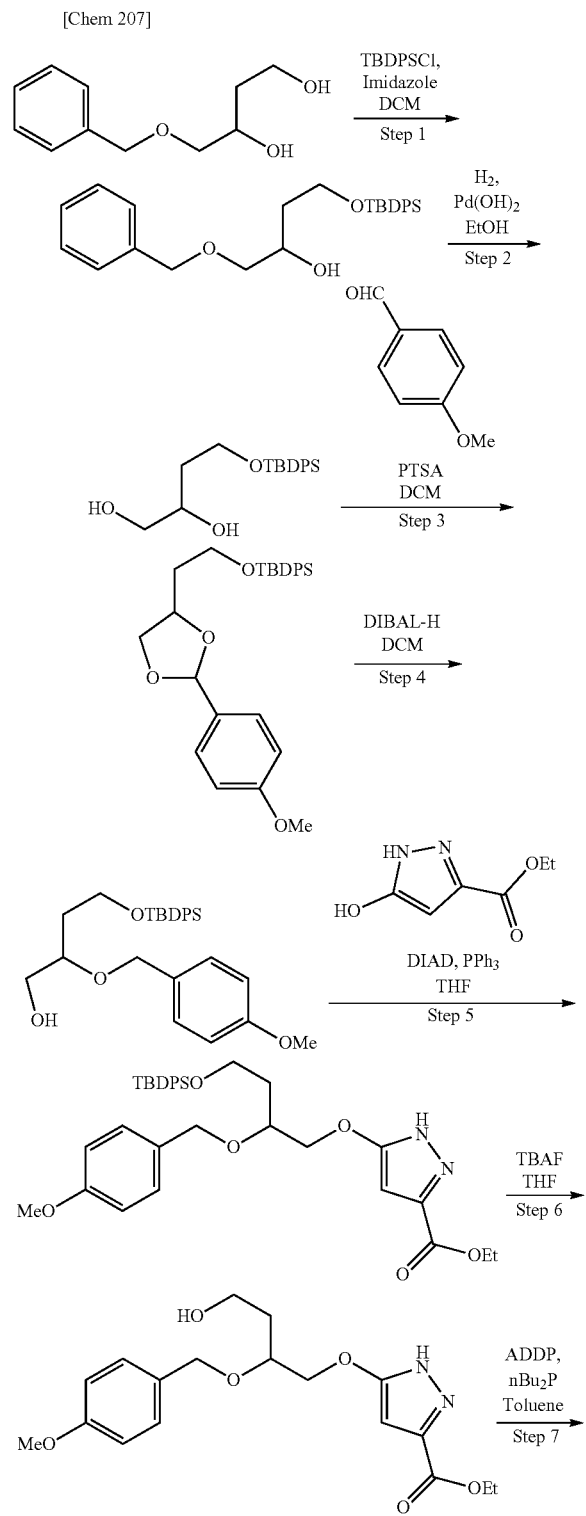

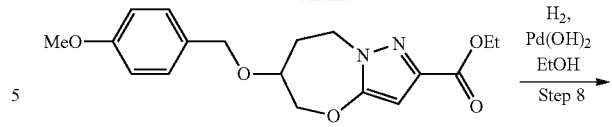

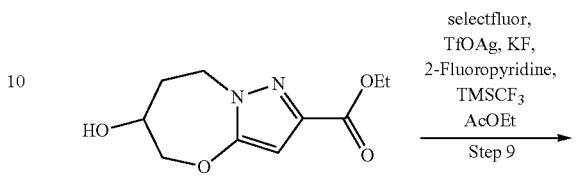

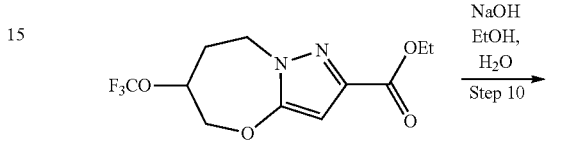

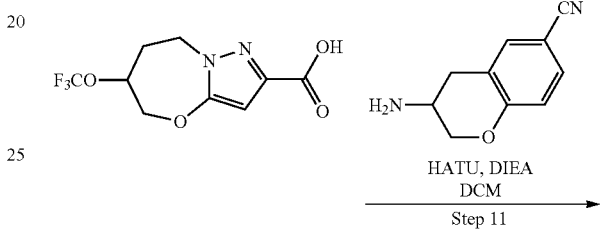

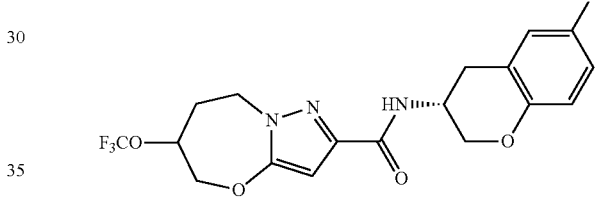

Step 1

1-(Benzyloxy)-4-((tert-butyldiphenylsilyl)oxy)butan-2-ol was obtained by a method similar to Step 1 in Example 85, using 4-(benzyloxy)butan-1,3-diol instead of butan-1,3-diol.

Step 2

4-((tert-Butyldiphenylsilyl)oxy)butan-1,2-diol was obtained by a method similar to Step 1 in Example 100, using 1-(benzyloxy)-4-((tert-butyldiphenylsilyl)oxy)butan-2-ol instead of ethyl 5-((benzyloxy)methyl-6,7-dihydro-5H-pyrazolo[5,1-b][1,3]oxazine-2-carboxylate.

Step 3

To a solution of 4-((tert-butyldiphenylsilyl)oxy)butan-1,2-diol (2.00 g, 5.81 mmol) in dichloromethane (24 mL) were was added p-toluene sulfonic acid (55 mg, 0.29 mmol) and 4-methoxybenzaldehyde (2.37 g, 17.4 mmol), and the mixture was stirred for 1 hour at room temperature. Saturated aqueous solution of sodium hydrogen carbonate and chloroform was added to the reaction solution, and the mixture was partitioned. After the organic layer was washed with saturated brine and the solvent was evaporated off under reduced pressure, the residue was purified by silica gel column chromatography to give tert-butyl (2-(2-(4-methoxyphenyl)-1,3-dioxolan-4-yl)ethoxy)diphenylsilane (amount 1.76 g, yield 66%).

Step 4

A solution of tert-butyl (2-(2-(4-methoxyphenyl)-1,3-dioxolan-4-yl)ethoxy)diphenylsilane (1.76 g, 3.80 mmol) in dichloromethane (20 mL) was cooled to −78° C., and 1 mol/L diisobutylaluminum hydride/n-hexane solution (5.33 mL, 5.33 mmol) was added to the solution. After stirring for 15 minutes, the mixture was warmed to 0° C. To the reaction solution, an aqueous solution of potassium sodium tartarate and chloroform were added, and the mixture was partitioned. Thereafter, the organic layer was dried over anhydrous sodium sulfate and the solvent was evaporated off under reduced pressure. The residue was purified by silica gel column chromatography to give 4-(tert-butyl (diphenyl) silyl)oxy-2-((4-methoxyphenyl)methoxy)butan-1-ol (amount 427 mg, yield 24%).

Step 5 to Step 6

Ethyl 5-(4-hydroxy-2-((4-methoxybenzyl)oxy)butoxy)-1H-pyrazole-3-carboxylate was obtained by a method similar to Step 2 to Step 3 in Example 85, using 4-(tert-butyl (diphenyl)silyl)oxy-2-((4-methoxyphenyl)methoxy)butan-1-ol instead of 4-((tert-butyldiphenylsilyl)oxy)butan-2-ol in Step 2.

Step 7

To a solution of ethyl 5-(4-hydroxy-2-((4-methoxybenzyl)oxy)butoxy)-1H-pyrazole-3-carboxylate (274 mg, 0.752 mmol) in toluene (15 mL) were added tri-N-butylphosphine (376 μL, 1.51 mmol) and 1,1'-(azodicarbonyl)dipiperidine (379 mg, 1.50 mmol), and the mixture was stirred for 1.5 hours at 80° C. The reaction solution was allowed to cool to room temperature, and water and ethyl acetate was added, and the mixture was partitioned. The organic layer was washed with saturated brine and dried over anhydrous magnesium sulfate, and then the solvent was evaporated off under reduced pressure. The residue was purified by silica gel column chromatography to give ethyl 6-((4-methoxybenzyl)oxy)-5,6,7,8-tetrahydropyrazolo[5,1-b][1,3]oxazepine-2-carboxylate (amount 198 mg, yield 76%).

Step 8

Ethyl 6-hydroxy-5,6,7,8-tetrahydropyrazolo[5,1-b][1,3]oxazepine-2-carboxylate was obtained by a method similar to Step 1 in Example 100, using 6-((4-methoxybenzyl)oxy)-5,6,7,8-tetrahydropyrazolo[5,1-b][1,3]oxazepine-2-carboxylate instead of ethyl 5-((benzyloxy)methyl-6,7-dihydro-5H-pyrazolo[5,1-b][1,3]oxazine-2-carboxylate.

Step 9 to Step 11

By a method similar to Example 247, N—((R)-6-cyanochroman-3-yl)-6-(trifluoromethoxy)-5,6,7,8-tetrahydropyrazolo[5,1-b][1,3]oxazepine-2-carboxamide was obtained, using ethyl 6-hydroxy-5,6,7,8-tetrahydropyrazolo[5,1-b][1,3]oxazepine-2-carboxylate instead of ethyl 2-(3-hydroxypropyl)-2,3-dihydropyrazolo[5,1-b]oxazole-6-carboxylate in Step 1.

The compounds of Example 253 were obtained by separating the compound of Example 252.

Example 254

Production of N—((R)-6-cyanochroman-3-yl)-6-(2,2,2-trifluoroethoxy)-5,6,7,8-tetrahydropyrazolo[5,1-b][1,3]oxazepine-2-carboxamide

[Chem 208]

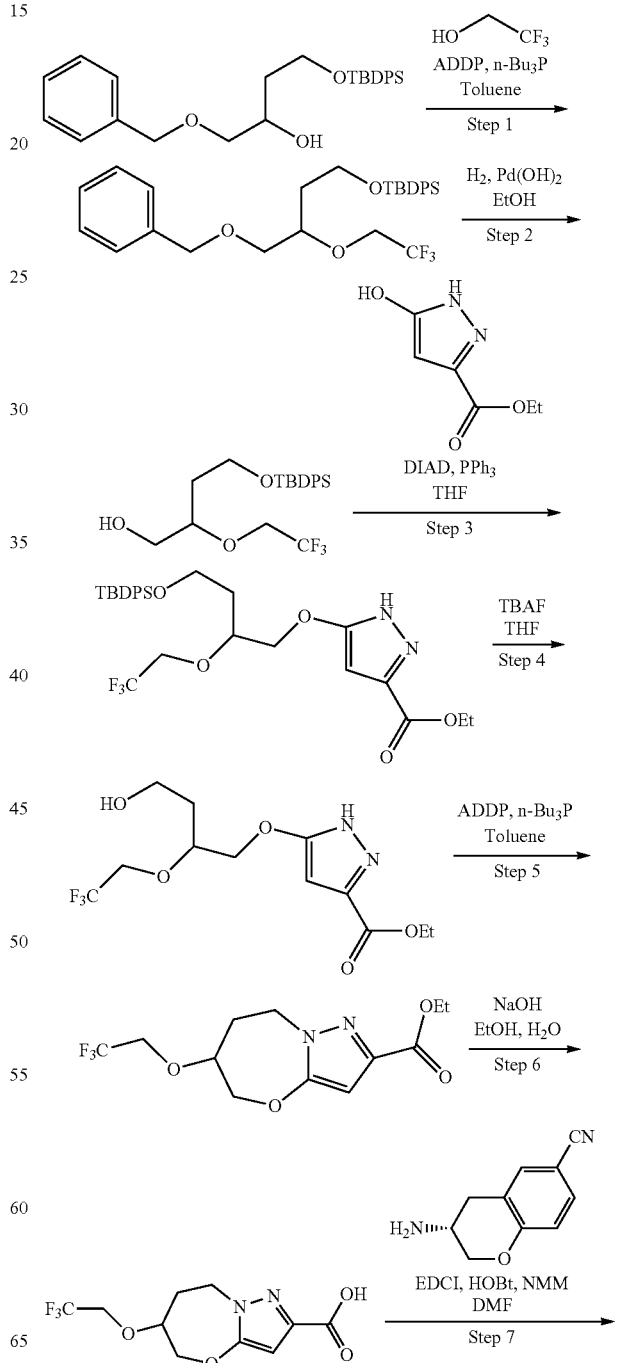

229
-continued

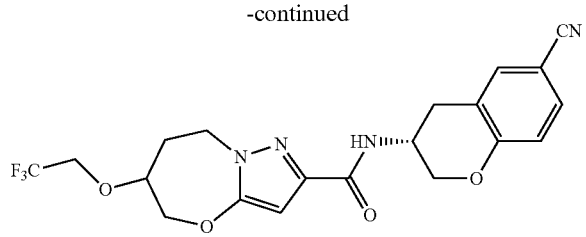

Step 1

By a method similar to Example 114, (4-(benzyloxy)-3-(2,2,2-trifluoroethoxy)butoxy) (tert-butyl)diphenylsilane was obtained, using 1-(benzyloxy)-4-((tert-butyldiphenylsilyl)oxy)butan-2-ol synthesized by a method described in Step 1 in Example 252 instead of N—((R)-6-cyanochroman-3-yl)-5-(hydroxymethyl)-6,7-dihydro-5H-pyrazolo[5,1-b][1,3]oxazine-2-carboxamide.

Step 2

By a method similar to Step 2 in Example 252, 4-(tert-butyldiphenylsilyl)oxy)-2-(2,2,2-trifluoroethoxy)butan-1-ol was obtained, using (4-(benzyloxy)-3-(2,2,2-trifluoroethoxy)butoxy) (tert-butyl)diphenylsilane instead of 1-(benzyloxy)-4-((tert-butyldiphenylsilyl)oxy)butan-2-ol.

Step 3 to Step 5

By a method similar to Step 5 to Step 7 in Example 252, ethyl 6-(2,2,2-trifluoroethoxy)-5,6,7,8-tetrahydropyrazolo[5,1-b][1,3]oxazepine-2-carboxylate was obtained, using 4-(tert-butyldiphenylsilyl)oxy)-2-(2,2,2-trifluoroethoxy)butan-1-ol instead of 4-(tert-butyl (diphenyl)silyl)oxy-2-((4-methoxyphenyl)methoxy)butan-1-ol in Step 5.

Step 6 to Step 7

By a method similar to Step 10 to Step 11 in Example 252, N—((R)-6-cyanochroman-3-yl)-6-(2,2,2-trifluoroethoxy)-5,6,7,8-tetrahydropyrazolo[5,1-b][1,3]oxazepine-2-carboxamide was obtained, using ethyl 6-(2,2,2-trifluoroethoxy)-5,6,7,8-tetrahydropyrazolo[5,1-b][1,3]oxazepine-2-carboxylate instead of ethyl 6-(trifluoromethoxy)-5,6,7,8-tetrahydropyrazolo[5,1-b][1,3]oxazepine-2-carboxylate in Step 10.

The compounds of Example 255 were obtained by separating the compound of Example 254.

Example 256

Production of N—((R)-6-chlorochroman-3-yl)-6-(2,2,2-trifluoroethoxy)-5,6,7,8-tetrahydropyrazolo[5,1-b][1,3]oxazepine-2-carboxamide (isomer A and isomer B)

[Chem 209]

To a suspension of 6-(2,2,2-trifluoroethoxy)-5,6,7,8-tetrahydropyrazolo[5,1-b][1,3]oxazepine-2-carboxylic acid (a mixture with 4 equivalents of sodium chloride) (26.0 mg, 0.0591 mmol) synthesized by a method described in Step 6 in Example 254, (R)-6-chlorochroman-3-amine (14.1 mg, 0.0768 mmol), 1-hydroxybenzotriazole (14.2 mg, 0.0927 mmol) and 1-ethyl-3-(3-dimethylaminopropyl)carbodiimide hydrochloride (17.8 mg, 0.0929 mmol) in N,N-dimethylformamide (0.5 mL), 4-methylmorpholine (41 µL, 0.373 mmol) was added. The mixture was stirred for 2 hours at room temperature. Water and ethyl acetate was added to the reaction solution, and the mixture was partitioned. After drying the organic layer with anhydrous sodium sulfate, the solvent was evaporated off under reduced pressure. The residue was purified by silica gel column chromatography and the diastereomers were separated to give N—((R)-6-chlorochroman-3-yl)-6-(2,2,2-trifluoroethoxy)-5,6,7,8-tetrahydropyrazolo[5,1-b][1,3]oxazepine-2-carboxamide (isomer A) (amount 2.7 mg, yield 10%) and N—((R)-6-chlorochroman-3-yl)-6-(2,2,2-trifluoroethoxy)-5,6,7,8-tetrahydropyrazolo[5,1-b][1,3]oxazepine-2-carboxamide (isomer B) (amount 2.9 mg, yield 11%).

The compound of Example 257 was synthesized from the compound synthesized in Step 6 in Example 254 under the scheme depicted in the figure below.

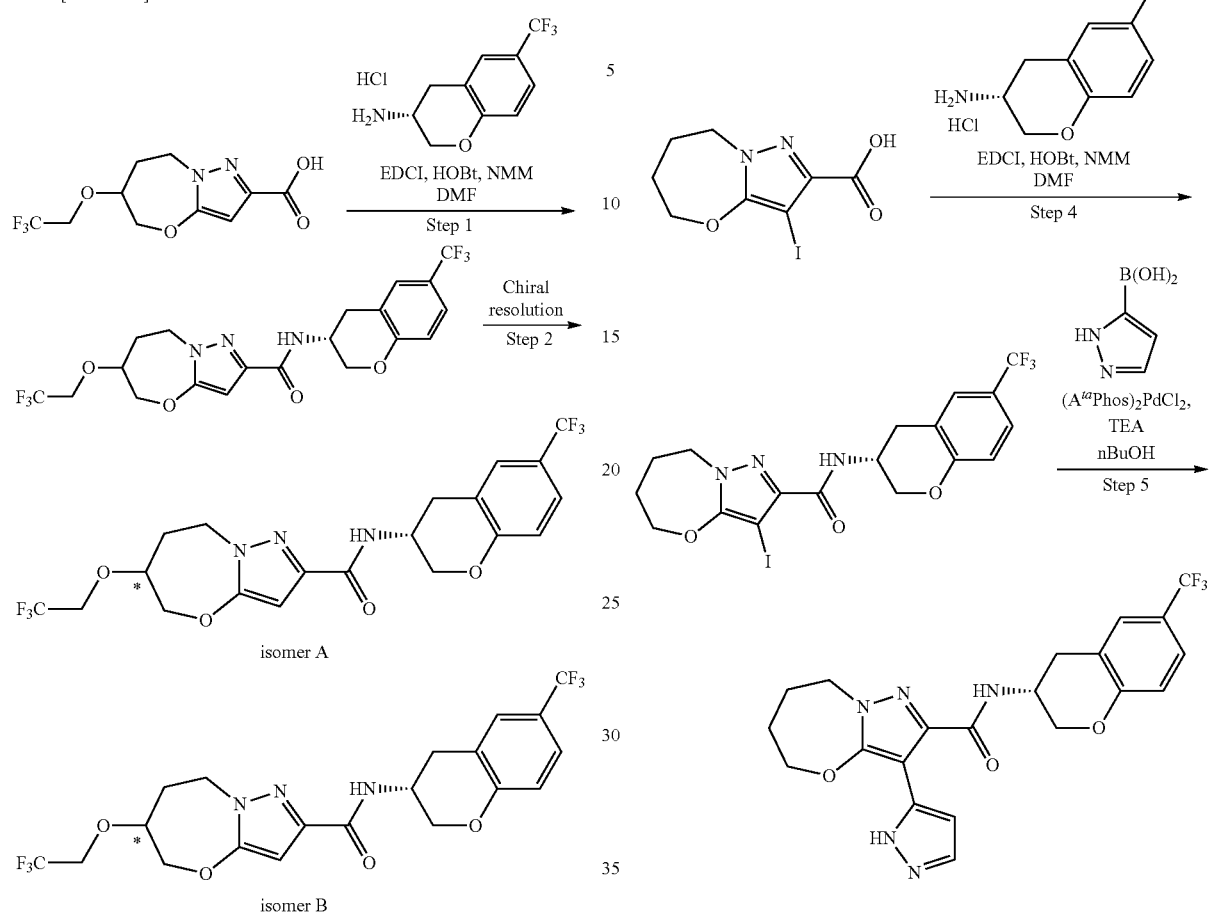

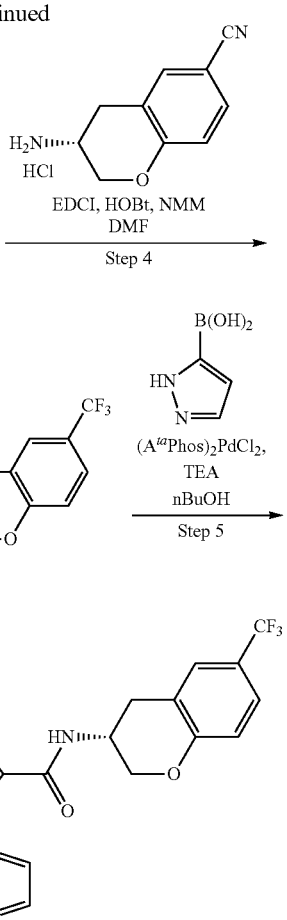

Example 258

Production of (R)-3-(1H-pyrazol-5-yl)-N-(6-(trifluoromethyl)chroman-3-yl)-5,6,7,8-tetrahydropyrazolo[5,1-b][1,3]oxazepine-2-carboxamide

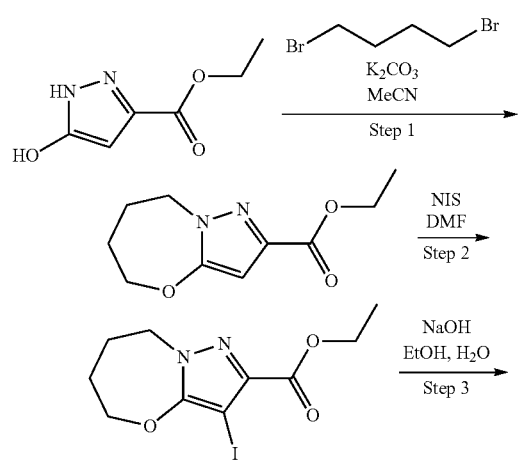

Step 1

To a solution of ethyl 5-hydroxy-1H-pyrazole-3-carboxylate (1.00 g, 6.40 mmol) in acetonitrile (13 mL) was added potassium carbonate (2.66 g, 19.2 mmol) and 1,4-dibromobutane (804 μL, 6.73 mmol). After sealing, the mixture was stirred for 15 hours at 100° C. The reaction solution was allowed to cool to room temperature, and after filtration, the filtrate was concentrated under reduced pressure. The residue was purified by silica gel column chromatography to give ethyl 5,6,7,8-tetrahydropyrazolo[5,1-b][1,3]oxazepine-2-carboxylate (amount 574 mg, yield 43%).

Step 2

Ethyl 3-iodo-5,6,7,8-tetrahydropyrazolo[5,1-b][1,3]oxazepine-2-carboxylate was obtained by a method similar to Example 14, using ethyl 5,6,7,8-tetrahydropyrazolo[5,1-b][1,3]oxazepine-2-carboxylate instead of N—((R)-chroman-3-yl)-6-(trifluoromethyl)-5,6,7,8-tetrahydroimidazo[1,2-a]pyridine-2-carboxamide.

Step 3 to Step 4

(R)-3-Iodo-N-(6-(trifluoromethyl)chroman-3-yl)-5,6,7,8-tetrahydropyrazolo[5,1-b][1,3]oxazepine-2-carboxamide was obtained by a method similar to Step 3 to Step 4 in Example 18, using ethyl 3-iodo-5,6,7,8-tetrahydropyrazolo[5,1-b][1,3]oxazepine-2-carboxylate instead of ethyl 3-(pyridin-2-yl)-5,6,7,8-tetrahydroimidazo[1,2-a]pyridine-2-carboxylate in Step 3, and using (R)-6-(trifluoromethyl)chroman-3-amine hydrochloride synthesized by a method described in Reference Example 43 instead of (R)-6-chlorochroman-3-amine hydrochloride in Step 4.

Step 5

To a solution of (R)-3-iodo-N-(6-(trifluoromethyl)chroman-3-yl)-5,6,7,8-tetrahydropyrazolo[5,1-b][1,3]oxazepine-2-carboxamide (20 mg, 0.039 mmol) in n-butanol (800 μL) were added 1H-pyrazol-5-ylboronic acid (8.8 mg, 0.079 mmol), triethylamine (22 μL, 0.16 mmol) and bis(di-tert-butyl (4-dimethylaminophenyl)phosphine)dichloropalladium (II) (2.8 mg, 0.0040 mmol). The mixture was stirred for 1 hour at 120° C. under microwave irradiation. The reaction solution was concentrated under reduced pressure, and the residue was purified by silica gel column chromatography to give (R)-3-(1H-pyrazol-5-yl)-N-(6-(trifluoromethyl)chroman-3-yl)-5,6,7,8-tetrahydropyrazolo[5,1-b][1,3]oxazepine-2-carboxamide (amount 13.6 mg, yield 77%).

Example 259

Production of (R)-3-(1H-pyrazol-5-yl)-N-(6-(trifluoromethyl)chroman-3-yl)-6,7-dihydro-4H-pyrazolo[5,1-c][1,4]oxazine-2-carboxamide

[Chem 212]

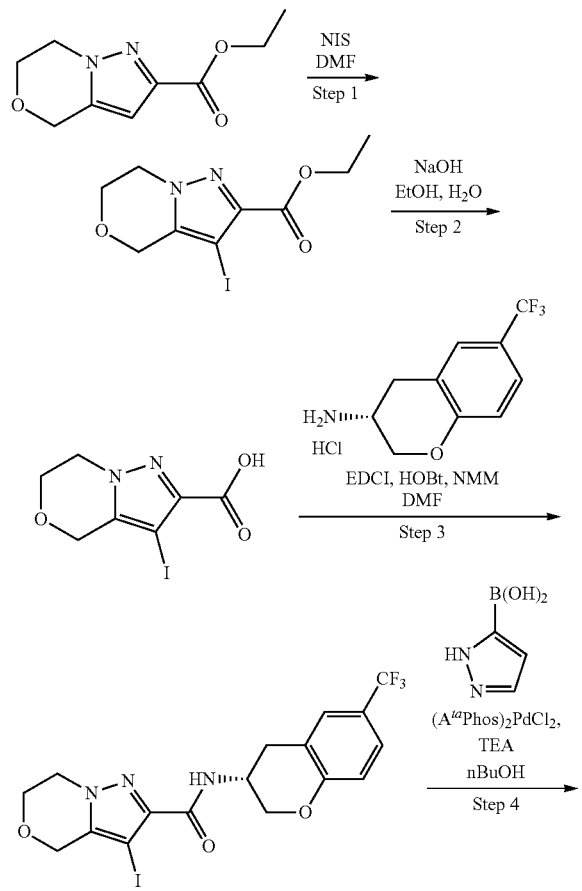

-continued

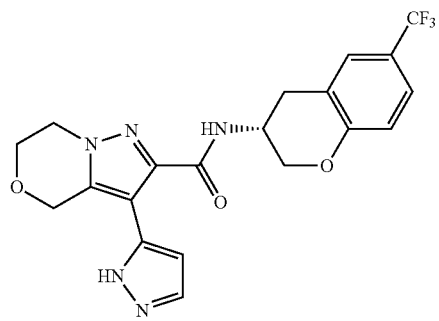

Step 1 to Step 4

(R)-3-(1H-Pyrazol-5-yl)-N-(6-(trifluoromethyl)chroman-3-yl)-6,7-dihydro-4H-pyrazolo[5,1-c][1,4]oxazine-2-carboxamide was obtained by a method similar to Step 2 to Step 5 in Example 258, using ethyl 6,7-dihydro-4H-pyrazolo[5,1-c][1,4]oxazine-2-carboxylate instead of ethyl 5,6,7,8-tetrahydropyrazolo[5,1-b][1,3]oxazepine-2-carboxylate in Step 2.

Example 260

Production of (R)-3-(pyridin-2-yl)-N-(6-(trifluoromethyl)chroman-3-yl)-6,7-dihydro-4H-pyrazolo[5,1-c][1,4]oxazine-2-carboxamide

[Chem 213]

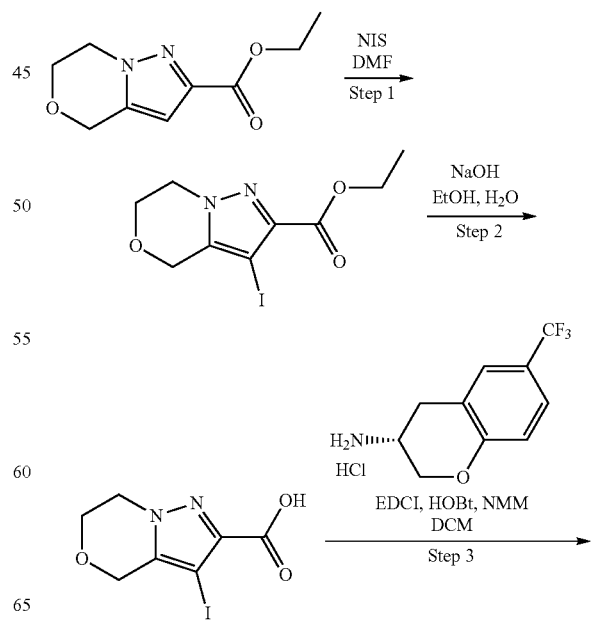

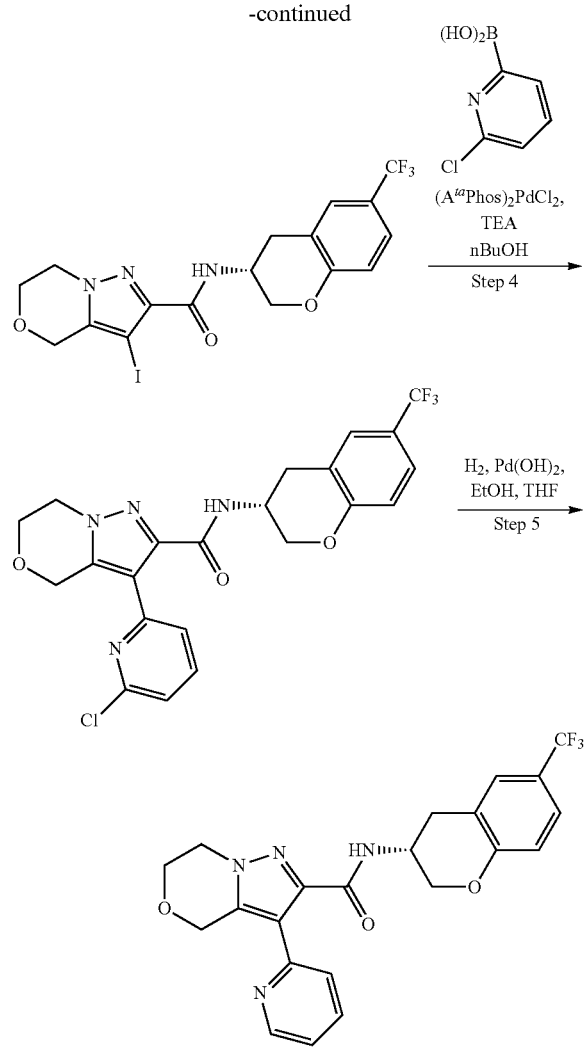

Step 1

To a solution of ethyl 6,7-dihydro-4H-pyrazolo[5,1-c][1,4]oxazine-2-carboxylate (400 mg, 2.04 mmol) in acetonitrile (6.8 mL), N-iodosuccineimide (1.38 g, 6.13 mmol) was added, and the mixture was stirred for 14 hours at 70° C. An aqueous solution of sodium thiosulfate and ethyl acetate were added to the reaction solution, and the mixture was partitioned. The organic layer was dried over anhydrous sodium sulfate and the solvent was evaporated off under reduced pressure. The residue was purified by silica gel column chromatography to give ethyl 3-iodo-6,7-dihydro-4H-pyrazolo[5,1-c][1,4]oxazine-2-carboxylate (amount 650 mg, yield 99%).

Step 2

To a solution of ethyl 3-iodo-6,7-dihydro-4H-pyrazolo[5,1-c][1,4]oxazine-2-carboxylate (200 mg, 0.621 mmol) in ethanol (6.2 mL), 4 mol/L aqueous solution of sodium hydroxide (0.62 mL, 2.5 mmol) was added, and the mixture was stirred for 2 hours at room temperature. To the reaction solution, 2 mol/L hydrochloric acid was added, and then the solvent was evaporated off under reduced pressure. Toluene was added to the residue and the solvent was evaporated off under reduced pressure to give 3-iodo-6,7-dihydro-4H-pyrazolo[5,1-c][1,4]oxazine-2-carboxylic acid (amount 325 mg, yield 99%) as a mixture with 4 equivalents of sodium chloride.

Step 3

To a suspension of 3-iodo-6,7-dihydro-4H-pyrazolo[5,1-c][1,4]oxazine-2-carboxylic acid (a mixture with 4 equivalents of sodium chloride) (325 mg, 0.616 mmol), (R)-6-(trifluoromethyl)chroman-3-amine hydrochloride (156 mg, 0.616 mmol) synthesized by a method described in Reference Example 43, 1-hydroxybenzotriazole (10.0 mg, 0.0739 mmol) and 1-ethyl-3-(3-dimethylaminopropyl)carbodiimide hydrochloride (142 mg, 0.0739 mmol) in dichloromethane (10 mL), 4-methylmorpholine (203 μL, 1.85 mmol) was added, and the mixture was stirred for 12 hours at room temperature. Water and ethyl acetate were added to the reaction solution, and the mixture was partitioned. After drying the organic layer with anhydrous sodium sulfate, the solvent was evaporated off under reduced pressure. The residue was purified by silica gel column chromatography to give (R)-3-iodo-N-(6-(trifluoromethyl)chroman-3-yl)-6,7-dihydro-4H-pyrazolo[5,1-c][1,4]oxazine-2-carboxamide (amount 267 mg, yield 88%).

Step 4

To a mixed solution of (R)-3-iodo-N-(6-(trifluoromethyl)chroman-3-yl)-6,7-dihydro-4H-pyrazolo[5,1-c][1,4]oxazine-2-carboxamide (60.0 mg, 0.122 mmol) and (6-chloropyridin-2-yl)boronic acid (28.7 mg, 0.182 mmol) in 1,4-dioxane (1 mL) and water (1 mL) were added cesium carbonate (119 mg, 0.365 mmol), bis(di-tert-butyl(4-dimethylaminophenyl)phosphine)dichloropalladium (II) (8.6 mg, 0.012 mmol). The mixture was stirred for 1 hour at 140° C. under microwave irradiation. Water and ethyl acetate was added to the reaction solution, and the mixture was partitioned. The organic layer was dried over anhydrous magnesium sulfate and the solvent was evaporated off under reduced pressure. The residue was purified by silica gel column chromatography to give (R)-3-(6-chloropyridin-2-yl)-N-(6-(trifluoromethyl)chroman-3-yl)-6,7-dihydro-4H-pyrazolo[5,1-c][1,4]oxazine-2-carboxamide (amount 9.4 mg, yield 33%).

Step 5

To a solution of (R)-3-(6-chloropyridin-2-yl)-N-(6-(trifluoromethyl)chroman-3-yl)-6,7-dihydro-4H-pyrazolo[5,1-c][1,4]oxazine-2-carboxamide (290 mg, 0.606 mmol) in tetrahydrofuran (6 mL) were added ethanol (6 mL) and 20% palladium hydroxide on carbon (128 mg). The mixture was stirred under pressurized conditions (balloon pressure) in hydrogen atmosphere for 2 hours at 50° C. After the reaction solution was filtered through celite, the solvent was evaporated off under reduced pressure. The residue was purified by silica gel column chromatography to give (R)-3-(pyridin-2-yl)-N-(6-(trifluoromethyl)chroman-3-yl)-6,7-dihydro-4H-pyrazolo[5,1-c][1,4]oxazine-2-carboxamide (amount 204 mg, yield 76%).

The compound of Example 261 was synthesized under the scheme depicted in the figure below.

[Chem 214]

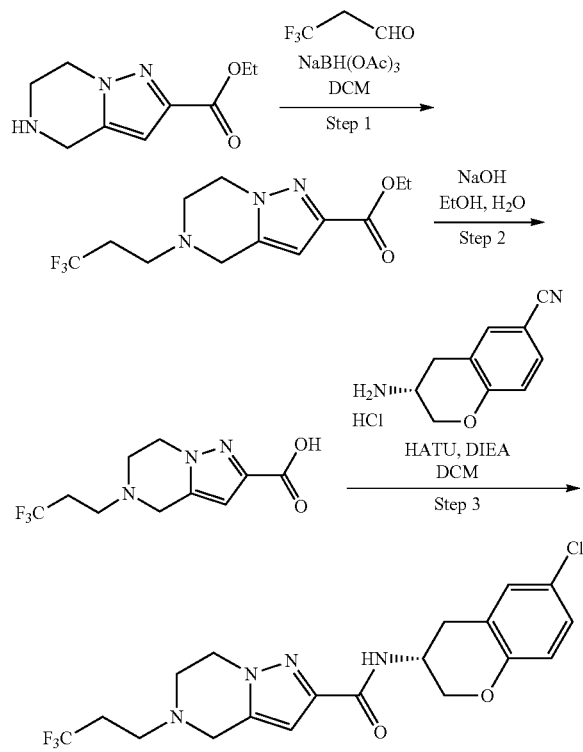

[Chem 216]

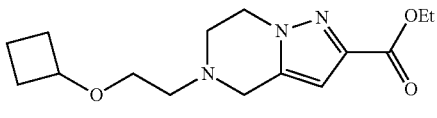

The compound of Example 265 was synthesized using the compound of Reference Example 70 and the compound of Reference Example 43 by methods similar to Step 2 and Step 3 in Example 261.

The compound of Example 266 was synthesized using the compound of Reference Example 70 and the compound of Reference Example 44 by methods similar to Step 2 and Step 3 in Example 261.

The compound of Example 267 was synthesized under the scheme depicted in the figure below.

[Chem 217]

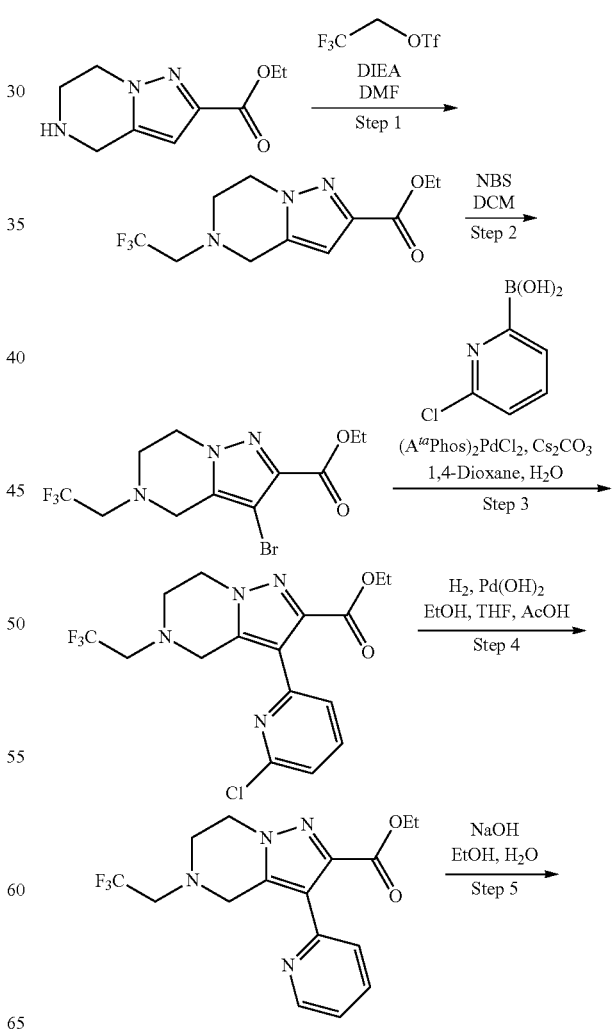

The compound of Example 262 was synthesized by a method similar to Example 261.

The compound of Reference Example 69 was synthesized under the scheme depicted in the figure below.

[Chem 215]

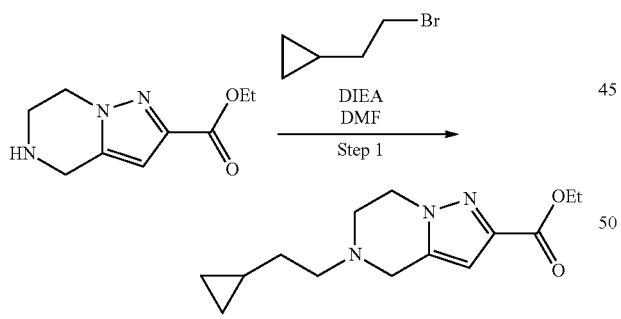

The compound of Example 263 was synthesized using the compound of Reference Example 69 and the compound of Reference Example 1 by methods similar to Step 2 and Step 3 in Example 261.

The compound of Example 264 was synthesized using the compound of Reference Example 69 and the compound of Reference Example 47 by methods similar to Step 2 and Step 3 in Example 261.

The compound of Reference Example 70 (shown in the figure below.) was synthesized by a method similar to Reference Example 69.

-continued

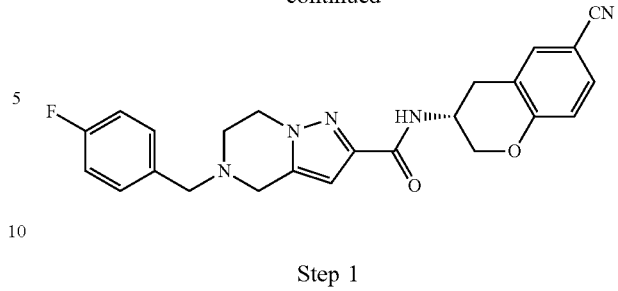

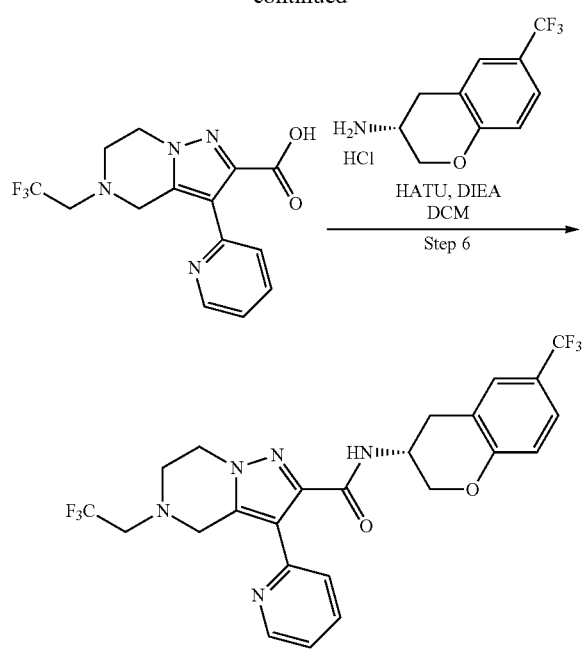

Example 268

Production of (R)—N-(6-cyanochroman-3-yl)-5-(4-fluorobenzyl)-4,5,6,7-tetrahydropyrazolo[1,5-a]pyrazine-2-carboxamide

[Chem 218]

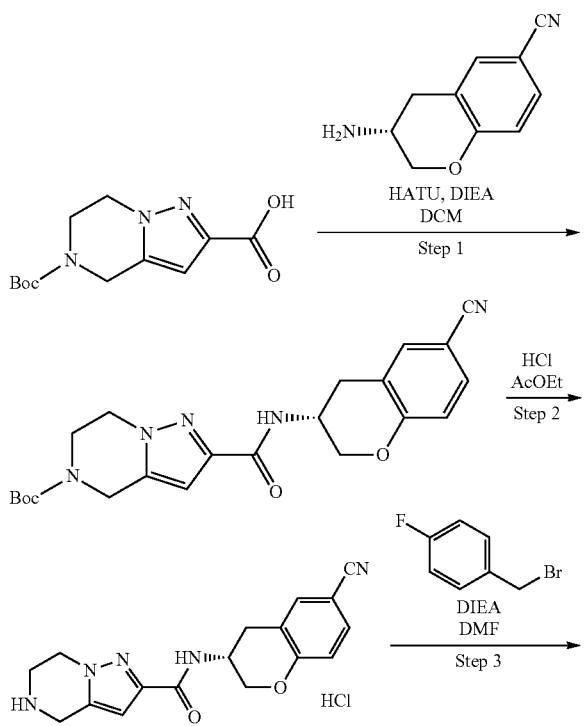

-continued

Step 1

To a solution of 5-(tert-butoxycarbonyl)-4,5,6,7-tetrahydropyrazolo[1,5-a]pyrazine-2-carboxylic acid (120 mg, 0.449 mmol) in dichloromethane (3 mL) were added HATU (188 mg, 0.494 mmol), N,N-diisopropylethylamine (386 μL, 2.24 mmol) and (R)-3-aminochroman-6-carbonitrile (104 mg, 0.494 mmol) synthesized by a method described in Reference Example 24.

The mixture was stirred for 12 hours at room temperature. The reaction solution was purified by silica gel column chromatography to give (R)-tert-butyl 2-((6-cyanochroman-3-yl)carbamoyl)-6,7-dihydropyrazolo[1,5-a]pyrazine-5 (4H)-carboxylate (amount 210 mg).

Step 2

To a solution of (R)-tert-butyl 2-((6-cyanochroman-3-yl)carbamoyl)-6,7-dihydropyrazolo[1,5-a]pyrazine-5 (4H)-carboxylate (210 mg, 0.496 mmol) in ethyl acetate (8 mL), 4 mol/L hydrogen chloride-ethyl acetate solution (8.0 mL, 32 mmol) was added, and the mixture was stirred for 2 hours at room temperature. The solvent was evaporated off under reduced pressure to give (R)—N-(6-cyanochroman-3-yl)-4,5,6,7-tetrahydropyrazolo[1,5-a]pyrazine-2-carboxamide hydrochloride (amount 178 mg, yield 100%).

Step 3

To a solution of (R)—N-(6-cyanochroman-3-yl)-4,5,6,7-tetrahydropyrazolo[1,5-a]pyrazine-2-carboxamide (15.0 mg, 0.0417 mmol) in N,N-dimethylformamide (208 μL) were added N,N-diisopropylethylamine (36 μL, 0.21 mmol) and 1-(bromomethyl)-4-fluorobenzene (15.8 mg, 0.0834 mmol). The mixture was stirred for 12 hours at 100° C. Water and chloroform was added to the reaction soltion, and the mixture was partitioned. After the organic layer was dried over sodium sulfate, the solvent was evaporated off under reduced pressure. The residue was purified by silica gel column chromatography to give (R)—N-(6-cyanochroman-3-yl)-5-(4-fluorobenzyl)-4,5,6,7-tetrahydropyrazolo[1,5-a]pyrazine-2-carboxamide (amount 16.0 mg, yield 89%).

The compound of Example 269 was synthesized by a method similar to Example 268.

The compound of Example 270 was synthesized by a method similar to Example 268.

The compound of Example 271 was synthesized by a method similar to Example 268.

The compound of Example 272 was synthesized by methods similar to those described in Example 268 and Reference Example 3.

The compound of Reference Example 71 (shown in the figure below.) was synthesized by methods similar to those described in Step 1 to Step 2 in Example 268 and in Reference Example 1.

[Chem 219]

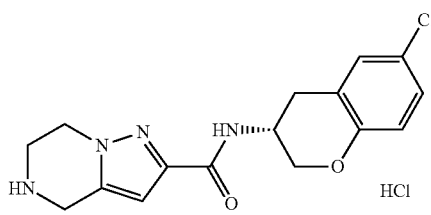

The compound of Example 273 was synthesized from the compound of Reference Example 71 by a method similar to Step 3 in Example 268.

The compound of Example 274 was synthesized from the compound of Reference Example 71 under the scheme depicted in the figure below.

[Chem 220]

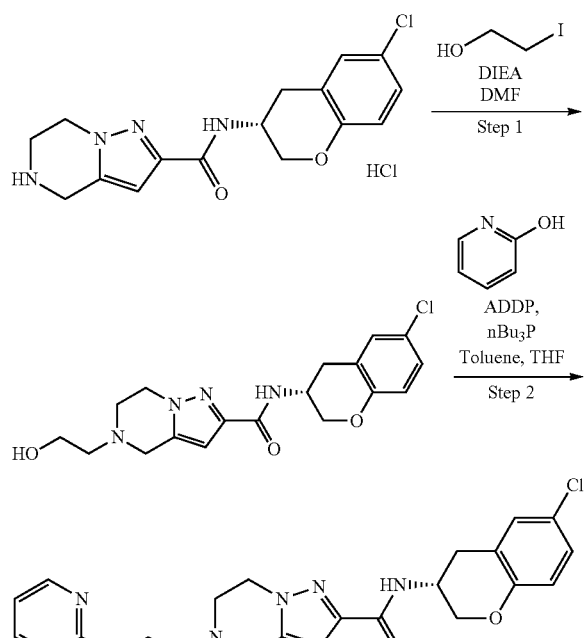

The compound of Example 275 was synthesized under the scheme depicted in the figure below.

[Chem 221]

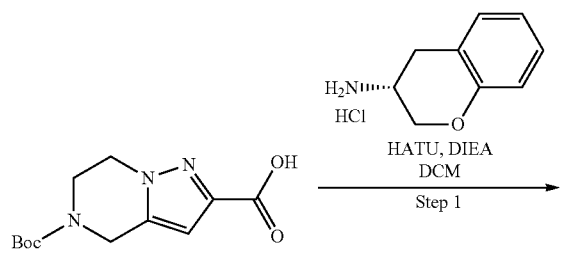

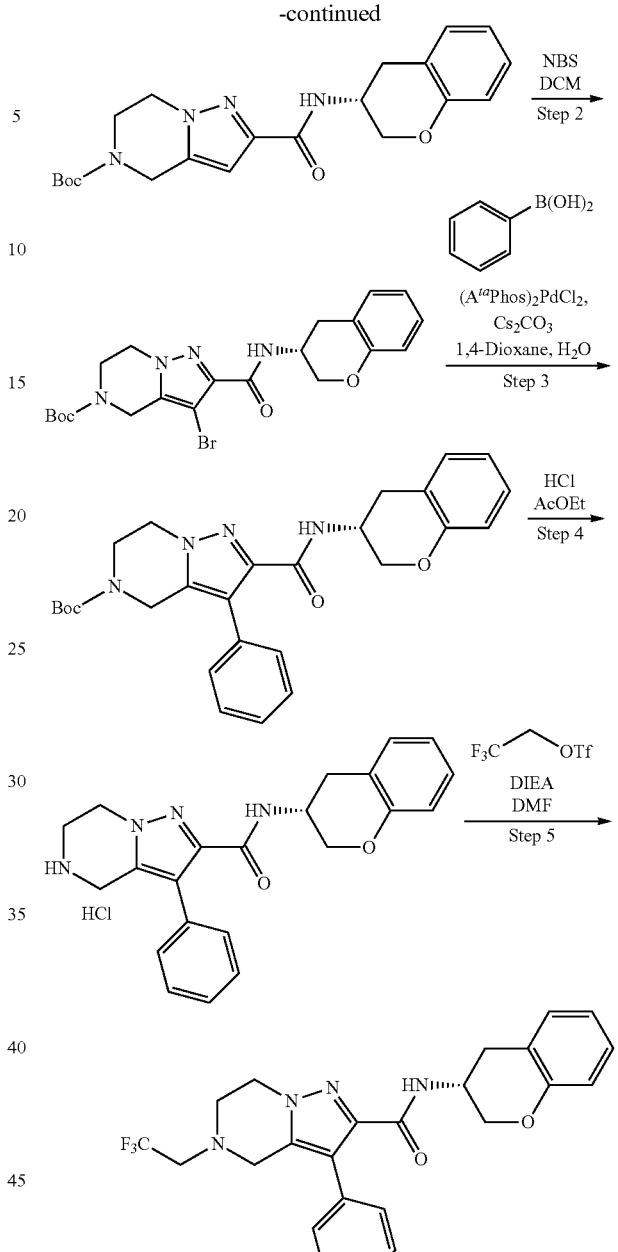

The compound of Reference Example 72 (shown in the figure below.) was synthesized by a method similar to Step 1 to Step 2 in Example 268.

[Chem 222]

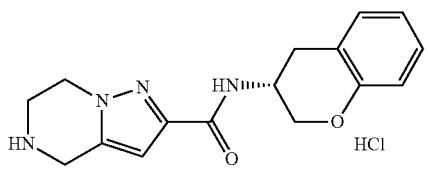

The compound of Example 276 was synthesized from the compound of Reference Example 72 under the scheme depicted in the figure below.

[Chem 223]

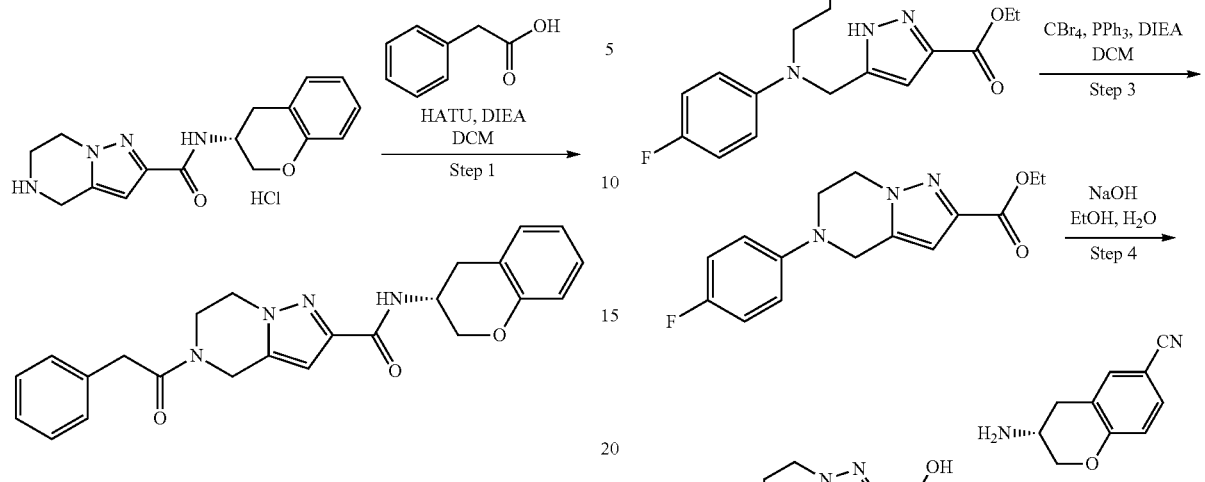

The compound of Example 277 was synthesized from the compound of Reference Example 72 under the scheme depicted in the figure below.

[Chem 224]

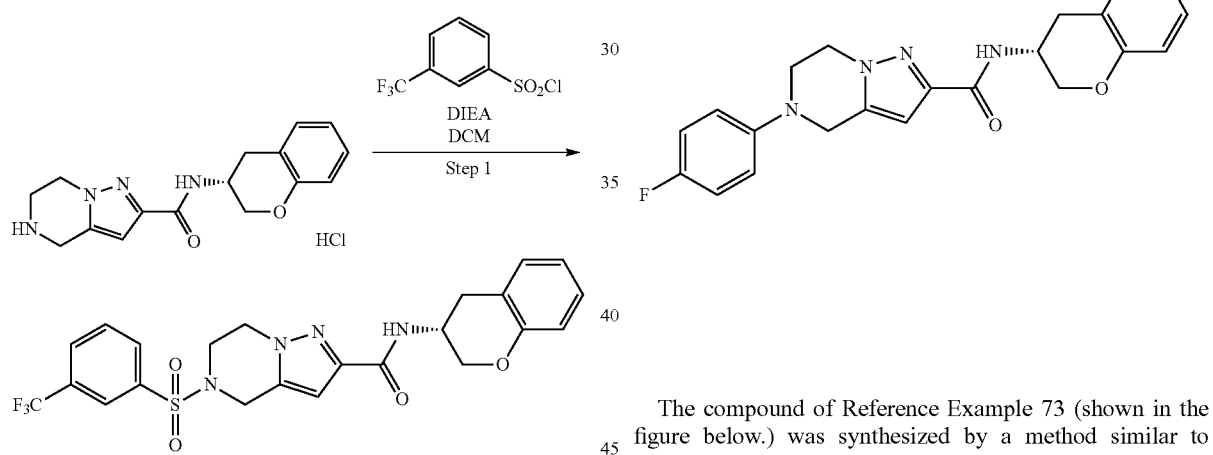

Example 278 was synthesized under the scheme depicted in the figure below.

[Chem 225]

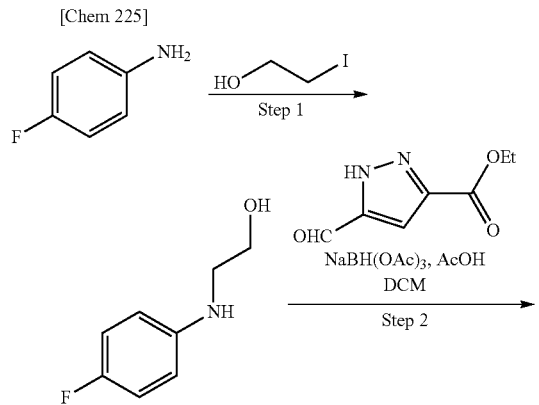

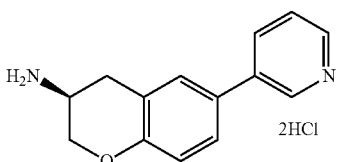

The compound of Reference Example 73 (shown in the figure below.) was synthesized by a method similar to Reference Example 27.

[Chem 226]

The compound of Example 279 was synthesized by methods similar to those described in Example 278 and Reference Example 73.

The compound of Example 280 was synthesized from the compound of Reference Example 71 under the scheme depicted in the figure below.

[Chem 227]

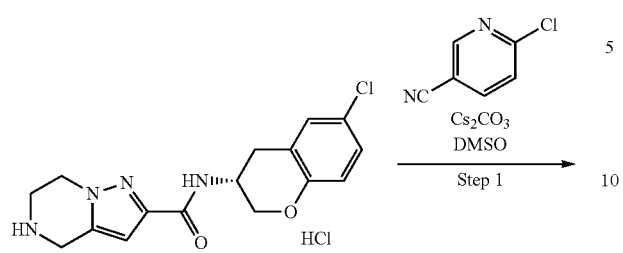
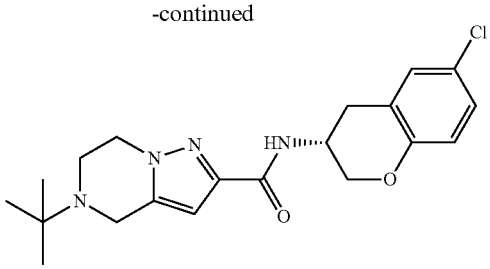
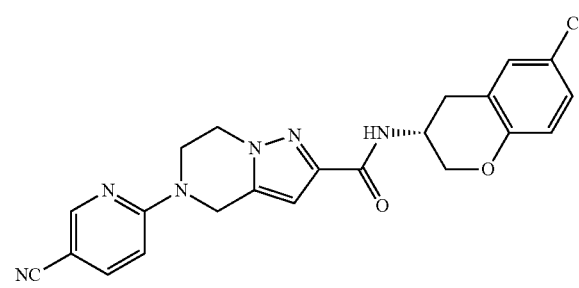

The compound of Example 281 was synthesized under the scheme depicted in the figure below.

[Chem 228]

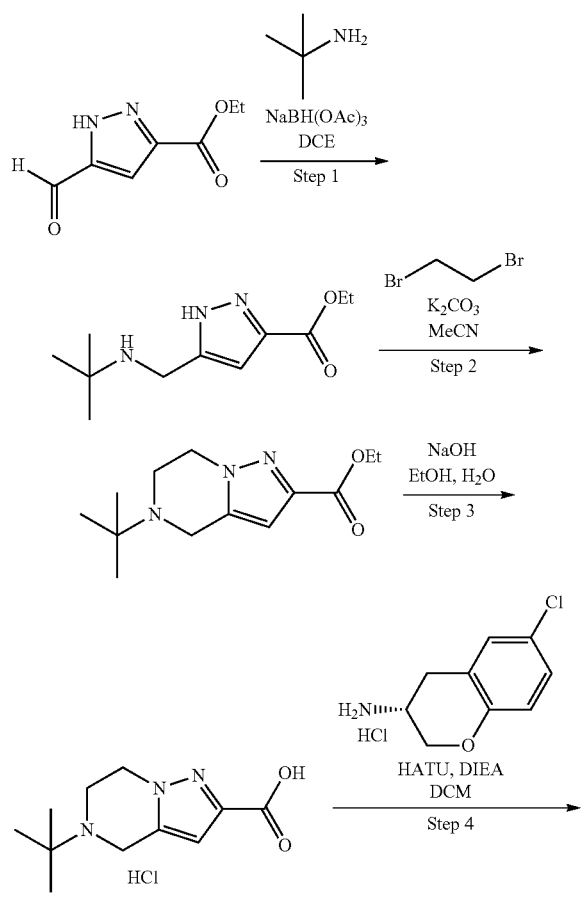

The compound of Example 282 was synthesized by methods similar to those described in Example 281 and Reference Example 24.

The compound of Example 283 was synthesized under the scheme depicted in the figure below.

[Chem 229]

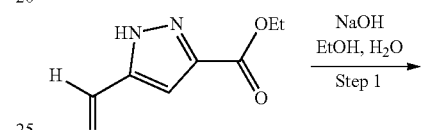
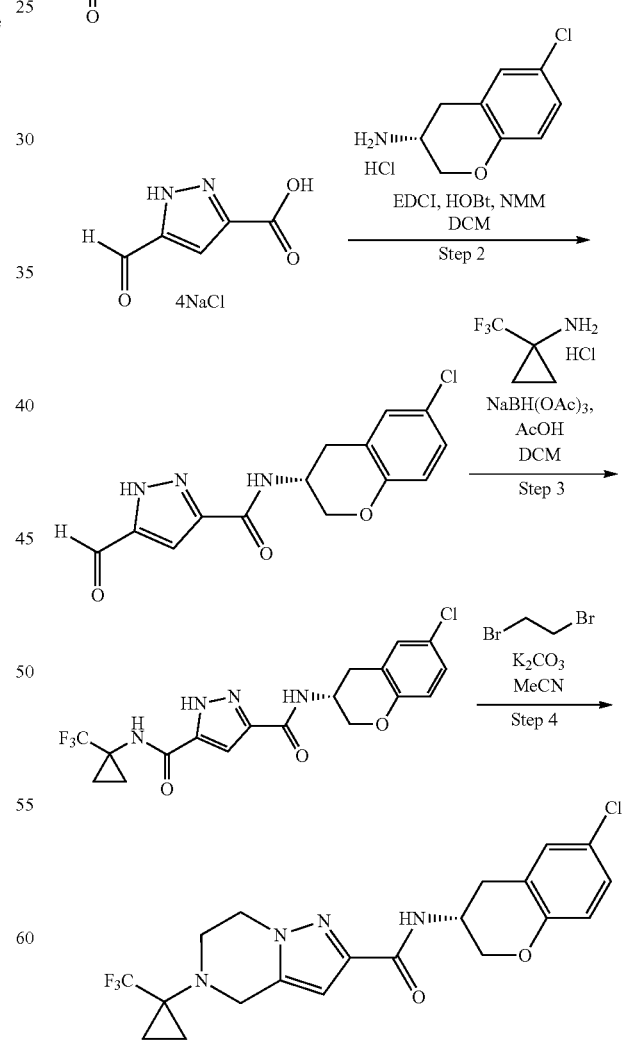

The compound of Example 284 was synthesized by a method similar to Example 283.

The compound of Example 285 was synthesized by a method similar to Example 283.

The compound of Reference Example 74 was synthesized under the scheme depicted in the figure below.

[Chem 230]

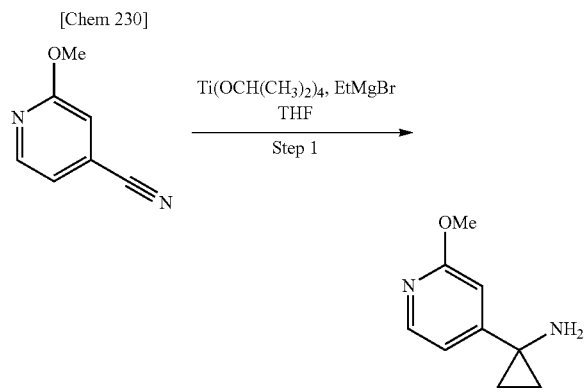

The compound of Example 286 was synthesized by a method similar to Example 283, using the compound of Reference Example 74 and the compound of Reference Example 24.

The compound of Example 287 was synthesized by a method similar to Step 6 to Step 8 in Example 70.

Example 288

Production of N—((R)-6-chlorochroman-3-yl)-6-(trifluoromethyl)-5,6,7,8-tetrahydroimidazo[1,2-a]pyridine-2-carboxamide (isomer A) hydrochloride

[Chem 231]

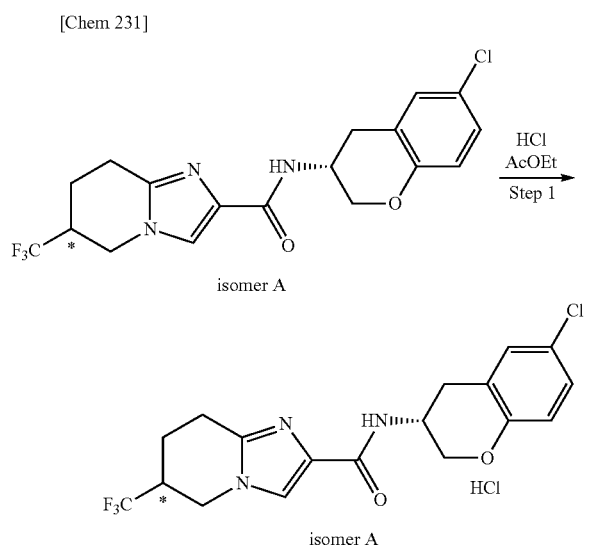

To a solution of N—((R)-6-chlorochroman-3-yl)-6-(trifluoromethyl)-5,6,7,8-tetrahydroimidazo[1,2-a]pyridine-2-carboxamide (isomer A) (170 mg, 0.425 mmol) synthesized by a method described in Example 2 in ethyl acetate (1 mL), 4 mol/L hydrogen chloride-ethyl acetate solution (1 mL, 4 mmol) was added, and the mixture was stirred for 10 minutes. The solvent was evaporated off under reduced pressure to give N—((R)-6-chlorochroman-3-yl)-6-(trifluoromethyl)-5,6,7,8-tetrahydroimidazo[1,2-a]pyridine-2-carboxamide (isomer A) hydrochloride (amount 185 mg, yield 100%).

The compound of Example 289 was synthesized from the compound of Example 81 under the scheme depicted in the figure below.

[Chem 232]

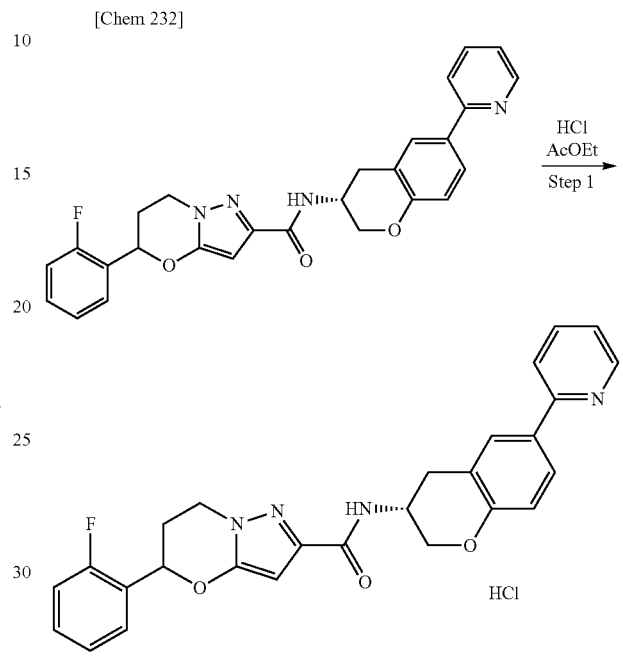

Example 290

Production of (R)—N-(6-cyanochroman-3-yl)-5-(4-fluorobenzyl)-4,5,6,7-tetrahydropyrazolo[1,5-a]pyrazine-2-carboxamide hydrochloride

[Chem 233]

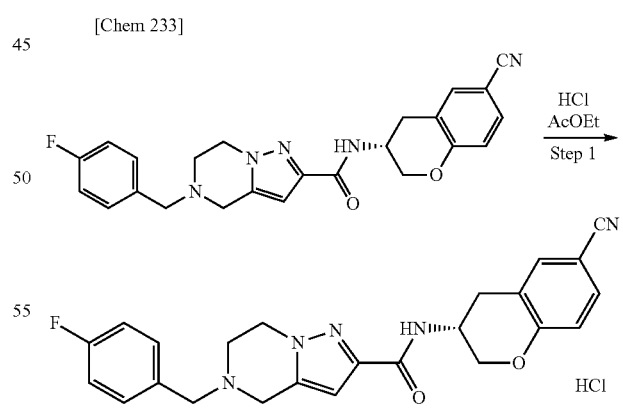

To a solution of (R)—N-(6-cyanochroman-3-yl)-5-(4-fluorobenzyl)-4,5,6,7-tetrahydropyrazolo[1,5-a]pyrazine-2-carboxamide (122 mg, 0.283 mmol) synthesized by a method described in Example 268 in ethyl acetate (2 mL), 4 mol/L hydrogen chloride-ethyl acetate solution (141 μL, 0.563 mmol) was added, and the mixture was stirred. n-Hexane (2 mL) was added, the precipitated solid was filtered, and then the solid was dried under reduced pressure to give (R)—N-(6-cyanochroman-3-yl)-5-(4-fluorobenzyl)-4,5,6,7-tetrahydropyrazolo[1,5-a]pyrazine-2-carboxamide hydrochloride (amount 96.4 mg, yield 73%).

In the tables below, on the compounds synthesized in Example 1 to Example 287, the chemical structures and instrumental analysis data are shown. Meanwhile, in the tables below, the asterisks (*) appearing in the structural formulae in the Examples denote that the corresponding asymmetric carbon has a single steric structure. Unless specifically stated otherwise, "Example" in the tables refers to the compound intended for production in each Example; for example, the data given for Example 1 shows the data of the compound intended for production in Example 1.

TABLE 1

| Example | Structural formula | NMR | MS |
|---|---|---|---|
| 1 | | 1H-NMR (CDCl$_3$) δ: 1.93-1.99 (1H, m), 2.32-2.36 (1H, m, 2.75-2.88 (3H, m), 3.03-3.08 (1H, m), 3.14-3.19 (1H, m), 3.96-4.03 (1H, m), 4.12-4.18 (2H, m), 4.26-4.30 (1H, m), 4.56-4.62 (1H, m), 6.74 (1H, d, J = 9.0 Hz), 6.80-6.83 (2H, m), 7.18 (1H, d, J = 7.6 Hz), 7.46 (1H, s). | |
| 2 (isomer A) | | 1H-NMR (CDCl$_3$) δ: 1.94 (1H, m), 2.34 (1H, m), 2.74-2.87 (3H, m), 3.02-3.19 (2H, m), 3.99 (1H, m), 4.13-4.22 (2H, m), 4.28 (1H, m), 4.60 (1H, m), 6.80 (1H, d, J = 8.7 Hz), 7.03 (1H, m), 7.07 (1H, dd, J = 8.9, 2.7 Hz), 7.17 (1H, d, J = 7.8 Hz), 7.46 (1H, s). | ESI-MS m/z: 400 [M + H]+ |
| 2 (isomer B) | | 1H-NMR (CDCl$_3$) δ: 1.95 (1H, m), 2.34 (1H, m), 2.73-2.87 (3H, m), 3.06 (1H, m), 3.15 (1H, m), 4.00 (1H, m), 4.13-4.23 (2H, m), 4.26 (1H, m), 4.60 (1H, m), 6.80 (1H, d, J = 8.7 Hz), 7.03 (1H, d, J = 2.5 Hz), 7.07 (1H, dd, J = 8.7, 2.6 Hz), 7.17 (1H, d, J = 8.2 Hz), 7.46 (1H, s). | ESI-MS m/z: 400 [M + H]+ |
| 3 | | 1H-NMR (CDCl$_3$) δ: 1.95 (1H, m), 2.34 (1H, m), 2.72-2.88 (2H, m), 2.96-3.35 (6H, m), 3.99 (1H, m), 4.15 (1H, m), 4.26-4.31 (2H, m), 5.27 (1H, m), 6.77 (1H, d, J = 9.7 Hz), 7.05-7.07 (2H, m), 7.43 (1H, s). | ESI-MS m/z: 414 [M + H]+ |
| 4 | | 1H-NMR (CDCl$_3$) δ: 1.97 (1H, m), 2.34 (1H, m), 2.73-2.87 (2H, m), 3.00-3.27 (6H, m), 3.99 (1H, m), 4.15 (1H, m), 4.26-4.32 (2H, m), 5.27 (1H, m), 6.77 (1H, d, J = 9.4 Hz), 7.06-7.07 (2H, m), 7.43 (1H, s). | ESI-MS m/z: 414 [M + H]+ |
| 5 | | 1H-NMR (CDCl$_3$) δ: 1.95 (1H, m), 2.34 (1H, m), 2.76-2.88 (3H, m), 3.06 (1H, m), 3.15 (1H, m), 3.99 (1H, m), 4.13-4.22 (2H, m), 4.28 (1H, m), 4.60 (1H, m), 6.75 (1H, d, J = 8.6 Hz), 7.15-7.18 (2H, m), 7.21 (1H, dd, J = 8.6, 2.4 Hz), 7.46 (1H, s). | ESI-MS m/z: 444, 446 [M + H]+ |

TABLE 1-continued

| Example | Structural formula | NMR | MS |
|---|---|---|---|
| 6 | | 1H-NMR (CDCl$_3$) δ: 1.94 (1H, m), 2.33 (1H, m), 2.75-2.84 (2H, m), 2.91 (1H, m), 3.05 (1H, m), 3.20 (1H, m), 3.99 (1H, m), 4.19 (1H, m), 4.25-4.30 (2H, m), 4.63 (1H, m), 6.56 (1H, t, J = 56.7 Hz), 6.93 (1H, d, J = 8.4 Hz), 7.16 (1H, d, J = 7.9 Hz), 7.21 (1H, s), 7.27 (1H, m), 7.46 (1H, s). | |
| 7 (isomer A) | | 1H-NMR (CDCl$_3$) δ: 1.94 (1H, m), 2.33 (1H, m), 2.76-2.84 (2H, m), 2.91 (1H, m), 3.05 (1H, m), 3.16 (1H, m), 3.99 (1H, m), 4.17-4.30 (3H, m), 4.63 (1H, m), 6.56 (1H, t, J = 56.7 Hz), 6.93 (1H, d, J = 8.4 Hz), 7.16 (1H, d, J = 7.8 Hz), 7.21 (1H, s), 7.27 (1H, m), 7.46 (1H, s). | ESI-MS m/z: 416 [M + H]+ |
| 7 (isomer B) | | 1H-NMR (CDCl$_3$) δ: 1.95 (1H, m), 2.33 (1H, m), 2.75-2.83 (2H, m), 2.90 (1H, m), 3.06 (1H, m), 3.20 (1H, m), 4.00 (1H, m), 4.19 (1H, m), 4.25-4.30 (2H, m), 4.63 (1H, m), 6.56 (1H, t, J = 56.7 Hz), 6.93 (1H, d, J = 8.4 Hz), 7.16 (1H, d, J = 7.8 Hz), 7.21 (1H, s), 7.27 (1H, m), 7.46 (1H, s). | ESI-MS m/z: 416 [M + H]+ |

TABLE 2

| Example | Structural formula | NMR | MS |
|---|---|---|---|
| 8 | | 1H-NMR (CDCl$_3$) δ: 1.98 (m, 1H), 2.36 (1H, m), 2.74-2.91 (3H, m), 3.04-3.17 (2H, m), 4.00 (1H, t, J = 11.5 Hz), 4.11-4.20 (2H, m), 4.28 (1H, dd, J = 4.2, 12.4 Hz), 4.68 (1H, m), 6.80 (1H, d, J = 8.0 Hz), 6.98 (1H, dd, J = 8.0, 1.2 Hz), 7.07 (1H, t, J = 8.0 Hz), 7.17 (1H, d, J = 7.9 Hz), 7.47 (1H, s). | ESI-MS m/z: 400 [M + H]+ |
| 9 (isomer A) | | 1H-NMR (CDCl$_3$) δ: 1.96 (1H, m), 2.36 (1H, m), 2.76-2.88 (3H, m), 3.05-3.14 (2H, m), 4.00 (1H, m), 4.10-4.20 12H, m), 4.28 (1H, m), 4.67 (1H, m), 6.85 (1H, dd, J = 8.2, 1.0 Hz), 7.01 (1H, t, J = 8.1 Hz), 7.16-7.18 (2H, m), 7.48 (1H, s). | ESI-MS m/z: 444, 446 [M + H]+ |

TABLE 2-continued

| Example | Structural formula | NMR | MS |
|---|---|---|---|
| 9 (isomer B) | (structure: 6-CF3-5,6,7,8-tetrahydroimidazo[1,2-a]pyridine-2-carboxamide linked to 8-bromo-chroman-3-yl) | 1H-NMR (CDCl3) δ: 1.95 (1H, m), 2.35 (1H, m), 2.77-2.68 (3H, m), 3.04-3.14 (2H, m), 4.00 (1H, m), 4.10-4.20 (2H, m), 4.28 (1H, m), 4.67 (1H, m), 6.85 (1H, dd, J = 8.2, 1.0 Hz), 7.01 (1H, t, J = 8.1 Hz), 7.16-7.19 (2H, m), 7.47 (1H, s). | ESI-MS m/z: 444, 446 [M + H]+ |
| 10 | (structure: 6-CF3-5,6,7,8-tetrahydroimidazo[1,2-a]pyridine-2-carboxamide linked to 8-cyclopropyl-chroman-3-yl) | 1H-NMR (CDCl3) δ: 0.60-0.64 (2H, m), 0.85-0.94 (2H, m), 1.70-1.79 (1H, m), 1.90-2.01 (1H, m), 2.32-2.41 (1H, m), 2.71-2.68 (2H, m), 2.95 (1H, dd, J = 17.0, 4.7 Hz), 3.02-3.12 (1H, m), 3.24 (1H, dd, J = 17.0, 6.1 Hz), 4.00 (1H, t, J = 10.8 Hz), 4.08-4.12 (1H, m), 4.20 (1H, dd, J = 10.6, 2.4 Hz), 4.28 (1H, dd, J = 12.6, 5.4 Hz), 4.67-4.70 (1H, m), 6.62 (1H, d, J = 7.5 Hz), 6.74 (1H, d, J = 8.0 Hz), 7.05 (1H, t, J = 7.8 Hz), 7.20-7.26 (1H, m), 7.47 (1H, s). | ESI-MS m/z: 406 [M + H]+ |
| 11 | (structure: 6-CF3-5,6,7,8-tetrahydroimidazo[1,2-a]pyridine-2-carboxamide linked to 6-ethyl-chroman-3-yl) | 1H-NMR (CDCl3) δ: 1.20 (3H, t, J = 7.6 Hz), 1.95 (1H, m), 2.34 (1H, m), 2.55 (2H, q, J = 7.6 Hz), 1.74-1.86 (3H, m), 3.06 (1H, m), 3.17 (1H, m), 3.99 (1H, m), 4.12 (1H, m), 4.19 (1H, m), 4.27 (1H, m), 4.61 (1H, m), 6.79 (1H, d, J = 8.3 Hz), 6.87 (1H, s), 6.95 (1H, dd, J = 8.3, 2.1 Hz), 7.20 (1H, d, J = 8.4 Hz), 7.45 (1H, s). | ESI-MS m/z: 394 [M + H]+ |
| 12 | (structure: 6-CF3-5,6,7,8-tetrahydroimidazo[1,2-a]pyridine-2-carboxamide linked to 6-bromo-chroman-3-yl) | 1H-NMR (CDCl3) δ: 1.95 (1H, m), 2.34 (1H, m), 2.75-2.89 (3H, m), 3.06 (1H, m), 3.15 (1H, m), 3.99 (1H, m), 4.13-4.22 (2H, m), 4.28 (1H, m), 4.60 (1H, m), 6.75 (1H, d, J = 8.6 Hz), 7.15-7.16 (2H, m), 7.21 (1H, dd, J = 8.6, 2.4 Hz), 7.46 (1H, s). | ESI-MS m/z: 444, 446 [M + H]+ |
| 13 | (structure: 6-CF3-5,6,7,8-tetrahydroimidazo[1,2-a]pyridine-2-carboxamide linked to 6-methoxy-chroman-3-yl) | 1H-NMR (CDCl3) δ: 1.94 (1H, m), 2.43 (1H, m), 2.74-2.87 (3H, m), 3.05 (1H, m), 3.17 (1H, m), 3.74 (3H, s), 3.99 (1H, m), 4.10-4.18 (2H, m), 4.27 (1H, m), 4.60 (1H, m), 6.58 (1H, d, J = 2.7 Hz), 6.70 (1H, dd, J = 8.9, 3.0 Hz), 6.80 (1H, d, J = 8.9 Hz), 7.22 (1H, d, J = 7.8 Hz), 7.45 (1H, s). | ESI-MS m/z: 396 [M + H]+ |
| 14 | (structure: 6-CF3-3-iodo-5,6,7,8-tetrahydroimidazo[1,2-a]pyridine-2-carboxamide linked to chroman-3-yl) | 1H-NMR (CDCl3) δ: 1.92 (1H, m), 2.35 (1H, m), 2.72-2.90 (3H, m), 3.08 (1H, m), 3.19 (1H, dd, J = 16.8, 5.4 Hz), 3.74 (1H, m), 4.14-4.24 (3H, m), 4.61 (1H, m), 6.86-6.91 (2H, m), 7.06 (1H, d, J = 7.4 Hz), 7.13 (1H, m), 7.31 (1H, d, J = 7.8 Hz). | ESI-MS m/z: 492 [M + H]+ |

TABLE 2-continued

| Example | Structural formula | NMR | MS |
|---|---|---|---|
| 15 | | 1H-NMR (CDCl₃) δ: 1.96 (1H, m), 2.33 (1H, m), 2.72 (1H, m), 2.80-2.90 (2H, m), 3.10-3.20 (2H, m), 3.89 (3H, d, J = 1.0 Hz), 4.09-4.23 (3H, m), 4.48 (1H, m), 4.55 (1H, m), 6.75 (1H, m), 6.86-6.91 (2H, m), 7.05 (1H, m), 7.12 (1H, m), 7.48 (1H, d, J = 8.2 Hz), 7.64-7.71 (2H, m). | ESI-MS m/z: 473 [M + H]+ |

TABLE 3

| Example | Structural formula | NMR | MS |
|---|---|---|---|
| 16 | | 1H-NMR (CDCl₃) δ: 1.92-1.93 (4H, m), 2.81-2.90 (3H, m), 3.12 (1H, dd, J = 16.6, 5.6 Hz), 3.68-3.70 (2H, m), 4.07-4.21 (2H, m), 4.54 (1H, m), 6.84-6.89 (2H, m), 7.03 (1H, d, J = 7.4 Hz), 7.11 (1H, m), 7.30 (1H, m), 7.39-7.44 (5H, m). | ESI-MS m/z: 374 [M + H]+ |
| 17 | | 1H-NMR (CDCl₃) δ: 1.93-1.95 (4H, m), 2.81-2.92 (3H, m), 3.10 (1H, dd, J = 16.7, 5.6 Hz), 3.91 (3H, s), 4.05 (2H, s), 4.11 (1H, m), 4.19 (1H, dd, J = 10.8, 2.0 Hz), 4.53 (1H, m), 6.72 (1H, d, J = 8.2 Hz), 6.79 (1H, d, J = 8.7 Hz), 7.01 (1H, d, J = 2.3 Hz), 7.06 (1H, dd, J = 8.7, 2.4 Hz), 7.42 (1H, d, J = 8.0 Hz), 7.54 (1H, d, J = 7.3 Hz), 7.66 (1H, t, J = 7.8 Hz), | ESI-MS m/z: 439 [M + H]+ |
| 18 | | 1H-NMR (CDCl₃) δ: 1.94 (4H, s), 2.81-2.88 (3H, m), 3.11 (1H, dd, J = 16.7, 5.8 Hz), 4.01 (2H, m), 4.09-4.20 (2H, m), 4.53 (1H, m), 6.79 (1H, d, J = 8.7 Hz), 7.02 (1H, s), 7.07 (1H, d, J = 7.4 Hz), 7.47 (1H, d, J = 8.5 Hz), 7.78 (1H, t, J = 7.7 Hz), 7.91 (1H, d, J = 8.0 Hz), 8.63 (1H, d, J = 4.0 Hz). | ESI-MS m/z: 409 [M + H]+ |

TABLE 3-continued

| Example | Structural formula | NMR | MS |
|---|---|---|---|
| 19 | | 1H-NMR (CDCl₃) δ: 1.94 (2H, m), 2.05 (2H, m), 2.87 (2H, q, J = 6.1 Hz), 2.97 (1H, dt, J = 16.7, 4.9 Hz), 3.23 (1H, dt, J = 16.7, 4.9 Hz), 4.15 (2H, q, J = 5.8 Hz), 4.28 (2H, m), 4.64 (1H, m), 6.52 (1H, d, J = 4.3 Hz), 6.95 (1H, m), 7.33 (1H, d, J = 2.9 Hz), 7.38 (1H, m), 7.66 (1H, d, J = 4.4 Hz), 7.70 (1H, m), 14.4 (1H, brs). | ESI-MS m/z: 432 [M + H]+ |
| 20 | | 1H-NMR (CDCl₃) δ: 1.94 (2H, m), 2.06 (2H, m), 2.87 (2H, t, J = 6.4 Hz), 2.93 (1H, dd, J = 16.8, 4.5 Hz), 3.21 (1H, dt, J = 16.5, 5.3 Hz), 3.82 (2H, q, J = 8.7 Hz), 4.15 (2H, d, J = 6.0 Hz), 4.20-4.27 (2H, m), 4.57 (2H, s), 4.64 (1H, m), 6.52 (1H, s), 6.89 (1H, d, J = 8.3 Hz), 7.06 (1H, s), 7.12 (1H, d, J = 8.4 Hz), 7.67 (1H, s), 7.74 (1H, d, J = 7.8 Hz), 14.5 (1H, brs). | ESI-MS m/z: 476 [M + H]+ |
| 21 | | 1H-NMR (CDCl₃) δ: 1.91-1.97 (2H, m), 2.04-2.10 (2H, m), 2.86-2.93 (3H, m), 3.18 (1H, dd, J = 16.9, 5.3 Hz), 4.16 (2H, t, J = 6.1 Hz), 4.21-4.23 (2H, m), 4.62 (1H, m), 6.53 (1H, d, J = 1.9 Hz), 6.82 (1H, d, J = 8.7 Hz), 7.05 (1H, d, J = 2.4 Hz), 7.09 (1H, dd, J = 8.7, 2.6 Hz), 7.67 (1H, d, J = 1.9 Hz), 7.72 (1H, d, J = 7.9 Hz). | ESI-MS m/z: 397 [M + H]+ |
| 22 | | 1H-NMR (CDCl₃) δ: 1.94-1.95 (4H, m), 2.56-2.94 (4H, m), 3.58 (2H, q, J = 7.1 Hz), 3.71 (2H, t, J = 5.4 Hz, 7.38-7.46 (9H, m).. | ESI-MS m/z: 414 [M + H]+ |
| 23 | | 1H-NMR (CDCl₃) δ: 2.05-2.15 (8H, m), 2.28 (1H, m), 2.93 (1H, m), 3.10 (1H, m), 3.23 (1H, m), 3.80 (1H, t, J = 11.7 Hz), 3.92 (1H, t, J = 12.7 Hz), 4.11 (1H, m), 4.24 (1H, dd, J = 12.6, 4.4 Hz), 4.57 (1H, m), 6.98-7.20 (4H, s), 7.33 (1H, m), 7.48 (1H, s). | ESI-MS m/z: 326 [M + H]+ |

TABLE 3-continued

| Example | Structural formula | NMR | MS |
|---|---|---|---|
| 24 | | 1H-NMR (CDCl₃) δ: 1.15-1.88 (12H, m), 2.11 (1H, m), 2.72 (1H, m), 2.85-2.96 (2H, m), 3.17 (1H, m), 3.61 (1H, m), 4.06-4.13 (2H, m), 4.25 (1H, m), 4.62 (1H, m), 6.85-6.89 (2H, m), 7.05 (1H, d, J = 6.6 Hz), 7.12 (1H, t, J = 7.7 Hz), 7.41 (1H, s). | ESI-MS m/z: 366 [M + H]+ |

TABLE 4

| Example | Structural formula | NMR | MS |
|---|---|---|---|
| 25 | | 1H-NMR (CDCl₃) δ: 2.08-2.14 (1H, m), 2.24-2.28 (1H, m), 2.81-2.91 (2H, m), 2.97-3.02 (1H, m), 3.17-3.22 (2H, m), 3.75 (1H, t, J = 8.0 Hz), 4.11-4.25 (3H, m), 4.56-4.66 (1H, m), 6.80-6.91 (2H, m), 7.03-7.40 (8H, m). | ESI-MS m/z: 408 [M + H]+ |
| 26 | | 1H-NMR (CDCl₃) δ: 2.05 (2H, m), 2.20 (2H, m), 2.34 (1H, m), 2.85-3.11 (3H, m), 3.41 (1H, m), 3.52 (1H, m), 3.69 (1H, m), 3.89 (2H, m), 3.98 (3H, s), 4.33 (1H, m), 6.89 (1H, m), 7.23-7.35 (5H, m), 7.41 (1H, m), 7.48 (1H, d, J = 11.8 Hz), 8.10 (1H, s). | ESI-MS m/z: 403 [M + H]+ |
| 27 | | 1H-NMR (CDCl₃) δ: 2.25 (2H, m), 2.81-3.01 (3H, m), 3.16 (1H, dd, J = 16.4, 5.4 Hz), 3.29 (1H, m), 3.86 (3H, s), 4.14 (1H, m), 4.24-4.33 (3H, m), 4.63 (1H, m), 6.63 (1H, d, J = 8.3 Hz), 6.79 (1H, d, J = 7.2 Hz), 6.85-6.90 (2H, m), 7.05 (1H, d, J = 7.4 Hz), 7.12 (1H, t, J = 7.7 Hz), 7.21 (1H, d, J = 8.1 Hz), 7.48 (1H, s), 7.54 (1H, t, J = 7.8 Hz). | ESI-MS m/z: 405 [M + H]+ |
| 28 | | 1H-NMR (CDCl₃) δ: 1.16-1.28 (2H, m), 1.56-1.91 (9H, m), 2.12-2.31 (3H, m), 2.69-2.81 (1H, m), 2.93-3.02 (1H, m), 3.56-3.64 (1H, m), 3.77-3.85 (1H, m), 3.90-3.99 (4H, m), 4.07-4.25 (2H, m), 4.33-4.39 (1H, m), 5.56-5.58 (1H, m), 6.24-6.30 (2H, m), 7.41-7.48 (2H, m). | ESI-MS m/z: 411 [M + H]+ |

TABLE 4-continued

| Example | Structural formula | NMR | MS |
|---|---|---|---|
| 29 | 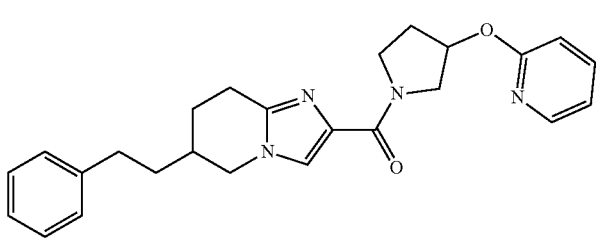 [SMILES: O=C(c1cn2c(n1)CCC(CCc1ccccc1)C2)N1CCC(Oc2ccccn2)C1] | 1H-NMR (CDCl₃) δ: 1.55-1.76 (4H, m), 2.01 (1H, m), 2.14-2.28 (3H, m), 2.66-2.83 (3H, m), 2.93-3.03 (1H, m), 3.54-3.62 (1H, m), 3.77-3.97 (2H, m), 4.05-4.38 (3H, m), 5.64 (1H, m), 6.68 (1H, dd, J = 8.3, 2.4 Hz), 6.85 (1H, t, J = 5.8 Hz), 7.18-7.32 (4H, m), 7.42 (1H, d, J = 10.2 Hz), 7.55 (1H, t, J = 7.7 Hz), 8.14 (1H, m). | ESI-MS m/z: 417 [M + H]+ |
| 30 | 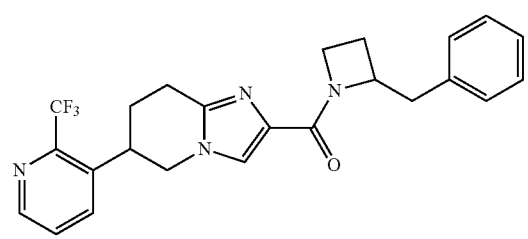 [SMILES: O=C(c1cn2c(n1)CCC(c1cccnc1C(F)(F)F)C2)N1CCC1Cc1ccccc1] | 1H-NMR (CDCl₃) δ: 2.01 (1H, m), 2.20-2.43 (3H, m), 2.88-3.17 (3H, m), 3.48-3.50 (2H, m), 3.98 (1H, m), 4.30-4.39 (3H, m), 4.79 (0.6H, m), 5.23 (0.4H, m), 7.20-7.32 (5H, m), 7.43-7.52 (2H, m), 7.61 (1H, d, J = 7.3 Hz), 7.88 (1H, t, J = 7.8 Hz). | ESI-MS m/z: 441 [M + H]+ |
| 31 | 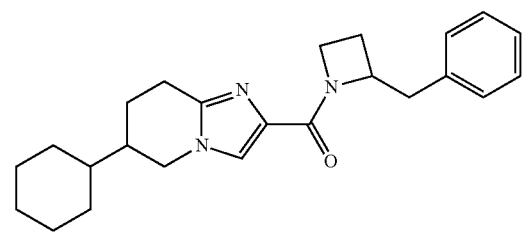 [SMILES: O=C(c1cn2c(n1)CCC(C1CCCCC1)C2)N1CCC1Cc1ccccc1] | 1H-NMR (CDCl₃) δ: 1.01-1.31 (6H, m), 1.68-1.84 (6H, m), 1.94-2.11 (2H, m), 2.26-2.35 (1H, m), 2.63-2.74 (1H, m), 2.93-3.07 (2H, m), 3.45-3.69 (1H, m), 3.64-3.69 (1H, m), 3.94-4.09 (2H, m), 4.31-4.41 (1H, m), 4.71-4.82 (1H, m), 5.20-5.23 (1H, m), 7.20-7.31 (5H, m), 7.39-7.45 (1H, m). | ESI-MS m/z: 378 [M + H]+ |
| 32 | 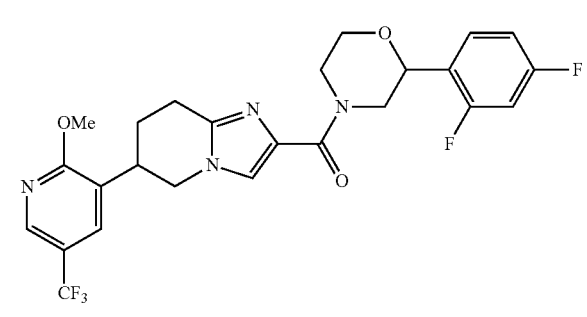 [SMILES: COc1ncc(C(F)(F)F)cc1C1CCc2nc(C(=O)N3CCOC(c4ccc(F)cc4F)C3)cn2C1] | 1H-NMR (CDCl₃) δ: 1.83 (2H, m), 2.23 (3H, m), 3.11 (1H, m), 3.38 (1H, m), 3.54 (1H, m), 3.76-3.89 (2H, m), 4.05 (3H, s), 4.35 (1H, dd, J = 12.1, 5.0 Hz), 4.63 (1H, m), 4.93 (1H, d, J = 11.0 Hz), 5.35 (1H, m), 6.83-6.95 (2H, m), 7.47 (1H, s), 7.49-7.53 (1H, s), 7.63 (1H, s), 8.40 (1H, s). | ESI-MS m/z: 523 [M + H]+ |
| 33 | 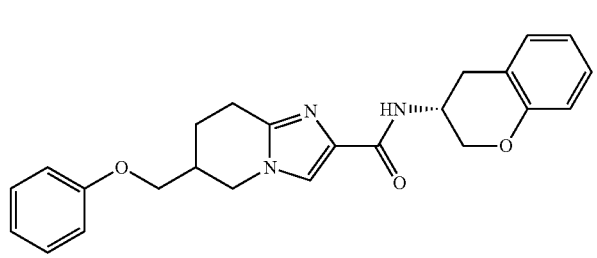 [SMILES: O=C(N[C@H]1COc2ccccc2C1)c1cn2c(n1)CCC(COc1ccccc1)C2] | 1H-NMR (CDCl₃) δ: 1.76-1.87 (1H, m), 2.12-2.17 (1H, m), 2.49-2.58 (1H, m), 2.76-2.90 (2H, m), 2.95-3.02 (1H, m), 3.15-3.20 (1H, m), 3.81-3.87 (1H, m), 3.90-3.95 (1H, m), 4.03-4.07 (1H, m), 4.11-4.15 (1H, m), 4.22-4.29 (2H, m), 4.58-4.64 (1H, m), 6.85-6.90 (4H, m), 6.96-7.00 (1H, m), 7.05 (1H, d, J = 6.6 Hz), 7.10-7.14 (1H, m), 7.19 (1H, d, J = 8.0 Hz), 7.28-7.32 (2H, m), 7.45 (1H, s) | ESI-MS m/z: 404 [M + H]+ |

TABLE 5

| Example | Structural formula | NMR | MS |
|---|---|---|---|
| 34 | | 1H-NMR (CDCl₃) δ: 1.18 (9H, m), 1.65 (1H, m), 2.02 (1H, m), 2.20 (1H, m), 2.75 (1H, m), 2.84-2.94 (2H, m), 3.18 (1H, m), 3.29 (1H, m), 3.43 (1H, m), 3.68 (1H, m), 4.10-4.16 (2H, m), 4.24 (1H, m), 4.62 (1H, m), 6.85-6.90 (2H, m), 7.05 (1H, d, J = 7.4 Hz), 7.12 (1H, t, J = 7.7 Hz), 7.18 (1H, d, J = 7.9 Hz), 7.42 (1H, s). | ESI-MS m/z: 384 [M + H]+ |
| 35 | | 1H-NMR (CDCl₃) δ: 0.94 (1H, m), 1.60-1.78 (3H, m), 2.02 (1H, m), 2.13 (1H, m), 2.24-2.45 (3H, m), 2.67-2.90 (3H, m), 3.18 (1H, m), 3.81 (1H, m), 4.09-4.16 (2H, m), 4.24 (1H, m), 4.61 (1H, m), 6.85-6.90 (2H, m), 7.05 (1H, d, J = 7.2 Hz), 7.12 (1H, t, J = 7.7 Hz), 7.19 (1H, d, J = 8.1 Hz), 7.44 (1H, s). | ESI-MS m/z: 370 [M + H]+ |
| 36 | | 1H-NMR (CDCl₃) δ: 0.98 (9H, s), 1.47-1.56 (1H, m), 1.57-1.76 (1H, m), 2.09-2.15 (1H, m), 2.61-2.70 (1H, m), 2.86 (1H, dd, J = 16.6, 5.4 Hz), 2.93-3.00 (1H, m), 3.17 (1H, dd, J = 16.6, 5.5 Hz), 3.66 (1H, dt, J = 12.0, 1.5 Hz), 4.05-4.14 (2H, m), 4.23-4.26 (1H, m), 4.62 (1H, m), 6.85-6.90 (2H, m), 7.04-7.06 (1H, m), 7.09-7.17 (2H, m), 7.41 (1H, s). | ESI-MS m/z: 354 [M + H]+ |
| 37 | | 1H-NMR (CDCl₃) δ: 1.99-2.06 (1H, m), 2.20-2.28 (1H, m), 2.78-3.01 (3H, m), 3.15-3.21 (1H, m), 3.84-3.98 (2H, m), 4.06-4.16 (4H, m), 4.22-4.25 (1H, m), 4.58-4.65 (1H, m), 6.85-6.90 (2H, m), 7.05 (1H, d, J = 7.3 Hz), 7.10-7.14 (1H, m), 7.19 (1H, d, J = 7.9 Hz), 7.42 (1H, s). | ESI-MS m/z: 396 [M + H]+ |
| 38 | | 1H-NMR (CDCl₃) δ: 2.03 (1H, m), 2.24 (1H, m), 2.80-2.87 (2H, m), 2.91-3.01 (1H, m), 3.14 (1H, m), 3.85-3.96 (2H, m), 4.10-4.23 (5H, m), 4.60 (1H, m), 6.80 (1H, d, J = 8.6 Hz), 7.03 (1H, d, J = 2.4 Hz), 7.07 (1H, dd, J = 8.9, 2.6 Hz), 7.17 (1H, d, J = 8.0 Hz), 7.42 (1H, s). | ESI-MS m/z: 430 [M + H]+ |
| 39 (isomer A) | | 1H-NMR (CDCl₃) δ: 2.03 (1H, m), 2.24 (1H, m), 2.80-2.87 (2H, m), 2.95 (1H, m), 3.14 (1H, m), 3.86-3.96 (2H, m), 4.11-4.23 (5H, m), 4.60 (1H, m), 6.79 (1H, d, J = 8.6 Hz), 7.03 (1H, d, J = 2.4 Hz), 7.07 (1H, dd, J = 8.7, 2.6 Hz), 7.17 (1H, d, J = 8.1 Hz), 7.42 (1H, s). | ESI-MS m/z: 430 [M + H]+ |
| 39 (isomer B) | | 1H-NMR (CDCl₃) δ: 2.03 (1H, m), 2.24 (1H, m), 2.79-2.87 (2H, m), 2.92-3.01 (1H, m), 3.14 (1H, m), 3.86-3.96 (2H, m), 4.10-4.23 (5H, m), 4.60 (1H, m), 6.80 (1H, d, J = 8.7 Hz), 7.02 (1H, d, J = 2.5 Hz), 7.07 (1H, dd, J = 8.7, 2.6 Hz), 7.17 (1H, d, J = 7.7 Hz), 7.42 (1H, s). | ESI-MS m/z: 430 [M + H]+ |

TABLE 5-continued

| Example | Structural formula | NMR | MS |
|---|---|---|---|
| 40 | 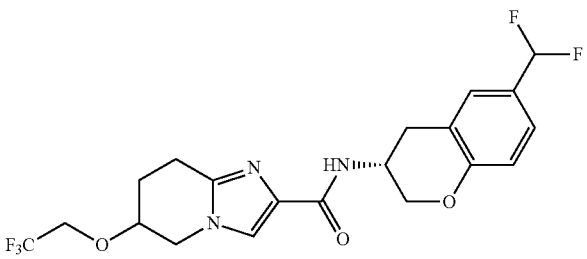 [SMILES: O=C(N[C@H]1COc2ccc(C(F)F)cc2C1)c1cn2c(n1)CCC(OCC(F)(F)F)C2] | 1H-NMR (CDCl₃) δ: 2.03 (1H, m), 2.24 (1H, m), 2.79-3.00 (3H, m), 3.19 (1H, m), 3.86-3.96 (2H, m), 4.11-4.20 (4H, m), 4.27 (1H, m), 4.63 (1H, m), 6.56 (1H, t, J = 56.8 Hz), 6.92 (1H, d, J = 8.4 Hz), 7.17 (1H, d, J = 8.0 Hz), 7.21 (1H, s), 7.26 (1H, m), 7.43 (1H, s). | ESI-MS m/z: 446 [M + H]+ |
| 41 | 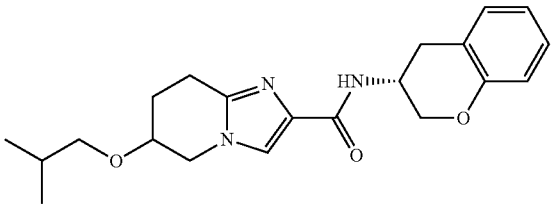 [SMILES: CC(C)COC1CCc2nc(C(=O)N[C@H]3COc4ccccc4C3)cn2C1] | 1H-NMR (CDCl₃) δ: 0.85-0.89 (6H, m), 1.81 (1H, m), 1.95 (1H, m), 2.17 (1H, m), 2.73-2.99 (3H, m), 3.15-3.31 (3H, m), 3.88 (1H, m), 4.03 (2H, d, J = 4.0 Hz), 4.13 (1H, m), 4.24 (1H, m), 4.62 (1H, m), 6.85-6.90 (2H, m), 7.05 (1H, d, J = 6.4 Hz), 7.12 (1H, m), 7.18 (1H, d, J = 7.8 Hz), 7.41 (1H, s). | ESI-MS m/z: 370 [M + H]+ |

TABLE 6

| Example | Structural formula | NMR | MS |
|---|---|---|---|
| 42 | 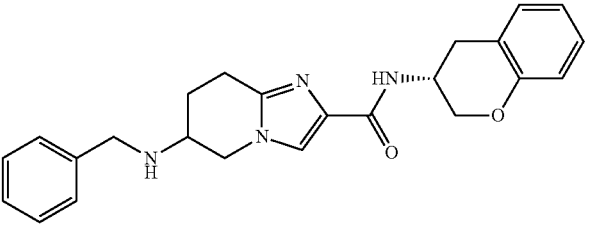 [SMILES: O=C(N[C@H]1COc2ccccc2C1)c1cn2c(n1)CCC(NCc1ccccc1)C2] | 1H-NMR (CDCl₃) δ: 1.85-1.94 (1H, m), 2.09-2.16 (1H, m), 2.73-3.01 (3H, m), 3.15-3.25 (2H, m), 3.73-3.78 (1H, m), 3.83-3.91 (2H, m), 4.09-4.15 (2H, m), 4.22-4.25 (1H, m), 4.58-4.65 (1H, m), 6.85-6.90 (2H, m), 7.05 (1H, d, J = 7.3 Hz), 7.10-7.14 (1H, m), 7.17 (1H, d, J = 8.0 Hz, 7.25-7.36 (5H, m), 7.38 (1H, s). | ESI-MS m/z: 403 [M + H]+ |
| 43 | 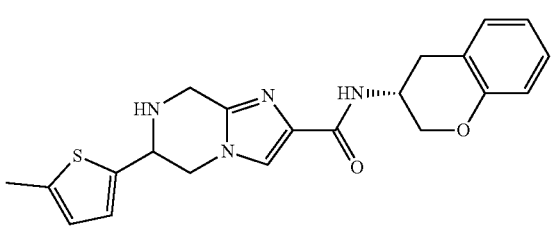 [SMILES: Cc1ccc(C2Cn3cc(C(=O)N[C@H]4COc5ccccc5C4)nc3CN2)s1] | 1H-NMR (CDCl₃) δ: 2.47 (3H, m), 2.86-2.90 (1H, m), 3.17-3.22 (1H, m), 3.99-4.06 (1H, m), 4.11-4.17 (3H, m), 4.19-4.25 (3H, m), 4.41-4.45 (1H, m), 4.58-4.65 (1H, m), 6.64 (1H, m), 6.81 (1H, d, J = 3.6 Hz), 6.86-6.91 (2H, m), 7.05-7.06 (1H, m), 7.12 (1H, t, J = 7.6 Hz), 7.17-7.21 (1H, m), 7.47 (1H, s). | |
| 44 | 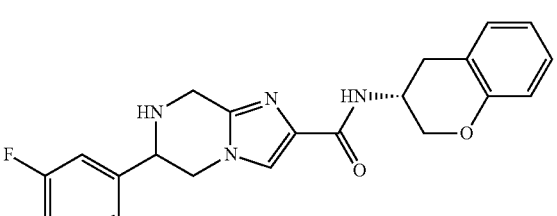 | 1H-NMR (CDCl₃) δ: 2.88 (1H, dd, J = 16.3, 5.0 Hz), 3.20 (1H, dd, J = 16.3, 5.0 Hz), 3.91 (1H, t, J = 12.2 Hz), 4.05-4.19 (4H, m), 4.23-4.28 (2H, m), 4.61-4.65 (1H, m), 6.86-6.91 (2H, m), 7.05 (1H, d, J = 7.6 Hz), 7.11-7.23 (4H, m), 7.31 (1H, ddd, J = 10.7, 7.6, 2.2 Hz), 7.46 (1H, s). | ESI-MS m/z: 411 [M + H]+ |

TABLE 6-continued

| Example | Structural formula | NMR | MS |
| --- | --- | --- | --- |
| 45 | | 1H-NMR (CDCl₃) δ: 2.17 (3H, s), 2.88 (1H, dd, J = 16.3, 5.0 Hz), 3.20 (1H, dd, J = 16.3, 5.0 Hz), 3.49 (1H, t, J = 12.2 Hz), 4.05-4.18 (4H, m), 4.21-4.26 (2H, m), 4.61-4.64 (1H, m), 6.86-6.91 (2H, m), 7.05-7.22 (6H, m), 7.44 (1H, s) | ESI-MS m/z: 425 [M + H]+ |
| 46 | | 1H-NMR (CDCl₃) δ: 2.27 (1H, brs), 2.55-2.91 (1H, m), 3.17-3.22 (1H, m), 4.11-4.29 (5H, m), 4.41-4.46 (2H, m), 4.60-4.65 (1H, m), 6.86-6.91 (2H, m), 7.06 (1H, d, J = 7.2 Hz), 7.13 (1H, t, J = 7.8 Hz), 7.20-7.23 (1H, m), 7.52 (1H, s), 7.66-7.72 (2H, m), 7.94 (1H, t, J = 7.8 Hz). | ESI-MS m/z: 444 [M + H]+ |
| 47 | | 1H-NMR (CDCl₃) δ: 2.26 (3H, s), 2.87 (1H, dd, J = 17.5, 5.7 Hz), 3.08-3.14 (1H, m), 3.84 (1H, dd, J = 16.4, 3.7 Hz), 4.02 (1H, dd, J = 16.1, 2.6 Hz), 4.11-4.24 (3H, m), 4.31-4.36 (1H, m), 4.38-4.45 (1H, m), 4.63-4.67 (1H, m), 6.62-6.70 (2H, m), 7.05-7.09 (1H, m), 7.17-7.20 (1H, m), 7.52 (1H, d, J = 2.9 Hz), 7.66-7.71 (2H, m), 7.94 (1H, t, J = 7.8 Hz). | ESI-MS m/z: 476 [M + H]+ |
| 48 | | 1H-NMR (CDCl₃) δ: 2.97 (2H, t, J = 7.3 Hz), 3.67 (2H, q, J = 7.0 Hz), 3.98 (1H, m), 4.13-4.30 (4H, m), 7.11 (1H, m), 7.34-7.49 (10H, m). | ESI-MS m/z: 415 [M + H]+ |
| 49 | | 1H-NMR (CDCl₃) δ: 0.92 (6H, d, J = 7.3 Hz), 1.22-1.41 (3H, m), 1.51-1.56 (2H, m), 2.87 (1H, dd, J = 16.3, 5.5 Hz), 3.00-3.04 (1H, m), 3.18 (1H, dd, J = 16.3, 5.5 Hz), 3.60 (1H, t, J = 12.4 Hz), 3.95-4.03 (2H, m), 4.11-4.16 (2H, m), 4.24 (1H, d, J = 10.7 Hz), 4.60-4.64 (1H, m), 6.85-6.90 (2H, m), 7.05 (1H, d, J = 7.3 Hz), 7.12 (1H, t, J = 7.3 Hz), 7.17 (1H, d, J = 7.3 Hz), 7.43 (1H, s) | ESI-MS m/z: 369 [M + H]+ |
| 50 | | 1H-NMR (CDCl₃) δ: 0.90 (3H, d, J = 6.6 Hz), 0.91 (3H, d, J = 7.3 Hz), 1.20-1.32 (2H, m), 1.35-1.44 (1H, m), 1.50-1.57 (1H, m), 1.62-1.71 (1H, m), 2.39 (3H, s), 2.84-2.90 (2H, m), 3.18 (1H, dd, J = 16.3, 5.5 Hz), 3.70 (1H, dd, J = 12.4, 4.2 Hz), 3.79 (1H, ddd, J = 12.4, 8.2, 1.5 Hz), 3.85 (1H, dd, J = 16.2, 3.8 Hz), 3.98 (1H, dd, J = 12.4, 4.2 Hz), 4.14 (1H, ddd, J = 10.7, 5.4, 1.5 Hz), 4.24 (1H, d, J = 10.7 Hz), 4.59-4.65 (1H, m), 6.85-6.90 (2H, m), 7.05 (1H, d, J = 7.3 Hz), 7.12 (1H, t, J = 7.3 Hz), 7.17 (1H, d, J = 8.5 Hz), 7.43 (1H, s) | ESI-MS m/z: 383 [M + H]+ |

TABLE 7

| Example | Structural formula | NMR | MS |
|---|---|---|---|
| 51 | | 1H-NMR (CDCl₃) δ: 1.08-1.13 (3H, m), 1.39-1.44 (2H, m), 1.46-1.57 (5H, m), 1.72-1.77 (3H, m), 2.86 (1H, dd, J = 16.3, 5.5 Hz), 3.00-3.05 (1H, m), 3.18 (1H, dd, J = 16.3, 5.5 Hz), 3.59 (1H, t, J = 12.4 Hz), 3.95-4.03 (2H, m), 4.10-4.15 (2H, m), 4.24 (1H, d, J = 10.7 Hz), 4.59-4.64 (1H, m), 6.85-6.90 (2H, m), 7.05 (1H, d, J = 7.3 Hz), 7.12 (1H, t, J = 7.3 Hz), 7.17 (1H, d, J = 7.3 Hz), 7.43 (1H, s). | ESI-MS m/z: 395 [M + H]+ |
| 52 | | 1H-NMR (CDCl₃) δ: 1.06-1.11 (3H, m), 1.35-1.42 (3H, m), 1.52-1.56 (4H, m), 1.72-1.76 (3H, m), 2.38 (3H, s), 2.84-2.90 (2H, m), 3.18 (1H, dd, J = 16.3, 5.5 Hz), 3.69 (1H, dd, J = 12.4, 4.2 Hz), 3.79 (1H, ddd, J = 12.4, 8.2, 1.5 Hz), 3.85 (1H, dd, J = 16.2, 3.8 Hz), 3.98 (1H, dd, J = 12.4, 4.2 Hz), 4.14 (1H, ddd, J = 10.7, 5.4, 1.5 Hz), 4.24 (1H, d, J = 10.7 Hz), 4.60-4.64 (1H, m), 6.85-6.90 (2H, m), 7.05 (1H, d, J = 7.3 Hz), 7.12 (1H, t, J = 7.3 Hz), 7.18 (1H, d, J = 7.3 Hz), 7.43 (1H, s). | ESI-MS m/z: 409 [M + H]+ |
| 53 | | 1H-NMR (CDCl₃) δ: 1.80-1.85 (2H, m), 2.70-2.81 (2H, m), 2.86 (1H, dd, J = 16.3, 5.0 Hz), 3.01-3.09 (1H, m), 3.18 (1H, dd, J = 16.3, 5.0 Hz), 3.63 (1H, t, J = 10.2 Hz), 3.95 (1H, dd, J = 16.3, 5.0 Hz), 4.00 (1H, dd, J = 12.4, 3.1 Hz), 4.11-4.16 (2H, m), 4.23 (1H, d, J = 10.7 Hz), 4.58-4.65 (1H, m), 6.85-6.90 (2H, m), 6.99 (2H, t, J = 8.7 Hz), 7.05 (1H, d, J = 7.3 Hz), 7.10-7.18 (4H, m), 7.42 (1H, s). | ESI-MS m/z: 421 [M + H]+ |
| 54 | | 1H-NMR (CDCl₃) δ: 1.63-1.72 (1H, m), 1.92-1.97 (1H, m), 2.39 (3H, s), 2.66-2.74 (2H, m), 2.87 (1H, dd, J = 16.3, 5.0 Hz), 2.95-2.97 (1H, m), 3.18 (1H, dd, J = 16.3, 5.0 Hz), 3.74-3.88 (3H, m), 3.98 (1H, dd, J = 12.4, 3.1 Hz), 4.14 (1H, ddd, J = 10.7, 5.4, 1.5 Hz), 4.23 (1H, d, J = 10.7 Hz), 4.59-4.65 (1H, m), 6.86-6.90 (2H, m), 6.98 (2H, t, J = 8.7 Hz), 7.05 (1H, d, J = 7.3 Hz), 7.11-7.19 (4H, m), 7.43 (1H, s). | ESI-MS m/z: 435 [M + H]+ |
| 55 | | 1H-NMR (CDCl₃) δ: 1.56 (1H, q, J = 7.6 Hz), 1.69-1.85 (2H, m), 2.05 (2H, s), 2.67 (2H, t, J = 7.5 Hz), 2.87 (1H, dd, J = 16.6, 5.3 Hz), 3.02-3.09 (1H, m), 3.16 (1H, dd, J = 16.5, 5.4 Hz), 3.57 (1H, t, J = 11.3 Hz), 3.92-4.00 (2H, m), 4.09-4.15 (2H, m), 4.23 (1H, d, J = 10.7 Hz), 4.58-4.64 (1H, m), 6.84-6.89 (2H, m), 7.03-7.29 (8H, m), 7.43 (1H, s). | ESI-MS m/z: 417 [M + H]+ |
| 56 | | 1H-NMR (CDCl₃) δ: 2.00 (1H, brs), 2.88 (1H, dd, J = 16.7, 4.9 Hz), 3.71-3.22 (1H, m), 3.97 (1H, t, J = 11.3 Hz), 4.11-4.27 (6H, m), 4.63 (1H, s), 6.89 (2H, t, J = 9.4 Hz), 7.06 (1H, d, J = 7.4 Hz), 7.13 (1H, t, J = 7.6 Hz), 7.21 (1H, m), 7.36-7.46 (6H, m). | ESI-MS m/z: 375 [M + H]+ |

TABLE 7-continued

| Example | Structural formula | NMR | MS |
|---|---|---|---|
| 57 | | 1H-NMR (CDCl₃) δ: 2.16 (3H, s), 2.89 (1H, dd, J = 16.7, 5.1 Hz), 3.20 (1H, d, J = 16.3 Hz), 3.49 (1H, dd, J = 15.7, 4.9 Hz), 3.57 (1H, m), 4.07-4.10 (3H, m), 4.14-4.17 (1H, m), 4.25 (1H, d, J = 10.6 Hz), 4.63 (1H, m), 6.89 (2H, t, J = 9.0 Hz), 7.06 (1H, d, J = 7.1 Hz), 7.13 (1H, t, J = 7.5 Hz), 7.22 (1H, m), 7.32-7.39 (5H, m), 7.45 (1H, s). | ESI-MS m/z: 389 [M + H]+ |
| 58 | | 1H-NMR (CDCl₃) δ: 2.18 (3H, s), 2.91 (2H, t, J = 7.5 Hz), 3.52 (1H, d, J = 15.6 Hz), 3.59 (1H, t, J = 7.1 Hz), 3.68 (2H, q, J = 7.0 Hz), 4.07-4.13 (3H, m), 7.11 (1H, t, J = 7.8 Hz), 7.20-7.46 (11H, m). | ESI-MS m/z: 361 [M + H]+ |
| 59 | | 1H-NMR (CDCl₃) δ: 1.23-1.38 (2H, m), 1.60-1.70 (4H, m), 1.79-1.93 (3H, m), 2.17 (1H, s), 2.78-2.89 (2H, m), 3.15-3.21 (1H, m), 3.66 (1H, t, J = 11.0 Hz), 3.94-4.05 (2H, m), 4.12-4.17 (2H, m), 4.24 (1H, d, J = 10.7 Hz), 4.61 (1H, m), 6.85-6.90 (2H, m), 7.05 (1H, d, J = 7.5 Hz), 7.10-7.17 (2H, m), 7.43 (1H, s). | ESI-MS m/z: 367 [M + H]+ |

TABLE 8

| Example | Structural formula | NMR | MS |
|---|---|---|---|
| 60 | | 1H-NMR (CDCl₃) δ: 2.00-2.14 (2H, m), 2.33-2.41 (1H, m), 3.44-3.52 (1H, m), 3.64-3.77 (1H, m), 3.87-4.02 (2H, m), 4.13-4.41 (4H, m), 4.65 (1H, m), 7.36-7.54 (10H, m). | ESI-MS m/z: 441 [M + H]+ |
| 61 | | 1H-NMR (CDCl₃) δ: 2.07 (1H, brs), 2.79-3.50 (2H, m), 3.79-3.85 (1H, m), 3.99 (1H, t, J = 11.1 Hz), 4.14-4.35 (5H, m), 4.61-4.84 (2H, m), 5.39-5.57 (1H, m), 7.37-7.50 (7H, m), 7.56-7.62 (2H, m), 7.73 (1H, s). | ESI-MS m/z: 457 [M + H]+ |

TABLE 8-continued

| Example | Structural formula | NMR | MS |
|---|---|---|---|
| 62 | | 1H-NMR (CDCl₃) δ: 2.18 (3H, s), 2.87 (2H, t, J = 7.1 Hz), 3.15-3.17 (4H, m), 3.48-3.53 (1H, m), 3.57-3.68 (3H, m), 3.85-3.87 (4H, m), 4.08-4.12 (3H, m), 6.75-6.80 (3H, m), 7.17-7.24 (2H, m), 7.33-7.43 (6H, m). | ESI-MS m/z: 446 [M + H]+ |
| 63 | | 1H-NMR (CDCl₃) δ: 2.18 (3H, s), 3.51-3.61 (2H, m), 4.08 (2H, d, J = 6.7 Hz), 4.11-4.23 (2H, m), 4.58-4.60 (2H, m), 5.01-5.09 (1H, m), 5.47-5.53 (1H, m), 6.98 (1H, d, J = 8.4 Hz), 7.28-7.41 (6H, m), 7.46 (1H, s), 7.76 (1H, t, J = 7.5 Hz). | ESI-MS m/z: 458 [M + H]+ |
| 64 | | 1H-NMR (CDCl₃) δ: 2.84 (1H, dd, J = 16.6, 4.5 Hz), 3.14 (1H, dd, J = 16.6, 5.4 Hz), 3.80 (2H, t, J = 5.1 Hz), 3.99 (2H, t, J = 5.1 Hz), 4.09-4.20 (2H, m), 4.54 (1H, m), 4.83 (2H, s), 6.85-6.90 (2H, m), 7.04 (1H, d, J = 7.4 Hz), 7.12 (1H, m), 7.30 (1H, m), 7.40-7.45 (5H, m). | ESI-MS m/z: 376 [M + H]+ |
| 65 | | 1H-NMR (CDCl₃) δ: 2.85 (1H, dd, J = 17.0, 4.4 Hz), 3.12 (1H, dd, J = 16.6, 5.4 Hz), 3.91 (3H, s), 4.02 (2H, t, J = 5.0 Hz), 4.13-4.24 (4H, m), 4.54 (1H, m), 4.84 (2H, s), 6.74 (1H, d, J = 7.7 Hz), 6.80 (1H, d, J = 8.7 Hz), 7.03 (1H, s), 7.07 (1H, d, J = 8.8 Hz), 7.45 (1H, d, J = 7.6 Hz), 7.66-7.73 (2H, m). | ESI-MS m/z: 441 [M + H]+ |
| 66 | | 1H-NMR (CDCl₃) δ: 2.84 (1H, dd, J = 16.7, 4.8 Hz), 3.13 (1H, dd, J = 17.0, 5.4 Hz), 4.02 (2H, t, J = 4.8 Hz), 4.13-4.20 (4H, m), 4.54 (1H, m), 4.84 (2H, s), 6.81 (1H, d, J = 8.7 Hz), 7.03 (1H, s), 7.08 (1H, d, J = 8.9 Hz), 7.29 (1H, m), 7.51 (1H, d, J = 7.8 Hz), 7.80 (1H, t, J = 7.8 Hz), 8.07 (1H, d, J = 7.8 Hz), 8.63 (1H, d, J = 4.2 Hz). | ESI-MS m/z: 411 [M + H]+ |

TABLE 8-continued

| Example | Structural formula | NMR | MS |
|---|---|---|---|
| 67 | | 1H-NMR (CDCl₃) δ: 2.92 (1H, dd, J = 16.7, 4.9 Hz), 3.18 (1H, dd, J = 16.8, 5.3 Hz), 4.02 (2H, t, J = 5.0 Hz), 4.17-4.28 (4H, m), 4.58 (1H, m), 4.84 (2H, s), 6.94 (1H, d, J = 8.5 Hz), 7.28 (1H, m), 7.32 (1H, s), 7.38 (1H, d, J = 8.6 Hz), 7.50 (1H, d, J = 8.0 Hz), 7.80 (1H dt, J = 1.8, 7.8 Hz), 8.07 (1H, dt, J = 1.0, 8.0 Hz), 8.62 (1H, m). | ESI-MS m/z: 445 [M + H]+ |
| 68 | | 1H-NMR (CDCl₃) δ: 2.21-2.30 (2H, m), 2.37 (3H, s), 2.80-2.92 (2H, m), 3.12 (1H, dd, J = 16.6, 4.5 Hz), 3.20 (1H, dd, J = 16.6, 5.5 Hz), 3.32 (1H, m), 4.09-4.30 (4H, m), 4.65 (1H, m), 6.55 (1H, s), 6.87-6.92 (2H, m), 7.06-7.19 (7H, m). | ESI-MS m/z: 388 [M + H]+ |

TABLE 9

| Example | Structural formula | NMR | MS |
|---|---|---|---|
| 69 | | 1H-NMR (CDCl₃) δ: 1.82-1.88 (2H, m), 2.01-2.08 (2H, m), 2.86 (1H, dd, J = 16.6, 4.6 Hz), 2.98-3.01 (2H, m), 3.16 (1H, dd, J = 16.7, 5.5 Hz), 3.90 (3H, s), 4.12-4.19 (4H, m), 4.57-4.65 (1H, m), 6.60 (1H, dd, J = 8.2, 0.68 Hz), 6.83-6.90 (2H, m), 7.04 (1H, d, J = 7.5 Hz), 7.09-7.14 (1H, m), 7.21-7.29 (1H, m), 7.40 (1H, dd, J = 7.4, 0.70 Hz), 7.54-7.59 (1H, m). | ESI-MS m/z: 405 [M + H]+ |
| 70 | | 1H-NMR (CDCl₃) δ: 2.34-2.50 (2H, m), 2.92 (1H, m), 3.18 (1H, m), 4.14-4.32 (4H, m), 4.65 (1H, m), 5.56 (1H, m), 6.12 (1H, s), 6.93-6.95 (2H, m), 7.11 (1H, m), 7.21 (1H, t, J = 7.6 Hz), 7.34-7.49 (4H, m). | ESI-MS m/z: 419 [M + H]+ |

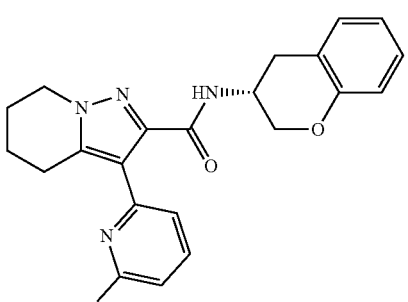
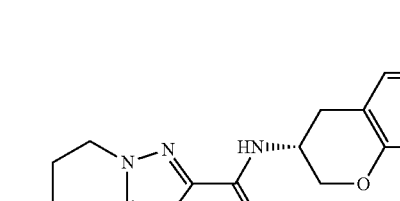

TABLE 9-continued

| Example | Structural formula | NMR | MS |
|---|---|---|---|
| 71 | (structure with 2-fluorophenyl, pyrazole fused ring, amide, bromo-chroman) | 1H-NMR (CDCl₃) δ: 2.39-2.48 (2H, m), 2.87 (1H, m), 3.16 (1H, m), 4.15-4.28 (4H, m), 4.63 (1H, m), 5.56 (1H, m), 6.11 (1H, s), 6.77 (1H, d, J = 8.7 Hz), 7.02 (1H, m), 7.10 (1H, m), 7.19-7.27 (3H, m), 7.36 (1H, m), 7.47 (1H, m). | ESI-MS m/z: 472, 474 [M + H]+ |
| 72 | (structure with 2-cyanophenyl, pyrazole fused ring, amide, cyano-chroman) | 1H-NMR (CDCl₃) δ: 2.32-2.43 (1H, m), 2.53-2.57 (1H, m), 2.93 (1H, dd, J = 17.1, 4.7 Hz), 3.19 (1H, dt, J = 16.6, 4.9 Hz), 4.21-4.35 (4H, m), 4.63-4.67 (1H, m), 5.59-5.62 (1H, m), 6.14 (1H, s), 6.90-6.98 (2H, m), 7.39-7.44 (2H, m), 7.49-7.55 (1H, m), 7.67-7.74 (3H, m). | ESI-MS m/z: 426 [M + H]+ |
| 73 | (structure with 2-methoxypyridin-4-yl, pyrazole fused ring, amide, cyano-chroman) | 1H-NMR (CDCl₃) δ: 2.30-2.49 (2H, m), 2.91 (1H, dd, J = 16.9, 4.8 Hz), 3.18 (1H, dd, J = 16.6, 5.2 Hz), 3.95 (3H, s), 4.09-4.32 (4H, m), 4.65 (1H, m), 5.24 (1H, d, J = 9.2 Hz), 6.13 (1H, s), 6.75 (1H, s), 6.86 (1H, d, J = 5.3 Hz), 6.93 (2H, d, J = 8.4 Hz), 7.37-7.43 (2H, m), 8.20 (1H, d, J = 5.3 Hz). | ESI-MS m/z: 432 [M + H]+ |
| 74 (isomer A) | (structure with 2-methoxypyridin-4-yl *, pyrazole fused ring, amide, cyano-chroman) | 1H-NMR (CDCl₃) δ: 2.36 (1H, m), 2.44 (1H, m), 2.91 (1H, dd, J = 16.7, 4.3 Hz), 3.18 (1H, dd, J = 16.8, 5.3 Hz), 3.95 (3H, s), 4.09-4.32 (4H, m), 4.64 (1H, m), 5.24 (1H, dd, J = 9.3, 2.5 Hz), 6.13 (1H, s), 6.75 (1H, s), 6.86 (1H, d, J = 4.4 Hz), 6.93 (2H, d, J = 8.4 Hz), 7.39 (1H, s), 7.41 (1H, dd, J = 16.8, 1.6 Hz), 8.19 (1H, d, J = 5.3 Hz). | ESI-MS m/z: 432 [M + H]+ |
| 74 (isomer B) | (structure with 2-methoxypyridin-4-yl *, pyrazole fused ring, amide, cyano-chroman) | 1H-NMR (CDCl₃) δ: 2.36 (1H, m), 2.44 (1H, m), 2.91 (1H, dd, J = 16.7, 4.3 Hz), 3.18 (1H, dd, J = 16.8, 5.3 Hz), 3.95 (3H, s), 4.11-4.30 (4H, m), 4.64 (1H, m), 5.24 (1H, dd, J = 9.3, 2.5 Hz), 6.13 (1H, s), 6.75 (1H, s), 6.86 (1H, d, J = 4.4 Hz), 6.93 (2H, d, J = 8.4 Hz), 7.39 (1H, s), 7.41 (1H, dd, J = 16.8, 1.6 Hz), 8.19 (1H, d, J = 5.3 Hz). | ESI-MS m/z: 432 [M + H]+ |

TABLE 9-continued

| Example | Structural formula | NMR | MS |
|---|---|---|---|
| 75 | (structure with 2-methoxypyridinyl, pyrazolo-oxazine, chromane-CN) | 1H-NMR (CDCl₃) δ: 2.24 (1H, m), 2.54 (1H, m), 2.92 (1H, dd, J = 16.9, 4.8 Hz), 3.18 (1H, dd, J = 16.6, 5.0 Hz), 3.99 (3H, s), 4.12 (1H, s), 4.18-4.32 (3H, m), 4.65 (1H, m), 5.47 (1H, d, J = 9.6 Hz), 6.11 (1H, s), 6.93-6.97 (3H, m), 7.39 (1H, s), 7.42 (1H, d, J = 8.5 Hz), 7.70 (1H, d, J = 7.4 Hz), 8.16 (1H, dd, J = 5.0, 1.4 Hz). | ESI-MS m/z: 432 [M + H]+ |
| 76 | (structure with 2-fluorophenyl, pyrazolo-oxazine, chromane-Et) | 1H-NMR (CDCl₃) δ: 1.20 (3H, t, J = 7.6 Hz), 2.3-2.49 (2H, m), 2.56 (2H, q, J = 7.6 Hz), 2.86 (1H, m), 3.17 (1H, m), 4.12-4.27 (4H, m), 4.64 (1H, m), 5.55 (1H, m), 6.11 (1H, s), 6.80 (1H, d, J = 8.3 Hz), 6.89 (1H, s), 6.96 (1H, d, J = 8.3 Hz), 7.07-7.12 (2H, m), 7.20 (1H, m), 7.35 (1H, m), 7.47 (1H, m). | ESI-MS m/z: 422 [M + H]+ |

TABLE 10

| Example | Structural formula | NMR | MS |
|---|---|---|---|
| 77 | (structure with phenyl, pyrazolo-oxazine, chromane-Cl) | 1H-NMR (CDCl₃) δ: 2.41-2.47 (2H, m), 2.91 (1H, dd, J = 17.5, 4.4 Hz), 3.13 (1H, dd, J = 17.6, 5.9 Hz), 4.15-4.24 (4H, m), 4.68 (1H, m), 5.27 (1H, m), 6.11 (1H, s), 6.82 (1H, dd, J = 8.2, 1.1 Hz), 6.99-7.03 (2H, m), 7.08 (1H, t, J = 8.0 Hz), 7.36-7.44 (5H, m). | ESI-MS m/z: 410 [M + H]+ |
| 78 | (structure with phenyl, pyrazolo-oxazine, chromane-OCF₃) | 1H-NMR (CDCl₃) δ: 2.41-2.47 (2H, m), 2.90 (1H, m), 3.12 (1H, dd, J = 17.4, 5.7 Hz), 4.14-4.19 (4H, m), 4.65 (1H, m), 5.27 (1H, m), 6.11 (1H, s), 6.83-6.86 (2H, m), 6.98 (1H, d, J = 8.1 Hz), 7.15 (1H, t, J = 8.3 Hz), 7.35-7.44 (5H, m). | ESI-MS m/z: 460 [M + H]+ |
| 79 | (structure with phenyl, pyrazolo-oxazine, phenethylamide-OEt) | 1H-NMR (CDCl₃) δ: 1.41 (3H, t, J = 6.6 Hz), 2.41-2.49 (2H, m), 2.88 (2H, t, J = 7.2 Hz), 3.66 (2H, q, J = 7.2 Hz), 4.03 (2H, q, J = 7.0 Hz), 4.16-4.28 (2H, m), 5.28 (1H, dd, J = 9.0, 3.6 Hz), 6.09 (1H, s), 6.75-6.88 (4H, m), 7.21 (1H, t, J = 8.1 Hz), 7.36-7.45 (5H, m). | ESI-MS m/z: 392 [M + H]+ |

TABLE 10-continued

| Example | Structural formula | NMR | MS |
|---|---|---|---|
| 80 | | 1H-NMR (CDCl₃) δ: 2.33-2.50 (2H, m), 2.98 (1H, dd, J = 16.6, 4.4 Hz), 3.26 (1H, dd, J = 16.7, 5.3 Hz), 4.13-4.30 (4H, m), 4.69 (1H, m), 5.56 (1H, m), 6.12 (1H, s), 6.99 (1H, d, J = 8.5 Hz), 7.05-7.12 (2H, m), 7.20 (1H, m), 7.32-7.39 (2H, m), 7.43-7.49 (4H, m), 8.61 (2H, d, J = 5.2 Hz). | ESI-MS m/z: 471 [M + H]+ |
| 81 | | 1H-NMR (CDCl₃) δ: 2.36-2.47 (2H, m), 2.97 (1H, dd, J = 16.5, 3.5 Hz), 3.27 (1H, dd, J = 16.4, 5.3 Hz), 4.13-4.28 (4H, m), 4.68 (1H, m), 5.55 (1H, d, J = 9.4 Hz), 6.11 (1H, s), 6.98 (1H, d, J = 8.3 Hz), 7.04-7.12 (2H, m), 7.16-7.22 (2H, m), 7.35 (1H, m), 7.46 (1H, m), 7.64-7.77 (4H, m), 8.64 (1H, d, J = 3.8 Hz). | ESI-MS m/z: 471 [M + H]+ |
| 82 | | 1H-NMR (CDCl₃) δ: 1.66 (1H, m), 2.33-2.49 (2H, m), 2.88 (1H, dd, J = 16.7, 4.2 Hz), 3.19 (1H, dd, J = 16.9, 5.3 Hz), 4.12-4.27 (4H, m), 4.59-4.65 (3H, m), 5.55 (1H, td, J = 9.5, 3.0 Hz), 6.11 (1H, s), 6.87 (1H, d, J = 8.3 Hz), 7.05-7.14 (4H, m), 7.20 (1H, tt, J = 7.6, 1.6 Hz), 7.35 (1H, m), 7.46 (1H, tt, J = 11.4, 1.9 Hz). | ESI-MS m/z: 424 [M + H]+ |
| 83 | | 1H-NMR (CDCl₃) δ: 1.24 (3H, t, J = 6.8 Hz), 2.34-2.48 (2H, m), 2.87 (1H, m), 3.19 (1H, dd, J = 5.3, 17.1 Hz), 3.55 (2H, q, J = 7.0 Hz), 4.14-4.27 (4H, m), 4.39 (2H, s), 4.63 (1H, m), 5.56 (1H, d, J = 9.5 Hz), 6.10 (1H, s), 6.85 (1H, d, J = 8.3 Hz), 7.03-7.12 (4H, m), 7.20 (1H, t, J = 7.6 Hz), 7.35 (1H, q, J = 6.9 Hz), 7.47 (1H, t, J = 7.4 Hz). | ESI-MS m/z: 452 [M + H]+ |
| 84 | | 1H-NMR (CDCl₃) δ: 1.59-1.70 (2H, m), 1.89-1.96 (2H, m), 2.38-2.49 (2H, m), 2.88 (1H, dd, J = 16.2, 3.8 Hz), 3.19 (1H, dd, J = 16.8, 5.6 Hz), 3.44 (2H, m), 3.59 (1H, m), 3.95-4.00 (2H, m), 4.10-4.27 (4H, m), 4.45 (2H, s), 4.64 (1H, m), 5.56 (1H, d, J = 9.5 Hz), 6.11 (1H, s), 6.86 (1H, d, J = 8.3 Hz), 7.04-7.13 (4H, m), 7.21 (1H, t, J = 7.2 Hz), 7.36 (1H, q, J = 6.9 Hz), 7.47 (1H, t, J = 7.6 Hz). | ESI-MS m/z: 508 [M + H]+ |
| 85 | | 1H-NMR (CDCl₃) δ: 1.46 (3H, d, J = 6.3 Hz), 2.06 (1H, m), 2.17 (1H, m), 2.84 (1H, dd, J = 16.8, 4.3 Hz), 3.14 (1H, dd, J = 16.8, 5.4 Hz), 4.02-4.19 (4H, m), 4.34 (1H, m), 4.60 (1H, m), 5.98 (1H, s), 6.80 (1H, d, J = 8.6 Hz), 6.99 (1H, d, J = 8.3 Hz), 7.03 (1H, d, J = 2.2 Hz), 7.08 (1H, dd, J = 8.7, 2.4 Hz). | ESI-MS m/z: 348 [M + H]+ |

TABLE 11

| Example | Structural formula | NMR | MS |
|---|---|---|---|
| 86 | | 1H-NMR (CDCl₃) δ: 1.46 (3H, d, J = 6.3 Hz), 2.05 (1H, m), 2.17 (1H, m), 2.84 (1H, dd, J = 16.9, 4.3 Hz), 3.14 (1H, dd, J = 16.7, 5.4 Hz), 4.07 (1H, m), 4.13-4.19 (3H, m), 4.34 (1H, m), 4.60 (1H, m), 5.98 (1H, s), 6.80 (1H, d, J = 8.6 Hz), 6.99 (1H, d, J = 8.5 Hz), 7.04 (1H, s), 7.08 (1H, dd, J = 8.7, 2.4 Hz). | ESI-MS m/z: 348 [M + H]+ |
| 87 | | 1H-NMR (CDCl₃) δ: 1.46 (3H, d, J = 6.3 Hz), 2.06 (1H, m, J = 3.9 Hz), 2.18 (1H, m), 2.84 (1H, dd, J = 16.9, 4.3 Hz), 3.14 (1H, dd, J = 16.8, 5.4 Hz), 4.07 (1H, m), 4.13-4.19 (3H, m), 4.34 (1H, m), 4.60 (1H, m), 5.98 (1H, s), 6.80 (1H, d, J = 8.7 Hz), 6.99 (1H, d, J = 7.9 Hz), 7.04 (1H, s), 7.08 (1H, dd, J = 8.7, 2.4 Hz). | ESI-MS m/z: 348 [M + H]+ |
| 88 | | 1H-NMR (CDCl₃) δ: 1.46 (3H, d, J = 6.3 Hz), 2.05 (1H, m), 2.17 (1H, m), 2.85 (1H, dd, J = 16.6, 4.1 Hz), 3.15 (1H, dd, J = 16.9, 5.4 Hz), 4.13 (1H, m), 4.13-4.19 (3H, m), 4.34 (1H, m), 4.61 (1H, m), 5.98 (1H, s), 6.76 (1H, d, J = 8.6 Hz), 6.98 (1H, d, J = 8.4 Hz), 7.18 (1H, s), 7.22 (1H, dd, J = 8.8, 2.2 Hz).. | ESI-MS m/z: 392, 394 [M + H]+ |
| 89 | | 1H-NMR (CDCl₃) δ: 1.46 (3H, d, J = 6.3 Hz), 2.06 (1H, m), 2.17 (1H, m), 2.85 (1H, dd, J = 16.9, 4.0 Hz), 3.15 (1H, dd, J = 17.0, 5.4 Hz), 4.06 (1H, m), 4.13-4.19 (3H, m), 4.34 (1H, m), 4.60 (1H, m), 5.98 (1H, s), 6.76 (1H, d, J = 8.6 Hz), 6.98 (1H, d, J = 7.8 Hz), 7.18 (1H, s), 7.21 (1H, d, J = 8.6 Hz). | ESI-MS m/z: 392, 394 [M + H]+ |
| 90 | | 1H-NMR (CDCl₃) δ: 1.05 (3H, t, J = 7.5 Hz), 1.72 (1H, m), 1.85 (1H, m), 2.05 (1H, m), 2.18 (1H, m), 2.84 (1H, dd, J = 16.8, 4.2 Hz), 3.14 (1H, dd, J = 16.9, 5.2 Hz), 4.01-4.19 (5H, m), 4.60 (1H, m), 5.99 (1H, s), 6.80 (1H, d, J = 8.7 Hz), 6.99 (1H, d, J = 7.9 Hz), 7.04 (1H, s), 7.08 (1H, dd, J = 8.6, 2.3 Hz). | ESI-MS m/z: 362 [M + H]+ |
| 91 | | 1H-NMR (CDCl₃) δ: 1.06 (3H, t, J = 7.5 Hz), 1.73 (1H, m), 1.81 (1H, m), 2.05 (1H, m), 2.18 (1H, m), 2.90 (1H, dd, J = 16.7, 4.5 Hz), 3.17 (1H, dd, J = 16.8, 5.1 Hz), 4.02-4.18 (3H, m), 4.21-4.31 (2H, m), 4.63 (1H, m), 5.99 (1H, s), 6.90-6.94 (2H, m), 7.38 (1H, s), 7.42 (1H, d, J = 8.5 Hz). | ESI-MS m/z: 353 [M + H]+ |
| 92 (isomer A) | | 1H-NMR (CDCl₃) δ: 1.06 (3H, t, J = 7.5 Hz), 1.64-1.88 (2H, m), 2.05 (1H, m), 2.19 (1H, m), 2.90 (1H, dd, J = 16.7, 5.1), 3.17 (1H, dd, J = 16.7, 5.1 Hz), 3.99-4.19 (3H, m), 4.21-4.33 (2H, m), 4.63 (1H, m), 6.00 (1H, s), 6.93 (2H, m), 7.38 (1H, s), 7.42 (1H, d, J = 8.6 Hz). | ESI-MS m/z: 353 [M + H]+ |

TABLE 11-continued

| Example | Structural formula | NMR | MS |
|---|---|---|---|
| 92 (isomer B) | | 1H-NMR (CDCl₃) δ: 1.06 (3H, t, J = 7.5 Hz), 1.64-1.88 (2H, m), 2.05 (1H, m), 2.19 (1H, m), 2.90 (1H, dd, J = 16.7, 5.1 Hz), 3.17 (1H, dd, J = 16.7, 5.1 Hz), 3.99-4.19 (3H, m), 4.21-4.33 (2H, m), 4.63 (1H, m), 6.00 (1H, s), 6.93 (2H, m), 7.38 (1H, s), 7.42 (1H, d, J = 8.6 Hz). | ESI-MS m/z: 353 [M + H]+ |
| 93 | | 1H-NMR (CDCl₃) δ: 1.05 (3H, t, J = 7.5 Hz), 1.72 (1H, m), 1.83 (1H, m), 2.00 (1H, m), 2.18 (1H, m), 2.96 (1H, dd, J = 16.8, 4.3 Hz), 3.24 (1H, dd, J = 16.7, 5.4 Hz), 4.01-4.28 (8H, m), 4.67 (1H, m), 6.00 (1H, s), 6.98 (1H, d, J = 8.4 Hz), 7.03 (1H, d, J = 8.0 Hz), 7.20 (1H, d, J = 2.1 Hz), 7.29 (1H, d, J = 2.3 Hz), 8.65 (2H, s). | ESI-MS m/z: 436 [M + H]+ |

TABLE 12

| Example | Structural formula | NMR | MS |
|---|---|---|---|
| 94 | | 1H-NMR (CDCl₃) δ: 0.98 (3H, t, J = 7.2 Hz), 1.48 (1H, m), 1.64 (1H, m), 1.80 (1H, m), 2.06 (1H, m), 2.18 (1H, m), 2.91 (1H, dd, J = 17.7, 5.2 Hz), 3.17 (1H, dd, J = 17.7, 6.9 Hz), 4.06 (1H, m), 4.12-4.32 (5H, m), 4.63 (1H, m), 5.98 (1H, s), 6.92 (2H, m), 7.38 (1H, s), 7.42 (1H, d, J = 8.7 Hz). | ESI-MS m/z: 367 [M + H]+ |
| 95 (isomer A) | | 1H-NMR (CDCl₃) δ: 0.98 (3H, t, J = 7.2 Hz), 1.48 (1H, m), 1.64 (1H, m), 1.80 (1H, m), 2.06 (1H, m), 2.18 (1H, m), 2.91 (1H, dd, J = 17.7, 5.2 Hz), 3.17 (1H, dd, J = 17.7, 6.9 Hz), 4.06 (1H, m), 4.12-4.32 (5H, m), 4.63 (1H, m), 5.98 (1H, s), 6.92 (2H, m), 7.38 (1H, s), 7.42 (1H, d, J = 8.7 Hz) | ESI-MS m/z: 367 [M + H]+ |
| 95 (isomer B) | | 1H-NMR (CDCl₃) δ: 0.98 (3H, t, J = 7.2 Hz), 1.48 (1H, m), 1.64 (1H, m), 1.80 (1H, m), 2.06 (1H, m), 2.18 (1H, m), 2.91 (1H, dd, J = 17.7, 5.2 Hz), 3.17 (1H, dd, J = 17.7, 6.9 Hz), 4.06 (1H, m), 4.12-4.32 (5H, m), 4.63 (1H, m), 5.98 (1H, s), 6.92 (2H, m), 7.38 (1H, s), 7.42 (1H, d, J = 8.7 Hz) | ESI-MS m/z: 367 [M + H]+ |

TABLE 12-continued

| Example | Structural formula | NMR | MS |
|---|---|---|---|
| 96 | | 1H-NMR (CDCl₃) δ: 0.12-0.16 (2H, m), 0.53-0.55 (2H, m), 0.84 (1H, m), 1.49 (1H, m), 1.81 (1H, m), 2.10 (1H, m), 2.28 (1H, m), 2.91 (1H, m), 3.17 (1H, m), 4.08 (1H, m), 4.15 (1H, m), 4.23-4.31 (3H, m), 4.63 (1H, m), 5.99 (1H, m), 6.92-6.94 (2H, m), 7.38 (1H, m), 7.42 (1H, m). | ESI-MS m/z: 379 [M + H]+ |
| 97 (isomer A) | | 1H-NMR (CDCl₃) δ: 0.12-0.16 (2H, m), 0.53-0.55 (2H, m), 0.84 (1H, m), 1.49 (1H, m), 1.81 (1H, m), 2.10 (1H, m), 2.28 (1H, m), 2.91 (1H, dd, J = 16.4, 4.5 Hz), 3.17 (1H, dd, J = 16.9, 5.2 Hz), 4.08 (1H, m), 4.16 (1H, m), 4.25-4.31 (3H, m), 4.63 (1H, m), 5.99 (1H, s), 6.92-6.94 (2H, m), 7.38 (1H, s), 7.42 (1H, d, J = 8.7 Hz). | ESI-MS m/z: 379 [M + H]+ |
| 97 (isomer B) | | 1H-NMR (CDCl₃) δ: 0.12-0.15 (2H, m), 0.53-0.55 (2H, m), 0.84 (1H, m), 1.49 (1H, m), 1.81 (1H, m), 2.11 (1H, m), 2.28 (1H, m), 2.90 (1H, m), 3.17 (1H, dd, J = 16.8, 4.8 Hz), 4.07 (1H, m), 4.17 (1H, m), 4.23-4.31 (3H, m), 4.63 (1H, m), 5.99 (1H, s), 6.92-6.94 (2H, m), 7.39 (1H, s), 7.42 (1H, d, J = 8.4 Hz). | ESI-MS m/z: 379 [M + H]+ |
| 98 | | 1H-NMR (CDCl₃) δ: 2.18-2.27 (2H, m), 2.84 (1H, dd, J = 17.0, 4.1 Hz), 3.14 (1H, dd, J = 17.0, 5.2 Hz), 3.66 (1H, dd, J = 10.3, 5.1 Hz), 3.75 (1H, dd, J = 10.3, 5.1 Hz), 4.07 (1H, m), 4.15-4.19 (3H, m), 4.37 (1H, m), 4.56-4.64 (3H, m), 6.02 (1H, s), 6.80 (1H, d, J = 8.6 Hz), 6.98 (1H, d, J = 7.9 Hz), 7.03 (1H, d, J = 2.2 Hz), 7.08 (1H, dd, J = 8.7, 2.4 Hz), 7.34 (5H, m). | ESI-MS m/z: 454 [M + H]+ |
| 99 | | 1H-NMR (CDCl₃) δ: 2.16-2.27 (2H, m), 2.90 (1H, dd, J = 16.7, 4.6 Hz), 3.17 (1H, dd, J = 16.8, 5.0 Hz), 3.67 (1H, dd, J = 10.3, 5.0 Hz), 3.75 (1H, dd, J = 10.3, 5.1 Hz), 4.06 (1H, m), 4.17 (1H, m), 4.23-4.31 (2H, m), 4.36 (1H, m), 4.60-4.65 (3H, m), 6.03 (1H, s), 6.90-6.94 (2H, m), 7.30-7.43 (7H, m). | ESI-MS m/z: 445 [M + H]+ |
| 100 | | 1H-NMR (CDCl₃) δ: 0.92 (3H, t, J = 7.4 Hz), 1.56-1.64 (2H, m), 2.15-2.29 (2H, m), 2.90 (1H, dd, J = 16.6, 4.8 Hz), 3.17 (1H, dd, J = 16.7, 5.3 Hz), 3.47 (1H, t, J = 6.6 Hz), 3.62 (1H, m), 3.72 (1H, dd, J = 10.5, 5.1 Hz), 4.04-4.37 (6H, m), 4.63 (1H, m), 6.02 (1H, s), 6.91-6.94 (2H, m), 7.38 (1H, s), 7.42 (1H, d, J = 8.5 Hz). | ESI-MS m/z: 397 [M + H]+ |

TABLE 13

| Example | Structural formula | NMR | MS |
| --- | --- | --- | --- |
| 101 (isomer A) | | 1H-NMR (CDCl₃) δ: 0.92 (3H, t, J = 7.3 Hz), 1.58-1.64 (2H, m), 2.14-2.27 (2H, m), 2.90 (1H, dd, J = 16.4, 4.2 Hz), 3.17 (1H, dd, J = 16.4, 4.6 Hz), 3.47 (2H, t, J = 6.6 Hz), 3.62 (1H, m), 3.72 (1H, m), 4.08 (1H, m), 4.17-4.36 (4H, m), 4.63 (1H, m), 6.02 (1H, s), 6.92-6.94 (2H, m), 7.38 (1H, s), 7.42 (1H, d, J = 8.5 Hz). | ESI-MS m/z: 397 [M + H]+ |
| 101 (isomer B) | | 1H-NMR (CDCl₃) δ: 0.92 (3H, t, J = 7.4 Hz), 1.57-1.66 (2H, m), 2.14-2.28 (2H, m), 2.90 (1H, dd, J = 16.9, 4.5 Hz), 3.17 (1H, dd, J = 16.7, 5.0 Hz), 3.47 (2H, t, J = 6.6 Hz), 3.62 (1H, m), 3.72 (1H, m), 4.08 (1H, m), 4.17-4.36 (4H, m), 4.63 (1H, m), 6.02 (1H, s), 6.92-6.94 (2H, m), 7.38 (1H, s), 7.42 (1H, d, J = 8.8 Hz). | ESI-MS m/z: 397 [M + H]+ |
| 102 | | 1H-NMR (CDCl₃) δ: 0.20-0.23 (2H, m), 0.54-0.58 (2H, m), 1.06 (1H, m), 2.16-2.29 (2H, m), 2.90 (1H, dd, J = 16.6, 4.9 Hz), 3.17 (1H, dd, J = 16.8, 5.1 Hz), 3.37 (2H, d, J = 6.9 Hz), 3.66 (1H, ddd, J = 10.5, 5.1, 1.7 Hz), 3.76 (1H, dd, J = 10.4, 5.2 Hz), 4.05-4.38 (5H, m), 4.63 (1H, m), 6.02 (1H, s), 6.91-6.94 (2H, m), 7.38 (1H, s), 7.42 (1H, dd, J = 8.6, 1.7 Hz). | ESI-MS m/z: 409 [M + H]+ |
| 103 (isomer A) | | 1H-NMR (CDCl₃) δ: 0.20-0.23 (2H, m), 0.54-0.58 (2H, m), 1.06 (1H, m), 2.14-2.27 (2H, m), 2.90 1H, dd, J = 16.7, 4.5 Hz), 3.17 (1H, dd, J = 16.8, 5.3 Hz), 3.37 (2H, d, J = 6.9 Hz), 3.65 (1H, dd, J = 10.4, 5.2 Hz), 3.76 (1H, dd, J = 10.4, 5.2 Hz), 4.06 (1H, m), 4.16-4.40 (4H, m), 4.63 (1H, m), 6.02 (1H, s), 6.90-6.94 (2H, m), 7.38 (1H, s), 7.42 (1H, d, J = 8.5 Hz). | ESI-MS m/z: 409 [M + H]+ |
| 103 (isomer B) | | 1H-NMR (CDCl₃) δ: 0.20-0.24 (2H, m), 0.54-0.58 (2H, m), 1.06 (1H, m), 2.15-2.30 (2H, m), 2.90 (1H, dd, J = 4.7, 16.7 Hz), 3.17 (1H, dd, J = 16.8, 5.0 Hz), 3.37 (2H, d, J = 6.9 Hz), 3.66 (1H, dd, J = 10.4, 5.2 Hz), 3.76 (1H, dd, J = 10.4, 5.2 Hz), 4.08 (1H, m), 4.17-4.39 (4H, m), 4.63 (1H, m), 6.02 (1H, s), 6.91-6.94 (2H, m), 7.38 (1H, s), 7.42 (1H, d, J = 8.5 Hz). | ESI-MS m/z: 409 [M + H]+ |
| 104 | | 1H-NMR (CDCl₃) δ: 2.20-2.28 (2H, m), 2.90 (1H, dd, J = 16.7, 4.9 Hz), 3.17 (1H, dd, J = 16.5, 5.0 Hz), 3.69 (1H, m), 3.76 (1H, dd, J = 10.4, 5.1 Hz), 4.09 (1H, m), 4.15-4.31 (3H, m), 4.38 (1H, m), 4.60-4.65 (3H, m), 6.03 (1H, s), 6.91-6.94 (2H, m), 6.98-7.05 (2H, m), 7.09 (1H, d, J = 7.7 Hz), 7.32 (1H, q, J = 6.8 Hz), 7.38 (1H, s), 7.42 (1H, dd, J = 8.5, 1.7 Hz). | ESI-MS m/z: 463 [M + H]+ |

TABLE 13-continued

| Example | Structural formula | NMR | MS |
| --- | --- | --- | --- |
| 105 | | 1H-NMR (CDCl₃) δ: 2.24-2.29 (2H, m), 2.85 (1H, dd, J = 16.6, 3.9 Hz), 3.15 (1H, dd, J = 16.8, 5.3 Hz), 3.82-3.90 (2H, m), 4.11 (1H, m), 4.19-4.24 (3H, m), 4.45 (1H, m), 4.61 (1H, m), 4.79 (2H, s), 6.03 (1H, s), 6.81 (1H, d, J = 8.7 Hz), 7.00 (1H, d, J = 8.1 Hz), 7.04 (1H, m), 7.08 (1H, dd, J = 8.8, 2.3 Hz), 7.59-7.65 (2H, m), 7.88 (1H, m). | ESI-MS m/z: 523 [M + H]+ |
| 106 | | 1H-NMR (CDCl₃) δ: 0.20-0.23 (2H, m), 0.53-0.58 (2H, m), 1.07 (1H, m), 2.14-2.30 (2H, m), 2.84 (1H, dd, J = 16.9, 4.2 Hz), 3.14 (1H, dd, J = 16.9, 5.3 Hz), 3.37 (2H, d, J = 6.9 Hz), 3.65 (1H, m), 3.76 (1H, m), 4.09 (1H, m), 4.18-4.22 (3H, m), 4.36 (1H, m), 4.60 (1H, m), 6.02 (1H, s), 6.81 (1H, d, J = 8.6 Hz), 6.99 (1H, d, J = 8.3 Hz), 7.04 (1H, s), 7.08 (1H, dd, J = 8.7, 2.4 Hz). | ESI-MS m/z: 418 [M + H]+ |
| 107 | | 1H-NMR (CDCl₃) δ: 0.21 (2H, d, J = 4.6 Hz), 0.56 (2H, d, J = 7.9 Hz), 1.07 (1H, m), 2.14-2.30 (2H, m), 2.95 (1H, m), 3.25 (1H, dd, J = 16.2, 5.3 Hz), 3.36-3.39 (2H, m), 3.66 (1H, m), 3.76 (1H, m), 4.03-4.30 (4H, m), 4.39 (1H, m), 4.67 (1H, m), 6.03 (1H, s), 7.02 (2H, d, J = 8.4 Hz), 7.31 (1H, s), 7.39 (1H, dd, J = 8.6, 2.0 Hz), 7.73 (1H, d, J = 8.0 Hz), 7.93 (1H, dd, J = 8.1, 2.2 Hz), 8.90 (1H, d, J = 1.9 Hz). | ESI-MS m/z: 486 [M + H]+ |

TABLE 14

| Example | Structural formula | NMR | MS |
| --- | --- | --- | --- |
| 108 | | 1H-NMR (CDCl₃) δ: 0.20-0.22 (2H, m), 0.55-0.57 (2H, m), 1.06 (1H, m), 2.13-2.29 (2H, m), 2.86 (1H, dd, J = 4.1, 16.8 Hz), 3.04 (2H, dt, J = 17.4, 4.4 Hz), 3.16 (1H, dd, J = 16.7, 5.4 Hz), 3.37 (2H, d, J = 6.9 Hz), 3.65 (1H, dd, J = 10.3, 5.3 Hz), 3.75 (1H, dd, J = 10.4, 5.2 Hz), 4.08 (1H, m), 4.14-4.22 (3H, m), 4.36 (1H, m), 4.61 (1H, m), 5.72-6.02 (2H, m), 6.84 (1H, d, J = 8.3 Hz), 6.93 (1H, s), 7.00-7.01 (2H, m). | ESI-MS m/z: 448 [M + H]+ |

TABLE 14-continued

| Example | Structural formula | NMR | MS |
|---|---|---|---|
| 109 (isomer A) | | 1H-NMR (CDCl₃) δ: 0.21 (2H, d, J = 4.5 Hz), 0.56 (2H, d, J = 7.9 Hz), 1.06 (1H, m), 2.13-2.29 (2H, m), 2.86 (1H, m), 3.04 (2H, dt, J = 17.3, 4.2 Hz), 3.16 (1H, dd, J = 16.9, 5.2 Hz), 3.37 (2H, d, J = 6.9 Hz), 3.65 (1H, m), 3.75 (1H, m), 4.05-4.21 (4H, m), 4.36 (1H, m), 4.61 (1H, m), 5.73-6.02 (2H, m), 6.84 (1H, d, J = 8.2 Hz), 6.94 (1H, s), 7.01 (2H, d, J = 8.3 Hz). | ESI-MS m/z: 448 [M + H]+ |
| 109 (isomer B) | | 1H-NMR (CDCl₃) δ: 0.22 (2H, d, J = 4.7 Hz), 0.56 (2H, d, J = 8.0 Hz), 1.07 (1H, m), 2.14-2.29 (2H, m), 2.86 (1H, dd, J = 16.8, 3.7 Hz), 3.04 (2H, dt, J = 17.5, 4.3 Hz), 3.16 (1H, dd, J = 16.7, 5.3 Hz), 3.37 (2H, d, J = 7.0 Hz), 3.65 (1H, m), 3.76 (1H, m), 4.07 (1H, m), 4.15-4.21 (3H, m), 4.35 (1H, m), 4.62 (1H, m), 5.73-6.02 (2H, m), 6.84 (1H, d, J = 8.4 Hz), 6.94 (1H, s), 7.01 (2H, d, J = 8.0 Hz). | ESI-MS m/z: 448 [M + H]+ |
| 110 | | 1H-NMR (CDCl₃) δ: 0.21 (2H, d, J = 4.6 Hz), 0.55 (2H, d, J = 7.9 Hz), 1.06 (1H, m), 2.12-2.28 (2H, m), 2.95 (1H, dd, J = 16.6, 4.1 Hz), 3.26 (1H, dd, J = 16.6, 5.3 Hz), 3.36 (2H, d, J = 6.8 Hz), 3.64 (1H, dd, J = 5.4, 9.9 Hz), 3.75 (1H, dd, J = 10.4, 5.2 Hz), 4.02-4.43 (5H, m), 4.68 (1H, m), 6.02 (1H, s), 6.97 (1H, d, J = 8.2 Hz), 7.02 (1H, d, J = 8.1 Hz), 7.18, (1H, m), 7.64-7.77 (4H, m), 8.64 (1H, d, J = 4.2 Hz). | ESI-MS m/z: 461 [M + H]+ |
| 111 (isomer A) | | 1H-NMR (CDCl₃) δ: 0.19-0.22 (2H, m), 0.53-0.57 (2H, m), 1.06 (1H, m), 2.12-2.29 (2H, m), 2.95 (1H, dd, J = 16.6, 4.0 Hz), 3.26 (1H, dd, J = 16.5, 5.3 Hz), 3.36 (2H, d, J = 6.9 Hz), 3.64 (1H, dd, J = 10.4, 5.2 Hz), 3.75 (1H, dd, J = 10.4, 5.2 Hz), 4.07 (1H, m), 4.18 (1H, m), 4.22-4.28 (2H, m), 4.36 (1H, m), 4.69 (1H, m), 6.02 (1H, s), 6.94-7.03 (2H, m), 7.18 (1H, m), 7.64-7.76 (4H, m), 8.64 (1H, m). | ESI-MS m/z: 461 [M + H]+ |
| 111 (isomer B) | | 1H-NMR (CDCl₃) δ: 0.20-0.23 (2H, m), 0.53-0.58 (2H, m), 1.06 (1H, m), 2.13-2.28 (2H, m), 2.96 (1H, dd, J = 16.5, 4.4 Hz), 3.26 (1H, dd, J = 16.5, 5.4 Hz), 3.37 (2H, d, J = 6.9 Hz), 3.65 (1H, m), 3.75 (1H, dd, J = 10.4, 5.2 Hz), 4.06 (1H, m), 4.19 (1H, m), 4.25-4.26 (2H, m), 4.35 (1H, m), 4.66 (1H, m), 6.02 (1H, s), 6.96-7.03 (2H, m), 7.18 (1H, m), 7.64-7.76 (4H, m), 8.64 (1H, m). | ESI-MS m/z: 461 [M + H]+ |

TABLE 14-continued

| Example | Structural formula | NMR | MS |
| --- | --- | --- | --- |
| 112 | | 1H-NMR (CDCl₃) δ: 0.29-0.43 (4H, m), 1.12 (3H, s), 2.13-2.33 (2H, m), 2.91 (1H, dd, J = 16.2, 4.8 Hz), 3.17 (1H, dd, J = 16.8, 5.5 Hz), 3.28-3.35 (2H, m), 3.63 (1H, dd, J = 10.3, 4.8 Hz), 3.75 (1H, dd, J = 10.6, 6.1 Hz), 4.08 (1H, m), 4.16-4.41 (4H, m), 4.63 (1H, m), 6.02 (1H, s), 6.88-6.95 (2H, m), 7.39 (1H, s), 7.42 (1H, dd, J = 8.7, 2.4 Hz). | ESI-MS m/z: 423 [M + H]+ |
| 113 (isomer A) | | 1H-NMR (CDCl₃) δ: 0.29-0.43 (4H, m), 1.12 (3H, s), 2.13-2.33 (2H, m), 2.91 (1H, dd, J = 16.2, 4.8 Hz), 3.17 (1H, dd, J = 16.8, 5.5 Hz), 3.28-3.35 (2H, m), 3.63 (1H, dd, J = 10.3, 4.8 Hz), 3.75 (1H, dd, J = 10.6, 6.1 Hz), 4.08 (1H, m), 4.16-4.41 (4H, m), 4.63 (1H, m), 6.02 (1H, s), 6.88-6.95 (2H, m), 7.39 (1H, s), 7.42 (1H, dd, J = 8.7, 2.4 Hz) | ESI-MS m/z: 423 [M + H]+ |
| 113 (isomer B) | | 1H-NMR (CDCl₃) δ: 0.29-0.43 (4H, m), 1.12 (3H, s), 2.13-2.33 (2H, m), 2.91 (1H, dd, J = 16.2, 4.8 Hz), 3.17 (1H, dd, J = 16.8, 5.5 Hz), 3.28-3.35 (2H, m), 3.63 (1H, dd, J = 10.3, 4.8 Hz), 3.75 (1H, dd, J = 10.6, 6.1 Hz), 4.08 (1H, m), 4.16-4.41 (4H, m), 4.63 (1H, m), 6.02 (1H, s), 6.88-6.95 (2H, m), 7.39 (1H, s), 7.42 (1H, dd, J = 8.7, 2.4 Hz) | ESI-MS m/z: 423 [M + H]+ |

TABLE 15

| Example | Structural formula | NMR | MS |
| --- | --- | --- | --- |
| 114 | | 1H-NMR (CDCl₃) δ: 2.23-2.27 (2H, m), 2.90 (1H, dd, J = 16.6, 4.8 Hz), 3.17 (1H, dd, J = 16.7, 5.2 Hz), 3.85-3.98 (4H, m), 4.09 (1H, m), 4.20-4.31 (3H, m), 4.37 (1H, m), 4.63 (1H, m), 6.03 (1H, s), 6.91-6.94 (2H, m), 7.38 (1H, s), 7.42 (1H, dd, J = 8.5, 1.9 Hz). | ESI-MS m/z: 437 [M + H]+ |
| 115 (isomer A) | | 1H-NMR (CDCl₃) δ: 2.24-2.27 (2H, m), 2.90 (1H, m), 3.17 (1H, dd, J = 16.8, 5.4 Hz), 3.84-3.97 (4H, m), 4.10 (1H, m), 4.18-4.31 (3H, m), 4.38 (1H, m), 4.63 (1H, m), 6.03 (1H, s), 6.91-6.94 (2H, m), 7.39 (1H, s), 7.42 (1H, d, J = 8.5 Hz). | ESI-MS m/z: 437 [M + H]+ |
| 115 (isomer B) | | 1H-NMR (CDCl₃) δ: 2.22-2.27 (2H, m), 2.91 (1H, dd, J = 16.8, 3.9 Hz), 3.17 (1H, dd, J = 16.7, 5.0 Hz), 3.85-3.98 (4H, m), 4.09 (1H, m), 4.19-4.31 (3H, m), 4.37 (1H, m), 4.64 (1H, m), 6.03 (1H, s), 6.91-6.94 (2H, m), 7.39 (1H, s), 7.42 (1H, d, J = 8.6 Hz). | ESI-MS m/z: 437 [M + H]+ |

TABLE 15-continued

| Example | Structural formula | NMR | MS |
| --- | --- | --- | --- |
| 116 | (structure) | 1H-NMR (CDCl₃) δ: 2.24-2.31 (2H, m), 2.91 (1H, m), 3.17 (1H, m), 4.06-4.15 (3H, m), 4.21-4.31 (4H, m), 4.41 (1H, m), 4.63 (1H, m), 6.04 (1H, s), 6.91-6.94 (2H, m), 7.39 (1H, s), 7.42 (1H, d, J = 8.5 Hz). | ESI-MS m/z: 505 [M + H]+ |
| 117 | (structure) | 1H-NMR (CDCl₃) δ: 2.23-2.33 (2H, m), 2.85 (1H, m), 3.15 (1H, dd, J = 16.8, 5.3 Hz), 4.07-4.25 (4H, m), 4.59-4.61 (4H, m), 6.05 (1H, s), 6.81 (2H, d, J = 8.6 Hz), 6.91 (1H, t, J = 6.1 Hz), 6.99 (1H, d, J = 7.8 Hz), 7.04 (1H, s), 7.08 (1H, dd, J = 8.8, 2.4 Hz), 7.60 (1H, t, J = 6.9 Hz), 8.13 (1H, d, J = 3.9 Hz). | ESI-MS m/z: 441 [M + H]+ |
| 118 | (structure) | 1H-NMR (CDCl₃) δ: 2.27-2.43 (2H, m), 2.91 (1H, dd, J = 16.4, 4.5 Hz), 3.18 (1H, m), 4.11-4.17 (2H, m), 4.24-4.32 (4H, m), 4.55-4.65 (2H, m), 6.06 (1H, s), 6.91-6.94 (4H, m), 7.00 (1H, t, J = 7.4 Hz), 7.31 (2H, t, J = 7.9 Hz), 7.39 (1H, s), 7.42 (1H, d, J = 8.4 Hz). | ESI-MS m/z: 431 [M + H]+ |
| 119 | (structure) | 1H-NMR (CDCl₃) δ: 2.14 (1H, m), 2.44 (1H, m), 2.90 (1H, dd, J = 16.7, 4.6 Hz), 3.08 (1H, dd, J = 14.1, 8.0 Hz), 3.16 (1H, m), 3.40 (1H, dd, J = 14.1, 5.0 Hz), 4.04 (1H, m), 4.14 (1H, m), 4.22-4.30 (3H, m), 4.62 (1H, m), 6.00 (1H, s), 6.89-6.93 (2H, m), 7.23-7.43 (7H, m). | ESI-MS m/z: 447 [M + H]+ |
| 120 | (structure) | 1H-NMR (CDCl₃) δ: 2.28-2.37 (2H, m), 2.85 (1H, dd, J = 16.7, 3.9 Hz), 3.15 (1H, dd, J = 16.8, 5.2 Hz), 4.09-4.33 (6H, m), 4.56-4.62 (2H, m), 6.05 (1H, s), 6.80-6.85 (3H, m), 7.01 (1H, d, J = 8.0 Hz), 7.04 (1H, s), 7.09 (1H, dd, J = 8.6, 2.3 Hz), 8.48 (2H, d, J = 4.8 Hz). | ESI-MS m/z: 441 [M + H]+ |

TABLE 15-continued

| Example | Structural formula | NMR | MS |
| --- | --- | --- | --- |
| 121 | | 1H-NMR (CDCl₃) δ: 2.02 (1H, m), 2.26 (1H, m), 2.34 (3H, s), 2.69 (1H, dd, J = 13.2, 6.6 Hz), 2.74 (1H, dd, J = 13.3, 5.7 Hz), 2.84 (1H, dd, J = 16.8, 4.0 Hz), 3.14 (1H, dd, J = 16.9, 5.2 Hz), 3.54-3.65 (2H, m), 3.97-4.13 (2H, m), 4.18 (2H, d, J = 2.8 Hz), 4.29 (1H, m), 4.60 (1H, m), 5.99 (1H, s), 6.80 (1H, d, J = 8.6 Hz), 6.97 (1H, d, J = 7.9 Hz), 7.03 (1H, s), 7.08 (1H, dd, J = 8.7, 2.3 Hz), 7.30-7.34 (5H, m). | ESI-MS m/z: 467 [M + H]+ |

TABLE 16

| Example | Structural formula | NMR | MS |
| --- | --- | --- | --- |
| 122 | | 1H-NMR (CDCl₃) δ: 2.13 (1H, m), 2.28 (1H, m), 2.50-2.60 (5H, m), 2.76 (1H, dd, J = 13.5, 6.2 Hz), 2.84 (1H, dd, J = 16.9, 4.2 Hz), 3.15 (1H, m), 3.72 (4H, t, J = 4.6 Hz), 4.04-4.19 (4H, m), 4.34 (1H, m), 4.60 (1H, m), 6.01 (1H, s), 6.81 (1H, d, J = 8.7 Hz), 6.99 (1H, d, J = 8.0 Hz), 7.04 (1H, s), 7.08 (1H, dd, J = 8.7, 2.4 Hz). | ESI-MS m/z: 433 [M + H]+ |
| 123 | | 1H-NMR (CDCl₃) δ: 1.22 (3H, dt, J = 7.0, 1.0 Hz), 2.12-2.28 (2H, m), 2.95 (1H, dd, J = 16.7, 4.2 Hz), 3.26 (1H, dd, J = 16.6, 5.2 Hz), 3.55-3.65 (3H, m), 3.71 (1H, dd, J = 10.4, 5.3 Hz), 4.06 (1H, m), 4.17 (1H, m), 4.26 (2H, s), 4.33 (1H, m), 4.66 (1H, m), 6.02 (1H, s), 6.97 (1H, d, J = 8.2 Hz), 7.02 (1H, d, J = 8.1 Hz), 7.18 (1H, m), 7.64-7.76 (4H, m), 8.64 (1H, d, J = 4.3 Hz). | ESI-MS m/z: 435 [M + H]+ |
| 124 (isomer A) | | 1H-NMR (CDCl₃) δ: 1.22 (3H, t, J = 7.0 Hz), 2.12-2.25 (2H, m), 2.95 (1H, dd, J = 16.4, 3.8 Hz), 3.26 (1H, dd, J = 16.7, 4.9 Hz), 3.55-3.65 (3H, m), 3.71 (1H, dd, J = 10.5, 5.3 Hz), 4.07 (1H, m), 4.17 (1H, m), 4.26 (2H, s), 4.34 (1H, m), 4.66 (1H, m), 6.02 (1H, s), 6.96-7.03 (2H, m), 7.18 (1H, t, J = 6.0 Hz), 7.65 (1H, d, J = 7.8 Hz), 7.70-7.76 (3H, m), 8.64 (1H, d, J = 4.5 Hz). | ESI-MS m/z: 435 [M + H]+ |
| 124 (isomer B) | | 1H-NMR (CDCl₃) δ: 1.22 (3H, t, J =7.0 Hz), 2.13-2.26 (2H, m), 2.96 (1H, dd, J = 16.6, 3.9 Hz), 3.26 (1H, dd, J = 16.6, 5.4 Hz), 3.55-3.65 (3H, m), 3.71 (1H, dd, J = 10.4, 5.2 Hz), 4.06 (1H, m), 4.15-4.36 (4H, m), 4.66 (1H, m), 6.02 (1H, s), 6.96-7.03 (2H, m), 7.18 (1H, m), 7.65 (1H, d, J = 7.9 Hz), 7.70-7.76 (3H, m), 8.64 (1H, d, J = 4.0 Hz). | ESI-MS m/z: 435 [M + H]+ |

TABLE 16-continued

| Example | Structural formula | NMR | MS |
|---|---|---|---|
| 125 | | 1H-NMR (CDCl$_3$) δ: 1.22 (3H, dt, J = 7.0, 1.0 Hz), 2.13-2.28 (2H, m), 2.98 (1H, dd, J = 16.7, 4.1 Hz), 3.25 (1H, dd, J = 16.7, 5.3 Hz), 3.55-3.65 (3H, m), 3.72 (1H, dd, J = 10.1, 4.9 Hz), 4.08 (1H, m), 4.15-4.38 (4H, m), 4.66 (1H, m), 6.03 (1H, s), 7.02 (2H, d, J = 8.4 Hz), 7.31 (1H, s), 7.39 (1H, dd, J = 8.5, 2.0 Hz), 7.73 (1H, d, J = 8.1 Hz), 7.93 (1H, dd, J = 8.1, 2.2 Hz), 8.89 (1H, d, J = 2.0 Hz). | ESI-MS m/z: 460 [M + H]+ |
| 126 | | 1H-NMR (CDCl$_3$) δ: 2.17-2.24 (2H, m), 2.86 (1H, dd, J = 16.7, 3.9 Hz), 3.04 (2H, dt, J = 17.3, 4.5 Hz), 3.17 (1H, dd, J = 16.8, 5.4 Hz), 3.84-3.98 (4H, m), 4.05-4.23 (4H, m), 4.37 (1H, m), 4.61 (1H, m), 5.73-6.03 (2H, m), 6.84 (1H, d, J = 8.3 Hz), 6.94 (1H, s), 7.01 (2H, d, J = 7.1 Hz). | ESI-MS m/z: 476 [M + H]+ |
| 127 (isomer A) | | 1H-NMR (CDCl$_3$) δ: 2.16-2.26 (2H, m), 2.86 (1H, dd, J = 16.6, 3.8 Hz), 3.04 (2H, dt, J = 17.4, 4.4 Hz), 3.17 (1H, dd, J = 16.8, 5.5 Hz), 3.84-3.97 (4H, m), 4.06-4.22 (4H, m), 4.37 (1H, m), 4.61 (1H, m), 5.73-6.03 (2H, m), 6.84 (1H, d, J = 8.3 Hz), 6.94 (1H, s), 7.01 (2H, d, J = 8.6 Hz). | ESI-MS m/z: 476 [M + H]+ |
| 127 (isomer B) | | 1H-NMR (CDCl$_3$) δ: 2.17-2.26 (2H, m), 2.86 (1H, dd, J = 16.7, 4.3 Hz), 3.04 (2H, dt, J = 17.4, 4.5 Hz), 3.17 (1H, dd, J = 16.8, 5.5 Hz), 3.84-3.98 (4H, m), 4.05-4.24 (4H, m), 4.36 (1H, m), 4.61 (1H, m), 5.73-6.03 (2H, m), 6.84 (1H, d, J = 8.3 Hz), 6.94 (1H, s), 7.00-7.03 (2H, m). | ESI-MS m/z: 476 [M + H]+ |
| 128 | | 1H-NMR (CDCl$_3$) δ: 2.22-2.26 (2H, m), 2.85-2.90 (1H, m), 3.15-3.21 (1H, m), 3.79-3.98 (6H, m), 4.06-4.14 (1H, m), 4.17-4.23 (3H, m), 4.35-4.40 (1H, m), 4.57 (2H, s), 4.60-4.64 (1H, m), 6.03 (1H, s), 6.87 (1H, d, J = 8.3 Hz), 7.00-7.05 (2H, m), 7.12 (1H, dd, J = 8.4, 2.0 Hz). | ESI-MS m/z: 524 [M + H]+ |

TABLE 17

| Example | Structural formula | NMR | MS |
|---|---|---|---|
| 129 (isomer A) | | 1H-NMR (CDCl$_3$) δ: 2.27 (2H, m), 2.85-2.89 (1H, m), 3.15-3.21 (1H, m), 3.78-3.97 (6H, m), 4.08-4.12 (1H, m), 4.20 (3H, m), 4.35-4.38 (1H, m), 4.57 (2H, s), 4.62 (1H, m), 6.03 (1H, s), 6.87 (1H, d, J = 8.5 Hz), 7.01 (1H, d, J = 8.2 Hz), 7.05 (1H, s), 7.12 (1H, d, J = 7.4 Hz). | ESI-MS m/z: 524 [M + H]+ |
| 129 (isomer B) | | 1H-NMR (CDCl$_3$) δ: 2.24 (2H, m), 2.85-2.89 (1H, m), 3.15-3.21 (1H, m), 3.78-3.97 (6H, m), 4.09-4.12 (1H, m), 4.21 (3H, m), 4.35-4.37 (1H, m), 4.57 (2H, s), 4.63 (1H, m), 6.03 (1H, s), 6.87 (1H, d, J = 8.3 Hz), 7.01 (1H, d, J = 8.2 Hz), 7.06 (1H, s), 7.12 (1H, d, J = 8.0 Hz). | ESI-MS m/z: 524 [M + H]+ |
| 130 | | 1H-NMR (CDCl$_3$) δ: 2.18-2.25 (2H, m), 2.96 (1H, m), 3.26 (1H, dd, J = 5.2, 16.6 Hz), 3.84-3.97 (4H, m), 4.08 (1H, m), 4.20 (1H, m), 4.26 (2H, d, J = 2.5 Hz), 4.36 (1H, m), 4.66 (1H, m), 6.03 (1H, s), 6.97 (1H, d, J = 8.3 Hz), 7.02 (1H, d, J = 8.0 Hz), 7.18 (1H, m), 7.65 (1H, d, J = 7.9 Hz), 7.70-7.76 (3H, m), 8.64 (1H, d, J = 4.3 Hz). | ESI-MS m/z: 489 [M + H]+ |
| 131 (isomer A) | | 1H-NMR (CDCl$_3$) δ: 2.16-2.25 (2H, m), 2.96 (1H, m), 3.26 (1H, dd, J = 16.5, 5.3 Hz), 3.83-3.97 (4H, m), 4.08 (1H, m), 4.18 (1H, m), 4.26 (2H, s), 4.36 (1H, m), 4.66 (1H, m), 6.03 (1H, s), 6.96-7.03 (2H, m), 7.18 (1H, t, J = 5.8 Hz), 7.64-7.76 (4H, m), 8.64 (1H, d, J = 4.5 Hz). | ESI-MS m/z: 489 [M + H]+ |
| 131 (isomer B) | | 1H-NMR (CDCl$_3$) δ: 2.18-2.25 (2H, m), 2.96 (1H, m), 3.26 (1H, dd, J = 16.6, 5.0 Hz), 3.84-3.97 (4H, m), 4.07 (1H, m), 4.20 (1H, m), 4.26 (2H, d, J = 3.0 Hz), 4.36 (1H, m), 4.66 (1H, m), 6.03 (1H, s), 6.96-7.03 (2H, m), 7.18 (1H, m), 7.64-7.76 (4H, m), 8.64 (1H, d, J = 4.7 Hz). | ESI-MS m/z: 489 [M + H]+ |

TABLE 17-continued

| Example | Structural formula | NMR | MS |
|---|---|---|---|
| 132 | | 1H-NMR (CDCl$_3$) δ: 2.16-2.27 (2H, m), 2.98 (1H, dd, J = 16.7, 4.6 Hz), 3.25 (1H, dd, J = 16.7, 5.2 Hz), 3.84-3.98 (4H, m), 4.10 (1H, m), 4.18-4.31 (3H, m), 4.37 (1H, m), 4.68 (1H, m), 6.04 (1H, s), 7.02 (2H, d, J = 8.5 Hz), 7.31 (1H, d, J = 2.2 Hz), 7.39 (1H, dd, J = 8.5, 2.3 Hz), 7.73 (1H, dd, J = 8.1, 0.7 Hz), 7.93 (1H, dd, J = 8.1, 2.3 Hz), 8.89 (1H, dd, J = 2.3, 0.7 Hz). | ESI-MS m/z: 514 [M + H]+ |
| 133 | | 1H-NMR (CDCl$_3$) δ: 2.25-2.29 (2H, m), 2.91 (1H, dd, J = 4.8, 16.5 Hz), 3.17 (1H, dd, J = 16.2, 5.1 Hz), 4.11-4.28 (6H, m), 4.45 (1H, m), 4.64 (1H, m), 6.06 (1H, s), 6.90-6.94 (2H, m), 7.39-7.43 (2H, m). | ESI-MS m/z: 423 [M + H]+ |
| 134 (isomer A) | | 1H-NMR (CDCl$_3$) δ: 2.18-2.31 (2H, m), 2.88-2.93 (1H, m), 3.17 (1H, dd, J = 16.7, 5.1 Hz), 4.01-4.30 (6H, m), 4.42-4.47 (1H, m), 4.62-4.64 (1H, m), 6.06 (1H, s), 6.90-6.94 (2H, m), 7.39-7.43 (2H, m). | ESI-MS m/z: 423 [M + H]+ |
| 134 (isomer B) | | 1H-NMR (CDCl$_3$) δ: 2.23-2.30 (2H, m), 2.91 (1H, dd, J = 16.5, 4.5 Hz), 3.17 (1H, dd, J = 16.7, 5.1 Hz), 4.08-4.31 (6H, m), 4.41-4.47 (1H, m), 4.63 (1H, m), 6.06 (1H, s), 6.91-6.94 (2H, m), 7.39-7.43 (2H, m). | ESI-MS m/z: 423 [M + H]+ |

TABLE 18

| Example | Structural formula | NMR | MS |
|---|---|---|---|
| 135 | | 1H-NMR (CDCl$_3$) δ: 2.23-2.28 (2H, m), 2.84-3.28 (4H, m), 4.10-4.25 (6H, m), 4.42-4.45 (1H, m), 4.62 (1H, m), 5.73-6.05 (2H, m), 6.84 (1H, m), 6.94 (1H, s), 7.00-7.02 (2H, m). | ESI-MS m/z: 462 [M + H]+ |

TABLE 18-continued

| Example | Structural formula | NMR | MS |
|---|---|---|---|
| 136 (isomer A) | | 1H-NMR (CDCl₃) δ: 2.28-2.30 (2H, m), 2.81-3.20 (4H, m), 4.09-4.26 (6H, m), 4.42-4.49 (1H, m), 4.61-4.63 (1H, m), 5.88 (1H, m), 6.05 (1H, s), 6.84 (1H, m), 6.94 (1H, s), 7.01 (2H, m). | ESI-MS m/z: 462 [M + H]+ |
| 136 (isomer B) | | 1H-NMR (CDCl₃) δ: 2.22-2.29 (2H, m), 2.84-3.20 (4H, m), 4.07-4.27 (6H, m), 4.41-4.45 (1H, m), 4.61-4.63 (1H, m), 5.87 (1H, m), 6.05 (1H, s), 6.85 (1H, m), 6.94 (1H, s), 7.01 (2H, m). | ESI-MS m/z: 462 [M + H]+ |
| 137 | | 1H-NMR (CDCl₃) δ: 2.18-2.25 (2H, m), 2.86 (1H, dd, J = 16.9, 3.7 Hz), 3.04 (2H, dt, J = 17.4, 4.4 Hz), 3.17 (1H, dd, J = 16.8, 5.3 Hz), 4.05-4.24 (6H, m), 4.41 (1H, m), 4.61 (1H, m), 5.73-6.04 (2H, m), 6.30 (1H, t, J = 73.5 Hz), 6.84 (1H, d, J = 8.3 Hz), 6.94 (1H, s), 7.00-7.02 (2H, m). | ESI-MS m/z: 444 [M + H]+ |
| 138 (isomer A) | | 1H-NMR (CDCl₃) δ: 2.16-2.29 (2H, m), 2.86 (1H, dd, J = 16.8, 4.1 Hz), 3.04 (2H, dt, J = 17.4, 4.5 Hz), 3.17 (1H, dd, J = 16.7, 5.5 Hz), 4.05-4.25 (6H, m), 4.41 (1H, m), 4.62 (1H, m), 5.88 (1H, tt, J = 56.7, 4.5 Hz), 6.04 (1H, s), 6.30 (1H, t, J = 73.4 Hz), 6.84 (1H, d, J = 8.3 Hz), 6.94 (1H, s), 7.00-7.02 (2H, m). | ESI-MS m/z: 444 [M + H]+ |
| 138 (isomer B) | | 1H-NMR (CDCl₃) δ: 2.17-2.28 (2H, m), 2.86 (1H, m), 3.04 (2H, dt, J = 17.4, 4.5 Hz), 3.17 (1H, dd, J = 16.8, 5.5 Hz), 4.05-4.26 (6H, m), 4.40 (1H, m), 4.62 (1H, m), 5.88 (1H, tt, J = 56.7, 4.5 Hz), 6.04 (1H, s), 6.30 (1H, t, J = 73.4 Hz), 6.84 (1H, d, J = 8.3 Hz), 6.94 (1H, s), 7.00-7.02 (2H, m). | ESI-MS m/z: 444 [M + H]+ |

TABLE 18-continued

| Example | Structural formula | NMR | MS |
| --- | --- | --- | --- |
| 139 | | 1H-NMR (CDCl₃) δ: 2.16-2.26 (2H, m), 2.87 (1H, dd, J = 16.8, 3.9 Hz), 3.18 (1H, dd, J = 16.7, 5.3 Hz), 3.82 (2H, q, J = 8.8 Hz), 4.05-4.14 (3H, m), 4.20-4.23 (3H, m), 4.41 (1H, m), 4.57-4.63 (3H, m), 6.04 (1H, s), 6.30 (1H, t, J = 73.4 Hz), 6.87 (1H, d, J = 8.3 Hz), 7.00-7.05 (2H, m), 7.12 (1H, d, J = 8.0 Hz). | ESI-MS m/z: 492 [M + H]+ |
| 140 (isomer A) | | 1H-NMR (CDCl₃) δ: 2.16-2.28 (2H, m), 2.87 (1H, dd, J = 16.8, 4.0 Hz), 3.18 (1H, dd, J = 16.7, 5.2 Hz), 3.82 (2H, q, J = 8.7 Hz), 4.05-4.14 (3H, m), 4.19-4.24 (3H, m), 4.41 (1H, s), 4.57 (2H, s), 4.63 (1H, m), 6.04 (1H, s), 6.30 (1H, t, J = 73.4 Hz), 6.87 (1H, d, J = 8.3 Hz), 7.01 (1H, d, J = 8.3 Hz), 7.05 (1H, s), 7.12 (1H, dd, J = 8.3, 2.0 Hz). | ESI-MS m/z: 492 [M + H]+ |
| 140 (isomer B) | | 1H-NMR (CDCl₃) δ: 2.18-2.27 (2H, m), 2.87 (1H, m), 3.18 (1H, dd, J = 16.9, 5.5 Hz), 3.82 (2H, q, J = 8.7 Hz), 4.05-4.14 (3H, m), 4.20-4.24 (3H, m), 4.40 (1H, m), 4.57 (2H, s), 4.62 (1H, m), 6.05 (1H, s), 6.30 (1H, t, J = 73.4 Hz), 6.88 (1H, d, J = 8.2 Hz), 7.01 (1H, d, J = 8.1 Hz), 7.05 (1H, s), 7.12 (1H, d, J = 8.1 Hz). | ESI-MS m/z: 492 [M + H]+ |

TABLE 19

| Example | Structural formula | NMR | MS |
| --- | --- | --- | --- |
| 141 | | 1H-NMR (CDCl₃) δ: 2.17-2.24 (2H, m), 2.82-2.88 (3H, m), 3.16 (1H, dd, J = 16.7, 5.3 Hz), 4.00-4.24 (8H, m), 4.41 (1H, m), 4.61 (1H, m), 6.00-6.48 (3H, m), 6.82 (1H, d, J = 8.3 Hz), 6.91 (1H, s), 6.97-7.33 (2H, m). | ESI-MS m/z: 474 [M + H]+ |
| 142 (isomer A) | | 1H-NMR (CDCl₃) δ: 2.16-2.26 (2H, m), 2.82-2.88 (3H, m), 3.16 (1H, dd, J = 16.7, 5.1 Hz), 4.00-4.23 (8H, m), 4.41 (1H, m), 4.61 (1H, m), 6.00-6.48 (3H, m), 6.82 (1H, d, J = 8.2 Hz), 6.91 (1H, s), 6.98-7.03 (2H, m). | ESI-MS m/z: 474 [M + H]+ |

TABLE 19-continued

| Example | Structural formula | NMR | MS |
|---|---|---|---|
| 142 (isomer B) | | 1H-NMR (CDCl₃) δ: 2.17-2.27 (2H, m), 2.82-2.88 (3H, m), 3.16 (1H, dd, J = 16.6, 5.3 Hz), 4.00-4.25 (8H, m), 4.40 (1H, m), 4.61 (1H, m), 6.00-6.48 (3H, m), 6.82 (1H, d, J = 8.3 Hz), 6.91 (1H, s), 6.98-7.03 (2H, m). | ESI-MS m/z: 474 [M + H]+ |
| 143 | | 1H-NMR (CDCl₃) δ: 2.03-2.25 (4H, m), 2.91 (1H, m), 3.17 (1H, m), 4.07-4.31 (6H, m), 4.38 (1H, m), 4.63 (1H, m), 6.01 (1H, m), 6.91-6.94 (2H, m), 7.38 (1H, m), 7.42 (1H, m). | ESI-MS m/z: 437 [M + H]+ |
| 144 (isomer A) | | 1H-NMR (CDCl₃) δ: 2.07-2.24 (4H, m), 2.91 (1H, m), 3.17 (1H, dd, J = 16.6, 5.2 Hz), 4.07-4.31 (6H, m), 4.38 (1H, m), 4.63 (1H, m), 6.01 (1H, s), 6.91-6.94 (2H, m), 7.38 (1H, s), 7.42 (1H, d, J = 8.7 Hz). | ESI-MS m/z: 437 [M + H]+ |
| 144 (isomer B) | | 1H-NMR (CDCl₃) δ: 2.09-2.24 (4H, m), 2.90 (1H, dd, J = 16.9, 5.0 Hz), 3.17 (1H, dd, J = 5.2, 16.7 Hz), 4.06-4.31 (6H, m), 4.37 (1H, m), 4.63 (1H, s), 6.02 (1H, s), 6.90-6.94 (2H, m), 7.39 (1H, s), 7.42 (1H, d, J = 8.6 Hz). | ESI-MS m/z: 437 [M + H]+ |
| 145 | | 1H-NMR (CDCl₃) δ: 2.04-2.18 (3H, m), 2.23 (1H, m), 2.91 (1H, m), 3.17 (1H, m), 4.02-4.19 (4H, m), 4.23-4.31 (2H, m), 4.38 (1H, m), 4.63 (1H, m), 6.01 (1H, m), 6.22 (1H, m), 6.91-6.94 (2H, m), 7.38 (1H, m), 7.42 (1H, m). | ESI-MS m/z: 419 [M + H]+ |
| 146 (isomer A) | | 1H-NMR (CDCl₃) δ: 1.99-2.16 (3H, m), 2.23 (1H, m), 2.91 (1H, dd, J = 16.7, 4.8 Hz), 3.17 (1H, dd, J = 5.2, 16.8 Hz), 4.02-4.20 (4H, m), 4.23-4.32 (2H, m), 4.38 (1H, m), 4.63 (1H, m), 6.01 (1H, s), 6.22 (1H, t, J = 74.4 Hz), 6.91-6.94 (2H, m), 7.38 (1H, s), 7.42 (1H, dd, J = 8.5, 2.0 Hz). | ESI-MS m/z: 419 [M + H]+ |

TABLE 19-continued

| Example | Structural formula | NMR | MS |
| --- | --- | --- | --- |
| 146 (isomer B) | (structure) | 1H-NMR (CDCl₃) δ: 2.01-2.17 (3H, m), 2.23 (1H, m), 2.91 (1H, m), 3.17 (1H, dd, J = 16.8, 5.1 Hz), 4.02-4.13 (3H, m), 4.18 (1H, m), 4.23-4.31 (2H, m), 4.37 (1H, m), 4.63 (1H, m), 6.01 (1H, s), 6.22 (1H, t, J = 74.4 Hz), 6.90-6.93 (2H, m), 7.39 (1H, s), 7.42 (1H, dd, J = 8.5, 2.0 Hz). | ESI-MS m/z: 419 [M + H]+ |

TABLE 20

| Example | Structural formula | NMR | MS |
| --- | --- | --- | --- |
| 147 | (structure) | 1H-NMR (CDCl₃) δ: 2.00-2.16 (3H, m), 2.22 (1H, m), 2.86 (1H, m), 2.99-3.09 (2H, m), 3.16 (1H, m), 4.02-4.21 (6H, m), 4.37 (1H, m), 4.61 (1H, m), 5.72-6.40 (3H, m), 6.84 (1H, m), 6.94 (1H, m), 7.00-7.02 (2H, m). | ESI-MS m/z: 458 [M + H]+ |
| 148 (isomer A) | (structure) | 1H-NMR (CDCl₃) δ: 2.00-2.15 (3H, m), 2.22 (1H, m), 2.86 (1H, m), 3.02 (2H, dt, J = 26.2, 4.4 Hz), 3.16 (1H, dd, J = 16.8, 5.4 Hz), 4.02-4.22 (6H, m), 4.37 (1H, m), 4.61 (1H, m), 5.72-6.40 (3H, m), 6.84 (1H, d, J = 8.3 Hz), 6.94 (1H, s), 7.01 (2H, m). | ESI-MS m/z: 458 [M + H]+ |
| 148 (isomer B) | (structure) | 1H-NMR (CDCl₃) δ: 2.00-2.16 (3H, m), 2.22 (1H, m), 2.86 (1H, m), 3.02 (2H, dt, J = 26.2, 4.2 Hz), 3.17 (1H, m), 4.03-4.21 (6H, m), 4.36 (1H, m), 4.62 (1H, m), 5.73-6.40 (3H, m), 6.84 (1H, d, J = 8.3 Hz), 6.94 (1H, s), 7.00-7.02 (2H, m). | ESI-MS m/z: 458 [M + H]+ |
| 149 | (structure) | 1H-NMR (CDCl₃) δ: 2.02-2.24 (4H, m), 2.87 (1H, m), 3.18 (1H, m), 3.79-3.85 (2H, m), 4.02-4.22 (6H, m), 4.37 (1H, m), 4.57-4.63 (3H, m), 6.00 (1H, m), 6.22 (1H, m), 6.87 (1H, m), 7.00 (1H, m), 7.05 (1H, m), 7.12 (1H, m). | ESI-MS m/z: 506 [M + H]+ |

TABLE 20-continued

| Example | Structural formula | NMR | MS |
|---|---|---|---|
| 150 (isomer A) | | 1H-NMR (CDCl₃) δ: 2.00-2.30 (4H, m), 2.87 (1H, m), 3.18 (1H, dd, J = 16.6, 5.1 Hz), 3.82 (2H, q, J = 8.7 Hz), 4.02-4.23 (6H, m), 4.38 (1H, m), 4.57 (2H, s), 4.63 (1H, m), 6.00 (1H, s), 6.22 (1H, t, J = 74.4 Hz), 6.87 (1H, d, J = 8.3 Hz), 7.00 (1H, d, J = 7.8 Hz), 7.05 (1H, s), 7.12 (1H, d, J = 7.8 Hz). | ESI-MS m/z: 506 [M + H]+ |
| 150 (isomer B) | | 1H-NMR (CDCl₃) δ: 2.00-2.25 (4H, m), 2.87 (1H, dd, J = 17.1, 4.3 Hz), 3.18 (1H, dd, J = 16.8, 5.4 Hz), 3.82 (2H, q, J = 8.8 Hz), 4.02-4.23 (6H, m), 4.37 (1H, m), 4.57 (2H, s), 4.62 (1H, m), 6.00 (1H, s), 6.22 (1H, t, J = 74.4 Hz), 6.87 (1H, d, J = 8.3 Hz), 7.01 (1H, d, J = 7.6 Hz), 7.05 (1H, s), 7.12 (1H, dd, J = 8.3, 2.0 Hz). | ESI-MS m/z: 506 [M + H]+ |
| 151 | | 1H-NMR (CDCl₃) δ: 2.14-2.27 (2H, m), 2.84 (1H, dd, J = 16.5, 4.0 Hz), 3.05-3.26 (5H, m), 4.04-4.22 (5H, m), 4.28 (1H, m), 4.61 (1H, m), 6.00 (1H, s), 6.81 (1H, d, J = 8.7 Hz), 6.98-7.09 (3H, m). | ESI-MS m/z: 445 [M + H]+ |
| 152 (isomer A) | | 1H-NMR (CDCl₃) δ: 2.16-2.23 (2H, m), 2.84 (1H, dd, J = 17.0, 4.3 Hz), 3.03-3.08 (2H, m), 3.15 (1H, dd, J = 16.9, 5.4 Hz), 3.26 (2H, q, J = 9.3 Hz), 4.09 (1H, m), 4.16-4.22 (3H, m), 4.28 (1H, m), 4.60 (1H, m), 6.01 (1H, s), 6.81 (1H, d, J = 8.7 Hz), 6.99 (1H, d, J = 7.2 Hz), 7.04 (1H, s), 7.08 (1H, dd, J = 8.7, 2.3 Hz). | ESI-MS m/z: 445 [M + H]+ |
| 152 (isomer B) | | 1H-NMR (CDCl₃) δ: 2.14-2.27 (2H, m), 2.85 (1H, m), 3.03-3.08 (2H, m), 3.15 (1H, m), 3.26 (2H, q, J = 9.3 Hz), 4.08 (1H, m), 4.18-4.22 (3H, m), 4.29 (1H, m), 4.61 (1H, m), 6.01 (1H, s), 6.81 (1H, d, J = 8.7 Hz), 6.99 (1H, d, J = 7.8 Hz), 7.04 (1H, s), 7.08 (1H, dd, J = 8.6, 2.4 Hz). | ESI-MS m/z: 445 [M + H]+ |

TABLE 21

| Example | Structural formula | NMR | MS |
|---|---|---|---|
| 153 (isomer A) | 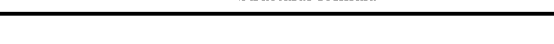 | 1H-NMR (CDCl₃) δ: 2.10-2.34 (4H, m), 2.76-2.90 (5H, m), 2.93-3.10 (2H, m), 3.14 (1H, dd, J = 16.7, 5.1 Hz), 4.08 (1H, m), 4.15-4.21 (3H, m), 4.31 (1H, m), 4.60 (1H, m), 6.01 (1H, s), 6.81 (1H, d, J = 8.6 Hz), 6.98 (1H, d, J = 8.3 Hz), 7.04 (1H, s), 7.08 (1H, d, J = 9.0 Hz). | ESI-MS m/z: 453 [M + H]+ |

TABLE 21-continued

| Example | Structural formula | NMR | MS |
|---|---|---|---|
| 153 (isomer B) | | 1H-NMR (CDCl₃) δ: 2.10-2.34 (4H, m), 2.77-2.90 (5H, m), 2.94-3.08 (2H, m), 3.15 (1H, m), 4.08 (1H, m), 4.19 (3H, d, J = 2.4 Hz), 4.29 (1H, m), 4.61 (1H, m), 6.01 (1H, s), 6.81 (1H, d, J = 8.6 Hz), 6.98 (1H, d, J = 7.8 Hz), 7.04 (1H, s), 7.08 (1H, d, J = 9.0 Hz). | ESI-MS m/z: 453 [M + H]+ |
| 154 (isomer A) | | 1H-NMR (CDCl₃) δ: 2.10-2.33 (4H, m), 2.76-2.90 (5H, m), 2.93-3.08 (2H, m), 3.18 (1H, dd, J = 16.5, 5.0 Hz), 3.82 (2H, q, J = 8.7 Hz), 4.08 (1H, m), 4.15-4.20 (3H, m), 4.30 (1H, m), 4.57 (2H, s), 4.62 (1H, m), 6.01 (1H, s), 6.87 (1H, d, J = 8.3 Hz), 7.00 (1H, d, J = 8.1 Hz), 7.04 (1H, s), 7.12 (1H, d, J = 8.0 Hz). | ESI-MS m/z: 531 [M + H]+ |
| 155 | | 1H-NMR (CDCl₃) δ: 2.20 (1H, m), 2.38 (1H, m), 2.91 (1H, dd, J = 17.7, 4.4 Hz), 3.12-3.22 (2H, m), 3.30 (1H, dd, J = 15.7, 6.3 Hz), 4.09 (1H, m), 4.07-4.17 (1H, m), 4.18-4.31 (3H, m), 4.63 (1H, m), 6.04 (1H, s), 6.93 (2H, m), 7.38 (1H, s), 7.42 (1H, d, J = 8.7 Hz). | ESI-MS m/z: 439 [M + H]+ |
| 156 (isomer A) | | 1H-NMR (CDCl₃) δ: 2.20 (1H, m), 2.38 (1H, m), 2.91 (1H, dd, J = 17.7, 4.4 Hz), 3.12-3.22 (2H, m), 3.30 (1H, dd, J = 15.7, 6.3 Hz), 4.09 (1H, m), 4.07-4.17 (1H, m), 4.18-4.31 (3H, m), 4.63 (1H, m), 6.04 (1H, s), 6.93 (2H, m), 7.38 (1H, s), 7.42 (1H, d, J = 8.7 Hz). | ESI-MS m/z: 439 [M + H]+ |
| 156 (isomer B) | | 1H-NMR (CDCl₃) δ: 2.20 (1H, m), 2.38 (1H, m), 2.91 (1H, dd, J = 17.7, 4.4 Hz), 3.12-3.22 (2H, m), 3.30 (1H, dd, J = 15.7, 6.3 Hz), 4.09 (1H, m), 4.07-4.17 (1H, m), 4.18-4.31 (3H, m), 4.63 (1H, m), 6.04 (1H, s), 6.93 (2H, m), 7.38 (1H, s), 7.42 (1H, d, J = 8.7 Hz). | ESI-MS m/z: 439 [M + H]+ |
| 157 | | 1H-NMR (CDCl₃) δ: 2.26-2.38 (2H, m), 2.84 (1H, dd, J = 16.7, 3.5 Hz), 3.15 (1H, dd, J = 16.9, 5.5 Hz), 4.08-4.19 (3H, m), 4.27 (1H, m), 4.38 (1H, m), 4.61 (1H, m), 5.82-6.10 (2H, m), 6.81 (1H, d, J = 8.7 Hz), 6.98-7.10 (3H, m). | ESI-MS m/z: 384 [M + H]+ |

TABLE 21-continued

| Example | Structural formula | NMR | MS |
|---|---|---|---|
| 158 (isomer A) | (structure) | 1H-NMR (CDCl$_3$) δ: 2.29-2.36 (2H, m), 2.84 (1H, dd, J = 16.8, 4.0 Hz), 3.15 (1H, dd, J = 16.8, 5.4 Hz), 4.08-4.30 (4H, m), 4.38 (1H, m), 4.61 (1H, m), 5.90 (1H, dt, J = 82.1, 3.4 Hz), 6.08 (1H, s), 6.81 (1H, d, J = 8.6 Hz), 6.99 (1H, d, J = 8.2 Hz), 7.04 (1H, s), 7.09 (1H, dd, J = 8.7, 2.4 Hz). | ESI-MS m/z: 384 [M + H]+ |
| 158 (isomer B) | (structure) | 1H-NMR (CDCl$_3$) δ: 2.26-2.38 (2H, m), 2.85 (1H, dd, J = 16.6, 3.7 Hz), 3.15 (1H, dd, J = 16.5, 5.1 Hz), 4.08-4.38 (4H, m), 4.36 (1H, m), 4.60 (1H, m), 5.83-6.11 (2H, m), 6.81 (1H, d, J = 8.7 Hz), 6.99 (1H, d, J = 7.1 Hz), 7.04 (1H, s), 7.09 (1H, dd, J = 8.7, 2.4 Hz). | ESI-MS m/z: 384 [M + H]+ |

TABLE 22

| Example | Structural formula | NMR | MS |
|---|---|---|---|
| 159 | (structure) | 1H-NMR (CDCl$_3$) δ: 2.26-2.38 (2H, m), 2.85 (1H, dd, J = 16.7, 3.7 Hz), 3.15 (1H, dd, J = 16.9, 5.4 Hz), 4.08-4.29 (4H, m), 4.37 (1H, m), 4.60 (1H, m), 5.90 (1H, dt, J = 82.3, 3.2 Hz), 6.08 (1H, s), 6.76 (1H, s, J = 8.6 Hz), 6.99 (1H, d, J = 7.8 Hz), 7.19 (1H, s), 7.22 (1H, dd, J = 8.6, 2.4 Hz). | ESI-MS m/z: 428, 430 [M + H]+ |
| 160 | (structure) | 1H-NMR (CDCl$_3$) δ: 2.28-2.38 (2H, m), 2.92 (1H, m), 3.21 (1H, m), 4.32 (1H, m), 4.22-4.42 (4H, m), 4.65 (1H, m), 5.83-6.10 (2H, m), 6.94-6.98 (2H, m), 7.33 (1H, m), 7.39 (1H, m). | ESI-MS m/z: 418 [M + H]+ |
| 161 (isomer A) | (structure) | 1H-NMR (CDCl$_3$) δ: 2.25-2.40 (2H, m), 2.92 (1H, dd, J = 16.9, 4.2 Hz), 3.21 (1H, dd, J = 16.9, 5.4 Hz), 4.12 (1H, m), 4.25-4.30 (3H, m), 4.39 (1H, m), 4.65 (1H, m), 5.82-6.10 (2H, m), 6.94-6.98 (2H, m), 7.33 (1H, s), 7.38 (1H, d, J = 8.6 Hz). | ESI-MS m/z: 418 [M + H]+ |

TABLE 22-continued

| Example | Structural formula | NMR | MS |
|---|---|---|---|
| 161 (isomer B) | | 1H-NMR (CDCl$_3$) δ: 2.28-2.35 (2H, m), 2.92 (1H, dd, J = 16.3, 4.1 Hz), 3.21 (1H, dd, J = 16.4, 5.2 Hz), 4.12 (1H, m), 4.25-4.30 (3H, m), 4.38 (1H, m), 4.65 (1H, m), 5.83-6.11 (2H, m), 6.94-6.98 (2H, m), 7.33 (1H, s), 7.39 (1H, d, J = 8.8 Hz). | ESI-MS m/z: 418 [M + H]+ |
| 162 | | 1H-NMR (CDCl$_3$) δ: 2.24-2.37 (2H, m), 2.87 (1H, m), 3.18 (1H, m), 3.77-3.86 (2H, m), 4.11 (1H, m), 4.20-4.21 (2H, m), 4.28 (1H, m), 4.38 (1H, m), 4.57-4.63 (3H, m), 5.82-6.30 (2H, m), 6.88 (1H, m), 7.01 (1H, m), 7.05 (1H, m), 7.12 (1H, m). | ESI-MS m/z: 462 [M + H]+ |
| 163 (isomer A) | | 1H-NMR (CDCl$_3$) δ: 2.25-2.37 (2H, m), 2.87 (1H, m), 3.18 (1H, dd, J = 16.9, 5.6 Hz), 3.82 (2H, q, J = 8.7 Hz), 4.12 (1H, m), 4.21 (2H, d, J = 2.1 Hz), 4.26 (1H, m), 4.38 (1H, m), 4.67 (2H, s), 4.62 (1H, m), 5.82-6.10 (2H, m), 6.88 (1H, d, J = 8.4 Hz), 7.01 (1H, d, J = 8.1 Hz) 7.05 (1H, s), 7.12 (1H, d, J = 8.7 Hz). | ESI-MS m/z: 462 [M + H]+ |
| 163 (isomer B) | | 1H-NMR (CDCl$_3$) δ: 2.26-2.39 (2H, m), 2.87 (1H, dd, J = 16.5, 4.0 Hz), 3.18 (1H, dd, J = 16.7, 5.4 Hz), 3.82 (2H, q, J = 8.8 Hz), 4.20 (2H, d, J = 2.92 Hz), 4.27 (1H, m), 4.37 (1H, m), 4.57 (2H, s), 4.63 (1H, m), 5.82-6.11 (2H, m), 6.88 (1H, d, J = 8.3 Hz), 7.01 (1H, d, J = 8.0 Hz), 7.05 (1H, s), 7.12 (1H, dd, J = 8.4, 2.0 Hz). | ESI-MS m/z: 462 [M + H]+ |
| 164 | | 1H-NMR (CDCl$_3$) δ: 2.25-2.38 (2H, m), 2.82-2.88 (3H, m), 3.17 (1H, m), 4.00-4.03 (2H, m), 4.07-4.18 (3H, m), 4.27 (1H, m), 4.38 (1H, m), 4.61 (1H, m), 5.82-6.38 (3H, m), 6.82 (1H, m), 6.91 (1H, m), 6.99 (1H, m), 7.03 (1H, m). | ESI-MS m/z: 444 [M + H]+ |
| 165 (isomer A) | | 1H-NMR (CDCl$_3$) δ: 2.26-2.37 (2H, m), 2.82-2.88 (3H, m), 3.17 (1H, dd, J = 16.6, 5.4 Hz), 4.01 (2H, t, J = 7.1 Hz), 4.09-4.16 (3H, m), 4.27 (1H, m), 4.38 (1H, m), 4.62 (1H, m), 5.82-6.38 (3H, m), 6.82 (1H, d, J = 8.3 Hz), 6.91 (1H, s), 6.99 (1H, d, J = 8.4 Hz), 7.03 (1H, d, J = 8.0 Hz). | ESI-MS m/z: 444 [M + H]+ |

TABLE 23

| Example | Structural formula | NMR | MS |
|---|---|---|---|
| 165 (isomer B) | | 1H-NMR (CDCl₃) δ: 2.26-2.39 (2H, m), 2.82-2.88 (3H, m), 3.17 (1H, dd, J = 16.7, 5.4 Hz), 4.01 (2H, t, J = 7.1 Hz), 4.07-4.18 (3H, m), 4.28 (1H, m), 4.37 (1H, m), 4.61 (1H, m), 5.82-6.38 (3H, m), 6.82 (1H, d, J = 8.3 Hz), 6.91 (1H, s), 6.99 (1H, dd, 8.4, 2.0 Hz), 7.03 (1H, d, J = 7.9 Hz). | ESI-MS m/z: 444 [M + H]+ |
| 166 | | 1H-NMR (CDCl₃) δ: 1.44-1.54 (6H, m), 2.17 (1H, m), 2.31 (1H, m), 2.84 (1H, dd, J = 16.7, 3.8 Hz), 3.15 (1H, dd, J = 16.5, 5.3 Hz), 4.03-4.13 (2H, m), 4.19 (2H, d, J = 3.0 Hz), 4.24 (1H, dd, J = 12.6, 5.9 Hz), 4.60 (1H, m), 6.03 (1H, s), 6.81 (1H, d, J = 8.6 Hz), 6.99 (1H, d, J = 8.1 Hz), 7.04 (1H, s), 7.08 (1H, dd, J = 8.7, 2.4 Hz). | ESI-MS m/z: 394 [M + H]+ |
| 167 | | 1H-NMR (CDCl₃) δ: 1.78 (3H, t, J = 19.1 Hz), 2.24-2.41 (2H, m), 2.85 (1H, m), 3.15 (1H, dd, J = 16.9, 5.3 Hz, 4.09 (1H, m), 4.19 (2H, d, J = 2.6 Hz), 4.23-4.29 (2H, m), 4.60 (1H, m), 8.07 (1H, s), 6.81 (1H, d, J = 6.7 Hz), 6.99 (1H, d, J = 8.0 Hz), 7.04 (1H, s), 7.08 (1H, dd, J = 8.6, 2.4 Hz). | ESI-MS m/z: 398 [M + H]+ |
| 168 | | 1H-NMR (CDCl₃) δ: 0.91-0.95 (6H, m), 1.44-1.77 (5H, m), 2.17-2.28 (2H, m), 2.65 (1H, m), 3.14 (1H, dd, J = 16.4, 5.2 Hz), 4.01-4.12 (2H, m), 4.15-4.25 (3H, m), 4.60 (1H, m), 6.01 (1H, s), 6.81 (1H, d, J = 8.7 Hz), 6.99 (1H, d, J = 8.0 Hz), 7.04 (1H, s), 7.08 (1H, d, J = 8.8 Hz). | ESI-MS m/z: 420 [M + H]+ |
| 169 | | 1H-NMR (CDCl₃) δ: 2.32-2.50 (2H, m), 2.84 (1H, dd, J = 16.0, 4.6 Hz), 3.15 (1H, dd, J = 17.4, 5.8 Hz), 4.09-4.24 (3H, m), 4.25-4.32 (1H, m), 4.58-4.62 (2H, m), 6.13 (1H, s), 6.81 (1H, d, J = 9.2 Hz), 6.96-7.10 (3H, m). | ESI-MS m/z: 402 [M + H]+ |
| 170 (isomer A) | | 1H-NMR (CDCl₃) δ: 2.29-2.51 (2H, m), 2.83 (1H, dd, J = 16.0, 4.6 Hz), 3.15 (1H, dd, J = 17.4, 5.8 Hz), 4.10-4.24 (3H, m), 4.25-4.32 (1H, m), 4.57-4.61 (2H, m), 6.13 (1H, s), 6.81 (1H, d, J = 9.2 Hz), 6.96-7.12 (3H, m). | ESI-MS m/z: 402 [M + H]+ |

TABLE 23-continued

| Example | Structural formula | NMR | MS |
|---|---|---|---|
| 170 (isomer B) | (structure with Cl-substituted chromane) | 1H-NMR (CDCl₃) δ: 2.29-2.49 (2H, m), 2.84 (1H, dd, J = 16.0, 4.6 Hz), 3.15 (1H, dd, J = 17.4, 5.8 Hz), 4.10-4.26 (3H, m), 4.27-4.34 (1H, m), 4.57-4.60 (2H, m), 6.13 (1H, s), 6.81 (1H, d, J = 9.2 Hz), 6.95-7.16 (3H, m). | ESI-MS m/z: 402 [M + H]+ |
| 171 | (structure with Br-substituted chromane) | 1H-NMR (CDCl₃) δ: 2.40-2.45 (2H, m), 2.81 (1H, dd, J = 17.0, 3.9 Hz), 3.16 (1H, dd, J = 16.7, 5.0 Hz), 4.16-4.23 (3H, m), 4.26-4.31 (1H, m), 4.56-4.61 (2H, m), 6.13 (1H, s), 6.77 (1H, d, J = 8.6 Hz), 6.99 (1H, d, J = 8.4 Hz), 7.19-7.24 (2H, m). | ESI-MS m/z: 446, 448 [M + H]+ |
| 172 | (structure with CHF₂-CH₂-substituted chromane) | 1H-NMR (CDCl₃) δ: 2.33-2.46 (2H, m), 2.86 (1H, dd, J = 16.9, 3.4 Hz), 3.04 (2H, dt, J = 17.4, 4.4 Hz), 3.17 (1H, dd, J = 16.8, 5.7 Hz), 4.10-4.19 (3H, m), 4.27 (1H, m), 4.55-4.65 (2H, m), 5.88 (1H, tt, J = 56.7, 4.5 Hz), 6.13 (1H, s), 6.85 (1H, s, J = 8.3 Hz), 6.94 (1H, s), 7.01 (2H, d, J = 8.4 Hz). | ESI-MS m/z: 432 [M + H]+ |

TABLE 24

| Example | Structural formula | NMR | MS |
|---|---|---|---|
| 173 (isomer A) | (structure with CHF₂-CH₂-substituted chromane) | 1H-NMR (CDCl₃) δ: 2.34-2.45 (2H, m), 2.86 (1H, m), 3.04 (2H, dt, J = 17.3, 4.5 Hz), 3.18 (1H, dd, J = 16.9, 5.3 Hz), 4.12-4.20 (3H, m), 4.26 (1H, m), 4.58-4.62 (2H, m), 5.88 (1H, m), 6.13 (1H, s), 6.85 (1H, d, J = 8.4 Hz), 6.94 (1H, s), 7.02 (2H, d, J = 8.8 Hz). | ESI-MS m/z: 432 [M + H]+ |
| 173 (isomer B) | (structure with CHF₂-CH₂-substituted chromane) | 1H-NMR (CDCl₃) δ: 2.35-2.74 (2H, m), 2.86 (1H, dd, J = 16.9, 3.8 Hz), 3.04 (2H, dt, J = 17.4, 4.5 Hz), 3.17 (1H, dd, J = 16.7, 6.4 Hz), 4.10-4.18 (3H, m), 4.29 (1H, m), 4.53-4.65 (2H, m), 5.88 (1H, tt, J = 56.7, 4.5 Hz), 6.13 (1H, s), 6.85 (1H, d, J = 8.3 Hz), 6.94 (1H, s), 7.01 (2H, dd, J = 8.4, 2.0 Hz). | ESI-MS m/z: 432 [M + H]+ |
| 174 | (structure with CN-pyridyl-substituted chromane) | 1H-NMR (CDCl₃) δ: 2.35-2.46 (2H, m), 2.98 (1H, dd, J = 16.3, 4.0 Hz), 3.26 (1H, dd, J = 17.1, 5.7 Hz), 4.10-4.19 (1H, m), 4.24-4.31 (3H, m), 4.55-4.61 (1H, m), 4.66-4.68 (1H, m), 6.15 (1H, s), 7.01-7.04 (2H, m), 7.32 (1H, s), 7.39 (1H, dd, J = 8.6, 2.4 Hz), 7.73 (1H, d, J = 8.1 Hz), 7.93 (1H, dd, J = 8.0, 2.1 Hz), 8.89 (1H, d, J = 1.8 Hz). | ESI-MS m/z: 470 [M + H]+ |

TABLE 24-continued

| Example | Structural formula | NMR | MS |
| --- | --- | --- | --- |
| 175 | | 1H-NMR (CDCl₃) δ: 2.33-2.47 (2H, m), 2.59 (3H, s), 2.97 (1H, dd, J = 15.6, 3.0 Hz), 3.25 (1H, dd, J = 16.6, 5.2 Hz), 4.12-4.19 (1H, m), 4.25-4.31 (3H, m), 4.54-4.60 (1H, m), 4.65-4.68 (1H, m), 6.14 (1H, s), 6.98 (1H, d, J = 8.4 Hz), 7.05 (1H, d, J = 7.8 Hz), 7.19 (1H, d, J = 8.1 Hz), 7.33-7.35 (1H, m), 7.71 (1H, dd, J = 8.1, 2.1 Hz), 8.67 (1H, d, J = 1.3 Hz). | ESI-MS m/z: 459 [M + H]+ |
| 176 | | 1H-NMR (CDCl₃) δ: 2.33-2.48 (2H, m), 2.96 (1H, dd, J = 16.3, 3.3 Hz), 3.25 (1H, dd, J = 16.2, 5.4 Hz), 4.05 (3H, s), 4.12-4.19 (1H, m), 4.25-4.30 (3H, m), 4.54-4.61 (1H, m), 4.66-4.68 (1H, m), 6.14 (1H, s), 6.98-7.05 (2H, m), 7.21 (1H, s), 7.26-7.30 (1H, m), 8.66 (2H, d, J = 1.3 Hz). | ESI-MS m/z: 476 [M + H]+ |
| 177 | | 1H-NMR (CDCl₃) δ: 1.42 (6H, s), 2.08 (2H, t, J = 6.5 Hz), 2.84 (1H, dd, J = 17.3, 4.2 Hz), 3.14 (1H, dd, J = 16.5, 5.3 Hz), 4.10 (2H, t, J = 6.5 Hz), 4.19 (2H, d, J = 3.1 Hz), 4.60-4.61 (1H, m), 5.97 (3H, s), 6.81 (1H, d, J = 8.6 Hz), 6.97-7.09 (3H, m). | ESI-MS m/z: 362 [M + H]+ |
| 178 | | 1H-NMR (CDCl₃) δ: 1.42 (6H, s), 2.08 (2H, t, J = 6.5 Hz), 2.91 (1H, dd, J = 17.0, 4.8 Hz), 3.17 (1H, dd, J = 17.0, 5.6 Hz), 4.10 (2H, s, J = 5.5 Hz), 4.26-4.32 (2H, m), 4.62-4.65 (1H, m), 5.97 (1H, s), 6.91-6.94 (2H, m), 7.39 (1H, s), 7.42 (1H, d, J = 8.5 Hz). | ESI-MS m/z: 353 [M + H]+ |
| 179 | | 1H-NMR (CDCl₃) δ: 1.42 (6H, d, J = 3.7 Hz), 2.08 (2H, t, J = 6.4 Hz), 2.98 (1H, dd, J = 16.1, 4.0 Hz), 3.26 (1H, dd, J = 16.5, 5.3 Hz), 4.09 (2H, t, J = 6.9 Hz), 4.23-4.31 (2H, m), 4.66-4.67 (1H, m), 5.98 (1H, s), 7.02 (2H, d, J = 8.5 Hz), 7.31 (1H, s), 7.39 (1H, dd, J = 6.5, 2.1 Hz, 7.73 (1H, d, J = 8.1 Hz), 7.93 (1H, dd, J = 8.1, 2.3 Hz), 8.89 (1H, d, J = 1.6 Hz). | ESI-MS m/z: 430 [M + H]+ |
| 180 | | 1H-NMR (CDCl₃) δ: 1.66-1.75 (1H, m), 1.91-2.04 (1H, m), 2.09-2.27 (4H, m), 2.36 (2H, m), 2.90 (1H, dd, J = 16.1, 5.0 Hz), 3.16 (1H, dd, J =17.0, 5.0 Hz), 4.10 (2H, t, J = 6.3 Hz), 4.21-4.32 (2H, m), 4.63 (1H, m), 6.00 (1H, s), 6.88-6.96 (2H, m), 7.38 (1H, s), 7.42 (1H, d, J = 8.4 Hz). | ESI-MS m/z: 365 [M + H]+ |

TABLE 25

| Example | Structural formula | NMR | MS |
|---|---|---|---|
| 181 | (structure) | 1H-NMR (CDCl₃) δ: 2.88 (1H, dd, J = 16.2, 4.0 Hz), 3.20 (1H, dd, J = 16.9, 4.3 Hz), 4.15-4.21 (3H, m), 4.57-4.65 (2H, m), 5.98 (1H, s), 6.18 (1H, dt, J = 12.4, 3.2 Hz), 6.86-6.91 (2H, m), 7.05-7.07 (2H, m), 7.13 (1H, t, J = 7.4 Hz), 7.37-7.44 (5H, m). | ESI-MS m/z: 362 [M + H]+ |
| 182 | (structure) | 1H-NMR (CDCl₃) δ: 2.91 (1H, dd, J = 16.6, 4.5 Hz), 3.18 (1H, dd, J = 17.1, 4.1 Hz), 4.18 (1H, m), 4.24-4.33 (2H, m), 4.59-4.68 (2H, m), 5.99 (1H, s), 6.20 (1H, dt, J = 12.5, 1.8 Hz), 6.91-6.98 (2H, m), 7.36-7.45 (7H, m). | ESI-MS m/z: 409 [M + H]+ |
| 183 | (structure) | 1H-NMR (CDCl₃) δ: 2.86 (1H, dd, J = 16.8, 5.2 Hz), 3.19 (1H, dd, J = 16.8, 5.6 Hz), 3.82 (2H, dd, J = 17.8, 9.7 Hz), 4.16-4.25 (2H, m), 4.36 (1H, dd, J = 10.5, 5.5 Hz), 4.50 (1H, t, J = 9.5 Hz), 4.57 (2H, s), 4.63 (1H, m), 5.50 (1H, m), 6.03 (1H, s), 6.88 (1H, d, J = 8.8 Hz), 7.00 (1H, d, J = 6.8 Hz), 7.05 (1H, s), 7.12 (1H, d, J = 8.8 Hz). | ESI-MS m/z: 466 [M + H]+ |
| 184 (isomer A) | (structure) | 1H-NMR (CDCl₃) δ: 2.86 (1H, dd, J = 16.8, 5.2 Hz), 3.19 (1H, dd, J = 16.8, 5.6 Hz), 3.82 (2H, dd, J = 17.8, 9.7 Hz), 4.16-4.25 (2H, m), 4.36 (1H, dd, J = 10.5, 5.5 Hz), 4.50 (1H, t, J = 9.5 Hz), 4.57 (2H, s), 4.63 (1H, m), 5.50 (1H, m), 6.03 (1H, s), 6.88 (1H, d, J = 8.8 Hz), 7.00 (1H, d, J = 6.8 Hz), 7.05 (1H, s), 7.12 (1H, d, J = 8.8 Hz). | ESI-MS m/z: 466 [M + H]+ |
| 184 (isomer B) | (structure) | 1H-NMR (CDCl₃) δ: 2.86 (1H, dd, J = 16.8, 5.2 Hz), 3.19 (1H, dd, J = 16.8, 5.6 Hz), 3.82 (2H, dd, J = 17.8, 9.7 Hz), 4.16-4.25 (2H, m), 4.36 (1H, dd, J = 10.5, 5.5 Hz), 4.50 (1H, t, J = 9.5 Hz), 4.57 (2H, s), 4.63 (1H, m), 5.50 (1H, m), 6.03 (1H, s), 6.88 (1H, d, J = 8.8 Hz), 7.00 (1H, d, J = 6.8 Hz), 7.05 (1H, s), 7.12 (1H, d, J = 8.8 Hz). | ESI-MS m/z: 466 [M + H]+ |
| 185 | (structure) | 1H-NMR (CDCl₃) δ: 0.15-0.19 (2H, m), 0.50-0.57 (2H, m), 1.02 (1H, m), 2.87 (1H, m), 3.18 (1H, m), 3.36 (2H, dd, J = 6.9, 3.8 Hz), 3.73-3.85 (4H, m), 4.14-4.20 (3H, m), 4.31 (1H, dt, J = 13.6, 4.4 Hz), 4.57 (2H, s), 4.63 (1H, m), 5.41 (1H, m), 5.91 (1H, s), 6.87 (1H, d, J = 8.3 Hz), 7.00-7.14 (2H, m), 7.11 (1H, dd, J = 8.3, 2.1 Hz). | ESI-MS m/z: 482 [M + H]+ |
| 186 (isomer A) | (structure) | 1H-NMR (CDCl₃) δ: 0.14-0.23 (2H, m), 0.49-0.57 (2H, m), 1.02 (1H, m), 2.87 (1H, dd, J = 16.8, 4.3 Hz), 3.18 (1H, dd, J = 16.6, 5.3 Hz), 3.36 (2H, d, J = 6.9 Hz), 3.73-3.85 (4H, m), 4.14-4.21 (3H, m), 4.30 (1H, t, J = 9.2 Hz), 4.56 (2H, s), 4.63 (1H, m), 5.41 (1H, m), 5.90 (1H, s), 6.87 (1H, d, J = 8.3 Hz), 7.00-7.04 (2H, m), 7.11 (1H, dd, J = 8.4, 2.0 Hz). | ESI-MS m/z: 482 [M + H]+ |

TABLE 25-continued

| Example | Structural formula | NMR | MS |
|---|---|---|---|
| 186 (isomer B) | | 1H-NMR (CDCl₃) δ: 0.19 (2H, s), 0.54 (2H, d, J = 7.8 Hz), 1.03 (1H, m), 2.86 (1H, m), 3.18 (1H, dd, J = 16.6, 5.0 Hz), 3.37 (2H, d, J = 6.9 Hz), 3.74-3.85 (4H, m), 4.16-4.20 (3H, m), 4.29 (1H, t, J = 9.1 Hz), 4.57 (2H, s), 4.63 (1H, m), 5.40 (1H, m), 5.90 (1H, s), 6.87 (1H, d, J = 8.3 Hz), 7.00 (1H, d, J = 8.2 Hz), 7.04 (1H, s), 7.11 (1H, s). | ESI-MS m/z: 482 [M + H]+ |
| 187 | | 1H-NMR (CDCl₃) δ: 2.84-2.89 (1H, m), 3.15-3.21 (1H, m), 3.20 (1H, d, J = 5.16 Hz), 3.82 (2H, q, J = 8.8 Hz), 3.89-3.99 (4H, m), 4.15-4.21 (3H, m), 4.31 (1H, dt, J = 14.1, 4.3 Hz), 4.57 (1H, s), 4.63 (1H, m), 5.42 (1H, m), 5.92 (1H, s), 6.87 (1H, d, J = 8.4 Hz), 7.00-7.04 (2H, m), 7.11 (1H, d, J = 8.6 Hz). | ESI-MS m/z: 510 [M + H]+ |

TABLE 26

| Example | Structural formula | NMR | MS |
|---|---|---|---|
| 188 (isomer A) | | 1H-NMR (CDCl₃) δ: 2.83-2.90 (1H, m), 3.15-3.23 (1H, m), 3.20 (1H, d, J = 5.16 Hz), 3.82 (2H, q, J = 8.8 Hz), 3.89-3.97 (4H, m), 4.15-4.23 (3H, m), 4.30 (1H, dt, J = 14.1, 4.3 Hz), 4.57 (1H, s), 4.65 (1H, m), 5.42 (1H, m), 5.92 (1H, s), 6.87 (1H, d, J = 8.4 Hz), 6.99-7.05 (2H, m), 7.11 (1H, d, J = 8.6 Hz). | ESI-MS m/z: 510 [M + H]+ |
| 188 (isomer B) | | 1H-NMR (CDCl₃) δ: 2.85-2.91 (1H, m), 3.14-3.25 (1H, m), 3.20 (1H, d, J = 5.2 Hz), 3.81 (2H, q, J = 8.8 Hz), 3.89-3.98 (4H, m), 4.16-4.23 (3H, m), 4.30 (1H, dt, J = 4.3, 14.1 Hz), 4.58 (1H, s), 4.65 (1H, m), 5.42 (1H, m), 5.92 (1H, s), 6.88 (1H, d, J = 8.4 Hz), 6.99-7.06 (2H, m), 7.11 (1H, d, J = 8.6 Hz). | ESI-MS m/z: 510 [M + H]+ |
| 189 | | 1H-NMR (CDCl₃) δ: 2.82-2.88 (3H, m), 3.16 (1H, dd, J = 16.7, 5.3 Hz), 3.89-4.03 (6H, m), 4.16-4.21 (3H, m), 4.32 (1H, dt, J = 9.3, 4.4 Hz), 4.61 (1H, m), 5.41 (1H, m), 5.92 (1H, s), 6.19 (1H, t, J = 74.8 Hz), 6.81 (1H, d, J = 8.4 Hz), 6.90 (1H, s), 6.97-7.03 (2H, m). | ESI-MS m/z: 492 [M + H]+ |
| 190 (isomer A) | | 1H-NMR (CDCl₃) δ: 2.82-2.88 (3H, m), 3.18 (1H, dd, J = 16.6, 5.4 Hz), 3.89-4.03 (6H, m), 4.16-4.20 (3H, m), 4.33 (1H, t, J = 9.3 Hz), 4.61 (1H, m), 5.42 (1H, m), 5.92 (1H, s), 6.19 (1H, t, J = 74.8 Hz), 6.81 (1H, d, J = 8.3 Hz), 6.90 (1H, s), 6.97-7.03 (2H, m). | ESI-MS m/z: 492 [M + H]+ |

TABLE 26-continued

| Example | Structural formula | NMR | MS |
|---|---|---|---|
| 190 (isomer B) | | 1H-NMR (CDCl₃) δ: 2.81-2.88 (3H, m), 3.16 (1H, dd, J = 16.7, 5.5 Hz), 3.90-4.03 (6H, m), 4.18-4.21 (3H, m), 4.31 (1H, t, J = 9.3 Hz), 4.61 (1H, m), 5.41 (1H, m), 5.92 (1H, s), 6.19 (1H, t, J = 74.8 Hz), 6.81 (1H, d, J = 8.3 Hz), 6.90 (1H, s), 6.97-7.02 (2H, m). | ESI-MS m/z: 492 [M + H]+ |
| 191 | | 1H-NMR (CDCl₃) δ: 2.86 (1H, m), 3.15-3.31 (3H, m), 3.91-3.98 (4H, m), 4.20 (3H, d, J = 2.3 Hz), 4.33 (1H, m), 4.63 (1H, m), 5.42 (1H, m), 5.92 (1H, s), 6.85 (1H, d, J = 8.3 Hz), 6.98-7.08 (3H, m). | ESI-MS m/z: 480 [M + H]+ |
| 192 (isomer B) | | 1H-NMR (CDCl₃) δ: 2.86 (1H, dd, J = 17.2, 3.6 Hz), 3.18 (1H, dd, J = 16.9, 5.1 Hz), 3.26 (2H, q, J = 10.8 Hz), 3.89-3.97 (4H, m), 4.20 (3H, s), 4.33 (1H, t, J = 9.5 Hz), 4.63 (1H, m), 5.42 (1H, m), 5.92 (1H, s), 6.85 (1H, d, J = 8.4 Hz), 6.97 (1H, s), 7.01 (1H, d, J = 7.3 Hz), 7.05 (1H, d, J = 8.2 Hz). | ESI-MS m/z: 480 [M + H]+ |
| 193 | | 1H-NMR (CDCl₃) δ: 2.59 (3H, s), 2.96 (1H, m), 3.26 (1H, m), 3.88-3.96 (4H, m), 4.17 (1H, m), 4.26-4.30 (3H, m), 4.67 (1H, m), 5.41 (1H, m), 5.92 (1H, s), 6.98-7.03 (2H, m), 7.73-7.76 (2H, m), 8.45 (1H, s), 8.83 (1H, s). | ESI-MS m/z: 490 [M + H]+ |
| 194 (isomer A) | | 1H-NMR (CDCl₃) δ: 2.58 (3H, s), 2.96 (1H, d, J = 17.0 Hz), 3.26 (1H, dd, J = 16.0, 3.8 Hz), 3.88-3.96 (4H, m), 4.16 (1H, t, J = 8.0 Hz), 4.27-4.34 (3H, m), 4.67 (1H, s), 5.41 (1H, s), 5.92 (1H, s), 6.99 (1H, d, J = 8.1 Hz), 7.02 (1H, d, J = 8.1 Hz), 7.73-7.76 (2H, m), 8.45 (1H, s), 8.83 (1H, s). | ESI-MS m/z: 490 [M + H]+ |

TABLE 27

| Example | Structural formula | NMR | MS |
|---|---|---|---|
| 194 (isomer B) | 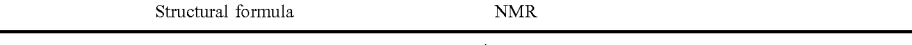 | 1H-NMR (CDCl₃) δ: 2.58 (3H, s), 2.96 (1H, d, J = 17.0 Hz), 3.26 (1H, dd, J = 16.0, 3.8 Hz), 3.88-3.96 (4H, m), 4.16 (1H, t, J = 8.0 Hz), 4.27-4.34 (3H, m), 4.67 (1H, s), 5.41 (1H, s), 5.92 (1H, s), 6.99 (1H, d, J = 8.1 Hz), 7.02 (1H, d, J = 8.1 Hz), 7.73-7.76 (2H, m), 8.45 (1H, s), 8.83 (1H, s). | ESI-MS m/z: 490 [M + H]+ |

TABLE 27-continued

| Example | Structural formula | NMR | MS |
|---|---|---|---|
| 195 | | 1H-NMR (CDCl₃) δ: 2.87 (1H, dd, J = 16.9, 3.7 Hz), 3.18 (1H, dd, J = 16.7, 5.2 Hz), 3.82 (2H, q, 8.7 Hz), 4.14-4.32 (5H, m), 4.38 (1H, dt, J = 4.2, 14.2 Hz), 4.57 (2H, s), 4.63 (1H, m), 5.48 (1H, s), 5.94 (1H, s), 6.87 (1H, d, J = 8.3 Hz), 7.00-7.05 (2H, m), 7.12 (1H, d, J = 8.4 Hz). | ESI-MS m/z: 496 [M + H]+ |
| 196 (isomer A) | | 1H-NMR (CDCl₃) δ: 2.87 (1H, dd, J = 17.0, 3.8 Hz), 3.18 (1H, dd, J = 16.7, 5.4 Hz), 3.82 (2H, q, J = 8.7 Hz), 4.15-4.32 (5H, m), 4.39 (1H, t, J = 9.4 Hz), 4.57 (2H, s), 4.63 (1H, m), 5.49 (1H, m), 5.95 (1H, s), 6.87 (1H, d, J = 8.3 Hz), 7.00-7.05 (2H, m), 7.12 (1H, dd, J = 8.3, 1.9 Hz). | ESI-MS m/z: 496 [M + H]+ |
| 196 (isomer B) | | 1H-NMR (CDCl₃) δ: 2.87 (1H, dd, J = 16.6, 4.1 Hz), 3.18 (1H, dd, J = 16.8, 5.4 Hz), 3.82 (2H, q, J = 8.7 Hz), 4.14-4.31 (5H, m), 4.40 (1H, dd, J = 10.0, 9.0 Hz), 4.57 (2H, s), 4.63 (1H, m), 5.49 (1H, m), 5.95 (1H, s), 6.87 (1H, d, J = 8.3 Hz), 7.00-7.05 (2H, m), 7.12 (1H, dd, J = 8.3, 2.0 Hz). | ESI-MS m/z: 496 [M + H]+ |
| 197 | | 1H-NMR (CDCl₃) δ: 2.85 (1H, dd, J = 16.8, 3.6 Hz), 3.04 (2H, dt, J = 17.4, 4.3 Hz), 3.17 (1H, dd, J = 16.7, 5.2 Hz), 4.11-4.32 (5H, m), 4.40 (1H, dt, J = 9.5, 4.1 Hz), 4.62 (1H, m), 5.48 (1H, m), 5.81 (1H, tt, J = 84.9, 4.5 Hz), 5.95 (1H, s), 6.84 (1H, d, J = 8.4 Hz), 6.94 (1H, s), 7.01 (2H, d, J = 7.8 Hz). | ESI-MS m/z: 448 [M + H]+ |
| 198 (isomer A) | | 1H-NMR (CDCl₃) δ: 2.85 (1H, m), 3.04 (2H, dt, J = 17.4, 4.5 Hz), 3.17 (1H, dd, J = 16.7, 5.4 Hz), 4.15-4.31 (5H, m), 4.40 (1H, m), 4.62 (1H, m), 5.49 (1H, m), 5.81 (1H, tt, J = 85.0, 4.5 Hz), 5.95 (1H, s), 6.84 (1H, d, J = 8.3 Hz), 6.91 (1H, s), 7.00-7.02 (2H, m). | ESI-MS m/z: 448 [M + H]+ |
| 198 (isomer B) | | 1H-NMR (CDCl₃) δ: 2.85 (1H, dd, J = 17.1, 4.0 Hz), 3.04 (2H, dt, J = 17.4, 4.5 Hz), 3.17 (1H, dd, J = 16.9, 5.4 Hz), 4.16-4.32 (5H, m), 4.39 (1H, t, J = 9.4 Hz), 4.62 (1H, m), 5.48 (1H, m), 5.81 (1H, tt, J = 85.1, 4.6 Hz), 5.95 (1H, s), 6.84 (1H, d, J = 8.4 Hz), 6.94 (1H, s), 7.01 (2H, d, J = 7.9 Hz). | ESI-MS m/z: 448 [M + H]+ |
| 199 | | 1H-NMR (CDCl₃) δ: 2.90 (1H, dd, J = 16.6, 4.6 Hz), 3.08-3.24 (5H, m), 4.12 (1H, m), 4.28 (2H, m), 4.36-4.41 (1H, m), 4.64 (1H, m), 5.51 (1H, m), 5.93 (1H, s), 6.91-6.94 (2H, m), 7.39 (1H, s), 7.43 (1H, d, J = 8.5 Hz). | ESI-MS m/z: 439 [M + H]+ |

TABLE 27-continued

| Example | Structural formula | NMR | MS |
| --- | --- | --- | --- |
| 200 (isomer A) | [structure: F₃C-CH₂-S-CH₂- attached to bicyclic pyrazolo-oxazoline, C(=O)NH-chromane-CN] | 1H-NMR (CDCl₃) δ: 2.90 (1H, m), 3.08-3.24 (5H, m), 4.12 (1H, m), 4.28 (2H, s), 4.39 (1H, t, J = 9.2 Hz), 4.64 (1H, m), 5.51 (1H, m), 5.93 (1H, s), 6.91-6.94 (2H, m), 7.38 (1H, s), 7.42 (1H, d, J = 8.6 Hz). | ESI-MS m/z: 439 [M + H]+ |

TABLE 28

| Example | Structural formula | NMR | MS |
| --- | --- | --- | --- |
| 200 (isomer B) | [structure: F₃C-CH₂-S-CH₂- attached to bicyclic pyrazolo-oxazoline, C(=O)NH-chromane-CN] | 1H-NMR (CDCl₃) δ: 2.90 (1H, dd, J = 17.1, 3.8 Hz), 3.08-3.24 (5H, m), 4.13 (1H, m), 4.28 (2H, s), 4.39 (1H, t, J = 9.1 Hz), 4.64 (1H, m), 5.51 (1H, m), 5.93 (1H, s), 6.90-6.94 (2H, m), 7.38 (1H, s), 7.42 (1H, d, J = 8.8 Hz). | ESI-MS m/z: 439 [M + H]+ |
| 201 | [structure: cyclopropylmethyl-O-CH₂CH₂- attached to bicyclic pyrazolo-oxazoline, C(=O)NH-chromane-CN] | 1H-NMR (CDCl₃) δ: 0.18 (2H, m), 0.53 (2H, m), 1.02 (1H, m), 2.18 (2H, m), 2.90 (1H, dd, J = 16.6, 4.2 Hz), 3.17 (1H, dd, J = 16.6, 5.0 Hz), 3.24-3.27 (2H, m), 3.63 (2H, t, J = 4.8 Hz), 4.01 (1H, t, J = 8.8 Hz), 4.23-4.36 (3H, m), 4.64 (1H, m), 5.45 (1H, m), 5.89 (1H, s), 6.92 (2H, d, J = 8.4 Hz), 7.38 (1H, s), 7.42 (1H, d, J = 8.7 Hz). | ESI-MS m/z: 409 [M + H]+ |
| 202 (isomer A) | [structure: cyclopropylmethyl-O-CH₂CH₂- attached to bicyclic pyrazolo-oxazoline, C(=O)NH-chromane-CN] | 1H-NMR (CDCl₃) δ: 0.18 (2H, m), 0.52 (2H, m), 1.01 (1H, m), 2.10-2.19 (2H, m), 2.90 (1H, dd, J = 17.2, 4.6 Hz), 3.17 (1H, dd, J = 16.4, 4.9 Hz), 3.26 (1H, dd, J = 6.8, 2.9 Hz), 3.62 (2H, t, J = 4.9 Hz), 4.01 (1H, t, J = 8.0 Hz), 4.24-4.36 (3H, m), 4.64 (1H, m), 5.45 (1H, m), 5.89 (1H, s), 6.92 (2H, d, J = 8.5 Hz), 7.38 (1H, s), 7.42 (1H, d, J = 8.6 Hz). | ESI-MS m/z: 409 [M + H]+ |
| 202 (isomer B) | [structure: cyclopropylmethyl-O-CH₂CH₂- attached to bicyclic pyrazolo-oxazoline, C(=O)NH-chromane-CN] | 1H-NMR (CDCl₃) δ: 0.18 (2H, m), 0.52 (2H, m), 1.01 (1H, m), 2.10-2.19 (2H, m), 2.90 (1H, dd, J = 17.2, 4.6 Hz), 3.17 (1H, dd, J = 16.4, 4.9 Hz), 3.26 (2H, dd, J = 6.8, 2.9 Hz), 3.62 (2H, t, J = 4.9 Hz), 4.01 (1H, t, J = 8.0 Hz), 4.24-4.36 (3H, m), 4.64 (1H, m), 5.45 (1H, m), 5.89 (1H, s), 6.92 (2H, d, J = 8.5 Hz), 7.38 (1H, s), 7.42 (1H, d, J = 8.6 Hz). | ESI-MS m/z: 409 [M + H]+ |
| 203 | [structure: cyclopropylmethyl-O-CH₂CH₂- attached to bicyclic pyrazolo-oxazoline, C(=O)NH-chromane-pyrimidine-OMe] | 1H-NMR (CDCl₃) δ: 0.18 (2H, m), 0.52 (2H, m), 1.02 (1H, m), 2.16 (2H, m), 2.94 (1H, dd, J = 16.6, 4.3 Hz), 3.22-3.27 (3H, m), 3.62 (2H, m), 4.01 (1H, m), 4.05 (3H, s), 4.25 (2H, m), 4.33 (1H, m), 4.66 (1H, m), 5.45 (1H, m), 6.90 (1H, s), 6.98 (1H, d, J = 8.5 Hz), 7.03 (1H, d, J = 7.7 Hz), 7.19 (1H, s), 7.28 (1H, m), 8.65 (2H, s). | ESI-MS m/z: 492 [M + H]+ |

TABLE 28-continued

| Example | Structural formula | NMR | MS |
|---|---|---|---|
| 204 (isomer A) | | 1H-NMR (CDCl₃) δ: 0.21 (2H, m), 0.54 (2H, m), 1.03 (1H, m), 2.17 (2H, m), 2.95 (1H, dd, J = 16.8, 4.0 Hz), 3.23 (1H, d, J = 5.1 Hz), 3.27 (2H, d, J = 6.5 Hz), 3.63 (2H, dd, J = 4.9, 1.6 Hz), 4.02 (1H, dd, J = 9.9, 1.9 Hz), 4.06 (3H, s), 4.26 (2H, d, J = 2.4 Hz), 4.33 (1H, dd, J = 9.8, 1.4 Hz), 4.67 (1H, m), 5.45 (1H, m), 5.91 (1H, s), 6.98 (1H, d, J = 8.4 Hz), 7.04 (1H, d, J = 8.0 Hz), 7.20 (1H, s), 7.28 (1H, m), 8.66 (2H, s). | ESI-MS m/z: 492 [M + H]+ |
| 204 (isomer B) | | 1H-NMR (CDCl₃) δ: 0.21 (2H, m), 0.54 (2H, m), 1.03 (1H, m), 2.17 (2H, m), 2.95 (1H, dd, J = 16.8, 4.0 Hz), 3.23 (1H, d, J = 5.1 Hz), 3.27 (2H, d, J = 6.5 Hz), 3.63 (2H, dd, J = 4.9, 1.6 Hz), 4.02 (1H, dd, J = 9.9, 1.9 Hz), 4.06 (3H, s), 4.26 (2H, d, J = 2.4 Hz), 4.33 (1H, dd, J = 9.8, 1.4 Hz), 4.67 (1H, m), 5.45 (1H, m), 5.91 (1H, s), 6.98 (1H, d, J = 8.4 Hz), 7.04 (1H, d, J = 8.0 Hz), 7.20 (1H, s), 7.28 (1H, m), 8.66 (2H, s). | ESI-MS m/z: 492 [M + H]+ |
| 205 | | 1H-NMR (CDCl₃) δ: 2.19 (2H, m), 2.90 (1H, m), 3.22 (1H, m), 3.80-3.86 (4H, m), 3.93-3.95 (4H, m), 4.22 (2H, s), 4.34 (1H, m), 4.64 (1H, m), 5.43 (1H, m), 5.89 (1H, s), 6.44 (1H, d, J = 2.2 Hz), 6.89 (1H, d, J = 8.2 Hz), 7.02 (1H, m), 7.35 (1H, d, J = 2.2 Hz), 7.51-7.54 (2H, m). | ESI-MS m/z: 492 [M + H]+ |
| 206 (isomer A) | | 1H-NMR (CDCl₃) δ: 2.18 (2H, m), 2.90 (1H, dd, J = 16.5, 3.9 Hz), 3.21 (1H, dd, J = 16.5, 5.2 Hz), 3.79-3.86 (4H, m), 3.92-3.96 (4H, m), 4.22 (2H, m), 4.34 (1H, t, J = 8.4 Hz), 4.64 (1H, m), 5.43 (1H, m), 5.89 (1H, s), 6.44 (1H, d, J = 2.2 Hz), 6.89 (1H, d, J = 8.4 Hz), 7.02 (1H, d, J = 8.1 Hz), 7.35 (1H, d, J = 2.2 Hz), 7.51 (1H, s), 7.54 (1H, d, J = 2.0 Hz). | ESI-MS m/z: 492 [M + H]+ |

TABLE 29

| Example | Structural formula | NMR | MS |
|---|---|---|---|
| 206 (isomer B) | | 1H-NMR (CDCl₃) δ: 2.18 (2H, m), 2.90 (1H, dd, J = 16.5, 3.0 Hz), 3.21 (1H, dd, J = 16.5, 5.2 Hz), 3.79-3.86 (4H, m), 3.92-3.96 (4H, m), 4.22 (2H, m), 4.34 (1H, t, J = 8.4 Hz), 4.64 (1H, m), 5.43 (1H, m), 5.89 (1H, s), 6.44 (1H, d, J = 2.2 Hz), 6.89 (1H, d, J = 8.4 Hz), 7.02 (1H, d, J = 8.1 Hz), 7.35 (1H, d, J = 2.2 Hz), 7.51 (1H, s), 7.54 (1H, d, J = 2.0 Hz). | ESI-MS m/z: 492 [M + H]+ |

TABLE 29-continued

| Example | Structural formula | NMR | MS |
| --- | --- | --- | --- |
| 207 (isomer A) | | 1H-NMR (CDCl$_3$) δ: 2.18 (2H, m), 2.95 (1H, d, J = 17.4 Hz), 3.26 (1H, dd, J = 17.0, 4.2 Hz), 3.80-3.86 (4H, m), 3.96 (1H, t, J = 8.2 Hz), 4.26 (2H, s), 4.33 (1H, t, J = 9.1 Hz), 4.66 (1H, m), 5.45 (1H, m), 5.89 (1H, s), 6.96 (1H, d, J = 8.0 Hz), 7.02 (1H, d, J = 7.6 Hz), 7.18 (1H, t, J = 5.4 Hz), 7.65 (1H, d, J = 7.6 Hz), 7.70-7.75 (3H, m), 8.65 (1H, s). | ESI-MS m/z: 489 [M + H]+ |
| 207 (isomer B) | | 1H-NMR (CDCl$_3$) δ: 2.18 (2H, m), 2.95 (1H, d, J = 17.4 Hz), 3.26 (1H, dd, J = 17.0, 4.2 Hz), 3.80-3.86 (4H, m), 3.96 (1H, t, J = 8.2 Hz), 4.26 (2H, s), 4.33 (1H, t, J = 9.1 Hz), 4.66 (1H, m), 5.42 (1H, m), 5.89 (1H, s), 6.96 (1H, d, J = 8.0 Hz), 7.02 (1H, d, J = 7.6 Hz), 7.18 (1H, t, J = 5.4 Hz), 7.65 (1H, d, J = 7.6 Hz), 7.70-7.75 (3H, m), 8.64 (1H, s). | ESI-MS m/z: 489 [M + H]+ |
| 208 | | 1H-NMR (CDCl$_3$) δ: 2.27 (2H, m), 2.90 (1H, dd, J = 4.5, 16.7 Hz), 3.17 (1H, dd, J = 16.7, 5.0 Hz), 3.95 (1H, m), 4.15-4.28 (4H, m), 4.40 (1H, m), 4.63 (1H, m), 5.44 (1H, m), 5.95 (1H, s), 6.93 (2H, d, J = 8.4 Hz), 7.38 (1H, s), 7.42 (1H, dd, J = 8.5, 1.7 Hz). | ESI-MS m/z: 423 [M + H]+ |
| 209 (isomer A) | | 1H-NMR (CDCl$_3$) δ: 2.26 (2H, m), 2.90 (1H, dd, J = 16.5, 4.4 Hz), 3.17 (1H, dd, J = 16.6, 5.0 Hz), 3.95 (1H, dd, J = 9.9, 7.6 Hz), 4.15-4.25 (3H, s), 4.28 (1H, m), 4.40 (1H, t, J = 8.4 Hz), 4.64 (1H, m), 5.45 (1H, m), 5.92 (1H, s), 6.91 (1H, s), 6.93 (1H, d, J = 8.4 Hz), 7.38 (1H, s), 7.42 (1H, d, J = 8.5 Hz). | ESI-MS m/z: 423 [M + H]+ |
| 209 (isomer B) | | 1H-NMR (CDCl$_3$) δ: 2.26 (2H, m), 2.90 (1H, dd, J = 16.5, 4.4 Hz), 3.17 (1H, dd, J = 16.6, 5.0 Hz), 3.95 (1H, dd, J = 9.9, 7.6 Hz), 4.15-4.25 (3H, s), 4.28 (1H, m), 4.40 (1H, t, J = 8.4 Hz), 4.64 (1H, m), 5.45 (1H, m), 5.92 (1H, s), 6.91 (1H, s), 6.93 (1H, d, J = 8.4 Hz), 7.38 (1H, s), 7.42 (1H, d, J = 8.5 Hz). | ESI-MS m/z: 423 [M + H]+ |
| 210 | | 1H-NMR (CDCl$_3$) δ: 2.26 (2H, m), 2.85 (1H, dd, J = 16.7, 3.9 Hz), 3.04 (3H, dt, J = 17.4, 4.6 Hz), 3.17 (1H, dd, J = 16.8, 5.4 Hz), 3.94 (1H, m), 4.12-4.26 (3H, m), 4.39 (1H, m), 4.62 (1H, m), 5.43 (1H, m), 5.88 (1H, m), 5.92 (1H, s), 6.81 (1H, q, J = 8.5 Hz), 6.93 (1H, s), 6.97-7.02 (2H, m). | ESI-MS m/z: 462 [M + H]+ |
| 211 (isomer A) | | 1H-NMR (CDCl$_3$) δ: 2.26 (2H, m), 2.85 (1H, dd, J = 17.1, 3.4 Hz), 3.04 (2H, td, J = 17.4, 4.4 Hz), 3.17 (1H, dd, J = 16.4, 5.0 Hz), 3.94 (1H, t, J = 7.7 Hz), 4.15-4.26 (4H, m), 4.40 (1H, t, J = 9.1 Hz), 4.62 (1H, m), 5.44 (1H, m), 5.88 (1H, m), 5.92 (1H, s), 6.84 (1H, d, J = 8.3 Hz), 6.93 (1H, s), 7.01 (2H, d, J = 8.2 Hz). | ESI-MS m/z: 462 [M + H]+ |

TABLE 29-continued

| Example | Structural formula | NMR | MS |
|---|---|---|---|
| 211 (isomer B) | | 1H-NMR (CDCl$_3$) δ: 2.26 (2H, m), 2.85 (1H, dd, J = 17.1, 3.4 Hz), 3.04 (2H, td, J = 17.4, 4.4 Hz), 3.17 (1H, dd, J = 16.4, 5.0 Hz), 3.94 (1H, t, J = 7.7 Hz), 4.15-4.26 (4H, m), 4.40 (1H, t, J = 9.1 Hz), 4.62 (1H, m), 5.44 (1H, m), 6.88 (1H, m), 5.92 (1H, s), 6.84 (1H, d, J = 8.3 Hz), 6.93 (1H, s), 7.01 (2H, d, J = 8.2 Hz). | ESI-MS m/z: 462 [M + H]+ |

TABLE 30

| Example | Structural formula | NMR | MS |
|---|---|---|---|
| 212 | | 1H-NMR (CDCl$_3$) δ: 2.25 (2H, m), 2.90 (1H, m), 3.22 (1H, m), 3.93 (4H, m), 4.15-4.23 (4H, m), 4.38 (1H, m), 4.64 (1H, m), 5.42 (1H, m), 5.91 (1H, s), 6.44 (1H, d, J = 1.9 Hz), 6.89 (1H, d, J = 7.6 Hz), 7.02 (1H, m), 7.35 (1H, d, J = 2.0 Hz), 7.52-7.54 (2H, m). | ESI-MS m/z: 478 [M + H]+ |
| 213 (isomer A) | | 1H-NMR (CDCl$_3$) δ: 2.25 (2H, m), 2.90 (1H, dd, J = 16.4, 3.6 Hz), 3.22 (1H, dd, J = 16.8, 5.0 Hz), 3.90-3.94 (4H, m), 4.14-4.25 (4H, m), 4.39 (1H, dd, J = 8.3, 1.6 Hz), 4.64 (1H, m), 5.43 (1H, m), 5.91 (1H, s), 6.44 (1H, d, J = 2.2 Hz), 6.89 (1H, d, J = 8.0 Hz), 7.02 (1H, d, J = 8.2 Hz), 7.35 (1H, d, J = 2.2 Hz), 7.51 (1H, s), 7.54 (1H, d, J = 2.1 Hz). | ESI-MS m/z: 478 [M + H]+ |
| 213 (isomer B) | | 1H-NMR (CDCl$_3$) δ: 2.25 (2H, m), 2.90 (1H, dd, J = 3.6, 16.4 Hz), 3.22 (1H, dd, J = 16.8, 5.0 Hz), 3.90-3.94 (4H, m), 4.14-4.25 (4H, m), 4.39 (1H, dd, J = 8.3, 1.6 Hz), 4.64 (1H, m), 5.43 (1H, m), 5.91 (1H, s), 6.44 (1JH, d, J = 2.2 Hz), 6.89 (1H, d, J = 8.0 Hz), 7.02 (1H, d, J = 8.2 Hz), 7.35 (1H, d, J = 2.2 Hz), 7.51 (1H, s), 7.54 (1H, d, J = 2.1 Hz). | ESI-MS m/z: 478 [M + H]+ |
| 214 | | 1H-NMR (CDCl$_3$) δ: 2.12-2.32 (2H, m), 2.87 (1H, dd, J = 16.8, 4.2 Hz), 3.18 (1H, dd, J = 16.8, 6.0 Hz), 3.80 (1H, d, J = 8.2 Hz), 3.84 (1H, d, J = 8.2 Hz), 3.94 (1H, dd, J = 10.8, 7.9 Hz), 4.03-4.13 (2H, m), 4.20 (2H, m), 4.38 (1H, dd, J = 9.5, 8.6 Hz), 4.56 (2H, s), 4.63 (1H, m), 5.43 (1H, m), 5.91 (1H, s), 6.22 (1H, t, J = 73.9 Hz), 6.87 (1H, d, J = 8.5 Hz), 7.01 (1H, d, J = 7.8 Hz), 7.04 (1H, s), 7.11 (1H, dd, J = 8.5, 1.5 Hz) | ESI-MS m/z: 492 [M + H]+ |

TABLE 30-continued

| Example | Structural formula | NMR | MS |
|---|---|---|---|
| 215 (isomer A) | | 1H-NMR (CDCl$_3$) δ: 2.12-2.32 (2H, m), 2.87 (1H, dd, J = 16.8, 4.2 Hz), 3.18 (1H, dd, J = 16.8, 6.0 Hz), 3.80 (1H, d, J = 8.2 Hz), 3.84 (1H, d, J = 8.2 Hz), 3.94 (1H, dd, J = 10.8, 7.9 Hz), 4.03-4.13 (2H, m), 4.20 (2H, m), 4.38 (1H, dd, J = 9.5, 8.6 Hz), 4.56 (2H, s), 4.63 (1H, m), 5.43 (1H, m), 5.91 (1H, s), 6.22 (1H, t, J = 73.9 Hz), 6.87 (1H, d, J = 8.5 Hz), 7.01 (1H, d, J = 7.8 Hz), 7.04 (1H, s), 7.11 (1H, dd, J = 8.5, 1.5 Hz). | ESI-MS m/z: 492 [M + H]+ |
| 215 (isomer B) | | 1H-NMR (CDCl$_3$) δ: 2.12-2.32 (2H, m), 2.87 (1H, dd, J = 16.8, 4.2 Hz), 3.18 (1H, dd, J = 16.8, 6.0 Hz), 3.80 (1H, d, J = 8.2 Hz), 3.84 (1H, d, J = 8.2 Hz), 3.94 (1H, dd, J = 10.8, 7.9 Hz), 4.03-4.13 (2H, m), 4.20 (2H, m), 4.38 (1H, dd, J = 9.5, 8.6 Hz), 4.56 (2H, s), 4.63 (1H, m), 5.43 (1H, m), 5.91 (1H, s), 6.22 (1H, t, J = 73.9 Hz), 6.87 (1H, d, J = 8.5 Hz), 7.01 (1H, d, J = 7.8 Hz), 7.04 (1H, s), 7.11 (1H, dd, J = 8.5, 1.5 Hz). | ESI-MS m/z: 492 [M + H]+ |
| 216 | | 1H-NMR (CDCl$_3$) δ: 2.13-2.31 (2H, m), 2.80-2.90 (3H, m), 3.16 (1H, dd, J = 16.8, 5.6 Hz), 3.92-4.14 (5H, m), 4.18 (2H, m), 4.37 (1H, t, J = 9.2 Hz), 4.61 (1H, m), 5.42 (1H, m), 5.91 (1H, s), 6.19 (1H, t, J = 72.3 Hz), 6.22 (1H, t, J = 72.3 Hz), 6.81 (1H, d, J = 8.0 Hz), 6.91 (1H, s), 6.95-7.05 (2H, m). | ESI-MS m/z: 474 [M + H]+ |
| 217 (isomer A) | | 1H-NMR (CDCl$_3$) δ: 2.13-2.31 (2H, m), 2.80-2.90 (3H, m), 3.16 (1H, dd, J = 16.8, 5.6 Hz), 3.92-4.14 (5H, m), 4.18 (2H, m), 4.37 (1H, t, J = 9.2 Hz), 4.61 (1H, m), 5.42 (1H, m), 5.91 (1H, s), 6.19 (1H, t, J = 72.3 Hz), 6.22 (1H, t, J = 72.3 Hz), 6.81 (1H, d, J = 8.0 Hz), 6.91 (1H, s), 6.95-7.05 (2H, m). | ESI-MS m/z: 474 [M + H]+ |
| 217 (isomer B) | | 1H-NMR (CDCl$_3$) δ: 2.13-2.31 (2H, m), 2.80-2.90 (3H, m), 3.16 (1H, dd, J = 16.8, 5.6 Hz), 3.92-4.14 (5H, m), 4.18 (2H, m), 4.37 (1H, t, J = 9.2 Hz), 4.61 (1H, m), 5.42 (1H, m), 5.91 (1H, s), 6.19 (1H, t, J = 72.3 Hz), 6.22 (1H, t, J = 72.3 Hz), 6.81 (1H, d, J = 8.0 Hz), 6.91 (1H, s), 6.95-7.05 (2H, m) | ESI-MS m/z: 474 [M + H]+ |

TABLE 31

| Example | Structural formula | NMR | MS |
|---|---|---|---|
| 218 | | 1H-NMR (CDCl$_3$) δ: 2.11-2.31 (2H, m), 2.85 (1H, dd, J = 17.0, 4.0 Hz), 3.04 (2H, td, J = 17.2, 5.0 Hz), 3.17 (1H, dd, J = 16.8, 5.2 Hz), 3.95 (1H, dd, J = 10.9, 8.5 Hz), 4.03-4.14 (2H, m), 4.18 (2H, m), 4.38 (1H, dd, J = 10.2, 8.3 Hz), 4.62 (1H, m), 5.39-5.47 (1H, m), 5.88 (1H, tt, J = 56.8, 4.3 Hz), 5.91 (1H, s), 6.22 (1H, t, J = 74.2 Hz), 6.84 (1H, d, J = 8.6 Hz), 6.93 (1H, s), 6.98-7.04 (2H, m). | ESI-MS m/z: 444 [M + H]+ |

TABLE 31-continued

| Example | Structural formula | NMR | MS |
|---|---|---|---|
| 219 (isomer A) | | 1H-NMR (CDCl₃) δ: 2.11-2.31 (2H, m), 2.86 (1H, dd, J = 17.0, 4.0 Hz), 3.04 (2H, td, J = 17.2, 5.0 Hz), 3.17 (1H, dd, J = 16.8, 5.2 Hz), 3.95 (1H, dd, J = 10.9, 8.5 Hz), 4.03-4.14 (2H, m), 4.18 (2H, m), 4.38 (1H, dd, J = 10.2, 8.3 Hz), 4.82 (1H, m), 5.39-5.47 (1H, m), 5.88 (1H, tt, J = 56.8, 4.3 Hz), 5.91 (1H, s), 6.22 (1H, t, J = 74.2 Hz), 6.84 (1H, d, J = 8.6 Hz), 6.93 (1H, s), 6.98-7.04 (2H, m). | ESI-MS m/z: 444 [M + H]+ |
| 219 (isomer B) | | 1H-NMR (CDCl₃) δ: 2.11-2.31 (2H, m), 2.85 (1H, dd, J = 17.0, 4.0 Hz), 3.04 (2H, td, J = 17.2, 5.0 Hz), 3.17 (1H, dd, J = 16.8, 5.2 Hz), 3.95 (1H, dd, J = 10.9, 8.5 Hz), 4.03-4.14 (2H, m), 4.18 (2H, m), 4.38 (1H, dd, J = 10.2, 8.3 Hz), 4.62 (1H, m), 5.39-5.47 (1H, m), 5.88 (1H, tt, J = 56.8, 4.3 Hz), 5.91 (1H, s), 6.22 (1H, t, J = 74.2 Hz), 6.84 (1H, d, J = 8.6 Hz), 6.93 (1H, s), 6.98-7.04 (2H, m). | ESI-MS m/z: 444 [M + H]+ |
| 220 | | 1H-NMR (CDCl₃) δ: 2.12-2.31 (2H, m), 2.88 (1H, dd, J = 17.2, 3.3 Hz), 3.20 (1H, dd, J = 17.1, 4.7 Hz), 3.90-3.98 (4H, m), 4.04-4.13 (2H, m), 4.21 (2H, m), 4.36 (1H, t, J = 9.4 Hz), 4.64 (1H, m), 5.42 (1H, m), 5.91 (1H, s), 6.22 (1H, t, J = 74.5 Hz), 6.87 (1H, d, J = 8.0 Hz), 7.04 (1H, d, J = 8.8 Hz), 7.15 (1H, s), 7.23 (1H, d, J = 8.4 Hz), 7.51 (1H, s), 7.67 (1H, s). | ESI-MS m/z: 460 [M + H]+ |
| 221 (isomer A) | | 1H-NMR (CDCl₃) δ: 2.12-2.31 (2H, m), 2.88 (1H, dd, J = 17.2, 3.3 Hz), 3.20 (1H, dd, J = 17.1, 4.7 Hz), 3.90-3.98 (4H, m), 4.04-4.13 (2H, m), 4.21 (2H, m), 4.36 (1H, t, J = 9.4 Hz), 4.64 (1H, m), 5.42 (1H, m), 5.91 (1H, s), 6.22 (1H, t, J = 74.5 Hz), 6.87 (1H, d, J = 8.0 Hz), 7.04 (1H, d, J = 8.8 Hz), 7.15 (1H, s), 7.23 (1H, d, J = 8.4 Hz), 7.51 (1H, s), 7.67 (1H, s) | ESI-MS m/z: 460 [M + H]+ |
| 221 (isomer B) | | 1H-NMR (CDCl₃) δ: 2.12-2.31 (2H, m), 2.88 (1H, dd, J = 17.2, 3.3 Hz), 3.20 (1H, dd, J = 17.1, 4.7 Hz), 3.90-3.98 (4H, m), 4.04-4.13 (2H, m), 4.21 (2H, m), 4.36 (1H, t, J = 9.4 Hz), 4.64 (1H, m), 5.42 (1H, m), 5.91 (1H, s), 6.22 (1H, t, J = 74.5 Hz), 6.87 (1H, d, J = 8.0 Hz), 7.04 (1H, d, J = 8.8 Hz), 7.15 (1H, s), 7.23 (1H, d, J = 8.4 Hz), 7.51 (1H, s), 7.67 (1H, s). | ESI-MS m/z: 460 [M + H]+ |

TABLE 31-continued

| Example | Structural formula | NMR | MS |
|---|---|---|---|
| 222 | | 1H-NMR (CDCl₃) δ: 2.13-2.30 (2H, m), 2.97 (1H, dd, J = 17.2, 3.4 Hz), 3.27 (1H, dd, J = 16.0, 3.4 Hz), 3.93 (1H, dd, J = 9.6, 8.2 Hz), 4.01-4.14 (2H, m), 4.28 (2H, m), 4.37 (1H, t, J = 9.3 Hz), 4.68 (1H, m), 5.43 (1H, m), 5.91 (1H, s), 6.22 (1H, t, J = 73.8 Hz), 6.98-7.04 (2H, m), 7.75-7.82 (2H, m), 8.45 (1H, s), 8.58 (1H, s), 8.96 (1H, s) | ESI-MS m/z: 458 [M + H]+ |
| 223 (isomer A) | | 1H-NMR (CDCl₃) δ: 2.13-2.30 (2H, m), 2.97 (1H, dd, J = 17.2, 3.4 Hz), 3.27 (1H, dd, J = 16.0, 3.4 Hz), 3.93 (1H, dd, J = 9.6, 8.2 Hz), 4.01-4.14 (2H, m), 4.28 (2H, m), 4.37 (1H, t, J = 9.3 Hz), 4.68 (1H, m), 5.43 (1H, m), 5.91 (1H, s), 6.22 (1H, t, J = 73.8 Hz), 6.98-7.04 (2H, m), 7.75-7.82 (2H, m), 8.45 (1H, s), 8.58 (1H, s), 8.96 (1H, s), | ESI-MS m/z: 458 [M + H]+ |
| 223 (isomer B) | | 1H-NMR (CDCl₃) δ: 2.13-2.30 (2H, m), 2.97 (1H, dd, J = 17.2, 3.4 Hz), 3.27 (1H, dd, J = 16.0, 3.4 Hz), 3.93 (1H, dd, J = 9.6, 8.2 Hz), 4.01-4.14 (2H, m), 4.28 (2H, m), 4.37 (1H, t, J = 9.3 Hz), 4.68 (1H, m), 5.43 (1H, m), 5.91 (1H, s), 6.22 (1H, t, J = 73.8 Hz), 6.98-7.04 (2H, m), 7.75-7.82 (2H, m), 8.45 (1H, s), 8.58 (1H, s), 8.96 (1H, s). | ESI-MS m/z: 458 [M + H]+ |

TABLE 32

| Example | Structural formula | NMR | MS |
|---|---|---|---|
| 224 (isomer A) | | 1H-NMR (CDCl₃) δ: 2.17 (2H, m), 2.87 (1H, d, J = 15.7 Hz), 3.18 (1H, dd, J = 16.4, 4.3 Hz), 3.63-3.85 (6H, m), 3.96 (1H, t, J = 8.9 Hz), 4.20 (2H, s), 4.34 (1H, t, J = 9.0 Hz), 4.56 (2H, s), 4.62 (1H, s), 5.44 (1H, t, J = 7.1 Hz), 5.84 (1H, t, J = 55.1 Hz), 5.89 (1H, s), 6.87 (1H, d, J = 8.2 Hz), 7.01 (1H, d, J = 8.2 Hz), 7.04 (1H, s), 7.11 (1H, d, J = 8.2 Hz). | ESI-MS m/z: 506 [M + H]+ |
| 224 (isomer B) | | 1H-NMR (CDCl₃) δ: 2.17 (2H, m), 2.87 (1H, d, J = 15.7 Hz), 3.18 (1H, dd, J = 16.4, 4.3 Hz), 3.63-3.85 (6H, m), 3.96 (1H, t, J = 8.9 Hz), 4.20 (2H, s), 4.34 (1H, t, J = 9.0 Hz), 4.56 (2H, s), 4.62 (1H, s), 5.44 (1H, t, J = 7.1 Hz), 5.84 (1H, t, J = 55.1 Hz), 5.89 (1H, s), 6.87 (1H, d, J = 8.2 Hz), 7.01 (1H, d, J = 8.2 Hz), 7.04 (1H, s), 7.11 (1H, d, J = 8.2 Hz). | ESI-MS m/z: 506 [M + H]+ |

TABLE 32-continued

| Example | Structural formula | NMR | MS |
|---|---|---|---|
| 225 | | 1H-NMR (CDCl$_3$) δ: 1.96 (1H, m), 2.13 (1H, m), 2.84 (1H, dd, J = 3.7, 16.9 Hz), 2.96 (2H, m), 3.14 (1H, m), 3.20 (2H, m), 3.93 (1H, m), 4.19 (2H, d, J = 2.7 Hz), 4.35 (1H, m), 4.60 (1H, m), 5.43 (1H, m), 5.89 (1H, s), 6.80 (1H, d, J = 8.7 Hz), 6.98 (1H, d, J = 7.3 Hz), 7.03 (1H, s), 7.08 (1H, dd, J = 8.7, 2.9 Hz). | ESI-MS m/z: 445 [M + H]+ |
| 226 (isomer A) | | 1H-NMR (CDCl$_3$) δ: 1.91-1.99 (1H, m), 2.08-2.17 (1H, m), 2.76-2.90 (1H, m), 2.93-3.02 (2H, m), 3.11-3.23 (3H, m), 3.93 (1H, t, J = 9.1 Hz), 4.18 (2H, m), 4.36 (1H, t, J = 9.1 Hz), 4.60 (1H, m), 5.44 (1H, m), 5.89 (1H, s), 6.80 (1H, d, J = 8.8 Hz), 6.99 (1H, d, J = 8.0 Hz), 7.03 (1H, s), 7.08 (1H, d, J = 8.8 Hz). | ESI-MS m/z: 445 [M + H]+ |
| 226 (isomer B) | | 1H-NMR (CDCl$_3$) δ: 1.91-1.99 (1H, m), 2.08-2.17 (1H, m), 2.81-2.86 (1H, m), 2.95-2.98 (2H, m), 3.12-3.21 (3H, m), 3.93 (1H, t, J = 8.8 Hz), 4.18 (2H, s), 4.35 (1H, t, J = 9.2 Hz), 4.61 (1H, m), 5.43 (1H, m), 5.89 (1H, s), 6.80 (1H, d, J = 8.7 Hz), 6.98 (1H, d, J = 7.8 Hz), 7.04 (1H, s), 7.08 (1H, d, J = 8.7 Hz). | ESI-MS m/z: 445 [M + H]+ |
| 227 | | 1H-NMR (CDCl$_3$) δ: 1.96 (1H, m), 2.11 (1H, m), 2.25 (3H, s), 2.82 (1H, m), 2.97 (2H, m), 3.12-3.23 (3H, m), 3.93 (1H, m), 4.16 (2H, d, J = 2.7 Hz), 4.35 (1H, m), 4.60 (1H, m), 5.42 (1H, m), 5.89 (1H, s), 6.76 (1H, d, J = 8.3 Hz), 6.86 (1H, s), 6.93 (1H, d, J = 8.2 Hz), 7.03 (1H, d, J = 8.0 Hz). | ESI-MS m/z: 425 [M + H]+ |
| 228 (isomer A) | | 1H-NMR (CDCl$_3$) δ: 1.90-1.96 (1H, m), 2.05-2.09 (1H, m), 2.26 (3H, s), 2.80-2.94 (1H, m), 2.89-3.02 (2H, m), 3.11-3.23 (3H, m), 3.91 (1H, t, J = 8.9 Hz), 4.16 (2H, m), 4.35 (1H, t, J = 9.1 Hz), 4.60 (1H, m), 5.43 (1H, m), 5.88 (1H, s), 6.77 (1H, d, J = 8.3 Hz), 6.85 (1H, s), 6.93 (1H, d, J = 8.3 Hz), 7.03 (1H, d, J = 8.5 Hz). | ESI-MS m/z: 425 [M + H]+ |
| 228 (isomer B) | | 1H-NMR (CDCl$_3$) δ: 1.93-2.00 (1H, m), 2.07-2.25 (1H, m), 2.25 (3H, s), 2.78-2.94 (1H, m), 2.90-3.02 (1H, m), 3.12-3.23 (1H, m), 3.93 (1H, t, J = 8.9 Hz), 4.16 (2H, m), 4.34 (1H, t, J = 9.1 Hz), 4.60 (1H, m), 5.42 (1H, m), 5.89 (1H, s), 6.76 (1H, d, J = 8.2 Hz), 6.86 (1H, s), 6.93 (1H, d, J = 8.2 Hz), 7.02 (1H, d, J = 8.3 Hz). | ESI-MS m/z: 425 [M + H]+ |

TABLE 32-continued

| Example | Structural formula | NMR | MS |
|---|---|---|---|
| 229 | 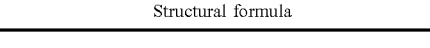 | 1H-NMR (CDCl$_3$) δ: 1.95 (1H, m), 2.11 (1H, m), 2.88-3.01 (3H, m), 3.16-3.23 (3H, m), 3.93 (1H, m), 4.25 (2H, d, J = 2.6 Hz), 4.35 (1H, m), 4.65 (1H, m), 5.44 (1H, m), 5.90 (1H, s), 6.93-6.97 (2H, m), 7.33 (1H, s), 7.38 (1H, d, J = 8.8 Hz). | ESI-MS m/z: 479 [M + H]+ |

TABLE 33

| Example | Structural formula | NMR | MS |
|---|---|---|---|
| 230 (isomer A) | | 1H-NMR (CDCl$_3$) δ: 1.91-1.99 (1H, m), 2.08-2.17 (1H, m), 2.88-3.00 (3H, m), 3.16-3.23 (3H, m), 3.90-3.92 (1H, m), 4.25 (2H, d, J = 2.9 Hz), 4.33-4.37 (1H, m), 4.61-4.68 (1H, m), 5.44 (1H, m), 5.90 (1H, s), 6.93-7.00 (2H, m), 7.33 (1H, s), 7.38 (1H, d, J = 8.7 Hz). | ESI-MS m/z: 479 [M + H]+ |
| 230 (isomer B) | | 1H-NMR (CDCl$_3$) δ: 1.91-1.99 (1H, m), 2.08-2.17 (1H, m), 2.92-3.02 (3H, m), 3.16-3.23 (3H, m), 3.90-3.92 (1H, m), 4.25 (2H, d, J = 2.9 Hz), 4.33-4.37 (1H, m), 4.61-4.68 (1H, m), 5.44 (1H, m), 5.90 (1H, s), 6.93-7.00 (2H, m), 7.33 (1H, s), 7.38 (1H, d, J = 8.7 Hz). | ESI-MS m/z: 479 [M + H]+ |
| 231 | | 1H-NMR (CDCl$_3$) δ: 1.96 (1H, m), 2.13 (1H, m), 2.84-3.01 (3H, m), 3.15-3.24 (3H, m), 3.81 (2H, q, J = 8.7 Hz), 3.93 (1H, m), 4.20 (2H, d, J = 2.8 Hz), 4.35 (1H, m), 4.56 (2H, s), 4.62 (1H, m), 5.42 (1H, m), 5.89 (1H, s), 6.87 (1H, d, J = 8.3 Hz), 7.00 (1H, d, J = 8.6 Hz), 7.04 (1H, m), 7.11 (1H, dd, J = 8.5, 2.0 Hz). | ESI-MS m/z: 523 [M + H]+ |
| 232 (isomer A) | | 1H-NMR (CDCl$_3$) δ: 1.97 (1H, m), 2.12 (1H, m), 2.84-3.03 (3H, m), 3.15-3.24 (3H, m), 3.81 (2H, q, J = 8.7 Hz), 3.93 (1H, t, J = 8.2 Hz), 4.20 (2H, s), 4.34 (1H, t, J = 9.0 Hz), 4.57 (2H, s), 4.63 (1H, m), 5.43 (1H, m), 5.89 (1H, s), 6.87 (1H, d, J = 8.3 Hz), 7.00 (1H, d, J = 8.0 Hz), 7.04 (1H, s), 7.11 (1H, d, J = 8.2 Hz). | ESI-MS m/z: 523 [M + H]+ |
| 232 (isomer B) | | 1H-NMR (CDCl$_3$) δ: 1.97 (1H, m), 2.12 (1H, m), 2.84-3.03 (3H, m), 3.15-3.24 (3H, m), 3.81 (2H, q, J = 8.7 Hz), 3.93 (1H, t, J = 8.2 Hz), 4.20 (2H, s), 4.34 (1H, t, J = 9.0 Hz), 4.57 (2H, s), 4.63 (1H, m), 5.43 (1H, m), 5.89 (1H, s), 6.87 (1H, d, J = 8.3 Hz), 7.00 (1H, d, J = 8.0 Hz), 7.04 (1H, s), 7.11 (1H, d, J = 8.2 Hz). | ESI-MS m/z: 523 [M + H]+ |

TABLE 33-continued

| Example | Structural formula | NMR | MS |
|---|---|---|---|
| 233 | | 1H-NMR (CDCl₃) δ: 1.80-1.90 (1H, m), 1.98-2.08 (1H, m), 2.67-2.88 (3H, m), 3.12-3.18 (1H, m), 3.56-3.62 (4H, m), 3.89-3.94 (1H, m), 4.18 (2H, m), 4.33-4.38 (1H, m), 4.58-4.63 (1H, m), 5.35-5.42 (1H, m), 5.88 (1H, s), 6.80 (1H, d, J = 8.7 Hz), 6.96-7.00 (1H, m), 7.03 (1H, d, J = 1.8 Hz), 7.08 (1H, dd, J = 18.6, 2.6 Hz). | ESI-MS m/z: 439 [M + H]+ |
| 234 (isomer A) | | 1H-NMR (CDCl₃) δ: 1.86 (1H, m), 1.99-2.04 (1H, m), 2.69-2.88 (3H, m), 3.15 (1H, dd, J = 16.7, 5.1 Hz), 3.57-3.63 (4H, m), 3.91 (1H, t, J = 9.0 Hz), 4.19 (2H, s), 4.36 (1H, t, J = 9.1 Hz), 4.61 (1H, m), 5.37-5.40 (1H, m), 5.89 (1H, s), 6.80 (1H, d, J = 8.8 Hz), 6.97-7.09 (3H, m). | ESI-MS m/z: 439 [M + H]+ |
| 234 (isomer B) | | 1H-NMR (CDCl₃) δ: 1.87 (1H, m), 2.02-2.08 (1H, m), 2.75-2.86 (3H, m), 3.15 (1H, dd, J = 17.1, 5.3 Hz), 3.57-3.64 (4H, m), 3.92 (1H, t, J = 8.8 Hz), 4.18 (2H, s), 4.35 (1H, t, J = 9.1 Hz), 4.61 (1H, m), 5.35-5.42 (1H, m), 5.89 (1H, s), 6.80 (1H, d, J = 8.8 Hz), 6.96-7.09 (3H, m). | ESI-MS m/z: 439 [M + H]+ |
| 235 | | 1H-NMR (CDCl₃) δ: 1.85-1.87 (1H, m), 1.98-2.05 (1H, m), 2.73-2.93 (3H, m), 3.18-3.23 (1H, m), 3.55-3.63 (4H, m), 3.89-3.94 (1H, m), 4.25-4.26 (2H, m), 4.33-4.38 (1H, m), 4.64-4.66 (1H ,m), 5.36-5.41 (1H, m), 5.89 (1H, s), 6.93-7.00 (2H, m), 7.33-7.39 (2H, m). | ESI-MS m/z: 473 [M + H]+ |

TABLE 34

| Example | Structural formula | NMR | MS |
|---|---|---|---|
| 236 (isomer A) | | 1H-NMR (CDCl₃) δ: 1.87 (1H, m), 1.99-2.06 (1H, m), 2.75-2.93 (3H, m), 3.18-3.23 (1H, m), 3.60 (4H, m), 3.91 (1H, t, J = 8.9 Hz), 4.26 (2H, s), 4.36 (1H, t, J = 9.0 Hz), 4.65 (1H, m), 5.36-5.46 (1H, m), 5.89 (1H, s), 6.93-6.97 (2H, m), 7.33 (1H, s), 7.38 (1H, d, J = 8.8 Hz). | ESI-MS m/z: 473 [M + H]+ |
| 236 (isomer B) | | 1H-NMR (CDCl₃) δ: 1.88 (1H, m), 1.98-2.08 (1H, m), 2.74-2.93 (3H, m), 3.18-3.23 (1H, m), 3.60 (4H, m), 3.92 (1H, t, J = 8.8 Hz), 4.25 (2H, s), 4.35 (1H, t, J = 9.0 Hz), 4.65 (1H, m), 5.35-5.44 (1H, m), 5.89 (1H, s), 6.93-6.95 (2H, m), 7.33 (1H, s), 7.38 (1H, d, J = 9.2 Hz). | ESI-MS m/z: 473 [M + H]+ |
| 237 | | 1H-NMR (CDCl₃) δ: 1.85-1.87 (1H, m), 2.02-2.05 (1H, m), 2.75-2.87 (5H, m), 3.12-3.19 (1H, m), 3.55-3.61 (3H, m), 3.88-3.94 (1H, m), 4.01 (2H, t, J = 7.2 Hz), 4.11-4.18 (3H, m), 4.31-4.38 (1H, m), 4.60-4.61 (1H, m), 5.36-5.40 (1H, m), 5.89 (1H, s), 6.19 (1H, t, J = 74.7 Hz), 6.81 (1H, dd, J = 8.2, 2.1 Hz), 6.90 (1H, s), 6.97-7.01 (2H, m). | ESI-MS m/z: 499 [M + H]+ |

TABLE 34-continued

| Example | Structural formula | NMR | MS |
|---|---|---|---|
| 238 (isomer A) | | 1H-NMR (CDCl$_3$) δ: 1H-NMR (CDCl3) 1.81-1.86 (1H, m), 1.93-2.13 (1H, m), 2.69-2.94 (5H, m), 3.06-3.13 (2H, m), 3.58 (2H, t, J = 11.9 Hz), 3.76 (1H, t, J = 11.9 Hz), 3.91 (1H, m), 4.01 (2H, t, J = 7.1 Hz), 4.18 (2H, s), 4.35 (1H, m), 4.61 (1H, s), 5.41 (1H, m), 5.89 (1H, s), 6.19 (1H, t, J = 74.8 Hz), 6.81 (1H, d, J = 8.2 Hz), 6.90 (1H, s), 6.97-7.02 (2H, m). | ESI-MS m/z: 499 [M + H]+ |
| 238 (isomer B) | | 1H-NMR (CDCl$_3$) δ: 1.81-1.86 (1H, m), 2.13-1.93 (1H, m), 2.81-2.93 (5H, m), 3.08-3.13 (2H, m), 3.59 (2H, t, J = 11.9 Hz), 3.77 (1H, t, J = 11.9 Hz), 3.92 (1H, m), 4.01 (2H, t, J = 7.1 Hz), 4.18 (2H, s), 4.34 (1H, m), 4.61 (1H, s), 5.40 (1H, m), 5.89 (1H, s), 6.19 (1H, t, J = 74.7 Hz), 6.81 (1H, d, 8.6 Hz), 6.90 (1H, s), 6.97-7.02 (2H, m) | ESI-MS m/z: 499 [M + H]+ |
| 239 | | 1H-NMR (CDCl$_3$) δ: 1.86-1.87 (1H, m), 2.01-2.06 (1H, m), 2.73-2.92 (5H, m), 3.14-3.19 (1H, m), 3.55-3.63 (4H, m), 3.87-3.99 (1H, m), 4.10 (2H, t, J = 7.3 Hz), 4.18 (2H, s), 4.32-4.38 (1H, m), 4.61-4.62 (1H, m), 5.37-5.39 (1H, m), 5.89 (1H, s), 6.82 (1H, d, J = 8.3 Hz), 6.89 (1H, s), 6.96-7.01 (2H, m). | ESI-MS m/z: 517 [M + H]+ |
| 240 (isomer A) | | 1H-NMR (CDCl$_3$) δ: 1.86-1.87 (1H, m), 2.01-2.04 (1H, m), 2.79-2.03 (5H, m), 3.08-3.13 (1H, m), 3.59 (4H, t, J = 11.5 Hz), 3.91 (1H, t, J = 8.7 Hz), 4.10 (2H, t, J = 9.1 Hz), 4.18 (2H, s), 4.35 (1H, t, J = 9.1 Hz), 4.61 (1H, m), 5.38 (1H, m), 5.89 (1H, s), 6.82 (1H, d, J = 8.1 Hz), 6.89 (1H, s), 6.96-7.01 (2H, m). | ESI-MS m/z: 517 [M + H]+ |
| 240 (isomer B) | | 1H-NMR (CDCl$_3$) δ: 1.86-1.87 (1H, m), 2.01-2.04 (1H, m), 2.70-2.96 (5H, m), 3.08-3.16 (1H, m), 3.59 (4H, t, J = 11.9 Hz), 3.91 (1H, t, J = 8.7 Hz), 4.10 (1H, t, J = 7.26 Hz), 4.18 (2H, s), 4.34 (1H, t, J = 9.1 Hz), 4.61 (1H, m), 5.37 (1H, m), 5.89 (1H, s), 6.82 (1H, d, J = 8.3 Hz), 6.90 (1H, s), 6.90-7.10 (2H, m). | ESI-MS m/z: 517 [M + H]+ |
| 241 (isomer A) | | 1H-NMR (CDCl$_3$) δ: 1.98 (1H, m), 2.10 (1H, m), 2.22-2.32 (2H, m), 2.60-2.76 (4H, m), 2.83-2.94 (3H, m), 3.15-3.30 (3H, m), 3.93 (1H, t, J = 8.9 Hz), 4.20 (2H, s), 4.36 (1H, t, J = 8.9 Hz), 4.62 (1H, m), 5.40 (1H, m), 5.89 (1H, s), 6.85 (1H, d, J = 8.2 Hz), 6.97-7.06 (3H, m). | ESI-MS m/z: 501 [M + H]+ |

TABLE 35

| Example | Structural formula | NMR | MS |
|---|---|---|---|
| 241 (isomer B) | (structure with 3,3-difluoropyrrolidine, pyrazole-oxazoline, chroman-CF3) | 1H-NMR (CDCl3) δ: 1.99 (1H, m), 2.11 (1H, m), 2.22-2.33 (2H, m), 2.63 (1H, m), 2.69-2.77 (3H, m), 2.83-2.98 (3H, m), 3.15-3.30 (3H, m), 3.94 (1H, t, J = 8.8 Hz), 4.20 (2H, s), 4.35 (1H, t, J = 9.0 Hz), 4.62 (1H, m), 5.39 (1H, m), 5.89 (1H, s), 6.85 (1H, d, J = 8.3 Hz), 6.97-7.06 (3H, m). | ESI-MS m/z: 501 [M + H]+ |
| 242 (isomer A) | (structure with 4,4-difluoropiperidine, pyrazole-oxazoline, chroman-CF3) | 1H-NMR (CDCl3) δ: 1.92-2.14 (6H, m), 2.55-2.64 (6H, m), 2.91 (1H, m), 3.20 (1H, m), 3.94 (1H, t, J = 8.8 Hz), 4.25 (2H, d, J = 2.8 Hz), 4.35 (1H, t, J = 9.1 Hz), 4.65 (1H, m), 5.39 (1H, m), 5.89 (1H, s), 6.93-6.97 (2H, m), 7.33 (1H, s), 7.38 (1H, d, J = 8.4 Hz). | ESI-MS m/z: 501 [M + H]+ |
| 242 (isomer B) | (structure with 4,4-difluoropiperidine, pyrazole-oxazoline, chroman-CF3) | 1H-NMR (CDCl3) δ: 1.93-2.17 (6H, m), 2.56-2.61 (6H, m), 2.91 (1H, dd, J = 16.9, 4.1 Hz), 3.21 (1H, dd, J = 17.0, 5.2 Hz), 3.95 (1H, t, J = 8.9 Hz), 4.25 (2H, d, J = 2.6 Hz), 4.34 (1H, t, J = 9.0 Hz), 4.65 (1H, m), 5.38 (1H, m), 5.89 (1H, s), 6.93-7.00 (2H, m), 7.33 (1H, s), 7.38 (1H, d, J = 9.0 Hz). | ESI-MS m/z: 501 [M + H]+ |
| 243 | (structure with F3C-S-CH2CH2-, pyrazole-oxazoline, chroman-CN) | 1H-NMR (CDCl3) δ: 2.07 (1H, m), 2.26 (1H, m), 2.82-2.94 (3H, m), 3.08-3.20 (3H, m), 3.91 (1H, m), 4.28 (2H, s), 4.38 (1H, m), 4.64 (1H, m), 5.44 (1H, m), 5.91 (1H, s), 6.93 (2H, d, J = 8.5 Hz), 7.38 (1H, s), 7.42 (1H, m). | ESI-MS m/z: 453 [M + H]+ |
| 244 (isomer A) | (structure with F3C-S-CH2CH2-, pyrazole-oxazoline, chroman-CN) | 1H-NMR (CDCl3) δ: 2.07 (1H, m), 2.25 (1H, m), 2.81-2.95 (3H, m), 3.07-3.20 (3H, m), 3.91 (1H, dd, J = 9.9, 7.6 Hz), 4.28 (2H, m), 4.38 (1H, t, J = 8.5 Hz), 4.64 (1H, m), 5.44 (1H, m), 5.91 (1H, s), 6.90 (1H, s), 6.93 (1H, d, J = 8.4 Hz), 7.38 (1H, s), 7.42 (1H, d, J = 8.7 Hz). | ESI-MS m/z: 453 [M + H]+ |
| 244 (isomer B) | (structure with F3C-S-CH2CH2-, pyrazole-oxazoline, chroman-CN) | 1H-NMR (CDCl3) δ: 2.07 (1H, m), 2.25 (1H, m), 2.81-2.95 (3H, m), 3.07-3.20 (3H, m), 3.91 (1H, dd, J = 9.9, 7.6 Hz), 4.28 (2H, m), 4.38 (1H, t, J = 8.5 Hz), 4.64 (1H, m), 5.44 (1H, m), 5.91 (1H, s), 6.90 (1H, s), 6.93 (1H, d, J = 8.4 Hz), 7.38 (1H, s), 7.42 (1H, d, J = 8.7 Hz). | ESI-MS m/z: 453 [M + H]+ |

TABLE 35-continued

| Example | Structural formula | NMR | MS |
|---|---|---|---|
| 245 | | 1H-NMR (CDCl₃) δ: 1.69-1.92 (2H, m), 1.92-2.09 (2H, m), 2.89 (1H, dd, J = 17.3, 5.7 Hz), 3.18 (1H, dd, J = 14.3, 5.2 Hz), 3.68 (2H, m), 3.77-3.93 (3H, m), 4.22-4.29 (2H, m), 4.34 (1H, t, J = 8.7 Hz), 4.64 (1H, m), 5.34 (1H, m), 5.89 (1H, s), 6.88-6.94 (2H, m), 7.38 (1H, s), 7.42 (1H, d, J = 8.7 Hz), | ESI-MS m/z: 451 [M + H]+ |
| 246 (isomer A) | | 1H-NMR (CDCl₃) δ: 1.69-1.92 (2H, m), 1.92-2.09 (2H, m), 2.89 (1H, dd, J = 17.3, 5.7 Hz), 3.18 (1H, dd, J = 14.3, 5.2 Hz), 3.68 (2H, m), 3.77-3.93 (3H, m), 4.22-4.29 (2H, m), 4.34 (1H, t, J = 8.7 Hz), 4.64 (1H, m), 5.34 (1H, m), 5.89 (1H, s), 6.88-6.94 (2H, m), 7.38 (1H, s), 7.42 (1H, d, J = 8.7 Hz), | ESI-MS m/z: 451 [M + H]+ |
| 246 (isomer B) | | 1H-NMR (CDCl₃) δ: 1.69-1.92 (2H, m), 1.92-2.09 (2H, m), 2.89 (1H, dd, J = 17.3, 5.7 Hz), 3.18 (1H, dd, J = 14.3, 5.2 Hz), 3.68 (2H, m), 3.77-3.93 (3H, m), 4.22-4.29 (2H, m), 4.34 (1H, t, J = 8.7 Hz), 4.64 (1H, m), 5.34 (1H, m), 5.89 (1H, s), 6.88-6.94 (2H, m), 7.38 (1H, s), 7.42 (1H, d, J = 8.7 Hz) | ESI-MS m/z: 451 [M + H]+ |

TABLE 36

| Example | Structural formula | NMR | MS |
|---|---|---|---|
| 247 (isomer A) | | 1H-NMR (CDCl₃) δ: 1.81-2.06 (4H, m), 2.89 (1H, dd, J = 17.0, 5.7 Hz), 3.18 (1H, dd, J = 17.3, 5.4 Hz), 3.90 (1H, d, J = 9.9, 7.5 Hz), 3.98-4.09 (2H, m), 4.28 (2H, m), 4.36 (1H, dd, J = 10.3, 7.4 Hz), 4.59-4.68 (1H, m), 5.28-5.37 (1H, m), 5.90 (1H, s), 6.89 (1H, m), 6.93 (1H, d, J = 8.0 Hz), 7.38 (1H, s), 7.42 (1H, dd, J = 8.7, 1.8 Hz), | ESI-MS m/z: 437 [M + H]+ |
| 247 (isomer B) | | 1H-NMR (CDCl₃) δ: 1.81-2.06 (4H, m), 2.89 (1H, dd, J = 17.0, 5.7 Hz), 3.18 (1H, dd, J = 17.3, 5.4 Hz), 3.90 (1H, d, J = 9.9, 7.5 Hz), 3.98-4.09 (2H, m), 4.28 (2H, m), 4.36 (1H, dd, J = 10.3, 7.4 Hz), 4.59-4.68 (1H, m), 5.28-5.37 (1H, m), 5.90 (1H, s), 6.89 (1H, m), 6.93 (1H, d, J = 8.0 Hz), 7.38 (1H, s), 7.42 (1H, dd, J = 8.7, 1.8 Hz). | ESI-MS m/z: 437 [M + H]+ |
| 248 (isomer A) | | 1H-NMR (CDCl₃) δ: 1.73-2.10 (4H, m), 2.89 (1H, dd, J = 16.7, 4.3 Hz), 3.17 (1H, dd, J = 17.4, 5.8 Hz), 3.86-3.99 (3H, m), 4.22-4.32 (2H, m), 4.34 (1H, t, J = 8.7 Hz), 4.68 (1H, m), 5.32 (1H, m), 5.90 (1H, s), 6.21 (1H, t, J = 75.0 Hz), 6.88-6.95 (1H, m), 6.89 (1H, m), 7.38 (1H, s), 7.42 (1H, dd, J = 8.7, 1.8 Hz). | ESI-MS m/z: 419 [M + H]+ |

TABLE 36-continued

| Example | Structural formula | NMR | MS |
|---|---|---|---|
| 248 (isomer B) | | 1H-NMR (CDCl₃) δ: 1.73-2.10 (4H, m), 2.89 (1H, dd, J = 16.7, 4.3 Hz), 3.17 (1H, dd, J = 17.4, 5.8 Hz), 3.86-3.99 (3H, m), 4.22-4.32 (2H, m), 4.34 (1H, t, J = 8.7 Hz), 4.68 (1H, m), 5.32 (1H, m), 5.90 (1H, s), 6.21 (1H, t, J = 75.0 Hz), 6.88-6.95 (1H, m), 6.89 (1H, m), 7.38 (1H, s), 7.42 (1H, dd, J = 8.7, 1.8 Hz) | ESI-MS m/z: 419 [M + H]+ |
| 249 | | 1H-NMR (CDCl₃) δ: 2.94-2.98 (1H, m), 3.23-3.26 (1H, m), 4.09-4.38 (4H, m), 4.72 (1H, m), 5.21 (2H, t, J = 8.2 Hz), 6.41 (1H, m), 6.97 (1H, m), 7.22-7.42 (2H, m), 7.57-7.77 (2H, m). | ESI-MS m/z: 420 [M + H]+ |
| 250 | | 1H-NMR (CDCl₃) δ: 1.69-1.71 (6H, m), 2.80 (1H, s), 2.99-3.03 (1H, m), 3.22-3.27 (1H, m), 4.07 (2H, m), 4.23-4.41 (2H, m), 4.70 (1H, s), 6.43 (1H, s), 6.92-6.99 (1H, m), 7.31-7.40 (3H, m), 7.58 (1H, s). | ESI-MS m/z: 448 [M + H]+ |
| 251 | | 1H-NMR (CDCl₃) δ: 1.86 (1H, m), 2.11-2.29 (3H, m), 2.92 (1H, d, J = 16.9 Hz), 3.18 (1H, dd, J = 16.6, 5.2 Hz), 4.15 (1H, t, J = 13.2 Hz), 4.24-4.32 (2H, m), 4.39 (1H, d, J = 14.6 Hz), 4.62-4.69 (2H, m), 6.27 (1H, s), 6.93-6.96 (2H, m), 7.34-7.44 (7H, m). | ESI-MS m/z: 415 [M + H]+ |
| 252 | | 1H-NMR (CDCl₃) δ: 2.13-2.26 (2H, m), 2.89-2.96 (1H, m), 3.15-3.20 (1H, m), 4.02-4.06 (1H, m), 4.11-4.18 (1H, m), 4.23-4.28 (3H, m), 4.41-4.47 (1H, m), 4.64-4.66 (2H, m), 6.30 (1H, s), 6.89-7.00 (2H, m), 7.39-7.44 (2H, m). | ESI-MS m/z: 423 [M + H]+ |

TABLE 36-continued

| Example | Structural formula | NMR | MS |
|---|---|---|---|
| 253 (isomer A) | (F₃CO-[7-membered ring with O, pyrazole]-C(O)NH-chroman-CN) | 1H-NMR (CDCl₃) δ: 2.10-2.26 (2H, m), 2.88-2.93 (1H, m), 3.18 (1H, dd, J = 16.8, 5.1 Hz), 4.05 (1H, d, J = 12.4 Hz), 4.13-4.18 (1H, m), 4.23-4.31 (3H, m), 4.41-4.47 (1H, m), 4.64 (2H, m), 6.30 (1H, s), 6.90 (1H, d, J = 7.3 Hz), 6.94 (1H, d, J = 8.5 Hz), 7.40 (1H, s), 7.43 (1H, d, J = 8.6 Hz). | ESI-MS m/z: 423 [M + H]+ |

TABLE 37

| Example | Structural formula | NMR | MS |
|---|---|---|---|
| 253 (isomer B) | (F₃CO-[7-membered ring with O, pyrazole]-C(O)NH-chroman-CN) | 1H-NMR (CDCl₃) δ: 2.09-2.26 (2H, m), 2.88-2.94 (1H, m), 3.17 (1H, dd, J = 16.7, 5.2 Hz), 4.03 (1H, d, J = 11.0 Hz), 4.13-4.19 (1H, m), 4.24-4.32 (3H, m), 4.41-4.48 (1H, m), 4.64 (2H, m), 6.30 (1H, s), 6.92-6.96 (2H, m), 7.39 (1H, s), 7.43 (1H, dd, J = 8.5, 2.0 Hz). | ESI-MS m/z: 423 [M + H]+ |
| 254 | (F₃C-CH₂-O-[7-membered ring with O, pyrazole]-C(O)NH-chroman-CN) | 1H-NMR (CDCl₃) δ: 2.05-2.07 (2H, m), 2.90 (1H, m), 3.18 (1H, m), 3.92-4.18 (6H, m), 4.24-4.31 (2H, m), 4.41-4.44 (1H, m), 4.63 (1H, m), 6.27 (1H, s), 6.89-6.95 (2H, m), 7.38-7.44 (2H, m). | ESI-MS m/z: 437 [M + H]+ |
| 255 (isomer A) | (F₃C-CH₂-O-[7-membered ring with O, pyrazole]-C(O)NH-chroman-CN) | 1H-NMR (CDCl₃) δ: 2.06-2.07 (2H, m), 2.90 (1H, dd, J = 4.8, 16.9 Hz), 3.18 (1H, dd, J = 16.8, 5.3 Hz), 3.92-4.17 (6H, m), 4.24-4.31 (2H, m), 4.40-4.46 (1H, m), 4.63 (1H, m), 6.27 (1H, s), 6.90 (1H, d, J = 7.9 Hz), 6.93 (1H, d, J = 8.4 Hz), 7.39 (1H, s), 7.43 (1H, d, J = 8.5 Hz). | ESI-MS m/z: 437 [M + H]+ |
| 256 (isomer A) | (F₃C-CH₂-O-[7-membered ring with O, pyrazole]-C(O)NH-chroman-Cl) | 1H-NMR (CDCl₃) δ: 2.05-2.07 (2H, m), 2.85 (1H, d, J = 17.1 Hz), 3.14 (1H, dd, J = 17.3, 5.0 Hz), 3.89-4.01 (4H, m), 4.09-4.19 (4H, m), 4.41-4.46 (1H, m), 4.61 (1H, m), 6.26 (1H, s), 6.82 (1H, d, J = 8.7 Hz), 6.99-7.10 (3H, m). | ESI-MS m/z: 446 [M + H]+ |
| 256 (isomer B) | (F₃C-CH₂-O-[7-membered ring with O, pyrazole]-C(O)NH-chroman-Cl) | 1H-NMR (CDCl₃) δ: 2.06-2.07 (2H, m), 2.82-2.87 (1H, m), 3.15 (1H, dd, J = 16.8, 4.7 Hz), 3.86-4.19 (8H, m), 4.39-4.46 (1H, m), 4.61 (1H, m), 6.26 (1H, s), 6.81 (1H, d, J = 8.5 Hz), 6.97-6.99 (1H, m), 7.05 (1H, s), 7.09 (1H, d, J = 8.6 Hz). | ESI-MS m/z: 446 [M + H]+ |

TABLE 37-continued

| Example | Structural formula | NMR | MS |
|---|---|---|---|
| 257 (isomer A) | | 1H-NMR (CDCl₃) δ: 2.06-2.07 (2H, m), 2.84-2.94 (1H, m), 3.15-3.24 (1H, m), 3.91-4.19 (6H, m), 4.25-4.27 (2H, m), 4.41-4.46 (1H, m), 4.64 (1H, s), 6.27 (1H, s), 6.95 (2H, d, J = 8.2 Hz), 7.34 (1H, s), 7.39 (1H, d, J = 8.9 Hz). | ESI-MS m/z: 480 [M + H]+ |
| 257 (isomer B) | | 1H-NMR (CDCl₃) δ: 2.05-2.07 (2H, m), 2.90-2.95 (1H, m), 3.20 (1H, dd, J = 16.1, 5.2 Hz), 3.91-4.18 (6H, m), 4.26 (2H, m), 4.40-4.46 (1H, m), 4.65 (1H, m), 6.26 (1H, s), 6.94-6.98 (2H, m), 7.33 (1H, s), 7.39 (1H, d, J = 8.2 Hz). | ESI-MS m/z: 480 [M + H]+ |
| 258 | | 1H-NMR (CDCl₃) δ: 1.86-1.94 (2H, m), 2.11-2.20 (2H, m), 2.97 (1H, m), 3.26 (1H, dd, J = 16.8, 5.5 Hz), 4.18-4.30 (7H, m), 4.70 (1H, m), 6.65 (1H, s), 6.98 (1H, d, J = 8.4 Hz), 7.36-7.46 (3H, m), 7.60 (1H, s). | ESI-MS m/z: 448 [M + H]+ |
| 259 | | 1H-NMR (CDCl₃) δ: 3.01-3.18 (1H, m), 3.18-3.29 (1H, m), 4.09-4.46 (6H, m), 4.71 (1H, m), 4.97 (2H, m), 6.06 (1H, s), 6.98 (1H, d, J = 8.8 Hz), 7.33-7.61 (3H, m), 7.62 (1H, s). | ESI-MS m/z: 434 [M + H]+ |

TABLE 38

| Example | Structural formula | NMR | MS |
|---|---|---|---|
| 260 | | 1H-NMR (CDCl₃) δ: 2.92-2.96 (1H, m), 3.19-3.26 (1H, m), 4.07-4.35 (6H, m), 4.71 (1H, m), 4.99 (2H, s), 6.96 (1H, m), 7.10 (1H, m), 7.31-7.43 (2H, m), 7.67-7.74 (2H, m), 8.21 (1H, m), 8.98 (1H, m). | ESI-MS m/z: 445 [M + H]+ |

TABLE 38-continued

| Example | Structural formula | NMR | MS |
| --- | --- | --- | --- |
| 261 | | 1H-NMR (CDCl₃) δ: 2.35-2.41 (2H, m), 2.80-2.88 (3H, m), 2.96 (2H, t, J = 5.6 Hz), 3.15 (1H, dd, J = 17.0, 5.2 Hz), 3.72 (2H, s), 4.14 (2H, t, J = 5.4 Hz), 4.19 (2H, d, J = 2.9 Hz), 4.59-4.67 (1H, m), 6.53 (1H, s), 6.81 (1H, d, J = 8.6 Hz), 6.99-7.13 (3H, m). | ESI-MS m/z: 429 [M + H]+ |
| 262 | | 1H-NMR (CDCl₃) δ: 2.32-2.45 (2H, m), 2.81-2.97 (5H, m), 3.13 (1H, dd, J = 17.4, 5.8 Hz), 3.73 (2H, s), 4.11-4.18 (4H, m), 4.65-4.73 (1H, m), 6.54 (1H, s), 6.81 (1H, dd, J = 8.1, 1.1 Hz), 6.95-7.10 (3H, m). | ESI-MS m/z: 429 [M + H]+ |
| 263 | | 1H-NMR (CDCl₃) δ: 0.04-0.10 (2H, m), 0.43-0.49 (2H, m), 0.65-0.76 (1H, m), 1.45 (2H, q, J = 8.0 Hz), 2.64 (2H, t, J = 7.7 Hz), 2.81-2.96 (3H, m), 3.15 (1H, dd, J = 16.8, 5.1 Hz), 3.68 (2H, s), 4.13 (2H, t, J = 5.5 Hz), 4.17-4.20 (2H, m), 4.59-4.65 (1H, m), 6.50 (1H, s), 6.78-6.84 (1H, m), 6.97-7.14 (3H, m). | ESI-MS m/z: 401 [M + H]+ |
| 264 | | 1H-NMR (CDCl₃) δ: 0.08 (2H, q, J = 5.7 Hz), 0.46 (2H, q, J = 6.6 Hz), 0.66-0.73 (1H, m), 1.42-1.49 (2H, m), 2.64 (2H, t, J = 7.6 Hz), 2.90-2.94 (3H, m), 3.15-3.25 (1H, m), 3.68 (2H, s), 4.13 (2H, t, J = 8.6 Hz), 4.22-4.28 (2H, m), 4.61-4.67 (1H, m), 6.51 (1H, s), 6.93-7.02 (2H, m), 7.33-7.41 (2H, m). | ESI-MS m/z: 435 [M + H]+ |
| 265 | | 1H-NMR (CDCl₃) δ: 1.47-1.71 (2H, m), 1.88-1.98 (2H, m), 2.18-2.23 (2H, m), 2.77 (2H, t, J = 5.3 Hz), 2.90-2.96 (1H, m), 3.00-3.03 (2H, m), 3.18-3.23 (1H, m), 3.52 (2H, t, J = 5.3 Hz), 3.76 (2H, s), 3.89-3.96 (1H, m), 4.14 (2H, t, J = 5.6 Hz), 4.21-4.29 (2H, m), 4.66 (1H, m), 6.51 (1H, s), 6.94-7.00 (2H, m), 7.33 (1H, s), 7.38 (1H, d, J = 9.7 Hz). | ESI-MS m/z: 465 [M + H]+ |
| 266 | | 1H-NMR (CDCl₃) δ: 1.47-1.76 (2H, m), 1.90-1.95 (2H, m), 2.19-2.21 (2H, m), 2.77 (2H, t, J = 5.4 Hz), 2.86-2.91 (1H, m), 3.01 (2H, t, J = 5.6 Hz), 3.16-3.21 (1H, m), 3.52 (2H, t, J = 5.3 Hz), 3.76 (2H, s), 3.82 (2H, q, J = 8.3 Hz), 3.93 (1H, m), 4.12-4.21 (4H, m), 4.57 (2H, s), 4.63 (1H, m), 6.51 (1H, s), 6.87 (1H, d, J = 8.4 Hz), 7.02-7.13 (3H, m). | ESI-MS m/z: 509 [M + H]+ |
| 267 | | 1H-NMR (CDCl₃) δ: 2.03 (1H, m), 2.87-3.05 (2H, m), 3.11-3.24 (4H, m), 4.03-3.08 (2H, m), 4.21-4.30 (3H, m), 4.66 (1H, m), 6.90-9.85 (1H, m), 7.06-7.09 (1H, m), 7.21 (1H, s), 7.31 (1H, m), 7.44-7.77 (2H, m), 8.18 (1H, m), 9.00 (1H, m). | ESI-MS m/z: 526 [M + H]+ |

TABLE 38-continued

| Example | Structural formula | NMR | MS |
|---|---|---|---|
| 268 | | 1H-NMR (CDCl$_3$) δ: 2.92 (3H, m), 3.17 (1H, dd, J = 16.8, 5.0 Hz), 3.67 (4H, m), 4.12 (2H, m), 4.23-4.32 (2H, m), 4.64 (1H, m), 6.49 (1H, s), 6.92-6.97 (2H, m), 7.03 (2H, t, J = 8.1 Hz), 7.31 (2H, t, J = 6.3 Hz), 7.38 (1H, s), 7.42 (1H, d, J = 8.6 Hz). | ESI-MS m/z: 432 [M + H]+ |

TABLE 39

| Example | Structural formula | NMR | MS |
|---|---|---|---|
| 269 | | 1H-NMR (CDCl$_3$) δ: 2.81 (4H, m), 2.89-2.99 (3H, m), 3.18 (1H, dd, J = 16.8, 4.9 Hz), 3.75 (2H, s), 4.14 (2H, t, J = 5.5 Hz), 4.24-4.32 (2H, m), 4.65 (1H, m), 6.53 (1H, s), 6.92-7.00 (4H, m), 7.16 (2H, m), 7.39 (1H, s), 7.42 (1H, d, J = 8.4 Hz). | ESI-MS m/z: 446 [M + H]+ |
| 270 | | 1H-NMR (CDCl$_3$) δ: 0.93 (6H, d, J = 6.6 Hz), 1.82 (1H, m), 2.29 (2H, d, J = 7.4 Hz), 2.86-2.96 (3H, m), 3.17 (1H, dd, J = 16.5, 5.2, Hz), 3.63 (2H, s), 4.12 (2H, t, J = 5.6 Hz), 4.23-4.32 (2H, m), 4.64 (1H, m), 6.51 (1H, s), 6.92-6.96 (2H, m), 7.38-7.43 (2H, m). | ESI-MS m/z: 380 [M + H]+ |
| 271 | | 1H-NMR (CDCl$_3$) δ: 1.45-1.62 (4H, m), 1.74 (2H, m), 1.93 (2H, m), 2.75 (1H, t, J = 7.5 Hz), 2.89-2.98 (3H, m), 3.17 (1H, dd, J = 16.7, 4.9 Hz), 3.73 (2H, m), 4.13 (2H, t, J = 5.6 Hz), 4.25-4.33 (2H, m), 4.64 (1H, m), 6.51 (1H, s), 6.92-6.95 (2H, m), 7.38 (1H, s), 7.42 (1H, dd, J = 8.4, 1.9 Hz). | ESI-MS m/z: 392 [M + H]+ |
| 272 | | 1H-NMR (CDCl$_3$) δ: 1.20 (9H, s), 2.75 (2H, t, J = 5.8 Hz), 2.91 (1H, dd, J = 17.6, 5.7 Hz), 3.03 (2H, t, J = 5.3 Hz), 3.20 (1H, dd, J = 16.5, 5.6 Hz), 3.55 (2H, t, J = 5.8 Hz), 3.77 (2H, s), 4.13 (2H, t, J = 5.5 Hz), 4.20-4.27 (2H, m), 4.65 (1H, m), 6.50 (1H, s), 6.56 (1H, t, J = 56.8 Hz), 6.93 (1H, d, J = 8.4 Hz), 7.01 (1H, d, J = 7.6 Hz), 7.22 (1H, s), 7.29 (1H, s). | ESI-MS m/z: 449 [M + H]+ |

TABLE 39-continued

| Example | Structural formula | NMR | MS |
|---|---|---|---|
| 273 | | 1H-NMR (CDCl₃) δ: 2.85 (1H, dd, J = 16.8, 4.3 Hz), 3.05 (2H, t, J = 4.8 Hz), 3.15 (1H, dd, J = 16.8, 5.3 Hz), 3.80 (4H, d, J = 3.1 Hz), 3.92 (3H, s), 4.13-4.22 (4H, m), 4.61 (1H, m), 6.50 (1H, s), 6.65 (1H, d, J = 8.2 Hz), 6.80 (1H, d, J = 8.6 Hz), 6.98 (1H, d, J = 7.2 Hz), 7.02-7.04 (2H, m), 7.08 (1H, dd, J = 8.7, 2.5 Hz), 7.56 (1H, t, J = 7.8 Hz). | ESI-MS m/z: 454 [M + H]+ |
| 274 | | 1H-NMR (CDCl₃) δ: 2.85 (1H, dd, J = 16.8, 4.2 Hz), 3.00 (2H, t, J = 5.5 Hz), 3.07 (2H, m), 3.15 (1H, dd, J = 16.8, 5.2 Hz), 3.84 (2H, s), 4.15 (2H, t, J = 5.5 Hz), 4.19 (2H, dd, J = 4.4, 1.8 Hz), 4.51 (2H, t, J = 5.5 Hz), 4.61 (1H, m), 6.51 (1H, m), 6.76 (1H, d, J = 8.4 Hz), 6.81 (1H, d, J = 8.7 Hz), 6.88 (1H, m), 7.01-7.04 (2H, m), 7.08 (1H, dd, J = 8.7, 2.6 Hz), 7.58 (1H, m), 8.14 (1H, ddd, J = 5.0, 2.0, 0.7 Hz). | ESI-MS m/z: 454 [M + H]+ |
| 275 | | 1H-NMR (CDCl₃) δ: 2.79-2.84 (1H, m), 3.10-3.23 (5H, m), 3.86 (2H, s), 4.15 (2H, d, J = 2.7 Hz), 4.19-4.23 (2H, m), 4.55-4.61 (1H, m), 6.83-7.04 (4H, m), 7.10-7.15 (1H, m), 7.27-7.35 (5H, m). | ESI-MS m/z: 457 [M + H]+ |
| 276 | | 1H-NMR (CDCl₃) δ: 2.84-2.89 (1H, m), 3.19 (1H, dd, J = 17.3, 5.2 Hz), 3.80-3.85 (4H, m), 4.08-4.13 (2H, m), 4.20 (2H, m), 4.62-4.64 (1H, m), 4.69 (1H, s), 4.83 (1H, s), 6.52-6.60 (1H, m), 6.86-6.92 (2H, m), 6.99-7.07 (2H, m), 7.14 (1H, t, J = 7.0 Hz), 7.21-7.35 (5H, m). | ESI-MS m/z: 417 [M + H]+ |
| 277 | | 1H-NMR (CDCl₃) δ: 2.86 (1H, dd, J = 16.9, 4.0 Hz), 3.19 (1H, dd, J = 17.0, 5.8 Hz), 3.65 (2H, t, J = 5.6 Hz), 4.18-4.20 (4H, m), 4.40 (2H, s), 4.60-4.65 (1H, m), 6.59 (1H, s), 6.87-6.92 (2H, m), 7.02-7.07 (2H, m), 7.14 (1H, t, J = 8.9 Hz), 7.73 (1H, t, J = 7.9 Hz), 7.90 (1H, d, J = 8.2 Hz), 8.01 (1H, d, J = 7.9 Hz), 8.08 (1H, s). | ESI-MS m/z: 507 [M + H]+ |

TABLE 40

| Example | Structural formula | NMR | MS |
|---|---|---|---|
| 278 | | 1H-NMR (CDCl₃) δ: 2.93 (1H, dd, J = 16.6, 5.0 Hz), 3.19 (1H, dd, J = 16.8, 5.1 Hz), 3.65 (2H, t, J = 6.0 Hz), 4.22 (2H, t, J = 5.4 Hz), 4.24-4.33 (2H, m), 4.36 (2H, s), 4.64-4.68 (1H, m), 6.63 (1H, s), 6.92-7.03 (6H, m), 7.39-7.44 (2H, m). | |
| 279 | | 1H-NMR (CDCl₃) δ: 2.95-3.03 (1H, m), 3.24-3.31 (1H, m), 3.64 (2H, t, J = 6.1 Hz), 4.23 (2H, t, J = 5.1 Hz), 4.27-4.32 (2H, m), 4.36 (2H, s), 4.67-4.72 (1H, m), 6.64 (1H, s), 6.93-7.11 (6H, m), 7.29-7.38 (3H, m), 7.81 (1H, td, J = 8.0, 1.9 Hz), 8.55 (1H, dd, J = 4.8, 1.5 Hz), 8.79 (1H, d, J = 2.0 Hz). | |
| 280 | | 1H-NMR (CDCl₃) δ: 2.86 (1H, dd, J = 16.8, 3.9 Hz), 3.16 (1H, dd, J = 16.8, 5.3 Hz), 4.21 (2H, m), 4.25 (4H, m), 4.63 (1H, m), 4.82 (2H, s), 6.68(1H, s), 6.70 (1H, d, J = 9.0 Hz), 6.81 (1H, d, J = 8.7 Hz), 7.04-7.10 (3H, m), 7.73 (1H, dd, J = 9.0, 2.3 Hz), 8.47 (1H, d, J = 2.1 Hz). | ESI-MS m/z: 435 [M + H]+ |
| 281 | | 1H-NMR (CDCl₃) δ: 1.16 (9H, m), 2.85 (1H, dd, J = 16.5, 4.0 Hz), 2.97 (2H, td, J = 5.7, 2.1 Hz), 3.15 (1H, dd, J = 16.7, 5.5 Hz), 3.81 (2H, s), 4.10 (2H, t, J = 5.4 Hz), 4.17-4.22 (2H, m), 4.59-4.63 (1H, m), 6.50 (1H, s), 6.79-6.81 (1H, m), 6.98-7.09 (3H, m). | ESI-MS m/z: 389 [M + H]+ |
| 282 | | 1H-NMR (CDCl₃) δ: 0.91 (2H, m), 1.05 (2H, m), 2.89 (1H, dd, J = 16.7, 5.0 Hz), 2.98 (2H, t, J = 5.5 Hz), 3.15 (1H, dd, J = 16.6, 5.2 Hz), 3.71 (2H, s), 4.05 (2H, t, J = 5.5 Hz), 4.20-4.31 (2H, m), 4.62 (1H, m), 6.47 (1H, s), 6.89-6.92 (2H, m), 7.04 (2H, t, J = 8.6 Hz), 7.30 (2H, m), 7.37 (1H, s), 7.40 (1H, d, J = 8.7 Hz). | ESI-MS m/z: 458 [M + H]+ |

TABLE 40-continued

| Example | Structural formula | NMR | MS |
| --- | --- | --- | --- |
| 283 | | 1H-NMR (CDCl₃) δ: 0.84 (1H, m), 0.94 (1H, m), 1.06 (1H, m), 1.15 (2H, m), 1.26 (1H, m), 2.87 (1H, m), 3.15 (1H, dt, J = 16.7, 5.5 Hz), 3.37 (1H, t, J = 5.2 Hz), 4.04 (2H, m), 4.13 (1H, s), 4.19 (2H, m), 4.62 (1H, m), 6.81 (1H, m), 6.97-7.10 (4H, m). | ESI-MS m/z: 441 [M + H]+ |
| 284 | | 1H-NMR (CDCl₃) δ: 0.77 (2H, m), 0.84 (2H, m), 2.34 (2H, m), 2.85 (1H, dd, J = 16.9, 3.9 Hz), 3.12-3.17 (3H, m), 3.88 (2H, s), 4.03 (2H, t, J = 5.4 Hz), 4.19 (2H, m), 4.61 (1H, m), 6.50 (1H, s), 6.80 (1H, d, J = 8.7 Hz), 6.99-7.09 (3H, m). | ESI-MS m/z: 455 [M + H]+ |
| 285 | | 1H-NMR (CDCl₃) δ: 1.50 (6H, s), 2.82-2.88 (3H, m), 3.15 (1H, dd, J = 11.4, 5.5 Hz), 3.86 (2H, s), 4.04 (2H, t, J = 5.5 Hz), 4.19 (2H, m), 4.62 (1H, m), 6.50 (1H, s), 6.80 (1H, d, J = 8.7 Hz), 7.00-7.09 (3H, m), 7.17 (1H, m), 7.65-7.67 (2H, m), 8.57 (1H, dt, J = 4.6, 1.3 Hz). | ESI-MS m/z: 452 [M + H]+ |
| 286 | | 1H-NMR (CDCl₃) δ: 0.88-1.09 (5H, m), 2.87-2.97 (1H, m), 3.04 (1H, t, J = 5.5 Hz), 3.17 (1H, m), 3.76-3.81 (2H, m), 3.94 (3H, s), 4.06 (1H, t, J = 5.4 Hz), 4.11 (1H, m), 4.21-4.34 (2H, m), 4.63 (1H, m), 6.67-6.73 (2H, m), 6.93 (2H, t, J = 9.1 Hz), 7.04-7.11 (1H, m), 7.37-7.44 (2H, m), 8.07-8.14 (1H, m). | ESI-MS m/z: 471 [M + H]+ |

TABLE 41

| Example | Structural formula | NMR | MS |
| --- | --- | --- | --- |
| 287 | | 1H-NMR (CDCl₃) δ: 1.24-1.28 (1H, m), 2.24-2.28 (1H, m), 2.87-2.91 (1H, m), 3.16-3.22 (1H, dd, J = 16.7, 5.5 Hz), 4.05-4.31 (4H, m), 4.48-4.64 (2H, m), 5.92 (1H, s), 6.87-7.15 (6H, m), 7.32-7.37 (4H, m). | ESI-MS m/z: 375 [M + H]+ |

The compound of Example 291 was synthesized from the compound of Example 9 by a method similar to Step 1 in Reference Example 3.

The compound of Example 292 was synthesized from the compound of Example 9 by a method similar to Step 1 to Step 3 in Reference Example 3.

The compound of Example 293 was synthesized from the compound of Example 9 by a method similar to Step 1 in Reference Example 3.

The compound of Example 294 was synthesized from the compound of Example 293 under the scheme depicted in the figure below.

[Chem 234]

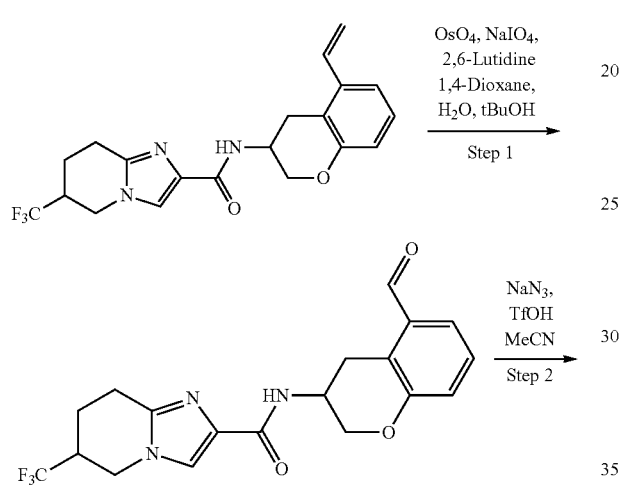

The compound of Example 295 was synthesized by a method similar to Example 11.

The compound of Example 296 was synthesized from the compound synthesized in Step 1 in Example 294 under the scheme depicted in the figure below.

[Chem 235]

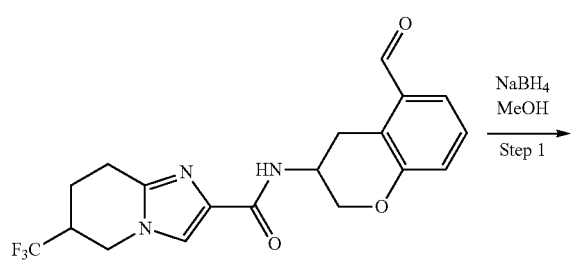

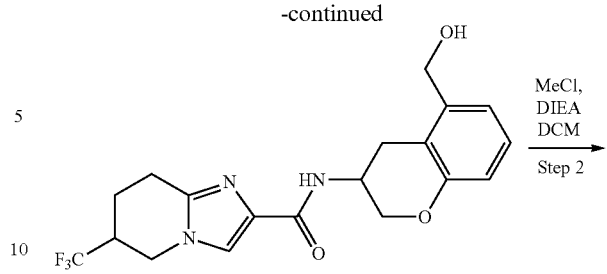

The compound of Example 297 was synthesized form the compound synthesized in Step 2 in Example 296 under the scheme depicted in the figure below.

[Chem 236]

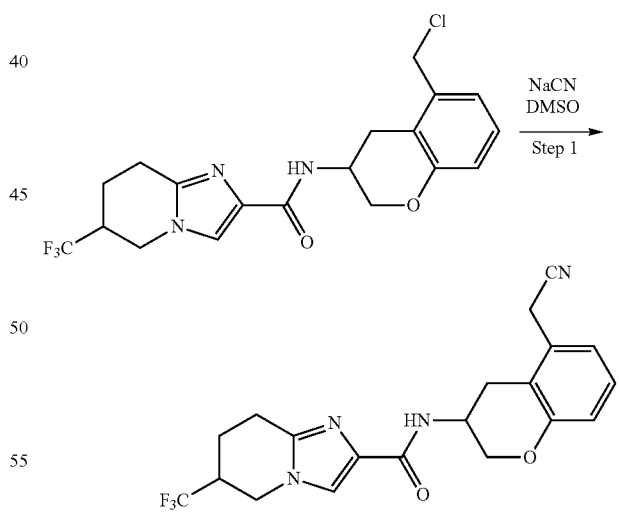

The compound of Example 298 was synthesized by methods similar to those described in Example 1 and Example 3.

The compound of Example 299 was synthesized by a method similar to Example 15.

The compound of Example 300 was synthesized from the compound synthesized in Example 14 under the scheme depicted in the figure below.

[Chem 237]

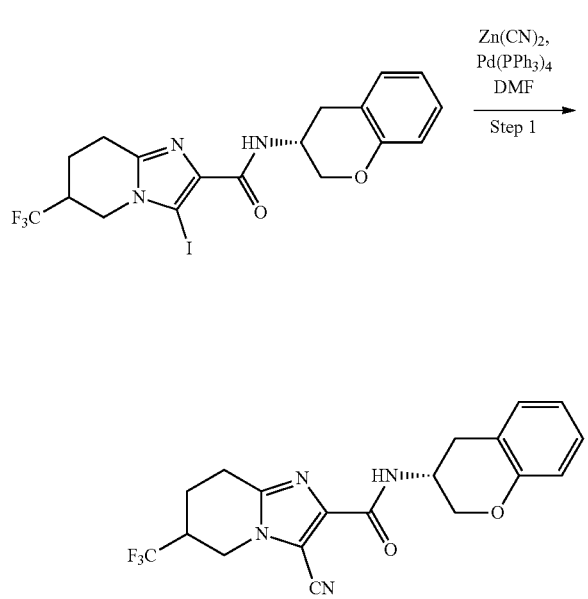

The compound of Example 301 was synthesized from the compound synthesized in Example 14 by a method similar to Example 29.

The compound of Example 302 was synthesized from the compound synthesized in Example 14 by a method similar to Step 2 in Reference Example 3.

The compound of Example 303 was synthesized by a method similar to Example 16.

The compound of Example 304 was synthesized by a method similar to Example 16.

The compound of Example 305 was synthesized by methods similar to those described in Example 18 and Reference Example 43.

The compound of Example 306 was synthesized by methods similar to those described in Example 18 and Reference Example 65.

The compound of Reference Example 75 (shown in the figure below.) was synthesized by a method similar to Example 26.

[Chem 238]

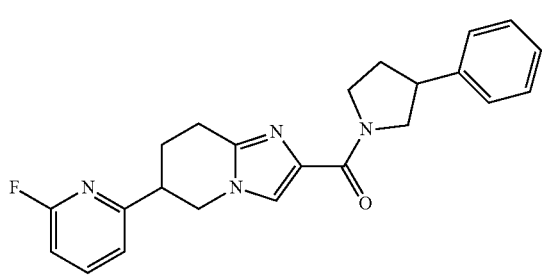

The compound of Example 307 was synthesized from the compound synthesized in Reference Example 75 under the scheme depicted in the figure below.

[Chem 239]

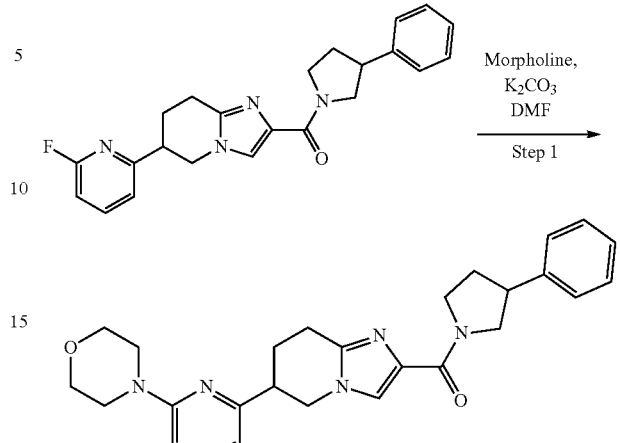

The compound of Example 308 was synthesized by a method similar to Example 307.

The compound of Example 309 was synthesized by a method similar to Example 307.

The compound of Example 310 was synthesized by a method similar to Example 307.

The compound of Example 311 was synthesized by a method similar to Example 307.

The compound of Example 312 was synthesized by methods similar to those described in Example 307 and Example 102.

The compound of Example 313 was synthesized from the compound synthesized in Reference Example 75 under the scheme depicted in the figure below.

[Chem 240]

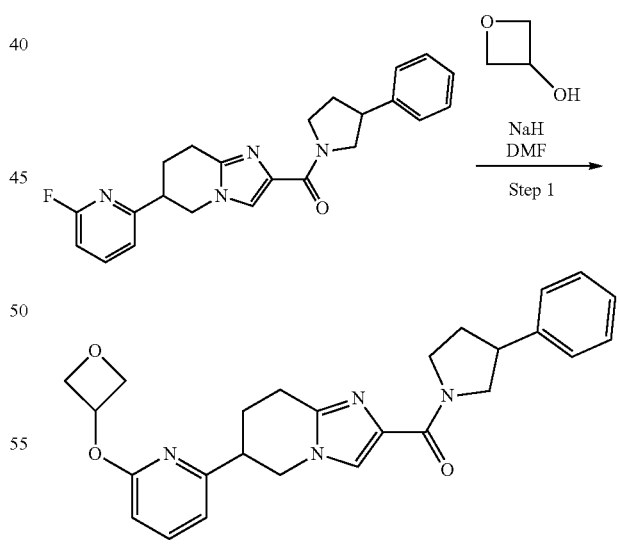

The compound of Example 314 was synthesized by a method similar to Example 27.

The compound of Example 315 was synthesized by a method similar to Example 26.

The compound of Example 316 was synthesized by a method similar to Example 26.

The compound of Example 317 was synthesized by a method similar to Example 29.

The compound of Example 318 was synthesized by a method similar to Example 30.

The compound of Example 319 was synthesized by methods similar to those described in Example 41, Example 168 and Example 157.

The compound of Example 320 was synthesized by methods similar to those described in Example 29 and Example 157.

The compound of Example 321 was synthesized by a method similar to Example 41.

The compound of Example 322 was synthesized from the compound synthesized in Step 1 in Example 42 under the scheme depicted in the figure below.

[Chem 241]

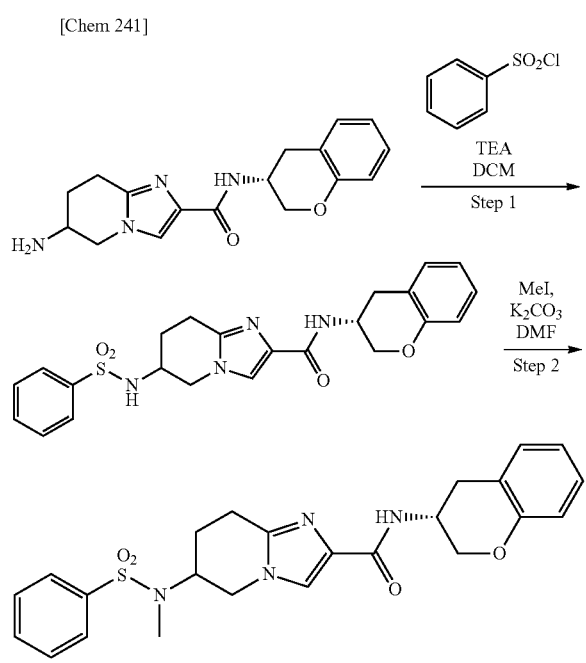

The compound of Example 323 was synthesized by a method similar to Example 62.

The compound of Example 324 was synthesized by a method similar to Example 43.

The compound of Example 325 was synthesized by methods similar to those described in Example 62 and Step 3 in Example 41.

The compound of Example 326 was synthesized by methods similar to those described in Example 43 and Example 45.

The compound of Example 327 was synthesized by a method similar to Example 325.

The compound of Example 328 was synthesized by a method similar to Example 49.

The compound of Reference Example 76 (3-(2-chlorophenyl)-3-fluoropyrrolidine hydrochloride) was synthesized under the scheme depicted in the figure below.

[Chem 242]

The compound of Example 329 was synthesized from the compound of Reference Example 21 and the compound of Reference Example 76 by a method similar to Step 3 in Example 56.

The compound of Example 330 was synthesized by a method similar to Example 62.

The compound of Example 331 was synthesized by a method similar to Example 62.

The compound of Example 332 was synthesized by methods similar to those described in Reference Example 18, Example 58 and Example 3.

The compound of Example 333 was synthesized by methods similar to those described in Example 59 and Example 45.

The compound of Reference Example 77 (shown in the figure below.) was synthesized by a method similar to Reference Example 4.

[Chem 243]

The compound of Example 334 was synthesized from the compound of Reference Example 21 and the compound of Reference Example 77 by a method similar to Step 3 in Example 100.

The compound of Example 335 was synthesized by methods similar to those described in Example 43 and Example 45.

The compound of Example 336 was synthesized by a method similar to Example 43.

The compound of Example 337 was synthesized by a method similar to Example 43.

Compound of Reference Example 78 ((R)—N-(Chroman-3-yl)-3-phenyl-5,6,7,8-tetrahydroimidazo[1,2-a]pyrazine-2-carboxamide) was synthesized under the scheme depicted in the figure below.

[Chem 244]

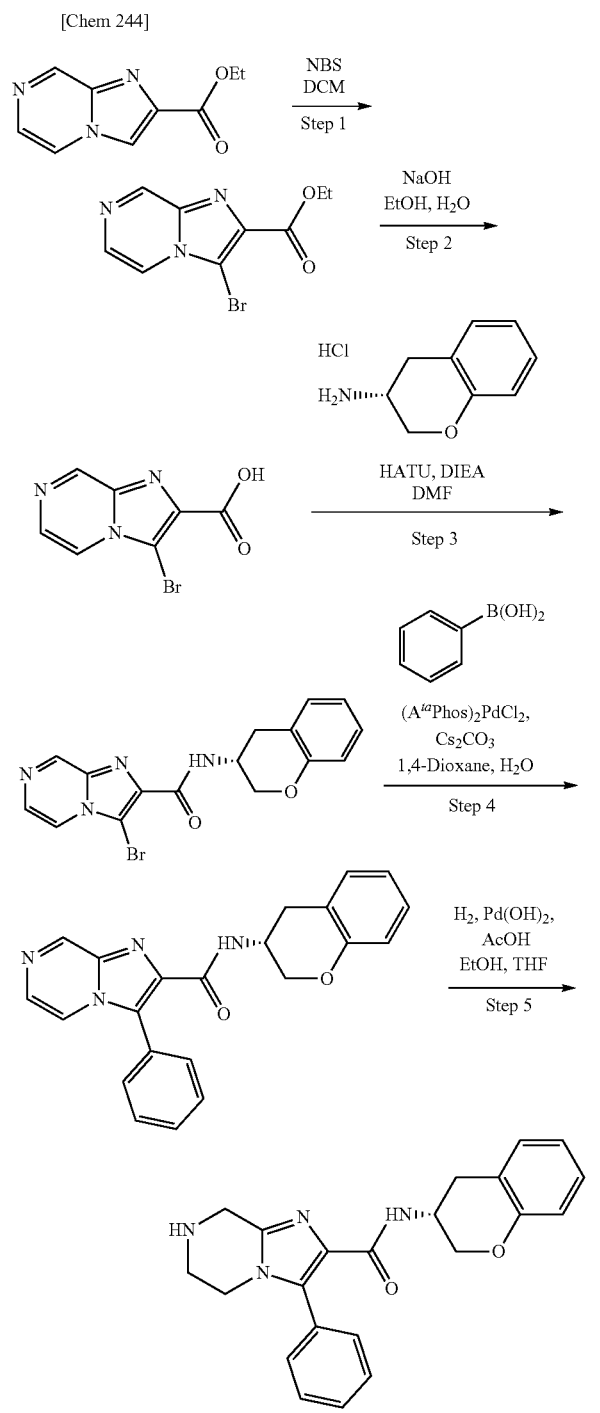

The compound of Example 338 was synthesized from the compound of Reference Example 78 by a method similar to Reference Example 69.

The compound of Example 339 was synthesized from the compound of Reference Example 78 by a method similar to Step 1 in Reference Example 1.

The compound of Reference Example 79 (6-phenyl-5,6-dihydro-8H-imidazo[2,1-c][1,4]oxazine-2-carboxylic acid) was synthesized under the scheme depicted in the figure below.

[Chem 245]

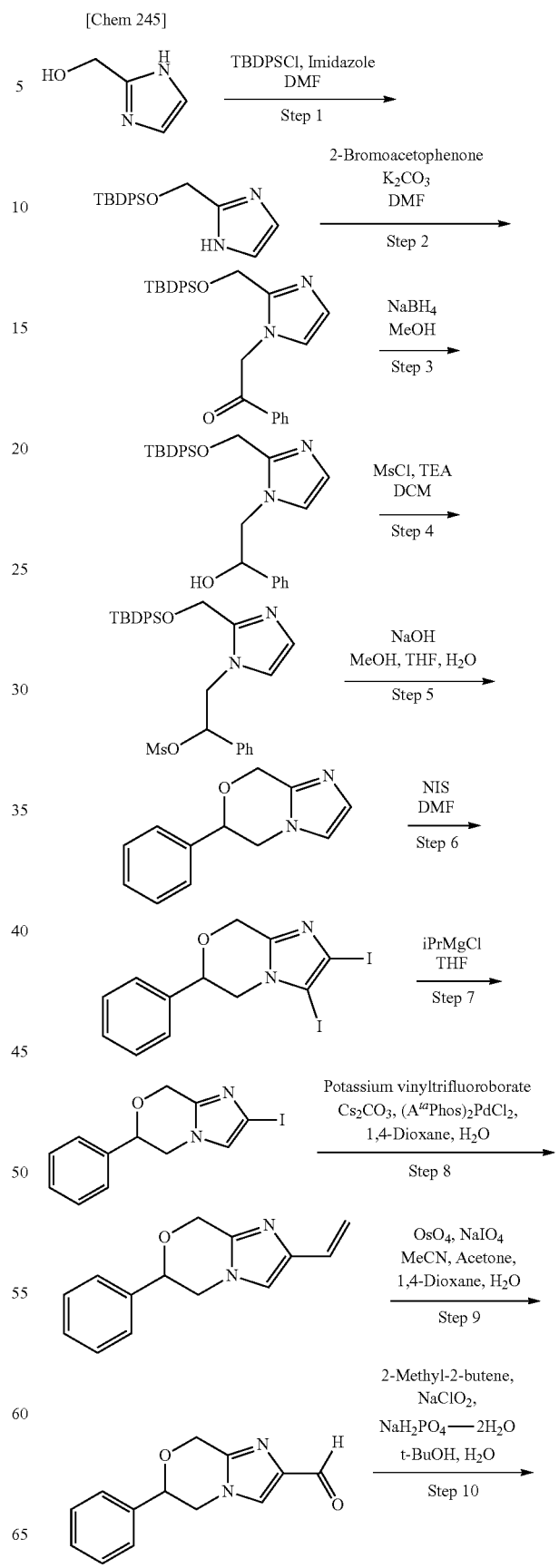

-continued

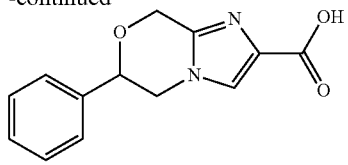

The compound of Example 340 was synthesized from the compound of Reference Example 79 by a method similar to Step 3 in Example 100.

The compound of Example 341 was synthesized by a method similar to Example 64 and Reference Example 24.

The compound of Reference Example 80 (shown in the figure below.) was synthesized by a method similar to Step 1 and Step 4 in Reference Example 3.

[Chem 246]

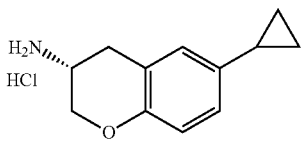

The compound of Example 342 was synthesized by methods similar to those described in Example 66 and Reference Example 80.

The compound of Example 343 was synthesized by methods similar to those described in Example 66 and Reference Example 52.

The compound of Example 344 was synthesized by methods similar to those described in Example 64 and Reference Example 1.

The compound of Example 345 was synthesized by methods similar to those described in Example 64 and Reference Example 43.

The compound of Example 346 was synthesized by methods similar to those described in Example 64 and Reference Example 43.

The compound of Example 347 was synthesized by a method similar to Example 69.

The compound of Example 348 was synthesized by methods similar to those described in Example 69 and Reference Example 1.

The compound of Example 349 was synthesized by a method similar to Example 70.

The compound of Example 350 was synthesized by a method similar to Example 70.

The compound of Example 351 was synthesized by a method similar to Example 70.

The compound of Example 352 was synthesized by a method similar to Example 70.

The compound of Example 353 was synthesized by a method similar to Example 70.

The compound of Example 354 was synthesized by a method similar to Example 70.

The compound of Example 355 was synthesized by a method similar to Example 70.

The compound of Example 356 was synthesized by a method similar to Example 70.

The compound of Example 357 was synthesized from the compound of Example 71 by a method similar to Step 1 in Reference Example 27.

The compound of Example 358 was synthesized by methods similar to those described in Example 70 and Reference Example 1.

The compounds of Example 359 and Example 360 were obtained by separating the compound of Example 70.

The compound of Example 361 was synthesized from the compound of Example 82 by a method similar to Step 2 to Step 3 in Example 296.

The compound of Example 362 was synthesized by methods similar to those described in Example 70 and Reference Example 1.

The compound of Example 363 was synthesized by a method similar to Example 70.

The compound of Example 364 was synthesized by methods similar to those described in Example 70 and Reference Example 24.

The compound of Example 365 was synthesized by a method similar to Example 361.

The compound of Example 366 was synthesized by methods similar to those described in Example 70 and Reference Example 24.

The compound of Example 367 was synthesized by methods similar to those described in Example 70 and Reference Example 1.

The compound of Example 368 was synthesized from the compound of Example 82 by methods similar to Step 2 in Example 296 and Step 1 in Example 122.

The compound of Example 369 was synthesized from the compound of Example 82 by a method similar to Step 2 to Step 3 in Example 296.

The compound of Example 370 was synthesized from the compound of Example 82 by a method similar to Step 2 to Step 3 in Example 296.

The compound of Example 371 was synthesized by methods similar to those described in Example 70 and Reference Example 1.

The compound of Example 372 was synthesized by methods similar to those described in Example 70 and Reference Example 24.

The compound of Example 373 was synthesized by methods similar to those described in Example 169 and Reference Example 24.

The compounds of Example 374 were obtained by separating the compound of Example 373.

The compound of Example 375 was synthesized by a methods similar to those described in Example 169 and Reference Example 73.

The compound of Example 376 was synthesized by a methods similar to those described in Example 169 and Reference Example 23.

The compound of Example 377 was synthesized from the compound of Example 171 by a method similar to Step 1 in Reference Example 27.

The compound of Example 378 was synthesized from the compound of Example 171 by a method similar to Step 1 in Reference Example 27.

The compound of Example 379 was synthesized from the compound synthesized in step 1 in Example 120 under the scheme depicted in the figure below.

[Chem 247]

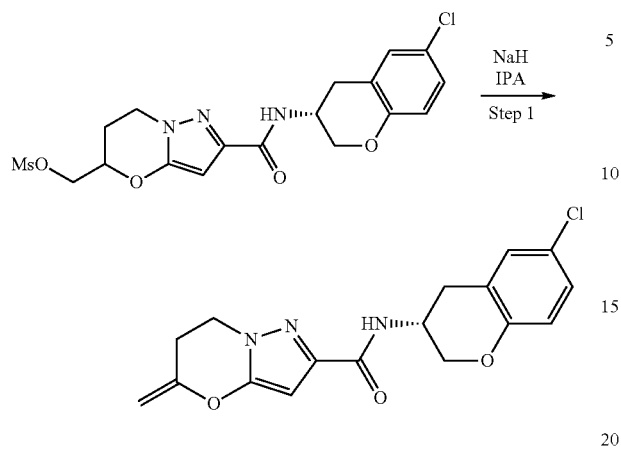

The compound of Example 380 was synthesized from the compound of Example 171 by a method similar to Step 1 in Reference Example 27.

The compound of Example 381 was synthesized from the compound synthesized in Step 1 in Example 117 by a method similar to Example 157.

The compound of Example 382 was synthesized from the compound of Example 171 by a method similar to Step 1 in Reference Example 27.

The compound of Example 383 was synthesized by methods similar to those described in Example 177 and Reference Example 28.

The compound of Example 384 was synthesized by methods similar to those described in Reference Example 34, Example 85 and Reference Example 24.

The compound of Reference Example 81 (6,6-difluoro5-methyl-6,7-dihydro-5H-pyrazolo[5,1-b][1,3]oxazine-2-carboxylic acid) was synthesized under the scheme depicted in the figure below.

[Chem 248]

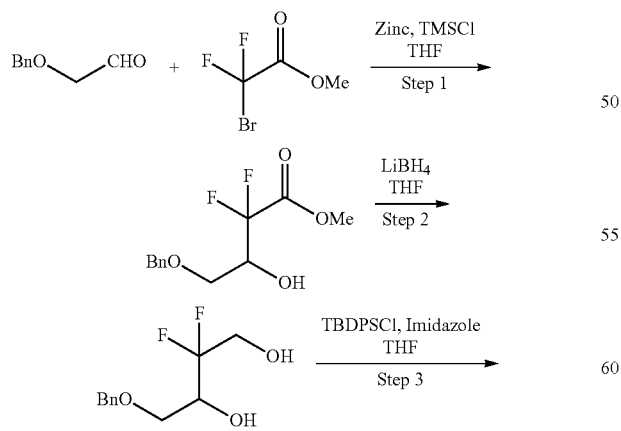

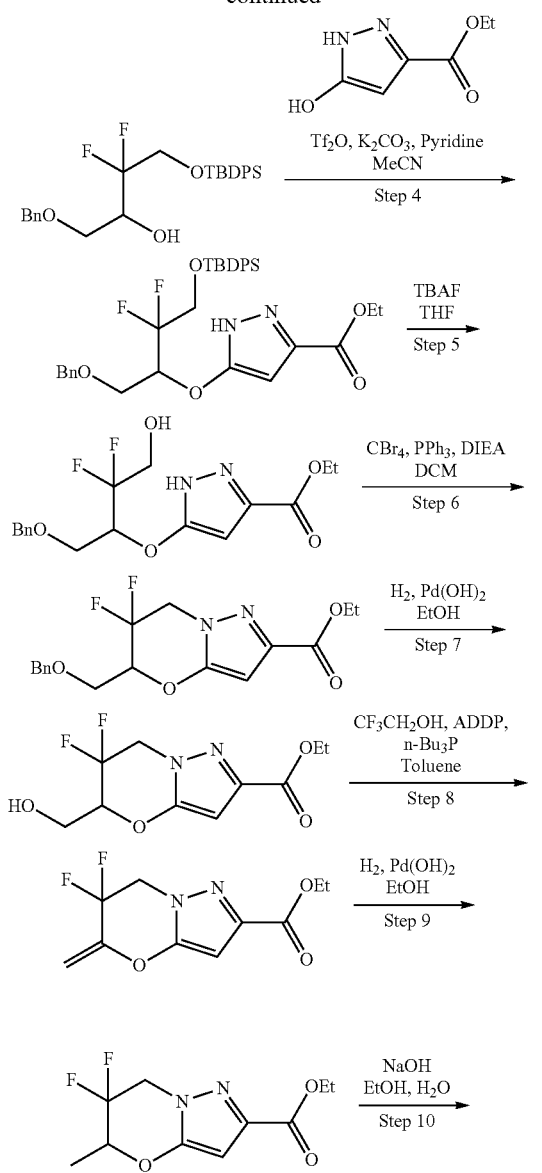

The compound of Example 385 was synthesized from the compound of Reference Example 81 and the compound of Reference Example 1 by a method similar to Step 3 in Example 100.

The compound of Example 386 was synthesized from the compound synthesized in Step 3 in Example 100 under the scheme depicted in the figure below.

[Chem 249]

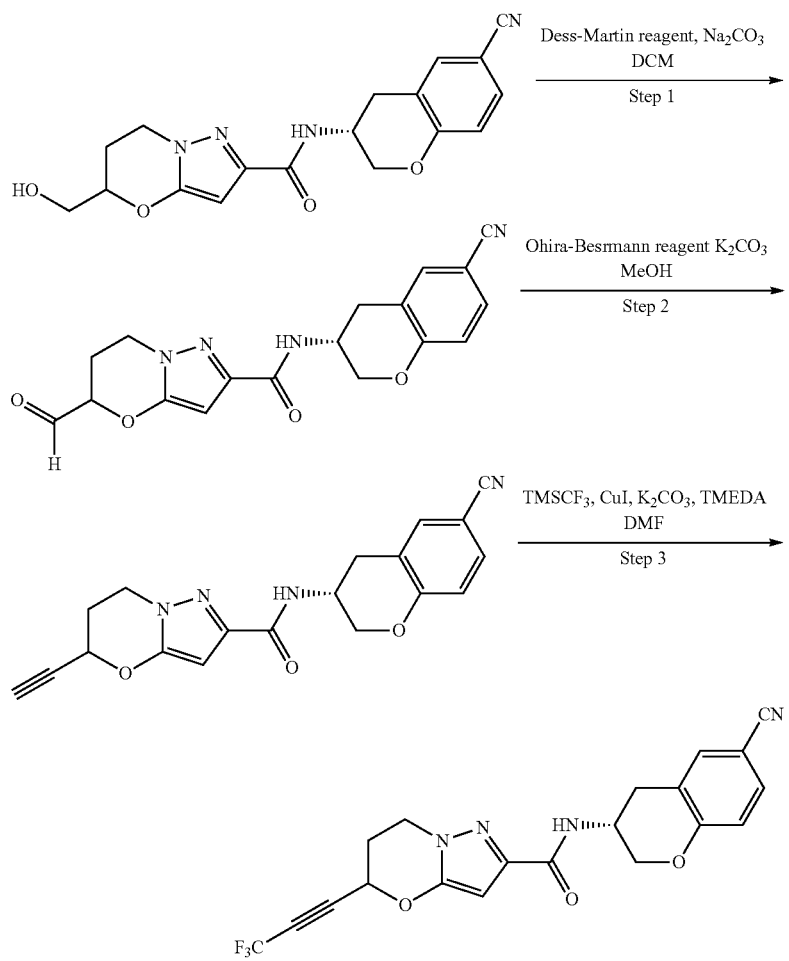

The compound of Reference Example 82 (1-cyclopropylpropane-1,3-diol) was synthesized under the scheme depicted in the figure below.

[Chem 250]

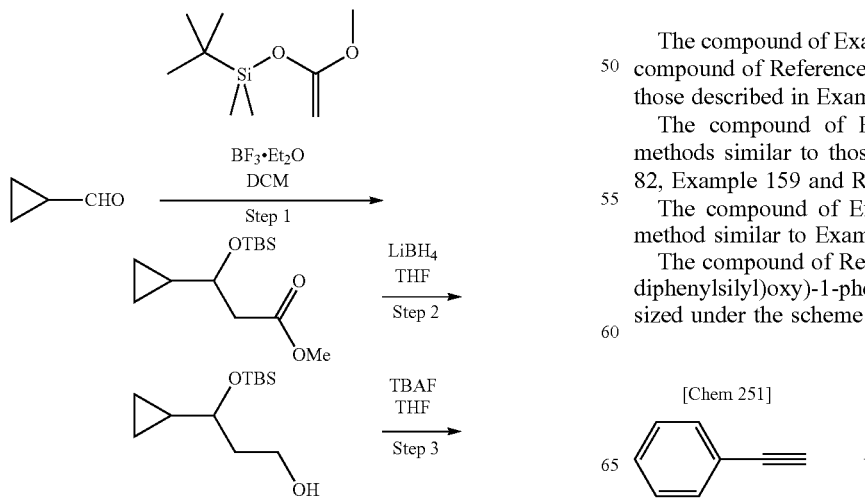

-continued

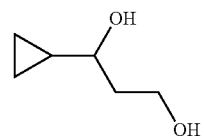

The compound of Example 387 was synthesized from the compound of Reference Example 82 by methods similar to those described in Example 159 and Reference Example 1.

The compound of Example 388 was synthesized by methods similar to those described in Reference Example 82, Example 159 and Reference Example 24.

The compound of Example 389 was synthesized by a method similar to Example 85.

The compound of Reference Example 83 (5-((tert-butyldiphenylsilyl)oxy)-1-phenylpent-1-yn-3-ol) was synthesized under the scheme depicted in the figure below.

[Chem 251]

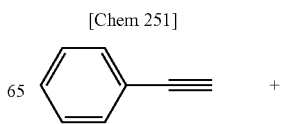

-continued

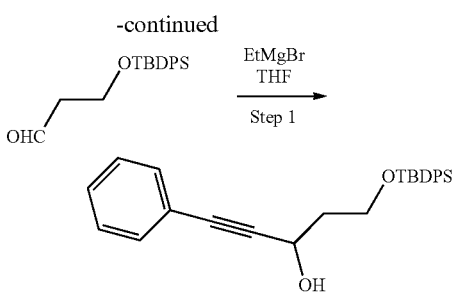

The compound of Example 390 was synthesized from the compound of Reference Example 83 by methods similar to those described in Example 85 and Reference Example 24.

The compound of Example 391 was synthesized from the compound of Example 171 by methods similar to those described in Example 82 and Example 83.

The compound of Example 392 was synthesized from the compound of Example 171 by a method similar to Step 2 in Example 117.

The compound of Example 393 was synthesized by methods similar to those described in Example 85 and Reference Example 24.

The compound of Example 394 was synthesized by methods similar to those described in Reference Example 83, Example 85 and Reference Example 24.

The compound of Example 395 was synthesized by methods similar to those described in Reference Example 82, Example 159 and Reference Example 1.

The compound of Example 396 was synthesized from the compound of Example 171 by a method similar to Step 1 in Reference Example 3.

The compound of Example 397 was synthesized from the compound of Example 396 by methods similar to those described in Step 1 in Reference Example 45 and Step 2 in Reference Example 44.

The compound of Reference Example 84 ((R)-6-(3-methoxy-3-ethylbut-1-yn-1-yl)chroman-3-amine) was synthesized from the compound synthesized in Step 1 in Reference Example 2 under the scheme depicted in the figure below.

[Chem 252]

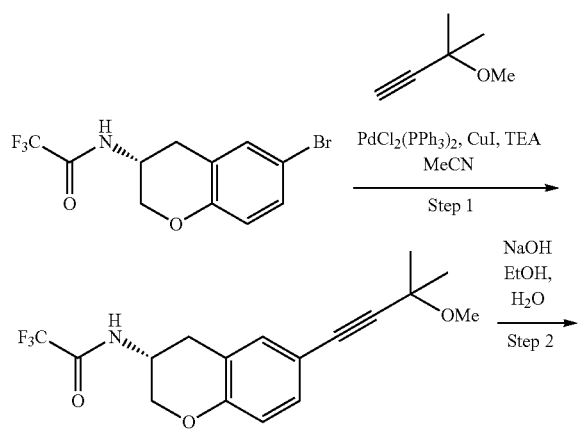

-continued

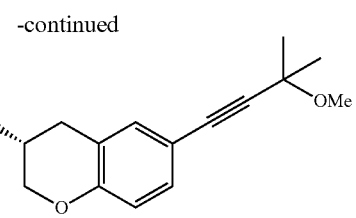

The compound of Example 398 was synthesized by methods similar to those described in Example 169 and Reference Example 84.

The compound of Example 399 was synthesized by a method similar to Example 391.

The compound of Example 400 was synthesized from the compound of Example 398 by a method similar to Step 2 in Example 1.

The compound of Example 401 was synthesized by methods similar to those described in Example 169, Reference Example 45 and Example 122.

The compound of Example 402 was synthesized by methods similar to those described in Reference Example 83, Example 85 and Reference Example 43.

The compound of Example 403 was synthesized by methods similar to those described in Example 177 and Reference Example 65.

The compound of Example 404 was synthesized by methods similar to those described in Reference Example 83, Example 85, Reference Example 3 and Reference Example 1.

The compound of Example 405 was synthesized from the compound synthesized in Step 6 in Example 159 and the compound of Reference Example 80 by a method similar to Step 8 in Example 70.

The compound of Reference Example 85 was synthesized by methods similar to those described in Reference Example 83, Example 85 and Reference Example 1.

[Chem 253]

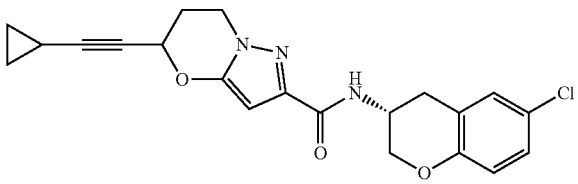

The compounds of Example 406 and Example 407 were obtained by separating the compound of Reference Example 85.

The compound of Example 408 was synthesized by methods similar to those described in Example 85 and Reference Example 24.

The compound of Example 409 was synthesized by a method similar to Example 157.

The compound of Example 410 was synthesized by a method similar to Example 100.

The compound of Example 411 was synthesized by methods similar to those described in Example 117 and Reference Example 24.

The compound of Example 412 was synthesized by a method similar to Example 114.

The compound of Example 413 was synthesized by methods similar to those described in Example 100 and Reference Example 1.

The compound of Example 414 was synthesized by methods similar to those described in Example 100 and Reference Example 28.

The compound of Example 415 was synthesized from the compound synthesized in Step 1 in Example 117 by a method similar to Step 1 to Step 2 in Example 122.

The compound of Reference Example 86 (2,3,5,6,6',7'-hexahydrospiro[pyran-4,5'-pyrazolo[5,1-b][1,3]oxazine]-2'-carboxylic acid) was synthesized under the scheme below.

[Chem 254]

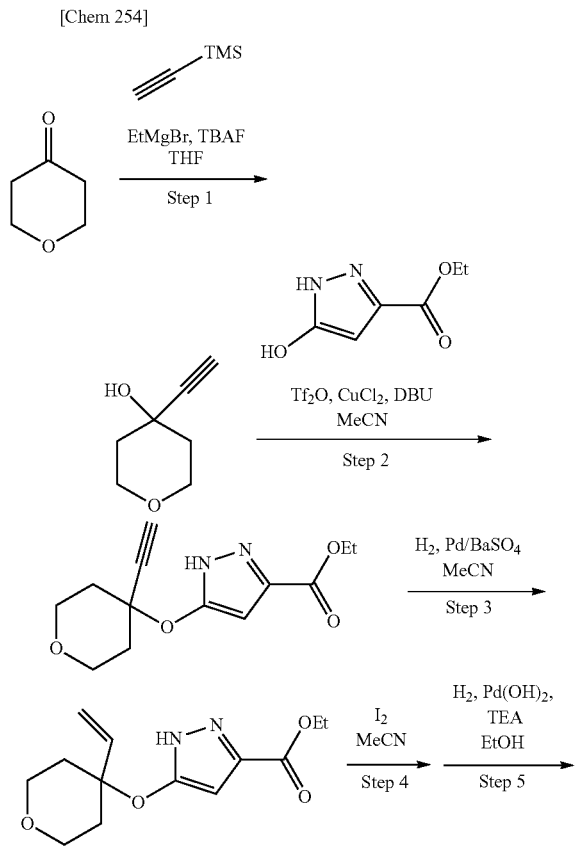

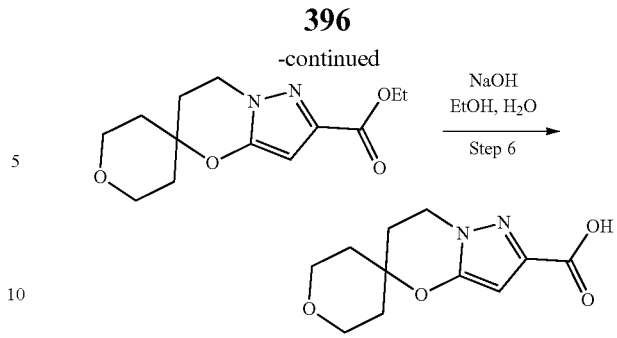

The compound of Example 416 was synthesized from the compound of Reference Example 86 and the compound of Reference Example 1 by a method similar to Step 8 in Example 70.

The compound of Example 417 was synthesized from the compound synthesized in Step 1 in Example 386 under the scheme depicted in the figure below.

[Chem 255]

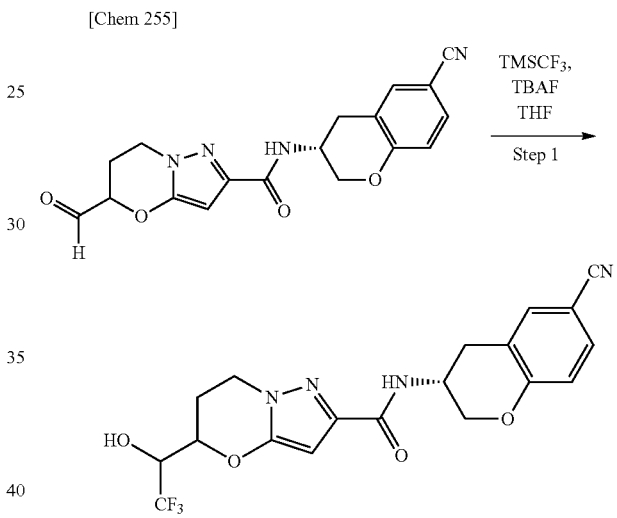

The compound of Example 418 was synthesized from the compound synthesized in Step 3 in Example 100 under the scheme depicted in the figure below.

[Chem 256]

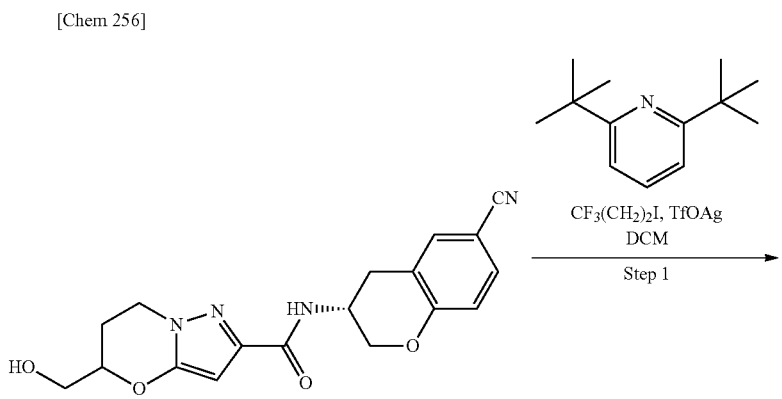

-continued

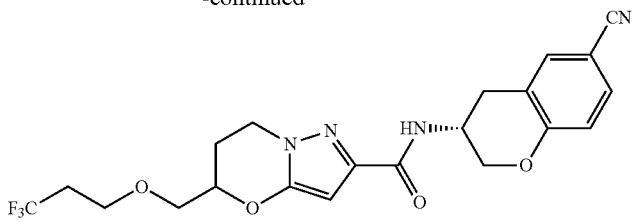

The compound of Reference Example 87 (5-(hydroxymethyl)-5-methyl-6,7-dihydro-5H-pyrazolo[5,1-b][1,3]oxazine-2-carboxylic acid) was synthesized under the scheme depicted in the figure below.

[Chem 257]

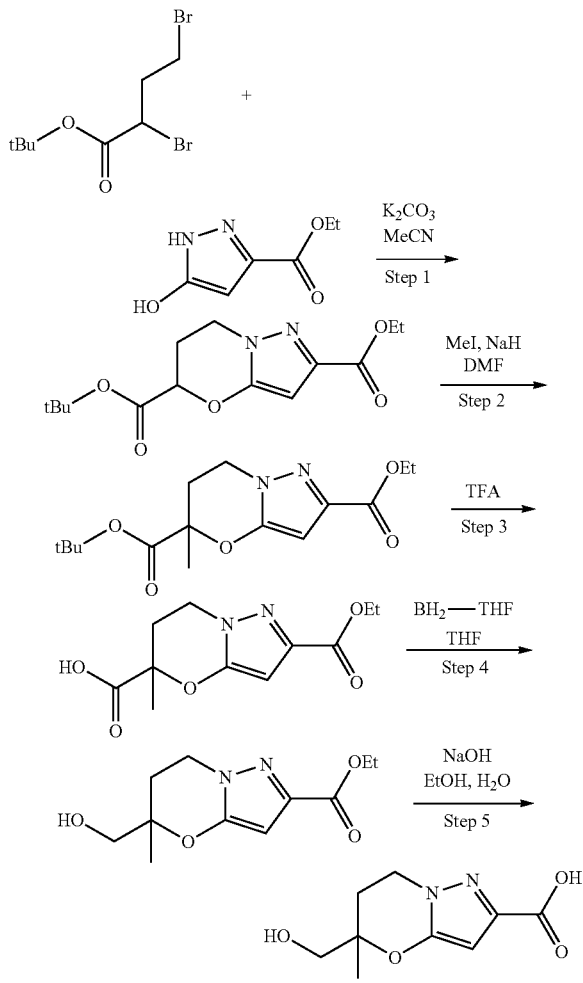

The compound of Example 419 was synthesized from the compound of Reference Example 87 by methods similar to Step 3 to Step 4 in Example 100.

The compound of Example 420 was synthesized from the compound of Reference Example 37 and the compound of Reference Example 1 by a method similar to Example 133.

The compound of Example 421 was synthesized from the compound of Reference Example 37 and the compound of Reference Example 32 by a method similar to Example 133.

The compound of Example 422 was synthesized by a method similar to Example 114.

The compounds of Example 423 and Example 424 were obtained by separating the compound of Example 422.

The compound of Example 425 was synthesized by methods similar to Example 100, Reference Example 2 and Step 1 in Reference Example 27.

The compound of Example 426 was synthesized by a method similar to Example 425.

The compound of Example 427 was synthesized by a method similar to Example 425.

The compound of Example 428 was synthesized by a method similar to Example 425.

The compound of Example 429 was synthesized by a method similar to Example 425.

The compound of Example 430 was synthesized by a method similar to Example 425.

The compound of Example 431 was synthesized by a method similar to Example 425.

The compound of Example 432 was synthesized from the compound of Reference Example 36 and the compound of Reference Example 43 by a method similar to Step 5 to Step 6 in Example 85.

The compound of Example 433 was synthesized from the compound of Reference Example 41 and the compound of Reference Example 43 by a method similar to Step 6 in Example 85.

The compound of Example 434 was synthesized by methods similar to those described in Reference Example 49, Example 85 and Reference Example 24.

The compound of Example 435 was synthesized by methods similar to those described in Example 434 and Reference Example 60.

The compound of Example 436 was synthesized from the compound of Reference Example 36 by methods similar to those described in Reference Example 84 and Step 5 to Step 6 in Example 85.

The compound of Example 437 was synthesized by methods similar to those described in Example 384 and Reference Example 48.

The compound of Example 438 was synthesized by methods similar to those described in Example 384 and Reference Example 44.

The compound of Example 439 was synthesized by methods similar to those described in Example 384, Example 157 and Reference Example 24.

The compound of Example 440 was synthesized by methods similar to those described in Example 122 and Reference Example 44.

The compound of Example 441 was synthesized from the compound of Reference Example 36 and the compound of Reference Example 52 by a method similar to Step 5 to Step 6 in Example 85.

The compound of Example 442 was synthesized from the compound of Reference Example 36 and the compound of Reference Example 1 by a method similar to Step 5 to Step 6 in Example 85.

The compound of Example 443 was synthesized by a method similar to Example 98.

The compound of Example 444 was synthesized by a method similar to those described in Example 85 and Example 69.

The compound of Example 445 was synthesized by methods similar to those described in Example 183 and Reference Example 2.

The compound of Example 446 was synthesized from the compound synthesized in Reference Example 68 by methods similar to those described in Example 249 and Reference Example 1.

The compound of Example 447 was synthesized by methods similar to those described in Example 183 and Reference Example 65.

The compound of Example 448 was synthesized from the compound synthesized in Step 1 in Example 187 by a method similar to Example 225.

The compound of Reference Example 88 (ethyl 2-(1,1-difluoro2-hydroxyethyl)-2,3-dihydropyrazolo[5,1-b]oxazole-6-carboxylate) was synthesized from the compound synthesized in Step 4 in Reference Example 81 under the scheme depicted in the figure below.

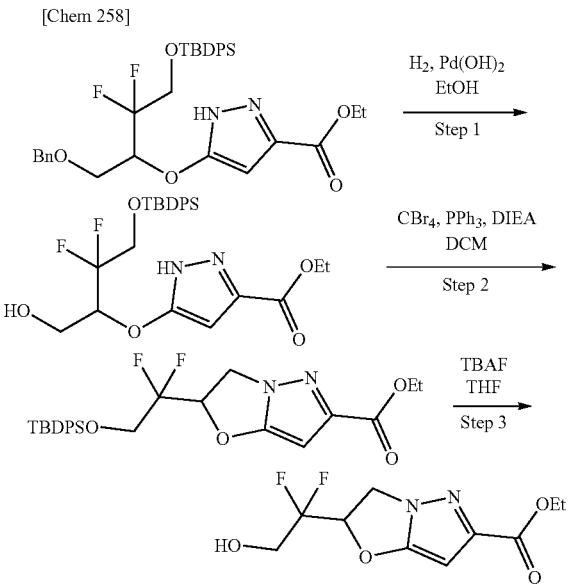

[Chem 258]

The compound of Example 449 was synthesized from the compound of Reference Example 88 by methods similar to those described in Reference Example 33 and Step 6 in Example 85.

The compound of Example 450 was synthesized from the compound synthesized in Step 1 in Example 187 by methods similar to those described in Step 2 in Example 117 and Step 2 to Step 3 in Example 100.

The compound of Example 451 was synthesized from the compound synthesized in Step 5 in Reference Example 55 by methods similar to those described in Reference Example 35 and Step 5 to Step 6 in Example 85.

The compound of Example 452 was synthesized from the compound synthesized in Step 1 in Example 187 by methods similar to those described in Example 225 and Reference Example 24.

The compound of Example 453 was synthesized from the compound synthesized in Step 1 in Reference Example 187 by methods similar to those described in in Reference Example 35 and Step 5 to Step 6 in Example 85.

The compound of Example 454 was synthesized from the compound of Reference Example 50 by a method similar to Step 3 in Example 100.

The compound of Example 455 was synthesized by methods similar to those described in Example 451 and Reference Example 24.

The compound of Example 456 was synthesized from the compound of Reference Example 55 and the compound of Reference Example 60 by a method similar to Step 3 in Example 100.

The compound of Example 457 was synthesized by methods similar to those described in Example 243 and Reference Example 56.

The compound of Example 458 was synthesized from the compound synthesized in Step 1 in Example 187 by methods similar to Step 1 in Example 225, Reference Example 64, Reference Example 43 and Step 3 in Example 100.

The compound of Example 459 was synthesized by methods similar to those described in Example 187 and Reference Example 48.

The compound of Example 460 was synthesized by methods similar to those described in Example 203 and Reference Example 59.

The compound of Example 461 was synthesized by methods similar to those described in Example 203 and Reference Example 56.

The compound of Example 462 was synthesized by methods similar to those described in Reference Example 38, Reference Example 65 and Step 3 in Example 100.

The compound of Example 463 was synthesized by methods similar to those described in Example 185 and Reference Example 80.

The compound of Example 464 was synthesized by methods similar to those described in Reference Example 49, Reference Example 50, Reference Example 24 and Step 3 in Example 100.

The compound of Example 465 was synthesized by methods similar to those described in Reference Example 49, Example 85 and Reference Example 24.

The compound of Example 466 was synthesized from the compound of Reference Example 55 and the compound of Reference Example 48 by a method similar to Step 3 in Example 100.

The compound of Example 467 was synthesized by methods similar to those described in Example 465 and Reference Example 60.

The compound of Example 468 was synthesized from the compound of Reference Example 50 and the compound of Reference Example 29 by a method similar to Step 3 in Example 100.

The compound of Example 469 was synthesized from the compound of Reference Example 50 and the compound of Reference Example 1 by a method similar to Step 3 in Example 100.

The compound of Example 470 was synthesized by methods similar to those described in Reference Example 49, Example 85 and Reference Example 24.

The compound of Example 471 was synthesized by similar methods described in Reference Example 49, Example 85 and Reference Example 48.

The compound of Example 472 was synthesized by similar methods described in Reference Example 49, Example 85 and Reference Example 44.

The compound of Example 473 was synthesized by similar methods described in Reference Example 49, Example 85 and Reference Example 59.

The compound of Example 474 was synthesized by similar methods described in Reference Example 49, Example 85 and Reference Example 60.

The compound of Example 475 was synthesized by similar methods described in Reference Example 49, Example 85 and Reference Example 53.

The compounds of Example 476 and Example 477 were synthesized by similar methods described in Example 241 and Reference Example 43.

The compound of Example 478 was synthesized by similar methods described in Step 1 in Example 224 and Reference Example 48.

The compound of Example 479 was synthesized by similar methods described in Step 1 in Example 224 and Reference Example 52.

The compound of Example 480 was synthesized by similar methods described in Example 251 and Reference Example 1.

The compound of Example 481 was synthesized by similar methods described in Example 258 and Reference Example 1.

The compound of Example 482 was synthesized by methods similar to those described in Example 254 and Reference Example 44.

The compound of Reference Example 89 (4-(((tert-butyldiphenylsilyl)oxy)-2-(trifluoromethyl)butan-1-ol) was synthesized under the scheme depicted in the figure below.

[Chem 259]

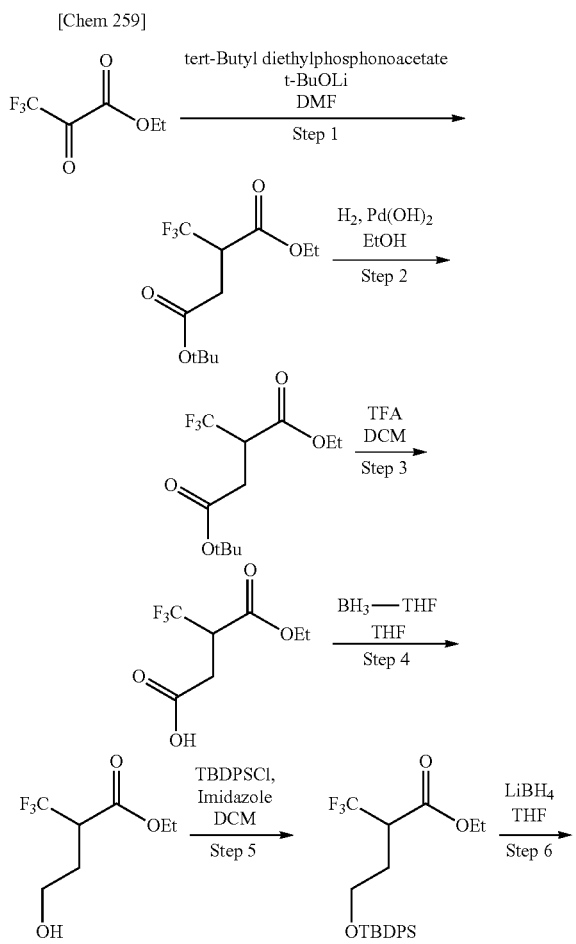

-continued

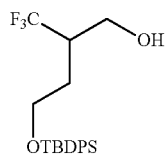

The compound of Example 483 was synthesized from the compound of Reference Example 89 by methods similar to those described in Step 2 to Step 6 in Example 85 and Reference Example 24.

The compound of Example 484 was synthesized by a method similar to Example 259.

The compound of Example 485 was synthesized by a method similar to Example 259.

The compound of Example 486 was synthesized by methods similar to those described in Example 16 and Reference Example 43.

The compound of Example 487 was synthesized from the compound of Reference Example 72 by a method similar to Step 1 in Example 266.

The compound of Example 488 was synthesized from the compound of Reference Example 72 by a method similar to Step 1 in Example 266.

The compound of Example 489 was synthesized by methods similar to those described in Example 487 and Reference Example 24.

The compound of Example 490 was synthesized from the compound of Reference Example 72 by a method similar to Step 1 in Example 266.

The compound of Example 491 was synthesized by methods similar to those described in Example 263 and Reference Example 24.

The compound of Example 492 was synthesized by methods similar to those described in Example 268 and Reference Example 3.

The compound of Example 493 was synthesized from the compound of Reference Example 71 by a method similar to Step 1 in Example 266.

The compound of Example 494 was synthesized from the compound of Reference Example 71 by methods similar to those described in Reference Example 69 and Example 157.

The compound of Example 495 was synthesized by methods similar to those described in Reference Example 69, Example 157 and Step 2 to Step 3 in Example 261.

The compound of Example 496 was synthesized by methods similar to those described in Reference Example 69 and Step 2 to Step 3 in Example 261.

The compound of Example 497 was synthesized by a method similar to Example 268.

The compound of Example 498 was synthesized by a method similar to Example 268.

The compound of Example 499 was synthesized by a method similar to Example 269.

The compound of Example 500 was synthesized by a method similar to Example 283.

The compound of Example 501 was synthesized by a method similar to Example 283.

The compound of Example 502 was synthesized by methods similar to those described in Example 283 and Reference Example 24.

The compound of Example 503 was synthesized by methods similar to those described in Example 283 and Reference Example 24.

The compound of Example 504 was synthesized from the compound of Reference Example 69 by methods similar to those described in Step 2 to Step 3 in Example 261 and Reference Example 48.

The compound of Example 505 was synthesized from the compound of Reference Example 69 by methods similar to those described in Step 2 to Step 3 in Example 261 and Reference Example 44.

The compound of Example 506 was synthesized by methods similar to those described in Example 261 and Reference Example 43.

The compound of Example 507 was synthesized by methods similar to those described in Example 261 and Reference Example 44.

The compound of Example 508 was synthesized by a method similar to Example 278.

The compound of Example 509 was synthesized by methods similar to those described in Example 275 and Reference Example 1.

The compound of Example 510 was synthesized by a method similar to Example 276.

The compound of Example 511 was synthesized by a method similar to Example 277.

The compound of Example 512 was synthesized by methods described in those similar to Example 64 and Reference Example 43.

The compound of Example 513 was synthesized by a method similar to Example 259.

The compound of Example 514 was synthesized by a method similar to Example 259.

The compound of Example 515 was synthesized by methods similar to those described in Example 259 and Reference Example 1.

The compound of Reference Example 90 (3-(6-ethylpyridin-2-yl)-6,7-dihydro-4H-pyrazolo[5,1-c][1,4]oxazine-2-carboxylic acid) was synthesized from the compound synthesized in Step 1 in Example 259 under the scheme depicted in the figure below.

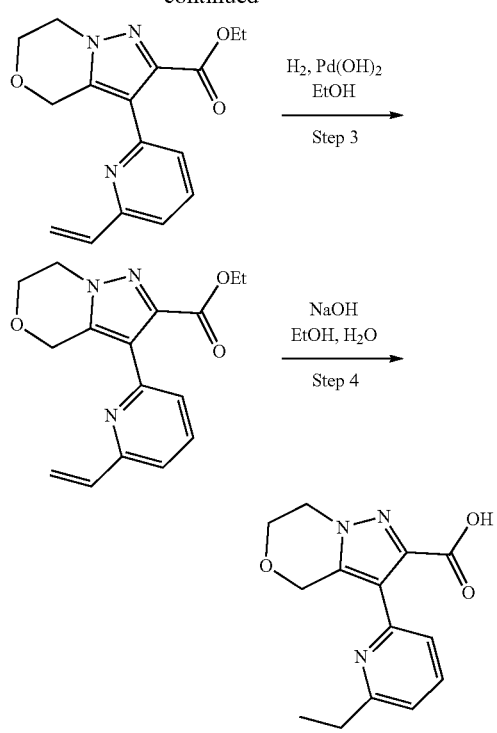

The compound of Example 516 was synthesized from the compound of Reference Example 90 by a method similar to Step 3 in Example 100.

The compound of Example 517 was synthesized by a method similar to Example 259.

The compound of Example 518 was synthesized by a method similar to Example 259.

The compound of Example 519 was synthesized from the compound of Example 514 under the scheme depicted in the figure below.

[Chem 260]

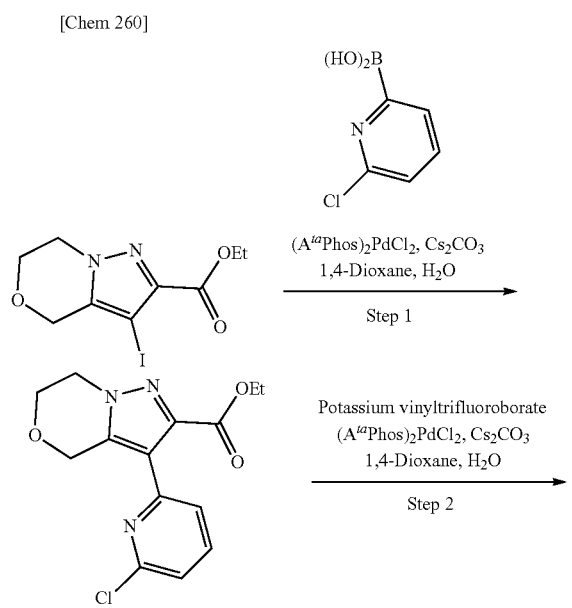

[Chem 261]

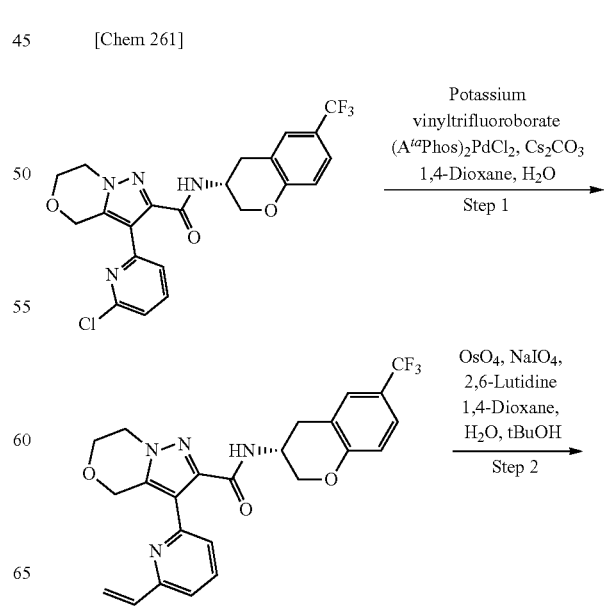

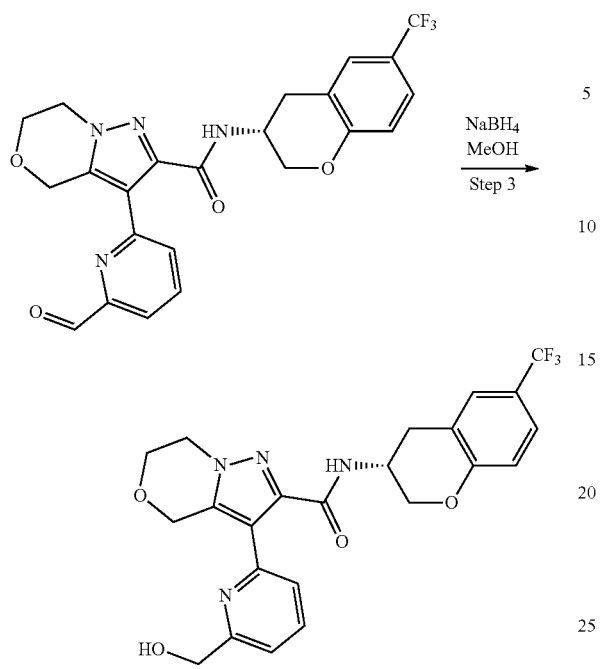

The compound of Example 520 was synthesized from the compound of Example 519 by a method similar to Example 114.

The compound of Example 521 was synthesized from the compound of Example 519 under the scheme depicted in the figure below.

[Chem 262]

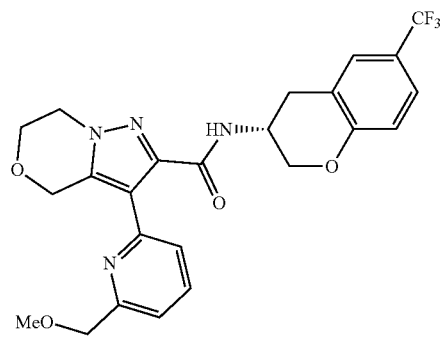

The compound of Example 522 was synthesized from the compound synthesized in Step 2 in Example 519 under the scheme depicted in the figure below.

[Chem 263]

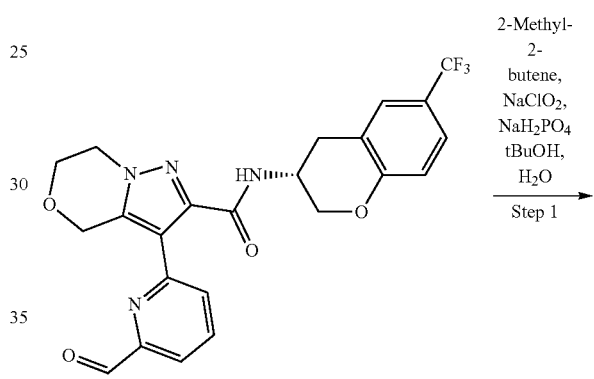

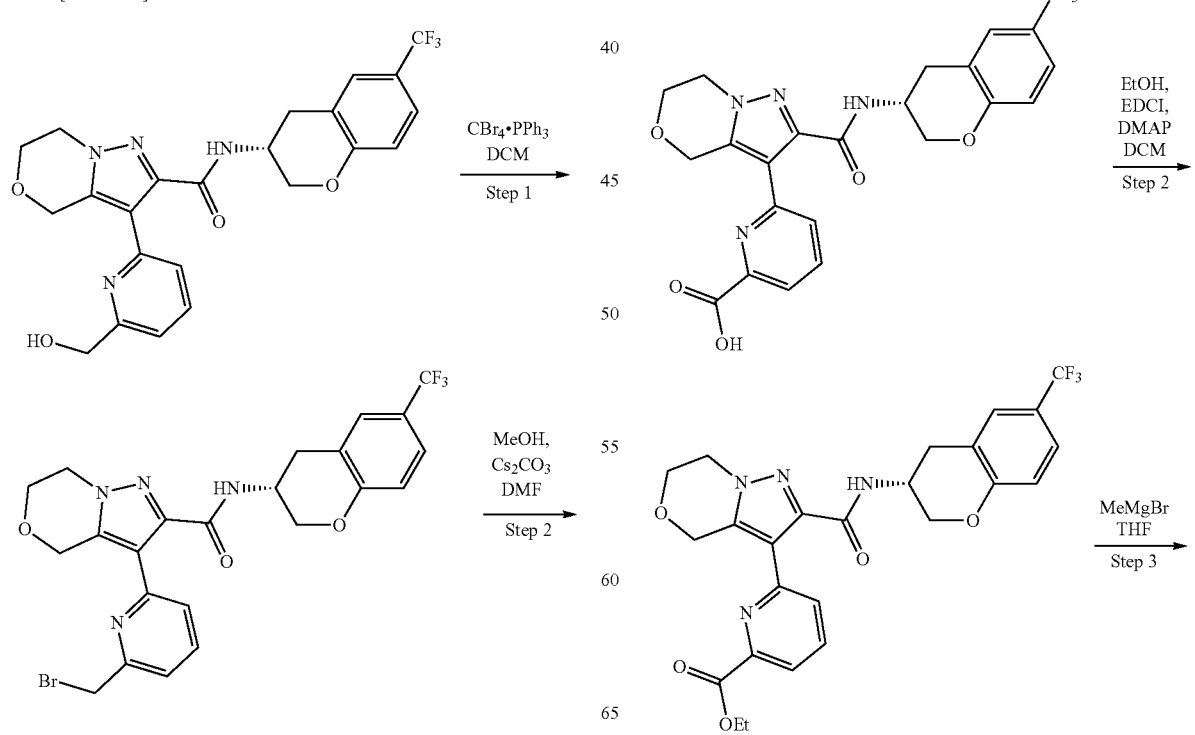

-continued
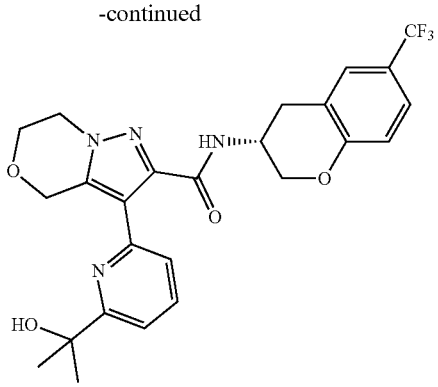
The compound of Example 523 was synthesized from the compound of Example 519 under the scheme depicted in the figure below.
The compound of Reference Example 91 (3-(6-methylpyridin-2-yl)-4,5,6,7-tetrahydropyrazolo[1,5-a]pyrimidine-2-carboxylic acid) was synthesized under the scheme depicted in the figure below.
[Chem 265]
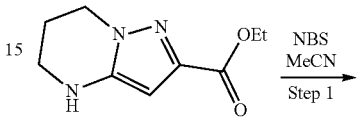
[Chem 264]
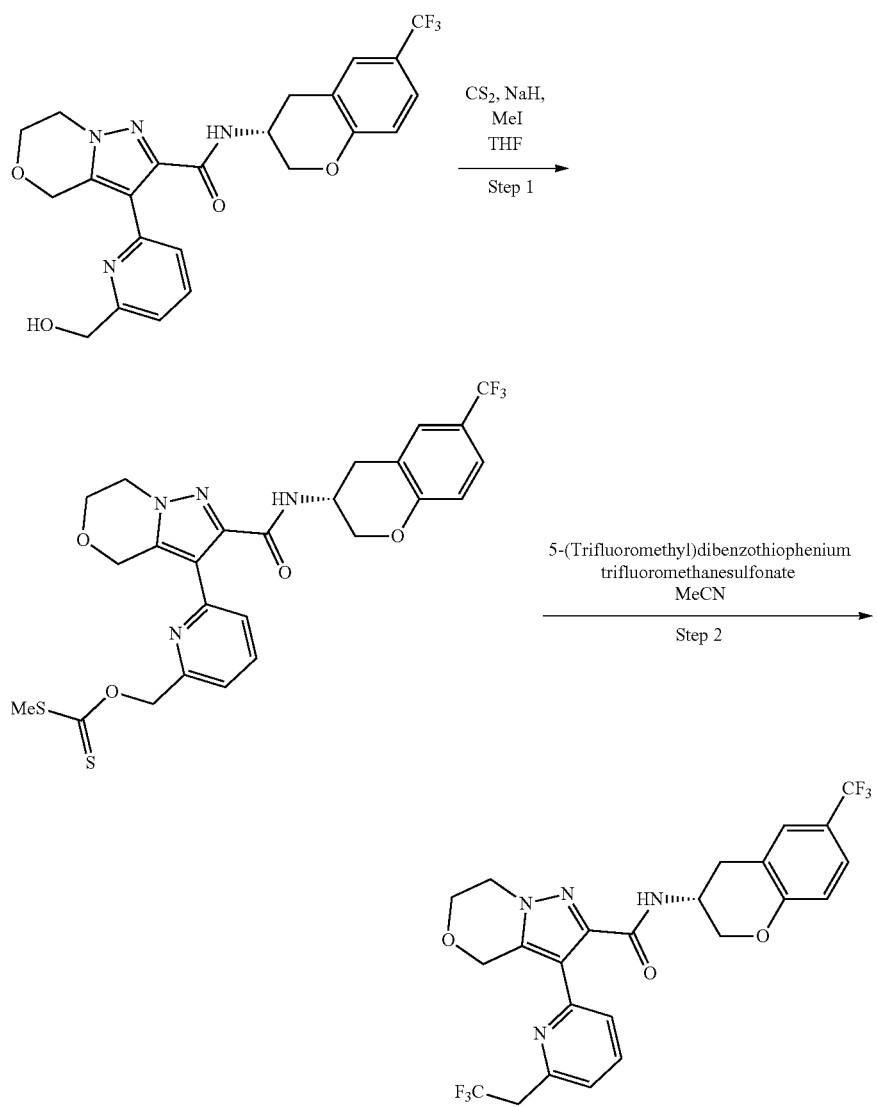

409

-continued

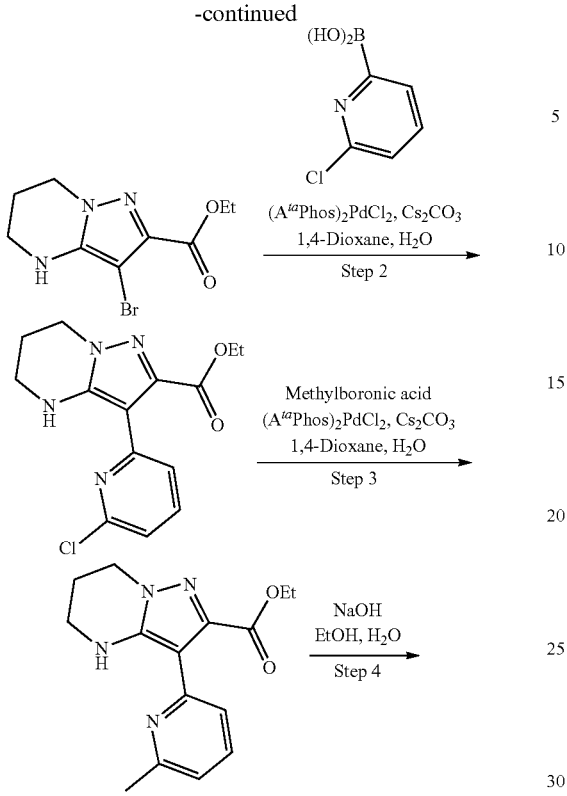

410

-continued

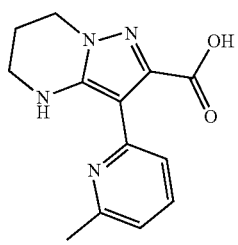

The compound of Example 524 was synthesized from the compound of Reference Example 91 and the compound of Reference Example 43 by a method similar to Step 3 in Example 100.

The compound of Example 525 was synthesized by methods similar to those described in Reference Example 91, Reference Example 44 and Step 3 in Example 100.

The compound of Example 526 was synthesized under the scheme depicted in the figure below.

[Chem 266]

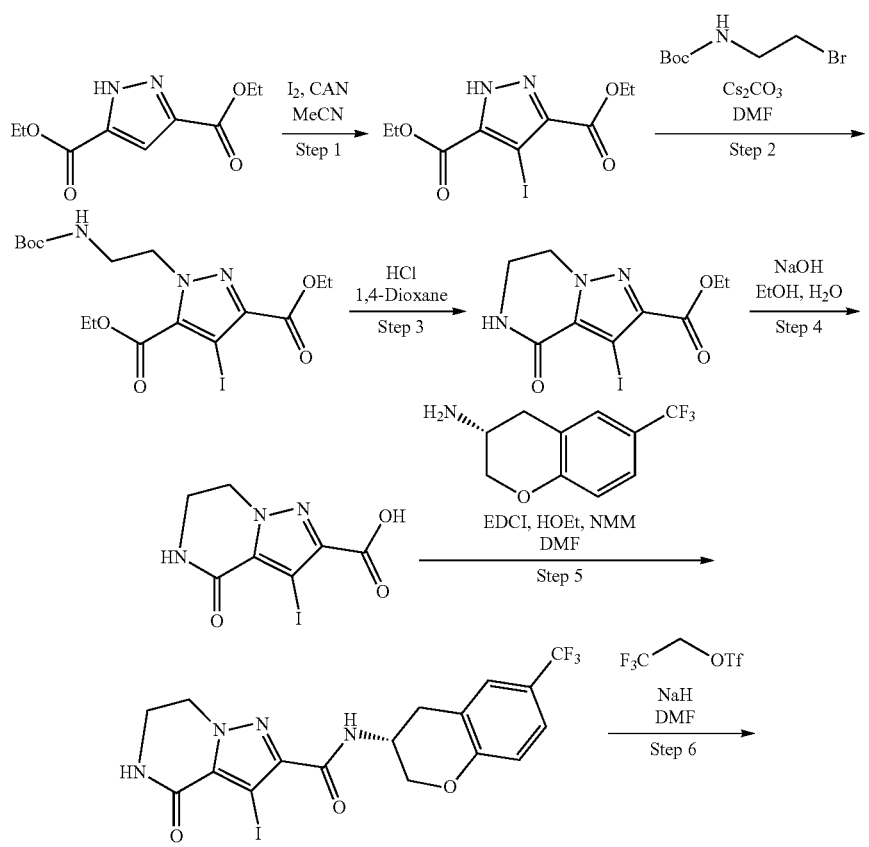

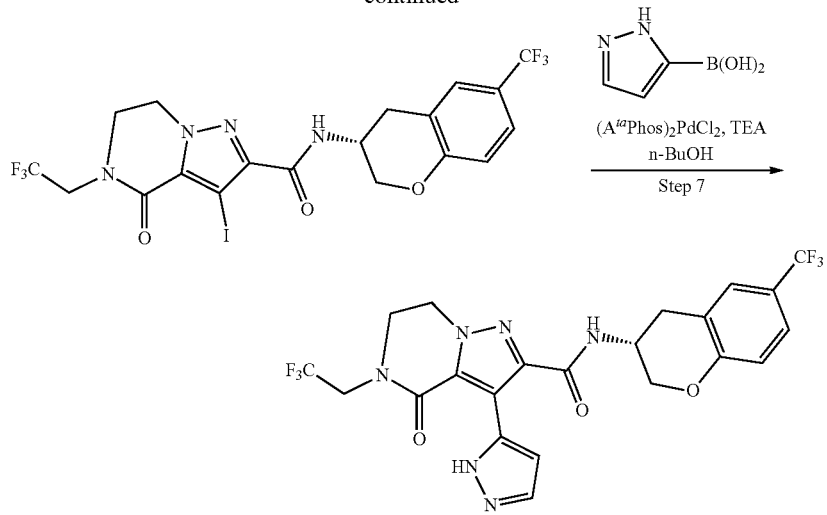

The compound of Example 527 was synthesized from the compound synthesized in Step 2 in Example 519 by a method similar to Step 1 in Reference Example 52.

The compound of Example 528 was synthesized by methods similar to those described in Steps 1 to 3 in Example 259 and Example 260.

The compounds of Reference Example 92 ((3S)-3-amino-6-(trifluoromethyl)chroman-4-ol (isomer A and isomer B)) were synthesized under the scheme depicted in the figure below.

[Chem 267]

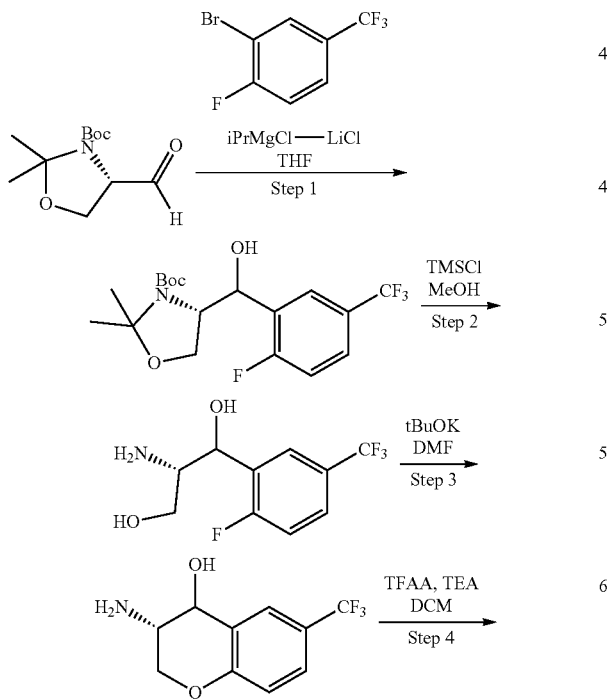

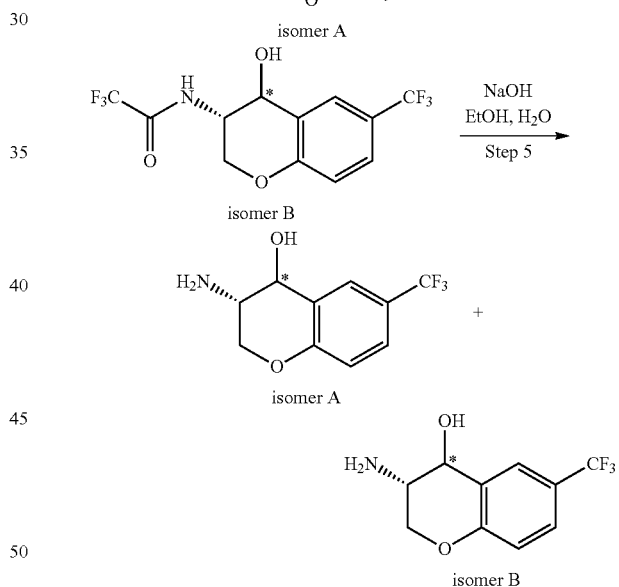

The compound of Example 529 was synthesized from the compound synthesized in Step 1 in Example 259 and the compound synthesized in Reference Example 92 (isomer A) by methods similar to those described in Step 2 to Step 4 in Example 259.

The compound of Example 530 was synthesized from the compound synthesized in Step 3 in Example 259 under the scheme depicted in the figure below.

[Chem 268]

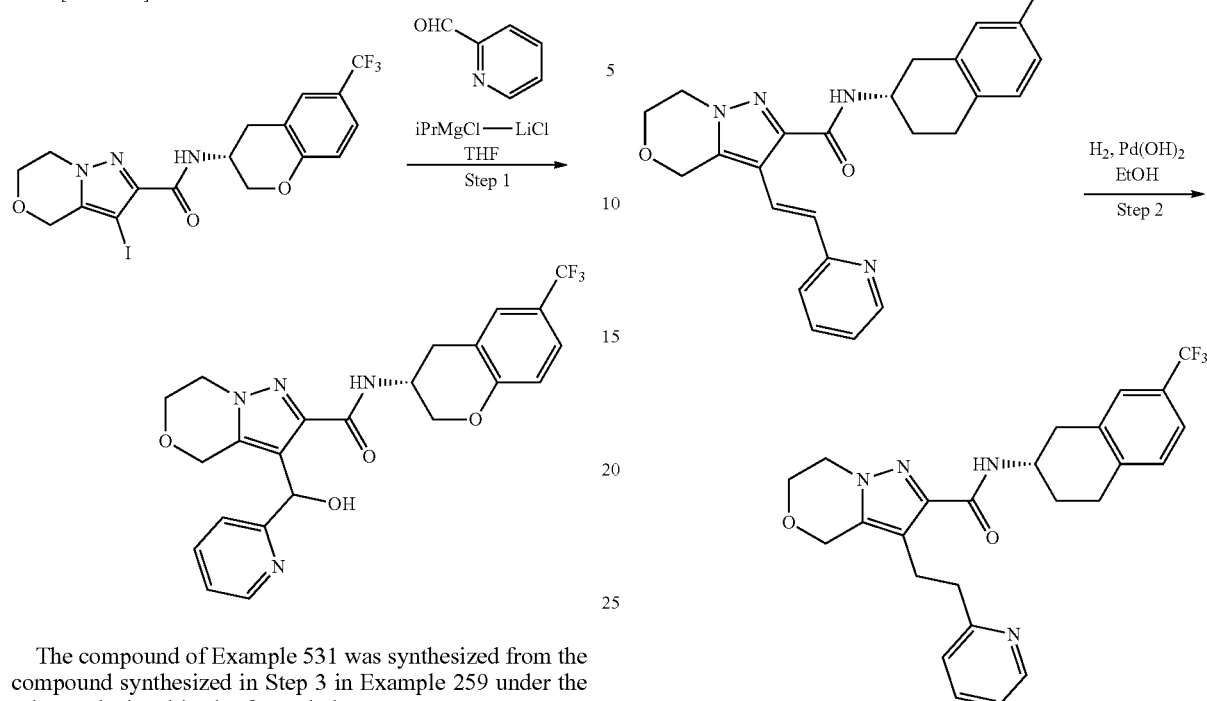

The compound of Example 531 was synthesized from the compound synthesized in Step 3 in Example 259 under the scheme depicted in the figure below.

[Chem 269]

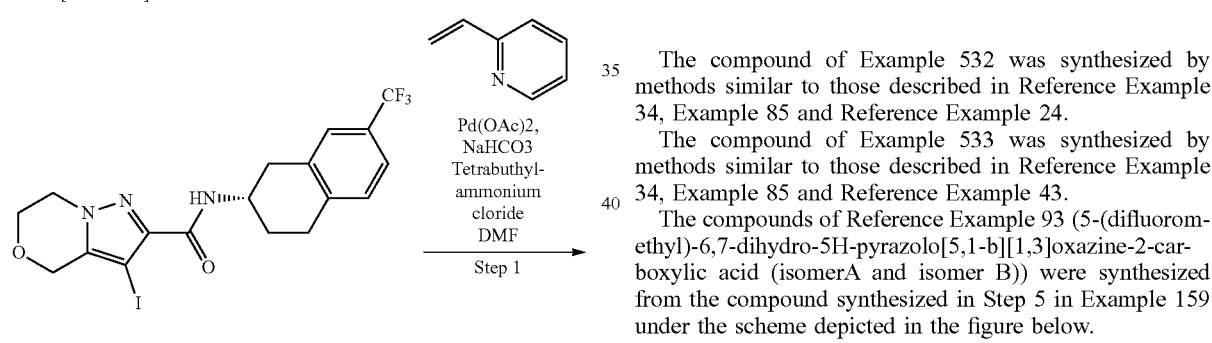

The compound of Example 532 was synthesized by methods similar to those described in Reference Example 34, Example 85 and Reference Example 24.

The compound of Example 533 was synthesized by methods similar to those described in Reference Example 34, Example 85 and Reference Example 43.

The compounds of Reference Example 93 (5-(difluoromethyl)-6,7-dihydro-5H-pyrazolo[5,1-b][1,3]oxazine-2-carboxylic acid (isomer A and isomer B)) were synthesized from the compound synthesized in Step 5 in Example 159 under the scheme depicted in the figure below.

[Chem 270]

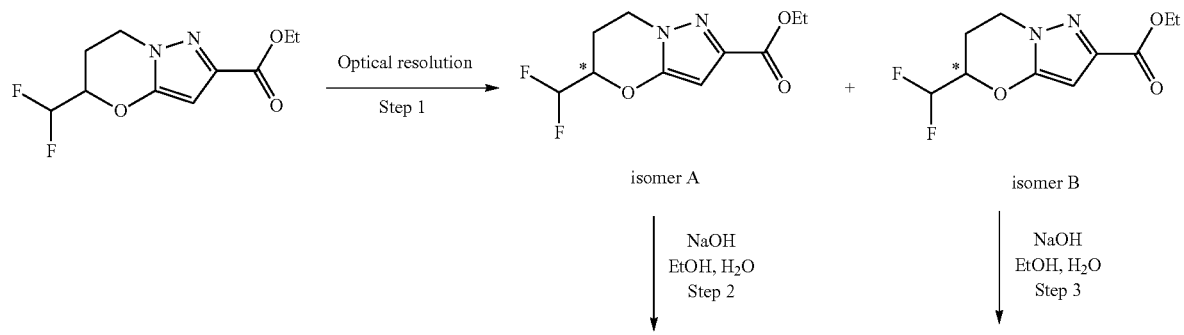

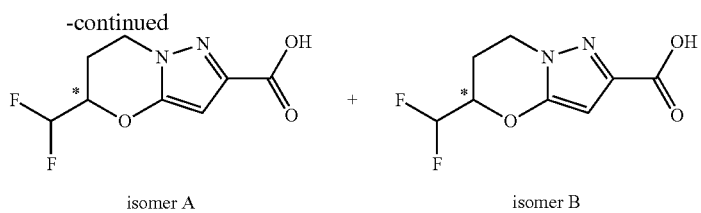

isomer A                              isomer B

The compounds of Example 534 (isomer A and isomer B) were synthesized from the compound of Reference Example 93 (isomer A) and the compound of Reference Example 92 (isomer A) by a method similar to Step 6 in Example 85.

The compound of Example 535 was synthesized from the compound of Example 534 (isomer A) under the scheme depicted in the figure below.

[Chem 271]

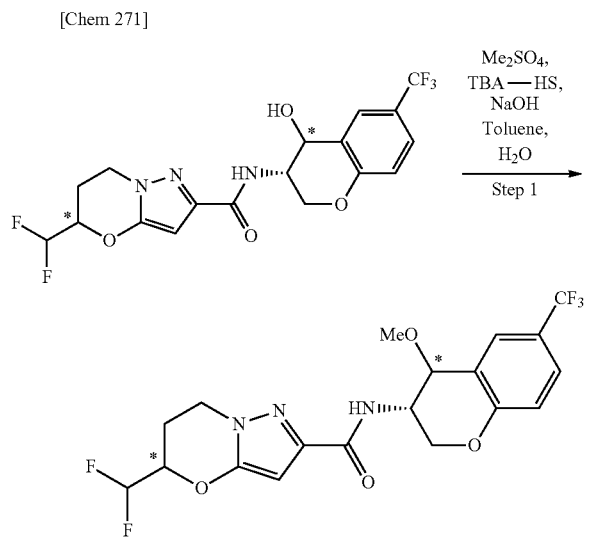

The compound of Example 536 was synthesized from the compound of Example 534 (isomer A) by a method similar to Example 114.

The compound of Example 537 was synthesized from the compound synthesized in Step 7 in Example 70 by a method similar to Step 3 in Example 100.

The compound of Reference Example 94 (1-((2,4-dihydroxybutoxy)methyl)cyclopropane-1-carbonitrile) was synthesized under the scheme depicted in the figure below.

[Chem 272]

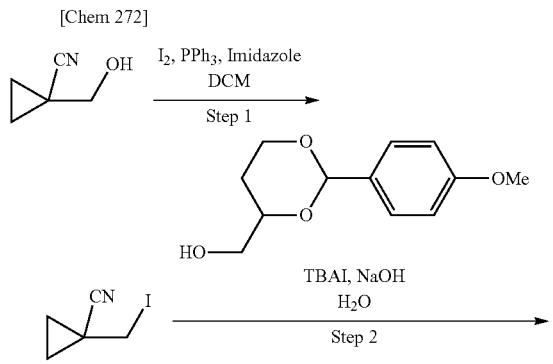

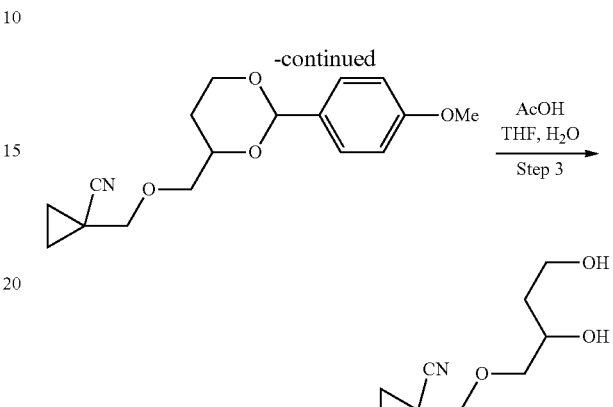

The compound of Example 538 was synthesized from the compound of Reference Example 94 by a method similar to Example 85.

The compound of Reference Example 95 (ethyl 6-((benzyloxy)methyl)-6,7-dihydro-5H-pyrazolo[5,1-b][1,3]oxazine-2-carboxylate) was synthesized under the scheme depicted in the figure below.

[Chem 273]

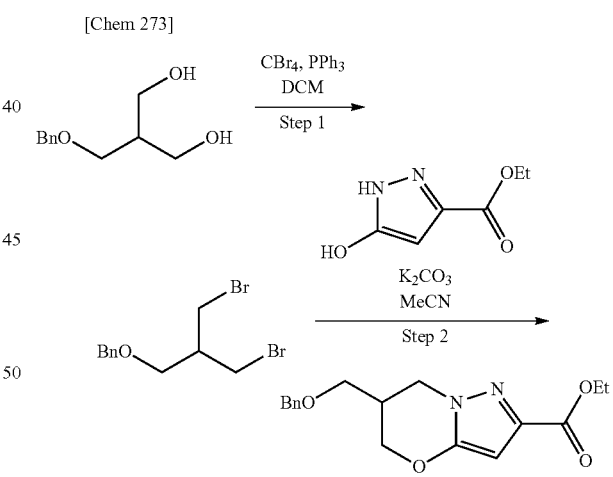

The compound of Example 539 was synthesized from the compound of Reference Example 95 by methods similar to those described in Example 100 and Reference Example 43.

The compound of Example 540 was synthesized by methods similar to those described in Reference Example 34, Example 169 and Reference Example 24.

The compound of Example 541 was synthesized by methods similar to those described in Example 449 and Reference Example 24.

The compound of Example 542 was synthesized from the compound of Reference Example 37 by a method similar to Step 3 in Example 100.

The compound of Reference Example 96 (4-((tert-butyl-diphenylsilyl)oxy)-2-methylbutan-1-ol) was synthesized under the scheme depicted in the figure below.

[Chem 274]

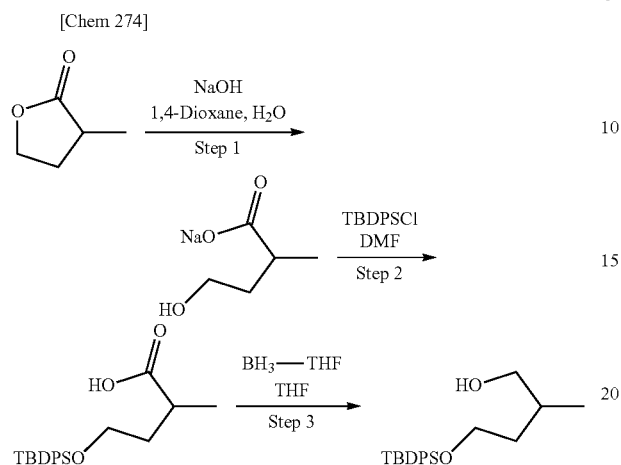

The compound of Example 543 was synthesized from the compound of Reference Example 96 by methods similar to those described in Example 85 and Reference Example 44.

The compound of Example 544 was synthesized from the compound of Example 534 under the scheme depicted in the figure below.

[Chem 275]

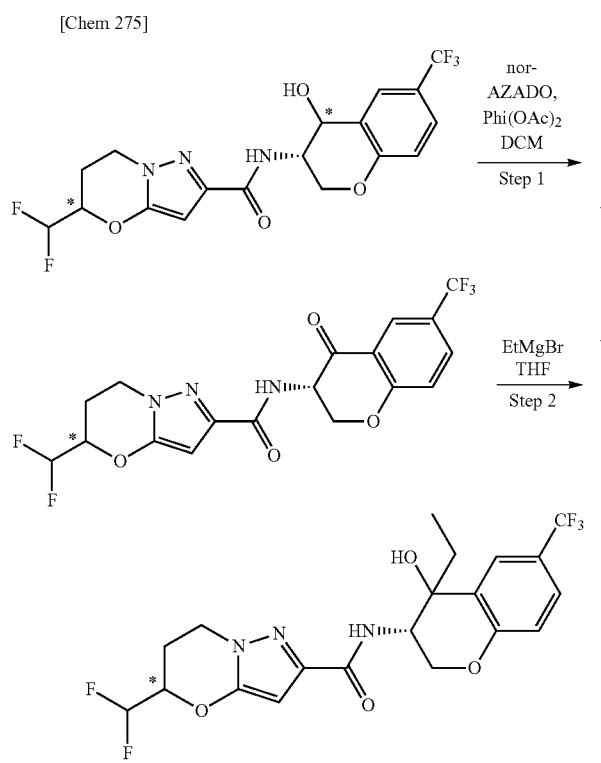

The compound of Example 545 was synthesized by a method similar to Example 543.

The compound of Example 546 was synthesized from the compound of Example 534 (isomer A) in a method similar to Step 1 in Reference Example 37.

The compounds of Example 547 (isomer A and isomer B) were synthesized by separating the compound of Example 540.

The compound of Reference Example 97 (6-(((2,2,2-trifluoroethyl)amino)methyl)-6,7-dihydro-5H-pyrazolo[5,1-b][1,3]oxazine-2-carboxylic acid) was synthesized from the compound of Reference Example 95 under the scheme depicted in the figure below.

[Chem 276]

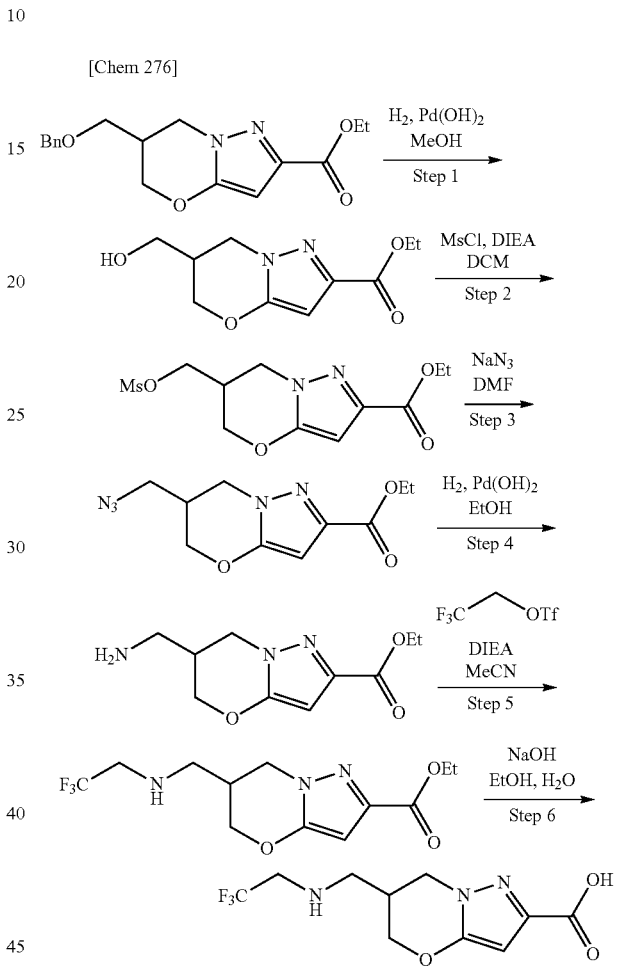

The compound of Example 548 was synthesized from the compound of Reference Example 95 by a method similar to Step 6 in Example 85.

The compound of Reference Example 98 (6-(trifluoromethyl)-3,4-dihydro-2H-pyrano[3,2-b]pyridin-3-amine hydrochloride) was synthesized under the scheme depicted in the figure below.

[Chem. 277]

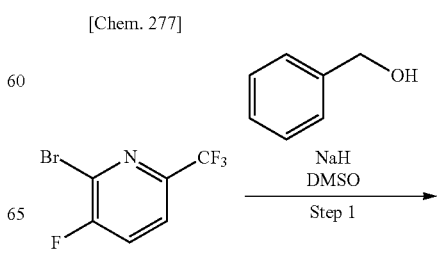

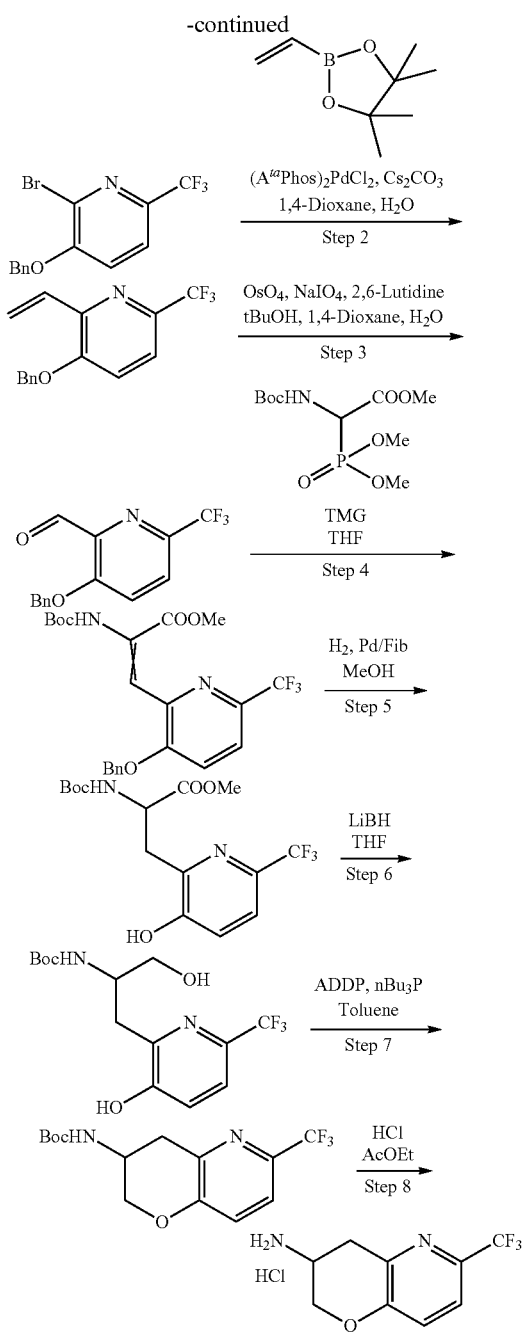

The compound of Example 549 was synthesized by methods similar to those described in Example 90 and Reference Example 98.

The compound of Example 550 was synthesized from the compound synthesized in Step 7 in Example 70 and the compound of Reference Example 98 by a method similar to Step 8 in Example 70.

The compound of Example 551 was synthesized from the compound of Reference Example 93 (isomer A) by a method similar to Step 6 in Example 85.

The compounds of Example 552 (isomer A and isomer B) were obtained by separating the compound of Example 532.

The compound of Example 553 was synthesized by methods similar to those described in Example 538 and Reference Example 43.

The compounds of Example 554 (isomer A and isomer B) were obtained by separating the compound of Example 553.

The compound of Reference Example 99 (6-((2,2,2-trifluoroethoxy)methyl)-5,6,7,8-tetrahydropyrazolo[5,1-b][1,3]oxazepine-2-carboxylic acid) was synthesized under the scheme depicted in the figure below.

[Chem 278]

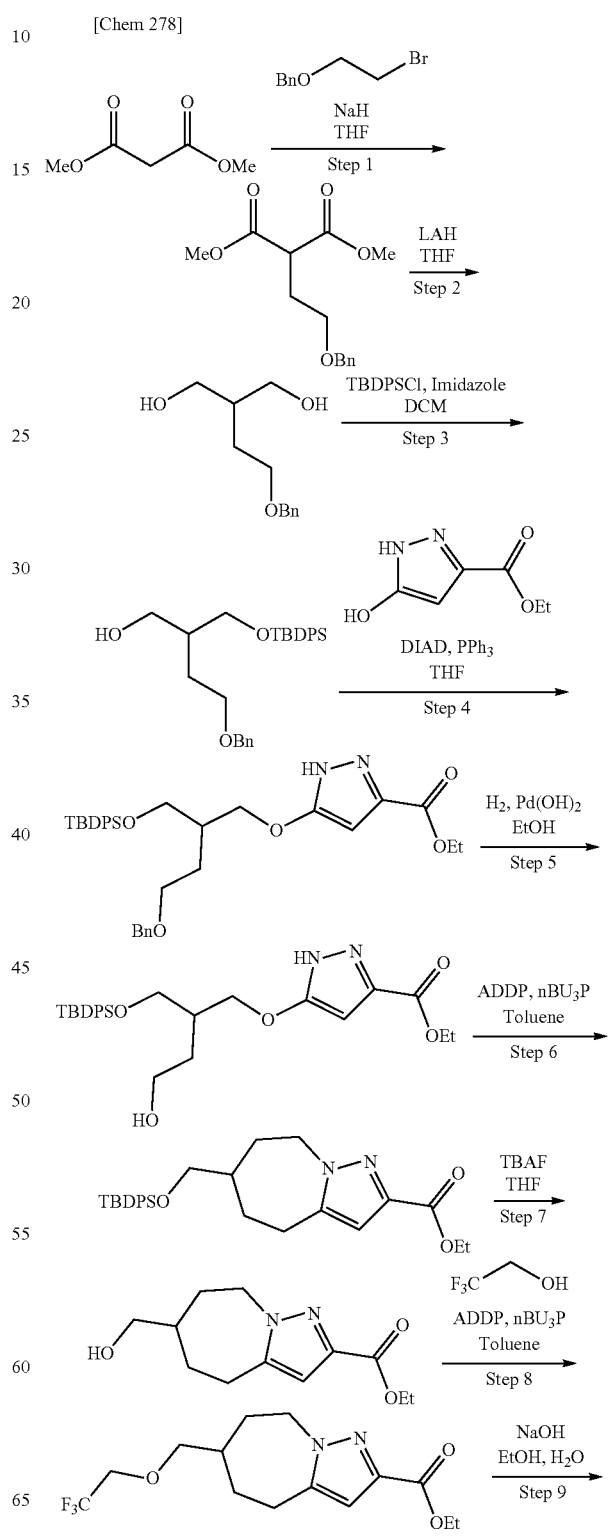

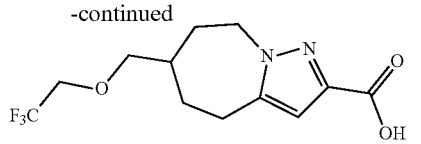

The compound of Example 555 was synthesized from the compound of Reference Example 99 by a method similar to Step 3 in Example 100.

The compound of Example 556 was synthesized from the compound of Reference Example 99 and from the compound of Reference Example 43 by a method similar to Step 3 in Example 100.

The compound of Example 557 was synthesized from the compound of Reference Example 99 and from the compound of Reference Example 48 by a method similar to Step 3 in Example 100.

The compound of Example 558 was synthesized from the compound of Reference Example 33 and the compound of Reference Example 92 (isomer A) by a method similar to Step 8 in Example 70.

The compound of Example 559 was synthesized from the compound of Reference Example 33 and the compound of Reference Example 92 (isomer B) by a method similar to Step 8 in Example 70.

The compound of Example 560 was synthesized from the compound of Reference Example 50 and the compound of Reference Example 92 (isomer A) by a method similar to Step 8 in Example 70.

The compound of Example 561 was synthesized from the compound of Reference Example 36 and the compound of Reference Example 92 (isomer A) by a method similar to Step 7 to Step 8 in Example 70.

The compounds of Example 562 were obtained by separating the compound synthesized by methods similar to those described in Step 3 to Step 5 in Reference Example 34, Example 169 and Reference Example 24.

The compounds of Example 563 (isomer A and isomer B) were obtained by separating the compound of Example 538.

The compound of Reference Example 100 (2-((tetrahydro-2H-pyran-4-yl)methyl)-2,3-dihydropyrazolo[5,1-b]oxazole-6-carboxylic acid) was synthesized under the scheme depicted in the figure below.

[Chem 279]

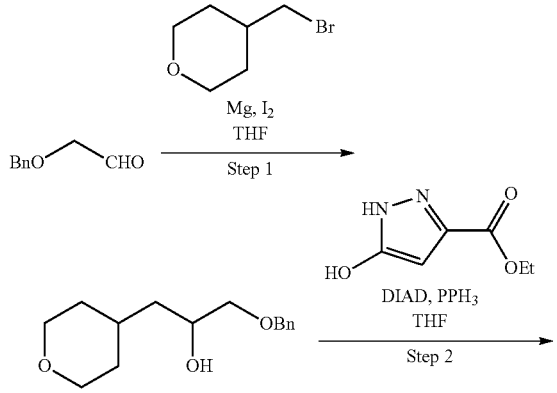

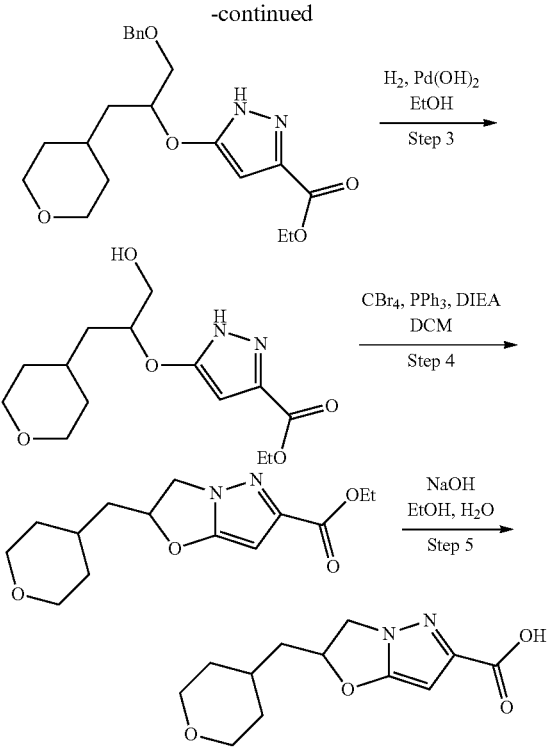

The compound of Example 564 was synthesized from the compound of Reference Example 100 and the compound of Reference Example 48 by a method similar to Step 8 in Example 70.

The compound of Example 565 was synthesized from the compound of Reference Example 100 and the compound of Reference Example 24 by a method similar to Step 8 in Example 70.

The compound of Reference Example 101 ((R)-6-iodochroman-3-amine) was synthesized from the compound synthesized in Step 1 in Reference Example 1 under the scheme depicted in the figure below.

[Chem 280]

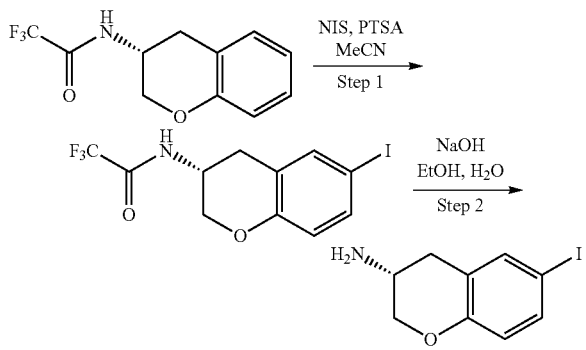

The compound of Example 566 was synthesized from the compound of Reference Example 93 (isomer A) and the compound of Reference Example 101 by a method similar to Step 8 in Example 70.

The compound of Example 567 was synthesized by methods similar to those described in Reference Example 34, Example 85 and Reference Example 48.

The compound of Example 568 was synthesized from the compound of Example 534 (isomer B) by a method similar to Example 535.

The compound of Example 569 was synthesized from the compound synthesized in Step 3 in Example 187 and the compound of Reference Example 92 (isomer A) by methods similar to those described in Step 8 in Example 70 and Example 535.

The compound of Example 570 was synthesized from the compound of Reference Example 36 and the compound of Reference Example 92 (isomer A) by methods similar to those described instep 7 to Step 8 in Example 70 and Example 535.

The compound of Example 571 was synthesized from the compound of Reference Example 33 by a method similar to Step 8 in Example 70.

The compounds of Example 572 (isomer A and isomer B) were obtained by separating the compound of Example 555.

The compound of Example 573 was synthesized by a method similar to Example 70.

The compound of Example 574 was synthesized from the compound of Reference Example 36 and the compound of Reference Example 4 by a method similar to Step 5 to Step 6 in Example 85.

The compounds of Example 575 (isomer A and isomer B) were obtained by separating the compound of Example 559.

The compounds of Example 576 (isomer A and isomer B) were obtained by separating the compound of Example 560.

The compounds of Example 577 (isomer A and isomer B) were obtained by separating the compound of Example 565.

The compound of Reference Example 102 (2-((cyclopropylmethoxy)methyl)-2,3-dihydroimidazo[2,1-b]oxazole-6-carboxylic acid) was synthesized under the scheme depicted in the figure below.

[Chem 281]

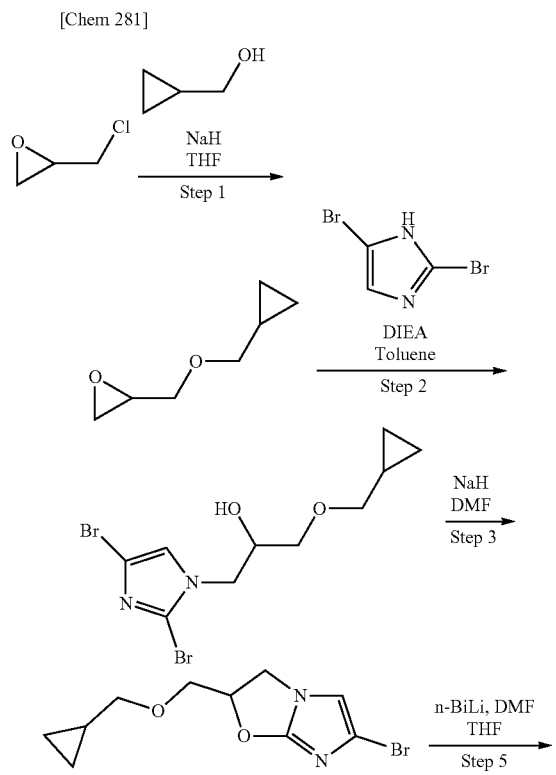

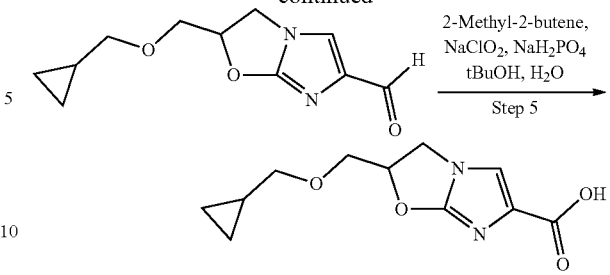

The compound of Example 578 was synthesized from the compound of Reference Example 102 and the compound of Reference Example 1 by a method similar to Step 8 in Example 70.

The compounds of Example 579 (isomer A and isomer B) were synthesized from the compound of Reference Example 93 (isomer A) and Reference Example 92 (isomer A) by methods similar to those described in Step 8 in Example 70 and Example 114.

The compound of Reference Example 103 (shown in the figure below.) was synthesized from the compound synthesized in Step 1 in Example 259 by a method similar to Reference Example 91.

[Chem 282]

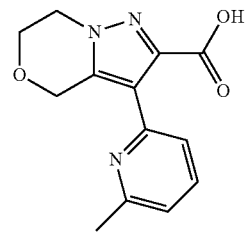

The compound of Example 580 was synthesized from the compound of Reference Example 103 and the compound of Reference Example 92 (isomer A) by a method similar to Step 3 in Example 100.

The compound of Example 581 was synthesized from the compound of Reference Example 90 and the compound of Reference Example 92 (isomer A) by a method similar to Step 3 in Example 100.

The compound of Example 582 was synthesized from the compound synthesized in Step 8 in Example 252 under the scheme depicted in the figure below.

[Chem 283]

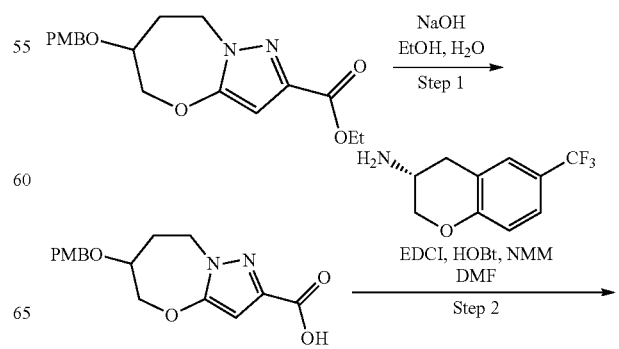

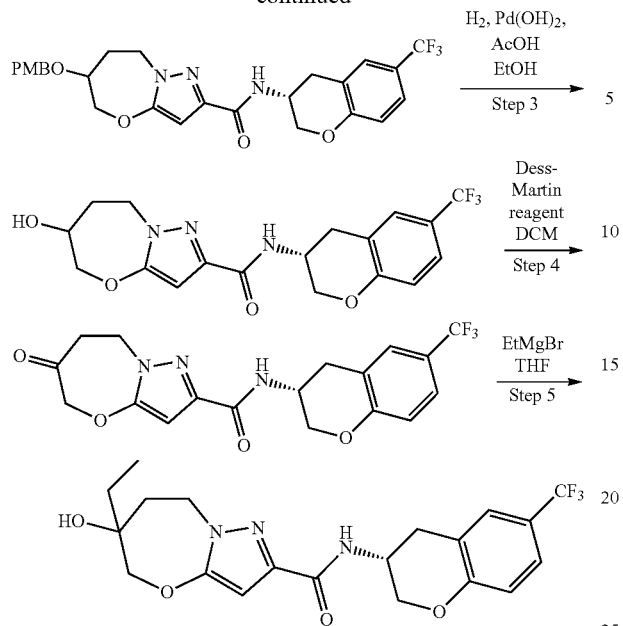

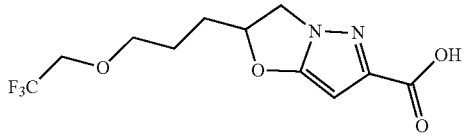

The compound of Example 583 was synthesized by methods similar to those described in Step 3 to Step 5 in Reference Example 34, Example 85 and Reference Example 43.

The compound of Example 584 was synthesized by methods similar to those described in Step 3 to Step 5 in Reference Example 34, Example 85 and Reference Example 1.

The compound of Example 585 was synthesized by methods similar to those described in Step 3 to Step 5 in Reference Example 34, Example 85 and Reference Example 24.

The compound of Example 586 was synthesized by methods similar to those described in Step 3 to Step 5 in Reference Example 34, Example 85 and Reference Example 48.

The compound of Example 587 was synthesized using the compound of Reference Example 92 (isomer A) by a method similar to one described in Example 199.

The compound of Example 588 was synthesized from the compound of Reference Example 55 and the compound of Reference Example 92 (isomer A) by a method similar to Step 8 in Example 70.

The compound of Example 589 was synthesized from the compound of Reference Example 55 and the compound of Reference Example 92 (isomer B) by a method similar to Step 8 in Example 70.

The compounds of Example 590 (isomer A and isomer B) were obtained by separating the compound of Example 564.

The compound of Reference Example 104 (shown in the figure below.) was synthesized from the compound synthesized in Step 7 in Example 245 by methods similar to those described in Example 114 and Step 7 in Example 70.

[Chem 284]

The compound of Example 591 was synthesized from the compound of Reference Example 104 and the compound of Reference Example 92 (isomer A) by a method similar to Step 8 in Example 70.

The compound of Example 592 was synthesized from the compound of Reference Example 104 and the compound of Reference Example 92 (isomer B) by a method similar to Step 8 in Example 70.

The compound of Example 593 was synthesized from the compound of Reference Example 92 (isomer A) by a method similar to Example 268.

The compound of Example 594 was synthesized from the compound of Reference Example 92 (isomer A) by methods similar to those described in Example 268 and Example 261.

The compound of Example 595 was synthesized from the compound synthesized in Step 6 in Example 201 and the compound of Reference Example 92 (isomer A) by a method similar to Step 8 in Example 70.

The compound of Example 596 was synthesized from the compound synthesized in Step 6 in Example 201 and the compound of Reference Example 92 (isomer B) by a method similar to Step 8 in Example 70.

The compounds of Example 597 (isomer A and isomer B) were obtained by separating the compound of Example 569.

The compounds of Example 598 (isomer A and isomer B) were obtained by separating the compound of Example 570.

The compound of Example 599 was synthesized using the compound of Reference Example 92 (isomer B) by a method similar to Example 90.

The compounds of Example 600 (isomer A and isomer B) were obtained by separating the compound of Example 588.

The compounds of Example 601 (isomer A and isomer B) were obtained by separating the compound of Example 557.

The compounds of Example 602 (isomer A and isomer B) were obtained by separating the compound synthesized from the compound of Reference Example 99 and Reference Example 44 by a method similar to Step 3 in Example 100.

The compounds of Example 603 (isomer A and isomer B) were obtained by separating the compound of Example 591

The compound of Reference Example 105 was synthesized from the compound synthesized in Step 2 in Example 245 under the scheme depicted in the figure below.

[Chem 285]

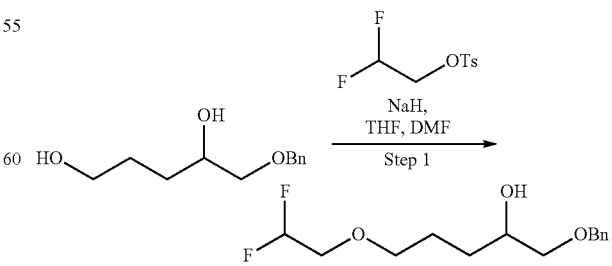

The compound of Reference Example 106 (shown in the figure below) was synthesized from the compound of Reference Example 105 by a method similar to one described in Step 5 to Step 8 in Example 245.

[Chem 286]

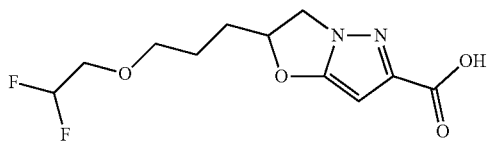

The compounds of Example 604 (isomer A and isomer B) were obtained by separating the compound synthesized using the compound of Reference Example 106 and Reference Example 24 by a method similar to Step 8 in Example 70.

The compound of Example 605 was synthesized from the compound of Reference Example 100 and Reference Example 44 by a method similar to Step 8 in Example 70.

The compound of Reference Example 107 (shown in the figure below) was synthesized by methods similar to those described in Step 3 to Step 5 in Reference Example 34 and Step 1 to Step 5 in Example 85.

[Chem 287]

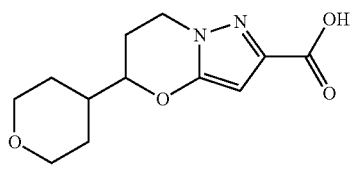

The compound of Example 606 was synthesized from the compound of Reference Example 107 and the compound of Reference Example 44 by a method similar to Step 8 in Example 70.

The compound of Example 607 was synthesized using the compound of Reference Example 106 and the compound of Reference Example 92 (isomer A) by a method similar to one described in Step 8 in Example 70.

The compounds of Example 608 (isomer A and isomer B) were obtained by separating the compound of Example 607.

The compound of Example 609 was synthesized using the compound of Reference Example 106 and the compound of Reference Example 92 (isomer B) by a method similar to Step 8 in Example 70.

The compounds of Example 610 (isomer A and isomer B) were obtained by separating the compound of Example 609.

The compound of Reference Example 108 (shown in the figure below) was synthesized by a method similar to the compound of Reference Example 107.

[Chem 288]

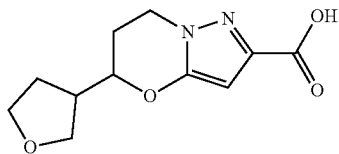

The compound of Example 611 was synthesized from the compound of Reference Example 108 and the compound of Reference Example 1 by a method similar to one described in Step 8 in Example 70.

The compound of Example 612 was synthesized from the compound of Reference Example 108 and the compound of Reference Example 43 by a method similar to one described in Step 8 in Example 70.

The compound of Example 613 was synthesized from the compound of Reference Example 108 and the compound of Reference Example 92 (isomer A) under the scheme depicted in the figure below.

[Chem 289]

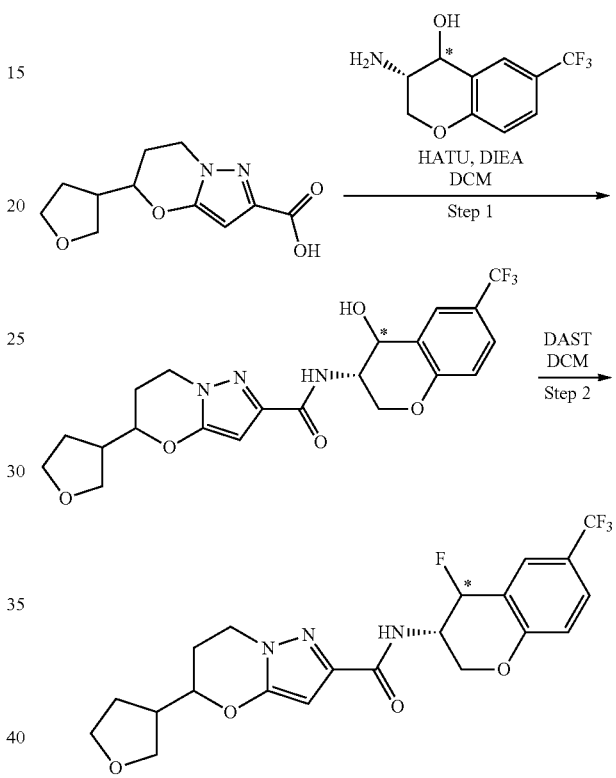

The compound of Example 614 was synthesized from the compound of Reference Example 108 and Reference Example 92 (isomer B) by a method similar to Example 613.

The compounds of Example 615 (isomer A and isomer B) were obtained by separating the compound of Example 606.

The compounds of Example 616 (isomer A and isomer B) were obtained by separating the compound of Example 592.

The compound of Reference Example 109 ((3S)-3-amino-4-fluorochroman-6-carbonitrile) was synthesized under the scheme depicted in the figure below.

[Chem 290]

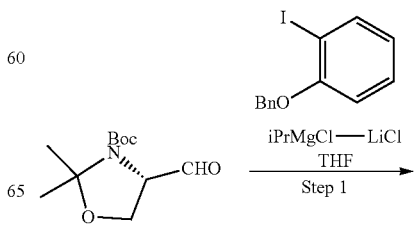

-continued

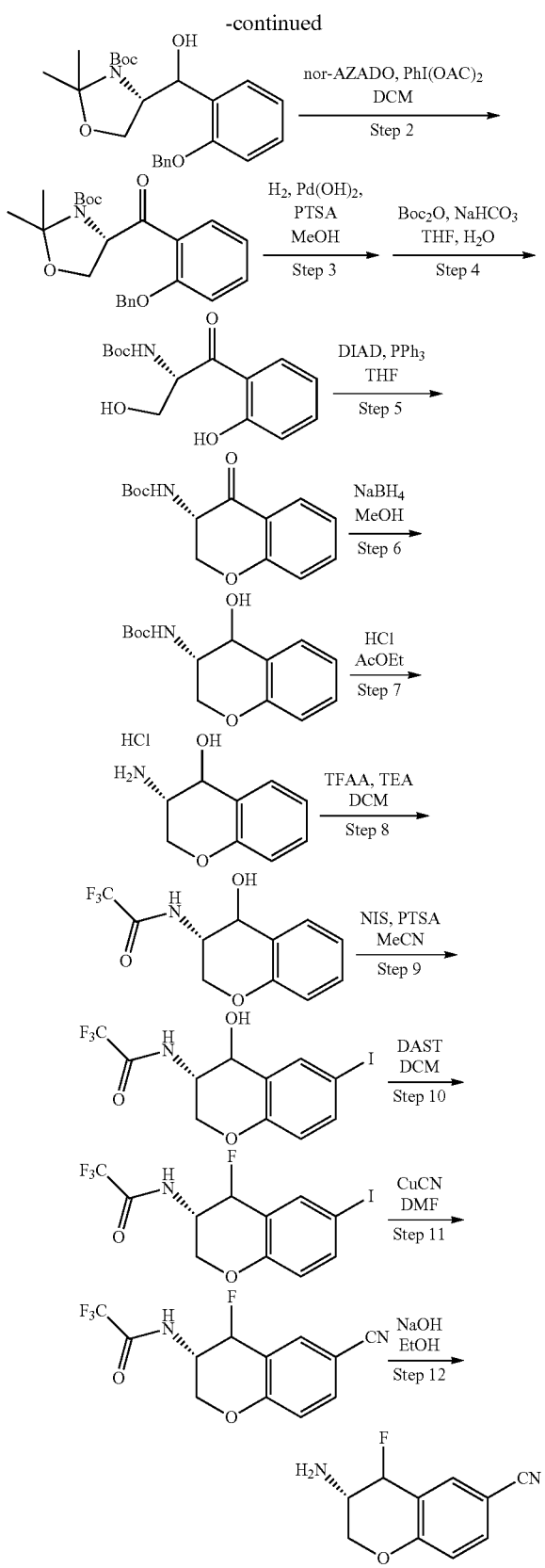

The compounds of Example 617 (isomer A, isomer B, isomer C and isomer D) were obtained by separating the compound synthesized from the compound of Reference Example 33 and the compound of Reference Example 109 by a method similar to Step 8 in Example 70.

The compound of Reference Example 110 (6-bromo-2-((cyclopropylmethoxy)methyl)-2-methyl-2,3-dihydropyrazolo[5,1-b]oxazole) was synthesized under the scheme depicted in the figure below.

[Chem 291]

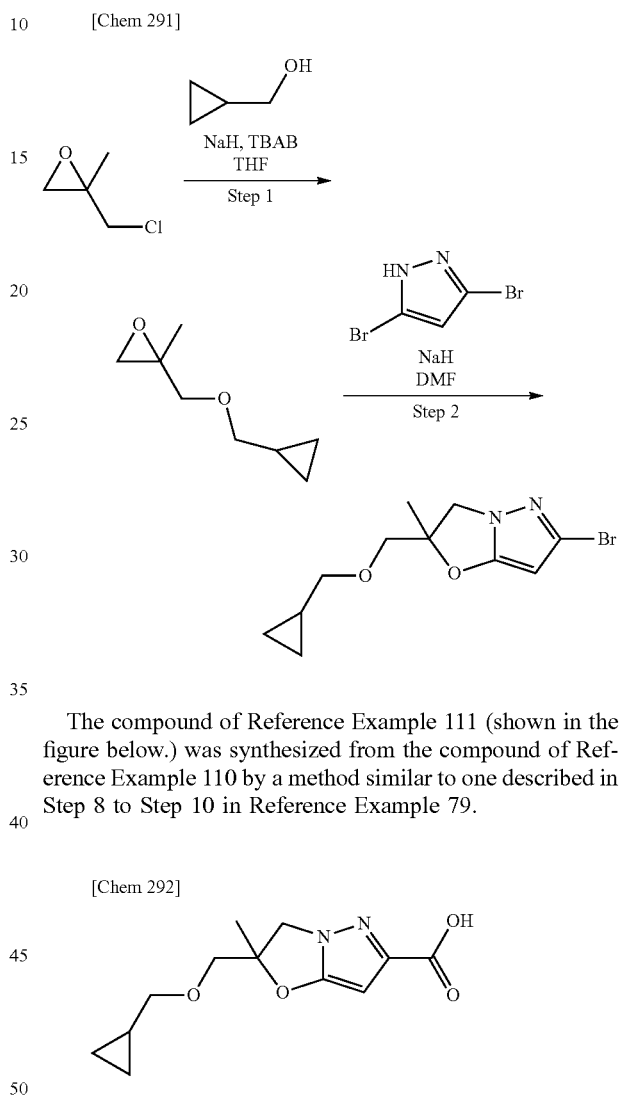

The compound of Reference Example 111 (shown in the figure below.) was synthesized from the compound of Reference Example 110 by a method similar to one described in Step 8 to Step 10 in Reference Example 79.

[Chem 292]

The compound of Example 618 was synthesized from the compound of Reference Example 111 and the compound of Reference Example 24 by a method similar to one described in Step 8 in Example 70.

The compound of Example 619 was synthesized from the compound of Reference Example 111 and the compound of Reference Example 48 by a method similar to one described in Step 8 in Example 70.

The compound of Reference Example 112 (shown in the figure below.) was synthesized by methods similar to those described in Step 3 to Step 5 in Reference Example 34 and Step 1 to Step 5 in Example 85.

[Chem 293]

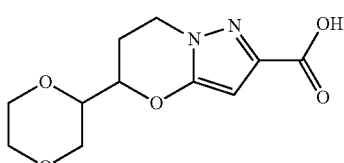

isomers A

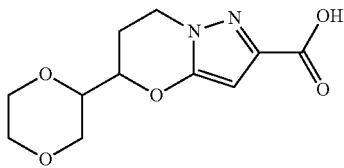

isomers B

The compound of Example 620 was synthesized from the compound of Reference Example 112 (isomers A) and the compound of Reference Example 43 by a method similar to one described in Step 8 in Example 70.

The compound of Example 621 was synthesized from the compound of Example 588 by a method similar to one described in Example 535.

The compounds of Example 622 (isomer A and isomer B) were obtained by separating the compound of Example 605.

The compound of Reference Example 113 (shown in the figure below.) was synthesized by a method similar to one described in Reference Example 100.

[Chem 294]

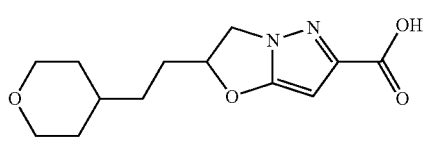

The compound of Example 623 was synthesized from the compound of Reference Example 113 and the compound of Reference Example 24 in a method similar to one described in Step 8 in Example 70.

The compound of Reference Example 114 (4-((tert-butyl-diphenylsilyl)oxy)-1-(2,2-difluoroethoxy)butan-2-ol) was synthesized under the scheme depicted in the figure below.

[Chem 295]

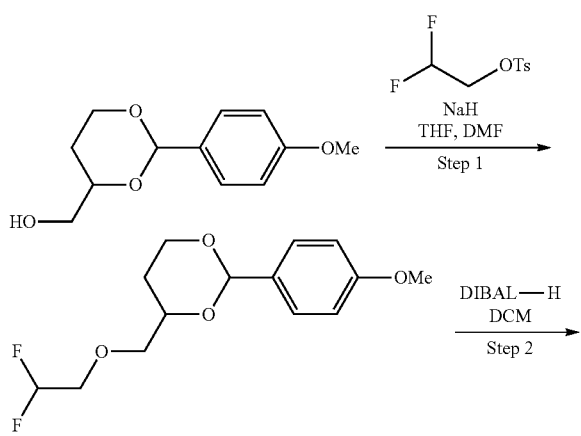

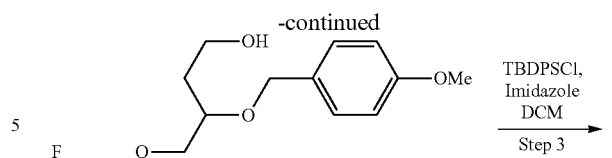

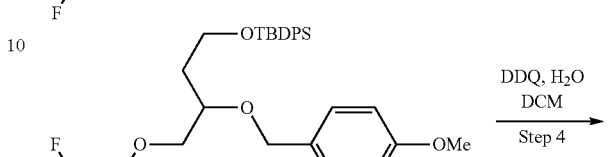

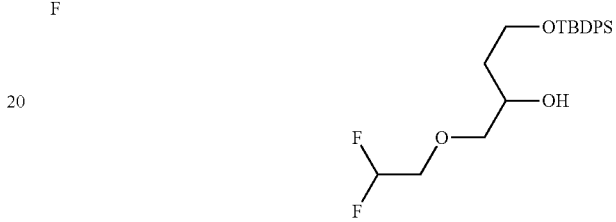

The compound of Reference Example 115 (shown in the figure below) was synthesized from the compound of Reference Example 114 by methods similar to those described in Step 2 to Step 5 in Example 85.

[Chem 296]

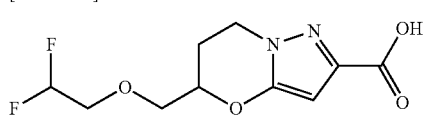

The compound of Example 624 was synthesized from the compound of Reference Example 115 and the compound of Reference Example 92 (isomer B) by methods similar to those described in Step 8 in Example 70 and Step 2 in Example 613.

The compound of Example 625 was synthesized from the compound of Reference Example 70 and the compound of Reference Example 92 (isomer A) by methods similar to those described in Step 7 to Step 8 in Example 70 and Step 2 in Example 613.

The compound of Reference Example 116 (shown in the figure below) was synthesized by a method similar to one described in Reference Example 4.

[Chem 297]

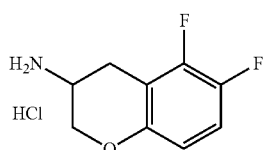

The compound of Example 626 was synthesized from the compound synthesized in Step 5 in Example 169 and the compound of Reference Example 116 by a method similar to one described in Step 8 in Example 70.

The compound of Example 627 was synthesized from the compound of Reference Example 36 and the compound of Reference Example 116 by a method similar to one described in Step 7 to Step 8 in Example 70.

The compound of Example 628 was synthesized from the compound of Reference Example 104 and the compound of Reference Example 116 in a method similar to one described in Step 8 in Example 70.

The compound of Example 629 was synthesized from the compound of Reference Example 55 and the compound of Reference Example 116 in a method similar to one described in Step 8 in Example 70.

The compound of Example 630 was synthesized from the compound of Reference Example 108 and the compound of Reference Example 44 in a method similar to one described in Step 8 in Example 70.

The compound of Example 631 was synthesized from the compound of Reference Example 112 (isomers A) and the compound of Reference Example 44 in a method similar to one described in Step 8 in Example 70.

The compound of Example 632 was synthesized from the compound of Reference Example 89 by methods similar to those described in Step 2 to Step 6 Example 85 and Reference Example 44.

The compound of Example 633 was synthesized from the compound of Reference Example 89 by methods similar to those described in Step 2 to Step 6 Example 85 and Reference Example 48

The compound of Example 634 was synthesized from the compound of Reference Example 99 and the compound of Reference Example 92 (isomer A) by methods similar to those described in Step 8 in Example 70 and Step 2 in Example 613.

The compound of Example 635 was synthesized from the compound of Reference Example 115 and Reference Example 44 in a method similar to one described in Step 8 in Example 70.

The compounds of Example 636 (isomer A and isomer B) were obtained by separating the compound of Example 595.

The compound of Reference Example 117 (shown in the figure below.) was synthesized using the compound of Reference Example 92 (isomer A) by a method similar to one described in Step 1 to Step 2 in Example 268.

[Chem 298]

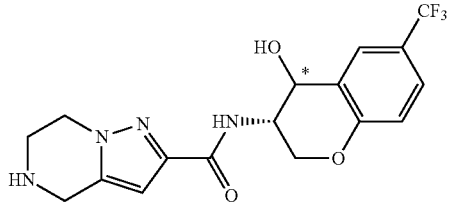

The compound of Example 637 was synthesized from the compound of Reference Example 117 by methods similar to those described in Step 1 in Example 261 and Step 2 in Example 613.

The compound of Example 638 was synthesized from the compound of Reference Example 112 (isomers B) and the compound of Reference Example 44 in a method similar to one described in Step 8 in Example 70.

The compound of Example 639 was synthesized from the compound synthesized in Step 6 in Example 201 and the compound of Reference Example 116 in a method similar to one described in Step 8 in Example 70.

The compound of Example 640 was synthesized from the compound of Reference Example 106 and the compound of Reference Example 116 in a method similar to one described in Step 8 in Example 70.

The compounds of Example 641 (isomer A and isomer B) were obtained by separating the compound of Example 587.

The compound of Example 642 was synthesized from the compound of Reference Example 117 by methods similar to those described in Reference Example 69 and Step 2 in Example 613.

The compound of Example 643 was synthesized from the compound of Reference Example 117 by a method similar to Reference Example 637.

The compound of Reference Example 118 (shown in the figure below.) was synthesized by a method similar to Step 1 in Example 267.

[Chem 299]

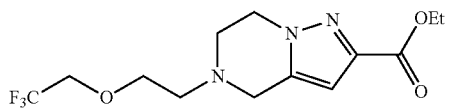

The compound of Example 644 was synthesized from the compound of Reference Example 118 and the compound of Reference Example 43 by a method similar to one described in Step 7 to Step 8 in Example 70.

The compound of Example 645 was synthesized from the compound of Reference Example 118 and the compound of Reference Example 92 (isomer B) by methods similar to those described in Step 2 to Step 3 in Example 100 and Step 2 in Example 613.

The compound of Reference Example 119 (shown in the figure below.) was synthesized using the compound of Reference Example 92 (isomer B) by methods similar to one described in Step 1 to Step 2 in Example 268.

[Chem 300]

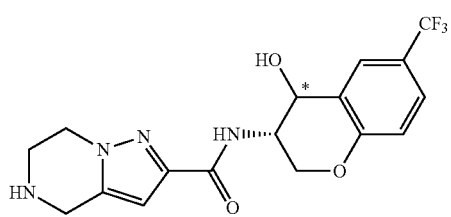

The compound of Example 646 was synthesized from the compound of Reference Example 119 by methods similar to those described in Reference Example 69 and Step 2 in Example 613.

The compound of Example 647 was synthesized from the compound of Reference Example 119 by methods similar to those described in Step 1 in Example 261 and Step 2 in Example 613.

The compound of Example 648 was synthesized from the compound synthesized in Step 5 in Example 169 and the compound of Reference Example 109 by a method similar to one described in Step 8 in Example 70.

The compound of Example 649 was synthesized from the compound of Reference Example 89 by methods similar to those described in Step 2 to Step 6 in Example 85 and Reference Example 109.

The compound of Example 650 was synthesized from the compound synthesized in Step 6 in Example 201 and the compound of Reference Example 109 by a method similar to Step 8 in Example 70.

The compound of Reference Example 120 (shown in the figure below.) was synthesized by a method similar to one described in the compound of Reference Example 107.

[Chem 301]

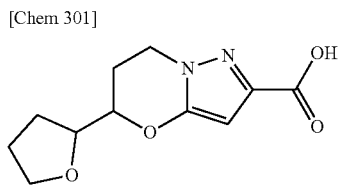

The compound of Example 651 was synthesized from the compound of Reference Example 120 and the compound of Reference Example 44 by a method similar to Step 8 in Example 70.

The compound of Example 652 was synthesized from the compound of Reference Example 117 by a method similar to Reference Example 69.

The compound of Example 653 was synthesized by methods similar to those described in Example 268 and Reference Example 43.

The compound of Example 654 was synthesized from the compound of Example 652 by a method similar to one described in Step 2 in Example 613.

The compound of Example 655 was synthesized by methods similar to those described in Reference Example 82, Example 159 and Reference Example 44.

The compound of Reference Example 121 (shown in the figure below.) was synthesized from the compound synthesized in Step 3 in Reference Example 92 by methods similar to those described in Step 1 and Step 3 in Reference Example 1 and Step 2 in Example 613.

[Chem 302]

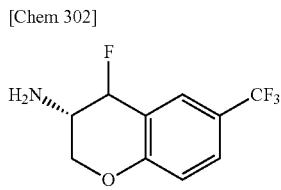

The compound of Example 656 was synthesized from the compound synthesized in Step 8 in Example 252 and the compound of Reference Example 121 under the scheme depicted in the figure below.

[Chem 303]

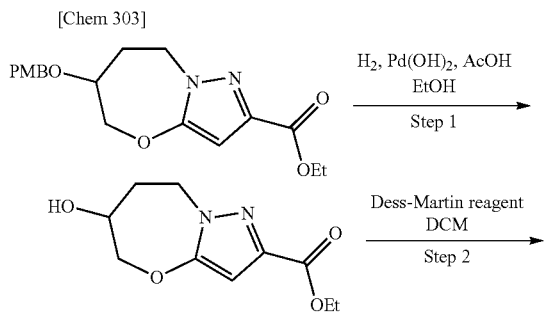

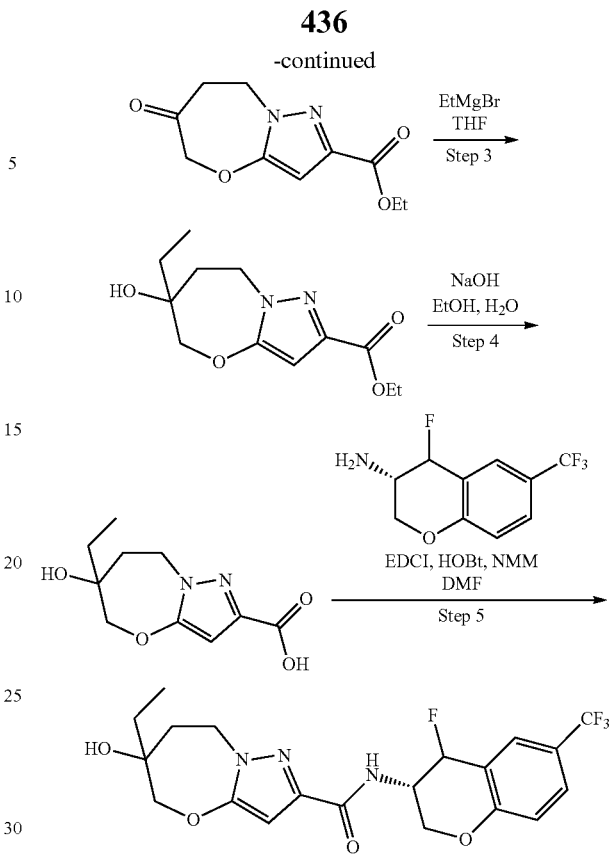

The compound of Reference Example 122 (2-((2-(2,2,2-trifluoroethoxy)ethoxy)methyl)-2,3-dihydropyrazolo[5,1-b]oxazole-6-carboxylic acid) was synthesized from the compound synthesized in Step 1 in Example 187 under the scheme depicted in the figure below.

[Chem 304]

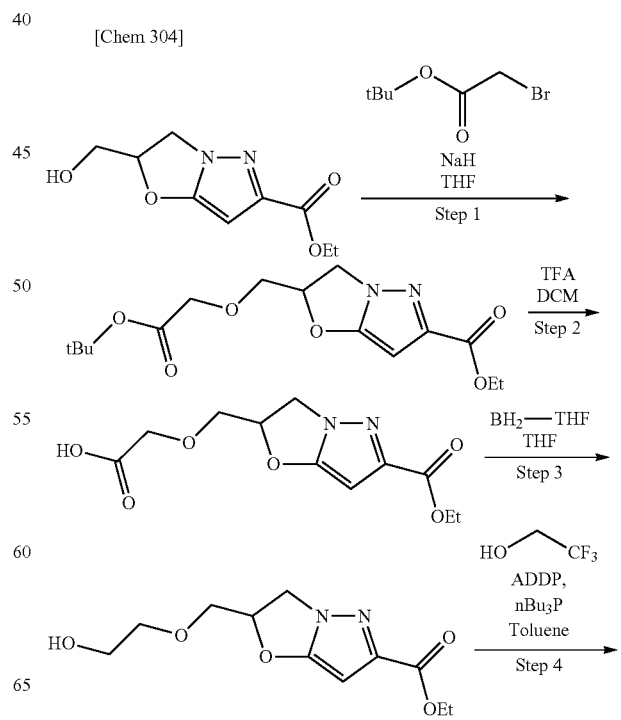

-continued

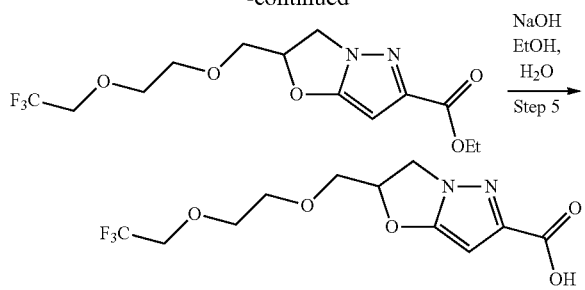

The compound of Example 657 was synthesized from the compound of Reference Example 122 and the compound of Reference Example 43 by a method similar to Step 3 in Example 100.

The compound of Example 658 was synthesized from the compound of Reference Example 122 and the compound of Reference Example 1 by a method similar to Step 3 in Example 100.

The compound of Example 659 was synthesized from the compound of Reference Example 122 and the compound of Reference Example 24 by a method similar to Step 3 in Example 100.

The compound of Example 660 was synthesized from the compound of Reference Example 122 and the compound of Reference Example 92 (isomer A) by a method similar to Step 3 in Example 100.

The compound of Example 661 was synthesized from the compound of Reference Example 122 and the compound of Reference Example 44 by a method similar to Step 3 in Example 100.

The compound of Reference Example 123 (shown in the figure below.) was synthesized from the compound synthesized in Step 1 in Example 100 by a method similar to Reference Example 122.

[Chem 305]

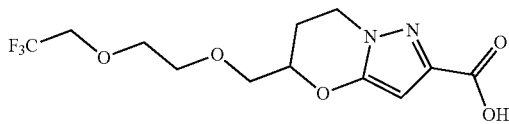

The compound of Example 662 was synthesized from the compound of Reference Example 123 and the compound of Reference Example 1 by a method similar to Step 8 in Example 70.

The compound of Example 663 was synthesized from the compound of Reference Example 123 and the compound of Reference Example 43 by a method similar to Step 8 in Example 70.

The compound of Example 664 was synthesized from the compound of Reference Example 123 and the compound of Reference Example 24 by a method similar to Step 8 in Example 70.

The compound of Example 665 was synthesized from the compound of Reference Example 123 and the compound of Reference Example 92 (isomer B) by methods similar to those described in Step 8 in Example 70 and Step 2 in Example 613.

The compound of Example 666 was synthesized by methods similar to those described in Example 268 and Reference Example 43.

The compound of Example 667 was synthesized from the compound of Reference Example 118 and the compound of Reference Example 44 by methods similar to those described in Step 7 to Step 8 in Example 70.

The compound of Example 668 was synthesized from the compound of Reference Example 120 and the compound of Reference Example 48 by a method similar to Step 8 in Example 70.

The compound of Example 669 was synthesized by methods similar to those described in Example 268 and Reference Example 43.

The compound of Example 670 was synthesized from the compound of Reference Example 119 by methods similar to those described in Step 1 in Example 261 and Step 2 in Example 613.

The compound of Example 671 was synthesized from the compound of Reference Example 119 by methods similar to those described in Reference Example 69 and Step 2 in Example 613.

The compound of Example 672 was synthesized from the compound of Reference Example 119 by methods similar to those described in Reference Example 69 and Step 2 in Example 613.

The compound of Example 673 was synthesized from the compound of Reference Example 119 by methods similar to those described in Reference Example 69 and Step 2 in Example 613.

The compound of Example 674 was synthesized by methods similar to those described in Reference Example 82, Example 159 and Reference Example 48.

The compound of Example 675 was synthesized from the compound of Reference Example 122 and the compound of Reference Example 92 (isomer B) was synthesized by a method similar to Step 3 in Example 100.

The compound of Example 676 was synthesized from the compound of Example 660 by a method similar to one described in Step 2 in Example 613.

The compound of Example 677 was synthesized from the compound of Reference Example 117 by a method similar to Reference Example 69.

The compound of Example 678 was synthesized from the compound of Reference Example 117 and the compound of Example 119 by methods similar to those described in Reference Example 69 and Step 2 in Example 613.

The compound of Example 679 was synthesized from the compound synthesized in Step 6 in Example 254 and the compound of Reference Example 92 (isomer B) by methods similar to those described in Step 8 in Example 70 and Step 2 in Example 613.

The compound of Reference Example 124 (shown in the figure below.) was synthesized from the compound synthesized in Step 8 in Example 252 by a method similar to Reference Example 122.

[Chem 306]

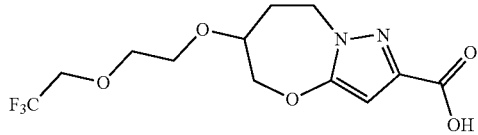

The compound of Example 680 was synthesized from the compound of Reference Example 124 and the compound of Reference Example 43 by a method similar to Step 8 in Example 70.

The compound of Example 681 was synthesized from the compound of Reference Example 124 and the compound of Reference Example 92 (isomer A) by a method similar to Step 8 in Example 70.

The compound of Example 682 was synthesized from the compound of Reference Example 124 and the compound of Reference Example 1 by a method similar to Step 8 in Example 70.

The compound of Example 683 was synthesized from the compound of Reference Example 99 and the compound of Reference Example 92 (isomer A) by methods similar to those described in Step 3 in Example 100 and Step 2 in Example 613.

In the tables below, on the compounds synthesized in Example 291 to Example 683, chemical structures and instrumental analysis data are shown.

TABLE 42

| Example | Structural formula | NMR | MS |
| --- | --- | --- | --- |
| 291 | | 1H-NMR (CDCl$_3$) δ: 1.94 (1H, m), 2.33 (1H, m), 2.65-2.85 (3H, m), 2.98-3.08 (2H, m), 3.98 (1H, m), 4.07-4.30 (3H, m), 4.55 (1H, m), 6.85 (1H, dd, J = 1.2, 7.4 Hz), 6.90 (1H, d, J = 8.0 Hz), 7.07 (1H, d, J = 8.4 Hz), 7.19 (1H, t, J = 7.8 Hz), 7.27-7.42 (6H, m). | ESI-MS m/z: 442 [M + H]+ |
| 292 | | 1H-NMR (CDCl$_3$) δ: 1.97 (1H, m), 2.34 (1H, m), 2.75-2.86 (2H, m), 2.95-3.10 (2H, m), 3.27 (1H, m), 4.00 (1H, t, J = 12.4 Hz), 4.14 (1H, m), 4.24-4.31 (2H, m), 4.66 (1H, m), 6.64 (1H, t, J = 55.6 Hz), 7.00 (1H, d, J = 8.0 Hz), 7.10 (1H, d, J = 7.4 Hz), 7.19-7.21 (2H, m), 7.47 (1H, s). | ESI-MS m/z: 416 [M + H]+ |
| 293 | | 1H-NMR (CDCl$_3$) δ: 1.94 (1H, m), 2.34 (1H, m), 2.82 (3H, m), 3.05 (1H, m), 3.14 (1H, dd, J = 5.8, 16.9 Hz), 3.99 (1H, t, J = 11.6 Hz), 4.15 (2H, m), 4.28 (1H, dd, J = 5.7, 12.5 Hz), 4.66 (1H, m), 5.30 (1H, dd, J = 1.2, 11.0 Hz), 5.63 (1H, dd, J = 1.3, 17.4 Hz), 6.79 (2H, m), 7.11 (2H, m), 7.22 (1H, d, J = 7.9 Hz), 7.46 (1H, s). | ESI-MS m/z: 392 [M + H]+ |
| 294 | | 1H-NMR (CDCl$_3$) δ: 1.96 (1H, m), 2.33 (1H, m), 2.74-3.08 (4H, m), 3.26 (1H, m), 3.96 (1H, m), 4.11-4.31 (3H, m), 4.66 (1H, m), 6.86-7.27 (4H, m), 7.47 (1H, m). | ESI-MS m/z: 391 [M + H]+ |
| 295 | | 1H-NMR (CDCl$_3$) δ: 1.20 (3H, t, J = 7.6 Hz), 1.94 (1H, m), 2.33 (1H, m), 2.55 (2H, q, J = 7.6 Hz), 2.74-2.86 (3H, m), 3.05 (1H, m), 3.16 (1H, m), 3.99 (1H, m), 4.12 (1H, m), 4.19 (1H, m), 4.27 (1H, m), 4.60 (1H, m), 6.79 (1H, d, J = 8.3 Hz), 6.87 (1H, s), 6.95 (1H, dd, J = 2.1, 8.3 Hz), 7.20 (1H, d, J = 8.0 Hz), 7.45 (1H, s). | ESI-MS m/z: 394 [M + H]+ |

TABLE 42-continued

| Example | Structural formula | NMR | MS |
|---|---|---|---|
| 296 | | 1H-NMR (CDCl₃) δ: 1.23 (3H, t, J = 7.0 Hz), 1.95 (1H, m), 2.34 (1H, m), 2.79-2.87 (3H, m), 3.06 (1H, m), 3.17 (1H, dd, J = 5.7, 16.9 Hz), 3.53 (2H, q, J = 7.0 Hz), 3.99 (1H, t, J = 11.6 Hz), 4.11 (1H, m), 4.20-4.30 (2H, m), 4.42 (2H, s), 4.65 (1H, m), 6.84 (1H, d, J = 8.1 Hz), 6.95 (1H, d, J = 6.5 Hz), 7.11 (1H, t, J = 7.8 Hz), 7.21 (1H, m), 7.46 (1H, s). | ESI-MS m/z: 424 [M + H]+ |
| 297 | | 1H-NMR (CDCl₃) δ: 1.95 (1H, m), 2.34 (1H, m), 2.75-2.85 (3H, m), 3.03-3.11 (2H, m), 3.59 (2H, s), 4.00 (1H, t, J = 10.9 Hz), 4.13-4.30 (3H, m), 4.68 (1H, m), 6.90 (1H, d, J = 8.2 Hz), 7.01 (1H, d, J = 7.2 Hz), 7.17 (1H, t, J = 7.9 Hz), 7.23 (1H, d, J = 8.4 Hz), 7.46 (1H, s). | ESI-MS m/z: 405 [M + H]+ |
| 298 | | 1H-NMR (CDCl₃) δ: 1.93 (1H, m), 2.32 (1H, m), 2.75-4.71 (11H, m), 5.26 (1H, m), 6.65 (1H, d, J = 8.6 Hz), 7.08 (1H, s), 7.15 (1H, dd, J = 2.3, 8.7 Hz), 7.22-7.32 (5H, m), 7.48 (1H, s). | ESI-MS m/z: 534 [M + H]+ |
| 299 | | 1H-NMR (CDCl₃) δ: 1.95 (1H, m), 2.34 (1H, m), 2.68 (1H, m), 2.80-2.91 (2H, m), 3.09-3.17 (2H, m), 3.70 (1H, t, J = 11.8 Hz), 3.91 (1H, dd, J = 4.2, 13.0 Hz), 4.08-4.20 (2H, m), 4.54 (1H, m), 6.85-6.90 (2H, m), 7.03 (1H, t, J = 6.1 Hz), 7.12 (1H, t, J = 7.7 Hz), 7.29 (1H, d, J = 8.4 Hz), 7.39-7.50 (5H, m). | ESI-MS m/z: 442 [M + H]+ |

TABLE 43

| Example | Structural formula | NMR | MS |
|---|---|---|---|
| 300 | 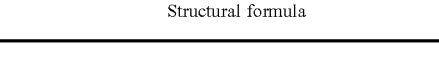 | 1H-NMR (CDCl₃) δ: 1.96 (1H, m), 2.34 (1H, m), 2.76-2.84 (2H, m), 2.90 (1H, dd, J = 4.9, 16.3 Hz), 3.06 (1H, m), 3.17 (1H, m), 4.00 (1H, m), 4.20-4.32 (3H, m), 4.63 (1H, m), 6.92 (1H, d, J = 8.6 Hz), 7.11 (1H, d, J = 7.7 Hz), 7.38 (1H, s), 7.42 (1H, dd, J = 2.0, 8.5 Hz), 7.47 (1H, s). | ESI-MS m/z: 391 [M + H]+ |

TABLE 43-continued

| Example | Structural formula | NMR | MS |
|---|---|---|---|
| 301 | | 1H-NMR (CDCl₃) δ: 1.74-1.78 (2H, m), 1.90 (1H, m), 2.32 (1H, m), 2.71-2.82 (2H, m), 2.86 (1H, dd, J = 4.6, 16.5 Hz), 2.99-3.11 (2H, m), 3.16-3.22 (2H, m), 3.46-3.52 (2H, m), 3.76 (1H, m), 4.11-4.23 (3H, m), 4.59 (1H, m), 4.75 (1H, t, J = 7.0 Hz), 6.86-6.91 (2H, m), 7.06 (1H, d, J = 7.6 Hz), 7.13 (1H, m), 7.40 (1H, d, J = 7.3 Hz). | ESI-MS m/z: 424 [M + H]+ |
| 302 | | 1H-NMR (CDCl₃) δ: 1.91 (1H, m), 2.32 (1H, m), 2.71-2.90 (3H, m), 3.07 (1H, m), 3.18 (1H, m), 3.91 (1H, t, J = 11.6 Hz), 4.15 (1H, m), 4.23 (1H, m), 4.33 (1H, dd, J = 5.4, 12.5 Hz), 4.59 (1H, m), 5.53 (1H, d, J = 12.3 Hz), 5.72 (1H, d, J = 18.4 Hz), 6.86-6.91 (2H, m), 7.05 (1H, d, J = 7.2 Hz), 7.13 (1H, m), 7.30-7.38 (2H, m). | ESI-MS m/z: 392 [M + H]+ |
| 303 | | 1H-NMR (CDCl₃) δ: 1.93-1.94 (4H, m), 2.84-2.89 (3H, m), 3.15 (1H, dd, J = 5.5, 16.5 Hz), 3.91 (3H, s), 4.04-4.05 (2H, m), 4.11 (1H, m), 4.22 (1H, m), 4.55 (1H, m), 6.72 (1H, dd, J = 0.8, 8.2 Hz), 6.85-6.89 (2H, m), 7.04 (1H, d, J = 1.0, 7.4 Hz), 7.12 (1H, m), 7.44 (1H, d, J = 8.0 Hz), 7.55 (1H, dd, J = 0.8, 7.4 Hz), 7.66 (1H, dd, J = 7.4, 8.2 Hz). | ESI-MS m/z: 405 [M + H]+ |
| 304 | | 1H-NMR (CDCl₃) δ: 1.82-1.95 (4H, m), 2.79-2.96 (3H, m), 3.13 (1H, dt, J = 5.4, 16.9 Hz), 3.51 (1H, m), 3.87 (1H, m), 4.03-4.22 (2H, m), 4.38 (1H, m), 4.51 (1H, m), 5.21 (1H, m), 6.85-6.90 (2H, m), 7.04 (1H, m), 7.09-7.14 (2H, m), 7.36 (1H, t, J = 7.8 Hz), 7.83 (1H, m), 8.22 (1H, dt, J = 1.6, 5.0 Hz). | ESI-MS m/z: 472 [M + H]+ |
| 305 | | 1H-NMR (CDCl₃) δ: 1.94 (4H, m), 2.89-2.93 (3H, m), 3.16 (1H, m), 4.02 (2H, m), 4.16 (1H, m), 4.26 (1H, m), 4.56 (1H, m), 6.93 (1H, d, J = 8.6 Hz), 7.26-7.38 (3H, m), 7.47 (1H, m), 7.78 (1H, t, J = 7.9 Hz), 7.91 (1H, d, J = 8.2 Hz), 8.63 (1H, d, J = 4.1 Hz). | ESI-MS m/z: 443 [M + H]+ |

TABLE 43-continued

| Example | Structural formula | NMR | MS |
|---|---|---|---|
| 306 | 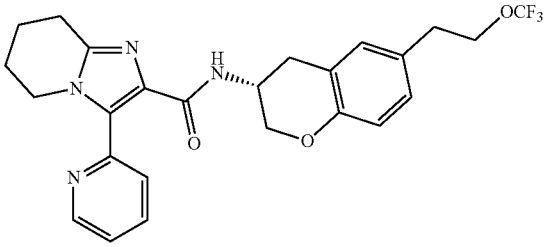 [SMILES: O=C(N[C@H]1COc2ccc(CCOC(F)(F)F)cc2C1)c1nc2n(c1-c1ccccn1)CCCC2] | 1H-NMR (CDCl₃) δ: 1.93 (3H, m), 2.81-2.92 (5H, m), 3.12 (1H, dd, J = 5.2, 16.7 Hz), 4.01-4.21 (7H, m), 4.54 (1H, m), 6.81 (1H, d, J = 8.3 Hz), 6.88 (1H, s), 6.96 (1H, d, J = 7.7 Hz), 7.24-7.26 (1H, m), 7.48 (1H, d, J = 7.8 Hz), 7.78 (1H, d, J = 7.7 Hz), 7.92 (1H, d, J = 7.8 Hz), 8.63 (1H, d, J = 4.8 Hz). | ESI-MS m/z: 487 [M + H]+ |
| 307 | 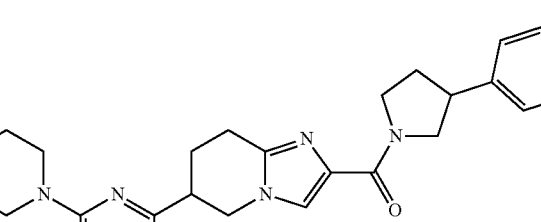 | 1H-NMR (CDCl₃) δ: 2.01-4.64 (22H, m), 6.51-6.61 (2H, m), 7.23-7.35 (5H, m), 7.46-7.51 (2H, m). | ESI-MS m/z: 458 [M + H]+ |
| 308 | 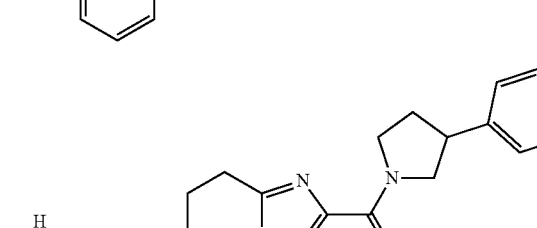 | 1H-NMR (CDCl₃) δ: 1.22-1.28 (3H, m), 2.01-4.61 (17H, m), 6.26 (1H, dd, J = 3.6, 8.3 Hz), 6.48 (1H, t, J = 6.7 Hz), 7.24-7.51 (7H, m). | ESI-MS m/z: 416 [M + H]+ |

TABLE 44

| Example | Structural formula | NMR | MS |
|---|---|---|---|
| 309 | 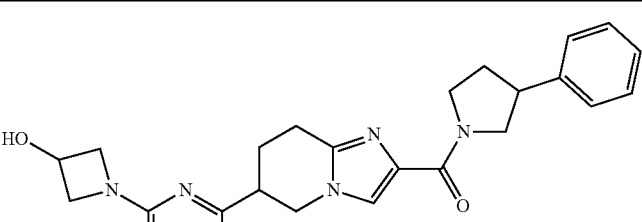 | 1H-NMR (CDCl₃) δ: 1.98-4.76 (20H, m), 6.20 (1H, dd, J = 3.7, 8.4 Hz), 6.52 (1H, t, J = 6.6 Hz), 7.26 (7H, s). | ESI-MS m/z: 444 [M + H]+ |
| 310 | 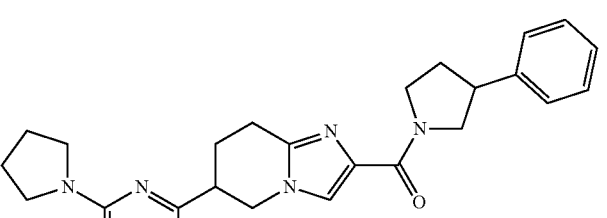 | 1H-NMR (CDCl₃) δ: 1.97-2.04 (6H, m), 2.16-2.39 (3H, m), 2.81-3.07 (2H, m), 3.21 (1H, m), 3.40-3.41 (4H, m), 3.69 (1H, m), 3.90 (1H, m), 3.99-4.64 (4H, m), 6.23 (1H, dd, J = 3.9, 8.3 Hz), 6.43 (1H, t, J = 6.7 Hz), 7.22-7.41 (6H, m), 7.49 (1H, d, J = 13.2 Hz). | ESI-MS m/z: 442 [M + H]+ |

TABLE 44-continued

| Example | Structural formula | NMR | MS |
| --- | --- | --- | --- |
| 311 | | 1H-NMR (CDCl₃) δ: 1.26 (6H, d, J = 6.16 Hz), 2.01-4.64 (20H, m), 6.51 (1H, dd, J = 3.5, 8.5 Hz), 6.56 (1H, t, J = 6.6 Hz), 7.22-7.35 (5H, m), 7.43-7.53 (2H, m). | ESI-MS m/z: 486 [M + H]+ |
| 312 | | 1H-NMR (CDCl₃) δ: 1.14-4.62 (28H, m), 6.49 (1H, t, J = 6.6 Hz), 6.54 (1H, dd, J = 3.6, 8.5 Hz), 7.22-7.35 (5H, m), 7.41 (1H, m), 7.49 (1H, d, J = 13.4 Hz). | ESI-MS m/z: 486 [M + H]+ |
| 313 | | 1H-NMR (CDCl₃) δ: 2.05-5.54 (19H, m), 6.70 (1H, m), 6.84 (1H, m), 7.24-7.33 (5H, m), 7.50 (1H, d, J = 14.4 Hz), 7.58 (1H, m). | ESI-MS m/z: 445 [M + H]+ |
| 314 | | 1H-NMR (CDCl₃) δ: 2.20-2.36 (2H, m), 2.86-2.95 (2H, m), 2.99-3.06 (1H, m), 3.19 (1H, dd, J = 5.7, 16.5 Hz), 3.46 (1H, m), 4.14 (1H, dd, J = 5.5, 10.8 Hz), 4.25 (1H, dd, J = 1.9, 10.7 Hz), 4.34 (2H, d, J = 8.0 Hz), 4.63 (1H, m), 6.86-6.90 (2H, m), 7.06 (1H, d, J = 7.5 Hz), 7.12 (1H, t, J = 7.7 Hz), 7.22 (1H, d, J = 6.8 Hz), 7.44 (1H, d, J = 7.8 Hz), 7.49 (1H, s), 7.61 (1H, d, J = 7.8 Hz), 7.86 (1H, t, J = 7.8 Hz). | ESI-MS m/z: 443 [M + H]+ |
| 315 | | 1H-NMR (CDCl₃) δ: 1.85-2.34 (6H, m), 2.74-3.14 (2H, m), 3.43 (1H, m), 3.89 (1H, m), 4.13-4.35 (4H, m), 5.37 (0.6H, m), 6.15 (0.4H, m), 7.05-7.22 (2H, m), 7.28-7.62 (5H, m), 7.86 (1H, m). | ESI-MS m/z: 441 [M + H]+ |

TABLE 44-continued

| Example | Structural formula | NMR | MS |
|---|---|---|---|
| 316 | | 1H-NMR (CDCl₃) δ: 2.17-2.42 (3H, m), 2.94 (1H, m), 3.07-3.18 (1H, m), 3.42 (1H, m), 3.54 (1H, m), 3.63-3.75 (1H, m), 3.82-3.97 (2H, m), 4.05 (3H, d, J = 4.4 Hz), 4.16 (1H, m), 4.35 (2H, m), 4.59 (1H, m), 7.23-7.35 (5H, m), 7.50 (1H, dd, J = 2.0, 12.3 Hz), 7.64 (1H, d, J = 6.2 Hz), 8.40 (1H, s). | ESI-MS m/z: 471 [M + H]+ |
| 317 | | 1H-NMR (CDCl₃) δ: 1.55-1.74 (3H, m), 1.97-2.12 (3H, m), 2.33 (1H, m), 2.62-2.79 (3H, m), 2.98 (1H, m), 3.41 (1H, m), 3.56-3.73 (2H, m), 3.83-4.18 (6H, m), 4.45 (1H, m), 6.70 (1H, dd, J = 3.1, 8.4 Hz), 7.22-7.34 (5H, m), 7.39-7.46 (2H, m), 7.98 (1H, m). | ESI-MS m/z: 431 [M + H]+ |

TABLE 45

| Example | Structural formula | NMR | MS |
|---|---|---|---|
| 318 | | 1H-NMR (CDCl₃) δ: 1.39-2.36 (14H, m), 2.76 (1H, m), 3.03-3.06 (2H, m), 3.49 (1H, m), 3.70 (1H, m), 3.94-4.11 (2H, m), 4.37 (1H, m), 4.77 (0.6H, m), 5.21 (0.4H, m), 7.20-7.31 (5H, m), 7.43 (1H, m). | ESI-MS m/z: 414 [M + H]+ |
| 319 | | 1H-NMR (CDCl₃) δ: 0.94-1.06 (6H, m), 1.63-2.18 (6H, m), 2.54-3.20 (5H, m), 3.80 (1H, m), 4.08 (1H, m), 4.24 (1H, m), 4.58-5.42 (2H, m), 6.85-6.90 (2H, m), 7.05 (1H, d, J = 7.4 Hz), 7.12 (1H, t, J = 7.7 Hz), 7.18 (1H, d, J = 7.6 Hz), 7.43 (1H, m). | ESI-MS m/z: 386 [M + H]+ |
| 320 | | 1H-NMR (CDCl₃) δ: 1.33 (3H, s), 1.39 (3H, s), 1.49-1.76 (5H, m), 1.96 (1H, m), 2.07 (1H, m), 2.73 (1H, m), 2.84-2.96 (2H, m), 3.18 (1H, dd, J = 5.5, 16.5 Hz), 3.56 (1H, t, J = 11.1 Hz), 4.06-4.15 (2H, m), 4.24 (1H, d, J = 10.6 Hz), 4.62 (1H, m), 6.85-6.90 (2H, m), 7.05 (1H, d, J = 7.4 Hz), 7.12 (1H, t, J = 7.7 Hz), 7.18 (1H, d, J = 8.0 Hz), 7.40 (1H, s). | ESI-MS m/z: 386 [M + H]+ |

TABLE 45-continued

| Example | Structural formula | NMR | MS |
|---|---|---|---|
| 321 | | 1H-NMR (CDCl$_3$) δ: 1.98 (1H, s), 2.20 (1H, m), 2.76-2.99 (3H, m), 3.18 (1H, dd, J = 5.6, 16.6 Hz), 3.71-3.82 (2H, m), 3.96-4.15 (6H, m), 4.24 (1H, dd, J = 2.3, 10.7 Hz), 4.62 (1H, m), 6.85-6.90 (2H, m), 7.05 (1H, d, J = 7.4 Hz), 7.12 (1H, t, J = 7.7 Hz), 7.18 (1H, d, J = 7.9 Hz), 7.41 (1H, s). | ESI-MS m/z: 426 [M + H]+ |
| 322 | | 1H-NMR (CDCl$_3$) δ: 1.74 (1H, m), 1.87 (1H, m), 2.73 (1H, m), 2.84 (3H, d, J = 1.7 Hz), 2.88 (1H, m), 2.96 (1H, m), 3.18 (1H, td, J = 5.4, 16.5 Hz), 3.83 (1H, m), 4.01 (1H, dd, J = 5.5, 12.3 Hz), 4.13 (1H, m), 4.22 (1H, m), 4.39 (1H, m), 4.61 (1H, m), 6.84-6.91 (2H, m), 7.04 (1H, t, J = 6.9 Hz), 7.10-7.17 (2H, m), 7.35 (1H, s), 7.55-7.59 (2H, m), 7.65 (1H, m), 7.82-7.85 (2H, m). | ESI-MS m/z: 467 [M + H]+ |
| 323 | | 1H-NMR (CDCl$_3$) δ: 2.16 (3H, m), 3.07 (2H, t, J = 7.1 Hz), 3.49 (1H, d, J = 15.6 Hz), 3.57 (1H, t, J = 7.2 Hz), 3.76 (2H, q, J = 6.8 Hz), 4.05-4.10 (3H, m), 7.05 (1H, m), 7.12 (1H, m), 7.7-7.21 (2H, m), 7.32-7.39 (6H, m), 7.43 (1H, s), 7.64 (1H, d, J = 7.8 Hz), 8.25 (1H, s). | |
| 324 | | 1H-NMR (CDCl$_3$) δ: 2.97 (2H, t, J = 7.2 Hz), 3.65-3.70 (2H, m), 4.18-4.31 (3H, m), 4.42-4.47 (2H, m, ), 7.11 (1H, m), 7.40-7.53 (5H, m), 7.68 (1H, d, J = 7.8 Hz), 7.71 (1H, d, J = 7.9 Hz), 7.95 (1H, t, J = 7.7 Hz) | ESI-MS m/z: 484 [M + H]+ |
| 325 | | 1H-NMR (CDCl$_3$) δ: 2.16 (3H, m), 2.90 (2H, t, J = 7.3 Hz), 3.51 (1H, m), 3.57-3.68 (4H, m), 4.04-4.13 (4H, m), 6.83 (1H, m), 6.95 (1H, m), 7.07-7.11 (4H, m), 7.26 (1H, m), 7.31-7.35 (2H, m), 7.43 (1H, s). | |
| 326 | | 1H-NMR (CDCl$_3$) δ: 2.27 (3H, s), 2.97 (2H, t, J = 7.3 Hz), 3.67 (2H, q, J = 7.0 Hz), 3.83 (1H, d, J = 16.1 Hz), 4.03 (1H, d, J = 16.1 Hz), 4.18 (1H, m), 4.31-4.44 (2H, m), 7.11 (1H, m), 7.42-7.51 (5H, m), 7.67-7.71 (2H, m), 7.95 (1H, t, J = 7.7 Hz). | ESI-MS m/z: 498 [M + H]+ |

TABLE 46

| Example | Structural formula | NMR | MS |
|---|---|---|---|
| 327 | | 1H-NMR (CDCl3) δ: 1.40-1.50 (2H, m), 1.77 (2H, m), 2.06 (1H, m), 2.18 (3H, s), 2.88 (2H, t, J = 7.3 Hz), 3.42-3.68 (6H, m), 3.79 (2H, d, J = 6.5 Hz), 4.08-4.13 (5H, m), 6.74-6.79 (2H, m), 6.83 (1H, d, J = 7.7 Hz), 7.12 (1H, t, J = 6.2 Hz), 7.21 (1H, t, J = 7.8 Hz), 7.33-7.40 (5H, m), 7.44 (1H, s). | |
| 328 | | 1H-NMR (CDCl$_3$) δ: 0.91 (9H, s), 1.23-1.28 (2H, m), 1.39 (1H, m), 1.48-1.54 (2H, m), 2.87 (1H, dd, J = 5.0, 16.4 Hz), 2.99 (1H, m), 3.18 (1H, m), 3.61 (1H, m), 3.95-4.04 (2H, m), 4.11-4.16 (2H, m), 4.24 (1H, d, J = 10.8 Hz), 4.62 (1H, m), 6.85-6.90 (2H, m), 7.05 (1H, d, J = 7.6 Hz), 7.12 (1H, m), 7.17 (1H, m), 7.43 (1H, s). | |
| 329 | | 1H-NMR (CDCl$_3$) δ: 1.26 (2H, m), 2.16 (1H, m), 2.20 (1H, s), 2.38 (1H, m), 2.85-3.10 (1H, m), 3.48-3.63 (2H, m), 4.07-4.28 (4H, m), 4.394.53 (1H, m), 4.64-4.77 (1H, m), 7.23-7.43 (8H, m), 7.52 (1H, m), 7.70 (1H, dd, J = 2.0, 7.4 Hz). | ESI-MS m/z: 439 [M + H]+ |
| 330 | | 1H-NMR (CDCl$_3$) δ: 2.18 (3H, s), 3.51-3.61 (2H, m), 4.08-4.23 (4H, m), 4.58-4.60 (2H, m), 5.03 (1H, m), 5.50 (1H, m), 6.98 (1H, d, J = 8.4 Hz), 7.30 (1H, d, J = 7.3 Hz), 7.34-7.41 (5H, m), 4.46 (1H, s), 7.75 (1H, t, J = 7.6 Hz). | ESI-MS m/z: 458 [M + H]+ |
| 331 | | 1H-NMR (CDCl$_3$) δ: 2.19 (3H, s), 3.52-3.62 (2H, m), 4.04-4.16 (5H, m), 7.33-7.42 (7H, m), 7.57 (1H, t, J = 7.8 Hz), 7.71 (1H, d, J = 7.9 Hz), 7.76 (1H, d, J = 7.8 Hz) 7.82 (1H, s). | ESI-MS m/z: 465 [M + H]+ |
| 332 | | 1H-NMR (CDCl$_3$) δ: 2.20 (3H, s), 3.06-3.11 (4H, m), 3.44-3.70 (4H, m), 4.07-4.25 (4H, m), 7.32-7.61 (10H, m). | ESI-MS m/z: 443 [M + H]+ |

TABLE 46-continued

| Example | Structural formula | NMR | MS |
|---|---|---|---|
| 333 | 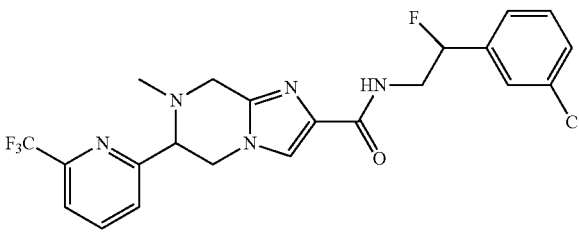 | 1H-NMR (CDCl₃) δ: 2.29 (3H, s), 3.58 (1H, m), 3.87 (1H, d, J = 16.1 Hz), 3.99-4.14 (2H, m), 4.20 (1H, m), 4.40 (1H, m), 5.70 (1H, dd, J = 6.6, 47.8 Hz), 7.45 (1H, m), 7.53 (1H, s), 7.51-7.55 (2H, m), 7.59-7.63 (2H, m), 7.67-7.73 (3H, m), 7.96 (1H, t, J = 7.8 Hz). | ESI-MS m/z: 516 [M + H]+ |
| 334 | 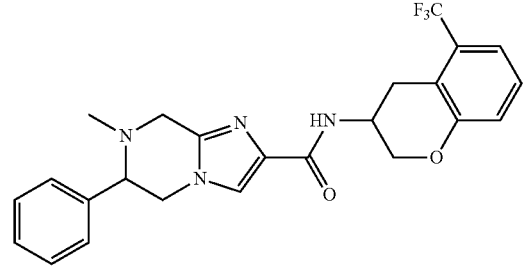 [SMILES: CN1Cc2nc(C(=O)NC3COc4cccc(C(F)(F)F)c4C3)cn2CC1c1ccccc1] | 1H-NMR (CDCl₃) δ: 2.17-2.19 (3H, m), 3.01-3.95 (5H, m), 4.08-4.31 (4H, m), 4.67-5.05 (1H, m), 6.95-7.25 (4H, m), 7.35-7.40 (5H, m), 7.46 (1H, s). | |
| 335 | 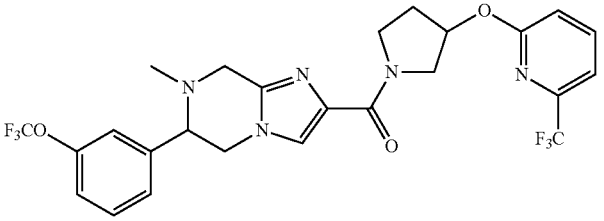 [SMILES: CN1Cc2nc(C(=O)N3CCC(Oc4cccc(C(F)(F)F)n4)C3)cn2CC1c1cccc(OC(F)(F)F)c1] | 1H-NMR (CDCl₃) δ: 2.19-2.31 (5H, m), 3.53-3.68 (2H, m), 3.77-3.95 (2H, m), 4.02-4.20 (4H, m), 4.30-4.40 (2H, m), 5.71 (1H, m), 6.88 (1H, d, J = 8.3 Hz), 7.22-7.25 (2H, m), 7.30 (1H, m), 7.43 (1H, m), 7.48 (1H, d, J = 8.3 Hz), 7.70 (1H, t, J = 7.8 Hz). | ESI-MS m/z: 556 [M + H]+ |

TABLE 47

| Example | Structural formula | NMR | MS |
|---|---|---|---|
| 336 | 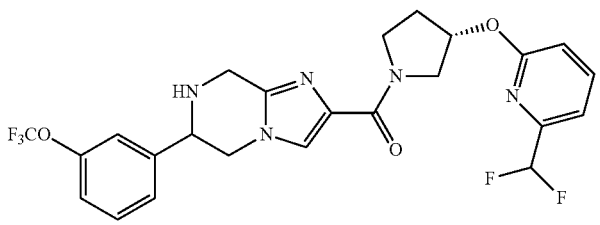 [SMILES: O=C(c1cn2c(n1)CNC(c1cccc(OC(F)(F)F)c1)C2)N1CC[C@H](Oc2cccc(C(F)F)n2)C1] | 1H-NMR (CDCl₃) δ: 2.17-2.28 (3H, m), 3.81-3.99 (3H, m), 4.11-4.37 (6H, m), 5.68 (1H, d, J = 19.5 Hz), 6.50 (1H, t, J = 55.6 Hz), 6.80 (1H, d, J = 7.4 Hz), 7.21 (1H, t, J = 7.4 Hz), 7.33-7.46 (3H, m), 7.50 (1H, d, J = 7.2 Hz), 7.68 (1H, t, J = 7.8 Hz). | ESI-MS m/z: 524 [M + H]+ |
| 337 | 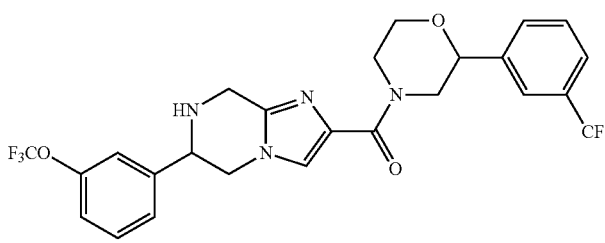 | 1H-NMR (CDCl₃) δ: 2.09 (1H, m), 3.82 (1H, td, J = 2.7, 11.7 Hz), 3.96 (1H, t, J = 11.0 Hz), 4.09-4.35 (6H, m), 4.62 (1H, d, J = 10.5 Hz), 4.77 (1H, m), 5.39-5.51 (1H, m), 7.23 (1H, dd, J = 1.0, 8.0 Hz), 7.35-7.51 (5H, m), 7.56 (1H, s), 7.50 (1H, t, J = 7.6 Hz), 7.73 (1H, s). | ESI-MS m/z: 541 [M + H]+ |

TABLE 47-continued

| Example | Structural formula | NMR | MS |
|---|---|---|---|
| 338 | | 1H-NMR (CDCl₃) δ: 2.83 (1H, dd, J = 4.9, 16.2 Hz), 3.07 (2H, t, J = 5.3 Hz), 3.13 (1H, dd, J = 5.6, 16.7 Hz), 3.18-3.25 (2H, m), 3.80 (2H, t, J = 5.3 Hz), 3.99 (2H, s), 4.09-4.20 (2H, m), 4.54 (1H, m), 6.85-6.90 (2H, m), 7.04 (1H, d, J = 7.3 Hz), 7.12 (1H, t, J = 7.5 Hz), 7.29 (1H, d, J = 8.2 Hz), 7.41-7.44 (5H, m). | ESI-MS m/z: 457 [M + H]+ |
| 339 | | 1H-NMR (CDCl₃) δ: 2.84 (1H, m), 3.15 (1H, dd, J = 5.7, 17.0 Hz), 3.85-3.95 (2H, m), 3.94 (1H, m), 4.04 (1H, m), 4.15-4.17 (2H, m), 4.55 (1H, m), 4.91 (2H, s), 6.87-6.91 (2H, m), 7.05 (1H, d, J = 7.4 Hz), 7.14 (1H, t, J = 7.6 Hz), 7.33 (1H, m), 7.42-7.49 (5H, m). | ESI-MS m/z: 471 [M + H]+ |
| 340 | | 1H-NMR (CDCl₃) δ: 1.24-1.48 (2H, m), 2.81 (1H, m), 3.16 (1H, m), 4.03-4.65 (4H, m), 4.85-5.08 (2H, m), 6.85-6.93 (2H, m), 7.02-7.23 (3H, m), 7.36-7.51 (5H, m), 7.68 (1H, m). | |
| 341 | | 1H-NMR (CDCl₃) δ: 2.91 (1H, dd, J = 5.1, 16.6 Hz), 3.16 (1H, dd, J = 5.1, 16.6 Hz), 4.05 (2H, t, J = 5.0 Hz), 4.20-4.31 (4H, m), 4.55 (1H, m), 4.82 (2H, s), 6.93 (1H, d, J = 8.5 Hz), 7.31 (1H, d, J = 8.0 Hz), 7.38 (1H, s), 7.41-7.43 (2H, m), 7.77 (1H, t, J = 7.8 Hz), 8.12 (1H, d, J = 7.7 Hz). | ESI-MS m/z: 436 [M + H]+ |
| 342 | | 1H-NMR (CDCl₃) δ: 0.60 (2H, d, J = 4.9 Hz), 0.88 (2H, d, J = 8.4 Hz), 1.81 (1H, m), 2.82 (1H, m), 3.12 (1H, dd, J = 5.5, 16.6 Hz), 4.02 (2H, t, J = 4.9 Hz), 4.10-4.20 (4H, m), 4.54 (1H, m), 4.84 (2H, s), 6.77-6.78 (2H, m), 6.84 (1H, d, J = 8.5 Hz), 7.28 (1H, m), 7.54 (1H, d, J = 8.0 Hz), 7.79 (1H, t, J = 7.5 Hz), 8.08 (1H, d, J = 7.7 Hz), 8.62 (1H, d, J = 4.8 Hz). | ESI-MS m/z: 417 [M + H]+ |
| 343 | | 1H-NMR (CDCl₃) δ: 2.86 (1H, dd, J = 4.8, 16.7 Hz), 3.15 (1H, dd, J = 5.5, 16.5 Hz), 3.26 (2H, q, J = 10.8 Hz), 4.02 (2H, t, J = 5.2 Hz), 4.13-4.23 (4H, m), 4.56 (1H, m), 4.84 (2H, s), 6.85 (1H, d, J = 8.4 Hz), 6.97 (1H, s), 7.05 (1H, d, J = 7.9 Hz), 7.26 (1H, m), 7.55 (1H, d, J = 8.2 Hz), 7.80 (1H, dt, J = 1.8, 7.8 Hz), 8.07 (1H, d, J = 7.9 Hz), 8.61 (1H, m). | ESI-MS m/z: 459 [M + H]+ |

TABLE 47-continued

| Example | Structural formula | NMR | MS |
|---|---|---|---|
| 344 | 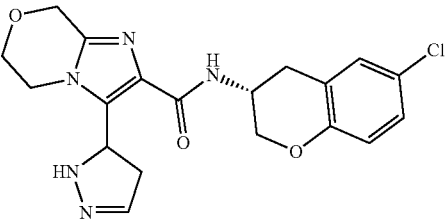 [SMILES: O=C(N[C@H]1COc2ccc(Cl)cc2C1)c1nc2n(c1C1CC=NN1)CCOC2] | 1H-NMR (CDCl₃) δ: 2.90 (1H, dd, J = 3.9, 16.9 Hz), 3.19 (1H, dd, J = 5.3, 16.9 Hz), 4.11 (2H, t, J = 5.2 Hz), 4.23-4.25 (4H, m), 4.63 (1H, m), 4.83 (2H, s), 6.54 (1H, s,), 6.83 (1H, d, J = 8.6 Hz), 7.05-7.11 (2H, m), 7.68-7.69 (2H, m), 14.4 (1H, s). | ESI-MS m/z: 400 [M + H]+ |

TABLE 48

| Example | Structural formula | NMR | MS |
|---|---|---|---|
| 345 | 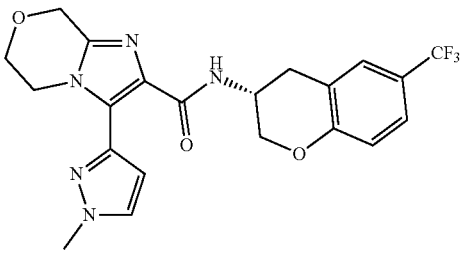 [SMILES: Cn1ccc(-c2c(C(=O)N[C@H]3COc4ccc(C(F)(F)F)cc4C3)nc3n2CCOC3)n1] | 1H-NMR (CDCl₃) δ: 2.92 (1H, d, J = 5.2, 16.6 Hz), 3.18 (1H, dd, J = 5.3, 16.5 Hz), 3.92 (3H, s), 4.02 (2H, t, J = 5.0 Hz), 4.18-4.29 (4H, m), 4.61 (1H, m), 4.82 (2H, s), 6.93 (1H, d, J = 8.6 Hz), 7.08 (1H, s), 7.31 (1H, s), 7.37 (1H, d, J = 8.8 Hz), 7.41 (1H, s), 7.48 (1H, d, J = 8.0 Hz). | ESI-MS m/z: 448 [M + H]+ |
| 346 | 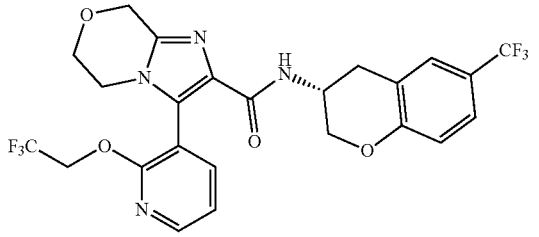 [SMILES: O=C(N[C@H]1COc2ccc(C(F)(F)F)cc2C1)c1nc2n(c1-c1cccnc1OCC(F)(F)F)CCOC2] | 1H-NMR (CDCl₃) δ: 2.89 (1H, m), 3.15 (1H, dt, J = 5.3, 17.4 Hz), 3.62 (1H, m), 3.97-4.05 (3H, m), 4.11-4.23 (2H, m), 4.40 (1H, m), 4.53 (1H, m), 4.79-4.89 (2H, m), 5.22 (1H, m), 6.94 (1H, d, J = 8.6 Hz), 7.14 (1H, dd, J = 5.0, 7.4 Hz), 7.29-7.39 (3H, m), (3H, m), 7.87 (1H, m), 8.25 (1H, dd, J = 1.7, 4.9 Hz). | ESI-MS m/z: 543 [M + H]+ |
| 347 | 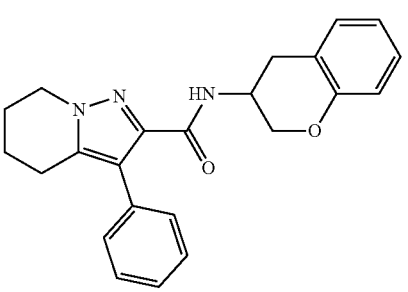 [SMILES: O=C(NC1COc2ccccc2C1)c1nn2c(c1-c1ccccc1)CCCC2] | 1H-NMR (CDCl₃) δ: 1.79-1.85 (2H, m), 2.03-2.08 (2H, m), 2.70 (1H, t, J = 6.3 Hz), 2.81 (1H, m), 3.12 (1H, dd, J = 5.3, 16.8 Hz), 4.11-4.21 (4H, m), 4.56 (1H, m), 6.82-6.92 (2H, m), 6.95 (1H, d, J = 7.5 Hz), 7.02 (1H, d, J = 7.6 Hz), 7.12 (1H, t, J = 7.4 Hz), 7.34 (4H, d, 3.9 Hz), 7.46 (1H, m). | ESI-MS m/z: 374 [M + H]+ |
| 348 | 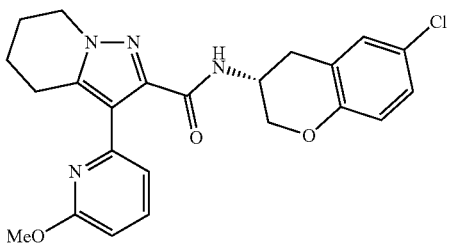 [SMILES: COc1cccc(-c2c(C(=O)N[C@H]3COc4ccc(Cl)cc4C3)nn3c2CCCC3)n1] | 1H-NMR (CDCl₃) δ: 1.84-1.87 (2H, m), 1.99-2.09 (2H, m), 2.83 (1H, m), 2.99 (2H, t, J = 6.4 Hz), 3.13 (1H, m), 3.90 (3H, s), 4.06-4.19 (4H, m), 4.58 (1H, m), 6.60 (1H, d, J = 8.4 Hz), 6.79 (1H, m), 7.01-7.07 (2H, m), 7.30 (1H, d, J = 7.8 Hz), 7.38 (1H, d, J = 7.4 Hz), 7.57 (1H, t, J = 7.8 Hz). | ESI-MS m/z: 439 [M + H]+ |

TABLE 48-continued

| Example | Structural formula | NMR | MS |
|---|---|---|---|
| 349 | | 1H-NMR (CDCl₃) δ: 2.40-2.44 (2H, m), 2.88 (1H, dd, J = 3.7, 16.7 Hz), 3.20 (1H, t, J = 5.3, 16.9 Hz), 4.17-4.24 (4H, m), 4.64 (1H, m), 5.26 (1H, m), 6.09 (1H, s), 6.87-6.92 (2H, m), 7.06 (2H, t, J = 6.7 Hz), 7.14 (1H, t, J = 7.7 Hz), 7.37-7.43 (5H, m). | ESI-MS m/z: 376 [M + H]+ |
| 350 | | 1H-NMR (CDCl₃) δ: 2.05-2.46 (4H, m), 3.44-4.29 (7H, m), 5.28 (1H, m), 6.09 (1H, s), 7.31-7.53 (9H, m). | ESI-MS m/z: 442 [M + H]+ |
| 351 | | 1H-NMR (CDCl₃) δ: 2.39-2.46 (2H, m), 2.79 (1H, dd, J = 3.9, 17.3 Hz), 3.00 (1H, dd, J = 5.9, 17.7 Hz), 3.80-3.82 (3H, m), 4.10-4.22 (4H, m), 4.62 (1H, m), 5.26 (1H, m), 6.09 (1H, s), 6.45-6.55 (2H, m), 7.00-7.12 (2H, m), 7.36-7.44 (5H, m). | ESI-MS m/z: 406 [M + H]+ |
| 352 | | 1H-NMR (CDCl₃) δ: 2.40-2.46 (2H, m), 2.87 (1H, dd, J = 3.7, 16.8 Hz), 3.17 (1H, dd, J = 5.7, 17.1 Hz), 4.15-4.26 (4H, m), (4H, s), 4.51 (1H, m), 5.27 (1H, m), 6.09 (1H, s), 6.77 (1H, m), 6.82-6.84 (2H, m), 7.04 (1H, d, J = 8.1 Hz), 7.35-7.44 (5H, m). | ESI-MS m/z: 394 [M + H]+ |
| 353 | | 1H-NMR (CDCl₃) δ: 2.41-2.46 (2H, m), 2.87 (1H, m), 3.11 (1H, dd, J = 6.3, 17.8 Hz), 4.10-4.27 (4H, m), 4.68 (1H, m), 5.27 (1H, m), 6.11 (1H, s), 6.86 (1H, d, J = 8.2 Hz), 7.07 (2H, t, J = 8.0 Hz), 7.19 (1H, d, J = 7.8 Hz), 7.36-7.44 (5H, m). | ESI-MS m/z: 454, 456 [M + H]+ |

TABLE 49

| Example | Structural formula | NMR | MS |
| --- | --- | --- | --- |
| 354 | | 1H-NMR (CDCl₃) δ: 2.41-2.45 (2H, m), 2.92 (1H, dd, J = 3.8, 17.0 Hz), 3.17 (1H, dd, J = 5.4, 17.1 Hz), 4.11-4.31 (4H, m), 4.65 (1H, m), 5.27 (1H, m), 6.09 (1H, s), 6.59 (1H, m), 6.73 (1H, m), 7.07 (1H, d, J = 7.9 Hz), 7.36-7.52 (5H, m). | ESI-MS m/z: 412 [M + H]+ |
| 355 | | 1H-NMR (CDCl₃) δ: 2.40-2.46 (2H, m), 2.86 (1H, dd, J = 4.1, 16.8 Hz), 3.16 (1H, dd, J = 4.9, 16.5 Hz), 4.18-4.23 (4H, m), 4.62 (1H, m), 5.27 (1H, m), 6.09 (1H, s), 6.81 (1H, d, J = 8.6 Hz), 7.00-7.10 (3H, m), 7.36-7.44 (5H, m). | ESI-MS m/z: 410 [M + H]+ |
| 356 | | 1H-NMR (CDCl₃) δ: 2.41-2.46 (2H, m), 2.88 (1H, dd, J = 4.7, 17.1 Hz), 3.10 (1H, dd, J = 5.8, 17.2 Hz), 4.18-4.23 (4H, m), 4.65 (1H, m), 5.27 (1H, m), 6.10 (1H, s), 6.63-6.70 (2H, m), 7.01 (1H, m), 7.09 (1H, m), 7.36-7.44 (5H, m). | ESI-MS m/z: 394 [M + H]+ |
| 357 | | 1H-NMR (CDCl₃) δ: 2.34-2.50 (2H, m), 5.99 (1H, dd, J = 4.2, 16.7 Hz), 3.27 (1H, dd, J = 5.1, 16.4 Hz), 4.11-4.31 (4H, m), 4.69 (1H, m), 5.56 (1H, m), 6.13 (1H, s), 7.02-7.13 (3H, m), 7.18-7.23 (1H, m), 7.29 (1H, s), 7.36 (1H, m), 7.47 (1H, qd, J = 1.6, 6.0 Hz), 8.90 (1H, s), 9.16 (1H, s). | ESI-MS m/z: 472 [M + H]+ |
| 358 | | 1H-NMR (CDCl₃) δ: 2.40-2.47 (2H, m), 2.86 (1H, dd, J = 3.7, 16.8 Hz), 3.16 (1H, dd, J = 5.2, 16.5 Hz), 4.20-4.30 (4H, m), 4.59-4.64 (1H, m), 5.29-5.33 (1H, m), 6.11 (1H, s), 6.82 (1H, d, J = 8.7 Hz), 7.01-7.10 (3H, m), 7.37 (1H, dd, J = 4.8, 7.9 Hz), 7.76 (1H, d, J = 8.7 Hz), 8.64-8.66 (2H, m). | ESI-MS m/z: 411 [M + H]+ |
| 359 | | 1H-NMR (CDCl₃) δ: 2.34-2.48 (2H, m), 2.92 (1H, m), 3.18 (1H, m), 4.14-4.33 (4H, m), 4.65 (1H, m), 5.56 (1H, m), 6.12 (1H, s), 6.93-6.96 (2H, m), 7.10 (1H, t, J = 9.4 Hz), 7.21 (1H, t, J = 7.4 Hz), 7.34-7.48 (4H, m). | ESI-MS m/z: 419 [M + H]+ |

TABLE 49-continued

| Example | Structural formula | NMR | MS |
| --- | --- | --- | --- |
| 360 | | 1H-NMR (CDCl₃) δ: 2.29-2.50 (2H, m), 2.88 (1H, m), 3.18 (1H, m), 4.14-4.32 (4H, m), 4.65 (1H, m), 5.56 (1H, m), 6.12 (1H, s), 6.93-6.96 (2H, m), 7.11 (1H, m), 7.21 (1H, m), 7.33-7.49 (4H, m). | ESI-MS m/z: 419 [M + H]+ |
| 361 | | 1H-NMR (CDCl₃) δ: 2.34-2.48 (2H, m), 2.88 (1H, dd, J = 4.2, 16.7 Hz), 3.19 (1H, dd, J = 5.4, 16.9 Hz), 3.38 (3H, s), 4.12-4.27 (4H, m), 4.35 (2H, s), 4.64 (1H, m), 5.55 (1H, d, J = 9.5 Hz), 6.10 (1H, s), 6.86 (1H, d, J = 8.3 Hz), 7.03-7.12 (4H, m), 7.20 (1H, t, J = 7.7 Hz), 7.35 (1H, q, J = 7.0 Hz), 7.47 (1H, t, J = 7.6 Hz). | ESI-MS m/z: 438 [M + H]+ |
| 362 | | 1H-NMR (CDCl₃) δ: 2.38 (1H, m), 2.52 (1H, m), 2.86 (1H, m), 3.16 (1H, dd, J = 5.3, 16.9 Hz), 4.17-4.31 (4H, m), 4.62 (1H, m), 5.34 (1H, dt, J = 2.8, 10.1 Hz), 6.16 (1H, s), 6.81 (1H, d, J = 8.7 Hz), 6.97-7.10 (3H, m), 7.55 (1H, d, J = 5.0 Hz), 7.73 (1H, s), 8.80 (1H, d, J = 5.0 Hz). | ESI-MS m/z: 479 [M + H]+ |

TABLE 50

| Example | Structural formula | NMR | MS |
| --- | --- | --- | --- |
| 363 | | 1H-NMR (CDCl₃) δ: 2.31-2.48 (2H, m), 3.21 (1H, m), 3.41 (1H, m), 4.10-4.37 (4H, m), 4.84 (1H, m), 5.54 (1H, m), 6.12 (1H, s), 7.09 (1H, m), 7.17-7.22 (2H, m), 7.31-7.48 (4H, m), 7.92 (1H, d, J = 9.2 Hz), 8.12 (1H, d, J = 8.5 Hz), 8.80 (1H, d, J = 4.2 Hz). | ESI-MS m/z: 445 [M + H]+ |
| 364 | | 1H-NMR (CDCl₃) δ: 2.38-2.44 (2H, m), 2.92 (1H, dd, J = 4.8, 16.6 Hz), 3.18 (1H, dd, J = 5.1, 16.7 Hz), 4.17-4.32 (4H, m), 4.65 (1H, m), 5.25 (1H, m), 6.09 (1H, s), 6.93-6.95 (2H, m), 7.11 (2H, t, J = 8.6 Hz), 7.36-7.44 (4H, m). | ESI-MS m/z: 419 [M + H]+ |

| Example | Structural formula | NMR | MS |
| --- | --- | --- | --- |
| 365 | | 1H-NMR (CDCl₃) δ: 1.18 (3H, t, J = 7.0 Hz), 1.41 (3H, d, J = 6.4 Hz), 2.35-2.49 (2H, m), 2.88 (1H, dd, J = 4.3, 16.9 Hz), 3.19 (1H, dd, J = 5.5, 16.9 Hz), 3.36 (2H, q, J = 7.0 Hz), 4.15-4.27 (4H, m, J = 4.93 Hz), 4.32 (1H, q, J = 6.5 Hz), 4.64 (1H, m), 5.56 (1H, m), 6.12 (1H, s), 6.85 (1H, d, J = 8.4 Hz), 7.00 (1H, s), 7.00-7.13 (3H, m), 7.21 (1H, m), 7.36 (1H, q, J = 7.1 Hz), 7.47 (1H, t, J = 7.0 Hz). | ESI-MS m/z: 466 [M + H]+ |
| 366 | | 1H-NMR (CDCl₃) δ: 2.29 (1H, dt, J = 2.2, 14.5 Hz), 2.86-2.98 (2H, m), 3.18 (1H, dd, J = 4.9, 16.8 Hz), 4.19-4.32 (4H, m), 4.65 (1H, m), 5.60 (1H, d, J = 11.9 Hz), 6.05 (1H, s), 6.93-6.98 (4H, m), 7.33-7.44 (3H, m). | ESI-MS m/z: 437 [M + H]+ |
| 367 | | 1H-NMR (CDCl₃) δ: 2.24 (1H, m), 2.54 (1H, m), 2.86 (1H, dd, J = 4.2, 16.8 Hz), 3.16 (1H, dd, J = 5.2, 16.8 Hz), 3.99 (3H, s), 4.08-4.15 (2H, m), 4.18-4.26 (2H, m), 4.62 (1H, m), 5.47 (1H, d, J = 9.5 Hz), 6.11 (1H, s), 6.81 (1H, d, J = 8.6 Hz), 6.95 (1H, m), 7.01-7.10 (3H, m), 7.70 (1H, d, J = 7.4 Hz), 8.16 (1H, d, J = 5.0 Hz). | ESI-MS m/z: 441 [M + H]+ |
| 368 | | 1H-NMR (CDCl₃) δ: 2.39-2.49 (6H, m), 2.87 (1H, m), 3.18 (1H, m), 3.40 (2H, s), 3.70-3.72 (4H, m), 410-4.28 (4H, m), 4.63 (1H, m), 5.56 (1H, m), 6.12 (1H, s), 6.83 (1H, d, J = 8.3 Hz), 7.01-7.13 (4H, m), 7.21 (1H, m), 7.36 (1H, m), 7.47 (1H, m). | ESI-MS m/z: 493 [M + H]+ |
| 369 | | 1H-NMR (CDCl₃) δ: 2.35-2.51 (9H, m), 2.86-2.92 (2H, m), 3.19 (1H, m), 3.49-3.64 (3H, m), 4.11-4.28 (5H, m), 4.63 (1H, m), 5.56 (1H, m), 6.11 (1H, s), 6.87 (1H, d, J = 8.3 Hz), 7.03 (1H, d, J = 7.9 Hz), 7.08-7.23 (4H, m), 7.36 (1H, m), 7.47 (1H, t, J = 7.4 Hz). | ESI-MS m/z: 495 [M + H]+ |

TABLE 50-continued

| Example | Structural formula | NMR | MS |
|---|---|---|---|
| 370 | | 1H-NMR (CDCl$_3$) δ: 2.34-2.47 (2H, m), 2.88 (1H, m), 2.96 (3H, s), 3.00 (3H, s), 3.19 (1H, m), 4.10-4.26 (6H, m), 4.50 (2H, s), 4.62 (1H, m), 5.56 (1H, m), 6.11 (1H, s), 6.86 (1H, d, J = 8.2 Hz), 7.03-7.15 (4H, m), 7.21 (1H, t, J = 7.8 Hz), 7.36 (1H, m), 7.47 (1H, t, J = 7.6 Hz). | ESI-MS m/z: 509 [M + H]+ |
| 371 | | 1H-NMR (CDCl$_3$) δ: 2.35-2.45 (2H, m), 2.86 (1H, m), 3.16 (1H, dd, J = 4.8, 17.1 Hz), 3.95 (3H, s), 4.20-4.24 (4H, m), 4.62 (1H, m), 5.22 (1H, d, J = 9.8 Hz), 6.07 (1H, s), 6.81 (2H, m), 7.00-7.13 (3H, m), 7.63 (1H, d, J = 8.2 Hz), 8.19 (1H, s). | ESI-MS m/z: 441 [M + H]+ |

TABLE 51

| Example | Structural formula | NMR | MS |
|---|---|---|---|
| 372 | | 1H-NMR (CDCl$_3$) δ: 1.39 (1H, t, J = 6.5 Hz), 2.26 (1H, m), 2.55 (1H, m), 2.92 (1H, dd, J = 4.3, 16.2 Hz), 3.18 (1H, dd, J = 4.7, 16.1 Hz), 4.12 (1H, m), 4.19-4.33 (3H, m), 4.44 (2H, m), 4.65 (1H, m), 5.49 (1H, d, J = 9.2 Hz), 6.12 (1H, s), 6.91-6.95 (3H, m), 7.39 (1H, s), 7.43 (1H, d, J = 8.8 Hz), 7.68 (1H, d, J = 6.8 Hz), 8.14 (1H, d, J = 4.6 Hz). | ESI-MS m/z: 446 [M + H]+ |
| 373 | | 1H-NMR (CDCl$_3$) δ: 2.41-2.46 (2H, m), 2.91 (1H, dd, J = 4.5, 16.6 Hz), 3.18 (1H, dd, J = 5.3, 16.5 Hz), 4.15 (1H, m), 4.25-4.31 (3H, m), 4.57-4.66 (2H, m), 6.14 (1H, s), 6.90-6.95 (2H, m), 7.26-7.44 (1H, m). | ESI-MS m/z: 393 [M + H]+ |
| 374 | | 1H-NMR (CDCl$_3$) δ: 2.41-2.46 (2H, m), 2.91 (1H, dd, J = 4.5, 16.6 Hz), 3.18 (1H, dd, J = 5.3, 16.5 Hz), 4.15 (1H, m), 4.25-4.31 (3H, m), 4.57-4.66 (2H, m), 6.14 (1H, s), 6.90-6.95 (2H, m), 7.26-7.44 (1H, m). | |

TABLE 51-continued

| Example | Structural formula | NMR | MS |
|---|---|---|---|
| 375 | | 1H-NMR (CDCl₃) δ: 2.37-2.46 (2H, m), 2.96 (1H, dd, J = 3.9, 16.8 Hz), 3.26 (1H, dd, J = 5.2, 16.8 Hz), 4.15 (1H, m), 4.26-4.30 (3H, m), 4.57 (1H, m), 4.67 (1H, m), 6.14 (1H, s), 6.99 (1H, d, J = 8.4 Hz), 7.05 (1H, d, J = 8.0 Hz), 7.29-7.35 (3H, m), 7.81 (1H, td, J = 2.0, 7.9 Hz), 8.55 (1H, dd, J = 1.4, 4.8 Hz), 8.79 (1H, d, J = 1.8 Hz). | ESI-MS m/z: 445 [M + H]+ |
| 376 | | 1H-NMR (CDCl₃) δ: 2.37-2.46 (2H, m), 2.96 (1H, m), 3.26 (1H, m), 4.14 (1H, m), 4.24-4.31 (3H, m), 4.57 (1H, m), 4.68 (1H, m), 6.14 (1H, s), 6.99 (1H, d, J = 8.5 Hz), 7.03 (1H, d, J = 8.0 Hz), 7.37 (1H, s), 7.45 (3H, d, J = 6.2 Hz), 8.61 (2H, d, J = 6.1 Hz). | ESI-MS m/z: 445 [M + H]+ |
| 377 | | 1H-NMR (CDCl₃) δ: 2.41-2.45 (2H, m), 2.92 (1H, m), 3.24 (1H, m), 3.98 (3H, s), 4.11-4.29 (4H, m), 4.57-4.67 (2H, m), 6.14 (1H, s), 6.93-6.97 (2H, m), 7.08 (1H, d, J = 8.1 Hz), 7.36 (1H, m), 7.56 (1H, dd, J = 1.6, 7.3 Hz), 8.13 (1H, dd, J = 1.7, 4.9 Hz). | ESI-MS m/z: 475 [M + H]+ |
| 378 | | 1H-NMR (CDCl₃) δ: 2.38-2.46 (2H, m), 2.94 (1H, m), 3.25 (1H, dd, J = 5.1, 16.6 Hz), 3.97 (3H, s), 4.15 (1H, m), 4.24-4.30 (3H, m), 4.57 (1H, m), 4.66 (1H, m), 6.14 (1H, s), 6.79 (1H, d, J = 8.6 Hz), 6.96 (1H, d, J = 8.4 Hz), 7.06 (1H, d, J = 7.9 Hz), 7.21 (1H, s), 7.30 (1H, m), 7.72 (1H, dd, J = 2.6, 8.6 Hz), 8.32 (1H, d, J = 2.2 Hz). | ESI-MS m/z: 475 [M + H]+ |
| 379 | | 1H-NMR (CDCl₃) δ: 2.79-2.87 (3H, m), 3.15 (1H, dd, J = 5.6, 16.8 Hz), 4.14 (2H, t, J = 6.3 Hz), 4.19 (2H, d, J = 2.8 Hz), 4.46 (1H, s), 4.61 (1H, m), 4.82 (1H, d, J = 1.7 Hz), 6.10 (1H, s), 6.81 (1H, d, J = 8.6 Hz), 6.99 (1H, d, J = 6.3 Hz), 7.04 (1H, s), 7.08 (1H, dd, J = 2.4, 8.7 Hz). | ESI-MS m/z: 346 [M + H]+ |

TABLE 51-continued

| Example | Structural formula | NMR | MS |
|---|---|---|---|
| 380 | | 1H-NMR (CDCl₃) δ: 2.37-2.46 (4H, m), 2.94 (1H, m), 3.24 (1H, m), 4.11-4.29 (8H, m), 4.55-4.65 (2H, m), 6.14 (1H, s), 6.95 (1H, d, J = 8.6 Hz), 7.05 (1H, d, J = 7.9 Hz), 7.14 (1H, s), 7.23 (1H, m), 8.47 (2H, s). | ESI-MS m/z: 501 [M + H]+ |

TABLE 52

| Example | Structural formula | NMR | MS |
|---|---|---|---|
| 381 | | 1H-NMR (CDCl₃) δ: 2.24-2.31 (2H, m), 2.85 (1H, m), 3.15 (1H, dd, J = 5.3, 16.9 Hz), 4.08-4.26 (4H, m), 4.42 (1H, m), 4.57-4.63 (2H, m), 4.70 (1H, m), 6.05 (1H, s), 6.81 (1H, d, J = 8.7 Hz), 7.00 (1H, d, J = 7.4 Hz), 7.04 (1H, s), 7.08 (1H, dd, J = 2.3, 8.6 Hz). | ESI-MS m/z: 366 [M + H]+ |
| 382 | | 1H-NMR (CDCl₃) δ: 2.41 (2H, m), 2.95 (1H, m), 3.26 (1H, dd, J = 5.5, 17.2 Hz), 4.12 (1H, m), 4.27 (3H, m), 4.56 (1H, m), 4.66 (1H, m), 6.13 (1H, s), 6.96-7.03 (2H, m), 7.18 (1H, m), 7.64-7.76 (4H, m), 8.64 (1H, d, J = 4.4 Hz). | ESI-MS m/z: 445 [M + H]+ |
| 383 | | 1H-NMR (CDCl₃) δ: 1.41 (6H, d, J = 2.9 Hz), 2.07 (2H, t, J = 7.3 Hz), 2.96 (1H, dd, J = 4.4, 16.7 Hz), 3.26 (1H, dd, J = 5.2, 16.8 Hz), 4.08 (2H, t, J = 6.5 Hz), 4.25-4.26 (2H, m), 4.66 (1H, m), 5.97 (1H, s), 6.97 (1H, d, J = 8.2 Hz), 7.02 (1H, d, J = 8.3 Hz), 7.18 (1H, t, J = 6.1 Hz), 7.64-7.76 (4H, m), 8.64 (1H, d, J = 4.8 Hz). | |
| 384 | | 1H-NMR (CDCl₃) δ: 2.04 (1H, m), 2.16 (1H, m), 2.59 (1H, dd, J = 6.7, 16.1 Hz), 3.05 (1H, d, J = 16.2 Hz), 3.41 (1H, m), 3.89 (1H, m), 4.02 (1H, m), 4.13 (1H, m), 4.21-4.30 (2H, m), 4.35 (1H, m), 4.62 (1H, m), 6.00 (1H, s), 6.86-6.93 (2H, m), 7.02 (1H, s), 7.30 (2H, s), 7.37-7.67 (3H, m). | ESI-MS m/z: 433 [M + H]+ |

TABLE 52-continued

| Example | Structural formula | NMR | MS |
|---|---|---|---|
| 385 | | 1H-NMR (CDCl₃) δ: 1.53 (3H, d, J = 6.6 Hz), 2.84 (1H, m), 3.15 (1H, dd, J = 5.0, 16.7 Hz), 4.11-4.23 (2H, m), 4.30-4.49 (3H, m), 4.60 (1H, m), 6.09 (1H, s), 6.82 (1H, d, J = 8.7 Hz), 6.98 (1H, m), 7.04 (1H, s), 7.09 (1H, m). | ESI-MS m/z: 384 [M + H]+ |
| 386 | | 1H-NMR (CDCl₃) δ: 2.41 (1H, m), 2.55 (1H, m), 2.98 (1H, dd, J = 16.7, 4.4 Hz), 3.17 (1H, br d, J = 16.7 Hz), 4.17-4.34 (4H, m), 4.64 (1H, m), 5.22 (1H, m), 6.12 (1H, s), 6.94 (1H, d, J = 8.5 Hz), 6.95 (1H, m), 7.39 (1H, m), 7.43 (1H, dd, J = 8.5, 2.2 Hz). | ESI-MS m/z: 417 [M + H]+ |
| 387 | | 1H-NMR (CDCl₃) δ: 0.35 (1H, m), 0.55 (1H, m), 0.62-0.76 (2H, m), 1.12 (1H, m), 2.18-2.32 (2H, m), 2.84 (1H, m), 3.14 (1H, m), 3.50 (1H, m), 4.05 (1H, m), 4.18-4.19 (3H, m), 4.60 (1H, m), 6.00 (1H, s), 6.80 (1H, d, J = 8.6 Hz), 6.98 (1H, d, J = 7.6 Hz), 7.04 (1H, s), 7.08 (1H, m). | ESI-MS m/z: 374 [M + H]+ |
| 388 | | 1H-NMR (CDCl₃) δ: 1.86-2.14 (8H, m), 2.58 (1H, m), 2.90 (1H, m), 3.17 (1H, m), 4.00-4.15 (3H, m), 4.22-4.31 (2H, m), 4.63 (1H, m), 6.00 (1H, s), 6.92-6.94 (2H, m), 7.38 (1H, s), 7.42 (1H, d, J = 8.5 Hz). | |
| 389 | | 1H-NMR (CDCl₃) δ: 0.98 (3H, t, J = 7.2 Hz), 1.41-168. (3H, m), 1.78 (1H, m), 2.05 (1H, m), 2.17 (1H, m), 2.84 (1H, dd, J = 16.8, 4.1 Hz), 3.14 (1H, dd, J = 16.8, 5.3 Hz), 4.00-4.26 (5H, m),, 4.60 (1H, m), 5.98 (1H, s), 6.80 (1H, d, J = 8.6 Hz), 6.99 (1H, m), 7.03 (1H, m), 7.07 (1H, dd, J = 8.6, 2.2 Hz). | ESI-MS m/z: 376 [M + H]+ |

TABLE 53

| Example | Structural formula | NMR | MS |
|---|---|---|---|
| 390 | | 1H-NMR (CDCl₃) δ: 2.42 (1H, m), 2.53 (1H, m), 2.91 (1H, dd, J = 16.7, 4.7 Hz), 3.14 (1H, dd, J = 16.7, 5.2 Hz), 4.16-4.32 (3H, m), 4.37 (1H, m), 4.64 (1H, m), 5.34 (1H, m), 6.10 (1H, s), 6.93 (1H, d, J = 8.5 Hz), 6.94 (1H, m), 6.95 (1H, s), 7.27-7.45 (7H, m). | ESI-MS m/z: 425 [M + H]+ |
| 391 | | 1H-NMR (CDCl₃) δ: 0.22 (2H, m) 0.54 (2H, q, J = 6.1 Hz), 1.10 (1H, m), 2.42-2.43 (2H, m), 2.86 (1H, d, J = 17.1 Hz), 3.18 (1H, dd, J = 5.2, 16.8 Hz), 3.31 (2H, d, J = 7.0 Hz), 4.13-4.28 (4H, m), 4.42 (2H, s), 4.59 (2H, m), 6.13 (1H, s), 6.85 (1H, d, J = 8.2 Hz), 7.00-7.06 (2H, m), 7.12 (1H, d, J = 7.8 Hz). | ESI-MS m/z: 452 [M + H]+ |
| 392 | | 1H-NMR (CDCl₃) δ: 2.41-2.44 (2H, m), 2.88 (1H, d, J = 13.5 Hz), 3.20 (1H, dd, J = 5.1, 17.2 Hz), 4.10-4.30 (4H, m), 4.56-4.63 (2H, m), 5.27 (2H, s), 6.13 (16, s), 6.79 (1H, d, J = 8.2 Hz), 6.87-6.90 (2H, m), 7.05 (1H, d, J = 7.7 Hz), 7.18 (1H, s), 7.23 (1H, m), 7.58 (1H, t, J = 6.8 Hz), 8.18 (1H, d, J = 4.4 Hz). | ESI-MS m/z: 475 [M + H]+ |
| 393 | | 1H-NMR (CDCl₃) δ: 1.02 (3H, d, J = 6.8 Hz), 1.05 (3H, d, J = 5.7 Hz), 1.99 (1H, m), 2.01-2.23 (2H, m), 2.90 (1H, dd, J = 16.6, 4.7 Hz), 3.17 (1H, dt, J = 16.7, 5.1 Hz), 3.92 (1H, m), 4.05 (1H, m), 4.11-4.34 (3H, m), 4.63 (1H, m), 5.99 (1H, s), 6.93 (1H, d, J = 8.5 Hz), 6.94 (1H, m), 7.38 (1H, s), 7.42 (1H, d, J = 8.5 Hz). | ESI-MS m/z: 367 [M + H]+ |
| 394 | | 1H-NMR (CDCl₃) δ: 1.41 (3H, m), 1.42 (3H, m), 2.30 (1H, m), 2.46 (1H, m), 2.91 (1H, dd, J = 16.6, 4.6 Hz), 3.17 (1H, dt, J = 16.6, 4.6 Hz), 3.26 (3H, m), 4.17 (1H, m), 4.21-4.35 (3H, m), 4.64 (1H, m), 5.17 (1H, m), 6.07 (1H, s), 6.93 (1H, m), 6.94 (1H, d, J = 8.6 Hz), 7.38 (1H, m), 7.42 (1H, d, J = 8.6 Hz). | ESI-MS m/z: 421 [M + H]+ |

TABLE 53-continued

| Example | Structural formula | NMR | MS |
|---|---|---|---|
| 395 | (structure) | 1H-NMR (CDCl₃) δ: 1.17-2.26 (9H, m), 2.84 (1H, br d, J = 16.8 Hz), 3.16 (1H, dd, J = 16.8, 5.2 Hz), 3.42 (2H, m), 3.97 (2H, m), 4.03-4.22 (4H, m), 4.30 (1H, m), 4.60 (1H, m), 5.98 (1H, s), 6.80 (1H, d, J = 8.6 Hz), 6.96 (1H, m), 7.04 (1H, s), 7.08 (1H, dd, J = 8.6, 2.2 Hz). | ESI-MS m/z: 432 [M + H]+ |
| 396 | (structure) | 1H-NMR (CDCl₃) δ: 2.36-2.47 (2H, m), 2.86 (1H, m), 3.18 (1H, m), 4.10-4.29 (4H, m), 4.54-4.64 (2H, m), 5.13 (1H, d, J = 11.0 Hz), 5.60 (1H, d, J = 17.6 Hz), 6.13 (1H, s), 6.62 (1H, dd, J = 10.9, 17.5 Hz), 6.84 (1H, d, J = 8.5 Hz), 7.03 (1H, d, J = 7.9 Hz), 7.10 (1H, s), 7.21 (1H, d, J = 8.4 Hz). | ESI-MS m/z: 394 [M + H]+ |
| 397 | (structure) | 1H-NMR (CDCl₃) δ: 2.33-2.45 (2H, m), 2.81-2.87 (2H, m), 3.15 (1H, dd, J = 5.4, 16.7 Hz), 3.47 (1H, t, J = 5.5 Hz), 3.67 (1H, m), 3.76-3.84 (3H, m), 4.10-4.20 (3H, m), 4.26 (1H, m), 4.54-4.62 (2H, m), 6.13 (1H, s), 6.81 (1H, d, J = 8.3 Hz), 6.91 (1H, s), 7.00 (2H, dd, J = 8.2, 17.9 Hz). | ESI-MS m/z: 494 [M + H]+ |
| 398 | (structure) | 1H-NMR (CDCl₃) δ: 1.52 (6H, s), 2.38-2.46 (2H, m), 2.83 (1H, m), 3.14 (1H, m), 3.41 (3H, s), 4.10-4.29 (4H, m), 4.55-4.63 (2H, m), 6.12 (1H, s), 6.81 (1H, d, J = 8.4 Hz), 6.96 (1H, d, J = 7.7 Hz), 7.17 (1H, s), 7.21 (1H, d, J = 8.5 Hz). | |

TABLE 54

| Example | Structural formula | NMS | MS |
|---|---|---|---|
| 399 | (structure) | 1H-NMR (CDCl₃) δ: 1.50 (1H, m), 1.71 (1H, q, J = 10.1 Hz), 1.97 (2H, m), 2.22 (2H, m), 2.40 (2H, m), 2.85 (1H, m), 3.18 (1H, m), 4.01 (1H, m), 4.11-4.28 (6H, m), 4.56-4.62 (2H, m), 6.12 (1H, s), 6.84 (1H, d, J = 8.3 Hz), 7.02 (1H, m), 7.05 (1H, s), 7.10 (1H, d, J = 7.7 Hz). | ESI-MS m/z: 452 [M + H]+ |

TABLE 54-continued

| Example | Structural formula | NMR | MS |
|---|---|---|---|
| 400 | | 1H-NMR (CDCl₃) δ: 1.20 (6H, s), 1.71-1.75 (2H, m), 2.36-2.46 (2H, m), 2.52-2.56 (2H, m), 2.83 (1H, m), 3.16 (1H, m), 3.22 (3H, s), 4.10-4.17 (3H, m), 4.28 (1H, m), 4.57-4.61 (2H, m), 6.13 (1H, s), 6.80 (1H, d, J = 8.3 Hz), 6.88 (1H, s), 6.96 (1H, d, J = 9.0 Hz), 7.04 (1H, d, J = 7.9 Hz). | ESI-MS m/z: 468 [M + H]+ |
| 401 | | 1H-NMR (CDCl₃) δ: 2.37-2.43 (2H, m), 2.58-2.92 (4H, m), 3.13-3.24 (2H, m), 3.54 (4H, t, J = 12.5 Hz), 4.11-4.28 (4H, m), 4.57-4.60 (2H, m), 6.13 (1H, s), 6.81 (1H, m), 6.87 (1H, m), 6.95 (1H, d, J = 7.4 Hz), 7.03 (1H, d, J = 8.2 Hz). | ESI-MS m/z: 487 [M + H]+ |
| 402 | | 1H-NMR (CDCl₃) δ: 0.68 (2H, m), 0.80 (2H, m), 1.25 (1H, m), 2.24 (1H, m), 2.39 (1H, m), 2.92 (1H, br d, J = 16.6 Hz), 3.20 (1H, dd, J = 16.6, 5.3 Hz), 4.12 (1H, m), 4.19-4.26 (3H, m), 4.65 (1H, m), 5.04 (1H, m), 6.05 (1H, s), 6.95 (1H, d, J = 6.6 Hz), 6.97 (1H, m), 7.33 (1H, s), 7.38 (1H, d, J = 8.6 Hz). | ESI-MS m/z: 432 [M + H]+ |
| 403 | | 1H-NMR (CDCl₃) δ: 1.42-1.44 (6H, d, J = 2.1 Hz), 2.08 (2H, t, J = 6.5 Hz), 2.82-2.92 (3H, m), 3.16 (1H, dd, J = 5.6, 16.6 Hz), 4.08-4.12 (4H, m), 4.17-4.22 (2H, m), 4.61 (1H, m), 5.97 (1H, s), 6.82 (1H, d, J = 8.3 Hz), 6.90 (1H, s), 6.96-7.02 (1H, m). | ESI-MS m/z: 440 [M + H]+ |
| 404 | | 1H-NMR (CDCl₃) δ: 2.09-2.44 (4H, m), 2.84 (1H, dd, J = 16.8, 4.2 Hz), 3.15 (1H, dd, J = 16.8, 4.6 Hz), 4.06-4.24 (3H, m), 4.44 (1H, m), 4.61 (1H, m), 4.63 (1H, m), 6.01 (1H, s), 6.12 (1H, tdd, J = 56., 6.5, 2.9 Hz), 6.81 (1H, d, J = 8.7 Hz), 6.99 (1H, m), 7.04 (1H, m), 7.08 (1H, dd, J = 8.7, 2.6 Hz) | ESI-MS m/z: 398 [M + H]+ |

TABLE 54-continued

| Example | Structural formula | NMR | MS |
|---|---|---|---|
| 405 | | 1H-NMR (CDCl₃) δ: 0.58-0.62 (2H, m), 0.87-0.91 (2H, m), 1.81 (1H, m), 2.24-2.38 (2H, m), 2.82 (1H, m), 3.15 (1H, m), 4.07-4.20 (3H, m), 4.27 (1H, m), 4.37 (1H, m), 4.60 (1H, m), 5.89 (1H, dt, J = 3.4, 82.0 Hz), 6.08 (1H, s), 6.77-6.79 (2H, m), 6.85 (1H, dd, J = 2.1, 8.5 Hz), 7.04 (1H, d, J = 8.2 Hz). | ESI-MS m/z: 390 [M + H]+ |
| 406 | | 1H-NMR (CDCl₃) δ: 0.68 (2H, m), 0.79 (2H, m), 1.23 (1H, m), 2.24 (1H, m), 2.38 (1H, m), 2.85 (1H, dd, J = 16.8, 4.2 Hz), 3.15 (1H, dd, J = 16.8, 5.4 Hz), 4.13 (1H, m), 4.19 (1H, m), 4.26 (1H, m), 4.61 (1H, m), 5.04 (1H, m), 5.41 (1H, m), 6.04 (1H, s), 6.81 (1H, d, J = 8.7 Hz), 7.00 (1H, m), 7.04 (1H, m), 7.08 (1H, dd, J = 8.7, 2.5 Hz). | ESI-MS m/z: 398 [M + H]+ |
| 407 | | 1H-NMR (CDCl₃) δ: 0.68 (2H, m), 0.79 (2H, m), 1.23 (1H, m), 2.24 (1H, m), 2.38 (1H, m), 2.85 (1H, dd, J = 16.8, 4.2 Hz), 3.15 (1H, dd, J = 16.8, 5.4 Hz), 4.13 (1H, m), 4.19 (1H, m), 4.26 (1H, m), 4.61 (1H, m), 5.04 (1H, m), 5.41 (1H, m), 6.04 (1H, s), 6.81 (1H, d, J = 8.7 Hz), 7.00 (1H, m), 7.04 (1H, m), 7.08 (1H, dd, J = 8.7, 2.5 Hz). | ESI-MS m/z: 398 [M + H]+ |

TABLE 55

| Example | Structural formula | NMR | MS |
|---|---|---|---|
| 408 | | 1H-NMR (CDCl₃) δ: 0.68 (2H, m), 0.79 (2H, m, 1.23 (1H, m), 2.24 (1H, m), 2.38 (1H, m), 2.85 (1H, dd, J = 16.8, 4.2 Hz), 3.15 (1H, dd, J = 16.8, 5.4 Hz), 4.13 (1H, m), 4.19 (1H, m), 4.26 (1H, m), 4.61 (1H, m), 5.04 (1H, m), 5.41 (1H, m), 6.04 (1H, s), 6.81 (1H, d, J = 8.7 Hz), 7.00 (1H, m), 7.04 (1H, m), 7.08 (1H, dd, J = 8.7, 2.5 Hz). | ESI-MS m/z: 398 [M + H]+ |

TABLE 55-continued

| Example | Structural formula | NMR | MS |
|---|---|---|---|
| 409 | | 1H-NMR (CDCl₃) δ: 1.25-1.31 (3H, m), 2.23-2.37 (2H, m), 2.84 (1H, m), 3.14 (1H, dd, J = 5.3, 16.8 Hz), 3.75 (1H, m, 3.95-4.13 (2H, m), 4.18-4.29 (4H, m), 4.60 (1H, m), 5.43 (1H, m), 6.05 (1H, d, J = 1.0 Hz), 6.81 (1H, d, J = 8.6 Hz), 6.99 (1H, d, J = 7.4 Hz), 7.04 (1H, s), 7.08 (1H, dd, J = 2.4, 8.7 Hz). | ESI-MS m/z: 410 [M + H]+ |
| 410 | | 1H-NMR (CDCl₃) δ: 1.68-1.77 (2H, m), 1.82-1.95 (2H, m), 2.01-2.06 (2H, m), 2.15-2.29 (2H, m), 2.58 (1H, m), 2.90 (1H, m), 3.17 (1H, m), 3.49 (2H, d, J = 6.7 Hz), 3.62 (1H, m), 3.72 (1H, m), 4.07 (1H, m), 4.16-4.35 (4H, m), 4.63 (1H, m), 6.02 (1H, s), 6.90-6.94 (2H, m), 7.38 (1H, s), 7.42 (1H, d, J = 8.5 Hz). | ESI-MS m/z: 423 [M + H]+ |
| 411 | | 1H-NMR (CDCl₃) δ: 2.27-2.36 (2H, m), 2.91 (1H, m), 3.17 (1H, m), 4.13 (1H, m), 4.22-4.31 (3H, m), 4.58-4.64 (4H, m), 6.05 (1H, s), 6.81 (1H, d, J = 8.3 Hz), 6.90-6.94 (3H, m), 7.39 (1H, s), 7.42 (1H, m), 7.61 (1H, m), 8.13 (1H, dd, J = 1.3, 4.9 Hz). | ESI-MS m/z: 432 [M + H]+ |
| 412 | | 1H-NMR (CDCl₃) δ: 2.24-2.26 (2H, m), 2.91 (1H, m), 3.17 (1H, m), 3.84-3.93 (2H, m), 4.00-4.13 (3H, m), 4.19-4.31 (3H, m), 4.37 (1H, m), 4.63 (1H, m), 6.03 (1H, s), 6.91-6.94 (2H, m), 7.39 (1H, s), 7.42 (1H, d, J = 8.6 Hz). | ESI-MS m/z: 487 [M + H]+ |
| 413 | | 1H-NMR (CDCl₃) δ: 1.24-1.38 (2H, m), 1.61-1.64 (2H, m), 1.86 (1H, m), 2.17-2.26 (2H, m), 2.84 (1H, dd, J = 3.9, 16.6 Hz), 3.14 (1H, dd, J = 5.5, 16.9 Hz), 3.35-3.41 (4H, m), 3.63 (1H, dd, J = 4.9, 10.3 Hz), 3.72 (1H, dd, J = 4.9, 10.5 Hz), 3.97 (2H, dd, J = 3.7, 11.2 Hz), 4.08 (1H, m), 4.18-4.21 (3H, m), 4.33 (1H, m), 4.60 (1H, m), 6.01 (1H, s), 6.81 (1H, d, J = 8.7 Hz), 6.99 (1H, d, J = 8.3 Hz), 7.04 (1H, s), 7.08 (1H, dd, J = 2.4, 8.6 Hz). | ESI-MS m/z: 462 [M + H]+ |

TABLE 55-continued

| Example | Structural formula | NMR | MS |
|---|---|---|---|
| 414 | | 1H-NMR (CDCl₃) δ: 2.17-2.23 (2H, m), 2.88 (1H, dd, J = 9.6, 15.7 Hz), 3.06 (1H, dd, J = 4.5, 15.6 Hz), 3.23 (1H, m), 3.38 (1H, m), 3.67 (1H, m), 3.74-3.78 (3H, m), 3.97 (1H, t, J = 9.8 Hz), 4.11 (1H, m), 4.20-4.26 (2H, m), 4.33-4.38 (3H, m), 4.45 (2H, t, J = 6.0 Hz), 4.55 (2H, t, J = 6.1 Hz), 4.64 (1H, m), 4.78-4.82 (4H, m), 5.70 (1H, s), 6.91 (1H, d, J = 8.5 Hz), 7.16 (1H, t, J = 5.9 Hz), 7.64-7.77 (4H, m), 8.64 (1H, d, J = 4.7 Hz). | ESI-MS m/z: 547 [M + H]+ |
| 415 | | 1H-NMR (CDCl₃) δ: 1.24 (3H, s), 1.25 (3H, s), 2.14 (1H, m), 2.31-2.34 (3H, m), 2.41-2.56 (3H, m), 2.68 (1H, dd, J = 5.5, 13.3 Hz), 2.84 (1H, dd, J = 4.1, 16.9 Hz), 3.14 (1H, dd, J = 4.3, 16.8 Hz), 3.74 (2H, t, J = 4.8 Hz), 4.08 (1H, m), 4.15-4.19 (3H, m), 4.31 (1H, m), 4.60 (1H, m), 6.00 (1H, s), 6.81 (1H, d, J = 8.7 Hz), 6.99 (1H, m), 7.04 (1H, s), 7.08 (1H, m). | ESI-MS m/z: 461 [M + H]+ |
| 416 | | 1H-NMR (CDCl₃) δ: 1.69-1.91 (4H, m), 1.96 (2H, m), 2.86 (1H, dd, J = 16.8, 4.2 Hz), 3.76 (1H, dd, J = 16.8, 5.6 Hz), 3.71-3.81 (3H, m), 3.82-3.97 (3H, m), 4.19 (2H, m), 4.62 (1H, m), 6.11 (1H, s), 6.81 (1H, d, J = 8.1 Hz), 6.99 (1H, m), 7.04 (1H, m), 7.09 (1H, br d, J = 8.1 Hz). | ESI-MS m/z: 404 [M + H]+ |

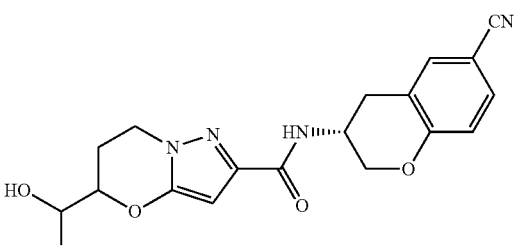

TABLE 56

| Example | Structural formula | NMS | MS |
|---|---|---|---|
| 417 | | 1H-NMR (CDCl₃) δ: 2.25 (1H, m), 2.43 (1H, m), 2.82 (1H, dd, J = 16.6, 3.6 Hz), 3.10 (1H, dd, J = 16.6, 5.0 Hz), 4.13 (1H, m), 4.12-4.25 (3H, m), 4.38 (2H, m), 4.54 (1H, m), 5.05 (1H, br s), 6.06 (1H, s), 6.86 (1H, d, J = 8.5 Hz), 6.98 (1H, d, J = 7.8 Hz), 7.31 (1H, m), 7.35 (1H, d, J = 8.5 Hz). | ESI-MS m/z: 423 [M + H]+ |
| 418 | | 1H-NMR (CDCl₃) δ: 2.43 (2H, m), 2.41 (2H, m), 2.91 (1H, dd, J = 16.7, 4.6 Hz), 3.17 (1H, dd, J = 16.7, 5.3 Hz), 3.66 (1H, dd, J = 10.7, 5.1 Hz), 3.72-3.79 (3H, m), 4.02-4.34 (5H, m), 4.63 (1H, m), 6.02 (1H, s), 6.91 (1H, m), 6.92 (1H, d, J = 8.7 Hz), 7.38 (1H, m), 7.42 (1H, d, J = 8.7 Hz). | ESI-MS m/z: 451 [M + H]+ |

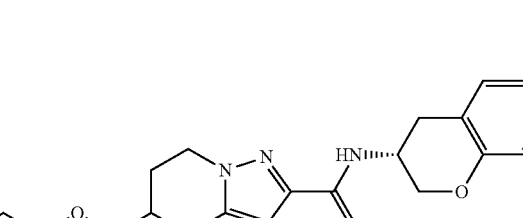

TABLE 56-continued

| Example | Structural formula | NMS | MS |
|---|---|---|---|
| 419 | | 1H-NMR (CDCl₃) δ: 0.17-0.18 (2H, m), 0.58-0.63 (2H, m), 1.00, (1H, m), 1.40 (3H, m), 2.04 (1H, m), 2.35 (1H, m), 2.91 (1H, m), 3.17 (1H, m), 3.31-3.35 (2H, m), 3.48-3.56 (2H, m), 4.04-4.18 (2H, m), 4.22-4.31 (2H, m), 4.63 (1H, m), 5.99 (1H, s), 6.92-6.94 (2H, m), 7.38 (1H, s), 7.42 (1H, d, J = 8.5 Hz). | ESI-MS m/z: 423 [M + H]+ |
| 420 | | 1H-NMR (CDCl₃) δ: 2.23-2.28 (2H, m), 2.84 (1H, m), 3.15 (1H, m), 4.09-4.26 (6H, m), 4.44 (1H, m), 4.61 (1H, m), 6.05 (1H, s), 6.81 (1H, d, J = 8.6 Hz), 6.99 (1H, d, J = 6.6 Hz), 7.04 (1H, s), 7.08 (1H, d, J = 8.7 Hz). | ESI-MS m/z: 432 [M + H]+ |
| 421 | | 1H-NMR (CDCl₃) δ: 2.23-2.29 (2H, m), 2.96 (1H, m), 3.25 (1H, dd, J = 5.4, 16.7 Hz), 4.11-4.25 (6H, m), 4.44 (1H, m), 4.66 (1H, m), 6.06 (1H, s), 6.99 (1H, d, J = 8.3 Hz), 7.04 (1H, d, J = 7.6 Hz), 7.20 (1H, s), 7.29 (2H, m), 8.65 (2H, s). | ESI-MS m/z: 506 [M + H]+ |
| 422 | | 1H-NMR (CDCl₃) δ: 2.26 (1H, m), 2.30 (1H, m), 2.91 (1H, dd, J = 16.8, 4.6 Hz), 2.98 (1H, dd, J = 14.8, 5.7 Hz), 3.06 (1H, dd, J = 14.8, 6.0 Hz), 3.11-3.30 (3H, m), 4.11 (1H, m), 4.06-4.33 (3H, m), 4.40 (1H, m), 4.64 (1H, m), 6.03 (1H, s), 6.93 (1H, d, J = 8.5 Hz), 6.94 (1H, m), 7.38 (1H, m), 7.42 (1H, dd, J = 8.5, 2.2 Hz). | ESI-MS m/z: 453 [M + H]+ |
| 423 | | 1H-NMR (CDCl₃) δ: 2.15-2.38 (2H, m), 2.91 (1H, dd, J = 16.8, 4.6 Hz), 2.98 (1H, dd, J = 14.0, 6.0 Hz), 3.06 (1H, dd, J = 14.0, 6.0 Hz), 3.12-3.29 (3H, m), 4.10 (1H, m), 4.16-4.36 (3H, m), 4.39 (1H, m), 4.63 (1H, m), 6.03 (1H, s), 6.93 (1H, d, J = 8.5 Hz), 6.94 (1H, m), 7.38 (1H, s), 7.42 (1H, d, J = 8.5 Hz). | ESI-MS m/z: 453 [M + H]+ |

TABLE 56-continued

| Example | Structural formula | NMR | MS |
|---|---|---|---|
| 424 | (structure) | 1H-NMR (CDCl₃) δ: 2.15-2.38 (2H, m), 2.91 (1H, dd, J = 16.8, 4.6 Hz), 2.98 (1H, dd, J = 14.0, 6.0 Hz), 3.06 (1H, dd, J = 14.0, 6.0 Hz), 3.12-3.29 (3H, m), 4.10 (1H, m), 4.16-4.36 (3H, m), 4.39 (1H, m), 4.63 (1H, m), 6.03 (1H, s), 6.93 (1H, d, J = 8.5 Hz), 6.94 (1H, m), 7.38 (1H, s), 7.42 (1H, d, J = 8.5 Hz). | ESI-MS m/z: 453 [M + H]+ |
| 425 | (structure) | 1H-NMR (CDCl₃) δ: 0.21 (2H, d, J = 4.6 Hz), 0.55 (2H, d, J = 8.0 Hz), 1.06 (1H, m), 2.13-2.29 (2H, m), 2.97 (1H, m), 3.26 (1H, dd, J = 5.2, 16.6 Hz), 3.37 (2H, d, J = 6.9 Hz), 3.65 (1H, dd, J = 5.2, 9.0 Hz), 3.75 (1H, dd, J = 5.3, 10.5 Hz), 4.07 (1H, m), 4.18 (1H, m), 4.28 (2H, m), 4.35 (1H, m), 4.67 (1H, m), 6.02 (1H, s), 6.72 (1H, d, J = 7.9 Hz), 7.02 (2H, m), 7.78 (1H, s), 8.45 (1H, d, J = 2.4 Hz), 8.58 (1H, t, J = 3.7 Hz), 8.96 (1H, d, J = 1.2 Hz). | ESI-MS m/z: 462 [M + H]+ |

TABLE 57

| Example | Structural formula | NMR | MS |
|---|---|---|---|
| 426 | (structure) | 1H-NMR (CDCl₃) δ: 0.21 (2H, m), 0.55 (2H, d, J = 6.8 Hz), 1.06 (1H, m), 2.18-2.27 (2H, m), 2.89 (1H, m), 3.21 (1H, m), 3.37 (2H, d, J = 6.3 Hz), 3.65 (1H, m), 3.74 (1H, m), 3.93 (3H, s), 4.06 (1H, m), 4.16-4.22 (3H, m), 4.35 (1H, m), 4.64 (1H, m), 6.01 (1H, s), 6.44 (1H, s), 6.89 (1H, d, J = 8.6 Hz), 7.02 (1H, d, J = 6.2 Hz), 7.35 (1H, s), 7.52-7.54 (2H, m). | ESI-MS m/z: 464 [M + H]+ |
| 427 | (structure) | 1H-NMR (CDCl₃) δ: 0.21 (2H, d, J = 4.7 Hz), 0.55 (2H, d, J = 7.5 Hz), 1.06 (1H, m), 2.21 (2H, m), 2.93 (1H, dd, J = 4.0, 16.5 Hz), 3.24 (1H, dd, J = 4.9, 17.0 Hz), 3.37 (2H, d, J = 7.0 Hz), 3.64 (1H, dd, J = 5.1, 10.0 Hz), 3.75 (1H, dd, J = 4.8, 10.5 Hz), 4.07 (1H, m), 4.17-4.24 (2H, m), 4.35 (1H, m), 4.66 (1H, m), 6.02 (1H, s), 6.94 (1H, d, J = 9.3 Hz), 7.02 (1H, d, J = 8.1 Hz), 7.39 (1H, s), 7.66-7.68 (2H, m), 8.85 (1H, s). | ESI-MS m/z: 467 [M + H]+ |

TABLE 57-continued

| Example | Structural formula | NMR | MS |
|---|---|---|---|
| 428 | | 1H-NMR (CDCl₃) δ: 0.21 (2H, d, J = 4.7 Hz), 0.55 (2H, d, J = 8.1 Hz), 1.06 (1H, m), 2.21 (2H, m), 2.92 (1H, dd, J = 3.9, 17.0 Hz), 3.21 (1H, dd, J = 5.1, 16.7 Hz), 3.37 (2H, d, J = 6.6 Hz), 3.65 (1H, m), 3.75 (1H, dd, J = 4.9, 10.4 Hz), 4.08 (1H, m), 4.19 (1H, m), 4.24 (2H, m), 4.36 (1H, m), 4.65 (1H, m), 6.03 (1H, s), 6.92 (1H, d, J = 8.5 Hz), 7.02 (1H, d, J = 8.1 Hz), 7.26 (1H, s), 7.35 (1H, dd, J = 2.1, 8.4 Hz), 7.96 (1H, s), 8.70 (1H, s). | ESI-MS m/z: 467 [M + H]+ |
| 429 | | 1H-NMR (CDCl₃) δ: 0.21 (2H, d, J = 5.0 Hz), 0.55 (2H, d, J = 7.9 Hz), 1.06 (1H, m), 2.21 (2H, m), 2.92 (1H, m), 3.22 (1H, m), 3.37 (2H, d, J = 7.0 Hz), 3.64 (1H, dd, J = 5.7, 10.3 Hz), 3.75 (1H, dd, J = 5.2, 10.4 Hz), 4.08 (1H, m), 4.16-4.24 (6H, m), 4.35 (1H, m), 4.65 (1H, m), 6.02 (1H, s), 6.93 (1H, d, J = 8.4 Hz), 7.02 (1H, d, J = 8.6 Hz), 7.49 (1H, s), 7.52 (1H, d, J = 8.5 Hz), 7.72 (1H, s). | ESI-MS m/z: 465 [M + H]+ |
| 430 | | 1H-NMR (CDCl₃) δ: 0.21 (2H, d, J = 4.6 Hz), 0.55 (2H, d, J = 7.9 Hz), 1.06 (1H, m), 2.12-2.29 (2H, m), 2.90 (1H, dd, J = 3.8, 16.5 Hz), 3.20 (1H, dd, J = 5.3, 16.7 Hz), 3.37 (2H, d, J = 6.8 Hz), 3.65 (1H, dd, J = 5.3, 10.4 Hz), 3.75 (1H, dd, J = 5.2, 10.4 Hz), 4.08 (1H, m), 4.17-4.24 (3H, m), 4.35 (1H, m), 4.64 (1H, m), 4.72 (2H, q, J = 8.4 Hz), 6.02 (1H, s), 6.89 (1H, d, J = 8.4 Hz), 7.04 (1H, d, J = 8.0 Hz), 7.17 (1H, s), 7.24 (1H, s), 7.65 (1H, s), 7.78 (1H, s). | ESI-MS m/z: 532 [M + H]+ |
| 431 | | 1H-NMR (CDCl₃) δ: 0.21 (2H, d, J = 3.9 Hz), 0.55 (2H, d, J = 7.2 Hz), 1.06 (1H, m), 2.17-2.28 (2H, m), 2.58 (3H, s), 2.97 (1H, m), 3.26 (1H, dd, J = 5.2, 16.2 Hz), 3.37 (2H, d, J = 6.8 Hz), 3.65 (1H, dd, J = 4.8, 9.9 Hz), 3.75 (1H, dd, J = 5.3, 10.8 Hz), 4.07 (1H, m), 4.17 (1H, m), 4.26 (2H, m), 4.35 (1H, m), 4.67 (1H, m), 6.02 (1H, s), 6.98-7.03 (2H, m), 7.73 (1H, s), 7.76 (1H, s), 8.45 (1H, s), 8.83 (1H, s). | ESI-MS m/z: 475 [M + H]+ |
| 432 | | 1H-NMR (CDCl₃) δ: 2.25 (2H, m), 2.91 (1H, dd, J = 16.8, 4.2 Hz), 3.20 (1H, dd, J = 16.8, 5.2 Hz), 3.83-4.00 (4H, m), 4.10 (1H, m), 4.17-4.30 (3H, m), 4.37 (1H, m), 4.64 (1H, m), 6.03 (1H, s), 6.95 (1H, d, J = 8.1 Hz), 6.98 (1H, m), 7.33 (1H, s), 7.38 (1H, d, J = 8.1 Hz). | ESI-MS m/z: 480 [M + H]+ |

TABLE 57-continued

| Example | Structural formula | NMR | MS |
|---|---|---|---|
| 433 | (structure) | 1H-NMR (CDCl₃) δ: 1.46-1.47 (3H, m), 2.06 (1H, m), 2.17 (1H, m), 2.87 (1H, m), 3.17 (1H, m), 3.26 (2H, q, J = 10.8 Hz), 4.07 (1H, m), 4.14-4.22 (3H, m), 4.35 (1H, m), 4.62 (1H, m), 5.99 (1H, s), 6.85 (1H, d, J = 8.4 Hz), 6.97-7.06 (3H, m). | ESI-MS m/z: 462 [M + H]+ |
| 434 | (structure) | 1H-NMR (CDCl₃) δ: 0.76 (2H, m), 1.04 (2H, m), 2.24 (2H, m), 2.91 (1H, dd, J = 16.7, 4.8 Hz), 3.12 (1H, dd, J = 16.7, 5.2 Hz), 3.62-3.71 (3H, m), 3.76 (1H, dd, J = 9.8, 4.6 Hz), 4.08 (1H, m), 4.21 (1H, m), 4.28 (2H, m), 4.34 (1H, m), 4.63 (1H, m), 6.01 (1H, s), 6.89-6.96 (2H, m), 7.38 (1H, m), 7.42 (1H, dd, J = 8.5, 2.1 Hz). | ESI-MS m/z: 477 [M + H]+ |

TABLE 58

| Example | Structural formula | NMR | MS |
|---|---|---|---|
| 435 | (structure) | 1H-NMR (CDCl₃) δ: 0.75 (2H, m), 1.04 (2H, m), 2.21 (2H, m), 2.97 (1H, dd, J = 16.6, 4.4 Hz), 3.27 (1H, dd, J = 16.6, 5.3 Hz), 3.62-3.69 (3H, m), 3.76 (1H, ddd, J = 10.1, 4.4, 0.5 Hz), 4.07 (1H, m), 4.19 (1H, m), 4.26-4.29 (1H, m), 4.33 (1H, m), 4.67 (1H, m), 5.41 (1H, m), 6.01 (1H, s), 6.97-7.05 (2H, m), 7.75-7.82 (2H, m), 7.01 (1H, m), 8.45 (1H, d, J = 2.5 Hz), 8.58 (1H, dd, J = 2.5, 1.6 Hz), 8.96 (1H, d, J = 1.5 Hz). | ESI-MS m/z: 530 [M + H]+ |
| 436 | (structure) | 1H-NMR (CDCl₃) δ: 2.24 (2H, m), 2.84 (1H, dt, J = 16.9, 3.3 Hz), 2.98 (1H, m), 3.15 (1H, dd, J = 16.8, 4.9 Hz), 3.78-3.99 (4H, m), 4.10 (1H, m), 4.17-4.26 (3H, m), 4.37 (1H, m), 4.60 (1H, m), 6.03 (1H, s), 6.78 (1H, dd, J = 22.7, 8.2 Hz), 6.97 (1H, t, J = 8.2 Hz), 7.23 (1H, m), 7.23 (1H, ddd, J = 22.7, 8.2, 2.6 Hz). | ESI-MS m/z: 436 [M + H]+ |
| 437 | (structure) | 1H-NMR (CDCl₃) δ: 1.50 (1H, m), 1.71 (1H, m), 1.67-1.75 (2H, m), 2.19-2.23 (4H, m), 2.86 (1H, m), 2.99-3.09 (2H, m), 3.16 (1H, m), 3.52 (1H, m), 3.62 (1H, m), 3.95-4.12 (2H, m), 4.17-4.21 (3H, m), 4.31 (1H, m), 4.61 (1H, m), 5.72-6.02 (2H, m), 6.84 (1H, d, J = 8.2 Hz), 8.94 (1H, s), 7.00-7.02 (2H, m). | ESI-MS m/z: 448 [M + H]+ |

TABLE 58-continued

| Example | Structural formula | NMR | MS |
|---|---|---|---|
| 438 | | 1H-NMR (CDCl₃) δ: 1.50 (1H, m), 1.71 (1H, m), 1.89-1.98 (2H, m), 2.17-2.22 (4H, m), 2.87 (1H, m), 3.18 (1H, m), 3.52 (1H, m), 3.62 (1H, m), 3.82 (2H, q, J = 8.8 Hz), 3.95-4.11 (2H, m), 4.16-4.23 (3H, m), 4.32 (1H, m), 4.57 (2H, s), 4.62 (1H, m), 6.02 (1H, s), 6.87 (1H, d, J = 8.2 Hz), 7.00 (1H, d, J = 7.2 Hz), 7.04 (1H, s), 7.12 (1H, d, J = 8.5 Hz). | ESI-MS m/z: 496 [M + H]+ |
| 439 | | 1H-NMR (CDCl₃) δ: 2.15-2.27 (2H, m), 2.28-2.58 (4H, m), 2.90 (1H, dd, J = 16.5, 4.6 Hz), 3.16 (1H, dd, J = 16.5, 5.2 Hz), 3.55 (1H, dd, J = 10.4, 4.7 Hz), 3.63 (1H, dd, J = 10.4, 5.2 Hz), 4.08 (1H, m), 4.15-4.41 (5H, m), 4.63 (1H, m), 5.20 (1H, m), 6.03 (1H, s), 6.89-6.96 (2H, m), 7.38 (1H, s), 7.42 (1H, d, J = 8.8 Hz). | ESI-MS m/z: 427 [M + H]+ |
| 440 | | 1H-NMR (CDCl₃) δ: 2.17-19 (2H, m), 2.85-2.91 (3H, m), 3.18 (1H, dd, J = 5.4, 16.7 Hz), 3.68-3.74 (4H, m), 3.82 (2H, q, J = 8.7 Hz), 4.05-4.20 (5H, m), 4.57 (2H, s), 4.62 (1H, m), 6.00 (1H, s), 6.87 (1H, d, J = 8.6 Hz), 7.00 (1H, d, J = 8.2 Hz), 7.05 (1H, s), 7.12 (1H, d, J = 8.4 Hz). | ESI-MS m/z: 517 [M + H]+ |
| 441 | | 1H-NMR (CDCl₃) δ: 2.24 (2H, m), 2.87 (1H, dd, J = 4.5, 17.4 Hz), 3.15-3.31 (3H, m), 3.84-3.98 (4H, m), 4.09 (1H, m), 4.16-4.22 (3H, m), 4.37 (1H, m), 4.62 (1H, m), 6.03 (1H, s), 6.86 (1H, d, J = 8.3 Hz), 6.98-7.06 (3H, m). | ESI-MS m/z: 494 [M + H]+ |
| 442 | | 1H-NMR (CDCl₃) δ: 2.20-2.26 (2H, m), 2.84 (1H, dd, J = 4.2, 16.9 Hz), 3.14 (1H, dd, J = 5.4, 16.8 Hz), 3.84-3.98 (4H, m), 4.09 (1H, m), 4.18-4.24 (3H, m), 4.37 (1H, m), 4.60 (1H, m), 6.02 (1H, s), 6.81 (1H, d, J = 8.7 Hz), 6.99 (1H, d, J = 7.8 Hz), 7.04 (1H, d, J = 2.5 Hz), 7.08 (1H, dd, J = 2.6, 8.7 Hz). | ESI-MS m/z: 446 [M + H]+ |
| 443 | | 1H-NMR (CDCl₃) δ: 2.17-2.25 (2H, m), 2.87 (1H, m), 3.18 (1H, m), 3.66 (1H, m), 3.74 (1H, m), 4.06 (1H, m), 4.14-4.22 (3H, m), 4.36 (1H, m), 4.60-4.62 (3H, m), 6.02 (1H, s), 6.86-6.91 (2H, m), 7.01-7.07 (2H, m), 7.13 (1H, t, J = 7.7 Hz), 7.29-7.38 (5H, m). | ESI-MS m/z: 420 [M + H]+ |

TABLE 59

| Example | Structural formula | NMR | MS |
|---|---|---|---|
| 444 | | 1H-NMR (CDCl₃) δ: 1.46 (3H, d, J = 6.2 Hz), 2.04 (1H, m), 2.22 (1H, m), 2.80 (1H, m), 3.09 (1H, m), 4.10-4.25 (4H, m), 4.38 (1H, m), 4.58 (1H, m), 6.77 (1H, d, J = 8.7 Hz), 6.92 (1H, d, J = 7.7 Hz), 7.00 (1H, s), 7.07 (1H, d, J = 8.7 Hz), 7.22 (1H, m), 7.31-7.34 (2H, m), 7.51 (2H, d, J = 7.8 Hz). | ESI-MS m/z: 424 [M + H]+ |
| 445 | | 1H-NMR (CDCl₃) δ: 2.84 (1H, br d, J = 16.9 Hz), 3.16 (1H, dd, J = 16.9, 5.2 Hz), 4.15-4.24 (2H, m), 4.36 (1H, dd, J = 10.7, 5.5 Hz), 4.52 (1H, t, J = 9.5 Hz), 4.60 (1H, m), 5.50 (1H, m), 6.02 (1H, m), 6.76 (1H, d, J = 8.6 Hz), 6.97 (1H, d, J = 8.0 Hz), 7.19 (1H, m), 7.22 (1H, br d, J = 8.8 Hz). | ESI-MS m/z: 433 [M + H]+ |
| 446 | | 1H-NMR (CDCl₃) δ: 1.53 (3H, m), 1.54 (3H, s), 2.09 (3H, s), 2.76 (1H, dd, J = 16.8, 4.0 Hz), 3.07 (1H, dd, J = 16.8, 5.3 Hz), 3.87 (2H, s), 4.11 (2H, m), 4.51 (1H, m), 6.72 (1H, d, J = 8.6 Hz), 6.89-6.97 (2H, m), 7.00 (1H, br d, J = 6.4 Hz). | ESI-MS m/z: 362 [M + H]+ |
| 447 | | 1H-NMR (CDCl₃) δ: 2.84 (1H, dt, J = 16.7, 4.0 Hz), 2.90 (1H, t, J = 7.2 Hz), 3.17 (1H, dd, J = 16.7, 5.4 Hz), 4.11 (2H, t, J = 7.2 Hz), 4.14-4.24 (2H, m), 4.36 (1H, m), 4.51 (1H, m), 4.61 (1H, m), 5.50 (1H, m,), 6.02 (1H, s), 6.83 (1H, br d, J =, 8.3 Hz), 6.90 (1H, br s), 6.98 (1H, dd, J = 8.5, 2.0 Hz), 7.01 (1H, m). | ESI-MS m/z: 466 [M + H]+ |
| 448 | | 1H-NMR (CDCl₃) δ: 1.62 (1H, s), 2.83 (1H, m), 3.06 (1H, m), 3.15 (1H, dd, J = 5.3, 16.8 Hz), 3.25 (3H, s), 4.11-4.18 (3H, m), 4.29 (1H, dt, J = 2.7, 9.1 Hz), 4.61 (1H, m), 5.38 (1H, m), 5.90 (1H, s), 6.80 (1H, d, J = 8.7 Hz), 6.99 (1H, d, J = 5.0 Hz), 7.04 (1H, s), 7.08 (1H, dd, J = 2.2, 8.7 Hz). | ESI-MS m/z: 431 [M + H]+ |
| 449 | | 1H-NMR (CDCl₃) δ: 0.18-0.22 (2H, m), 0.54 (2H, t, J = 8.9 Hz), 1.02 (1H, m), 2.84 (1H, m), 3.15 (1H, m), 3.32-3.41 (2H, m), 3.77-3.98 (2H, m), 4.19 (2H, s), 4.38 (1H, m), 4.48 (1H, m), 4.61 (1H, m), 5.59 (1H, m), 5.95 (1H, s), 6.81 (1H, d, J = 8.8 Hz), 6.99 (1H, d, J = 4.2 Hz), 7.04 (1H, s), 7.08 (1H, d, J = 8.8 Hz). | ESI-MS m/z: 454 [M + H]+ |

TABLE 59-continued

| Example | Structural formula | NMR | MS |
|---|---|---|---|
| 450 | | 1H-NMR (CDCl₃) δ: 2.90 (1H, m), 3.18 (1H, dd, J = 5.3, 16.5 Hz), 4.22-4.31 (3H, m), 4.40 (1H, t, J = 9.5 Hz), 4.62-4.73 (3H, m), 5.65 (1H, m), 5.93 (1H, s), 6.75 (1H, dd, J = 4.9, 8.3 Hz), 6.92-6.94 (3H, m), 7.38 (1H, s), 7.42 (1H, d, J = 8.5 Hz), 7.60 (1H, t, J = 7.7 Hz), 8.12 (1H, m). | ESI-MS m/z: 418 [M + H]+ |
| 451 | | 1H-NMR (CDCl₃) δ: 2.40 (1H, m), 2.48 (1H, m), 2.83 (1H, d, J = 16.9 Hz), 3.14 (1H, dd, J = 5.1, 16.9 Hz), 3.76 (1H, m), 4.18 (2H, s), 4.26 (1H, m), 4.38 (2H, m), 4.59 (1H, m), 5.15 (1H, m), 5.90 (1H, s), 6.26 (1H, s), 6.79 (1H, d, J = 8.6 Hz), 6.98 (1H, d, J = 7.0 Hz), 7.03 (1H, s), 7.07 (1H, d, J = 8.8 Hz), 7.42 (1H, s), 7.54 (1H, s). | ESI-MS m/z: 414 [M + H]+ |
| 452 | | 1H-NMR (CDCl₃) δ: 1.06 (3H, t, J = 7.1 Hz), 2.80 (2H, q, J = 7.1 Hz), 2.90 (1H, dd, J = 4.4, 16.6 Hz), 3.01 (1H, m), 3.08-3.20 (4H, m), 4.13 (1H, m), 4.23-4.31 (3H, m), 4.64 (1H, m), 5.34 (1H, m), 5.90 (1H, s), 6.92-6.94 (2H, m), 7.38 (1H, s), 7.42 (1H, d, J = 8.6 Hz). | ESI-MS m/z: 450 [M + H]+ |

TABLE 60

| Example | Structural formula | NMR | KS |
|---|---|---|---|
| 453 | | 1H-NMR (CDCl₃) δ: 2.82 (1H, dd, J = 3.6, 17.1 Hz), 3.13 (1H, dd, J = 5.2, 16.8 Hz), 4.12-4.18 (3H, m), 4.33 (1H, m), 4.55-4.59 (3H, m), 5.63 (1H, m), 5.89 (1H, m), 6.27 (1H, d, J = 2.0 Hz), 6.80 (1H, d, J = 8.6 Hz), 6.95 (1H, d, J = 7.6 Hz), 7.03 (1H, s), 7.07 (1H, d, J = 8.7 Hz), 7.47 (1H, s), 7.52 (1H, s). | ESI-MS m/z: 400 [M + H]+ |
| 454 | | 1H-NMR (CDCl₃) δ: 0.18 (2H, s), 0.54 (2H, d, J = 7.8 Hz), 1.02 (1H, s), 2.90 (1H, dd, J = 4.4, 16.5 Hz), 3.17 (1H, m), 3.37 (2H, dd, J = 3.2, 6.8 Hz), 3.77-3.79 (2H, m), 4.18 (1H, m), 4.23-4.33 (3H, m), 4.64 (1H, m), 5.41 (1H, m), 5.91 (1H, s), 6.93 (2H, d, J = 8.4 Hz), 7.38 (1H, s), 7.42 (1H, d, J = 8.6 Hz). | ESI-MS m/z: 395 [M + H]+ |

TABLE 60-continued

| Example | Structural formula | NMR | KS |
|---|---|---|---|
| 455 | 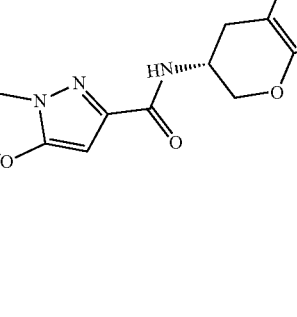 | 1H-NMR (CDCl₃) δ: 2.44 (1H, m), 2.52 (1H, m), 2.89 (1H, br d, J = 16.8 Hz), 3.17 (1H, dd, J = 16.7, 5.1 Hz), 3.83 (1H, m), 4.27 (2H, m), 4.33 (1H, m), 4.40 (2H, m), 4.63 (1H, m), 5.21 (1H, m), 5.93 (1H, s), 6.91 (1H, m), 6.92 (1H, d, J = 8.6 Hz), 7.37 (1H, s), 7.42 (1H, d, J = 8.6 Hz), 7.70 (1H, m), 7.74 (1H, s). | ESI-MS m/z: 473 [M + H]+ |
| 456 | 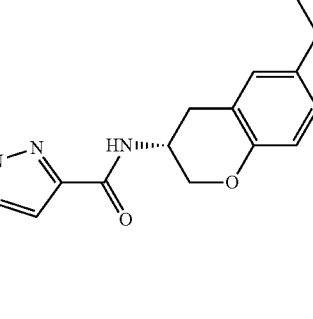 | 1H-NMR (CDCl₃) δ: 2.19 (2H, m), 2.97 (1H, dd, J = 4.5, 16.7 Hz), 3.27 (1H, dd, J = 5.6, 17.2 Hz), 3.83 (4H, m), 3.96 (1H, m), 4.28 (2H, s), 4.34 (1H, m), 4.68 (1H, m), 5.44 (1H, m), 5.90 (1H, s), 7.00 (2H, d, J = 7.7 Hz), 7.77 (1H, s), 7.80 (1H, s), 8.45 (1H, d, J = 1.9 Hz), 8.58 (1H, s), 8.96 (1H, s). | ESI-MS m/z: 490 [M + H]+ |
| 457 | 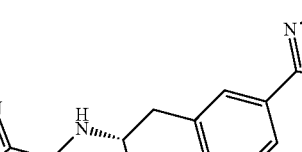 | 1H-NMR (CDCl₃) δ: 2.05 (1H, m), 2.24 (1H, m), 2.84-2.92 (3H, m), 3.11 (2H, m), 3.22 (1H, dd, J = 4.4, 17.2 Hz), 3.86-3.93 (4H, m), 4.22 (2H, m), 4.36 (1H, m), 4.64 (1H, m), 5.41 (1H, m), 5.89 (1H, s), 6.44 (1H, d, J = 2.0 Hz), 6.89 (1H, d, J = 8.2 Hz), 7.02 (1H, m), 7.35 (1H, d, J = 2.0 Hz), 7.51 (1H, s), 7.54 (1H, s). | ESI-MS m/z: 508 [M + H]+ |
| 458 | 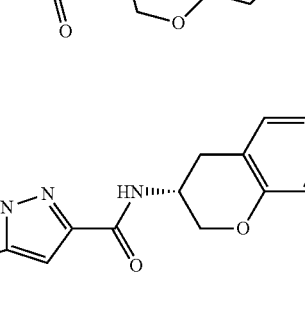 | 1H-NMR (CDCl₃) δ: 1.18 (3H, m), 1.20 (3H, m), 2.33 (2H, m), 2.49 (2H, m), 2.73 (2H, m), 2.91 (1H, dd, J = 16.7, 3.9 Hz), 3.21 (1H, dd, J = 16.7, 5.3 Hz), 3.70 (2H, m), 4.11-4.35 (4H, m), 4.66 (1H, m), 5.40 (1H, m), 5.89 (1H, s), 6.94 (1H, d, J = 8.5 Hz), 6.98 (1H, m), 7.33 (1H, s), 7.38 (1H, d, J = 8.5 Hz). | ESI-MS m/z: 481 [M + H]+ |
| 459 |  | 1H-NMR (CDCl₃) δ: 2.85 (1H, m), 3.04 (2H, dt, J = 4.5, 17.4 Hz), 3.17 (1H, dd, J = 5.5 16.6 Hz), 3.89-3.98 (4H, m), 4.16-4.21 (3H, m), 4.32 (1H, dt, J = 4.0, 9.3 Hz), 4.62 (1H, m), 5.41 (1H, m), 5.88 (1H, tt, J = 4.5, 56.3 Hz), 5.92 (1H, s), 6.84 (1H, d, J = 8.4 Hz), 6.93 (1H, s), 7.01 (2H, d, J = 8.0 Hz). | ESI-MS m/z: 462 [M + H]+ |

TABLE 60-continued

| Example | Structural formula | NMR | KS |
|---|---|---|---|
| 460 | | 1H-NMR (CDCl₃) δ: 0.18 (2H, m), 0.52 (2H, m), 1.02 (1H, m), 2.16 (2H, m), 2.88 (1H, m), 3.20 (1H, dd, J = 5.0, 16.9 Hz), 3.26 (2H, d, J = 6.6 Hz), 3.62 (2H, m), 3.93 (3H, s), 4.00 (1H, m), 4.21 (2H, s), 4.33 (1H, m), 4.64 (1H, m), 5.44 (1H, m), 5.89 (1H, s), 6.87 (1H, d, J = 8.4 Hz), 7.04 (1H, d, J = 8.5 Hz), 7.15 (1H, m), 7.22 (1H, d, J = 8.3 Hz), 7.51 (1H, s), 7.67 (1H, s). | ESI-MS m/z: 464 [M + H]+ |
| 461 | | 1H-NMR (CDCl₃) δ: 0.18 (2H, m), 0.53 (2H, m), 1.02 (1H, m), 2.16 (2H, m), 2.89 (1H, m), 3.19-3.27 (3H, m), 3.62 (2H, m), 3.93 (3H, s), 3.99 (1H, m), 4.22 (2H, s), 4.32 (1H, m), 4.64 (1H, m), 5.44 (1H, m), 5.88 (1H, s), 6.44 (1H, d, J = 2.1 Hz), 6.89 (1H, d, J = 8.2 Hz), 7.02 (1H, d, J = 7.8 Hz), 7.35 (1H, d, J = 2.0 Hz), 7.51-7.53 (2H, m). | ESI-MS m/z: 464 [M + H]+ |

TABLE 61

| Example | Structural formula | NMR | MS |
|---|---|---|---|
| 462 | | 1H-NMR (CDCl₃) δ: 2.82-2.92 (3H, m), 3.16 (1H, dd, J = 5.0, 16.5 Hz), 4.08-4.24 (7H, m), 4.36 (1H, m), 4.61 (1H, m), 5.46 (1H, m), 5.93 (1H, s), 6.36 (1H, dt, J = 5.6, 109.3 Hz), 6.82 (1H, d, J = 8.3 Hz), 6.90 (1H, s), 6.97-7.03 (2H, m). | ESI-MS m/z: 478 [M + H]+ |
| 463 | | 1H-NMR (CDCl₃) δ: 0.15-0.21 (2H, m), 0.51-0.62 (4H, m), 0.86-0.91 (2H, m), 1.02 (1H, m), 1.81 (1H, m), 2.81 (1H, d, J = 15.6 Hz), 3.14 (1H, m), 3.37 (2H, dd, J = 2.7, 6.9 Hz), 3.73-3.82 (2H, m), 4.14-4.19 (3H, m), 4.29 (1H, dt, J = 4.0, 9.2 Hz), 4.60 (1H, m), 5.40 (1H, m), 5.90 (1H, m), 6.76-6.78 (2H, m), 6.84 (1H, dd, J = 2.0, 8.4 Hz), 7.02 (1H, m). | ESI-MS m/z: 410 [M + H]+ |
| 464 | | 1H-NMR (CDCl₃) δ: 1.63-1.72 (2H, m), 1.77-1.93 (2H, m), 1.96-2.04 (2H, m), 2.53 (1H, m), 2.90 (1H, m), 3.17 (1H, dd, J = 5.1, 16.7 Hz), 3.47-3.50 (2H, m), 3.74-3.75 (2H, m), 4.17 (1H, m), 4.23-4.31 (3H, m), 4.64 (1H, m), 5.39 (1H, m), 5.91 (1H, s), 6.91-6.94 (2H, m), 7.38 (1H, s), 7.42 (1H, d, J = 8.5 Hz). | ESI-MS m/z: 409 [M + H]+ |

TABLE 61-continued

| Example | Structural formula | NMR | MS |
|---|---|---|---|
| 465 | | 1H-NMR (CDCl₃) δ: 0.72 (2H, m), 1.02 (2H, m), 2.17 (2H, m), 2.89 (1H, dd, J = 17.3, 4.5 Hz), 3.17 (1H, dd, J = 17.3, 5.1 Hz), 3.47 (1H, dd, J = 10.8, 6.4 Hz), 3.59 (1H, d, J = 10.6 Hz), 3.58-3.68 (2H, m), 4.01 (1H, dd, J = 9.8, 9.4 Hz), 4.24-4.29 (2H, m), 4.34 (1H, m), 4.65 (1H, m), 5.42 (1H, m), 5.89 (1H, s), 6.86-6.97 (2H, m), 7.38 (1H, s), 7.42 (1H, dd, J = 8.4, 2.0 Hz). | ESI-MS m/z: 477 [M + H]+ |
| 466 | | 1H-NMR (CDCl₃) δ: 2.19 (2H, m), 2.84 (1H, d, J = 15.4 Hz), 3.03 (2H, t, J = 17.3 Hz), 3.16 (1H, dd, J = 4.7, 17.1 Hz), 3.80-3.86 (4H, m), 3.96 (1H, m), 4.18 (2H, s), 4.35 (1H, m), 4.61 (1H, m), 5.43 (1H, m), 5.73-6.02 (2H, m), 6.83 (1H, dd, J = 1.8, 8.2 Hz), 6.93 (1H, s), 7.00 (2H, d, J = 8.3 Hz). | ESI-MS m/z: 476 [M + H]+ |
| 467 | | 1H-NMR (CDCl₃) δ: 0.71 (2H, m), 1.01 (2H, m), 2.16 (2H, m), 2.97 (1H, dd, J = 16.9, 3.7 Hz), 3.27 (1H, dd, J = 16.9, 5.2 Hz), 3.47 (1H, dd, J = 11.0, 6.2 Hz), 3.55 (1H, dd, J = 11.0, 1.6 Hz), 3.57-3.69 (2H, m), 3.99 (1H, m), 4.24-4.29 (1H, m), 4.32 (1H, m), 4.68 (1H, m), 5.41 (1H, m), 5.89 (1H, s), 6.97-7.05 (2H, m), 7.78-7.82 (2H, m), 7.01 (1H, m), 8.45 (1H, d, J = 2.5 Hz), 8.58 (1H, t, J = 1.8 Hz), 8.96 (1H, d, J = 1.2 Hz). | ESI-MS m/z: 530 [M + H]+ |
| 468 | | 1H-NMR (CDCl₃) δ: 0.15-0.20 (2H, m), 0.50-0.57 (2H, m), 1.02 (1H, m), 2.95 (1H, m), 3.25 (1H, dd, J = 4.7, 16.6 Hz), 3.36 (2H, t, J = 6.6 Hz), 3.75-3.81 (2H, m), 4.05 (3H, s), 4.18 (1H, m), 4.25-4.33 (3H, m), 4.67 (1H, m), 5.41 (1H, m), 5.92 (1H, s), 6.98 (1H, d, J = 8.4 Hz), 7.03 (1H, m), 7.19 (1H, s), 7.29 (1H, m), 8.66 (2H, s). | ESI-MS m/z: 478 [M + H]+ |
| 469 | | 1H-NMR (CDCl₃) δ: 0.15-0.21 (2H, m), 0.51-0.57 (2H, m), 1.02 (1H, m), 2.84 (1H, d, J = 16.6 Hz), 3.15 (1H, dd, J = 5.4, 16.6 Hz), 3.37 (2H, dd, J = 3.2, 6.9 Hz), 3.74-3.82 (2H, m), 4.15-4.19 (3H, m), 4.30 (1H, m), 4.61 (1H, m), 5.41 (1H, m), 5.92 (1H, s), 6.80 (1H, d, J = 8.7 Hz), 7.00-7.09 (3H, m). | ESI-MS m/z: 404 [M + H]+ |
| 470 | | 1H-NMR (CDCl₃) δ: 1.49 (1H, m), 1.69 (1H, m), 1.82-1.89 (2H, m), 2.08-2.19 (4H, m), 2.90 (1H, m), 3.17 (1H, m), 3.50 (2H, t, J = 5.5 Hz), 3.89 (1H, t, J = 7.3 Hz), 4.00 (1H, t, J = 8.4 Hz), 4.27-4.35 (3H, m), 4.64 (1H, m), 5.43 (1H, m), 5.89 (1H, s), 6.92 (2H, d, J = 8.4 Hz), 7.38-7.43 (2H, m). | ESI-MS m/z: 409 [M + H]+ |

TABLE 62

| Example | Structural formula | NMR | MS |
|---|---|---|---|
| 471 | | 1H-NMR (CDCl$_3$) δ: 1.51 (1H, m), 1.69 (1H, m), 1.82-1.90 (2H, m), 2.05-2.21 (4H, m), 2.85 (1H, dd, J = 3.9, 16.4 Hz), 3.06 (2H, dt, J = 4.5, 26.1 Hz), 3.17 (1H, dd, J = 5.4, 16.5 Hz), 3.48-3.50 (2H, m), 3.90 (1H, m), 3.99 (1H, m), 4.19 (2H, s), 4.33 (1H, m), 4.62 (1H, m), 5.41 (1H, m), 5.73-6.02 (2H, m), 6.83 (1H, d, J = 8.3 Hz), 6.93 (1H, s), 7.00 (2H, d, J = 8.2 Hz). | ESI-MS m/z: 448 [M + H]+ |
| 472 | | 1H-NMR (CDCl$_3$) δ: 1.49 (1H, m), 1.70 (1H, m), 1.83-1.90 (2H, m), 2.07-2.19 (4H, m), 2.86 (1H, m), 3.18 (1H, m), 3.49-3.51 (2H, m), 3.81 (2H, q, J = 8.8 Hz), 3.89 (1H, t, J = 7.1 Hz), 3.99 (1H, m), 4.20 (2H, s), 4.32 (1H, dt, J = 4.2, 9.0 Hz), 4.56 (2H, s), 4.63 (1H, m), 5.43 (1H, m), 5.89 (1H, s), 6.87 (1H, d, J = 8.5 Hz), 7.00 (1H, d, J = 7.7 Hz), 7.04 (1H, s), 7.11 (1H, d, J = 8.2 Hz). | ESI-MS m/z: 496 [M + H]+ |
| 473 | | 1H-NMR (CDCl$_3$) δ: 1.50 (1H, m), 1.68 (1H, m), 1.80-1.89 (2H, m), 2.04-2.21 (4H, m), 2.88 (1H, dd, J = 3.9, 16.7 Hz), 3.20 (1H, dd, J = 5.3, 16.7 Hz), 3.48-3.51 (2H, m), 3.88-4.01 (5H, m), 4.21 (2H, d, J = 2.8 Hz), 4.32 (1H, m), 4.64 (1H, m), 5.42 (1H, m), 5.89 (1H, s), 6.87 (1H, d, J = 8.4 Hz), 7.04 (1H, d, J = 8.1 Hz), 7.14 (1H, d, J = 1.3 Hz), 7.23 (1H, dd, J = 2.2, 8.4 Hz), 7.51 (1H, s), 7.67 (1H, s). | ESI-MS m/z: 464 [M + H]+ |
| 474 | | 1H-NMR (CDCl$_3$) δ: 1.51 (1H, m), 1.68 (1H, m), 1.82-1.89 (2H, m), 2.05-2.21 (4H, m), 2.97 (1H, m), 3.27 (1H, m), 3.48-3.51 (2H, m), 3.89 (1H, m), 3.98 (1H, m), 4.27-4.35 (3H, m), 4.68 (1H, m), 5.42 (1H, m), 5.89 (1H, s), 6.99-7.02 (2H, m), 7.78-7.80 (2H, m), 8.45 (1H, d, J = 2.5 Hz), 8.58 (1H, t, J = 2.0 Hz), 8.96 (1H, d, J = 1.4 Hz). | ESI-MS m/z: 462 [M + H]+ |
| 475 | | 1H-NMR (CDCl$_3$) δ: 1.51 (1H, m), 1.69 (1H, m), 1.82-1.89 (2H, m), 2.05-2.18 (4H, m), 2.50-2.59 (3H, m), 2.96 (1H, m), 3.26 (1H, dd, J = 5.3, 16.8 Hz), 3.48-3.50 (2H, m), 3.89 (1H, m), 3.98 (1H, m), 4.20-4.34 (3H, m), 4.67 (1H, m), 5.43 (1H, m), 5.89 (1H, s), 6.97-7.03 (2H, m), 7.73-7.75 (2H, m), 8.45 (1H, s), 8.83 (1H, s). | ESI-MS m/z: 476 [M + H]+ |
| 476 | | 1H-NMR (CDCl$_3$) δ: 1.98 (1H, m), 2.10 (1H, m), 2.21-2.32 (2H, m), 2.62 (1H, m), 2.69-2.76 (3H, m), 2.86-2.94 (3H, m), 3.20 (1H, dd, J = 5.1, 16.8 Hz), 3.93 (1H, t, J = 8.8 Hz), 4.26 (2H, s), 4.36 (1H, t, J = 9.0 Hz), 4.65 (1H, m), 5.40 (1H, m), 5.89 (1H, s), 6.93-7.09 (2H, m), 7.33 (1H, s), 7.38 (1H, d, J = 8.6 Hz). | ESI-MS m/z: 487 [M + H]+ |

TABLE 62-continued

| Example | Structural formula | NMR | MS |
|---|---|---|---|
| 477 | | 1H-NMR (CDCl₃) δ: 1.99 (1H, m), 2.11 (1H, m), 2.22-2.33 (2H, m), 2.63 (1H, m), 2.69-2.77 (3H, m), 2.86-2.93 (3H, m), 3.21 (1H, dd, J = 5.5, 16.8 Hz), 3.94 (1H, t, J = 9.0 Hz), 4.25 (2H, d, J = 2.6 Hz), 4.35 (1H, t, J = 9.1 Hz), 4.65 (1H, m), 5.39 (1H, m), 5.89 (1H, s), 6.93-6.96 (2H, m), 7.33 (1H, s), 7.38 (1H, d, J = 8.6 Hz). | ESI-MS m/z: 487 [M + H]+ |
| 478 | | 1H-NMR (CDCl₃) δ: 2.17 (2H, m), 2.85 (1H, dd, J = 3.4, 16.7 Hz), 3.03 (2H, td, J = 4.3, 17.4 Hz), 3.17 (1H, dd, J = 5.2, 16.7 Hz), 3.63-3.75 (4H, m), 3.97 (1H, m), 4.19 (2H, s), 4.34 (1H, m), 4.61 (1H, m), 5.43 (1H, m), 5.70-6.03 (3H, m), 6.83 (1H, d, J = 8.3 Hz), 6.83 (1H, d, J = 8.3 Hz), 6.93 (1H, s), 7.01 (2H, d, J = 8.0 Hz). | ESI-MS m/z: 458 [M + H]+ |
| 479 | | 1H-NMR (CDCl₃) δ: 2.18 (2H, m), 2.86 (1H, m), 3.15-3.30 (3H, m), 3.63-3.75 (4H, m), 3.97 (1H, m), 4.20 (2H, s), 4.35 (1H, m), 4.62 (1H, m), 5.43 (1H, m), 5.84 (1H, m), 5.90 (1H, s), 6.85 (1H, d, J = 8.4 Hz), 6.97-7.06 (3H, m). | ESI-MS m/z: 476 [M + H]+ |

TABLE 63

| Example | Structural formula | NMR | MS |
|---|---|---|---|
| 480 | | 1H-NMR (CDCl₃) δ: 1.88 (1H, m), 2.03-2.25 (3H, m), 2.86 (1H, m), 3.15 (1H, m), 4.14 (1H, t, J = 12.3 Hz), 4.20 (2H, d, J = 2.9 Hz), 4.40 (1H, d, J = 14.4 Hz), 4.59-4.69 (2H, m), 6.26 (1H, s), 6.82 (1H, m), 7.00-7.05 (2H, m), 7.09 (1H, d, J = 8.7 Hz), 7.35-7.41 (6H, m). | ESI-MS m/z: 424 [M + H]+ |
| 481 | | 1H-NMR (CDCl₃) δ: 1.88 (2H, m), 2.06 (2H, m), 2.76-2.81 (1H, m), 3.06-3.13 (1H, m), 4.04 (2H, m), 4.15 (2H, m), 4.26 (2H, m), 4.57 (1H, m), 6.77 (1H, m), 6.92 (1H, d, J = 8.20 Hz), 7.00 (1H, s), 7.07 (1H, d, J = 8.20 Hz), 7.27 (1H, m), 7.13-7.35 (2H, m), 7.44-7.47 (2H, m). | ESI-MS m/z: 424 [M + H]+ |

TABLE 63-continued

| Example | Structural formula | NMR | MS |
|---|---|---|---|
| 482 | | 1H-NMR (CDCl₃) δ: 2.05-2.07 (2H, m), 2.88 (1H, m), 3.18 (1H, m), 3.83 (2H, q, J = 8.8 Hz), 3.91-4.16 (6H, m), 4.21 (2H, s), 4.43 (1H, m), 4.57 (2H, s), 4.61 (1H, m), 6.26 (1H, s), 6.88 (1H, d, J = 8.9 Hz), 7.01-7.05 (2H, m), 7.12 (1H, d, J = 7.9 Hz). | ESI-MS m/z: 524 [M + H]+ |
| 483 | | 1H-NMR (CDCl₃) δ: 1.91 (1H, m), 2.30 (1H, m), 2.82 (1H, m), 2.91 (1H, m), 3.18 (1H, m), 3.80 (1H, m), 4.09 (1H, m), 4.27-4.29 (2H, m), 4.45 (1H, m), 4.56 (1H, ), 4.64 (1H, ), 6.28 (1H, s), 6.91-7.00 (2H, m), 7.39 (1H, s), 7.43 (1H, m). | ESI-MS m/z: 407 [M + H]+ |
| 484 | | 1H-NMR (CDCl₃) δ: 2.96 (1H, m), 3.22 (1H, m), 3.91 (3H, s), 4.13 (2H, d, J = 4.9 Hz), 4.19 (2H, d, J = 5.0 Hz), 4.28 (2H, s), 4.66 (1H, m), 5.17 (2H, s), 6.60 (1H, d, J = 8.6 Hz), 6.95 (1H, d, J = 8.8 Hz), 7.34 (2H, s), 7.39 (1H, d, J = 8.6 Hz), 7.60 (1H, t, J = 7.9 Hz), 7.91 (1H, d, J = 7.5 Hz). | ESI-MS m/z: 475 [M + H]+ |
| 485 | | 1H-NMR (CDCl₃) δ: 2.94-2.99 (1H, m), 3.20-3.26 (1H, m), 4.13 (2H, m), 4.18 (2H, m), 4.29 (2H, m), 4.64 (1H, m), 5.11 (2H, s), 6.96 (1H, m), 7.15 (1H, m), 7.35-7.41 (3H, m), 7.66 (1H, m), 8.34 (1H, m). | ESI-MS m/z: 479 [M + H]+ |
| 486 | | 1H-NMR (CDCl₃) δ: 2.30-2.55 (2H, m), 2.94-2.95 (1H, m), 3.22-3.28 (1H, m), 4.15-4.19 (2H, m), 4.30 (2H, m), 4.44-4.46 (2H, m), 4.69 (1H, m), 6.56 (1H, m), 6.97 (1H, d, J = 8.5 Hz), 7.44-7.58 (3H, m), 7.64-7.69 (2H, m). | ESI-MS m/z: 434 [M + H]+ |
| 487 | | 1H-NMR (CDCl₃) δ: 2.88 (1H, m), 3.16-3.25 (5H, m), 3.95 (2H, s), 4.13-4.16 (2H, m), 4.19-4.21 (2H, m), 4.64 (1H, m), 6.53 (1H, s), 6.87-6.92 (2H, m), 7.06 (2H, d, J = 7.7 Hz), 7.13 (1H, t, J = 7.8 Hz). | ESI-MS m/z: 431 [M + H]+ |

TABLE 63-continued

| Example | Structural formula | NMR | MS |
|---|---|---|---|
| 488 | | 1H-NMR (CDCl₃) δ: 2.20-2.39 (3H, m), 2.65-2.74 (4H, m), 2.85-2.93 (3H, m), 3.19 (1H, dd, J = 5.1, 16.6 Hz), 3.66 (2H, s), 4.12 (2H, t, J = 5.6 Hz), 4.16-4.24 (2H, m), 4.64 (1H, m), 6.51 (1H, s), 6.87-6.92 (2H, m), 7.04-7.07 (2H, m), 7.13 (1H, t, J = 7.7 Hz). | ESI-MS m/z: 403 [M + H]+ |

TABLE 64

| Example | Structural formula | NMR | MS |
|---|---|---|---|
| 489 | | 1H-NMR (CDCl₃) δ: 2.92 (1H, dd, J = 4.8, 16.5 Hz), 3.15-3.26 (5H, m), 3.96 (2H, s), 4.16 (2H, t, J = 5.5 Hz), 4.24-4.32 (2H, m), 4.64 (1H, m), 6.54 (1H, s), 6.92-6.96 (2H, m), 7.39-7.44 (2H, m). | ESI-MS m/z: 456 [M + H]+ |
| 490 | | 1H-NMR (CDCl₃) δ: 0.15-0.23 (4H, m), 0.38-0.48 (4H, m), 0.63-0.68 (2H, m), 1.26 (1H, m), 2.62 (2H, d, J = 6.6 Hz), 2.89-2.93 (3H, m), 3.18 (1H, m), 3.68 (2H, s), 4.11 (2H, t, J = 5.5 Hz), 4.18-4.22 (2H, m), 4.63 (1H, m), 6.49 (1H, s), 6.86-6.91 (2H, m), 7.04-7.07 (2H, m), 7.12 (1H, t, J = 8.0 Hz). | ESI-MS m/z: 407 [M + H]+ |
| 491 | | 1H-NMR (CDCl₃) δ: 0.06 (2H, q, J = 5.0 Hz), 0.44-0.48 (2H, m), 0.70 (1H, m), 1.45 (2H, q, J = 7.3 Hz), 2.65 (2H, t, J = 7.6 Hz), 2.89-2.94 (3H, m), 3.17 (1H, dd, J = 5.5, 16.6 Hz), 3.68 (2H, s), 4.13 (2H, t, J = 5.6 Hz), 4.22-4.32 (2H, m), 4.64 (1H, m), 6.51 (1H, s), 6.92-6.95 (2H, m), 7.38-7.43 (2H, m). | ESI-MS m/z: 392 [M + H]+ |
| 492 | | 1H-NMR (CDCl₃) δ: 2.91 (1H, m), 3.00 (2H, m), 3.19 (1H, m), 3.75 (2H, d, J = 4.9 Hz), 3.87 (2H, d, J = 5.4 Hz), 4.15 (2H, m), 4.23 (2H, m), 4.63 (1H, m), 6.40-6.70 (2H, m), 6.92 (1H, t, J = 7.8 Hz), 7.01 (1H, m), 7.23 (3H, m), 7.41 (1H, t, J = 5.8 Hz), 7.69 (1H, m), 8.58 (1H, m). | ESI-MS m/z: 440 [M + H]+ |
| 493 | | 1H-NMR (CDCl₃) δ: 2.85 (1H, dd, J = 3.9, 16.9 Hz), 3.01-3.03 (4H, m), 3.06-3.18 (1H, m), 3.80 (2H, s), 4.15 (2H, t, J = 5.5 Hz), 4.19 (2H, d, J = 2.8 Hz), 4.61 (1H, m), 6.54 (1H, s), 6.81 (1H, d, J = 8.7 Hz), 7.01-7.10 (3H, m). | |
| 494 | | 1H-NMR (CDCl₃) δ: 0.88 (1H, m), 1.27 (2H, m), 1.99 (1H, m), 2.47 (2H, m), 2.66 (1H, m), 2.85-3.08 (4H, m), 3.16 (1H, m), 3.71 (2H, s), 4.13-4.32 (3H, m), 4.63 (1H, m), 6.52 (1H, d, J = 11.3 Hz), 6.82 (1H, m), 7.05 (2H, m), 7.29 (1H, s). | ESI-MS m/z: 437 [M + H]+ |

TABLE 64-continued

| Example | Structural formula | NMR | MS |
|---|---|---|---|
| 495 | | 1H-NMR (CDCl₃) δ: 0.59 (2H, m), 0.68 (2H, m), 1.40 (1H, m), 2.86 (1H, dd, J = 4.2, 17.1 Hz), 2.99 (2H, t, J = 13.2 Hz), 3.15 (3H, m), 3.91 (2H, s), 4.14 (2H, t, J = 5.5 Hz), 4.19 (2H, d, J = 3.0 Hz), 4.62 (1H, m), 6.52 (1H, s), 6.81 (1H, d, J = 8.6 Hz), 7.01-7.10 (3H, m). | ESI-MS m/z: 437 [M + H]+ |
| 496 | | 1H-NMR (CDCl₃) δ: 1.58-1.66 (4H, m), 1.76-1.91 (2H, m) 2.05 (2H, m, 2.30 (1H, m), 2.44 (2H, m), 2.88-2.94 (3H, m), 3.17 1H, dd, J = 5.2, 16.7 Hz), 3.65 (2H, s), 4.12 (2H, t, J = 5.5 Hz), 4.22-4.32 (2H, m), 4.64 (1H, m), 6.51 (1H, s), 6.92-6.96 (2H, m), 7.38 (1H, s), 7.42 (1H, dd, J = 2.1, 8.5 Hz). | ESI-MS m/z: 406 [M + H]+ |
| 497 | | 1H-NMR (CDCl₃) δ: 2.91 (1H, dd, J = 4.5, 16.3 Hz), 2.97 (2H, t, J = 6.0 Hz), 3.17 (1H, dd, J = 5.2, 16.7 Hz), 3.72 (2H, s), 3.79 (2H, s), 4.13 (2H, t, J = 5.2 Hz), 4.22-4.32 (2H, m), 4.63 (1H, m), 6.50 (1H, s), 6.92 (1H, d, J = 8.5 Hz), 6.95 (1H, d, J = 7.8 Hz), 7.07 (1H, m), 7.14 (1H, td, J = 1.1, 7.5 Hz), 7.29 (1H, m), 7.37-7.43 (3H, m). | ESI-MS m/z: 432 [M + H]+ |

TABLE 65

| Example | Structural formula | NMR | MS |
|---|---|---|---|
| 498 | | 1H-NMR (CDCl₃) δ: 1.72 (2H, m), 1.81-1.97 (2H, m), 2.10 (2H, m), 2.53-2.63 (3H, m), 2.86-2.96 (3H, m), 3.17 (1H, dd, J = 5.2, 16.5 Hz), 3.63 (2H, s), 4.11 (2H, t, J = 5.6 Hz), 4.22-4.32 (2H, m), 4.64 (1H, m), 6.50 (1H, s), 6.93 (1H, d, J = 8.5 Hz), 6.95 (1H, s), 7.38 (1H, s), 7.42 (1H, dd, J = 2.0, 8.5 Hz). | ESI-MS m/z: 392 [M + H]+ |
| 499 | | 1H-NMR (CDCl₃) δ: 2.89-2.97 (3H, m), 3.18 (1H, dd, J = 5.2, 16.7 Hz), 3.73 (2H, s), 3.89 (2H, s), 4.14 (2H, t, J = 5.4 Hz), 4.23-4.33 (2H, m), 4.65 (1H, m), 6.50 (1H, s), 6.93 (1H, d, J = 8.5 Hz), 6.97 (1H, d, J = 7.8 Hz), 7.38-7.43 (3H, m), 7.54 (1H, t, J = 7.5 Hz), 7.67 (1H, d, J = 7.8 Hz), 7.76 (1H, d, J = 7.8 Hz). | ESI-MS m/z: 482 [M + H]+ |
| 500 | | 1H-NMR (CDCl₃) δ: 1.14 (4H, m), 2.84 (1H, dd, J = 4.5, 17.0 Hz), 3.14 (1H, dd, J = 5.3, 16.9 Hz), 3.24 (2H, t, J = 5.3 Hz), 3.96 (2H, s), 4.07 (2H, t, J = 5.5 Hz), 4.14-4.21 (2H, m), 4.60 (1H, m), 6.47 (1H, s), 6.80 (1H, d, J = 8.7 Hz), 6.97-7.08 (3H, m), 7.17 (1H, m), 7.28 (1H, s), 7.65 (1H, td, J = 1.8, 7.7 Hz), 8.58 (1H, d, J = 3.9 Hz). | ESI-MS m/z: 450 [M + H]+ |
| 501 | | 1H-NMR (CDCl₃) δ: 1.50 (6H, s), 2.84 (2H, t, J = 5.2 Hz), 2.92 (1H, dd, J = 5.0, 16.7 Hz), 3.17 (1H, dd, J = 5.1, 16.7 Hz), 3.86 (1H, s), 4.04 (2H, t, J = 5.2 Hz), 4.23-4.32 (2H, m), 4.64 (1H, m), 6.51 (1H, s), 6.92-6.96 (2H, m), 7.17 (1H, q, J = 3.7 Hz), 7.38 (1H, s), 7.42 (1H, d, J = 8.6 Hz), 7.66 (2H, d, J = 3.7 Hz), 8.57 (1H, d, J = 4.6 Hz). | ESI-MS m/z: 443 [M + H]+ |

TABLE 65-continued

| Example | Structural formula | NMR | MS |
|---|---|---|---|
| 502 | | 1H-NMR (CDCl₃) δ: 0.04 (2H, m), 0.47 (2H, m), 0.73 (1H, m), 1.17 (6H, s), 1.41 (2H, d, J = 6.4 Hz), 2.91 (1H, dd, J = 4.9, 16.4 Hz), 2.98 (2H, t, J = 5.8 Hz), 3.17 (1H, dd, J = 5.2, 16.5 Hz), 3.83 (2H, s), 4.08 (2H, t, J = 5.4 Hz), 4.22-4.33 (2H, m), 4.64 (1H, m), 6.51 (1H, s), 6.92-6.96 (2H, m), 7.38 (1H, s), 7.42 (1H, dd, J = 1.7, 8.5 Hz). | ESI-MS m/z: 420 [M + H]+ |
| 503 | | 1H-NMR (CDCl₃) δ: 2.25-2.38 (2H, m), 2.91 (1H, dd, J = 4.9, 16.5 Hz), 3.12-3.20 (3H, m), 3.89 (2H, s), 4.03 (1H, t, J = 5.2 Hz), 4.23-4.31 (3H, m), 4.64 (1H, m), 6.51 (1H, s), 6.92-6.94 (2H, m), 7.38 (1H, s), 7.42 (1H, d, J = 8.4 Hz). | ESI-MS m/z: 446 [M + H]+ |
| 504 | | 1H-NMR (CDCl₃) δ: 0.06 (2H, q, J = 5.0 Hz), 0.43-0.48 (2H, m), 0.71 (1H, m), 1.45 (2H, t, J = 7.4 Hz), 2.64 (2H, t, J = 7.6 Hz), 2.84-2.93 (3H, m), 3.06 (2H, dt, J = 4.5, 26.1 Hz), 3.17 (1H, dd, J = 5.5, 16.7 Hz), 3.68 (2H, s), 4.11-4.23 (4H, m), 4.63 (1H, m), 5.88 (1H, m), 6.51 (1H, s), 6.84 (1H, d, J = 8.3 Hz), 6.94 (1H, s), 7.00-7.05 (2H, m). | ESI-MS m/z: 431 [M + H]+ |
| 505 | | 1H-NMR (CDCl₃) δ: 0.06-0.07 (2H, m), 0.45-0.47 (2H, m), 0.70 (1H, m), 1.45 (2H, q, J = 7.4 Hz), 2.64 (2H, t, J = 7.6 Hz), 2.86-2.93 (3H, m), 3.18 (1H, m), 3.68 (2H, s), 3.81 (2H, t, J = 8.8 Hz), 4.13 (2H, t, J = 5.6 Hz), 4.20-4.24 (2H, m), 4.57 (2H, s), 4.64 (1H, m), 6.51 (1H, s), 6.87 (1H, d, J = 8.6 Hz), 7.02-7.05 (2H, m), 7.11 (1H, d, J = 8.1 Hz). | ESI-MS m/z: 479 [M + H]+ |
| 506 | | 1H-NMR (CDCl₃) δ: 2.32-2.44 (2H, m), 2.80-2.84 (2H, m), 2.90-2.97 (3H, m), 3.18-3.22 (1H, m), 3.72 (2H, s), 4.11-4.16 (2H, m), 4.26 (2H, m), 4.66 (1H, m), 6.53 (1H, s), 6.93-7.00 (2H, m), 7.33 (1H, s), 7.39-7.45 (1H, m). | ESI-MS m/z: 463 [M + H]+ |

TABLE 66

| Example | Structural formula | NMR | MS |
|---|---|---|---|
| 507 | 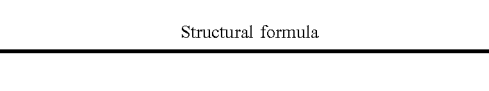 | 1H-NMR (CDCl₃) δ: 2.32-2.45 (2H, m), 2.77-2.90 (3H, m), 2.95 (2H, m), 3.16-3.21 (1H, m), 3.72 (2H, s), 3.78-3.88 (2H, m), 4.10-4.17 (2H, m), 4.21 (2H, m), 4.57 (2H, s), 4.64 (1H, m), 6.53 (1H, s), 6.88 (1H, d, J = 8.3 Hz), 7.00-7.05 (2H, m), 7.12 (1H, d, J = 8.3 Hz). | ESI-MS m/z: 507 [M + H]+ |

TABLE 66-continued

| Example | Structural formula | NMR | MS |
|---|---|---|---|
| 508 | | 1H-NMR (CDCl₃) δ: 2.89 (1H, m), 3.21 (1H, m), 3.65 (2H, t, J = 5.5 Hz), 4.21-4.23 (4H, m), 4.36 (2H, s), 4.65 (1H, m), 6.63 (1H, s), 6.87-6.95 (4H, m), 6.98-7.16 (5H, m). | ESI-MS m/z: 393 [M + H]+ |
| 509 | | 1H-NMR (CDCl₃) δ: 2.77 (1H, m), 3.06-3.23 (5H, m), 3.86 (2H, s), 4.10-4.24 (4H, m), 4.56 (1H, m), 6.77 (1H, d, J = 8.7 Hz), 6.90 (1H, d, J = 8.6 Hz), 7.00 (1H, m), 7.07 (1H, dd, J = 2.3, 8.5 Hz), 7.30-7.37 (5H, m). | ESI-MS m/z: 491 [M + H]+ |
| 510 | | 1H-NMR (CDCl₃) δ: 2.71 (2H, q, J = 8.1 Hz), 2.88 (1H, m), 2.97-3.01 (2H, m), 3.20 (1H, dd, J = 5.5, 16.8 Hz), 3.77 (1H, m), 3.99-4.09 (3H, m), 4.21 (2H, d, J = 3.0 Hz), 4.59 (1H, s), 4.64 (1H, m), 4.80 (1H, s), 6.56 (1H, m), 6.87-6.92 (2H, m), 7.06-7.07 (2H, m), 7.12-7.24 (6H, m). | ESI-MS m/z: 431 [M + H]+ |
| 511 | | 1H-NMR (CDCl₃) δ: 2.87 (1H, dd, J = 4.1, 16.5 Hz), 3.19 (1H, dd, J = 5.3, 16.6 Hz), 3.82 (2H, t, J = 5.5 Hz), 4.19-4.21 (4H, m), 4.50 (2H, s), 4.63 (1H, m), 6.58 (1H, s), 6.87-6.92 (2H, m), 7.04-7.07 (2H, m), 7.14 (1H, m), 7.75-7.78 (2H, m), 7.93 (1H, m), 8.23 (1H, m). | ESI-MS m/z: 507 [M + H]+ |
| 512 | | 1H-NMR (CDCl₃) δ: 2.37 (3H, s), 2.97 (1H, m), 3.23 (1H, dd, J = 4.9, 16.8 Hz), 4.09-4.18 (2H, m), 4.20-4.21 (2H, m), 4.28 (2H, s), 4.66 (1H, m), 4.82 (2H, s), 6.33 (1H, s), 6.96 (1H, d, J = 8.5 Hz), 7.34 (1H, s), 7.39 (1H, d, J = 8.2 Hz), 7.49 (1H, s), 7.63 (1H, d, J = 7.8 Hz). | ESI-MS m/z: 448 [M + H]+ |
| 513 | | 1H-NMR (CDCl₃) δ: 2.94-2.99 (1H, m), 3.20-3.26 (1H, s), 4.12 (2H, m), 4.18-4.21 (2H, m), 4.29 (2H, m), 4.64-4.69 (1H, m), 5.12 (2H, s), 6.73-6.77 (1H, m), 6.96-7.00 (1H, m), 7.35-7.43 (3H, m), 7.76-7.82 (1Hm), 8.24-8.29 (1H, m). | ESI-MS m/z: 463 [M + H]+ |

TABLE 66-continued

| Example | Structural formula | NMR | MS |
|---|---|---|---|
| 514 | | 1H-NMR (CDCl₃) δ: 2.94-2.99 (1H, m), 3.20-3.25 (1H, m), 4.13 (2H, m), 4.18 (2H, m), 4.29 (2H, m), 4.62-4.70 (1H, m), 5.11 (2H, s), 6.95-6.99 (1H, m), 7.14-7.16 (1H, m), 7.35-7.41 (3H, m), 7.64-7.68 (1H, m), 8.32-8.35 (1H, m). | ESI-MS m/z: 479 [M + H]+ |
| 515 | | 1H-NMR (CDCl₃) δ: 2.87-2.90 (1H, m), 3.10-3.19 (1H, m), 4.06-4.28 (6H, m), 4.46-4.51 (1H, m), 5.00 (2H, s), 6.73-6.82 (1H, m), 7.00-7.11 (3H, m), 7.69-7.79 (2H, m), 8.30 (1H, m), 8.81 (1H, m). | ESI-MS m/z: 411 [M + H]+ |

TABLE 67

| Example | Structural formula | NMR | MS |
|---|---|---|---|
| 516 | | 1H-NMR (CDCl₃) δ: 1.30 (3H, t, J = 7.60 Hz), 2.79 (2H, t, J = 7.60 Hz), 2.92-2.97 (1H, m), 3.15-3.21 (1H, m), 4.13-4.20 (4H, m), 4.23-4.33 (2H, m), 4.64 (1H, m), 5.08 (2H, s), 6.91-6.93 (1H, m), 7.00-7.02 (1H, m), 7.38-7.43 (2H, m), 7.55-7.58 (1H, m), 7.60-7.64 (1H, m), 7.90-7.92 (1H, m). | ESI-MS m/z: 430 [M + H]+ |
| 517 | | 1H-NMR (CDCl₃) δ: 2.91 (1H, dd, J = 3.3, 16.9 Hz), 3.17 (1H, dd, J = 5.3, 17.0 Hz), 4.11-4.28 (6H, m), 4.62 (1H, m), 4.87 (2H, s), 6.91 (1H, d, J = 8.6 Hz), 7.07 (1H, d, J = 7.6 Hz), 7.31 (1H, s), 7.36 (1H, d, J = 8.5 Hz), 7.41 (1H, m), 7.73 (1H, dd, J = 1.7, 8.4 Hz), 7.82 (1H, d, J = 8.4 Hz), 7.86 (1H, s), 8.16 (1H, d, J = 7.5 Hz), 8.91 (1H, m). | ESI-MS m/z: 495 [M + H]+ |

TABLE 67-continued

| Example | Structural formula | NMR | MS |
|---|---|---|---|
| 518 | | 1H-NMR (CDCl₃) δ: 2.99 (1H, m), 3.23 (1H, dd, J = 5.7, 17.1 Hz), 3.78 (3H, s), 4.10-4.12 (2H, m), 4.22-4.24 (2H, m), 4.26-4.35 (2H, m), 4.71 (1H, m), 4.97 (2H, s), 6.63 (1H, d, J = 2.3 Hz), 6.93 (1H, d, J = 8.4 Hz), 7.31-7.38 (3H, m), 8.62 (1H, d, J = 7.9 Hz). | ESI-MS m/z: 448 [M + H]+ |
| 519 | | 1H-NMR (CDCl₃) δ: 2.97 (1H, dd, J = 4.0, 16.7 Hz), 3.22 (1H, dd, J = 5.3, 16.9 Hz), 3.46 (1H, m), 4.10-4.15 (2H, m), 4.19-4.21 (2H, m), 4.28 (2H, m), 4.65 (1H, m), 4.75 (2H, s), 5.04 (2H, s), 6.95 (1H, d, J = 8.6 Hz), 7.11 (1H, d, J = 7.7 Hz), 7.34-7.40 (3H, m), 7.72 (1H, t, J = 7.8 Hz), 8.08 (1H, d, J = 7.8 Hz). | ESI-MS m/z: 475 [M + H]+ |
| 520 | | 1H-NMR (CDCl₃) δ: 2.96 (1H, dd, J = 4.2, 16.8 Hz), 3.22 (1H, dd, J = 5.3, 16.7 Hz), 3.94 (2H, m), 4.11-4.14 (2H, m), 4.18-4.21 (2H, m), 4.28 (2H, d, J = 3.2 Hz), 4.65 (1H, m), 4.75 (2H, s), 5.05 (2H, s), 6.95 (1H, d, J = 8.6 Hz), 7.29 (1H, d, J = 7.6 Hz), 7.34 (1H, s), 7.36-7.40 (2H, m), 7.75 (1H, t, J = 7.8 Hz), 8.18 (1H, d, J = 8.0 Hz). | ESI-MS m/z: 557 [M + H]+ |
| 521 | | 1H-NMR (CDCl₃) δ: 1.55 (6H, s), 2.97 (1H, dd, J = 4.3, 16.8 Hz), 3.22 (1H, dd, J = 5.3, 16.8 Hz), 4.13-4.15 (2H, m), 4.18-4.21 (2H, m), 4.29 (2H, m), 4.58 (1H, s), 4.65 (1H, m), 5.05 (2H, s), 6.96 (1H, d, J = 8.5 Hz), 7.22 (1H, s), 7.25 (1H, dd, J = 0.8, 7.8 Hz), 7.35 (1H, s), 7.39 (1H, d, J = 6.9 Hz), 7.74 (1H, t, J = 7.9 Hz), 8.13 (1H, dd, J = 0.8, 7.9 Hz). | ESI-MS m/z: 503 [M + H]+ |
| 522 | | 1H-NMR (CDCl₃) δ: 2.97 (1H, dd, J = 4.5, 17.0 Hz), 3.21 (1H, dd, J = 5.3, 16.8 Hz), 3.46 (2H, s), 4.11-4.28 (7H, m), 4.54-4.68 (3H, m), 5.05 (2H, s), 6.95 (1H, d, J = 8.5 Hz), 7.26-7.28 (1H, m), 7.34 (1H, s), 7.38 (1H, m), 7.50 (1H, d, J = 7.7 Hz), 7.73 (1H, t, J = 7.8 Hz), 8.07 (1H, d, J = 7.9 Hz). | ESI-MS m/z: 489 [M + H]+ |

TABLE 67-continued

| Example | Structural formula | NMR | MS |
|---|---|---|---|
| 523 | 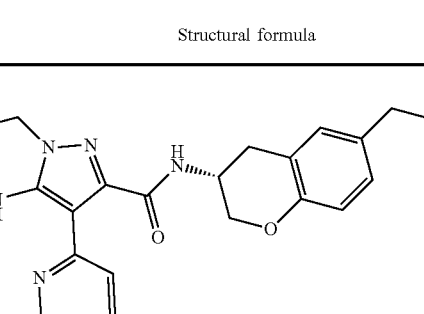 | 1H-NMR (CDCl₃) δ: 2.97 (1H, dd, J = 4.3, 16.8 Hz), 3.23 (1H, dd, J = 5.4, 16.7 Hz), 3.55 (2H, m), 4.11-4.14 (2H, m), 4.18-4.20 (2H, m), 4.29 (2H, d, J = 3.3 Hz), 4.65 (1H, m), 5.07 (2H, s), 6.96 (1H, d, J = 8.6 Hz), 7.15 (1H, d, J = 7.6 Hz), 7.30 (1H, d, J = 9.0 Hz), 7.35 (1H, s), 7.39 (1H, d, J = 8.5 Hz), 7.71 (1H, t, J = 7.8 Hz), 8.31 (1H, d, J = 8.0 Hz). | ESI-MS m/z: 527 [M + H]+ |
| 524 | | 1H-NMR (CDCl₃) δ: 2.18 (2H, m), 2.50 (3H, s), 2.93-2.99 (1H, m), 3.19-3.25 (1H, q, J = 7.34 Hz), 3.46 (2H, m), 4.09 (2H, m), 4.21-4.33 (2H, m), 4.62-4.69 (1H, m), 6.85 (1H, m), 6.95 (1H, m), 7.23 (1H, m), 7.21-7.38 (2H, m), 7.47 (1H, s), 7.54 (1H, m), 8.32 (1H, m). | ESI-MS m/z: 458 [M + H]+ |

TABLE 68

| Example | Structural formula | NMR | MS |
|---|---|---|---|
| 525 | 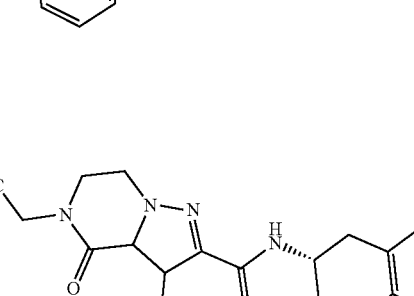 | 1H-NMR (CDCl₃) δ: 2.14-2.20 (2H, m), 2.89-2.94 (1H, m), 3.18-3.23 (1H, m), 3.44 (2H, m), 3.78-3.86 (2H, m), 4.07-4.11 (2H, m), 4.24 (2H, m), 4.59 (2H, s), 4.60-4.66 (2H, m), 6.83-6.88 (1H, m), 6.96-6.99 (1H, m), 7.04-7.06 (1H, m), 7.10-7.21 (1H, m), 7.31-7.40 (2H, m), 7.62-7.66 (1H, m), 8.40-8.41 (1H, m), 8.51-8.53 (1H, m). | ESI-MS m/z: 488 [M + H]+ |
| 526 | | 1H-NMR (CDCl₃) δ: 2.96 (1H, d, J = 16.8 Hz), 3.24 (1H, d, J = 16.1 Hz), 3.90 (2H, s), 4.19-4.43 (6H, m), 4.69 (1H, s), 6.96 (1H, d, J = 8.0 Hz), 7.30-7.62 (6H, m). | ESI-MS m/z: 529 [M + H]+ |

TABLE 68-continued

| Example | Structural formula | NMR | MS |
|---|---|---|---|
| 527 | | 1H-NMR (CDCl₃) δ: 2.97 (1H, m), 3.23 (1H, m), 4.07-4.37 (6H, m), 4.65 (1H, m), 4.92-5.09 (4H, m), 6.97 (1H, d, J = 8.8 Hz), 7.26-7.41 (4H, m), 7.82 (1H, t, J = 7.8 Hz), 8.31 (1H, m). | ESI-MS m/z: 543 [M + H]+ |
| 528 | | 1H-NMR (CDCl₃) δ: 2.03 (2H, m), 2.87 (1H, d, J = 18.1 Hz), 3.18 (1H, dd, J = 5.8, 16.5 Hz), 4.05 (2H, m), 4.21 (1H, d, J = 5.5 Hz), 4.28 (1H, m), 4.54 (2H, m), 4.68 (3H, m), 6.94 (1H, d, J = 8.5 Hz), 7.14 (1H, m), 7.32 (1H, s), 7.39 (1H, d, J = 8.3 Hz), 7.48 (1H, d, J = 7.9 Hz), 7.71 (1H, td, J = 1.8, 7.8 Hz), 8.19 (1H, d, J = 4.1 Hz), 8.84 (1H, d, J = 7.6 Hz). | ESI-MS m/z: 459 [M + H]+ |
| 529 | | 1H-NMR (CDCl₃) δ: 2.86 (1H, d, J = 4.8 Hz), 3.91 (3H, s), 4.13-4.15 (2H, m), 4.21-4.27 (3H, m), 4.38 (1H, dd, J = 3.8, 11.0 Hz), 4.67 (1H, m), 4.96 (1H, t, J = 8.1 Hz), 5.18 (2H, d, J = 3.0 Hz), 6.61 (1H, d, J = 7.7 Hz), 6.98 (1H, d, J = 8.8 Hz), 7.49 (1H, d, J = 10.6 Hz), 7.55 (1H, d, J = 7.7 Hz), 7.60 (1H, t, J = 7.9 Hz), 7.66 (1H, d, J = 1.6 Hz), 7.87 (1H, d, J = 7.8 Hz). | ESI-MS m/z: 491 [M + H]+ |
| 530 | | 1H-NMR (CDCl₃) δ: 2.92 (1H, m), 3.22 (1H, m), 4.01-4.13 (4H, m), 4.26 (2H, d, J = 12.7 Hz), 4.59-4.65 (2H, m), 4.82 (1H, d, J = 15.4 Hz), 6.02 (1H, s), 6.53 (1H, m), 6.95 (1H, d, J = 8.2 Hz), 7.16 (1H, s), 7.27-7.40 (3H, m), 7.68 (2H, s), 8.45 (1H, s). | ESI-MS m/z: 475 [M + H]+ |
| 531 | | 1H-NMR (CDCl₃) δ: 2.95 (1H, dd, J = 4.1, 16.6 Hz), 3.07 (4H, s), 3.23 (1H, dd, J = 5.4, 16.7 Hz), 3.93-3.96 (2H, m), 4.02-4.05 (2H, m), 4.28 (2H, m), 4.35 (2H, s), 4.67 (1H, m), 6.96 (1H, d, J = 8.5 Hz), 7.06-7.12 (3H, m), 7.35 (1H, s), 7.39 (1H, d, J = 8.6 Hz), 7.53 (1H, td, J = 1.8, 7.6 Hz), 8.52 (1H, m). | ESI-MS m/z: 473 [M + H]+ |

TABLE 68-continued

| Example | Structural formula | NMR | MS |
|---|---|---|---|
| 532 | | 1H-NMR (CDCl₃) δ: 0.71 (2H, m), 1.11 (2H, m), 2.16-2.36 (2H, m), 2.90 (1H, dd, J = 16.8, 5.0 Hz), 3.17 (1H, dd, J = 16.6, 5.3 Hz), 3.77-3.84 (3H, m), 3.89 (1H, dd, J = 10.5, 5.1 Hz), 4.10 (1H, m), 4.16-4.33 (3H, m), 4.39 (1H, m), 4.63 (1H, m), 6.03 (1H, s), 6.92 (1H, m), 6.93 (1H, d, J = 8.5 Hz), 7.39 (1H, m), 7.42 (1H, dd, J = 8.5, 2.0 Hz). | ESI-MS m/z: 427 [M + H]+ |
| 533 | | 1H-NMR (CDCl₃) δ: 1.11 (2H, m), 2.16-2.40 (2H, m), 2.92 (1H, dd, J = 16.8, 4.4 Hz), 3.19 (1H, dd, J = 16.7, 5.3 Hz), 3.72-3.84 (3H, m), 3.88 (1H, dd, J = 10.5, 5.1 Hz), 4.09 (1H, m), 4.16-4.29 (3H, m), 4.39 (1H, m), 4.65 (1H, m), 6.03 (1H, s), 6.95 (1H, d, J = 8.6 Hz), 6.97 (1H, m), 7.33 (1H, m), 7.38 (1H, d, J = 8.6 Hz). | ESI-MS m/z: 470 [M + H]+ |

TABLE 69

| Example | Structural formula | NMR | MS |
|---|---|---|---|
| 534 (isomer A) | | 1H-NMR (CDCl₃) δ: 2.23-2.39 (2H, m), 3.18 (1H, s), 4.12 (1H, m), 4.18-4.26 (2H, m), 4.33-4.44 (2H, m), 4.63 (1H, m), 4.91 (1H, d, J = 3.5 Hz), 5.97 (1H, m), 6.10 (1H, s), 6.97 (1H, d, J = 8.6 Hz), 7.30 (1H, d, J = 8.8 Hz), 7.48 (1H, dd, J = 2.1, 8.6 Hz), 7.58 (1H, d, J = 1.6 Hz). | ESI-MS m/z: 434 [M + H]+ |
| 534 (isomer B) | | 1H-NMR (CDCl₃) δ: 2.24-2.39 (2H, m), 3.12 (1H, s), 4.12 (1H, m), 4.23-4.32 (2H, m), 4.34-4.46 (2H, m), 4.50 (1H, dd, J = 2.2, 11.3 Hz), 4.76 (1H, t, J = 3.8 Hz), 5.96 (1H, m), 6.08 (1H, s), 6.97-7.03 (2H, m), 7.49 (1H, dd, J = 2.1, 8.7 Hz), 7.65 (1H, d, J = 1.8 Hz). | ESI-MS m/z: 434 [M + H]+ |
| 535 | | 1H-NMR (CDCl₃) δ: 2.30 (2H, m), 3.42 (3H, m), 4.10 (1H, m), 4.16-4.33 (5H, m), 4.64 (1H, m), 5.92 (1H, td, J =, 54.5, 3.4 Hz), 6.09 (1H, s), 6.90 (1H, d, J = 9.0 Hz), 7.12 (1H, m), 7.44 (1H, d, J = 9.0 Hz), 7.45 (1H, s). | ESI-MS m/z: 448 [M + H]+ |

TABLE 69-continued

| Example | Structural formula | NMR | MS |
|---|---|---|---|
| 536 | 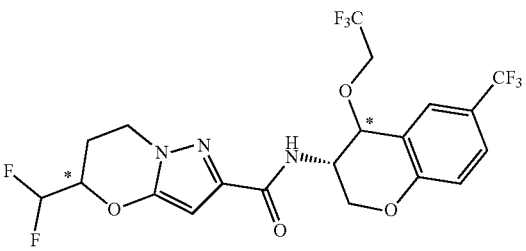 [SMILES: O=C(N[C@H]1COc2ccc(C(F)(F)F)cc2C1OCC(F)(F)F)c1cc2n(n1)CCC(C(F)F)O2] | 1H-NMR (CDCl₃) δ: 1.56 (3H, m), 1.68 (3H, m), 2.33 (1H, m), 4.07-4.44 (3H, m), 4.49 (1H, m), 5.95 (1H, dd, J = 49.3, 3.4 Hz), 6.06 (1H, s), 7.04 (1H, m), 7.05 (1H, d, J = 8.6 Hz), 7.52 (1H, dd, J = 8.6, 2.0 Hz), 7.55 (1H, m). | ESI-MS m/z: 516 [M + H]+ |
| 537 | 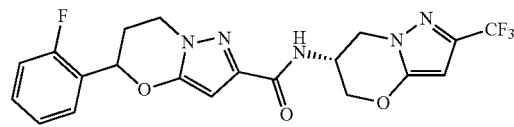 [SMILES: O=C(N[C@H]1COc2cc(C(F)(F)F)nn2C1)c1cc2n(n1)CCC(c1ccccc1F)O2] | 1H-NMR (CDCl₃) δ: 2.38-2.50 (2H, m), 4.10-4.29 (2H, m), 4.34-4.37 (2H, m), 4.43-4.47 (2H, m), 4.86 (1H, m), 5.58 (1H, m), 5.86 (1H, s), 6.13 (1H, s), 7.11 (1H, m), 7.20-7.39 (3H, m), 7.47 (1H, m). | ESI-MS m/z: 452 [M + H]+ |
| 538 | 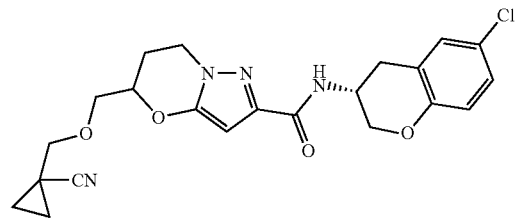 [SMILES: N#CC1(COCC2CCn3nc(C(=O)N[C@H]4COc5ccc(Cl)cc5C4)cc3O2)CC1] | 1H-NMR (CDCl₃) δ: 0.98 (2H, m), 1.32 (2H, m), 2.18-2.36 (2H, m), 2.85 (1H, dd, J = 16.8, 4.3 Hz), 3.14 (1H, dd, J = 16.7, 5.3 Hz), 3.55 (2H, m), 3.76 (1H, ddd, J = 10.5, 4.8, 1.2 Hz), 3.83 (1H, dd, J = 10.5, 5.1 Hz), 4.10 (1H, m), 4.16-4.28 (3H, m), 4.38 (1H, m), 4.61 (1H, m), 6.01 (1H, s), 6.81 (1H, d, J = 8.7 Hz), 6.99 (1H, d, J = 7.8 Hz), 7.04 (1H, d, J = 2.6 Hz), 7.08 (1H, dd, J = 8.7, 2.5 Hz). | ESI-MS m/z: 443 [M + H]+ |
| 539 | 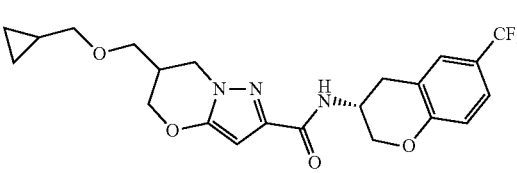 | 1H-NMR (CDCl₃) δ: 0.17-0.21 (2H, m), 0.50-0.56 (2H, m), 1.02 (1H, m), 2.60 (1H, m), 2.92 (1H, m), 3.20 (1H, dd, J = 5.4, 16.7 Hz), 3.28 (2H, dd, J = 2.8, 6.8 Hz), 3.51 (2H, dd, J = 2.1, 6.5 Hz), 4.00 (1H, m), 4.15-4.21 (2H, m), 4.24-4.26 (2H, m), 4.34 (1H, dd, J = 3.1, 11.2 Hz), 4.64 (1H, m), 6.02 (1H, s), 6.94-6.97 (2H, m), 7.33 (1H, s), 7.38 (1H, m). | ESI-MS m/z: 452 [M + H]+ |
| 540 | 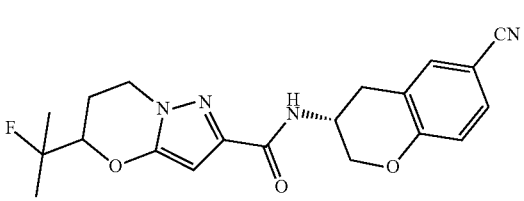 [SMILES: CC(C)(F)C1CCn2nc(C(=O)N[C@H]3COc4ccc(C#N)cc4C3)cc2O1] | 1H-NMR (CDCl₃) δ: 1.47 (3H, m), 1.51 (3H, m), 2.17 (1H, m), 2.31 (1H, m), 2.91 (3H, dd, J = 16.7, 4.7 Hz), 3.17 (1H, dd, J = 16.7, 5.3 Hz), 4.08-4.13 (2H, m), 4.21-4.34 (3H, m), 4.63 (1H, m), 6.04 (1H, s), 6.92 (1H, d, J = 8.5 Hz), 6.96 (1H, m), 7.38 (1H, d, J = 2.0 Hz), 7.42 (1H, dd, J = 8.5, 2.0 Hz). | ESI-MS m/z: 385 [M + H]+ |
| 541 | 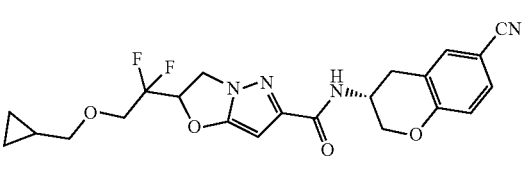 [SMILES: N#Cc1ccc2c(c1)C[C@@H](NC(=O)c1cc3n(n1)CC(C(F)(F)COCC1CC1)O3)CO2] | 1H-NMR (CDCl₃) δ: 0.16-0.22 (2H, m), 0.51-0.58 (2H, m), 1.01 (1H, m), 2.90 (1H, dd, J = 4.7, 16.6 Hz), 3.17 (1H, m), 3.32-3.42 (2H, m), 3.77-3.98 (2H, m), 4.23-4.30 (2H, m), 4.38 (1H, m), 4.49 (1H, dd, J = 6.2, 10.5 Hz), 4.63 (1H, m), 5.59 (1H, m), 5.96 (1H, s), 6.90-6.94 (2H, m), 7.38 (1H, s), 7.43 (1H, dd, J = 1.8, 8.5 Hz). | ESI-MS m/z: 445 [M + H]+ |

TABLE 70

| Example | Structural formula | NMR | MS |
|---|---|---|---|
| 542 | | 1H-NMR (CDCl3) δ: 2.27-2.40 (3H, m), 2.59 (1H, m), 2.89 (1H, dd, J = 5.1, 17.2 Hz), 3.39-3.48 (2H, m), 3.96 (1H, m), 4.16-4.30 (5H, m), 4.48 (1H, m), 6.06 (1H, s), 6.73 (1H, m), 6.96-7.05 (3H, m). | ESI-MS m/z: 446 [M + H]+ |
| 543 | | 1H-NMR (CDCl3) δ: 0.96-1.00 (3H, m), 1.96 (1H, m), 2.19 (1H, m), 2.85-2.96 (2H, m), 3.18 (1H, m), 3.44 (1H, m), 3.83 (2H, dq, J = 1.4, 11.7 Hz), 4.04 (1H, m), 4.17-4.23 (3H, m), 4.29 (1H, m), 4.57 (2H, s), 4.62 (1H, m), 6.22 (1H, s), 6.88 (1H, d, J = 8.3 Hz), 7.01 (1H, m), 7.05 (1H, s), 7.12 (1H, dd, J = 2.1, 8.3 Hz). | ESI-MS m/z: 440 [M + H]+ |
| 544 | | 1H-NMR (CDCl3) δ: 1.06 (3H, d, J = 7.4 Hz), 1.88 (1H, m), 2.06 (1H, m), 2.35 (2H, m), 4.13 (1H, m), 4.23-4.31 (2H, m), 4.33-4.45 (2H, m), 4.52 (1H, dd, J =10.8, 3.0 Hz), 4.64 (1H, m), 5.97 (1H, td, J = 55.1, 3.4 Hz), 6.10 (1H, s), 6.76 (1H, d, J = 9.2 Hz), 6.99 (1H, 8.6 Hz), 7.49 (1H, dd, J = 8.6, 1.8 Hz), 7.79 (1H, d, J = 1.8 Hz). | ESI-MS m/z: 462 [M + H]+ |
| 545 | | 1H-NMR (CDCl3) δ: 0.58 (2H, t, J = 5.2 Hz), 0.68 (2H, t, J = 5.3 Hz), 1.66 (2H, m), 2.88 (1H, m), 3.18 (1H, dd, J = 5.4, 16.7 Hz), 3.74 (2H, s), 3.82 (2H, q, J = 8.7 Hz), 4.21-4.24 (4H, m), 4.57 (2H, s), 4.64 (1H, m), 6.24 (1H, s), 6.88 (1H, d, J = 8.3 Hz), 7.00-7.05 (2H, m), 7.12 (1H, dd, J = 2.0, 8.3 Hz). | ESI-MS m/z: 452 [M + H]+ |
| 546 | | 1H-NMR (CDCl3) δ: 2.39 (2H, m), 4.18 (1H, m), 4.27 (1H, m), 4.31-4.47 (3H, m), 4.85 (1H, m), 5.39 (1H, d, J = 3.1 Hz), 5.98 (1H, td, J =, 55.1, 3.5 Hz), 6.11 (1H, s), 7.01 (1H, d, J = 8.6 Hz), 7.04 (1H, m), 7.56 (1H, m), 7.57 (1H, d, J = 8.6 Hz). | ESI-MS m/z: 502 [M + H]+ |
| 547 (isomer A) | | 1H-NMR (CDCl3) δ: 1.47 (3H, m), 1.51 (3H, m), 2.17 (1H, m), 2.31 (1H, m), 2.91 (1H, dd, J = 16.7, 4.7 Hz), 3.17 (1H, dd, J = 16.7, 5.3 Hz), 4.08-4.13 (2H, m), 4.21-4.34 (3H, m), 4.63 (1H, m), 6.04 (1H, s), 6.92 (1H, d, J = 8.5 Hz), 6.96 (1H, m), 7.38 (1H, d, J = 2.0 Hz), 7.42 (1H, dd, J = 8.5, 2.0 Hz). | ESI-MS m/z: 385 [M + H]+ |
| 547 (isomer B) | | 1H-NMR (CDCl3) δ: 1.47 (3H, m), 1.51 (3H, m), 2.17 (1H, m), 2.31 (1H, m, 2.91 (1H, dd, J =16.7, 4.7 Hz), 3.17 (1H, dd, J = 16.7, 5.3 Hz), 4.08-4.13 (2H, m), 4.21-4.34 (3H, m), 4.63 (1H, m), 6.04 (1H, s), 6.92 (1H, d, J = 8.5 Hz), 6.96 (1H, m), 7.38 (1H, d, J = 2.0 Hz), 7.42 (1H, dd, J = 8.5, 2.0 Hz). | ESI-MS m/z: 385 [M + H]+ |

TABLE 70-continued

| Example | Structural formula | NMR | MS |
|---|---|---|---|
| 548 | | 1H-NMR (CDCl₃) δ: 1.37 (1H, m), 2.38 (1H, m), 2.80-2.90 (3H, m), 3.11-3.24 (3H, m), 3.93 (1H, m), 4.11-4.24 (4H, m), 4.35 (1H, dd, J = 3.0, 11.1 Hz), 4.60 (1H, m), 6.01 (1H, s), 6.81 (1H, d, J = 8.7 Hz), 6.98 (1H, d, J = 8.0 Hz), 7.04 (1H, d, J = 2.4 Hz), 7.08 (1H, dd, J = 2.5, 8.7 Hz). | ESI-MS m/z: 445 [M + H]+ |
| 549 | | 1H-NMR (CDCl₃) δ: 1.06 (3H, t, J = 7.5 Hz), 1.67-1.88 (2H, m), 2.07 (1H, m), 2.18 (1H, m), 3.10 (1H, dd, J = 17.6, 4.5 Hz), 3.39 (1H, dd, J = 17.6, 6.5 Hz), 4.02-4.19 (3H, m), 4.22-4.36 (2H, m), 4.75 (1H, m), 6.00 (1H, s), 6.90 (1H, d, J = 7.7 Hz), 7.28 (1H, d, J = 8.5 Hz), 7.48 (1H, d, J = 8.5 Hz). | ESI-MS m/z: 397 [M + H]+ |

TABLE 71

| Example | Structural formula | NMR | MS |
|---|---|---|---|
| 550 | | 1H-NMR (CDCl₃) δ: 2.39 (1H, m), 2.48 (1H, m), 3.12 (1H, dd, J = 17.6, 4.8 Hz), 3.40 (1H, dd, J = 17.6, 5.6 Hz), 4.13-4.37 (4H, m), 4.77 (1H, m), 5.57 (1H, dd, J = 9.5, 2.4 Hz), 6.13 (1H, s), 6.94 (1H, d, J = 7.4 Hz), 7.11 (1H, dd, J = 10.2, 8.5 Hz), 7.21 (1H, d, J = 7.4 Hz), 7.29 (1H, d, J = 8.5 Hz), 7.37 (1H, m), 7.44-7.52 (2H, m). | ESI-MS m/z: 463 [M + H]+ |
| 551 | | 1H-NMR (CDCl₃) δ: 2.34 (2H, m), 2.98 (1H, dd, J = 17.7, 4.4 Hz), 3.11 (1H, dd, J = 17.7, 5.3 Hz), 3.83 (3H, s), 4.19-4.32 (3H, m), 4.39 (1H, m), 4.66 (1H, m), 5.97 (1H, td, J = 54.8, 3.4 Hz), 6.09 (1H, s), 7.01 (1H, d, J = 8.6 Hz), 6.73 (1H, d, J = 8.8 Hz), 6.92 (1H, d, J = 7.2 Hz), 7.38 (1H, d, J = 8.8 Hz). | ESI-MS m/z: 448 [M + H]+ |
| 552 (isomer A) | | 1H-NMR (CDCl₃) δ: 0.71 (2H, m), 1.11 (2H, m), 2.16-2.36 (2H, m), 2.90 (1H, dd, J = 16.8, 5.0 Hz), 3.17 (1H, dd, J = 16.6, 5.3 Hz), 3.77-3.84 (3H, m), 3.89 (1H, dd, J = 10.5, 5.1 Hz), 4.10 (1H, m), 4.16-4.33 (3H, m), 4.39 (1H, m), 4.63 (1H, m), 6.03 (1H, s), 6.92 (1H, m), 6.93 (1H, d, J = 8.5 Hz), 7.39 (1H, m), 7.42 (1H, dd, J = 8.5, 2.0 Hz). | ESI-MS m/z: 427 [M + H]+ |

TABLE 71-continued

| Example | Structural formula | NMR | MS |
|---|---|---|---|
| 552 (isomer B) | | 1H-NMR (CDCl₃) δ: 0.71 (2H, m), 1.11 (2H, m), 2.16-2.36 (2H, m), 2.90 (1H, dd, J =16.8, 5.0 Hz), 3.17 (1H, dd, J = 16.6, 5.3 Hz), 3.77-3.84 (3H, m), 3.89 (1H, dd, J = 10.5, 5.1 Hz), 4.10 (1H, m), 4.16-4.33 (3H, m), 4.39 (1H, m), 4.63 (1H, m), 6.03 (1H, s), 6.92 (1H, m), 6.93 (1H, d, J = 8.5 Hz), 7.39 (1H, m), 7.42 (1H, dd, J = 8.5, 2.0 Hz). | ESI-MS m/z: 427 [M + H]+ |
| 553 | | 1H-NMR (CDCl₃) δ: 0.98 (2H, m), 1.31 (2H, m), 2.16-2.39 (2H, m), 2.93 (1H, dd, J = 16.8, 4.6 Hz), 3.19 (1H, dd, J = 16.7, 5.4 Hz), 3.54 (2H, m), 3.74 (1H, dd J = 20.4, 5.0 Hz), 3.84 (1H, dd, J = 10.4, 4.8 Hz), 4.11 (1H, m), 4.17-4.29 (3H, m), 4.39 (1H, m), 4.64 (1H, m), 6.02 (1H, s), 6.94 (1H, d, J = 8.5 Hz), 6.98 (1H, d, J = 7.9 Hz), 7.33 (1H, d, J = 1.4 Hz), 7.38 (1H, dd, J = 8.5, 1.4 Hz). | ESI-MS m/z: 477 [M + H]+ |
| 554 (isomer A) | | 1H-NMR (CDCl₃) δ: 0.98 (2H, m), 1.31 (2H, m), 2.16-2.39 (2H, m), 2.93 (1H, dd, J = 16.8, 4.6 Hz), 3.19 (1H, dd, J = 16.7, 5.4 Hz), 3.54 (2H, m), 3.74 (1H, dd J = 20.4, 5.0 Hz), 3.84 (1H, dd, J = 10.4, 4.8 Hz), 4.11 (1H, m), 4.17-4.29 (3H, m), 4.39 (1H, m), 4.64 (1H, m), 6.02 (1H, s), 6.94 (1H, d, J = 8.5 Hz), 6.98 (1H, d, J = 7.9 Hz), 7.33 (1H, d, J = 1.4 Hz), 7.38 (1H, dd, J = 8.5, 1.4 Hz). | ESI-MS m/z: 477 [M + H]+ |
| 554 (isomer B) | | 1H-NMR (CDCl₃) δ: 0.98 (2H, m), 1.31 (2H, m), 2.16-2.39 (2H, m), 2.93 (1H, dd, J =16.8, 4.6 Hz), 3.19 (1H, dd, J = 16.7, 5.4 Hz), 3.54 (2H, m), 3.74 (1H, dd J = 20.4, 5.0 Hz), 3.84 (1H, dd, J = 10.4, 4.8 Hz), 4.11 (1H, m), 4.17-4.29 (3H, m), 4.39 (1H, m), 4.64 (1H, m), 6.02 (1H, s), 6.94 (1H, d, J = 8.5 Hz), 6.98 (1H, d, J = 7.9 Hz), 7.33 (1H, d, J = 1.4 Hz), 7.38 (1H, dd, J = 8.5, 1.4 Hz). | ESI-MS m/z: 477 [M + H]+ |
| 555 | | 1H-NMR (CDCl₃) δ: 1.74 (1H, m), 2.02 (1H, m), 2.39 (1H, m), 2.91 (1H, dd, J = 4.4, 16.4 Hz), 3.17 (1H, dd, J = 5.3, 16.7 Hz), 3.59-3.68 (2H, m), 3.74-3.85 (3H, m), 4.09 (1H, m), 4.23-4.33 (4H, m), 4.64 (1H, m), 6.24 (1H, s), 6.90-6.95 (2H, m), 7.39 (1H, s), 7.43 (1H, dd, J = 2.1, 8.5 Hz). | ESI-MS m/z: 451 [M + H]+ |
| 556 | | 1H-NMR (CDCl₃) δ: 1.73 (1H, m), 2.00 (1H, m), 2.37 (1H, m), 2.92 (1H, dd, J = 3.4, 16.2 Hz), 3.20 (1H, dd, J = 5.2, 16.9 Hz), 3.60-3.68 (2H, m), 3.73-3.85 (3H, m), 4.09 (1H, m), 4.22-4.33 (4H, m), 4.65 (1H, m), 6.24 (1H, s), 6.94-6.98 (2H, m), 7.33 (1H, s), 7.38 (1H, d, J = 8.6 Hz). | ESI-MS m/z: 493 [M + H]+ |

TABLE 72

| Example | Structural formula | NMR | MS |
|---|---|---|---|
| 557 | | 1H-NMR (CDCl₃) δ: 1.73 (1H, m), 2.02 (1H, m), 2.38 (1H, m), 2.87 (1H, m), 3.05 (1H, m), 3.02-3.08 (2H, m), 3.19 (1H, m), 3.64-3.68 (2H, m), 3.72-3.82 (3H, m), 4.08 (1H, m), 4.19 (2H, s), 4.28-4.33 (2H, m), 4.61 (1H, m), 5.88 (1H, dt, 4.7, 53.7 Hz), 6.23 (1H, s), 6.85 (1H, d, J = 8.4 Hz), 6.93 (1H, s), 7.01 (2H, d, J = 13.1 Hz). | ESI-MS m/z: 490 [M + H]+ |
| 558 | | 1H-NMR (CDCl₃) δ: 0.20-0.24 (2H, m), 0.54-0.58 (2H, m), 1.07 (1H, m), 2.08-2.27 (2H, m), 3.37 (2H, d, J = 6.9 Hz), 3.53 (1H, m), 3.65 (1H, m), 3.76 (1H, dd, J = 5.2, 10.4 Hz), 3.93-4.23 (3H, m), 4.31-4.39 (2H, m), 4.62 (1H, m), 4.91 (1H, t, J = 4.0 Hz), 6.04 (1H, s), 6.96 (1H, d, J = 8.6 Hz), 7.32 (1H, d, J = 8.1 Hz), 7.47 (1H, dd, J = 2.1, 8.6 Hz), 7.55 (1H, s). | ESI-MS m/z: 468 [M + H]+ |
| 559 | | 1H-NMR (CDCl₃) δ: 0.19-0.23 (2H, m), 0.54-0.57 (2H, m), 1.06 (1H, m), 1.61 (1H, s), 2.10-2.30 (2H, m), 3.36 (2H, dd, J = 1.6, 6.9 Hz), 3.65 (1H, m), 3.75 (1H, dd, J = 5.1, 10.5 Hz), 4.07 (1H, m), 4.18 (1H, m), 4.28-4.38 (2H, m), 4.44 (1H, m), 4.49 (1H, d, J = 11.4 Hz), 4.76 (1H, s), 6.01 (1H, s), 7.01 (2H, d, J = 8.5 Hz), 7.48 (1H, d, J = 7.9 Hz), 7.65 (1H, d, J = 1.9 Hz). | ESI-MS m/z: 468 [M + H]+ |
| 560 | | 1H-NMR (CDCl₃) δ: 0.17-0.20 (2H, m), 0.52-0.57 (2H, m), 1.03 (1H, m), 3.07 (1H, m), 3.37 (2H, dd, J = 1.3, 6.9 Hz), 3.74-3.82 (2H, m), 4.14-4.36 (4H, m), 4.64 (1H, m), 4.92 (1H, s), 5.41 (1H, m), 5.92 (1H, d, J = 2.2 Hz), 6.97 (1H, d, J = 8.6 Hz), 7.28 (1H, m), 7.48 (1H, dd, J = 2.1, 8.7 Hz), 7.62 (1H, d, J = 8.4 Hz). | ESI-MS m/z: 454 [M + H]+ |
| 561 | | 1H-NMR (CDCl₃) δ: 2.15-2.25 (2H, m), 3.54 (1H, m), 3.84-3.98 (4H, m), 4.05-4.23 (3H, m), 4.32-4.40 (2H, m), 4.62 (1H, m), 4.91 (1H, t, J = 4.0 Hz), 6.05 (1H, d, J = 1.0 Hz), 6.97 (1H, d, J = 8.6 Hz), 7.32 (1H, d, J = 8.7 Hz), 7.48 (1H, dd, J = 2.0, 8.7 Hz), 7.53 (1H, s). | ESI-MS m/z: 496 [M + H]+ |
| 562 | | 1H-NMR (CDCl₃) δ: 2.19 (1H, m), 2.36 (1H, m), 2.50 (1H, m), 2.71 (1H, m), 2.91 (1H, dd, J = 16.7, 4.7 Hz), 3.17 (1H, dd, J = 16.8, 5.2 Hz), 4.09-4.33 (4H, m), 4.53 (1H, m), 4.62 (1H, m), 6.03 (1H, s), 6.93 (1H, d, J = 8.5 Hz), 6.94 (1H, m), 7.38 (1H, d, J = 2.0 Hz), 7.42 (1H, dd, J = 8.5, 2.0 Hz). | ESI-MS m/z: 407 [M + H]+ |
| 563 (isomer A) | | 1H-NMR (CDCl₃) δ: 0.98 (2H, m), 1.32 (2H, m), 2.18-2.36 (2H, m), 2.85 (1H, dd, J = 16.8, 4.3 Hz), 3.14 (1H, dd, J = 16.7, 5.3 Hz), 3.55 (2H, m), 3.76 (1H, ddd, J = 10.5, 4.8, 1.2 Hz), 3.83 (1H, dd, J = 10.5, 5.1 Hz), 4.10 (1H, m), 4.16-4.28 (3H, m), 4.38 (1H, m), 4.61 (1H, m), 6.01 (1H, s), 6.81 (1H, d, J = 8.7 Hz), 6.99 (1H, d, J = 7.8 Hz), 7.04 (1H, d, J = 2.6 Hz), 7.08 (1H, dd, J = 8.7, 2.6 Hz). | ESI-MS m/z: 443 [M + H]+ |

TABLE 72-continued

| Example | Structural formula | NMR | MS |
|---|---|---|---|
| 563 (isomer B) | | 1H-NMR (CDCl₃) δ: 0.98 (2H, m), 1.32 (2H, m), 2.18-2.36 (2H, m), 2.85 (1H, dd, J = 16.8, 4.3 Hz), 3.14 (1H, dd, J = 16.7, 5.3 Hz), 3.55 (2H, m), 3.76 (1H, ddd, J = 10.5, 4.8, 1.2 Hz), 3.83 (1H, dd, J = 10.5, 5.1 Hz), 4.10 (1H, m), 4.16-4.28 (3H, m), 4.38 (1H, m), 4.61 (1H, m), 6.01 (1H, s), 6.81 (1H, d, J = 8.7 Hz), 6.99 (1H, d, J = 7.8 Hz), 7.04 (1H, d, J = 2.6 Hz), 7.08 (1H, dd, J = 8.7, 2.6 Hz). | ESI-MS m/z: 443 [M + H]+ |
| 564 | | 1H-NMR (CDCl₃) δ: 1.30-1.45 (2H, m), 1.63-1.74 (3H, m), 1.86 (1H, m), 1.97 (1H, m), 2.85 (1H, dd, J = 4.1, 16.9 Hz), 3.04 (2H, dt, J = 4.5, 17.4 Hz), 3.17 (1H, dd, J = 5.5, 16.8 Hz), 3.39-3.44 (2H, m), 3.85 (1H, m), 3.95-4.01 (2H, m), 4.19 (2H, d, J = 2.9 Hz), 4.34 (1H, m), 4.62 (1H, m), 5.38 (1H, m), 5.88 (1H, m), 5.89 (1H, s), 6.83 (1H, d, J = 8.3 Hz), 6.93 (1H, s), 7.00 (2H, d, J = 8.2 Hz). | ESI-MS m/z: 448 [M + H]+ |

TABLE 73

| Example | Structural formula | NMR | MS |
|---|---|---|---|
| 565 | | 1H-NMR (CDCl₃) δ: 1.31-1.45 (2H, m), 1.63-1.74 (3H, m), 1.87 (1H, m), 1.99 (1H, m), 2.90 (1H, m), 3.17 (1H, dd, J = 5.2, 16.6 Hz), 3.38-3.45 (2H, m), 3.85 (1H, m), 3.95-4.01 (2H, m), 4.26-4.28 (2H, m), 4.34 (1H, m), 4.63 (1H, m), 5.39 (1H, m), 5.89 (1H, s), 6.90-6.94 (2H, m), 7.38 (1H, s), 7.42 (1H, dd, J = 2.0, 8.5 Hz). | ESI-MS m/z: 409 [M + H]+ |
| 566 | | 1H-NMR (CDCl₃) δ: 2.25-2.40 (2H, m), 2.83 (1H, m), 3.14 (1H, dd, J = 5.3, 16.8 Hz), 4.08-4.22 (3H, m), 4.27 (1H, m), 4.38 (1H, m), 4.60 (1H, m), 5.96 (1H, m), 6.08 (1H, s), 6.65 (1H, d, J = 8.6 Hz), 6.98 (1H, d, J = 7.9 Hz), 7.37 (1H, s), 7.40 (1H, dd, J = 2.1, 8.6 Hz). | ESI-MS m/z: 476 [M + H]+ |
| 567 | | 1H-NMR (CDCl₃) δ: 0.70 (2H, m), 1.10 (2H, m), 2.14-2.33 (2H, m), 2.86 (1H, dd, J = 17.4, 4.4 Hz), 3.04 (2H, td, 17.4, 4.5 Hz), 3.16 (1H, dd, J = 16.7, 5.5 Hz), 3.75-3.85 (3H, m), 3.88 (1H, dd, J = 10.6, 5.1 Hz), 4.08 (1H, m), 4.14-4.27 (3H, m), 4.39 (1H, m), 4.61 (1H, m), 5.88 (1H, tt, J = 56.4, 4.6 Hz), 6.02 (1H, s), 6.83 (1H, d, J = 8.3 Hz), 6.94 (1H, d, J = 2.0 Hz), 7.00 (1H, dd, J = 8.3, 2.0 Hz), 7.03 (1H, m). | ESI-MS m/z: 466 [M + H]+ |
| 568 | | 1H-NMR (CDCl₃) δ: 2.36 (2H, m), 3.49 (3H, m), 4.18 (1H, m), 4.24-4.46 (5H, m), 4.67 (1H, m), 5.98 (1H, td, J =, 54.3, 3.5 Hz), 6.10 (1H, s), 6.97 (1H, d, J = 8.3 Hz), 7.21 (1H, d, J = 8.5 Hz), 7.51 (1H, d, J = 8.3 Hz), 7.52 (1H, m). | ESI-MS m/z: 448 [M + H]+ |

TABLE 73-continued

| Example | Structural formula | NMR | MS |
|---|---|---|---|
| 569 | | 1H-NMR (CDCl₃) δ: 3.49 (3H, d, J = 1.1 Hz), 3.91-4.00 (4H, m), 4.21-4.29 (3H, m), 4.34-4.40 (2H, m), 4.70 (1H, m), 5.44 (1H, m), 5.94 (1H, s), 6.97 (1H, d, J = 9.0 Hz), 7.20 (1H, d, J = 8.6 Hz), 7.50-7.51 (2H, m). | ESI-MS m/z: 496 [M + H]+ |
| 570 | | 1H-NMR (CDCl₃) δ: 2.23-2.29 (2H, m), 3.49 (3H, s), 3.86-3.99 (4H, m), 4.14 (1H, m), 4.24-4.32 (3H, m), 4.34 (1H, d, J = 3.6 Hz), 4.39 (1H, m), 4.70 (1H, m), 6.05 (1H, s), 6.97 (1H, d, J = 9.2 Hz), 7.21 (1H, d, J = 8.4 Hz), 7.50-7.51 (2H, m). | ESI-MS m/z: 510 [M + H]+ |
| 571 | | 1H-NMR (CDCl₃) δ: 0.22 (2H, m), 0.55 (2H, m), 1.06 (1H, m), 1.46 (1H, m), 2.09-2.33 (2H, m), 3.35-3.39 (2H, m), 3.66 (1H, m), 3.76 (1H, m), 3.96-4.31 (3.5H, m), 4.31-4.46 (2H, m), 4.60 (0.5H, m), 4.67 (0.5H, m), 4.84 (0.5H, m), 5.99 (0.5H, s), 6.04 (0.5H, s), 6.78-6.89 (1H, m), 7.03 (1H, m), 7.14-7.22 (1H, m), 7.24-7.37 (1H, m). | ESI-MS m/z: 434 [M + H]+ |
| 572 (isomer A) | | 1H-NMR (CDCl₃) δ: 1.73 (1H, m), 2.01 (1H, m), 2.38 (1H, m), 2.91 (1H, dd, J = 5.0, 17.0 Hz), 3.17 (1H, dd, J = 4.9, 16.8 Hz), 3.59-3.67 (2H, m), 3.74-3.85 (3H, m), 4.09 (1H, m), 4.24-4.34 (4H, m), 4.63 (1H, m), 6.24 (1H, s), 6.91-7.00 (2H, m), 7.39 (1H, s), 7.43 (1H, dd, J = 2.0, 8.5 Hz). | ESI-MS m/z: 451 [M + H]+ |
| 572 (isomer B) | | 1H-NMR (CDCl₃) δ: 1.74 (1H, m), 2.01 (1H, m), 2.38 (1H, m), 2.90 (1H, dd, J = 4.8, 16.5 Hz), 3.17 (1H, dd, J = 5.2, 16.7 Hz), 3.60-3.68 (2H, m), 3.75-3.85 (3H, m), 4.09 (1H, m), 4.23-4.33 (4H, m), 4.63 (1H, m), 6.24 (1H, s), 6.90-6.94 (2H, m), 7.39 (1H, s), 7.43 (1H, dd, J = 2.0, 8.5 Hz). | ESI-MS m/z: 451 [M + H]+ |

TABLE 74

| Example | Structural formula | NMR | MS |
|---|---|---|---|
| 573 | | 1H-NMR (CDCl₃) δ: 2.44 (2H, m), 4.11-4.67 (5H, m), 4.53 (0.5H, m), 4.65 (0.5H, m), 4.75 (0.5H, m), .4.92 (0.5H, m), 5.56 (1H, m), 6.06-6.14 (1H, m), 6.92-7.01 (1H, m), 7.04-7.15 (2H, m), 7.16-7.22 (1H, m), 7.37 (1H, m), 7.42-7.54 (2H, m), 7.70 (1H, m). | ESI-MS m/z: 435 [M + H]+ |
| 574 | | 1H-NMR (CDCl₃) δ: 2.25 (2H, m), 2.78-2.94 (1H, m), 2.95-3.17 (1H, m), 3.84-3.99 (4H, m), 4.02-4.40 (5H, m), 4.51-4.74 (1H, m), 6.04 (1H, s), 6.82 (1H, m), 6.95-7.03 (2H, m), 7.09 (1H, m). | ESI-MS m/z: 446 [M + H]+ |

TABLE 74-continued

| Example | Structural formula | NMR | MS |
|---|---|---|---|
| 575 (isomer A) | | 1H-NMR (CDCl₃) δ: 0.20-0.24 (2H, m), 0.54-0.59 (2H, m), 1.07 (1H, m), 2.11-2.30 (2H, m), 3.25 (1H, s), 3.38 (2H, d, J = 6.9 Hz), 3.65 (1H, dd, J = 5.2, 10.4 Hz), 3.76 (1H, dd, J = 5.2, 10.4 Hz), 4.04-4.26 (3H, m), 4.33-4.40 (2H, m), 4.64 (1H, m), 4.91 (1H, s), 6.04 (1H, s), 6.97 (1H, d, J = 8.6 Hz), 7.29 (1H, m), 7.48 (1H, dd, J = 2.1, 8.6 Hz), 7.59 (1H, s). | ESI-MS m/z: 468 [M + H]+ |
| 575 (isomer B) | | 1H-NMR (CDCl₃) δ: 0.20-0.24 (2H, m), 0.53-0.59 (2H, m), 1.07 (1H, m), 2.15-2.29 (2H, m), 3.23 (1H, s), 3.38 (2H, d, J = 6.9 Hz), 3.66 (1H, dd, J = 5.2, 10.5 Hz), 3.76 (1H, dd, J = 5.1, 10.5 Hz), 4.04 (1H, m), 4.18-4.23 (2H, m), 4.33-4.39 (2H, m), 4.64 (1H, m), 4.92 (1H, s), 6.04 (1H, s), 6.97 (1H, d, J = 8.6 Hz), 7.29 (1H, m), 7.48 (1H, dd, J = 2.1, 8.6 Hz), 7.60 (1H, s). | ESI-MS m/z: 468 [M + H]+ |
| 576 (isomer A) | | 1H-NMR (CDCl₃) δ: 0.17-0.21 (2H, m), 0.52-0.57 (2H, m), 1.03 (1H, m), 2.95 (1H, s), 3.37 (2H, d, J = 6.9 Hz), 3.75-3.83 (2H, m), 4.17-4.23 (2H, m), 4.29-4.36 (2H, m), 4.65 (1H, m), 4.93 (1H, s), 5.42 (1H, m), 5.92 (1H, s), 6.97 (1H, d, J = 8.6 Hz), 7.25 (1H, m), 7.48 (1H, dd, J = 2.2, 8.6 Hz), 7.65 (1H, d, J = 2.0 Hz). | ESI-MS m/z: 454 [M + H]+ |
| 576 (isomer B) | | 1H-NMR (CDCl₃) δ: 0.17-0.21 (2H, m), 0.52-0.57 (2H, m), 1.03 (1H, m), 3.03 (1H, s), 3.38 (2H, d, J = 6.9 Hz), 3.79 (2H, dd, J = 1.5, 4.7 Hz), 4.17-4.36 (4H, m), 4.64 (1H, m), 4.92 (1H, t, J = 4.0 Hz), 5.41 (1H, m), 5.92 (1H, s), 6.97 (1H, d, J = 8.6 Hz), 7.28 (1H, m), 7.48 (1H, dd, J = 2.0, 8.8 Hz), 7.62 (1H, d, J = 1.6 Hz). | ESI-MS m/z: 454 [M + H]+ |
| 577 (isomer A) | | 1H-NMR (CDCl₃) δ: 1.31-1.45 (2H, m), 1.62-1.74 (3H, m), 1.87 (1H, m), 1.98 (1H, m), 2.90 (1H, dd, J = 4.7, 16.7 Hz), 3.17 (1H, dd, J = 5.1, 16.8 Hz), 3.41 (2H, dt, J = 2.2, 11.8 Hz), 3.85 (1H, dd, J = 7.9, 9.8 Hz), 3.95-4.01 (2H, m), 4.26-4.37 (3H, m), 4.64 (1H, m), 5.39 (1H, m), 5.89 (1H, s), 6.90-6.94 (2H, m), 7.38 (1H, d, J = 1.8 Hz), 7.42 (1H, dd, J = 2.1, 8.5 Hz). | ESI-MS m/z: 409 [M + H]+ |
| 577 (isomer B) | | 1H-NMR (CDCl₃) δ: 1.31-1.46 (2H, m), 1.63-1.75 (3H, m), 1.87 (1H, m), 1.99 (1H, m), 2.90 (1H, dd, J = 4.5, 16.9 Hz), 3.17 (1H, dd, J = 5.4, 16.9 Hz), 3.42 (1H, dt, J = 2.2, 11.8 Hz), 3.85 (1H, dd, J = 8.0, 9.8 Hz), 3.96-4.01 (2H, m), 4.26-4.36 (3H, m), 4.64 (1H, m), 5.38 (1H, m), 5.89 (1H, s), 6.90-6.94 (2H, m), 7.38 (1H, d, J = 1.8 Hz), 7.42 (1H, dd, J = 2.0, 8.5 Hz). | ESI-MS m/z: 409 [M + H]+ |
| 578 | | 1H-NMR (CDCl₃) δ: 0.14-0.19 (2H, m), 0.49-0.56 (2H, m), 1.00 (1H, m), 2.82 (1H, d, J = 4.6, 16.7 Hz), 3.12 (1H, m), 3.33-3.38 (2H, m), 3.76-3.78 (2H, m), 4.11-4.15 (2H, m), 4.18-4.25 (2H, m), 4.57 (1H, m), 5.35 (1H, m), 6.78 (1H, d, J = 8.7 Hz), 7.02-7.08 (3H, m), 7.27 (1H, s). | ESI-MS m/z: 404 [M + H]+ |

TABLE 75

| Example | Structural formula | NMR | MS |
|---|---|---|---|
| 579 (isomer A) | | 1H-NMR (CDCl₃) δ: 2.39 (2H, m), 4.06-4.15 (1H, m), 4.20 (1H, m), 4.33-4.40 (2H, m), 4.42 (1H, m), 4.78 (1H, m), 5.51 (1H, dd, J = 54.9, 2.0 Hz), 6.00 (1H, m), 6.13 (1H, s), 7.02 (1H, d, J = 8.6 Hz), 7.17 (1H, d, J = 8.8 Hz), 7.58 (1H, d, J = 8.6 Hz), 7.63 (1H, m). | ESI-MS m/z: 436 [M + H]+ |
| 579 (isomer B) | | 1H-NMR (CDCl₃) δ: 2.17-2.44 (2H, m), 4.11 (1H, m), 4.24 (1H, m), 4.33-4.48 (3H, m), 4.70 (1H, m), 5.42 (1H, dd, J = 54.9, 2.0 Hz), 5.95 (1H, m), 6.08 (1H, s), 6.93 (1H, d, J = 8.8 Hz), 7.08 (1H, d, J = 8.6 Hz), 7.58 (1H, d, J = 8.6 Hz), 7.65 (1H, m). | ESI-MS m/z: 436 [M + H]+ |
| 580 | | 1H-NMR (CDCl₃) δ: 2.53 (3H, s), 3.31 (1H, s), 4.07-4.35 (6H, m), 4.67 (1H, m), 4.94 (1H, d, J = 3.6 Hz), 5.03 (2H, s), 6.95 (1H, d, J = 8.6 Hz), 7.01 (1H, d, J = 7.6 Hz), 7.47 (1H, dd, J = 2.1, 8.7 Hz), 7.60 (1H, t, J = 7.8 Hz), 7.63 (1H, d, J = 1.8 Hz), 7.77 (1H, d, J = 7.9 Hz), 8.05 (1H, d, J = 8.0 Hz). | ESI-MS m/z: 475 [M + H]+ |
| 581 | | 1H-NMR (CDCl₃) δ: 1.30 (3H, t, J = 7.6 Hz), 2.80 (2H, q, J = 7.6 Hz), 3.01 (1H, s), 4.12-4.37 (6H, m), 4.67 (1H, m), 4.95 (1H, m), 5.09 (2H, d, J = 3.3 Hz), 6.99 (2H, m), 7.48 (1H, dd, J = 2.3, 8.7 Hz), 7.61 (1H, t, J = 7.8 Hz), 7.65 (1H, m), 7.80 (1H, d, J = 8.4 Hz), 7.91 (1H, d, J = 7.7 Hz). | ESI-MS m/z: 489 [M + H]+ |
| 582 | | 1H-NMR (CDCl₃) δ: 0.98 (3H, dt, J = 3.6, 11.4 Hz), 1.26-1.61 (2H, m), 1.80 (1H, m), 1.91 (1H, m), 2.22 (1H, d, J = 4.7 Hz), 2.92 (1H, m), 3.20 (1H, m), 3.71 (1H, dd, J = 4.8, 12.2 Hz), 4.02 (1H, d, J = 12.3 Hz), 4.15 (1H, m), 4.25 (2H, s), 4.33 (1H, m), 4.65 (1H, m, J = 4.0 Hz), 6.26 (1H, s), 6.94-7.00 (2H, m), 7.33 (1H, s), 7.39 (1H, d, J = 8.5 Hz). | ESI-MS m/z: 426 [M + H]+ |
| 583 | | 1H-NMR (CDCl₃) δ: 1.41-1.61 (3H, m), 1.88 (2H, m), 2.08 (1H, m), 2.19 (1H, m), 2.92 (1H, dd, J = 16.7, 4.4 Hz), 3.20 (1H, dd, J = 16.7, 4.9 Hz), 3.41 (2H, m), 3.95 (1H, m), 4.04 (3H, m), 4.14-4.29 (3H, m), 4.64 (1H, m), 5.99 (1H, s), 6.94 (1H, d, J = 8.5 Hz), 6.97 (1H, m), 7.33 (1H, m), 7.37 (1H, d, J = 8.5 Hz) | ESI-MS m/z: 452 [M + H]+ |

TABLE 75-continued

| Example | Structural formula | NMR | MS |
|---|---|---|---|
| 584 | (structure) | 1H-NMR (CDCl₃) δ: 1.41-1.64 (3H, m), 1.88 (2H, m), 2.06 (1H, m), 2.20 (1H, m), 2.84 (1H, dd, J = 16.3, 4.4 Hz), 3.15 (1H, dd, J = 16.3, 4.9 Hz), 3.41 (2H, m), 3.94 (1H, m), 4.04 (3H, m), 4.14-4.25 (3H, m), 4.59 (1H, m), 5.98 (1H, s), 6.80 (1H, d, J = 8.7 Hz), 6.99 (1H, m), 7.04 (1H, d, J = 2.1 Hz), 7.08 (1H, d, J = 8.7 Hz). | ESI-MS m/z: 418 [M + H]+ |
| 585 | (structure) | 1H-NMR (CDCl₃) δ: 1.44-1.63 (3H, m), 1.88 (2H, m), 2.07 (1H, m), 2.20 (1H, m), 2.90 (1H, dd, J = 16.7, 4.7 Hz), 3.17 (1H, dd, J = 16.7, 4.6 Hz), 3.41 (2H, m), 3.96 (1H, m), 4.05 (3H, m), 4.14-4.34 (3H, m), 4.64 (1H, m), 6.00 (1H, s), 6.93 (1H, d, J = 8.5 Hz), 6.94 (1H, m), 7.38 (1H, d, J = 2.0 Hz), 7.42 (1H, dd, J = 8.5, 2.0 Hz). | ESI-MS m/z: 409 [M + H]+ |
| 586 | (structure) | 1H-NMR (CDCl₃) δ: 1.45-1.63 (3H, m), 1.89 (2H, m), 2.07 (1H, m), 2.19 (1H, m), 2.90 (1H, dd, J = 16.7, 4.2 Hz), 3.04 (2H, td, J = 17.4, 4.4 Hz), 3.16 (1H, dd, J = 16.7, 4.8 Hz), 3.42 (2H, m), 3.94 (1H, m), 4.04 (3H, m), 4.13-4.24 (3H, m), 4.61 (1H, m), 5.88 (1H, tt, J = 53.3, 4.5 Hz), 5.99 (1H, s), 6.63 (1H, d, J = 8.3 Hz), 6.95 (1H, d, J = 1.8 Hz), 7.00 (1H, dd, J = 8.3, 1.8 Hz), 7.03 (1H, m). | ESI-MS m/z: 448 [M + H]+ |

TABLE 76

| Example | Structural formula | NMR | MS |
|---|---|---|---|
| 587 | (structure) | 1H-NMR (CDCl₃) δ: 2.99 (1H, m), 3.09-3.15 (2H, m), 3.21 (H, q, J = 9.7 Hz), 4.11 (1H, m), 4.20 (1H, m), 4.33-4.41 (2H, m), 4.64 (1H, m), 4.92 (1H, s), 5.51 (1H, m), 5.94 (1H, d, J = 1.9 Hz), 6.97 (1H, d, J = 8.6 Hz), 7.29 (1H, m), 7.49 (1H, dd, J = 2.2, 8.7 Hz), 7.63 (1H, dd, J = 1.8, 6.5 Hz). | ESI-MS m/z: 498 [M + H]+ |
| 588 | (structure) | 1H-NMR (CDCl₃) δ: 2.18-2.22, (2H, m), 3.01 (1H, m), 3.81-3.87 (4H, m), 3.97 (1H, m), 4.20 (1H, t, J = 9.8 Hz), 4.35 (2H, dd, J = 3.6, 10.8 Hz), 4.64 (1H, m), 4.92 (1H, m), 5.45 (1H, m), 5.91 (1H, s), 6.97 (1H, d, J = 8.7 Hz), 7.29 (1H, m), 7.48 (1H, dd, J = 2.1, 8.6 Hz), 7.62 (1H, s). | ESI-MS m/z: 496 [M + H]+ |
| 589 | (structure) | 1H-NMR (CDCl₃) δ: 2.15-2.23 (2H, m), 3.49 (1H, m), 3.79-3.86 (4H, m), 3.96 (1H, m), 4.28-4.37 (2H, m), 4.47-4.51 (2H, m), 4.75 (1H, m), 5.43 (1H, m), 5.89 (1H, s), 6.99-7.02 (2H, m), 7.48 (1H, dd, J = 2.1, 8.6 Hz), 7.64 (1H, s). | ESI-MS m/z: 496 [M + H]+ |

TABLE 76-continued

| Example | Structural formula | NMR | MS |
|---|---|---|---|
| 590 (isomer A) | | 1H-NMR (CDCl$_3$) δ: 1.30-1.45 (2H, m), 1.63-1.74 (3H, m), 1.86 (1H, m), 1.98 (1H, m), 2.85 (1H, dd, J = 4.1, 16.7 Hz), 3.04 (2H, dt, J = 4.5, 17.4 Hz), 3.17 (1H, dd, J = 5.5, 16.8 Hz), 3.41 (2H, dt, J = 2.2, 11.8 Hz), 3.84 (1H, dd, J = 7.9, 9.7 Hz), 3.95-4.00 (2H, m), 4.19 (2H, d, J = 2.9 Hz), 4.34 (1H, dd, J = 8.2, 9.7 Hz), 4.62 (1H, m), 5.38 (1H, m), 5.88 (1H, m), 5.89 (1H, s), 6.83 (1H, d, J = 8.3 Hz), 6.93 (1H, s), 7.01 (2H, d, J = 8.1 Hz). | ESI-MS m/z: 448 [M + H]+ |
| 590 (isomer B) | | 1H-NMR (CDCl$_3$) δ: 1.31-1.46 (2H, m), 1.63-1.74 (3H, m), 1.86 (1H, m), 1.99 (1H, m), 2.85 (1H, dd, J = 4.0, 16.7 Hz), 3.04 (2H, dt, J = 4.5, 17.4 Hz), 3.17 (1H, dd, J = 5.3, 16.8 Hz), 3.40 (2H, dt, J = 2.1, 17.7 Hz), 3.85 (1H, dd, J = 8.0, 9.7 Hz), 3.95-4.00 (2H, m), 4.19 (2H, d, J = 2.8 Hz), 4.33 (1H, dd, J = 8.2, 9.7 Hz), 4.62 (1H, m), 5.37 (1H, m), 5.87 (1H, m), 5.89 (1H, s), 6.83 (1H, d, J = 8.3 Hz), 6.93 (1H, s), 7.00 (2H, d, J = 8.4 Hz). | ESI-MS m/z: 496 [M + H]+ |
| 591 | | 1H-NMR (CDCl$_3$) δ: 1.84 (2H, m), 1.99 (2H, m), 3.26 (1H, m), 3.69 (2H, m), 3.77-4.01 (3H, m), 4.17-4.36 (3H, m), 4.61 (1H, m), 4.91 (1H, t, J = 4.2 Hz), 5.32 (1H, m), 5.89 (1H, m), 6.94 (1H, d, J = 8.6 Hz), 7.29 (1H, d, J = 8.3 Hz), 7.47 (1H, dd, J = 8.7, 1.9 Hz), 7.61 (1H, m). | ESI-MS m/z: 510 [M + H]+ |
| 592 | | 1H-NMR (CDCl$_3$) δ: 1.81 (2H, m), 1.99 (2H, m), 3.53 (1H, m), 3.68 (2H, m), 3.77-3.93 (3H, m), 4.26-4.37 (3H, m), 4.44 (1H, m), 4.49 (1H, m), 4.75 (1H, t, J = 3.9 Hz), 5.32 (1H, m), 5.87 (1H, s), 7.00 (1H, d, J = 8.7 Hz), 7.01 (1H, m), 7.48 (1H, dd, J = 8.7, 1.9 Hz), 7.54 (1H, d, J = 2.0 Hz). | ESI-MS m/z: 510 [M + H]+ |
| 593 | | 1H-NMR (CDCl$_3$) δ: 0.05-0.08 (2H, m), 0.45-0.48 (2H, m), 0.71 (1H, m), 1.46-1.51 (2H, m), 2.64-2.68 (2H, m), 2.86 (1H, d, J = 4.8 Hz), 2.93-2.94 (2H, m), 3.69 (2H, d, J = 4.2 Hz), 4.15-4.25 (3H, m), 4.35 (1H, m), 4.67 (1H, m), 4.93 (1H, m), 6.53 (1H, s), 6.97 (1H, m), 7.28 (1H, m), 7.49 (1H, m), 7.63 (1H, m). | ESI-MS m/z: 451 [M + H]+ |
| 594 | | 1H-NMR (CDCl$_3$) δ: 2.36-2.42 (2H, m), 2.79-2.86 (3H, m), 2.96-2.99 (2H, m), 3.74 (2H, s), 4.17-4.24 (3H, m), 4.36 (1H, dd, J = 3.8, 11.5 Hz), 4.67 (1H, m), 4.94 (1H, t, J = 3.9 Hz), 6.55 (1H, s), 6.98 (1H, m), 7.30 (1H, m), 7.50 (1H, m), 7.64 (1H, m). | ESI-MS m/z: 478 [M + H]+ |

TABLE 77

| Example | Structural formula | NMR | MS |
|---|---|---|---|
| 595 | (structure) | 1H-NMR (CDCl₃) δ: 0.17-0.21 (2H, m), 0.51-0.56 (2H, m), 1.03 (1H, m), 2.10-2.23 (2H, m), 3.10 (1H, m), 3.27 (2H, d, J = 6.9 Hz), 3.63 (2H, t, J = 6.1 Hz), 3.99 (1H, m), 4.20 (1H, dd, J = 9.1, 10.6 Hz), 4.31-4.36 (2H, m), 4.64 (1H, m), 4.92 (1H, s), 5.46 (1H, m), 5.90 (1H, s), 6.97 (1H, d, J = 8.6 Hz), 7.29 (1H, s), 7.48 (1H, dd, J = 2.1, 8.7 Hz), 7.62 (1H, s). | ESI-MS m/z: 468 [M + H]+ |
| 596 | (structure) | 1H-NMR (CDCl₃) δ: 0.15-0.20 (2H, m), 0.48-0.55 (2H, m), 1.02 (1H, m), 2.09-2.22 (2H, m), 3.21-3.33 (3H, m), 3.62 (2H, q, J = 5.5 Hz), 4.00 (1H, m), 4.26-4.35 (2H, m), 4.44 (1H, m), 4.50 (1H, dd, J = 1.8, 11.4 Hz), 4.75 (1H, s), 5.45 (1H, m), 5.88 (1H, s), 6.98-7.01 (2H, m), 7.48 (1H, m), 7.64 (1H, s). | ESI-MS m/z: 468 [M + H]+ |
| 597 (isomer A) | (structure) | 1H-NMR (CDCl₃) δ: 3.49 (3H, s), 3.94 (2H, q, J = 8.5 Hz), 3.99 (2H, d, J = 4.2 Hz), 4.23-4.29 (3H, m), 4.34-4.39 (2H, m), 4.70 (1H, m), 5.44 (1H, m), 5.94 (1H, s), 6.97 (1H, d, J = 8.6 Hz), 7.20 (1H, d, J = 8.2 Hz), 7.49-7.52 (2H, m). | ESI-MS m/z: 496 [M + H]+ |
| 597 (isomer B) | (structure) | 1H-NMR (CDCl₃) δ: 3.49 (3H, s), 3.94 (2H, q, J = 8.5 Hz), 3.99 (2H, d, J = 4.2 Hz), 4.21-4.29 (3H, m), 4.32-4.41 (2H, m), 4.69 (1H, m), 5.44 (1H, m), 5.94 (1H, s), 6.97 (1H, d, J = 9.0 Hz), 7.20 (1H, d, J = 8.4 Hz), 7.49-7.51 (2H, m). | ESI-MS m/z: 496 [M + H]+ |
| 598 (isomer A) | (structure) | 1H-NMR (CDCl₃) δ: 2.23-2.29 (2H, m), 3.49 (3H, s), 3.86-4.00 (4H, m), 4.14 (1H, m), 4.25-4.32 (3H, m), 4.34 (1H, d, J = 3.6 Hz), 4.39 (1H, m), 4.70 (1H, m), 6.05 (1H, s), 6.97 (1H, d, J = 9.2 Hz), 7.21 (1H, d, J = 8.8 Hz), 7.49-7.51 (2H, m). | ESI-MS m/z: 510 [M + H]+ |
| 598 (isomer B) | (structure) | 1H-NMR (CDCl₃) δ: 2.23-2.29 (2H, m), 3.49 (3H, s), 3.86-3.98 (4H, m), 4.15 (1H, m), 4.24-4.32 (3H, m), 4.34 (1H, d, J = 3.6 Hz), 4.39 (1H, m), 4.70 (1H, m), 6.05 (1H, s), 6.97 (1H, d, J = 9.3 Hz), 7.21 (1H, d, J = 8.6 Hz), 7.50-7.51 (2H, m). | ESI-MS m/z: 510 [M + H]+ |
| 599 | (structure) | 1H-NMR (CDCl₃) δ: 1.06 (3H, t, J = 7.5 Hz), 1.72 (1H, m), 1.81 (1H, m), 2.01 (1H, m), 2.13 (1H, m), 3.84 (1H, m), 4.00 (1H, m), 4.04-4.25 (3H, m), 4.35 (1H, dd, J = 10.7, 3.5 Hz), 4.62 (1H, m), 4.90 (1H, t, J = 3.9 Hz), 6.02 (1H, s), 6.92 (1H, d, J = 8.6 Hz), 7.34 (1H, d, J = 8.1 Hz), 7.47 (1H, dd, J = 8.7, 2.1 Hz), 7.51 (1H, d, J = 2.1 Hz). | ESI-MS m/z: 412 [M + H]+ |
| 600 (isomer A) | (structure) | 1H-NMR (CDCl₃) δ: 2.16-2.25 (2H, m), 2.92 (1H, m), 3.79-3.87 (4H, m), 3.98 (1H, t, J = 8.9 Hz), 4.21 (1H, dd, J = 8.8, 10.8 Hz), 4.33-4.39 (2H, m), 4.65 (1H, m), 4.93 (1H, s), 5.46 (1H, m), 5.91 (1H, s), 6.97 (1H, d, J = 8.5 Hz), 7.27 (1H, m), 7.48 (1H, dd, J = 2.1, 8.7 Hz), 7.64 (1H, s). | ESI-MS m/z: 496 [M + H]+ |
| 600 (isomer B) | (structure) | 1H-NMR (CDCl₃) δ: 2.16-2.26 (2H, m), 2.97 (1H, m), 3.81-3.87 (4H, m), 3.99 (1H, dd, J = 7.8, 10.1 Hz), 4.20 (1H, dd, J = 9.0, 10.8 Hz), 4.33-4.37 (2H, m), 4.64 (1H, m), 4.92 (1H, s), 5.45 (1H, m), 5.91 (1H, s), 6.97 (1H, d, J = 8.6 Hz), 7.28 (1H, m), 7.48 (1H, dd, J = 2.1, 8.7 Hz), 7.62 (1H, d, J = 1.7 Hz). | ESI-MS m/z: 496 [M + H]+ |

TABLE 78

| Example | Structural formula | NMR | MS |
|---|---|---|---|
| 601 (isomer A) | | 1H-NMR (CDCl₃) δ: 1.73 (1H, m), 1.99 (1H, m), 2.38 (1H, m), 2.86 (1H, dd, J = 4.4, 16.9 Hz), 3.04 (2H, dt, J = 4.5, 17.4 Hz), 3.17 (1H, dd, J = 5.4, 16.8 Hz), 3.59-3.67 (2H, m), 3.74-3.85 (3H, m), 4.08 (1H, m), 4.18-4.19 (2H, m), 4.28-4.34 (2H, m), 4.61 (1H, m), 5.81 (1H, tt, J = 4.5, 85.1 Hz), 6.23 (1H, s), 6.85 (1H, d, J = 8.3 Hz), 6.94 (1H, s), 7.01 (2H, dd, J = 2.2, 8.4 Hz). | ESI-MS m/z: 490 [M + H]+ |
| 601 (isomer B) | | 1H-NMR (CDCl₃) δ: 1.73 (1H, m), 2.00 (1H, m), 2.38 (1H, m), 2.86 (1H, dd, J = 4.4, 16.7 Hz), 2.99-3.09 (2H, m, J = 7.9 Hz), 3.17 (1H, dd, J = 5.4, 16.8 Hz), 3.58-3.67 (2H, m), 3.73-3.85 (3H, m), 4.09 (1H, m), 4.18-4.19 (2H, m), 4.28-4.34 (2H, m), 4.61 (1H, m), 5.88 (1H, tt, J = 4.5, 56.8 Hz), 6.23 (1H, s), 6.85 (1H, d, J = 8.3 Hz), 6.94 (1H, s), 7.00-7.04 (2H, m). | ESI-MS m/z: 490 [M + H]+ |
| 602 (isomer A) | | 1H-NMR (CDCl₃) δ: 1.73 (1H, m), 2.00 (1H, m), 2.38 (1H, m), 2.87 (1H, dd, J = 4.3, 16.8 Hz), 3.18 (1H, dd, J = 5.4, 16.6 Hz), 3.59-3.67 (2H, m), 3.75-3.85 (5H, m), 4.08 (1H, m), 4.20 (2H, d, J = 2.9 Hz), 4.27-4.33 (2H, m), 4.57 (2H, s), 4.62 (1H, m), 6.23 (1H, s), 6.88 (1H, d, J = 8.3 Hz), 7.01 (1H, d, J = 8.8 Hz), 7.05 (1H, m), 7.12 (1H, dd, J = 2.1, 8.4 Hz). | ESI-MS m/z: 538 [M + H]+ |
| 602 (isomer B) | | 1H-NMR (CDCl₃) δ: 1.72 (1H, m), 1.99 (1H, m), 2.38 (1H, m), 2.88 (1H, dd, J = 4.1, 16.4 Hz), 3.18 (1H, dd, J = 5.3, 16.8 Hz), 3.58-3.66 (2H, m), 3.73-3.86 (5H, m), 4.09 (1H, m), 4.21 (2H, d, J = 2.8 Hz), 4.27-4.33 (2H, m), 4.57 (2H, s), 4.62 (1H, m), 6.23 (1H, s), 6.88 (1H, d, J = 8.3 Hz), 7.00-7.05 (2H, m), 7.12 (1H, dd, J = 2.0, 8.4 Hz). | ESI-MS m/z: 538 [M + H]+ |
| 603 (isomer A) | | 1H-NMR (CDCl₃) δ: 1.84 (2H, m), 1.99 (2H, m), 3.42 (1H, d, J = 4.9 Hz), 3.69 (2H, m), 3.77-3.87 (3H, m), 4.20 (1H, dd, J = 10.7, 9.2 Hz), 4.27 (1H, dd, J = 10.7, 9.8 Hz), 4.34 (1H, dd, J = 10.6, 3.0 Hz), 4.61 (1H, m), 4.91 (1H, t, J = 4.2 Hz), 5.32 (1H, m), 5.89 (1H, s), 6.94 (1H, d, J = 8.6 Hz), 7.29 (1H, d, J = 8.3 Hz), 7.47 (1H, dd, J = 8.7, 1.9 Hz), 7.61 (1H, d, J = 1.9 Hz). | ESI-MS m/z: 510 [M + H]+ |
| 603 (isomer B) | | 1H-NMR (CDCl₃) δ: 1.84 (2H, m), 1.99 (2H, m), 3.42 (1H, d, J = 4.9 Hz), 3.69 (2H, m), 3.77-3.87 (3H, m), 4.17-4.28 (2H, m), 4.34 (1H, dd, J = 10.8, 3.0 Hz), 4.61 (1H, m), 4.91 (1H, t, J = 4.2 Hz), 5.32 (1H, m), 5.89 (1H, s), 6.94 (1H, d, J = 8.6 Hz), 7.29 (1H, d, J = 8.3 Hz), 7.47 (1H, dd, J = 8.7, 1.9 Hz), 7.61 (1H, d, J = 1.9 Hz). | ESI-MS m/z: 510 [M + H]+ |
| 604 (isomer A) | | 1H-NMR (CDCl₃) δ: 1.79 (2H, m), 1.99 (2H, m), 2.89 (1H, dd, J = 16.8, 4.5 Hz), 3.17 (1H, dd, J = 16.9, 5.1 Hz), 3.52-3.73 (4H, m), 3.89 (1H, dd, J = 9.8, 7.7 Hz), 4.23-4.30 (2H, m), 4.33 (1H, dd, J = 9.8, 8.3 Hz), 4.64 (1H, m), 5.38 (1H, m), 5.85 (1H, tt, J = 55.4, 4.0 Hz), 5.89 (1H, s), 6.92 (1H, d, J = 7.7 Hz), 6.93 (1H, d, J = 8.5 Hz), 7.38 (1H, d, J = 2.1 Hz), 7.42 (1H, dd, J = 8.5, 2.1 Hz). | ESI-MS m/z: 433 [M + H]+ |

TABLE 78-continued

| Example | Structural formula | NMR | MS |
|---|---|---|---|
| 604 (isomer B) | (structure) | 1H-NMR (CDCl$_3$) δ: 1.79 (2H, m), 1.99 (2H, m), 2.89 (1H, dd, J = 16.8, 4.5 Hz), 3.17 (1H, dd, J = 16.9, 5.1 Hz), 3.52-3.73 (4H, m), 3.89 (1H, dd, J = 9.8, 7.7 Hz), 4.23-4.30 (2H, m), 4.33 (1H, dd, J = 9.8, 8.3 Hz), 4.64 (1H, m), 5.38 (1H, m), 5.85 (1H, tt, J = 55.4, 4.0 Hz), 5.89 (1H, s), 6.92 (1H, d, J = 7.7 Hz), 6.93 (1H, d, J = 8.5 Hz), 7.38 (1H, d, J = 2.1 Hz), 7.42 (1H, dd, J = 8.5, 2.1 Hz). | ESI-MS m/z: 433 [M + H]+ |
| 605 | (structure) | 1H-NMR (CDCl$_3$) δ: 1.33-1.43 (2H, m), 1.62-1.75 (3H, m), 1.86 (1H, m), 1.98 (1H, m), 2.86 (1H, dd, J = 4.0, 16.7 Hz), 3.16 (1H, dd, J = 5.6, 16.6 Hz), 3.41 (2H, t, J = 11.2 Hz,), 3.78-3.87 (3H, m), 3.97-4.01 (2H, m), 4.20 (2H, d, J = 2.9 Hz), 4.33 (1H, m), 4.56 (2H, s), 4.63 (1H, m), 5.38 (1H, m), 5.89 (1H, s), 6.87 (1H, d, J = 8.3 Hz), 7.00 (1H, d, J = 7.5 Hz), 7.04 (1H, s), 7.11 (1H, dd, J = 2.0, 8.4 Hz). | ESI-MS m/z: 496 [M + H]+ |

TABLE 79

| Example | Structural formula | NMR | MS |
|---|---|---|---|
| 606 | (structure) | 1H-NMR (CDCl$_3$) δ: 1.44-1.66 (3H, m), 1.82-1.97 (2H, m), 2.07 (1H, m), 2.19 (1H, m), 2.87 (1H, dd, J = 16.7, 4.2 Hz), 3.17 (1H, dd, J = 16.7, 5.4 Hz), 3.35-3.45 (2H, m), 3.79 (1H, d, J = 8.7 Hz), 3.85 (1H, d, J = 8.7 Hz), 3.94 (1H, m), 3.99-4.08 (3H, m), 4.14-4.24 (3H, m), 4.57 (2H, s), 4.62 (1H, s), 5.98 (1H, s), 6.94 (1H, d, J = 8.5 Hz), 6.87 (1H, d, J = 8.3 Hz), 7.05 (1H, d, J = 1.8 Hz), 7.12 (1H, dd, J = 8.3, 1.8 Hz). | ESI-MS m/z: 496 [M + H]+ |
| 607 | (structure) | 1H-NMR (CDCl$_3$) δ: 1.80 (2H, m), 2.00 (2H, m), 3.55-3.72 (4H, m), 3.76 (1H, m), 3.83-3.96 (1H, m), 4.07-4.24 (2H, m), 4.34 (1H, dd, J = 10.7, 3.6 Hz), 4.63 (1H, m), 4.92 (1H, m), 5.33 (1H, m), 5.86 (1H, tt, J = 55.6, 4.0), 5.86 (1H, s), 6.95 (1H, d, J = 8.6 Hz), 7.28 (1H, m), 7.48 (1H, dd, J = 8.6, 1.8 Hz), 7.60 (0.5H, d, J = 1.8 Hz), 7.63 (0.5H, d, J = 1.8 Hz). | ESI-MS m/z: 492 [M + H]+ |
| 608 (isomer A) | (structure) | 1H-NMR (CDCl$_3$) δ: 1.80 (2H, m), 2.00 (2H, m), 3.36 (1H, br s), 3.55-3.72 (4H, m), 3.84 (1H, dd, J = 9.9, 7.7 Hz), 4.15-4.39 (3H, m), 4.62 (1H, m), 4.92 (1H, m), 5.33 (1H, m), 5.86 (1H, tt, J = 55.6, 4.0), 5.89 (1H, s), 6.96 (1H, d, J = 8.6 Hz), 7.28 (1H, d, J = 8.1 Hz), 7.48 (1H, dd, J = 8.6, 1.8 Hz), 7.63 (1H, d, J = 1.8 Hz). | ESI-MS m/z: 492 [M + H]+ |
| 608 (isomer B) | (structure) | 1H-NMR (CDCl$_3$) δ: 1.80 (2H, m), 2.00 (2H, m), 3.44 (1H, br s), 3.55-3.72 (4H, m), 3.84 (1H, dd, J = 9.9, 7.7 Hz), 4.15-4.39 (3H, m), 4.62 (1H, m), 4.92 (1H, m), 5.33 (1H, m), 5.86 (1H, tt, J = 55.6, 4.0), 5.89 (1H, s), 6.96 (1H, d, J = 8.6 Hz), 7.28 (1H, d, J = 8.1 Hz), 7.48 (1H, dd, J = 8.6, 1.8 Hz), 7.63 (1H, d, J = 1.8 Hz). | ESI-MS m/z: 492 [M + H]+ |

TABLE 79-continued

| Example | Structural formula | NMR | MS |
| --- | --- | --- | --- |
| 609 | | 1H-NMR (CDCl₃) δ: 1.57-1.80 (2H, m), 1.90 (2H, m), 3.46-3.65 (4H, m), 3.74-3.85 (2H, m), 4.20-4.30 (2H, m), 4.38 (1H, m), 4.67 (1H, m), 4.92 (1H, m), 5.25 (1H, m), 5.78 (1H, m), 5.80 (1H, s), 6.93 (1H, d, J = 8.6 Hz), 6.96 (1H, m), 7.40 (1H, dd, J = 8.6, 1.8 Hz), 7.58 (1H, m). | ESI-MS m/z: 492 [M + H]+ |
| 610 (isomer A) | | 1H-NMR (CDCl₃) δ: 1.80 (2H, m), 2.00 (2H, m), 3.55-3.72 (4H, m), 3.84 (1H, br s), 3.84 (1H, dd, J = 9.9, 7.7 Hz), 4.20 (1H, dd, J = 10.8, 9.1 Hz), 4.29 (1H, dd, J = 8.7, 8.3 Hz), 4.34 (1H, dd, J = 10.7, 3.6 Hz), 4.62 (1H, m), 4.92 (1H, m), 5.33 (1H, m), 5.86 (1H, tt, J = 55.6, 4.0), 5.89 (1H, s), 6.96 (1H, d, J = 8.6 Hz), 7.28 (1H, d, J = 8.1 Hz), 7.48 (1H, dd, J = 8.6, 1.8 Hz), 7.63 (1H, d, J = 1.8 Hz). | ESI-MS m/z: 492 [M + H]+ |
| 610 (isomer B) | | 1H-NMR (CDCl₃) δ: 1.80 (2H, m), 2.00 (2H, m), 3.55-3.72 (4H, m), 3.84 (1H, dd, J = 9.9, 7.7 Hz), 4.06 (1H, br s), 4.20 (1H, dd, J = 10.8, 9.1 Hz), 4.29 (1H, dd, J = 8.7, 8.3 Hz), 4.34 (1H, dd, J = 10.7, 3.6 Hz), 4.62 (1H, m), 4.92 (1H, m), 5.33 (1H, m), 5.86 (1H, tt, J = 55.6, 4.0), 5.89 (1H, s), 6.96 (1H, d, J = 8.6 Hz), 7.28 (1H, d, J = 8.1 Hz), 7.48 (1H, dd, J = 8.6, 1.8 Hz), 7.63 (1H, d, J = 1.8 Hz). | ESI-MS m/z: 492 [M + H]+ |
| 611 | | 1H-NMR (CDCl₃) δ: 1.66 (1H, m), 1.90-2.29 (3H, m), 2.56 (1H, m), 2.84 (1H, dd, J = 16.9, 4.2 Hz), 3.14 (1H, dd, J = 16.8, 5.3 Hz), 3.60-3.99 (4H, m), 4.00-4.23 (5H, m), 4.60 (1H, m), 5.97-6.01 (1H, m), 6.94 (1H, d, J = 8.5 Hz), 7.00 (1H, d, J = 8.7 Hz), 7.03 (1H, d, J = 2.5 Hz), 7.07 (1H, dd, J = 8.5, 2.5 Hz). | ESI-MS m/z: 404 [M + H]+ |
| 612 | | 1H-NMR (CDCl₃) δ: 1.66 (1H, m), 1.90-2.29 (3H, m), 2.55 (1H, m), 2.91 (1H, dd, J = 16.8, 4.4 Hz), 3.19 (1H, dd, J = 16.8, 5.2 Hz), 3.60-3.99 (4H, m), 4.00-4.29 (5H, m), 4.64 (1H, m), 5.98-6.02 (1H, m), 6.94 (1H, d, J = 8.5 Hz), 6.98 (1H, d, J = 7.8 Hz), 7.33 (1H, d, J = 1.8 Hz), 7.38 (1H, dd, J = 8.5, 1.8 Hz). | ESI-MS m/z: 438 [M + H]+ |

TABLE 80

| Example | Structural formula | NMR | MS |
| --- | --- | --- | --- |
| 613 | | 1H-NMR (CDCl₃) δ: 1.6 (1H, m), 1.87-2.33 (3H, m), 2.56 (1H, m), 3.58-4.20 (8H, m), 4.21-4.50 (2H, m), 4.65-4.87 (1H, m), 5.33-5.62 (1H, m), 5.96-6.07 (1H, m), 6.95 (0.5H, m), 7.00-7.10 (1H, m), 7.18 (0.5H, m), 7.55-7.68 (1H, m). | ESI-MS m/z: 456 [M + H]+ |
| 614 | | 1H-NMR (CDCl₃) δ: 1.6 (1H, m), 1.87-2.33 (3H, m), 2.56 (1H, m), 3.58-4.20 (8H, m), 4.21-4.50 (2H, m), 4.65-4.87 (1H, m), 5.33-5.62 (1H, m), 5.96-6.07 (1H, m), 6.93 (0.5H, m), 6.99-7.09 (1H, m), 7.18 (0.5H, m), 7.56-7.68 (1H, m). | ESI-MS m/z: 456 [M + H]+ |

TABLE 80-continued

| Example | Structural formula | NMR | MS |
|---|---|---|---|
| 615 (isomer A) | | 1H-NMR (CDCl₃) δ: 1.44-1.66 (3H, m), 1.82-1.97 (2H, m), 2.07 (1H, m), 2.19 (1H, m), 2.87 (1H, dd, J = 16.7, 4.2 Hz), 3.17 (1H, dd, J = 16.7, 6.4 Hz), 3.36-3.46 (2H, m), 3.79 (1H, d, J = 8.7 Hz), 3.85 (1H, d, J = 8.7 Hz), 3.94 (1H, m), 3.99-4.08 (3H, m), 4.14-4.24 (3H, m), 4.57 (2H, s), 4.62 (1H, m), 5.98 (1H, s), 6.94 (1H, d, J = 8.5 Hz), 6.87 (1H, d, J = 8.3 Hz), 7.05 (1H, d, J = 1.8 Hz), 7.12 (1H, dd, J = 8.3, 1.8 Hz). | ESI-MS m/z: 496 [M + H]+ |
| 615 (isomer B) | | 1H-NMR (CDCl₃) δ: 1.44-1.66 (3H, m), 1.82-1.97 (2H, m), 2.07 (1H, m), 2.19 (1H, m), 2.87 (1H, dd, J = 16.7, 4.2 Hz), 3.17 (1H, dd, J = 16.7, 5.4 Hz), 3.35-3.45 (2H, m), 3.79 (1H, d, J = 8.7 Hz), 3.85 (1H, d, J = 8.7 Hz), 3.94 (1H, m), 3.99-4.08 (3H, m), 4.14-4.24 (3H, m), 4.57 (2H, s), 4.62 (1H, m), 5.98 (1H, s), 6.94 (1H, d, J = 8.5 Hz), 6.87 (1H, d, J = 8.3 Hz), 7.05 (1H, d, J = 1.8 Hz), 7.12 (1H, dd, J = 8.3, 1.8 Hz). | ESI-MS m/z: 496 [M + H]+ |
| 616 (isomer A) | | 1H-NMR (CDCl₃) δ: 1.70-1.92 (2H, m), 1.96-2.07 (2H, m), 3.60-3.75 (2H, m), 3.80 (2H, m), 3.88 (1H, m), 4.07 (1H, br s), 4.27-4.34 (2H, m), 4.43-4.54 (2H, m), 4.75 (1H, m), 5.31 (1H, m), 5.87 (1H, s), 6.96 (1H, d, J = 8.6 Hz), 7.03 (1H, d, J = 7.6 Hz), 7.48 (1H, dd, J = 8.6, 1.8 Hz), 7.64 (1H, d, J = 1.8 Hz). | ESI-MS m/z: 510 [M + H]+ |
| 616 (isomer B) | | 1H-NMR (CDCl₃) δ: 1.70-1.92 (2H, m), 1.96-2.07 (2H, m), 3.60-3.75 (2H, m), 3.80 (2H, m), 3.88 (1H, m), 4.07 (1H, br s), 4.27-4.34 (2H, m), 4.43-4.54 (2H, m), 4.75 (1H, m), 5.31 (1H, m), 5.87 (1H, s), 6.96 (1H, d, J = 8.6 Hz), 7.03 (1H, d, J = 7.6 Hz), 7.48 (1H, dd, J = 8.6, 1.8 Hz), 7.64 (1H, d, J = 1.8 Hz). | ESI-MS m/z: 510 [M + H]+ |
| 617 (isomer A) | | 1H-NMR (CDCl₃) δ: 0.23 (2H, m), 0.57 (2H, m), 1.07 (1H, m), 2.14-2.37 (2H, m), 3.39 (2H, d, J = 6.9 Hz), 3.68 (1H, dd, J = 10.2, 6.2 Hz), 3.78 (1H, dd, J = 10.2, 5.2 Hz), 4.05-4.48 (5H, m), 4.62-4.98 (1H, m), 5.48 (1H, dd, J = 54.2, 1.7 Hz), 6.06 (1H, s), 7.02 (1H, d, J = 8.8 Hz), 7.16 (1H, m), 7.60 (1H, dt, J = 8.8, 1.7 Hz), 7.68 (1H, t, J = 1.7 Hz). | ESI-MS m/z: 427 [M + H]+ |
| 617 (isomer B) | | 1H-NMR (CDCl₃) δ: 0.23 (2H, m), 0.57 (2H, m), 1.07 (1H, m), 2.14-2.37 (2H, m), 3.39 (2H, d, J = 6.9 Hz), 3.68 (1H, dd, J = 10.2, 6.2 Hz), 3.78 (1H, dd, J = 10.2, 5.2 Hz), 4.05-4.48 (5H, m), 4.62-4.98 (1H, m), 5.48 (1H, dd, J = 54.2, 1.7 Hz), 6.06 (1H, s), 7.02 (1H, d, J = 8.8 Hz), 7.16 (1H, m), 7.60 (1H, dt, J = 8.8, 1.7 Hz), 7.68 (1H, t, J = 1.7 Hz). | ESI-MS m/z: 427 [M + H]+ |
| 617 (isomer C) | | 1H-NMR (CDCl₃) δ: 0.23 (2H, m), 0.57 (2H, m), 1.07 (1H, m), 2.14-2.37 (2H, m), 3.39 (2H, d, J = 6.9 Hz), 3.68 (1H, dd, J = 10.2, 5.2 Hz), 3.78 (1H, dd, J = 10.2, 5.2 Hz), 4.05-4.48 (5H, m), 4.62-4.98 (1H, m), 5.48 (1H, dd, J = 54.2, 1.7 Hz), 6.06 (1H, s), 7.02 (1H, d, J = 8.8 Hz), 7.16 (1H, m), 7.60 (1H, dt, J = 8.8, 1.7 Hz), 7.68 (1H, t, J = 1.7 Hz). | ESI-MS m/z: 427 [M + H]+ |

TABLE 81

| Example | Structural formula | NMR | MS |
|---|---|---|---|
| 617 (isomer D) | | 1H-NMR (CDCl₃) δ: 0.23 (2H, m), 0.57 (2H, m), 1.07 (1H, m), 2.14-2.37 (2H, m), 3.39 (2H, d, J = 6.9 Hz), 3.68 (1H, dd, J = 10.2, 5.2 Hz), 3.78 (1H, dd, J = 10.2, 5.2 Hz), 4.05-4.48 (5H, m), 4.62-4.98 (1H, m), 5.48 (1H, dd, J = 54.2, 1.7 Hz), 6.06 (1H, s), 7.02 (1H, d, J = 8.8 Hz), 7.16 (1H, m), 7.60 (1H, dt, J = 8.8, 1.7 Hz), 7.68 (1H, t, J = 1.7 Hz). | ESI-MS m/z: 427 [M + H]+ |

TABLE 81-continued

| Example | Structural formula | NMR | MS |
|---|---|---|---|
| 618 | | 1H-NMR (CDCl₃) δ: 0.11-0.20 (2H, m), 0.46-0.55 (2H, m), 0.99 (1H, m), 1.60 (3H, s), 2.90 (1H, dd, J = 4.5, 16.8 Hz), 3.17 (1H, dd, J = 2.0, 10.4 Hz), 3.64 (1H, dd, J = 3.9, 6.8 Hz), 3.58 (1H, dd, J = 2.0, 10.4 Hz), 3.64 (1H, dd, J = 3.6, 10.4 Hz), 3.89 (1H, dd, J = 1.9, 9.8 Hz), 4.23-4.35 (3H, m), 4.64 (1H, m), 5.88 (1H, s), 6.93 (2H, d, J = 8.5 Hz), 7.38 (1H, s), 7.42 (1H, dd, J = 2.0, 8.5 Hz). | ESI-MS m/z: 409 [M + H]+ |
| 619 | | 1H-NMR (CDCl₃) δ: 0.11-0.20 (2H, m), 0.46-0.55 (2H, m), 0.99 (1H, m), 1.60 (3H, s), 2.85 (1H, dd, J = 4.2, 16.8 Hz), 3.04 (2H, dt, J = 4.5, 17.4 Hz), 3.17 (1H, dd, J = 5.4, 16.8 Hz, ), 3.34 (2H, dd, J = 4.8, 6.8 Hz), 3.56-3.65 (2H, m), 3.89 (1H, dd, J = 3.8, 9.8 Hz), 4.19 (2H, s), 4.32 (1H, dd, J = 3.4, 9.8 Hz), 4.62 (1H, m), 5.72-6.03 (2H, m), 6.83 (1H, d, J = 8.3 Hz), 6.93 (1H, s), 7.00 (2H, dd, J = 2.0, 8.2 Hz). | ESI-MS m/z: 448 [M + H]+ |
| 620 | | 1H-NMR (CDCl₃) δ: 2.13 (1H, m), 2.32 (1H, m), 2.91 (1H, dd, J = 16.8, 4.4 Hz), 3.19 (1H, dd, J = 16.8, 5.4 Hz), 3.60-3.91 (7H, m), 4.07 (1H, m), 4.15-4.30 (4H, m), 4.64 (1H, m), 6.04 (1H, s), 6.94 (1H, d, J = 8.6 Hz), 6.98 (1H, d, J = 8.0 Hz), 7.32 (1H, d, J = 1.8 Hz), 7.38 (1H, dd, J = 8.6, 1.8 Hz). | ESI-MS m/z: 454 [M + H]+ |
| 621 | | 1H-NMR (CDCl₃) δ: 2.17-2.28 (2H, m), 3.49 (3H, s), 3.61-3.88 (4H, m), 4.02 (1H, m), 4.25-4.29 (2H, m), 4.34 (1H, d, J = 3.6 Hz), 4.41 (1H, m), 4.69 (1H, m), 5.46 (1H, m), 5.92 (1H, s), 6.97 (1H, d, J = 9.3 Hz), 7.21 (1H, d, J = 8.4 Hz), 7.49-7.51 (2H, m). | ESI-MS m/z: 510 [M + H]+ |
| 622 (isomer A) | | 1H-NMR (CDCl₃) δ: 1.30-1.45 (2H, m), 1.63-1.74 (3H, m), 1.85 (1H, m), 1.98 (1H, m), 2.86 (1H, m), 3.18 (1H, dd, J = 5.5, 16.7 Hz), 3.41 (2H, dt, J = 2.2, 11.8 Hz), 3.78-3.86 (3H, m), 3.95-4.01 (2H, m), 4.20 (2H, d, J = 2.9 Hz), 4.34 (1H, dd, J = 8.2, 9.7 Hz), 4.56 (2H, s), 4.62 (1H, m), 5.38 (1H, m), 5.89 (1H, s), 6.87 (1H, d, J = 8.3 Hz), 7.00 (1H, d, J = 8.2 Hz), 7.04 (1H, s), 7.11 (1H, dd, J = 2.0, 8.3 Hz). | ESI-MS m/z: 496 [M + H]+ |
| 622 (isomer B) | | 1H-NMR (CDCl₃) δ: 1.31-1.45 (2H, m), 1.63-1.74 (3H, m), 1.86 (1H, m), 1.99 (1H, m), 2.86 (1H, m), 3.18 (1H, dd, J = 5.5, 16.8 Hz), 3.42 (2H, dt, J = 2.2, 11.8 Hz), 3.78-3.87 (3H, m), 3.95-4.01 (2H, m), 4.20 (2H, d, J = 2.9 Hz), 4.34 (1H, dd, J = 8.2, 9.7 Hz), 4.56 (2H, s), 4.62 (1H, m), 5.37 (1H, m), 5.89 (1H, s), 6.87 (1H, d, J = 8.3 Hz), 7.00 (1H, d, J = 7.9 Hz), 7.04 (1H, s), 7.11 (1H, dd, J = 2.0, 8.3 Hz). | ESI-MS m/z: 496 [M + H]+ |
| 623 | | 1H-NMR (CDCl₃) δ: 1.23-1.38 (4H, m), 1.45-1.54 (3H, m), 1.82-1.97 (2H, m), 2.90 (1H, dd, J = 4.5, 17.0 Hz), 3.17 (1H, dd, J = 5.2, 16.6 Hz), 3.37 (2H, t, J = 11.7 Hz), 3.88 (1H, m), 3.96 (2H, dd, J = 4.0, 11.3 Hz), 4.24-4.34 (3H, m), 4.64 (1H, m), 5.27 (1H, m), 5.89 (1H, s), 6.90-6.94 (2H, m), 7.38 (1H, s), 7.42 (1H, dd, J = 2.0, 8.5 Hz). | ESI-MS m/z: 423 [M + H]+ |

TABLE 81-continued

| Example | Structural formula | NMR | MS |
|---|---|---|---|
| 624 | (structure) | 1H-NMR (CDCl₃) δ: 2.18-2.31 (2H, m), 3.70-3.92 (4H, m), 4.02-4.21 (2H, m), 4.22-4.46 (3H, m), 4.66-4.83 (1H, m), 5.35-5.59 (1H, m), 5.70-6.06 (1H, m), 6.03 (0.5H, s), 6.07 (0.5H, s), 6.93 (0.5H, m), 7.03 (0.5H, m), 7.07 (0.5H, m), 7.18 (0.5H, m), 7.53-7.69 (2H, m). | ESI-MS m/z: 480 [M + H]+ |

TABLE 82

| Example | Structural formula | NMR | MS |
|---|---|---|---|
| 625 | (structure) | 1H-NMR (CDCl₃) δ: 1.45-1.57 (1H, m), 1.68-1.75 (2H, m), 1.87-1.99 (2H, m), 2.16-2.25 (2H, m), 2.74-2.81 (2H, m), 2.93-3.07 (2H, m), 3.49-3.55 (2H, m), 3.73-3.79 (2H, m), 3.88-3.98 (1H, m), 4.09-4.15 (1H, m), 4.21 (1H, m), 4.35-4.45 (1H, m), 4.69-4.86 (1H, m), 5.38-5.59 (1H, m), 6.51-6.55 (1H, m), 6.95-7.22 (2H, m), 7.57-7.65 (2H, m). | ESI-MS m/z: 483 [M + H]+ |
| 626 | (structure) | 1H-NMR (CDCl₃) δ: 2.35-2.54 (2H, m), 2.92 (1H, dd, J = 16.8, 3.9 Hz), 3.11 (1H, dd, J = 16.8, 5.7 Hz), 4.10-4.21 (3H, m), 4.27 (1H, m), 4.53-4.69 (2H, m), 6.14 (1H, s), 6.62 (1H, m), 6.95 (1H, q, J = 9.3 Hz), 7.00 (1H, m). | ESI-MS m/z: 404 [M + H]+ |
| 627 | (structure) | 1H-NMR (CDCl₃) δ: 2.19-2.29 (2H, m), 2.92 (1H, dd, J = 16.8, 4.1 Hz), 3.11 (1H, dd, J = 16.8, 5.7 Hz), 3.83-3.99 (4H, m), 4.06-4.25 (4H, m), 4.37 (1H, m), 4.63 (1H, m), 6.04 (1H, s), 6.61 (1H, m), 6.94 (1H, q, J = 9.3 Hz), 7.00 (1H, m). | ESI-MS m/z: 448 [M + H]+ |
| 628 | (structure) | 1H-NMR (CDCl₃) δ: 1.69-1.94 (2H, m), 1.95-2.11 (2H, m), 2.92 (1H, dd, J = 16.8, 3.6 Hz), 3.10 (1H, dd, J = 16.8, 5.7 Hz), 3.82 (2H, m), 3.69 (2H, m), 3.89 (1H, m), 4.10-4.21 (2H, m), 4.34 (1H, m), 4.64 (1H, m), 5.33 (1H, m), 5.89 (1H, s), 6.61 (1H, m), 6.94 (1H, q, J = 9.3 Hz), 6.98 (1H, m). | ESI-MS m/z: 462 [M + H]+ |
| 629 | (structure) | 1H-NMR (CDCl₃) δ: 2.14-2.24 (2H, m), 2.91 (1H, dd, J = 16.8, 3.9 Hz), 3.10 (1H, dd, J = 16.8, 5.6 Hz), 3.78-3.88 (4H, m), 3.98 (1H, m), 4.10-4.21 (2H, m), 4.36 (1H, m), 4.64 (1H, m), 5.45 (1H, m), 5.91 (1H, s), 6.61 (1H, m), 6.94 (1H, q, J = 9.3 Hz), 6.99 (1H, m). | ESI-MS m/z: 448 [M + H]+ |
| 630 | (structure) | 1H-NMR (CDCl₃) δ: 1.69 (1H, m), 1.91-2.31 (3H, m), 2.57 (1H, m), 2.88 (1H, dd, J = 16.7, 4.3 Hz), 3.19 (1H, dd, J = 16.7, 5.4 Hz), 3.60-4.26 (11H, m), 4.55-4.72 (3H, m), 5.98-6.04 (1H, m), 6.88 (1H, m), 7.04 (1H, m), 7.06 (1H, s), 7.13 (1H, m). | ESI-MS m/z: 482 [M + H]+ |
| 631 | (structure) | 1H-NMR (CDCl₃) δ: 2.16 (1H, m), 2.40 (1H, m), 2.88 (1H, dd, J = 16.7, 4.3 Hz), 3.95 (1H, dd, J = 16.7, 5.4 Hz), 3.46-3.90 (8H, m), 3.99-4.28 (6H, m), 4.58 (2H, s), 4.63 (1H, m), 6.02 (1H, s), 6.88 (1H, m), 7.04 (1H, m), 7.07 (1H, s), 7.13 (1H, m). | ESI-MS m/z: 498 [M + H]+ |

TABLE 82-continued

| Example | Structural formula | NMR | MS |
| --- | --- | --- | --- |
| 632 | | 1H-NMR (CDCl₃) δ: 1.91 (1H, m), 2.30 (1H, m), 2.78-2.90 (2H, m), 3.19 (1H, dd, J = 5.1, 17.0 Hz), 3.76-3.86 (3H, m), 4.08 (1H, m), 4.20-4.21 (2H, m), 4.45 (1H, m), 4.53-4.57 (3H, m), 4.62 (1H, m), 6.28 (1H, s), 6.88 (1H, d, J = 8.4 Hz), 7.00-7.06 (2H, m), 7.12 (1H, dd, J = 2.1, 8.3 Hz). | ESI-MS m/z: 494 [M + H]+ |
| 633 | | 1H-NMR (CDCl₃) δ: 1.91 (1H, m), 2.30 (1H, m), 2.78-2.88 (2H, m), 3.04 (2H, dt, J = 4.5, 17.5 Hz), 3.17 (1H, dd, J = 5.4, 16.7 Hz), 3.80 (1H, m), 4.10 (1H, m), 4.19 (2H, d, J = 2.8 Hz), 4.46 (1H, m), 4.55 (1H, m), 4.62 (1H, m), 5.88 (1H, m), 6.28 (1H, s), 6.85 (1H, d, J = 8.4 Hz), 6.94 (1H, s), 7.00-7.02 (2H, m). | ESI-MS m/z: 446 [M + H]+ |

TABLE 83

| Example | Structural formula | NMR | MS |
| --- | --- | --- | --- |
| 634 | | 1H-NMR (CDCl₃) δ: 1.77 (1H, m), 2.03 (1H, m), 2.37 (1H, m), 3.58-4.85 (11H, m), 5.47 (1H, m), 6.25 (1H, m), 6.91-7.19 (2H, m), 7.57-7.66 (2H, m). | ESI-MS m/z: 512 [M + H]+ |
| 635 | | 1H-NMR (CDCl₃) δ: 2.16-2.27 (2H, m), 2.87 (1H, dd, J = 16.7, 4.3 Hz), 3.18 (1H, dd, J = 16.7, 5.4 Hz), 3.71-3.88 (6H, m), 4.02-4.25 (4H, m), 4.36 (1H, m), 4.57 (2H, s), 4.62 (1H, m), 5.70-6.06 (1H, m), 6.02 (1H, s), 6.87 (1H, d, J = 8.3 Hz), 7.01 (1H, m), 7.04 (1H, d, J = 1.8 Hz), 7.12 (1H, dd, J = 8.6, 1.8 Hz). | ESI-MS m/z: 506 [M + H]+ |
| 636 (isomer A) | | 1H-NMR (CDCl₃) δ: 0.17-0.21 (2H, m), 0.49-0.56 (2H, m), 1.03 (1H, m), 2.09-2.23 (2H, m), 3.08 (1H, s), 3.23-3.31 (2H, m), 3.60-3.66 (2H, m), 3.98 (1H, m), 4.21 (1H, dd, J = 8.9, 10.9 Hz), 4.31-4.36 (2H, m), 4.64 (1H, m), 4.92 (1H, d, J = 3.8 Hz), 5.46 (1H, m), 5.90 (1H, s), 6.96 (1H, d, J = 8.6 Hz), 7.28 (1H, s), 7.48 (1H, dd, J = 2.2, 8.6 Hz), 7.63 (1H, s). | ESI-MS m/z: 468 [M + H]+ |
| 636 (isomer B) | | 1H-NMR (CDCl₃) δ: 0.18-0.21 (2H, m), 0.52-0.56 (2H, m), 1.03 (1H, m), 2.10-2.24 (2H, m), 3.09 (1H, s), 3.24-3.31 (2H, m), 3.62-3.65 (2H, m), 4.01 (1H, dd, J = 7.9, 10.0 Hz), 4.20 (1H, dd, J = 9.1, 10.8 Hz), 4.28-4.36 (2H, m), 4.64 (1H, m), 4.92 (1H, d, J = 3.8 Hz), 5.45 (1H, m), 5.90 (1H, s), 6.97 (1H, d, J = 8.6 Hz), 7.29 (1H, s), 7.48 (1H, dd, J = 2.1, 8.7 Hz), 7.61 (1H, d, J = 1.9 Hz). | ESI-MS m/z: 468 [M + H]+ |
| 637 | | 1H-NMR (CDCl₃) δ: 1.68-1.74 (3H, m), 1.84-1.91 (3H, m), 2.83 (1H, m), 3.10-3.16 (2H, m), 3.38-3.46 (2H, m), 3.90-4.54 (6H, m), 4.68-4.86 (1H, m), 5.38-5.59 (1H, m), 6.56-6.60 (1H, m), 6.96-7.22 (2H, m), 7.57-7.65 (2H, m). | ESI-MS m/z: 469 [M + H]+ |

TABLE 83-continued

| Example | Structural formula | NMR | MS |
|---|---|---|---|
| 638 | | 1H-NMR (CDCl3) δ: 2.13 (1H, m), 2.34 (1H, m), 2.88 (1H, dd, J = 16.7, 4.3 Hz), 3.95 (1H, dd, J = 16.7, 5.4 Hz), 3.46-3.90 (8H, m), 3.59-4.28 (6H, m), 4.58 (2H, s), 4.63 (1H, m), 6.05 (1H, s), 6.88 (1H, m), 7.04 (1H, m), 7.07 (1H, s), 7.13 (1H, m). | ESI-MS m/z: 498 [M + H]+ |
| 639 | | 1H-NMR (CDCl3) δ: 0.18 (2H, m), 0.53 (2H, m), 1.02 (1H, m), 2.06-2.25 (2H, m), 2.92 (1H, dd, J = 16.8, 3.9 Hz), 3.10 (1H, dd, J = 16.8, 5.7 Hz), 3.22-3.31 (2H, m), 3.58-3.66 (2H, m), 4.02 (1H, m), 4.09-4.21 (2H, m), 4.34 (1H, m), 4.63 (1H, m), 5.45 (1H, m), 5.90 (1H, s), 6.61 (1H, m), 6.94 (1H, q, J = 9.3 Hz), 6.99 (1H, m). | ESI-MS m/z: 420 [M + H]+ |
| 640 | | 1H-NMR (CDCl3) δ: 1.70-1.89 (2H, m), 1.90-2.06 (2H, m), 2.92 (1H, dd, J = 16.8, 3.6 Hz), 3.10 (1H, dd, J = 16.8, 5.7 Hz), 3.55-3.71 (4H, m), 3.89 (1H, m), 4.09-4.21 (2H, m), 4.33 (1H, m), 4.64 (1H, m), 5.33 (1H, m), 5.68-6.02 (1H, m), 5.89 (1H, s), 6.61 (1H, m), 6.94 (1H, q, J = 9.3 Hz), 6.98 (1H, m). | ESI-MS m/z: 444 [M + H]+ |
| 641 (isomer A) | | 1H-NMR (CDCl3) δ: 2.95 (1H, s), 3.14 (2H, t, J = 5.4 Hz), 3.21 (2H, q, J = 9.8 Hz), 4.12 (1H, dd, J = 7.1, 10.1 Hz), 4.20 (1H, dd, J = 9.0, 10.8 Hz), 4.33-4.39 (2H, m), 4.64 (1H, m), 4.92 (1H, d, J = 3.8 Hz), 5.51 (1H, m), 5.95 (1H, s), 6.97 (1H, d, J = 8.7 Hz), 7.29 (1H, s), 7.49 (1H, dd, J = 2.1, 8.6 Hz), 7.62 (1H, d, J = 1.8 Hz). | ESI-MS m/z: 498 [M + H]+ |

TABLE 84

| Example | Structural formula | NMR | MS |
|---|---|---|---|
| 641 (isomer B) | | 1H-NMR (CDCl3) δ: 2.95 (1H, s), 3.13 (2H, dd, J = 1.9, 5.6 Hz), 3.21 (2H, q, J = 9.7 Hz), 4.12 (1H, m, 4.20 (1H, dd, J = 8.9, 10.9 Hz), 4.33-4.41 (2H, m), 4.64 (1H, m), 4.93 (1H, d, J = 3.8 Hz), 5.51 (1H, m), 5.94 (1H, s), 6.97 (1H, d, J = 8.6 Hz), 7.28 (1H, s), 7.49 (1H, dd, J = 2.2, 8.7 Hz), 7.64 (1H, d, J = 1.9 Hz). | ESI-MS m/z: 498 [M + H]+ |
| 642 | | 1H-NMR (CDCl3) δ: 1.26-1.84 (5H, m), 2.47 (2H, m), 3.02 (2H, m), 3.36-3.44 (2H, m), 3.76 (2H, m), 3.98 (2H, m), 4.09-4.46 (4H, m), 4.69-4.87 (1H, m), 5.38-5.58 (1H, m), 6.53-6.58 (1H, m), 6.95-7.22 (2H, m), 7.57-7.65 (2H, m). | ESI-MS m/z: 483 [M + H]+ |
| 643 | | 1H-NMR (CDCl3) δ: 2.89-2.95 (2H, m), 3.65-3.71 (2H, m), 3.84 (1H, m), 4.09-4.44 (5H, m), 4.69-4.82 (4H, m), 5.39-5.59 (1H, m), 6.55-6.59 (1H, m), 6.96-7.23 (2H, m), 7.57-7.66 (2H, m). | ESI-MS m/z: 441 [M + H]+ |
| 644 | | 1H-NMR (CDCl3) δ: 2.83 (2H, t, J = 5.2 Hz), 2.93 (1H, dd, J = 4.7, 17.4 Hz), 3.03 (2H, m), 3.21 (1H, dd, J = 5.5, 16.8 Hz), 3.78 (2H, s), 3.81-3.90 (4H, m), 4.14 (2H, m), 4.26 (2H, m), 4.66 (1H, m), 6.52 (1H, s), 6.95 (1H, d, J = 8.5 Hz), 7.00 (1H, d, J = 8.5 Hz), 7.33 (1H, s), 7.38 (1H, d, J = 8.6 Hz) | ESI-MS m/z: 493 [M + H]+ |

TABLE 84-continued

| Example | Structural formula | NMR | MS |
|---|---|---|---|
| 645 | | 1H-NMR (CDCl₃) δ: 2.81-2.88 (2H, m), 2.95-3.09 (2H, m), 3.71-3.91 (6H, m), 4.09-4.49 (4H, m), 4.69-4.87 (1H, m), 5.38-5.59 (1H, m), 6.51-6.56 (1H, m), 6.95-7.22 (2H, m), 7.57-7.65 (2H, m). | ESI-MS m/z: 511 [M + H]+ |
| 646 | | 1H-NMR (CDCl₃) δ: 2.42-2.53 (1H, m), 2.63-2.80 (2H, m), 2.91-3.08 (3H, m), 3.69-3.85 (2H, m), 4.08-4.57 (5H, m), 4.66-4.86 (2H, m), 5.04-5.13 (1H, m), 5.38-5.58 (1H, m), 6.48-6.55 (1H, m), 6.95-7.22 (2H, m), 7.57-7.65 (2H, m). | ESI-MS m/z: 455 [M + H]+ |
| 647 | | 1H-NMR (CDCl₃) δ: 2.31-2.46 (2H, m), 2.79-3.02 (4H, m), 3.70-3.76 (2H, m), 4.09-4.48 (4H, m), 4.69-4.87 (1H, m), 5.38-5.59 (1H, m), 6.53-6.57 (1H, m), 6.95-7.22 (2H, m), 7.57-7.65 (2H, m). | ESI-MS m/z: 481 [M + H]+ |
| 648 | | 1H-NMR (CDCl₃) δ: 2.39-2.54 (2H, m), 4.06-4.28 (2H, m), 4.28-4.46 (2H, m), 4.62 (1H, m), 4.78 (1H, m), 5.50 (1H, dd, J = 54.1, 1.8 Hz), 6.17 (1H, s), 7.02 (1H, d, J = 8.6 Hz), 7.15 (1H, d, J = 8.8 Hz), 7.61 (1H, dt, J = 8.6, 2.0 Hz), 7.68 (1H, t, J = 2.0 Hz). | ESI-MS m/z: 411 [M + H]+ |
| 649 | | 1H-NMR (CDCl₃) δ: 1.91-2.03 (2H, m), 2.36 (1H, m), 2.85 (1H, m), 3.86 (1H, m), 4.07-4.24 (2H, m), 4.39 (1H, m), 4.48-4.64 (1H, m), 4.79 (1H, m), 5.50 (1H, dd, J = 54.0, 1.8 Hz), 6.32 (1H, s), 7.02 (1H, d, J = 8.6 Hz), 7.15 (1H, d, J = 8.8 Hz), 7.61 (1H, dt, J = 8.6, 2.0 Hz), 7.69 (1H, t, J = 2.0 Hz). | ESI-MS m/z: 425 [M + H]+ |

TABLE 85

| Example | Structural formula | NMR | MS |
|---|---|---|---|
| 650 | | 1H-NMR (CDCl₃) δ: 0.23 (2H, m), 0.57 (2H, m), 1.08 (1H, m), 2.14-2.37 (2H, m), 3.39 (2H, d, J = 6.9 Hz), 3.68 (1H, dd, J = 10.2, 5.2 Hz), 3.78 (1H, dd, J = 10.2, 5.2 Hz), 4.05-4.48 (5H, m), 4.69-4.85 (1H, m), 5.48 (1H, dd, J = 54.0, 2.0 Hz), 6.06 (1H, s), 7.01 (1H, d, J = 8.6 Hz), 7.16 (1H, d, J = 8.9 Hz), 7.60 (1H, dt, J = 8.6, 2.0 Hz), 7.68 (1H, t, J = 2.0 Hz). | ESI-MS m/z: 427 [M + H]+ |
| 651 | | 1H-NMR (CDCl₃) δ: 1.86-1.99 (3H, m), 2.03-2.18 (2H, m), 2.70-2.90 (1H, m), 3.15 (1H, m), 3.77-4.24 (11H, m), 4.46-4.65 (3H, m), 5.80-6.04 (1H, m), 6.86 (1H, dd, J = 8.2, 7.0 Hz), 7.02 (1H, m), 7.04 (1H, br s), 7.12 (1H, m). | ESI-MS m/z: 482 [M + H]+ |

TABLE 85-continued

| Example | Structural formula | NMR | MS |
|---|---|---|---|
| 652 | | 1H-NMR (CDCl₃) δ: 0.20 (2H, m), 0.55 (2H, m), 1.07 (1H, m), 2.82 (2H, t, J = 5.4 Hz), 2.98-3.06 (3H, m), 3.31 (2H, d, J = 6.9 Hz), 3.66 (2H, t, J = 5.4 Hz), 3.79 (2H, d, J = 3.9 Hz), 4.16-4.24 (3H, m), 4.35 (1H, m), 4.66 (1H, m), 4.93 (1H, t, J = 4.2 Hz), 6.53 (1H, s), 6.97 (1H, d, J = 8.4 Hz), 7.29 (1H, m), 7.48 (1H, m), 7.63 (1H, m). | ESI-MS m/z: 481 [M + H]+ |
| 653 | | 1H-NMR (CDCl₃) δ: 1.29 (2H, m), 1.68 (2H, m), 1.78 (1H, m), 2.40 (2H, d, J = 7.2 Hz), 2.89-2.95 (3H, m), 3.21 (1H, dd, J = 5.3, 16.5 Hz), 3.39 (2H, td, J = 1.9, 11.8 Hz), 3.65 (2H, s), 3.97 (2H, dd, J = 3.5, 12.0 Hz), 4.12 (2H, t, J = 5.4 Hz), 4.22-4.29 (2H, m), 4.66 (1H, m), 6.51 (1H, s), 6.95 (1H, d, J = 8.6 Hz), 7.00 (1H, d, J = 7.9 Hz), 7.33 (1H, s), 7.38 (1H, d, J = 8.7 Hz). | ESI-MS m/z: 465 [M + H]+ |
| 654 | | 1H-NMR (CDCl₃) δ: 0.17-0.23 (2H, m), 0.51-0.58 (2H, m), 1.06 (1H, m), 2.78-2.84 (2H, m), 2.95-3.08 (2H, m), 3.29-3.33 (2H, m), 3.63-3.71 (2H, m), 3.75-3.81 (2H, m), 4.09-4.45 (4H, m), 4.69-4.87 (1H, m), 5.38-5.59 (1H, m), 6.51-6.55 (1H, m), 6.95-7.22 (2H, m), 7.57-7.65 (2H, m). | ESI-MS m/z: 483 [M + H]+ |
| 655 | | 1H-NMR (CDCl₃) δ: 1.24-1.42 (2H, m), 1.49 (1H, m), 1.63 (1H, m), 1.69-1.93 (3H, m), 2.00-2.19 (2H, m), 2.87 (1H, dd, J = 4.0, 16.9 Hz), 3.18 (1H, dd, J = 5.6, 17.0 Hz), 3.39-3.45 (2H, m), 3.82 (2H, q, J = 8.7 Hz), 3.96-3.98 (2H, m), 4.02-4.22 (4H, m), 4.29 (1H, m), 4.55-4.63 (3H, m), 5.99 (1H, s), 6.87 (1H, d, J = 8.3 Hz), 7.00-7.04 (2H, m), 7.11 (1H, dd, J = 1.9, 8.3 Hz). | ESI-MS m/z: 510 [M + H]+ |
| 656 | | 1H-NMR (CDCl₃) δ: 0.93-1.01 (3H, m), 1.52-1.63 (2H, m), 1.75-1.99 (2H, m), 2.29 (1H, m), 3.72 (1H, m), 3.99-4.47 (5H, m), 4.76 (1H, m), 5.43 (0.4H, m), 5.51 (0.6H, d, J = 54.4 Hz), 6.25 (0.4H, s), 6.29 (0.6H, s), 6.91-7.19 (2H, m), 7.52-7.66 (2H, m). | ESI-MS m/z: 444 [M + H]+ |
| 657 | | 1H-NMR (CDCl₃) δ: 2.88 (1H, m), 3.19 (1H, m), 3.70-3.85 (8H, m), 4.14-4.33 (4H, m), 4.64 (1H, m), 5.40 (1H, m), 5.91 (1H, s), 6.93-6.97 (2H, m), 7.33 (1H, s), 7.38 (1H, m). | ESI-MS m/z: 510 [M + H]+ |
| 658 | | 1H-NMR (CDCl₃) δ: 2.83 (1H, dd, J = 4.2, 16.9 Hz), 3.14 (1H, dd, J = 5.3, 16.5 Hz), 3.71-3.85 (8H, m), 4.14-4.19 (3H, m), 4.30 (1H, dt, J = 2.9, 9.3 Hz), 4.60 (1H, m), 5.41 (1H, m), 5.90 (1H, s), 6.80 (1H, m), 6.99 (1H, m), 7.03 (1H, m), 7.08 (1H, m). | ESI-MS m/z: 476 [M + H]+ |

TABLE 86

| Example | Structural formula | NMR | MS |
|---|---|---|---|
| 659 | | 1H-NMR (CDCl₃) δ: 2.89 (1H, dd, J = 4.4, 16.9 Hz), 3.17 (1H, dd, J = 5.3, 16.8 Hz), 3.71-3.86 (8H, m), 4.18-4.33 (4H, m), 4.63 (1H, m), 5.41 (1H, m), 5.91 (1H, s), 6.92-6.94 (2H, m), 7.38 (1H, s), 7.42 (1H, m). | ESI-MS m/z: 467 [M + H]+ |
| 660 | | 1H-NMR (CDCl₃) δ: 2.88 (1H, d, J = 4.9 Hz), 3.74-3.76 (4H, m), 3.80-3.87 (4H, m), 4.17-4.23 (2H, m), 4.30-4.35 (2H, m), 4.65 (1H, m), 4.92 (1H, m), 6.42 (1H, m), 5.92 (1H, s), 6.97 (1H, d, J = 8.7 Hz), 7.24 (1H, m), 7.48 (1H, m), 7.65 (1H, m). | ESI-MS m/z: 526 [M + H]+ |
| 661 | | 1H-NMR (CDCl₃) δ: 2.84 (1H, m), 3.16 (1H, m), 3.71-3.85 (10H, m), 4.09-4.32 (4H, m), 4.56-4.64 (3H, m), 5.40 (1H, m), 5.90 (1H, s), 6.86 (1H, m), 6.99-7.14 (3H, m). | ESI-MS m/z: 554 [M + H]+ |
| 662 | | 1H-NMR (CDCl₃) δ: 2.14-2.27 (2H, m), 2.84 (1H, dd, J = 17.8, 4.6 Hz), 3.14 (1H, dd, J = 17.8, 7.7 Hz), 3.72 (3H, m), 3.79 (3H, m), 3.88 (2H, m), 4.04-4.13 (1H, m), 4.15-4.26 (3H, m), 4.36 (1H, m), 4.60 (1H, m), 6.02 (1H, s), 6.81 (1H, d, J = 8.7 Hz), 7.00 (1H, d, J = 8.8 Hz), 7.04 (1H, d, J = 2.6 Hz), 7.08 (1H, dd, J = 8.7, 2.6 Hz). | ESI-MS m/z: 490 [M + H]+ |
| 663 | | 1H-NMR (CDCl₃) δ: 2.14-2.28 (2H, m), 2.92 (1H, dd, J = 16.6, 4.4 Hz), 3.20 (1H, dd, J = 16.6, 5.3 Hz), 3.72 (3H, m), 3.79 (3H, m), 3.88 (2H, m), 4.04-4.13 (1H, m), 4.15-4.29 (3H, m), 4.36 (1H, m), 4.63 (1H, m), 6.02 (1H, s), 6.94 (1H, d, J = 8.6 Hz), 6.97 (1H, d, J = 7.8 Hz), 7.33 (1H, d, J = 1.8 Hz), 7.38 (1H, dd, J = 8.6, 1.8 Hz). | ESI-MS m/z: 524 [M + H]+ |
| 664 | | 1H-NMR (CDCl₃) δ: 2.14-2.28 (2H, m), 2.92 (1H, dd, J = 16.6, 5.1 Hz), 3.15 (1H, dd, J = 16.6, 5.4 Hz), 3.72 (3H, m), 3.79 (3H, m), 3.89 (2H, m), 4.04-4.13 (1H, m), 4.15-4.29 (3H, m), 4.36 (1H, m), 4.63 (1H, m), 6.02 (1H, s), 6.93 (1H, d, J = 8.4 Hz), 6.94 (1H, m), 7.38 (1H, d, J = 2.0 Hz), 7.42 (1H, dd, J = 8.5, 2.0 Hz). | ESI-MS m/z: 481 [M + H]+ |
| 665 | | 1H-NMR (CDCl₃) δ: 2.12-2.32 (2H, m), 3.66-3.97 (9H, m), 4.03-4.21 (2H, m), 4.22-4.27 (3H, m), 4.63-4.87 (1H, m), 5.33-5.61 (1H, m), 6.01 (0.5H, s), 6.06 (0.5H, s), 6.94 (0.5H, m), 6.99-7.10 (1H, m), 7.18 (0.5H, m), 7.54-7.67 (1H, m). | ESI-MS m/z: 542 [M + H]+ |
| 666 | | 1H-NMR (CDCl₃) δ: 2.81 (2H, t, J = 5.3 Hz), 2.93 (1H, dd, J = 4.6, 16.8 Hz), 3.02 (2H, td, J = 2.0, 5.4 Hz), 3.21 (1H, dd, J = 5.4, 16.8 Hz), 3.66-3.77 (6H, m), 4.14 (2H, t, J = 5.5 Hz), 4.21-4.30 (2H, m), 4.65 (1H, m), 5.88 (1H, m), 6.52 (1H, s), 6.95 (1H, d, J = 8.6 Hz), 7.00 (1H, d, J = 7.8 Hz), 7.33 (1H, s), 7.38 (1H, m). | ESI-MS m/z: 475 [M + H]+ |

TABLE 86-continued

| Example | Structural formula | NMR | MS |
|---|---|---|---|
| 667 | | 1H-NMR (CDCl$_3$) δ: 2.82-2.91 (3H, m), 3.02 (2H, d, J = 5.6 Hz), 3.18 (1H, dd, J = 5.0, 17.0 Hz), 3.77-3.90 (8H, m), 4.14 (2H, t, J = 5.6 Hz), 4.17-4.24 (2H, m), 4.57 (2H, s), 4.64 (1H, m), 6.52 (1H, s), 6.87 (1H, d, J = 8.3 Hz), 7.05 (2H, s), 7.12 (1H, dd, J = 1.9, 8.4 Hz). | ESI-MS m/z: 537 [M + H]+ |

TABLE 87

| Example | Structural formula | NMR | MS |
|---|---|---|---|
| 668 | | 1H-NMR (CDCl$_3$) δ: 1.86-2.40 (5H, m), 2.71-2.88 (2H, m), 2.96-3.20 (3H, m), 3.15 (1H, m), 3.76-4.24 (7H, m), 4.43-4.45 (1H, m), 5.69-6.03 (1H, m), 5.99-6.03 (1H, m), 6.83 (1H, m), 6.93 (1H, br s), 6.97-7.06 (2H, m). | ESI-MS m/z: 434 [M + H]+ |
| 669 | | 1H-NMR (CDCl$_3$) δ: 1.63 (1H, m), 2.04 (1H, m), 2.46-2.55 (3H, m), 2.87-2.99 (3H, m), 3.21 (1H, dd, J = 5.5, 16.6 Hz), 3.56 (1H, dd, J = 4.8, 8.7 Hz), 3.69 (2H, t, J = 4.3 Hz), 3.75 (1H, q, J = 8.2 Hz), 3.82-3.90 (2H, m), 4.13 (2H, t, J = 5.5 Hz), 4.22-4.29 (2H, m), 4.66 (1H, m), 6.52 (1H, s), 6.95 (1H, d, J = 8.6 Hz), 7.00 (1H, d, J = 8.0 Hz), 7.33 (1H, s), 7.38 (1H, d, J = 8.5 Hz). | ESI-MS m/z: 451 [M + H]+ |
| 670 | | 1H-NMR (CDCl$_3$) δ: 1.87-1.99 (1H, m), 2.08-2.19 (1H, m), 2.81-3.07 (3H, m), 3.26 (1H, m), 3.62-4.04 (6H, m), 4.09-4.48 (4H, m), 4.69-4.85 (1H, m), 5.38-5.59 (1H, m), 6.52-6.56 (1H, m), 6.95-7.22 (2H, m), 7.57-7.65 (2H, m). | ESI-MS m/z: 455 [M + H]+ |
| 671 | | 1H-NMR (CDCl$_3$) δ: 1.15-1.19 (6H, m), 2.75-2.82 (2H, m), 2.96-3.08 (2H, m), 3.54-3.65 (3H, m), 3.74-3.80 (2H, m), 4.09-4.45 (4H, m), 4.69-4.87 (1H, m), 5.38-5.59 (1H, m), 6.50-6.55 (1H, m), 6.95-7.22 (2H, m), 7.57-7.65 (2H, m). | ESI-MS m/z: 471 [M + H]+ |
| 672 | | 1H-NMR (CDCl$_3$) δ: 1.18-1.30 (2H, m), 1.64 (1H, m), 1.81-1.95 (2H, m), 2.33-2.46 (2H, m), 2.78-3.00 (2H, m), 3.13-3.21 (2H, m), 3.38-3.46 (1H, m), 3.56-3.73 (2H, m), 3.83-3.98 (2H, m), 4.07-4.47 (4H, m), 4.69-4.87 (1H, m), 5.38-5.59 (1H, m), 6.50-6.54 (1H, m), 6.95-7.22 (2H, m), 7.57-7.65 (2H, m). | ESI-MS m/z: 483 [M + H]+ |
| 673 | | 1H-NMR (CDCl$_3$) δ: 1.63 (1H, m), 2.03 (1H, m), 2.48-2.57 (3H, m), 2.87-2.99 (2H, m), 3.54-3.91 (6H, m), 4.09-4.45 (4H, m), 4.68-4.87 (1H, m), 5.38-5.59 (1H, m), 6.51-6.55 (1H, m), 6.95-7.22 (2H, m), 7.57-7.65 (2H, m). | ESI-MS m/z: 469 [M + H]+ |

TABLE 87-continued

| Example | Structural formula | NMR | MS |
|---|---|---|---|
| 674 | | 1H-NMR (CDCl₃) δ: 1.24-1.42 (2H, m), 1.49 (1H, m), 1.82 (1H, m), 1.71 (1H, m), 1.76-1.93 (2H, m), 2.00-2.19 (2H, m), 2.86 (1H, m), 3.04 (2H, dt, J = 4.4, 17.4 Hz), 3.16 (1H, dd, J = 5.3, 17.0 Hz), 3.42 (2H, tt, J = 1.8, 11.8 Hz), 3.95-3.99 (2H, m), 4.03-4.21 (4H, m), 4.30 (1H, m), 4.61 (1H, m), 5.88 (1H, tt, J = 4.5, 56.7 Hz), 5.99 (1H, s), 6.84 (1H, d, J = 8.3 Hz), 6.93 (1H, s), 6.99-7.01 (2H, m). | ESI-MS m/z: 462 [M + H]+ |
| 675 | | 1H-NMR (CDCl₃) δ: 3.39 (1H, m), 3.71-3.85 (8H, m), 4.18 (1H, m), 4.26-4.32 (1H, m), 4.42 (1H, m), 4.49 (1H, m), 4.74 (1H, m), 5.40 (1H, m), 5.89 (1H, s), 6.99-7.02 (2H, m), 7.48 (1H, m), 7.65 (1H, m). | ESI-MS m/z: 526 [M + H]+ |
| 676 | | 1H-NMR (CDCl₃) δ: 3.72-3.91 (8H, m), 4.07-4.44 (4H, m), 4.68-4.84 (1H, m), 5.36-5.58 (2H, m), 5.92 (1H, m), 6.89-7.13 (2H, m), 7.57-7.65 (2H, m). | ESI-MS m/z: 528 [M + H]+ |

TABLE 88

| Example | Structural formula | NMR | MS |
|---|---|---|---|
| 677 | | 1H-NMR (CDCl₃) δ: 2.85 (2H, t, J = 5.2 Hz), 3.02-3.08 (3H, m), 3.78-3.90 (6H, m), 4.16 (2H, m), 4.22 (1H, m), 4.35 (1H, m), 4.66 (1H, m), 4.92 (1H, t, J = 4.2 Hz), 6.54 (1H, s), 6.97 (1H, d, J = 8.6 Hz), 7.30 (1H, d, J = 8.3 Hz), 7.48 (1H, dd, J = 2.2, 8.6 Hz), 7.62 (1H, s). | ESI-MS m/z: 509 [M + H]+ |
| 678 | | 1H-NMR (CDCl₃) δ: 2.79-2.86 (2H, m), 2.97-3.08 (2H, m), 3.65-3.80 (6H, m), 4.08-4.47 (4H, m), 4.69-4.87 (1H, m), 5.38-5.59 (1H, m), 5.72-6.04 (1H, m), 6.51-6.55 (1H, m), 6.95-7.22 (2H, m), 7.57-7.65 (2H, m). | ESI-MS m/z: 493 [M + H]+ |
| 679 | | 1H-NMR (CDCl₃) δ: 2.01-2.15 (2H, m), 3.90-4.21 (7H, m), 4.34-4.54 (2H, m), 4.76 (1H, m), 5.43 (0.4H, m), 5.51 (0.6H, m), 6.26 (0.4H, s), 6.30 (0.6H, s), 6.90-7.18 (2H, m), 7.57-7.65 (2H, m). | ESI-MS m/z: 498 [M + H]+ |
| 680 | | 1H-NMR (CDCl₃) δ: 1.96-2.07 (2H, m), 2.92 (1H, dd, J = 16.7, 6.1 Hz), 3.21 (1H, br d, J = 16.7 Hz), 3.73-4.17 (10H, m), 4.19-4.28 (2H, m), 4.42 (1H, m), 4.65 (1H, m), 6.49 (1H, s), 6.92-7.02 (2H, m), 7.33 (1H, br s), 7.39 (1H, m). | ESI-MS m/z: 524 [M + H]+ |
| 681 | | 1H-NMR (CDCl₃) δ: 1.96-2.11 (2H, m), 3.03-3.19 (1H, m), 3.69-3.85 (5H, m), 3.87-4.25 (6H, m), 4.29-4.47 (2H, m), 4.64 (1H, m), 4.92 (1H, m), 6.25-6.26 (1H, m), 6.97 (1H, d, J = 8.6 Hz), 7.25-7.32 (1H, m), 7.48 (1H, dd, J = 8.6, 1.8 Hz), 7.64 (1H, d, J = 1.8 Hz). | ESI-MS m/z: 540 [M + H]+ |

TABLE 88-continued

| Example | Structural formula | NMR | MS |
|---|---|---|---|
| 682 | [structure with F₃C, O, pyrazole, chromane-Cl] | 1H-NMR (CDCl₃) δ: 1.96-2.11 (2H, m), 2.85 (1H, m), 3.15 (1H, m), 3.72-3.83 (5H, m), 3.85-4.23 (7H, m), 4.40 (1H, m), 4.60 (1H, m), 6.24 (1H, s), 6.81 (1H, dd, J = 8.6, 2.0 Hz), 8.99 (1H, m), 7.04 (1H, m), 7.08 (1H, m). | ESI-MS m/z: 490 [M + H]+ |
| 683 | [structure with F₃C, O, pyrazole, HO, chromane-CF₃] | 1H-NMR (CDCl₃) δ: 1.75 (1H, m), 2.02 (1H, m), 2.39 (1H, m), 2.79 (1H, dd, J = 4.7, 18.5 Hz), 3.62-3.67 (2H, m), 3.76-3.86 (3H, m), 4.13 (1H, m), 4.21 (1H, m), 4.33-4.36 (3H, m), 4.65 (1H, m), 4.93 (1H, brs), 6.25 (1H, s), 6.97 (1H, d, J = 8.6 Hz), 7.26-7.31 (1H, m), 7.49 (1H, m), 7.65 (1H, s). | ESI-MS m/z: 510 [M + H]+ |

Test Example 1: Human Nav1.7 Inhibitory Activity Evaluation

A cell line in which human Nav1.7 and human Navβ1 subunits were stably expressed in HEK293A cells was used. Dulbecco's Modified Eagle Medium (DMEM) supplemeted with 10% fetal bovine serum, 600 µg/ml geneticin, and 2 µg/ml blasticidin S were used as culture medium under the conditions of 37° C. and 5% $CO_2$ in T175 flasks to carry out culturing. When 60-80% confluence was reached, the cells were detached and a cell suspension of about $0.5$-$5.0 \times 10^6$ cells/mL was prepared. The amount of current through human Nav1.7 was recorded using a fully automatic patch clamp device QPatch16X (Sophion Biosciences) at room temperature. As the extracellular solution, the solution of 145 mM NaCl, 4 mM KCl, 1 mM $MgCl_2$, 2 mM $CaCl_2$, 10 mM Glucose, 10 mM 4-(2-hydroxyethyl)-1-piperazine ethanesulfonic acid (HEPES) at pH 7.4 was used. As the intracellular solution, the solution of 135 mM CsF, ⅕ mM glycol ether diaminetetraacetic acid (EGTA)/CsOH, 10 mM HEPES, 10 mM NaCl at pH 7.3 was used. The test compounds were dissolved in dimethyl sulfoxide (DMSO) and diluted with the extracellular solution to attain the DMSO concentration of 0.1% at the time of assay.

The current response was obtained at a sampling frequency of 25 kHz, and noise was removed with a 3 kHz low-pass filter. The holding potential was −100 mV. Correction of the leakage current was carried out by applying a step pulse of −120 mV before the test pulse. In order to investigate inhibitory action of the test compound, the following test pulse was given: Namely, after depolarizing pulse of −10 mV was applied for 50 milliseconds, it was fixed at −120 mV for 500 milliseconds; a potential at which about 30-40% of the channel was inactivated was maintained for 15 seconds, then fixed again at −120 mV for 100 milliseconds, and finally a −10 mV depolarization pulse was given for 50 milliseconds. Test pulses were given before and after the test compound addition.

The inhibitory activity of the test compound was determined based on the amount of inward current generated by the second depolarization pulse, and the 50% inhibitory concentration ($IC_{50}$) was calculated from the concentration-response curve. $IC_{50}$ values are shown in Tables 89 to 98 below.

Compounds with $IC_{50}$ values of less than 1 µM are indicated by the letter "A", and compounds with $IC_{50}$ values less than 10 µM are indicated by the letter "B".

Meanwhile, unless otherwise stated, "Example" in the table refers to the compound intended for production in each Example; for example, the evaluation result for Example 1 shows the evaluation result of the compound intended for production in Example 1.

Test Example 2: Human Nav1.5 Inhibitory Activity Evaluation

A cell line in which human Nav1.5 was stably expressed in HEK293 cells was used. DMEM supplemeted with 15% fetal bovine serum, 500 µg/ml geneticin, 100 units/ml penicillin, 100 µg/ml streptomycin, 20 mM HEPES was used as culture medium under the conditions of 37° C. and 5% $CO_2$ in T175 flasks to carry out culturing. When 60-80% confluence was reached, a cell suspension of about $0.5$-$5.0 \times 10^6$ cells/mL was prepared. The amount of current through human Nav1.5 was recorded using a fully automatic patch clamp device QPatch16X at room temperature. As the extracellular solution, 145 mM NaCl, 4 mM KCl, 1 mM $MgCl_2$, 2 mM $CaCl_2$, 10 mM Glucose, and 10 mM HEPES at pH 7.4 was used. As the intracellular solution, 135 mM CsF, ⅕ mM EGTA/CsOH, 10 mM HEPES, and 10 mM NaCl at pH 7.3 was used. The test compounds were dissolved in DMSO and diluted with the extracellular solution to attend the DMSO concentration of 0.1% at the time of assay.

The current response was obtained at a sampling frequency of 25 kHz, and noise was removed with a 3 kHz low-pass filter. The holding potential was −80 mV. Correction of the leakage current was carried out by applying a step pulse of −100 mV before the test pulse. In order to investigate human Nav1.5 inhibitory effect of the test compound, test pulses imitating the action potential of cardiomyocytes were continuously given 20 times. The test pulses were given before and after the test compound addition.

The inhibitory activity of the test compound was determined based on the amount of inward current generated by the 20th depolarization pulse, and the 50% inhibitory concentration ($IC_{50}$) was calculated from the concentration-response curve.

The $IC_{50}$ values of inhibitory action of the test compounds are shown in Tables 89 to 98 below.

Compounds with an $IC_{50}$ value of less than 1 µM are indicated by the letter "A", compounds with an $IC_{50}$ value of 1 µM or more and less than 3 µM are indicated by the letter "B" and compounds with an $IC_{50}$ value of 3 µM or more is indicated by the letter "C".

Test Example 3: Effect on Acute Pain

Six-week old male ICR mice were used for the test. Test compounds were orally administered at 1-10 mg/kg and the mice were habituated to a clear observation cage for 60 minutes. The mice were lightly restrained under no anesthesia and 20 µL of 80 µg/mL (0.8% ethanol-saline) capsaicin solution was injected subcutaneously into the plantar surface of rihgt hind paw of mice. The mice were returned to the observation cage and, from just after that, the duration of pain-related behavior (licking, shaking) occurring in the right hind limb was measured as the reaction time for 5 minutes.

The inhibition rate of the test compound was determined by the following calculation formula.

Test compound inhibition rate (%)=100×[1−(response time of test compound administered group/response time of vehicle control group)]

The effect of the test compound on an acute pain is shown in Table 99 below. Compounds with an inhibition rate of 30% or more are indicated by the letter "A", and compounds with an inhibition rate of 20% or more and less than 30% are indicated by the letter "B" and compounds with an inhibition rate of 10% or more but less than 20% is indicated by the letter "C".

Test Example 4: Effect on a Neuropathic Pain

Five-week old male ICR mice were used for the test. The skin and muscles were incised to expose the sixth lumbar vertebra under isoflurane anesthesia, and the right transverse process was removed. The L5 spinal nerve was isolated from the surrounding tissue to cut out, and then the incision site was sutured.

The 50% pain threshold of the plantar surface was determined by referring to the method of Chaplan S R et al. (J Neurosci Methods 1994, 53: 55-63) using von Frey filaments (0.008 g, 0.02 g, 0.04 g, 0.07 g, 0.16 g, 0.4 g and 0.6 g). First, the mice were placed in a measurement case with a lattice scaffold and habituatedd until the animal settled; 0.07 g of filament was pressed against the plantar surface for about 3 seconds. If withdrawal behavior was observed, the filament with the stimulation intensity one level lower was used to apply stimulation, and conversely, if the withdrawal behavior was not detected, the filament with the stimulation intensity one level higher was used to apply stimulation. By repeating this operation, starting from 2 times before and after the presence or absence of escape behavior changed, the results for a total of 6 times were recorded, to calculate a 50% pain threshold using the following calculation formula.

50% pain threshold (g)=$(10^{[Xf+\kappa\delta]}/10000)$

Xf is the value of the stimulus intensity of the filament used in the last stimulation (log value), κ is the value derived from the pattern of presence/absence of withdrawal behavior for 6 times, and δ is the difference in stimulus intensity (log value) between the filaments used (here 0.365).

Animals that showed as a 50% pain threshold of the affected limb plantar surface of 0.16 g or more before the surgery and 0.08 g or less after 1 week after the surgery were used as allodynia-developed animals for evaluation of the test substance.

Each of the present inventive compounds, for example, Example 70, isomer A of Example 103, isomer A of Example 134, isomer A of Example 161, Example 288, and Example 290, increased the 50% pain threshold at a dose of 10 mg/kg or less in single oral administration, and showed antiallodynic effect.

TABLE 89

| Example | NaV1.7 $IC_{50}$ | NaV1.5 $IC_{50}$ |
|---|---|---|
| 1 | B | C |
| 2 (isomer A) | A | B |
| 2 (isomer B) | A | C |
| 3 | A | B |
| 4 | B | C |
| 5 | A | B |
| 6 | B | B |
| 7 (isomer A) | A | B |
| 7 (isomer B) | A | C |
| 8 | A | C |
| 9 (isomer A) | B | C |
| 9 (isomer B) | A | C |
| 10 | B | |
| 11 | A | C |
| 12 | A | B |
| 13 | B | |
| 14 | B | C |
| 15 | A | |
| 16 | A | A |
| 17 | A | B |
| 18 | A | |
| 19 | A | A |
| 20 | A | A |
| 21 | A | A |
| 22 | B | C |
| 23 | B | C |
| 24 | A | |
| 25 | B | B |
| 26 | B | C |
| 27 | A | A |
| 28 | B | C |
| 29 | B | B |
| 30 | B | C |
| 31 | A | |
| 32 | B | B |
| 33 | A | B |
| 34 | B | C |
| 35 | A | B |
| 36 | A | C |
| 37 | B | C |
| 38 | B | C |
| 39 (isomer A) | B | B |
| 39 (isomer B) | B | C |
| 40 | B | C |
| 41 | B | C |
| 42 | B | |
| 43 | B | C |
| 44 | B | C |
| 45 | B | |
| 46 | B | B |
| 47 | B | C |
| 48 | B | C |
| 49 | B | C |
| 50 | B | |
| 51 | A | B |
| 52 | A | B |
| 53 | B | |
| 54 | B | |
| 55 | A | B |
| 56 | B | |
| 57 | A | A |
| 58 | B | C |
| 59 | B | C |
| 60 | B | C |
| 61 | B | C |
| 62 | B | C |
| 63 | B | |
| 64 | B | A |
| 65 | A | A |

TABLE 89-continued

| Example | NaV1.7 IC$_{50}$ | NaV1.5 IC$_{50}$ |
| --- | --- | --- |
| 66 | B | A |
| 67 | A | A |
| 68 | B | C |
| 69 | B | |
| 70 | A | B |
| 71 | A | A |
| 72 | A | C |
| 73 | B | |
| 74 (isomer A) | A | C |
| 74 (isomer B) | A | |
| 75 | A | C |

TABLE 90

| Example | NaV1.7 IC$_{50}$ | NaV1.5 IC$_{50}$ |
| --- | --- | --- |
| 76 | A | C |
| 77 | A | C |
| 78 | B | C |
| 79 | B | C |
| 80 | A | C |
| 81 | A | C |
| 82 | B | |
| 83 | A | B |
| 84 | B | C |
| 85 | A | C |
| 86 | A | C |
| 87 | B | C |
| 88 | A | |
| 89 | A | |
| 90 | A | B |
| 91 | B | C |
| 92 (isomer A) | A | C |
| 92 (isomer B) | A | C |
| 93 | A | |
| 94 | A | B |
| 95 (isomer A) | A | C |
| 95 (isomer B) | A | C |
| 96 | A | B |
| 97 (isomer A) | A | |
| 97 (isomer B) | A | C |
| 98 | A | |
| 99 | A | |
| 100 | B | C |
| 101 (isomer A) | A | C |
| 101 (isomer B) | B | C |
| 102 | A | C |
| 103 (isomer A) | A | C |
| 103 (isomer B) | B | C |
| 104 | A | |
| 105 | A | A |
| 106 | A | |
| 107 | B | |
| 108 | A | B |
| 109 (isomer A) | A | B |
| 109 (isomer B) | B | C |
| 110 | A | C |
| 111 (isomer A) | A | B |
| 111 (isomer B) | A | B |
| 112 | A | C |
| 113 (isomer A) | A | B |
| 113 (isomer B) | A | A |
| 114 | B | C |
| 115 (isomer A) | B | C |
| 115 (isomer B) | B | |
| 116 | A | |
| 117 | A | A |
| 118 | A | A |
| 119 | A | |
| 120 | B | |
| 121 | B | |
| 122 | B | C |
| 123 | B | C |
| 124 (isomer A) | A | C |
| 124 (isomer B) | B | C |

TABLE 90-continued

| Example | NaV1.7 IC$_{50}$ | NaV1.5 IC$_{50}$ |
| --- | --- | --- |
| 125 | B | C |
| 126 | A | B |
| 127 (isomer A) | A | C |
| 127 (isomer B) | A | C |
| 128 | A | B |
| 129 (isomer A) | A | C |
| 129 (isomer B) | A | B |
| 130 | B | C |
| 131 (isomer A) | A | B |
| 131 (isomer B) | B | C |
| 132 | B | |
| 133 | A | B |
| 134 (isomer A) | A | B |
| 134 (isomer B) | B | C |
| 135 | A | B |
| 136 (isomer A) | A | A |
| 136 (isomer B) | A | B |
| 137 | A | C |
| 138 (isomer A) | A | |
| 138 (isomer B) | B | |
| 139 | A | C |

TABLE 91

| Example | NaV1.7 IC$_{50}$ | NaV1.5 IC$_{50}$ |
| --- | --- | --- |
| 140 (isomer A) | A | C |
| 140 (isomer B) | A | B |
| 141 | A | C |
| 142 (isomer A) | A | B |
| 142 (isomer B) | A | C |
| 143 | A | C |
| 144 (isomer A) | A | |
| 144 (isomer B) | A | C |
| 145 | A | C |
| 146 (isomer A) | B | |
| 146 (isomer B) | A | C |
| 147 | A | C |
| 148 (isomer A) | A | |
| 148 (isomer B) | A | C |
| 149 | A | B |
| 150 (isomer A) | A | |
| 150 (isomer B) | A | B |
| 151 | A | B |
| 152 (isomer A) | A | C |
| 152 (isomer B) | A | C |
| 153 (isomer A) | A | B |
| 153 (isomer B) | A | |
| 154 (isomer A) | B | |
| 155 | B | C |
| 156 (isomer A) | A | C |
| 156 (isomer B) | B | |
| 157 | B | C |
| 158 (isomer A) | A | C |
| 158 (isomer B) | B | |
| 159 | A | C |
| 160 | A | C |
| 161 (isomer A) | A | C |
| 161 (isomer B) | B | |
| 162 | A | C |
| 163 (isomer A) | A | B |
| 163 (isomer B) | B | |
| 164 | A | C |
| 165 (isomer A) | A | |
| 165 (isomer B) | B | |
| 166 | A | |
| 167 | A | B |
| 168 | B | C |
| 169 | A | B |
| 170 (isomer A) | A | B |
| 170 (isomer B) | A | A |
| 171 | A | B |
| 172 | B | C |
| 173 (isomer A) | A | C |
| 173 (isomer B) | B | |

TABLE 91-continued

| Example | NaV1.7 IC$_{50}$ | NaV1.5 IC$_{50}$ |
|---|---|---|
| 174 | A | C |
| 175 | B | C |
| 176 | B | |
| 177 | A | B |
| 178 | B | C |
| 179 | B | |
| 180 | B | |
| 181 | A | C |
| 182 | B | C |
| 183 | B | |
| 184 (isomer A) | A | B |
| 184 (isomer B) | B | |
| 185 | A | C |
| 186 (isomer A) | B | C |
| 186 (isomer B) | A | B |
| 187 | A | C |
| 188 (isomer A) | A | A |
| 188 (isomer B) | A | C |
| 189 | A | C |
| 190 (isomer A) | A | C |
| 190 (isomer B) | A | |
| 191 | A | |
| 192 (isomer B) | A | |
| 193 | B | |
| 194 (isomer A) | B | |
| 194 (isomer B) | A | C |
| 195 | A | C |
| 196 (isomer A) | A | B |
| 196 (isomer B) | A | C |
| 197 | A | C |
| 198 (isomer A) | B | |

TABLE 92

| Example | NaV1.7 IC$_{50}$ | NaV1.5 IC$_{50}$ |
|---|---|---|
| 198 (isomer B) | A | C |
| 199 | B | C |
| 200 (isomer A) | B | C |
| 200 (isomer B) | A | C |
| 201 | A | B |
| 202 (isomer A) | A | C |
| 202 (isomer B) | A | A |
| 203 | A | C |
| 204 (isomer A) | A | C |
| 204 (isomer B) | A | B |
| 205 | B | C |
| 206 (isomer A) | A | |
| 206 (isomer B) | A | C |
| 207 (isomer B) | A | B |
| 208 | A | A |
| 209 (isomer A) | B | |
| 209 (isomer B) | A | A |
| 210 | A | |
| 211 (isomer A) | A | |
| 211 (isomer B) | A | A |
| 212 | A | C |
| 213 (isomer A) | A | C |
| 213 (isomer B) | A | C |
| 214 | A | B |
| 215 (isomer A) | A | B |
| 215 (isomer B) | A | B |
| 216 | A | |
| 217 (isomer A) | A | B |
| 217 (isomer B) | A | A |
| 218 | A | C |
| 219 (isomer A) | B | C |
| 219 (isomer B) | A | B |
| 220 | B | B |
| 221 (isomer A) | B | C |
| 221 (isomer B) | A | B |
| 222 | A | C |
| 223 (isomer A) | B | |
| 223 (isomer B) | A | B |
| 224 (isomer A) | A | C |

TABLE 92-continued

| Example | NaV1.7 IC$_{50}$ | NaV1.5 IC$_{50}$ |
|---|---|---|
| 224 (isomer B) | A | B |
| 225 | A | B |
| 226 (isomer A) | A | C |
| 226 (isomer B) | A | B |
| 227 | A | B |
| 228 (isomer A) | A | C |
| 228 (isomer B) | B | |
| 229 | A | B |
| 230 (isomer A) | A | C |
| 230 (isomer B) | B | |
| 231 | A | C |
| 232 (isomer A) | A | B |
| 232 (isomer B) | A | C |
| 233 | A | A |
| 234 (isomer A) | A | C |
| 234 (isomer B) | A | A |
| 235 | B | |
| 236 (isomer A) | A | B |
| 236 (isomer B) | A | B |
| 237 | A | |
| 238 (isomer A) | A | |
| 238 (isomer B) | A | |
| 239 | A | |
| 240 (isomer A) | B | |
| 240 (isomer B) | B | |
| 241 (isomer A) | A | |
| 242 (isomer A) | A | |
| 242 (isomer B) | A | |
| 243 | A | C |
| 244 (isomer A) | A | B |
| 244 (isomer B) | A | A |
| 245 | A | B |
| 246 (isomer A) | A | B |
| 246 (isomer B) | A | C |
| 247 (isomer A) | A | B |
| 247 (isomer B) | A | B |
| 248 (isomer A) | A | B |
| 248 (isomer B) | B | |
| 249 | B | |

TABLE 93

| Example | NaV1.7 IC$_{50}$ | NaV1.5 IC$_{50}$ |
|---|---|---|
| 250 | B | |
| 251 | A | C |
| 252 | A | C |
| 253 (isomer A) | B | |
| 253 (isomer B) | B | |
| 255 (isomer A) | B | |
| 256 (isomer A) | A | C |
| 256 (isomer B) | A | B |
| 257 (isomer A) | A | C |
| 257 (isomer B) | A | C |
| 258 | A | A |
| 259 | A | |
| 260 | A | C |
| 261 | A | A |
| 262 | B | C |
| 263 | A | B |
| 264 | A | |
| 265 | A | C |
| 266 | A | C |
| 267 | B | A |
| 268 | A | C |
| 269 | A | |
| 270 | B | |
| 271 | B | |
| 272 | B | C |
| 273 | A | C |
| 274 | B | |
| 275 | A | B |
| 276 | B | C |
| 277 | B | C |
| 278 | A | B |

TABLE 93-continued

| Example | NaV1.7 IC$_{50}$ | NaV1.5 IC$_{50}$ |
|---|---|---|
| 279 | A | C |
| 280 | B | A |
| 281 | B | C |
| 282 | A | B |
| 283 | A | A |
| 284 | A | A |
| 285 | A | B |
| 286 | B |   |
| 287 | B | C |

TABLE 94

| Example | NaV1.7 IC$_{50}$ | NaV1.5 IC$_{50}$ |
|---|---|---|
| 291 | B | C |
| 292 | A | B |
| 293 | B |   |
| 294 | B | C |
| 295 | A | C |
| 296 | B |   |
| 297 | B |   |
| 298 | A | B |
| 299 | A |   |
| 300 | B |   |
| 301 | B |   |
| 302 | B |   |
| 303 | A | B |
| 304 | B | C |
| 305 | A | B |
| 306 | A |   |
| 307 | B | B |
| 308 | B | B |
| 309 | B |   |
| 310 | B |   |
| 311 | B | C |
| 312 | B | C |
| 313 | B | C |
| 314 | A |   |
| 315 | B |   |
| 316 | B | B |
| 317 | B | C |
| 318 | B | C |
| 319 | B |   |
| 320 | B |   |
| 321 | B | C |
| 322 | B |   |
| 323 | B |   |
| 324 | B | C |
| 325 | A | C |
| 326 | B | C |
| 327 | B | C |
| 328 | B | B |
| 329 | A |   |
| 330 | B |   |
| 331 | B | B |
| 332 | B | C |
| 333 | B | C |
| 334 | B | B |
| 335 | B |   |
| 336 | B | B |
| 337 | B | C |
| 338 | B | C |
| 339 | B |   |
| 340 | B | C |
| 341 | A |   |
| 342 | A |   |
| 343 | A | B |
| 344 | A |   |
| 345 | A | B |
| 346 | B |   |
| 347 | B |   |
| 348 | A |   |
| 349 | A | B |
| 350 | B | C |
| 351 | A | C |

TABLE 94-continued

| Example | NaV1.7 IC$_{50}$ | NaV1.5 IC$_{50}$ |
|---|---|---|
| 352 | A | C |
| 353 | B | C |
| 354 | B |   |
| 355 | A |   |
| 356 | A | C |
| 357 | A | C |
| 358 | B | C |
| 359 | A | C |
| 360 | A | C |
| 361 | A | C |
| 362 | B | C |
| 363 | B |   |
| 364 | A | B |
| 365 | B |   |
| 366 | A | B |
| 367 | A |   |
| 368 | B |   |
| 369 | B |   |
| 370 | B |   |

TABLE 95

| Example | NaV1.7 IC$_{50}$ | NaV1.5 IC$_{50}$ |
|---|---|---|
| 371 | A |   |
| 372 | A |   |
| 373 | B | C |
| 374 | A | C |
| 375 | A | C |
| 376 | B |   |
| 377 | B |   |
| 378 | B | C |
| 379 | A |   |
| 380 | B |   |
| 381 | B |   |
| 382 | B | C |
| 383 | A | C |
| 384 | A |   |
| 385 | B |   |
| 386 | A | C |
| 387 | A |   |
| 388 | A |   |
| 389 | A | B |
| 390 | B |   |
| 391 | A | C |
| 392 | A | B |
| 393 | B |   |
| 394 | B |   |
| 395 | A |   |
| 396 | A |   |
| 397 | A |   |
| 398 | B |   |
| 399 | A |   |
| 400 | A | C |
| 401 | B | C |
| 402 | A | C |
| 403 | A |   |
| 404 | A |   |
| 405 | A |   |
| 406 | A |   |
| 407 | A |   |
| 408 | B |   |
| 409 | A |   |
| 410 | A |   |
| 411 | A | C |
| 412 | A | B |
| 413 | A |   |
| 414 | B |   |
| 416 | B |   |
| 417 | B |   |
| 418 | B |   |
| 419 | B |   |
| 420 | A |   |
| 421 | A | C |
| 422 | B | C |

TABLE 95-continued

| Example | NaV1.7 IC$_{50}$ | NaV1.5 IC$_{50}$ |
|---|---|---|
| 423 | A | |
| 424 | B | |
| 425 | A | C |
| 426 | B | C |
| 427 | A | B |
| 428 | A | C |
| 429 | B | C |
| 430 | A | |
| 431 | A | |
| 432 | A | B |
| 433 | A | |
| 434 | A | |
| 435 | A | |
| 436 | A | |
| 437 | A | B |
| 438 | A | |
| 439 | B | |
| 440 | B | |
| 441 | A | |
| 442 | A | |
| 444 | A | |
| 445 | A | C |
| 446 | B | |
| 447 | A | C |
| 448 | A | B |
| 449 | A | |
| 450 | B | C |

TABLE 96

| Example | NaV1.7 IC$_{50}$ | NaV1.5 IC$_{50}$ |
|---|---|---|
| 451 | A | B |
| 452 | B | |
| 453 | B | |
| 454 | B | C |
| 455 | A | |
| 456 | A | B |
| 457 | A | C |
| 458 | A | |
| 459 | A | C |
| 460 | A | C |
| 461 | A | B |
| 462 | A | C |
| 463 | A | |
| 464 | A | C |
| 465 | A | |
| 466 | A | B |
| 467 | A | |
| 468 | A | C |
| 469 | A | |
| 470 | A | B |
| 471 | A | |
| 472 | A | |
| 473 | A | |
| 474 | A | |
| 475 | A | |
| 476 | A | |
| 477 | A | |
| 478 | A | |
| 479 | A | |
| 480 | B | |
| 481 | A | C |
| 482 | A | |
| 483 | B | |
| 484 | A | |
| 485 | A | |
| 486 | A | |
| 487 | A | B |
| 488 | B | C |
| 489 | B | C |
| 490 | B | C |
| 491 | B | C |
| 492 | B | C |
| 493 | A | B |

TABLE 96-continued

| Example | NaV1.7 IC$_{50}$ | NaV1.5 IC$_{50}$ |
|---|---|---|
| 494 | A | B |
| 495 | A | C |
| 496 | A | B |
| 497 | A | C |
| 498 | A | |
| 499 | A | B |
| 500 | B | B |
| 501 | B | |
| 502 | B | B |
| 503 | B | |
| 504 | A | B |
| 505 | A | |
| 506 | A | B |
| 507 | A | C |
| 508 | A | |
| 509 | B | |
| 510 | B | |
| 511 | B | |
| 512 | B | |
| 513 | A | |
| 514 | A | |
| 515 | A | |
| 516 | B | |
| 517 | B | |
| 518 | A | B |
| 519 | B | |
| 520 | A | |
| 521 | A | |
| 522 | A | |
| 523 | A | |
| 524 | B | |
| 525 | B | |
| 526 | B | |
| 527 | A | |
| 528 | B | |
| 529 | A | |
| 530 | B | C |

TABLE 97

| Example | NaV1.7 IC$_{50}$ | NaV1.5 IC$_{50}$ |
|---|---|---|
| 531 | B | B |
| 532 | B | C |
| 533 | A | |
| 534 (isomer A) | B | |
| 534 (isomer B) | B | |
| 535 | A | C |
| 536 | B | |
| 537 | B | |
| 538 | A | C |
| 539 | B | |
| 540 | A | B |
| 541 | A | C |
| 542 | B | |
| 543 | B | C |
| 544 | B | |
| 545 | A | |
| 546 | A | |
| 547 (isomer A) | B | C |
| 547 (isomer B) | B | |
| 548 | B | |
| 549 | B | |
| 550 | A | |
| 551 | B | |
| 552 (isomer A) | B | C |
| 552 (isomer B) | B | |
| 553 | B | |
| 554 (isomer A) | A | C |
| 554 (isomer B) | B | |
| 555 | A | |
| 556 | A | |
| 557 | A | |
| 558 | A | |
| 559 | B | |

TABLE 97-continued

| Example | NaV1.7 IC$_{50}$ | NaV1.5 IC$_{50}$ |
|---|---|---|
| 560 | A | |
| 561 | B | |
| 562 | B | |
| 563 (isomer A) | B | B |
| 563 (isomer B) | A | C |
| 564 | B | |
| 565 | A | |
| 566 | A | |
| 567 | A | |
| 568 | A | C |
| 569 | A | |
| 570 | A | |
| 571 | B | |
| 572(isomer A) | B | C |
| 572(isomer B) | B | C |
| 573 | B | |
| 574 | A | |
| 575(isomer A) | A | B |
| 575(isomer B) | B | |
| 576(isomer A) | A | C |
| 576(isomer B) | A | C |
| 577(isomer A) | B | |
| 577(isomer B) | B | |
| 578 | B | |
| 579(isomer A) | A | B |
| 579(isomer B) | A | |
| 580 | A | |
| 581 | A | |
| 582 | B | |
| 583 | A | |
| 584 | A | |
| 585 | B | |
| 586 | A | |
| 587 | B | |
| 588 | A | |
| 589 | B | |
| 590(isomer A) | A | |
| 590(isomer B) | A | |
| 591 | A | |
| 592 | B | |
| 593 | B | B |
| 594 | B | |
| 595 | A | |
| 596 | A | |
| 597(isomer A) | A | C |
| 597(isomer B) | A | B |
| 598(isomer A) | A | |

TABLE 98

| Example | NaV1.7 IC$_{50}$ | NaV1.5 IC$_{50}$ |
|---|---|---|
| 598 (isomer B) | A | B |
| 599 | A | |
| 600 (isomer A) | B | |
| 600 (isomer B) | A | B |
| 601 (isomer A) | B | |
| 601 (isomer B) | B | C |
| 602 (isomer A) | A | C |
| 602 (isomer B) | A | |
| 603 (isomer A) | A | |
| 603 (isomer B) | A | C |
| 604 (isomer A) | A | B |
| 604 (isomer B) | B | |
| 605 | A | |
| 606 | A | |
| 607 | A | |
| 608 (isomer A) | A | C |
| 608 (isomer B) | A | C |
| 609 | B | |
| 610 (isomer A) | A | C |
| 610 (isomer B) | B | |
| 611 | A | |
| 612 | B | |
| 613 | A | |

TABLE 98-continued

| Example | NaV1.7 IC$_{50}$ | NaV1.5 IC$_{50}$ |
|---|---|---|
| 614 | A | |
| 615 (isomer A) | A | B |
| 615 (isomer B) | A | C |
| 616 (isomer A) | A | B |
| 616 (isomer B) | B | |
| 617 (isomer A) | A | C |
| 617 (isomer B) | B | |
| 617 (isomer C) | B | C |
| 617 (isomer D) | B | |
| 618 | B | |
| 619 | B | |
| 620 | A | |
| 621 | A | |
| 622 (isomer A) | A | C |
| 622 (isomer B) | A | C |
| 623 | A | |
| 624 | A | |
| 625 | A | |
| 626 | B | |
| 627 | B | |
| 628 | A | |
| 629 | A | |
| 630 | A | |
| 631 | A | |
| 632 | A | |
| 633 | A | |
| 634 | A | |
| 635 | A | |
| 636 (isomer A) | A | |
| 636 (isomer B) | A | |
| 637 | B | |
| 638 | B | |
| 639 | A | |
| 640 | A | |
| 641 (isomer A) | B | |
| 641 (isomer B) | B | |
| 642 | B | |
| 643 | B | |
| 644 | A | |
| 645 | A | |
| 646 | A | |
| 647 | A | |
| 648 | B | |
| 649 | B | |
| 650 | A | |
| 651 | A | |
| 652 | B | |
| 653 | B | |
| 654 | A | |
| 655 | A | |
| 656 | B | |
| 657 | A | |
| 658 | A | |
| 659 | B | |
| 660 | B | |
| 661 | A | |
| 662 | A | |
| 663 | A | |
| 664 | B | |
| 665 | A | |
| 666 | B | |
| 667 | A | |
| 668 | B | |
| 669 | B | |
| 670 | A | |
| 671 | A | |
| 672 | A | |
| 673 | A | |
| 674 | B | |

TABLE 98-continued

| Example | NaV1.7 IC$_{50}$ | NaV1.5 IC$_{50}$ |
|---|---|---|
| 675 | B | |
| 676 | A | |
| 677 | B | |
| 678 | A | |
| 679 | A | |
| 680 | B | |
| 681 | B | |
| 682 | B | |
| 683 | B | C |

TABLE 99

| Example | Inhibition rate (%) |
|---|---|
| 37 | B |
| 40 | B |
| 44 | A |
| 48 | A |
| 60 | B |
| 61 | B |
| 70 | A |
| 74 (isomer A) | A |
| 92 (isomer A) | A |
| 92 (isomer B) | A |
| 101 (isomer A) | C |
| 103 (isomer A) | A |
| 115 (isomer A) | A |
| 129 (isomer A) | A |
| 134 (isomer A) | A |
| 144 (isomer B) | A |
| 161 (isomer A) | A |
| 204 (isomer A) | A |
| 213 (isomer B) | B |
| 244 (isomer A) | B |
| 260 | A |
| 288 | A |
| 289 | C |
| 290 | A |

INDUSTRIAL APPLICABILITY

The present inventive heteroaromatic amide derivative represented by the general formula (I) or the general formula (I-E2) or a salt thereof has a strong Nav1.7 inhibitory effect and a lower Nav1.5 inhibitory effect, so that it is useful as an active ingredient of a therapeutic agent and/or prophylactic for various diseases associated with Nav1.7 with less concern about side effects derived from Nav1.5. For example, the present inventive heteroaromatic amide derivative or a salt thereof is useful as an analgesic for various diseases with pain.

The invention claimed is:
1. A heteroaromatic amide derivative or salt thereof represented by formula (I-E2):

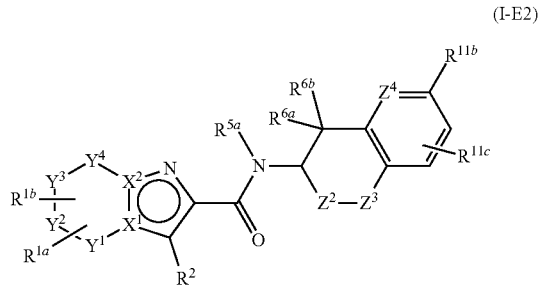

(I-E2)

wherein,
$X^1$—$X^2$ is N—C or C—N,
$Y^1$, $Y^2$, $Y^3$ and $Y^4$ together form
—OCR$^{4a}$HCH$_2$CH$_2$—, —OCR$^{4a}$R$^{4b}$CH$_2$CH$_2$—,
—OCH$_2$CH$_2$—, —OCR$^{4a}$HCH$_2$—, —OCR$^{4a}$R$^{4b}$CH$_2$—,
—OCH$_2$CH$_2$CH$_2$CH$_2$—, —OCR$^{4a}$HCH$_2$CH$_2$CH$_2$—,
—OCH$_2$CR$^{4a}$HCH$_2$CH$_2$—,
—OCH$_2$CR$^{4a}$R$^{4b}$CH$_2$CH$_2$—,
—CH$_2$OCH$_2$CH$_2$—, —CH$_2$OCH$_2$CH$_2$CH$_2$—,
—CH$_2$CH$_2$OCH$_2$—, —CH$_2$CR$^{4a}$HOCH$_2$—
—CH$_2$CH$_2$CH$_2$CH$_2$—, —CH$_2$CR$^{4a}$HCH$_2$CH$_2$—,
—NHCH$_2$CH$_2$CH$_2$—,
—NHCR$^{4a}$HCH$_2$CH$_2$—,
—CH$_2$NR$^{4c}$CH$_2$CH$_2$—,
—CH$_2$CH$_2$NR$^{4c}$CH$_2$—, —CH$_2$CR$^{4a}$HNR$^{4c}$CH$_2$—, or —CH$_2$CR$^{4a}$HNHCH$_2$—,
$R^{4a}$, $R^{4b}$ and $R^{4c}$ are, independently from each other and from $R^{1a}$ and $R^{1b}$, a hydroxy group, a $C_1$-$C_6$ alkyl group, a $C_1$-$C_6$ alkyl group optionally substituted by a hydroxy group, a $C_1$-$C_6$ haloalkyl group, a $C_1$-$C_6$ haloalkyl group optionally substituted by a hydroxy group, a $C_1$-$C_6$ alkoxy group, a $C_1$-$C_6$ haloalkoxy group, a $C_1$-$C_4$ alkoxy-$C_1$-$C_4$ alkyl group optionally substituted by a $C_1$-$C_4$ haloalkoxy group, a $C_1$-$C_4$ haloalkoxy-$C_1$-$C_4$ alkyl group, a $C_1$-$C_6$ haloalkylcarbonyl group, a $C_3$-$C_7$ cycloalkyl group optionally substituted by a halogen atom, a $C_1$-$C_4$ haloalkyl group, a heterocycloalkyl group, a $C_2$-$C_6$ alkynyl group optionally substituted by a halogen atom or a methoxy group, a $C_1$-$C_4$ haloalkoxy-$C_1$-$C_4$ alkoxy group, a $C_1$-$C_4$ haloalkylthio-$C_1$-$C_4$ alkyl group, —(CH$_2$)$_q$NR$^{b1}$R$^{b2}$ wherein R$^{b1}$ and R$^{b2}$ are, independently of each other, a hydrogen atom, a $C_1$-$C_4$ alkyl group, or a $C_1$-$C_4$ haloalkyl group, and q is 1, or 2 or a group represented by formula (I-B)

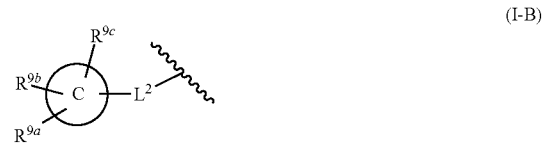

(I-B)

wherein,
ring C is a $C_3$-$C_7$ cycloalkyl, an azetidinyl, a pyrrolidinyl, a piperidyl, a morpholino, a phenyl, a thienyl, a pyrazolyl, a pyridyl, an oxetanyl, a tetrahydrofuranyl, a tetrahydropyranyl, or a dioxanyl,
$L^2$ is a single bond, —C≡C—,
—(CR$^{10a}$R$^{10b}$)$_{r1}$(CR$^{10c}$R$^{10d}$)$_{r2}$(CR$^{10e}$R$^{10f}$)$_{r3}$ (CR$^{10g}$R$^{10h}$)$_{r4}$—,
—(CR$^{10a}$R$^{10b}$)$_{r1}$(CR$^{10c}$R$^{10d}$)$_{r2}$O(CR$^{10e}$R$^{10f}$)$_{r3}$ (CR$^{10g}$R$^{10h}$)$_{r4}$—,
—(CR$^{10a}$R$^{10b}$)$_{r1}$(CR$^{10c}$R$^{10d}$)$_{r2}$NRC(CR$^{10e}$R$^{10f}$)$_{r3}$ (CR$^{10g}$R$^{10h}$)$_{r4}$—,
—(CR$^{10a}$R$^{10b}$)$_{r1}$(CR$^{10c}$R$^{10d}$)$_{r2}$CO(CR$^{10e}$R$^{10f}$)$_{r3}$ (CR$^{10g}$R$^{10h}$)$_{r4}$—;
(CR$^{10a}$R$^{10b}$)$_{r1}$(CR$^{10c}$R$^{10d}$)$_{r2}$S(CR$^{10e}$R$^{10f}$)$_{r3}$(CR$^{10g}$R$^{10h}$)$_{r4}$—;
—(CR$^{10a}$R$^{10b}$)$_{r1}$(CR$^{10c}$R$^{10d}$)$_{r2}$SO$_2$(CR$^{10e}$R$^{10f}$)$_{r3}$ (CR$^{10g}$R$^{10h}$)$_{r4}$—, or
(CR$^{10a}$R$^{10b}$)$_{r1}$(CR$^{10c}$R$^{10d}$)$_{r2}$SO$_2$NR$^c$(CR$^{10e}$R$^{10f}$)$_{r3}$ (CR$^{10g}$R$^{10h}$)$_{r4}$—, wherein $R^c$ is a hydrogen atom; or a $C_1$-$C_4$ alkyl group,
$R^{10a}$, $R^{10b}$, $R^{10c}$, $R^{10d}$, $R^{10e}$, $R^{10f}$, $R^{10g}$, and $R^{10h}$ are, independently from each other, a hydrogen atom, a halogen atom, a $C_1$-$C_4$ alkyl group, or a $C_3$-$C_7$ cycloalkyl group, $R^{10a}$ and $R^{10b}$ optionally form, together with the carbon atom bonded thereto, a 3- to 7-membered monocyclic ring;

r1, r2, r3 and r4 are, independently from each other, 0, 1, or 2, $R^{9a}$, Rob and $R^{9c}$ are, independently from each other, a hydrogen atom, a halogen atom, a cyano group, a $C_1$-$C_6$ alkyl group, a $C_1$-$C_6$ haloalkyl group, or a $C_1$-$C_6$ alkoxy group,

(I-C)

$R^{4a}$ and $R^{4b}$ optionally form, together with the carbon atom bonded thereto, a 3- to 7-membered monocyclic ring, or $R^{4a}$ and $R^{4b}$ optionally together form formula (I-D):

(I-D)

wherein $R^{4d}$ and $R^{4e}$ are, a hydrogen atom, $R^{1a}$ and $R^{1b}$ are, independently from each other, a hydrogen atom, a halogen atom, or a $C_1$-$C_4$ alkyl group, $R^2$ is a phenyl, a pyrazolyl, a pyridyl, or a pyrazinyl, wherein each is optionally substituted by a halogen atom, a $C_1$-$C_4$ alkyl group, a 2,2,2-trifluoroethoxy group, or a $C_1$-$C_4$ alkoxy group, a hydrogen atom, a halogen atom, a cyano group, a $C_2$-$C_6$ alkenyl group, or a $C_1$-$C_6$ alkyl group optionally substituted by a hydroxy group or a pyridinyl, $Z^2$-$Z^3$ is $CH_2O$, $R^{5a}$ is a hydrogen atom, a $C_1$-$C_6$ alkyl group, a heterocycloalkyl-$C_1$-$C_4$ alkyl group, or an aralkyl group, $R^{6a}$ and $R^{6b}$ are, independently from each other, a hydrogen atom, a halogen atom, a hydroxy group, a $C_1$-$C_4$ alkyl group, a $C_1$-$C_4$ alkoxy group, or a $C_1$-$C_4$ haloalkoxy group, $Z^4$ is C—$R^{11a}$ or a nitrogen atom, $R^{11a}$ is a hydrogen atom, a halogen atom, a cyano group, a cyanomethyl group, a $C_1$-$C_6$ haloalkyl group, a $C_1$-$C_6$ alkoxy group, a $C_1$-$C_6$ haloalkoxy group, a $C_1$-$C_4$ alkoxy-$C_1$-$C_4$ alkyl group, a $C_3$-$C_7$ cycloalkyl group, or a $C_2$-$C_6$ alkenyl group, $R^{11b}$ and $R^{11c}$ are, independently from each other, a hydrogen atom, a halogen atom, a cyano group, a $C_1$-$C_6$ alkyl group optionally substituted by a hydroxy group, a $C_1$-$C_6$ haloalkyl group, a $C_1$-$C_6$ alkoxy group, a $C_1$-$C_4$ alkoxy-$C_1$-$C_4$ alkyl group, a $C_1$-$C_4$ alkoxy-$C_1$-$C_4$ alkyl group substituted by a dimethylamino group or a dimethylaminocarbonyl group, a $C_1$-$C_4$ haloalkoxy-$C_1$-$C_4$ alkyl group, a $C_2$-$C_6$ alkenyl group optionally substituted by methoxy group, or a group represented by formula (I-A)

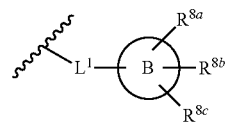
(I-A)

wherein,
ring B is a $C_3$-$C_7$ cycloalkyl, an azetidinyl, a morpholino, a pyrazolyl, a thiazolyl, a triazolyl, a pyridyl, a pyrazinyl, a tetrahydropyranyl, or a pyrimidinyl, $L^1$ is a single bond, —$CH_2$—, —$CH_2R^{a4}O$—, —$CH_2CH_2$, or —$CH_2OCH_2$, $R^{8a}$, $R^{8b}$ and $R^{8c}$ are, independently from each other, a hydrogen atom, a halogen atom, a cyano group, a $C_1$-$C_6$ alkyl group, a $C_1$-$C_6$ haloalkyl group, a $C_1$-$C_6$ alkoxy group, or a heterocycloalkyl group, with a proviso that at least one of $Y^1$, $Y^2$, $Y^3$, or $Y^4$ is —$CR^{4a}R^{4b}$—, —$CR^{4a}H$—, —$CH_2CR^{4a}R^{4b}$—, —$CH_2CR^{4a}H$—, or —$NR^{4c}$— when $R^2$ is a hydrogen atom, with a proviso that $R^2$ is a hydrogen atom when $X^1$—$X^2$ is C—N and $Y^1$, $Y^2$, $Y^3$ and $Y^4$ together form —$OCR^{4a}HCH_2CH_2$— or —$OCR^{4a}R^{4b}CH_2CH_2$.

2. The heteroaromatic amide derivative or salt thereof according to claim 1, wherein in the formula (I-E2),
$X^1$—$X^2$ is C—N,
$Y^1$, $Y^2$, $Y^3$ and $Y^4$ together form
—$OCR^{4a}HCH_2CH_2$—, —$OCR^{4a}R^{4b}CH_2CH_2$—, —$OCH_2CH_2$—,
—$OCR^{4a}HCH_2$—, —$OCR^{4a}R^{4b}CH_2$—,
—$OCH_2CH_2CH_2CH_2$—, —$OCR^{4a}HCH_2CH_2$—, —$OCH_2CR^{4a}HCH_2CH_2$—,
—$CH_2OCH_2CH_2$—, —$CH_2OCH_2CH_2CH_2$—, —$CH_2CR^{4a}HCH_2CH_2$—,
—$NHCH_2CH_2CH_2$—, —$NHCR^{4a}HCH_2CH_2$—, or —$CH_2NR^4CH_2CH_2$.

3. The heteroaromatic amide derivative or salt thereof according to claim 1, wherein in the formula (I-E2),
$Z^2$-$Z^3$ is —$CH_2O$—,
$R^{6a}$ and $R^{6b}$, independently from each other, are a hydrogen atom, a fluorine atom, a hydroxy group or a methoxy group,
$R^{11a}$ and $R^{11c}$ are each a hydrogen atom.

4. The heteroaromatic amide derivative or salt thereof according to claim 1, wherein in the formula (I-E2),
$X^1$—$X^2$ is C—N,
$Y^1$, $Y^2$, $Y^3$ and $Y^4$ together form
—$OCR^{4a}HCH_2CH_2$—, —$OCR^{4a}HCH_2$—,
—$OCR^{4a}HCH_2CH_2CH_2$—, —$CH_2CR^{4a}HCH_2CH_2$—,
$NHCR^{4a}HCH_2CH_2$—, or —$CH_2NR^4CH_2CH_2$.

5. The heteroaromatic amide derivative or salt thereof according to claim 1, wherein in the formula (I-E2),
$X^1$—$X^2$ is N—C,
$Y^1$, $Y^2$, $Y^3$ and $Y^4$ together form
—$CH_2CR^{4a}HOCH_2$—, —$CH_2CR^{4a}HCH_2CH_2$—,
—$CH_2CR^{4a}R^{4b}CH_2CH_2$—,
—$CH_2CH_2NR^4CH_2$—, —$CH_2CR^{4a}HNR_4CH_2$—, or
—$CH_2CR^{4a}HNHCH_2$—, with a proviso that ring C is not a phenyl ring when $Y^1$, $Y^2$, $Y^3$ and $Y^4$ together form $-CH_2CR^{4a}HCH_2CH_2-$, $R^2$ is a hydrogen atom, $R^{4a}$ is a group represented by the formula (I-B), and $L^2$ is a single bond.

6. The heteroaromatic amide derivative or salt thereof according to claim 1, wherein in the formula (I-E2), $Z^2$-$Z^3$ is $-CH_2O-$, $R^{6a}$, $R^{6b}$, and $R^{11c}$ are each a hydrogen atom, $R^{11a}$ is a hydrogen atom or a halogen atom.

7. A pharmaceutical composition containing the heteroaromatic amide derivative or salt thereof according to claim 1.

8. The heteroaromatic amide derivative or salt thereof according to claim 1, wherein the compound represented by the formula (I-E2) is any one of the following:

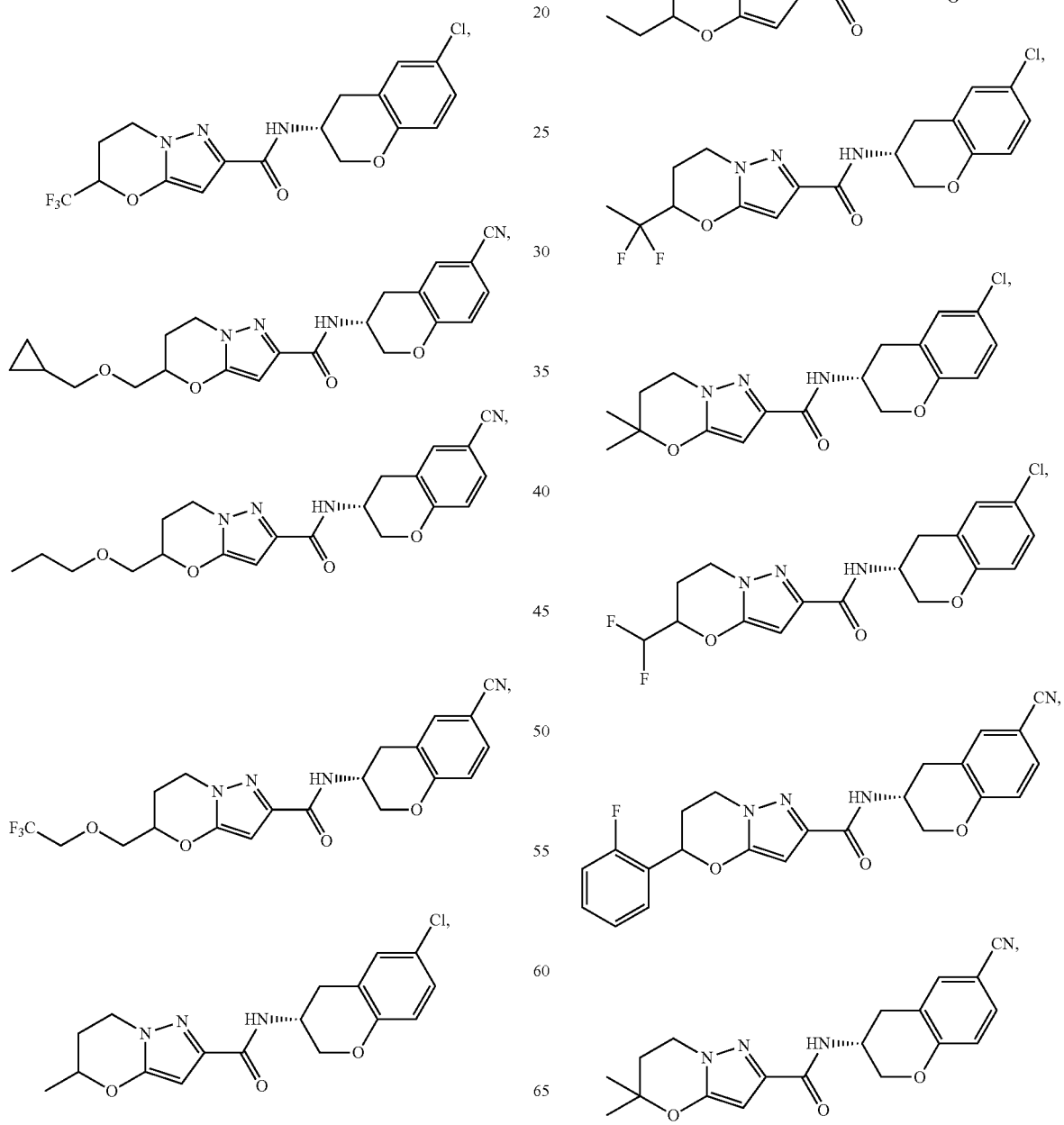

603
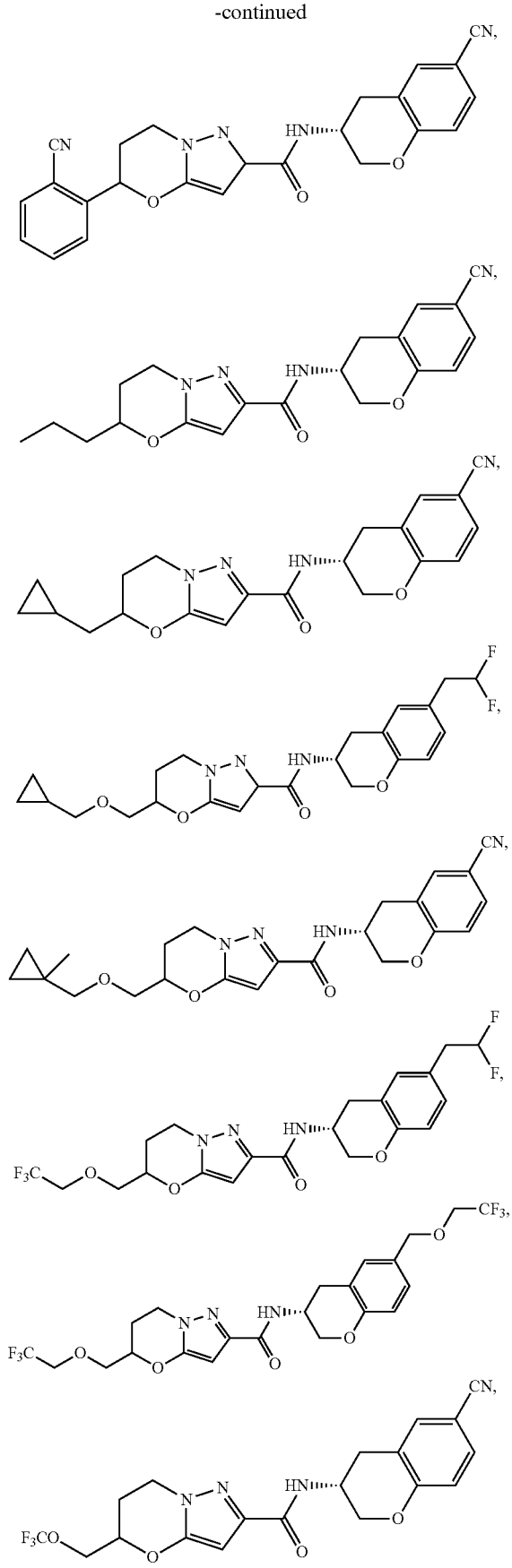
604
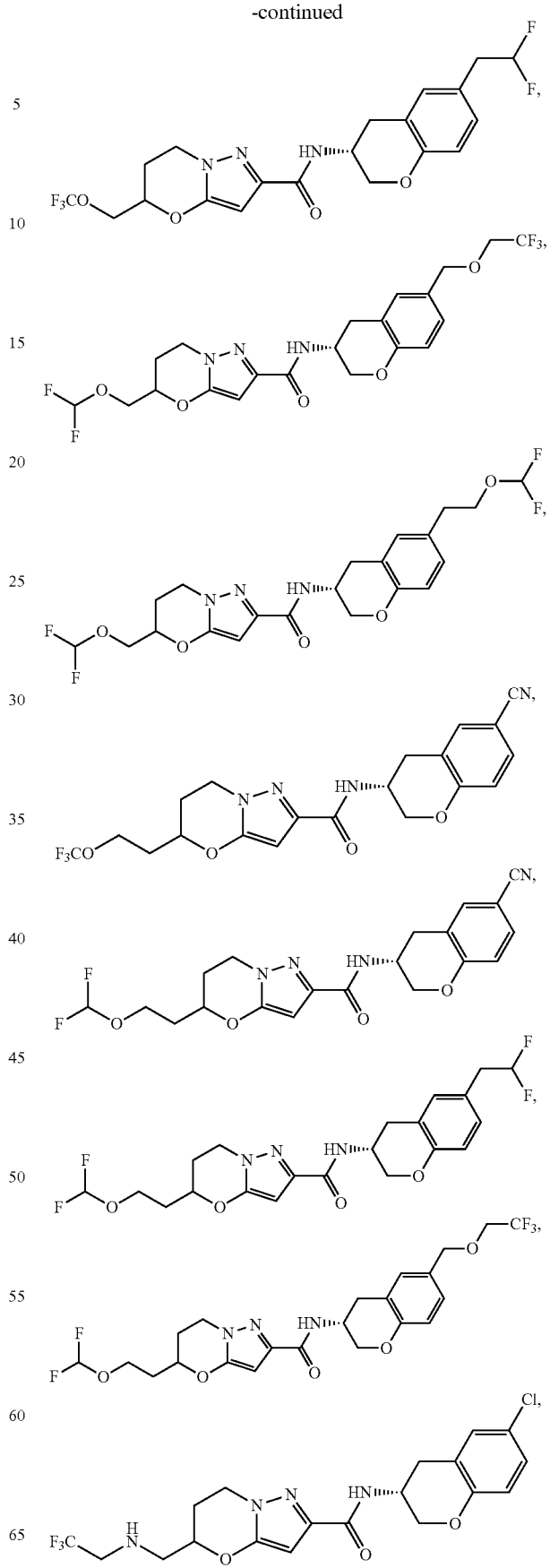

605
-continued
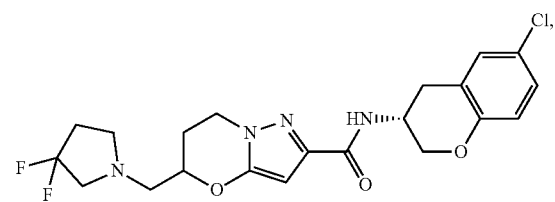
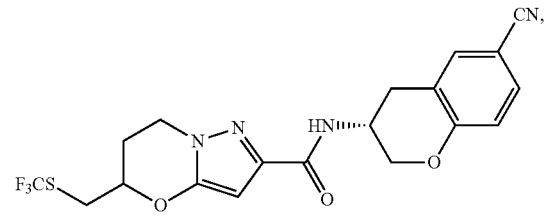
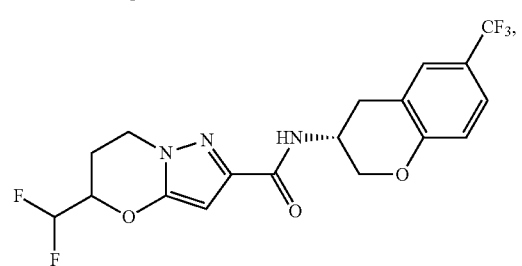
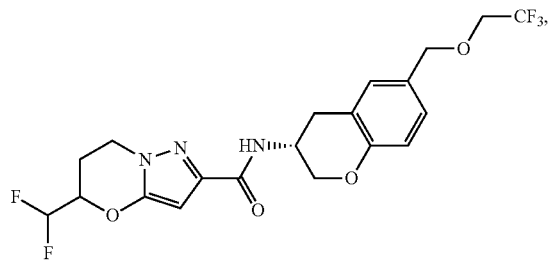
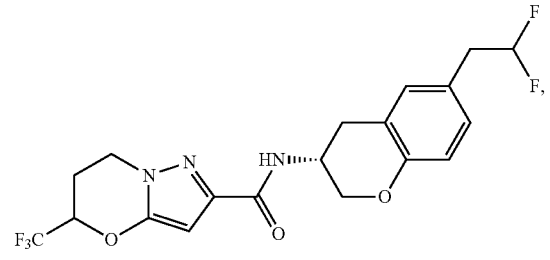
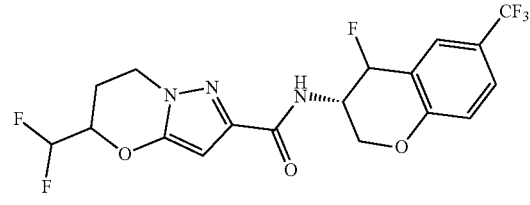
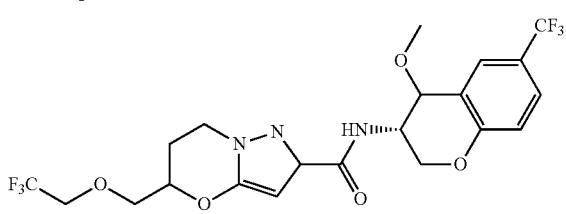
606
-continued
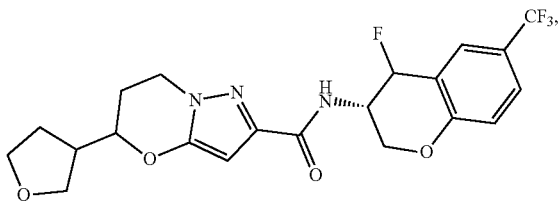
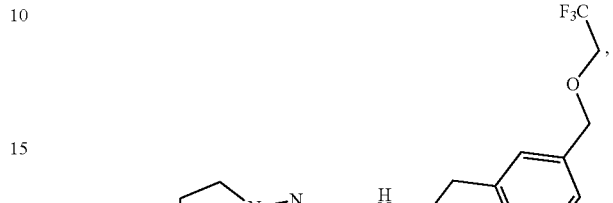
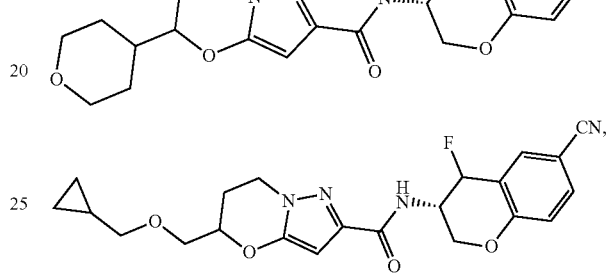
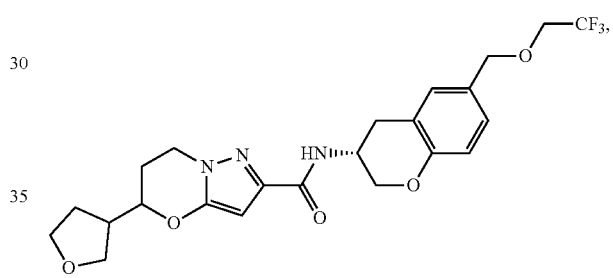
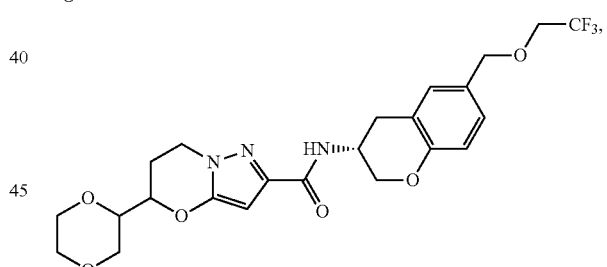
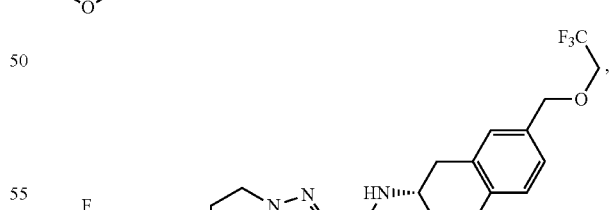
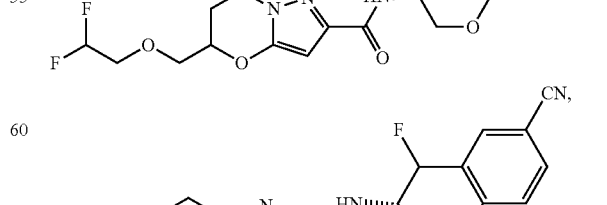
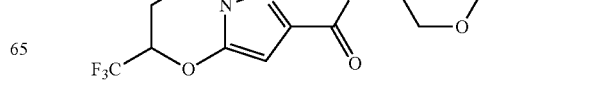

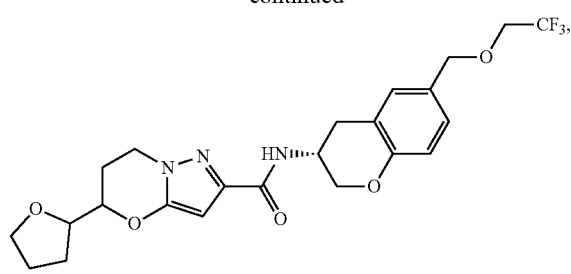
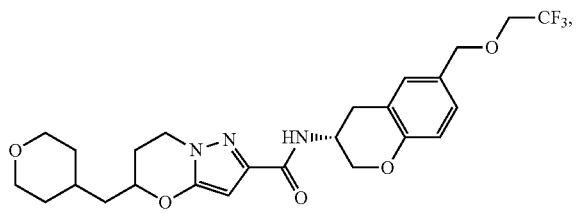
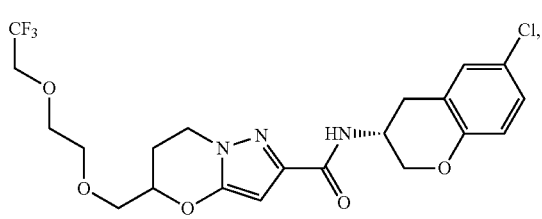
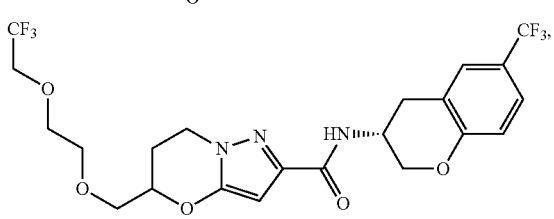
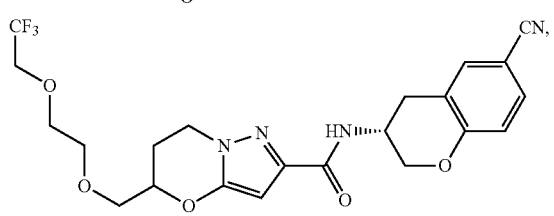
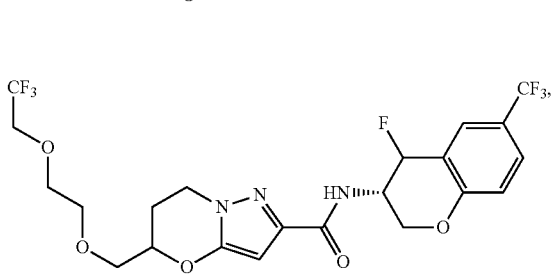
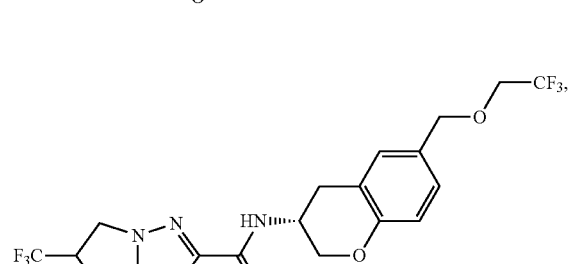
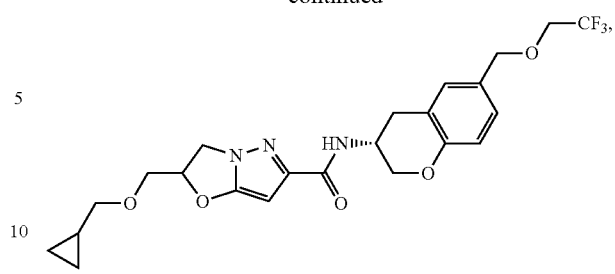
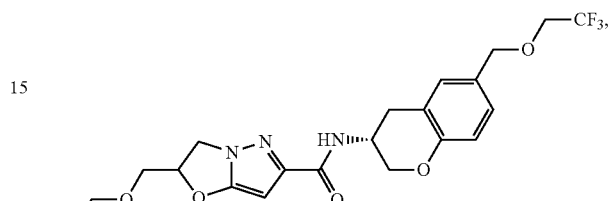
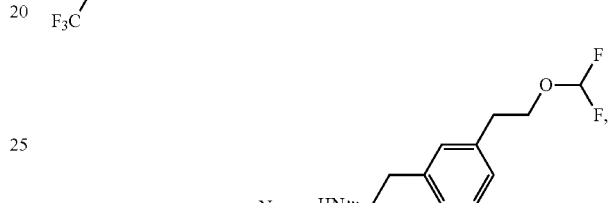
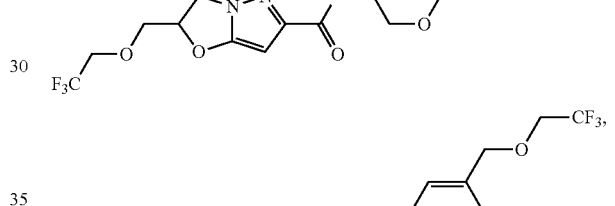
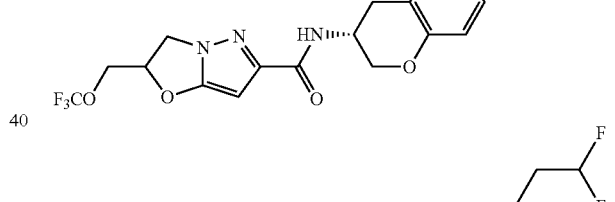
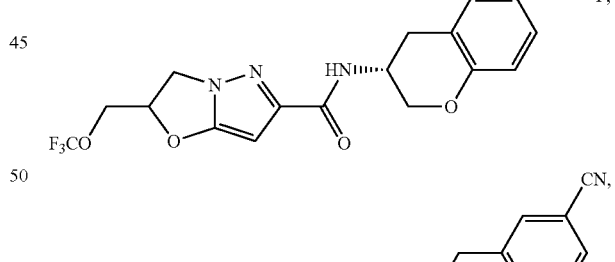
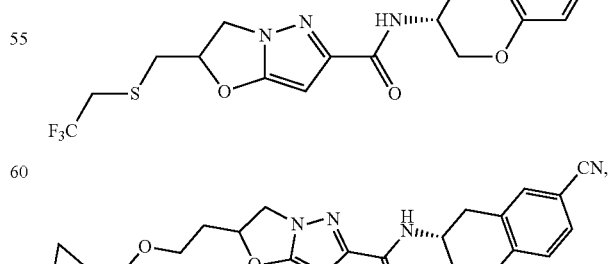

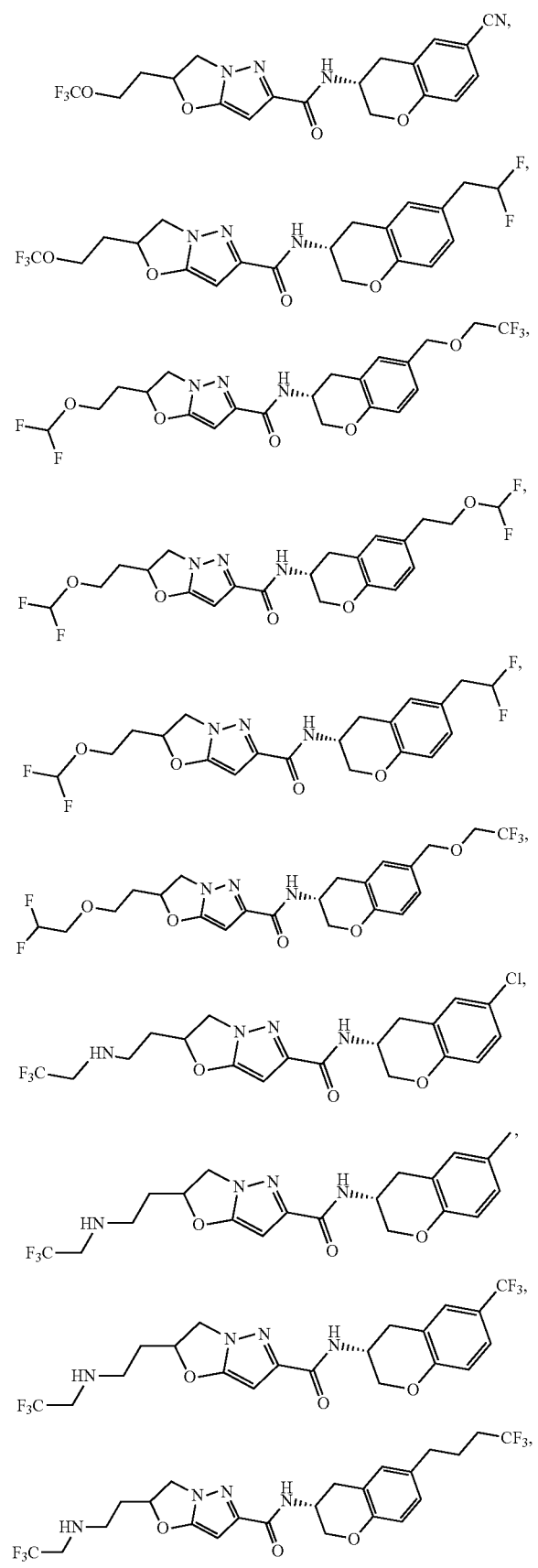
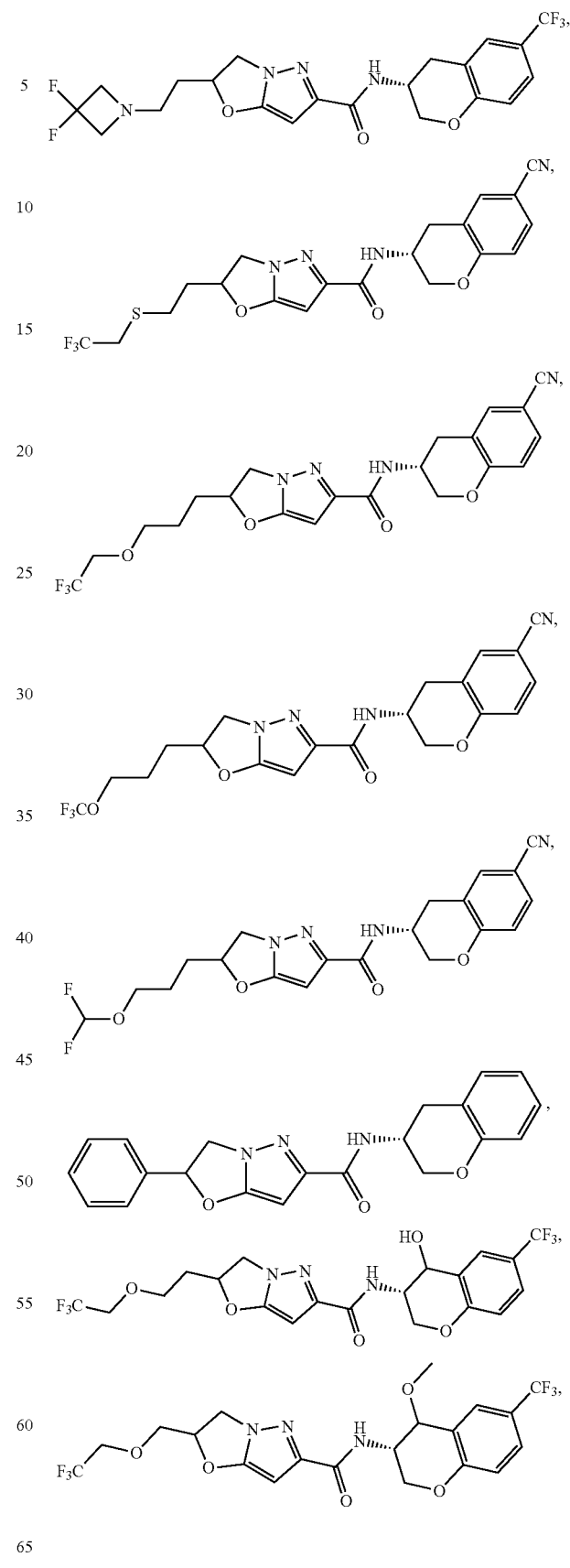

611
-continued
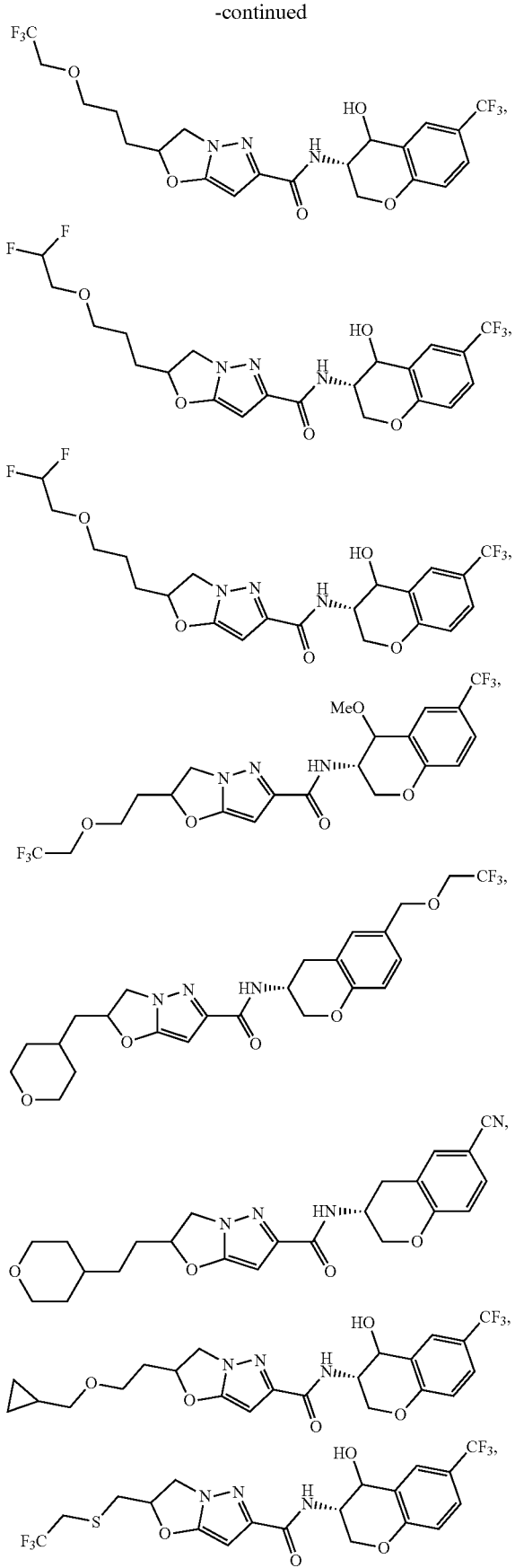
612
-continued
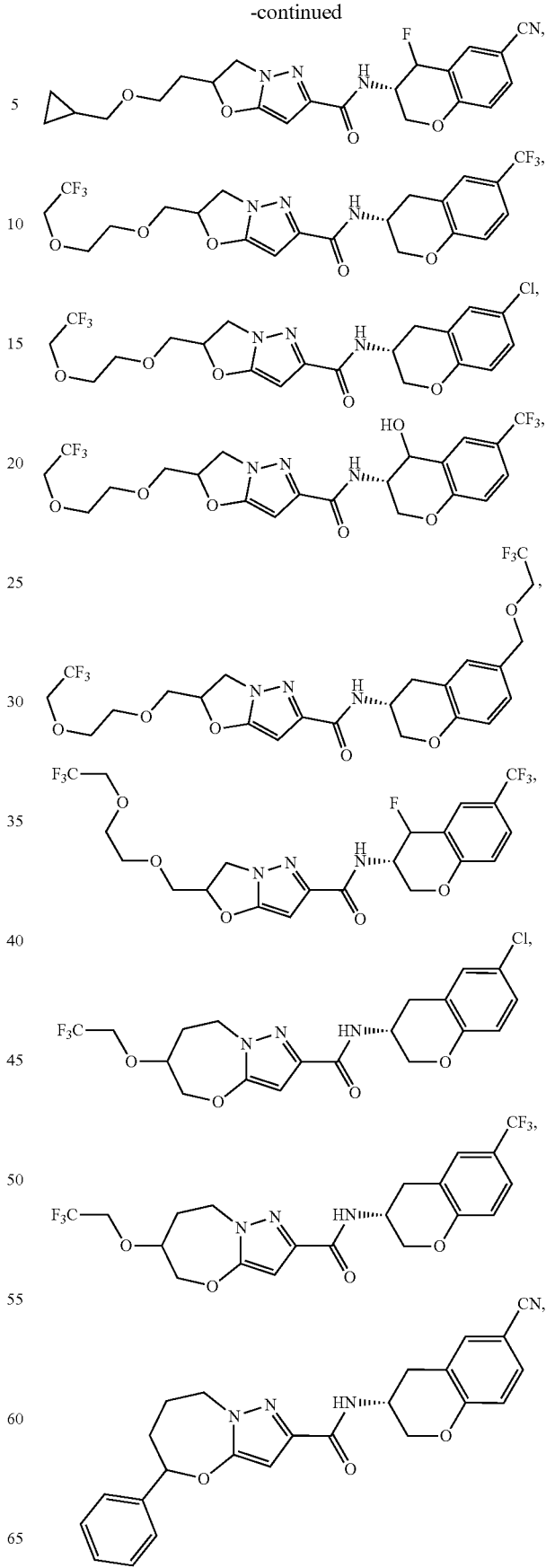

-continued
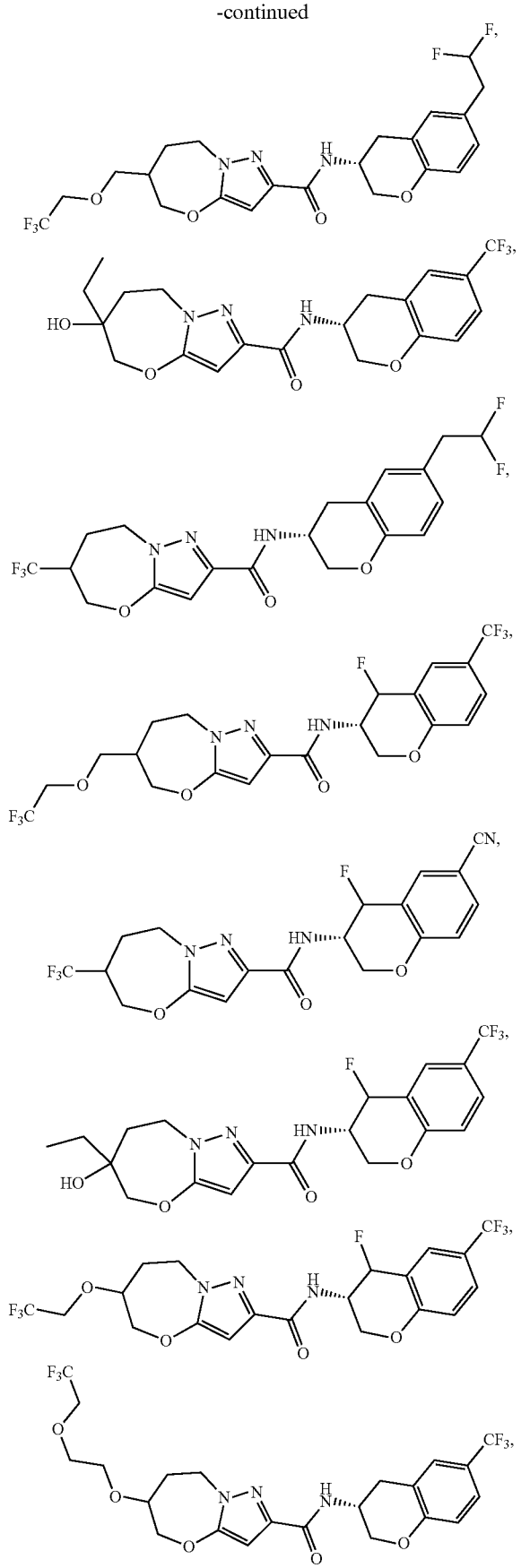
-continued
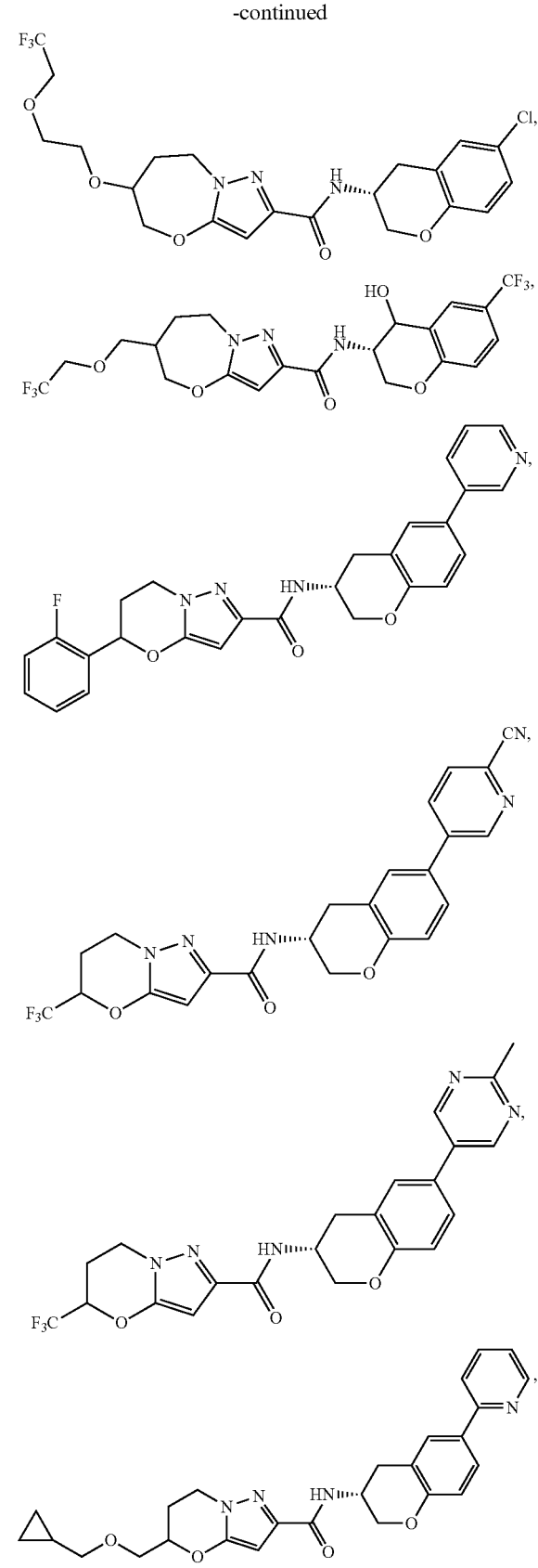

615
-continued
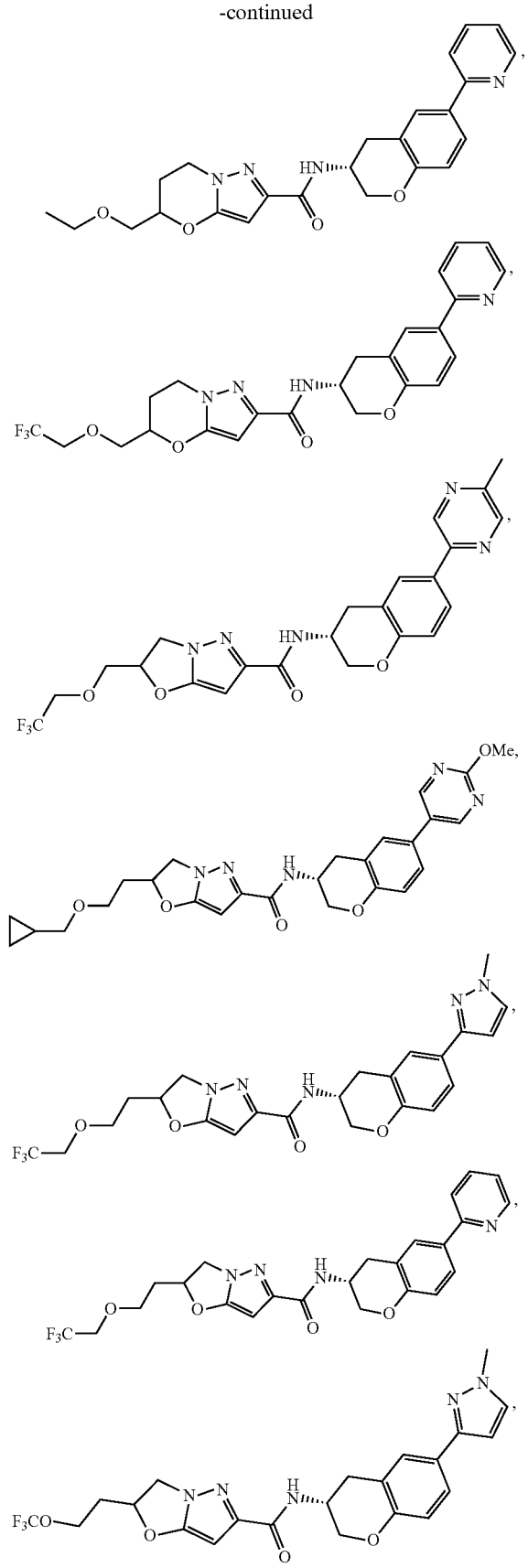
616
-continued
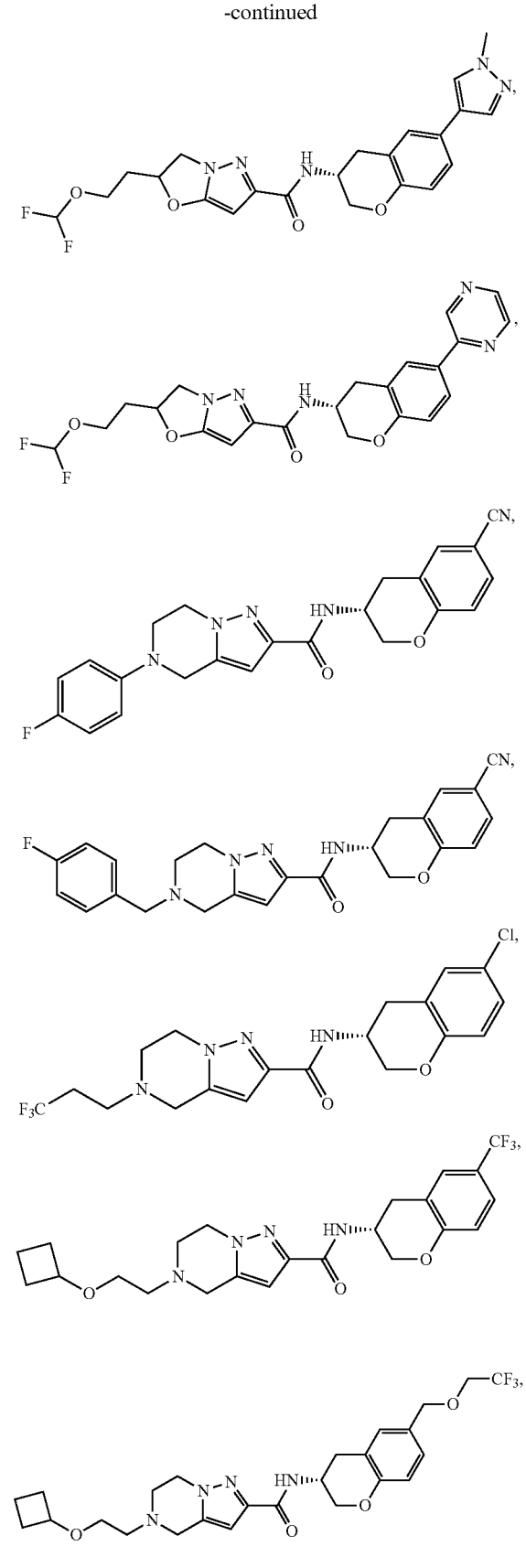

-continued
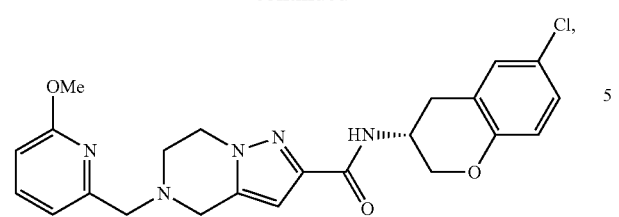
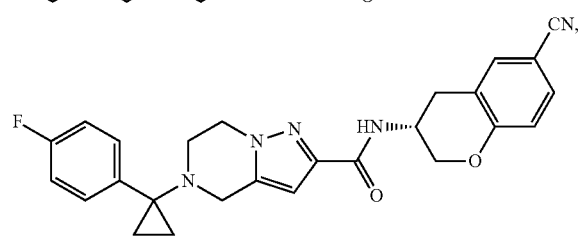
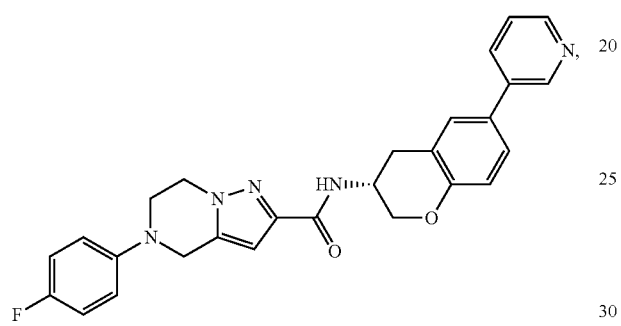
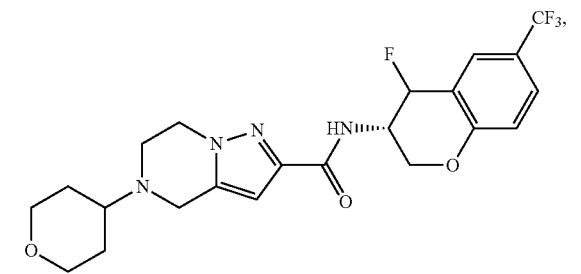
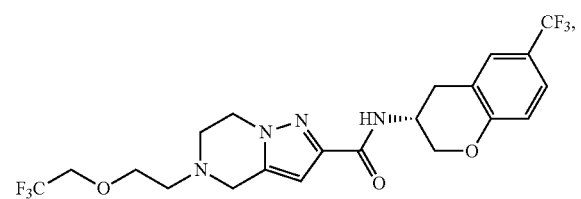
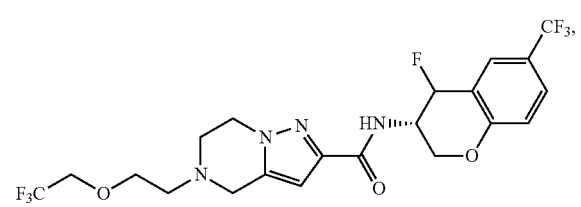
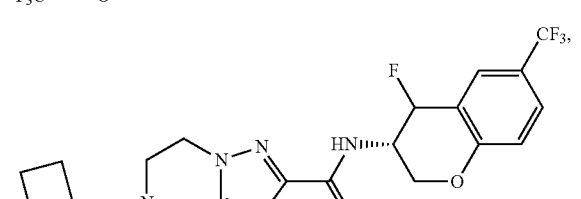
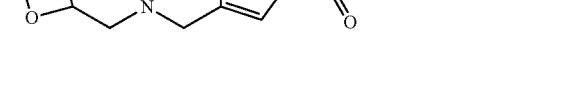
-continued
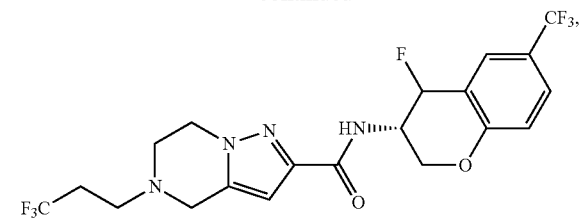
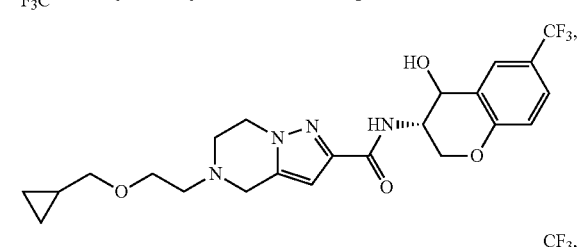
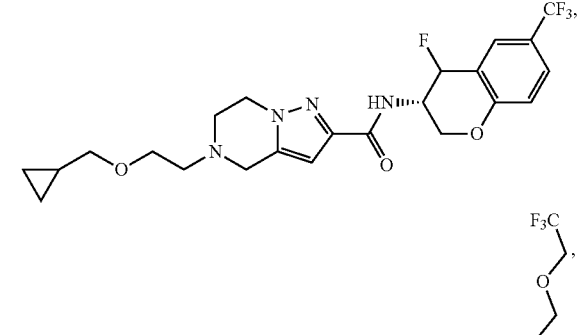
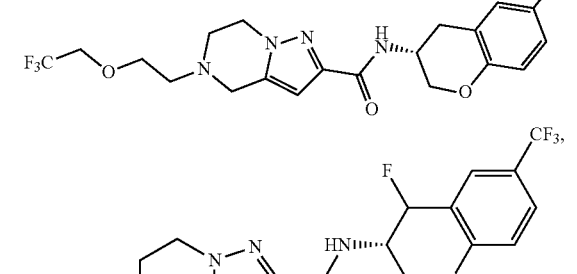
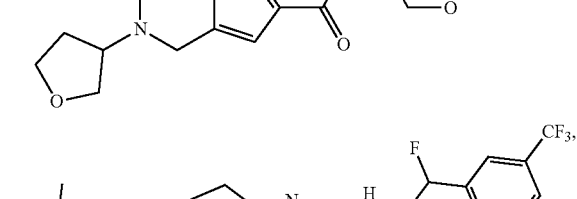
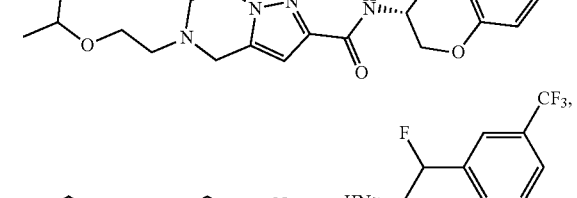
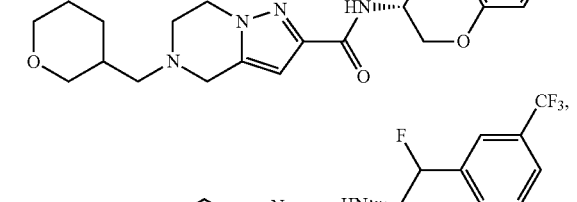

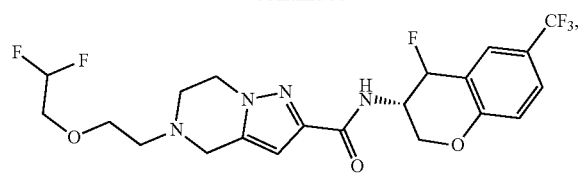
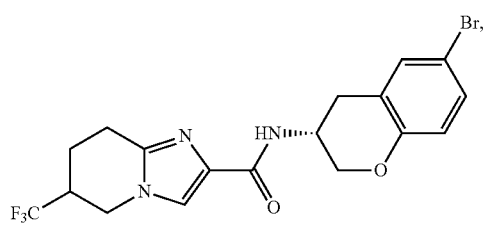
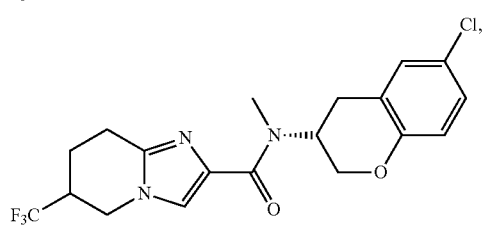
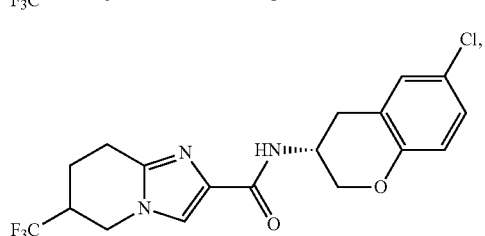
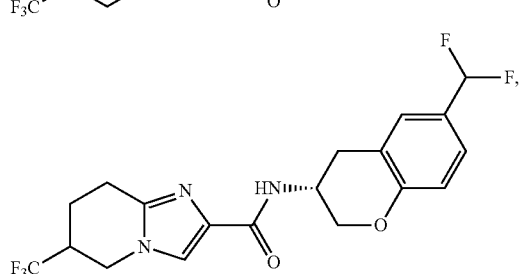
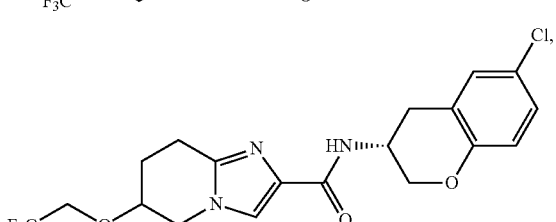
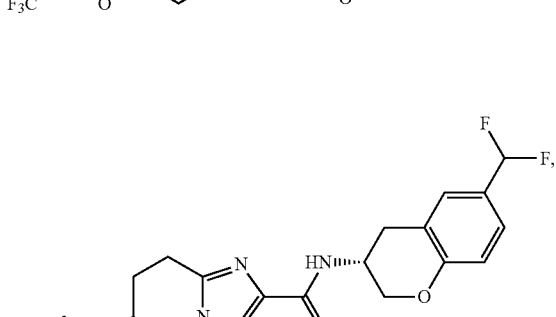
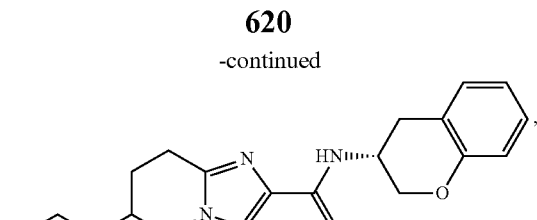
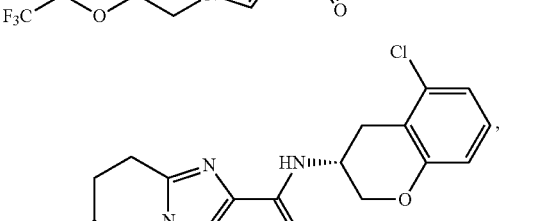
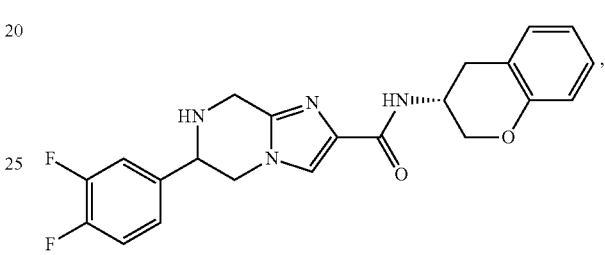
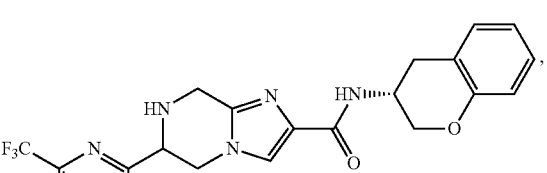
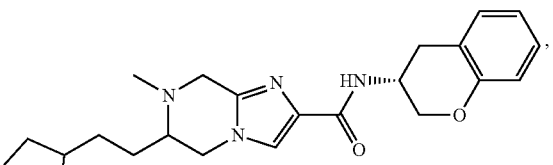
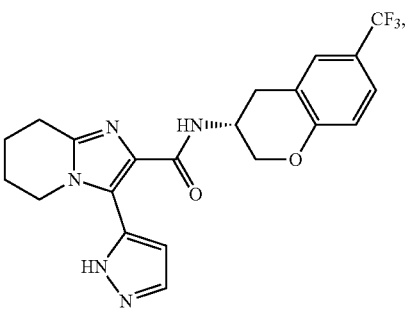

621
-continued
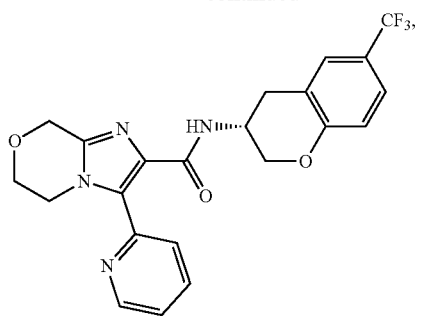
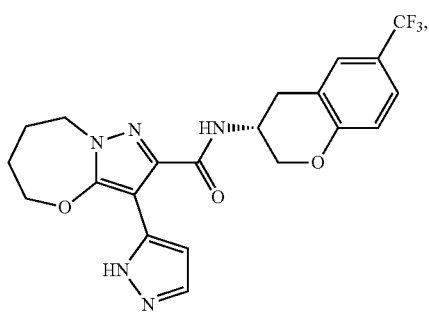
622
-continued
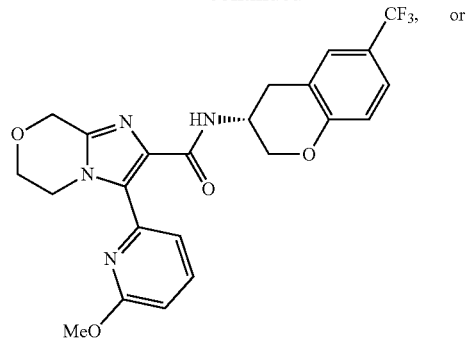
* * * * *